US012215157B2

(12) United States Patent
Chang et al.

(10) Patent No.: US 12,215,157 B2
(45) Date of Patent: Feb. 4, 2025

(54) MULTI-SPECIFIC BINDING PROTEINS THAT BIND CD33, NKG2D, AND CD16, AND METHODS OF USE

(71) Applicant: Dragonfly Therapeutics, Inc., Waltham, MA (US)

(72) Inventors: Gregory P. Chang, Medford, MA (US); Ann F. Cheung, Lincoln, MA (US); Asya Grinberg, Lexington, MA (US); Dhruv Kam Sethi, Belmont, MA (US); William Haney, Wayland, MA (US); Bianka Prinz, Lebanon, NH (US); Bradley M. Lunde, Lebanon, NH (US); Ronnie Wei, Weston, MA (US); Daniel Fallon, Winchester, MA (US); Steven O'Neil, Wayland, MA (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 503 days.

(21) Appl. No.: 16/971,104

(22) PCT Filed: Feb. 20, 2019

(86) PCT No.: PCT/US2019/018751
§ 371 (c)(1),
(2) Date: Aug. 19, 2020

(87) PCT Pub. No.: WO2019/164930
PCT Pub. Date: Aug. 29, 2019

(65) Prior Publication Data
US 2021/0101976 A1    Apr. 8, 2021

Related U.S. Application Data

(60) Provisional application No. 62/632,756, filed on Feb. 20, 2018, provisional application No. 62/677,137, filed on May 28, 2018.

(51) Int. Cl.
*C07K 16/28* (2006.01)

(52) U.S. Cl.
CPC ........ *C07K 16/283* (2013.01); *C07K 2317/31* (2013.01); *C07K 2317/522* (2013.01); *C07K 2317/55* (2013.01); *C07K 2317/565* (2013.01); *C07K 2317/622* (2013.01); *C07K 2317/92* (2013.01)

(58) Field of Classification Search
CPC .................... C07K 16/2803; C07K 16/2851
USPC ...................................................... 424/178.1
See application file for complete search history.

(56) References Cited

U.S. PATENT DOCUMENTS

| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,129,914 A | 10/2000 | Weiner et al. |
| 6,210,670 B1 | 4/2001 | Berg |
| 6,294,167 B1 | 9/2001 | Lindhofer et al. |
| 6,572,856 B1 | 6/2003 | Taylor et al. |
| 6,737,056 B1 | 5/2004 | Presta |
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,592,562 B2 | 11/2013 | Kannan et al. |
| 8,658,765 B2 | 2/2014 | Martin, Jr. et al. |
| 8,759,494 B2 | 6/2014 | Bachmann |
| 8,784,821 B1 | 7/2014 | Kufer et al. |

(Continued)

FOREIGN PATENT DOCUMENTS

| CA | 2990511 A1 | 12/2016 |
| CN | 101945893 A | 1/2011 |

(Continued)

OTHER PUBLICATIONS

Smits et al.(Expert Opin Biol Ther. Sep. 2016 ; 16(9): 1105-1112. doi:10.1080/14712598.2016.1195364).*
Rabia et al (Biochem Eng J. Sep. 15, 2018;137:365-374. doi: 10.1016/j.bej.2018.06.003. Epub Jun. 5, 2018).*
Altshuler et al.,(Biochemistry (Moscow), 75(13):1584-1605 (2010)).*
Marks et al., (J. Biol. Chem. 295(29) 9823-9837 (2020)).*
Ahmad et al., 2012, "scFv antibody: principles and clinical application," Clinical and Developmental Immunology 2012: 1-16.

(Continued)

*Primary Examiner* — Lynn A Bristol
(74) *Attorney, Agent, or Firm* — Jones Day

(57) ABSTRACT

Multi-specific binding proteins that bind to and kill human cancer cells expressing CD33 (Siglec-3) are described, as well as pharmaceutical compositions and therapeutic methods useful for the treatment of CD33 expressing cancer. The invention relates to multi-specific binding proteins that bind to human cancer cells expressing CD33 and exhibit high potency and maximum lysis of target cells compared to anti-CD33 monoclonal antibodies. The multi-specific binding proteins comprise a CD33-binding domain, an NKG2D-binding domain and a CD16-binding domain.

40 Claims, 36 Drawing Sheets

Specification includes a Sequence Listing.

(56) References Cited

U.S. PATENT DOCUMENTS

| | | |
|---|---|---|
| 8,796,420 B2 | 8/2014 | Martin, Jr. et al. |
| 8,840,888 B2 | 9/2014 | Nagorsen et al. |
| 8,931,406 B2 | 1/2015 | Detloff et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Radar et al. |
| 9,334,331 B2 | 5/2016 | Igawa et al. |
| 9,447,185 B2 | 9/2016 | Romagne et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,421,807 B2 | 9/2019 | Gonzalez et al. |
| 10,526,409 B2 | 1/2020 | Urso et al. |
| 11,124,582 B2 | 9/2021 | Ambrogelly et al. |
| 11,787,864 B2 | 10/2023 | Cheung et al. |
| 11,834,506 B2 | 12/2023 | Chang et al. |
| 11,884,733 B2 | 1/2024 | Chang et al. |
| 11,939,384 B1 | 3/2024 | Chang et al. |
| 2002/0103345 A1 | 8/2002 | Zhu |
| 2002/0193569 A1 | 12/2002 | Hanna |
| 2003/0095965 A1 | 5/2003 | Van Beneden et al. |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2010/0310463 A1 | 12/2010 | Cicortas Gunnarsson et al. |
| 2011/0008355 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Kreudenstein |
| 2012/0171173 A1 | 7/2012 | Ideno et al. |
| 2012/0195900 A1 | 8/2012 | Ghayur et al. |
| 2012/0251554 A1 | 10/2012 | Bachmann et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Inserm et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |

(56) References Cited

U.S. PATENT DOCUMENTS

| | | |
|---|---|---|
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1* | 12/2017 | Loew .............. C07K 14/70596 |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Yu et al. |
| 2018/0237541 A1 | 8/2018 | Kim et al. |
| 2018/0273633 A1 | 9/2018 | Jiang et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1* | 11/2019 | Chang ..................... A61P 13/12 |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1* | 7/2020 | Chang ..................... A61P 35/00 |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0376034 A1* | 12/2020 | Chang ................ A61K 39/4613 |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1* | 3/2021 | Chang ................ C07K 16/2803 |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1* | 7/2021 | Chang ..................... A61P 35/00 |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Begelow et al. |
| 2022/0119533 A1 | 4/2022 | Cheung et al. |
| 2022/0119534 A1* | 4/2022 | Baruah ................... A61P 35/02 |
| 2022/0153848 A1 | 5/2022 | Chang et al. |
| 2022/0195065 A1 | 6/2022 | Chang et al. |
| 2022/0378831 A1* | 12/2022 | Valamehr ......... C07K 14/70578 |
| 2022/0380459 A1* | 12/2022 | Chang ................ C07K 16/2803 |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 102378768 A | 3/2012 |
| CN | 105814084 | 7/2016 |
| CN | 105906722 A | 8/2016 |
| DE | 102013019352 A1 | 9/2015 |
| EP | 0627940 A1 | 12/1994 |
| EP | 0845998 A1 | 6/1998 |
| EP | 0871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 | 9/2013 |
| KR | 10-2014-0067944 | 6/2014 |
| RU | 2588668 C2 | 7/2016 |
| RU | 2593720 C2 | 8/2016 |
| RU | 2608504 C2 | 1/2017 |
| TW | 201305207 | 2/2013 |
| WO | WO 1988/008854 A1 | 11/1988 |
| WO | WO 1989/006544 A1 | 7/1989 |
| WO | WO 1996/027011 | 9/1996 |
| WO | WO 2001/071005 A2 | 9/2001 |
| WO | WO 2004/056873 A1 | 7/2004 |
| WO | WO 2005/003172 | 1/2005 |
| WO | WO 2005/009465 | 2/2005 |
| WO | WO 2005/105849 | 11/2005 |
| WO | WO 2006/037960 A2 | 4/2006 |
| WO | WO 2007/002905 | 1/2007 |
| WO | WO 2007/042573 | 4/2007 |
| WO | WO 2007/055926 A1 | 5/2007 |
| WO | WO 2007/097812 A2 | 8/2007 |
| WO | WO 2009/077483 A1 | 6/2009 |
| WO | WO 2009/089004 | 7/2009 |
| WO | WO 2010/017103 A2 | 2/2010 |
| WO | WO2010/080124 A2 | 7/2010 |
| WO | WO 2011/014659 | 2/2011 |
| WO | WO 2011/036183 | 3/2011 |
| WO | WO 2011/075636 A2 | 6/2011 |
| WO | WO 2011/076922 | 6/2011 |
| WO | WO 2011/109400 | 9/2011 |
| WO | WO 2011/131746 | 10/2011 |
| WO | WO 2011/143545 | 11/2011 |
| WO | WO 2012/006490 A2 | 1/2012 |
| WO | WO 2012/025530 | 3/2012 |
| WO | WO 2012/032080 | 3/2012 |
| WO | WO 2012/034039 A2 | 3/2012 |
| WO | WO 2012/045752 A1 | 4/2012 |
| WO | WO 2012/058768 | 5/2012 |
| WO | WO 2012/115241 | 8/2012 |
| WO | WO 2012/125850 A1 | 9/2012 |
| WO | WO 2012/158818 A2 | 11/2012 |
| WO | WO 2012/162482 A1 | 11/2012 |
| WO | WO 2013/013700 A1 | 1/2013 |
| WO | WO 2013/036799 A2 | 3/2013 |
| WO | WO 2013/092001 | 6/2013 |
| WO | WO 2013/113615 A1 | 8/2013 |
| WO | WO 2013/173496 A2 | 11/2013 |
| WO | WO 2013/192594 A2 | 12/2013 |
| WO | WO 2014/001324 A1 | 1/2014 |
| WO | WO 2014/012085 | 1/2014 |
| WO | WO 2014/079000 | 5/2014 |
| WO | WO 2014/084607 | 6/2014 |
| WO | WO 2014/110601 | 7/2014 |
| WO | WO 2014/124326 | 8/2014 |
| WO | WO 2014/131712 A1 | 9/2014 |
| WO | WO 2014/144763 A2 | 9/2014 |
| WO | WO 2014/145806 A2 | 9/2014 |
| WO | WO 2014/159940 A1 | 10/2014 |
| WO | WO 2014/165818 A2 | 10/2014 |
| WO | WO 2014/198748 A1 | 12/2014 |
| WO | WO 2015/009856 | 1/2015 |
| WO | WO 2015/036582 A2 | 3/2015 |
| WO | WO 2015/036606 | 3/2015 |

(56) References Cited

FOREIGN PATENT DOCUMENTS

| | | |
|---|---|---|
| WO | WO 2015/063187 A1 | 5/2015 |
| WO | WO 2015/070061 A1 | 5/2015 |
| WO | WO 2015/089344 A1 | 6/2015 |
| WO | WO 2015/095412 A1 | 6/2015 |
| WO | WO 2015/095539 A1 | 6/2015 |
| WO | WO 2015/095972 | 7/2015 |
| WO | WO 2015/150447 | 10/2015 |
| WO | WO 2015/153765 A1 | 10/2015 |
| WO | WO 2015/153912 A1 | 10/2015 |
| WO | WO 2015/158636 A1 | 10/2015 |
| WO | WO 2015/169781 A1 | 11/2015 |
| WO | WO 2015/181282 A1 | 12/2015 |
| WO | WO 2015/184203 A1 | 12/2015 |
| WO | WO 2015/184207 * | 12/2015 |
| WO | WO 2015/184207 A1 | 12/2015 |
| WO | WO 2015/197582 | 12/2015 |
| WO | WO 2015/197593 A1 | 12/2015 |
| WO | WO 2015/197598 | 12/2015 |
| WO | WO 2016/001810 | 1/2016 |
| WO | WO 2016/011571 | 1/2016 |
| WO | WO 2016/023909 A1 | 2/2016 |
| WO | WO 2016/025880 A1 | 2/2016 |
| WO | WO 2016/028672 A1 | 2/2016 |
| WO | WO 2016/032334 | 3/2016 |
| WO | WO 2016/070959 | 5/2016 |
| WO | WO 2016/090278 | 6/2016 |
| WO | WO 2016/097408 | 6/2016 |
| WO | WO 2016/100533 | 6/2016 |
| WO | WO 2016/109774 | 7/2016 |
| WO | WO 2016/115274 | 7/2016 |
| WO | WO 2016/122701 | 8/2016 |
| WO | WO 2016/134371 A2 | 8/2016 |
| WO | WO 2016/135041 | 9/2016 |
| WO | WO 2016/135066 A1 | 9/2016 |
| WO | WO 2016/142768 | 9/2016 |
| WO | WO 2016/146702 A1 | 9/2016 |
| WO | WO 2016/161390 A1 | 10/2016 |
| WO | WO 2016/164369 | 10/2016 |
| WO | WO 2016/164637 A1 | 10/2016 |
| WO | WO 2016/166629 A1 | 10/2016 |
| WO | WO 2016/184592 A1 | 11/2016 |
| WO | WO 2016/187220 | 11/2016 |
| WO | WO 2016/191305 A1 | 12/2016 |
| WO | WO 2016/196237 A1 | 12/2016 |
| WO | WO 2016/201300 A1 | 12/2016 |
| WO | WO 2016/201388 A2 | 12/2016 |
| WO | WO 2016/201389 | 12/2016 |
| WO | WO 2016/207273 A2 | 12/2016 |
| WO | WO 2016/207278 A1 | 12/2016 |
| WO | WO 2017/005732 A1 | 1/2017 |
| WO | WO 2017/008169 | 1/2017 |
| WO | WO 2017/021349 A1 | 2/2017 |
| WO | WO 2017/048824 A1 | 3/2017 |
| WO | WO 2017/075432 A2 | 5/2017 |
| WO | WO 2017/079694 | 5/2017 |
| WO | WO 2017/081190 | 5/2017 |
| WO | WO 2017/083545 | 5/2017 |
| WO | WO 2017/114694 | 7/2017 |
| WO | WO 2017/124002 A1 | 7/2017 |
| WO | WO 2017/125897 A1 | 7/2017 |
| WO | WO 2017/143406 A1 | 8/2017 |
| WO | WO 2017/165464 | 9/2017 |
| WO | WO 2017/165683 A1 | 9/2017 |
| WO | WO 2017/177337 A1 | 10/2017 |
| WO | WO 2017/180813 | 10/2017 |
| WO | WO 2017/211873 A1 | 12/2017 |
| WO | WO 2017/218707 A2 | 12/2017 |
| WO | WO 2018/045090 | 3/2018 |
| WO | WO 2018/098365 A2 | 5/2018 |
| WO | WO 2018/119171 A1 | 6/2018 |
| WO | WO 2018/148445 | 8/2018 |
| WO | WO 2018/148447 | 8/2018 |
| WO | WO 2018/148566 | 8/2018 |
| WO | WO 2018/148610 | 8/2018 |
| WO | WO 2018/152516 | 8/2018 |
| WO | WO 2018/152518 | 8/2018 |
| WO | WO 2018/152530 | 8/2018 |
| WO | WO 2018/152547 | 8/2018 |
| WO | WO 2018/157147 A1 | 8/2018 |
| WO | WO 2018/201051 | 11/2018 |
| WO | WO 2018/217799 | 11/2018 |
| WO | WO 2018/217945 | 11/2018 |
| WO | WO 2018/217947 | 11/2018 |
| WO | WO 2019/028027 | 2/2019 |
| WO | WO 2019/028283 | 2/2019 |
| WO | WO 2019/035939 | 2/2019 |
| WO | WO 2019/040727 | 2/2019 |
| WO | WO 2019/051308 A1 | 3/2019 |
| WO | WO 2019/055677 | 3/2019 |
| WO | WO 2019/157332 | 8/2019 |
| WO | WO 2019/157366 | 8/2019 |
| WO | WO 2019/164929 | 8/2019 |
| WO | WO 2019/164930 | 8/2019 |
| WO | WO 2019/195408 | 10/2019 |
| WO | WO 2019/195409 | 10/2019 |
| WO | WO 2019/217332 | 11/2019 |
| WO | WO 2019/222449 | 11/2019 |
| WO | WO 2019/231920 | 12/2019 |
| WO | WO 2020/033630 | 2/2020 |
| WO | WO 2020/086758 | 4/2020 |
| WO | WO 2020/172189 | 8/2020 |
| WO | WO 2021/041878 | 3/2021 |
| WO | WO 2021/216916 | 10/2021 |
| WO | WO 2021/226193 | 11/2021 |
| WO | WO 2022/031965 | 2/2022 |
| WO | WO 2022/187539 | 9/2022 |
| WO | WO 2023/056252 | 4/2023 |
| WO | WO 2023/107956 | 6/2023 |
| WO | WO 2023/154796 | 8/2023 |
| WO | WO 2023/168384 | 9/2023 |

OTHER PUBLICATIONS

Atwell et al., 1997, "Stable heterodimers from remodeling the domain interface of a homodimer using a phage display library", J. Mol. Biol., 270(1):26-35.

Averdam et al., 2009, "A novel system of polymorphic and diverse NK cell receptors in primates", PLoS Genetics, 5(10): e1000688.

Baek et al., 2014, "Construction of a large synthetic human Fab antibody library on yeast cell surface by optimized yeast mating", Journal of Microbiology and Biotechnology, 24(3):408-420.

Bendayan et al., 1995, "Possibilities of False Immunocytochemical Results Generated by The Use of Monoclonal Antibodies: The Example of the Anti-proinsulin Antibody," J. Histochem. Cytochem. 43:881-886.

Bostrom, et al., 2009, "Improving Antibody Binding Affinity and Specificity for Therapeutic Development," Methods and Protocols 525:353-376.

Brinkmann et al. (2017) "The making of bispecific antibodies," MABS 9(2)182-212.

Bryceson et al. (2006) "Synergy among receptors on resting NK cells for the activation of natural cytotoxicity and cytokine secretion," Blood 107(1):159-166.

Busfield et al. (2014) "Targeting of acute myeloid leukemia in vitro and in vivo with an anti-CD123 mAb engineered for optimal ADCC," Leukemia 28 (11): 2213-2221.

Cai et al., 2014, "Autonomous stimulation of cancer cell plasticity by the human NKG2D lymphocyte receptor coexpressed with its ligands on cancer cells", PLOS One, 9(10):e108942.

Chen et al. (1995) "Enhancement and destruction of antibody function by somatic mutation: unequal occurrence is controlled by V gene combinatorial associations," The EMBO Journal 14(12):2784-2794.

Chen et al. (1999) "Selection and Analysis of an Optimized Anti-VEGF Antibody: Crystal Structure of an Affinity-matured Fab in Complex with Antigen," J. Mol. Biol. 293:865-881.

Chen et al., 2017, "Targeting FLT3 by chimeric antigen receptor T ccells for the treatment of acute myeloid leuikemia", Leukemia, 31(8): 1830-1834.

(56) References Cited

OTHER PUBLICATIONS

Chen X. et al. (2013) "Fusion protein linkers: property, design and functionality" Advanced drug delivery reviews, 65(10):1357-1369.
Cho et al., 2010, "Delivery of NKG2D ligand using an anti-HER2 antibody-NKG2D ligand fusion protein results in an enhanced innate and adaptive antitumor response", Cancer Research, 70(24):10121-10130.
Choi et al. (2013) "A Heterodimeric Fc-Based Bispecific Antibody Simultaneously Targeting VEGFR-2 and Met Exhibits Potent Antitumor Activity," Mol Cancer Ther, 12(12):2748-2759.
Choi et al., 2015, "Engineering of immunoglobin Fc heterodimers using yeast surface-displayed combinatorial Fc library screening", PloS One, vol. 10, article No. 30145349:1-20.
Chu et al. Blood. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," 124(21) (5 pages).
Colman P. M. (1994) "Effects of amino acid sequence changes on antibody-antigen interactions" Research in Immunology 145(1):33-36.
Davis et al. (1999) "Therapy of B-Cell Lymphoma with Anti-CD20 Antibodies Can Result in the Loss of CD20 Antigen Expression, " Clinical Cancer Research 5:611-615.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084.
Dickopf et al. (2020) "Format and geometries matter: Structure-based design defines the functionality of bispecific antibodies," Computational and Structural Biotechnology Journal 18:1221-1227.
Ding et al., 2018, "Fusion proteins of NKG2DL in cancer immunotherapy", International J of Molecular Sciences, 19(1):177.
Edwards et al. (2003) "The Remarkable Flexibility of the Human Antibody Repertoire; Isolation of Over One Thousand Different Antibodies to a Single Protein, BLyS," J. Mol. Biol. 334:103-118.
Elliott et al., 2014, "Antiparallel conformation of knob and hole aglycosylated half-antibody homodimers is mediated by a CH2-CH3 hydrophobic interaction", J. Mol. Biol., 426(9):1947-57.
Epling-Burnette et al., 2004, "Dysregulated NK receptor expression in patients with lymphoproliferative disease of granular lymphocytes", Blood, 13(9):3431-3439.
Extended European Search Report dated Mar. 18, 2021 for EP App. No. 18840650.8 (14247-472-227).
Felices et al., 2016, "Generation of BiKEs and TriKEs to Improve NK Cell-Mediated Targeting of Tumor Cells" Methods Mol. Biol., vol. 1441:333-346.
Gantke et al. (2017) "Trispecific antibodies for CD16A-directed NK cell engagement and dual-targeting of tumor cells," Protein Engineering, Design & Selection 38(9):673-684.
Gantke et al., 2016, Trispecific antibodies for selective CD16A-directed NK-cell engagement in multiple myeloma, Blood, 128(22):4513-4513 (abstract only).
Gauthier et al. (2019) "Multifunctional Natural Killer Cell Engagers Targeting NKp46 Trigger Protective Tumor Immunity," Cell 177(7):1701-1713.
Germain et al., 2005, "MHC class I-related chain A conjugated to antitumor antibodies can sensitize tumor cells to specific lysis by natural killer cells", Clinical Cancer Research, Amer. Assoc. for Cancer Research, 11(20):7516-7522.
Glas et al. (1997) "Analysis of rearranged immunoglobulin heavy chain variable region genes obtained from a bone marrow transplant (BMT) recipient," Clinical & Experimental Immunology 107(2):372-380.
Gleason et al., "CD16xCD33 bispecific killer cell engager (BiKE) activates NK cells against primary MDS and MDSC CD33+ targets." Blood, The Journal of the American Society of Hematology 123.19 (2014): 3016-3026.

Gleason et al., 2012, "Bispecific and Trispecific Killer Cell Engagers Directly Activate Human NK Cells through CD16 Signaling and Induce Cytotoxicity and Cytokine Production," Molecular Cancer Therapeutics 11 (12): 2674-2684.
Gonzales, et al. (2005) "Minimizing the Immunogenicity of Antibodies for Clinical Application," Tumour Biol. 26(1):31-43.
Gooden et al. (2012) "Infiltrating CTLs are bothered by HLA-E on tumors," OncoImmunology, 1(1):92-93.
Ha et al., 2016, "Immunoglobin Fc heterodimer platform technology: from design to applications in therapeutic antibodies and proteins", Frontiers in Immunology, 7(394):1-16.
Henry et al. (2004) "A Prostate-Specific Membrane Antigen-Targeted Monoclonal Antibody- Chemotherapeutic Conjugate Designed for the Treatment of Prostate Cancer," Cancer Research 64:7995-8001.
Henry et al. (2017) "Stability-Diversity Tradeoffs Impose Fundamental Constraints on Selection of Synthetic Human VH/VL Single-Domain Antibodies from In Vitro Display Libraries," Frontiers in Immunology, 8:1-15.
Hezareh et al. (2001) "Effector Function Activities of a Panel of Mutants of a Broadly Neutralizing Antibody against Human Immunodeficiency Virus Type 1," Journal of Virology 75 (24):12161-12168.
Hlavacek et al., 1999, "Steric Effects on Multivalent Ligand-Receptor Binding: Exclusion of Ligand Sites by Bound Cell Surface Receptors," Biophysical Journal, 76(6): 3031-3043.
Hoseini et al. (2017) "Acute myeloid leukemia targets for bispecific antibodies," Blood Cancer Journal 7(2):e522-e522.
International Search Report and Written Opinion dated Aug. 23, 2018 for PCT/US2018/018768 (14247-426-228).
International Search Report and Written Opinion dated Aug. 29, 2019 for PCT/US2019/018748 (14247-427-228).
Jachimowicz et al., 2011, "Induction of In Vitro and In Vivo NK Cell Cytotoxicity Using High-Avidity Immunoligands Targeting Prostate-Specific Membrane Antigen in Prostate Carcinoma," Mol Cancer Thera, 10(6): 1036-1045.
Junttila et al. (2014) "Antitumor Efficacy of a Bispecific Antibody That Targets HER2 and Activates T Cells," Cancer Research 74(19):5561-5571.
Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," Leukemia 26:830-834.
Kellner et al., 2015, "Enhancing natural killer cell-mediated lysis of lymphoma cells by combining therapeutic antibodies with CD20-specific immunoligands engaging NKG2D or NKp30," OncoImmunology 5 (1): e1058459.
Kennedy et al. (2002) "Incidence and nature of CD20-negative relapses following rituximab therapy in aggressive B-cell non-Hodgkin's lymphoma: a retrospective review," British Journal of Haematology 119:412-416.
Kijanka et al. (2013) "Rapid optical imaging of human breast tumour xenografts using anti-HER2 VHHs site-directly conjugated to IRDye 800CW for image-guided surgery," Eur J Nucl Med Mol Imaging 40:1718-1729.
Kim et al. (2014) "Mutational approaches to improve the biophysical properties of human singledomain antibodies," Biochimica et Biophysica Acta, 1844:1983-2001.
Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.
Koerner et al. (2015) "Induction of NK and T Cell Immune Responses Against Leukemia Cells By Bispecific NKG2D-CD16 and -CD3 Fusion Proteins," Blood 126(23):2558, Abstract 606.
Krieg et al. (2005) "Functional Analysis of B and T Lymphocyte Attenuator Engagement on CD4+ and CD8+ T Cells," The Journal of Immunology 175(10):6420-6427.
Kunik et al. (2012) "Structural consensus among antibodies defines the antigen binding site," PLoS Comput Biol. 8(2):e1002388. Epub Feb. 23, 2012.

(56) References Cited

OTHER PUBLICATIONS

Kwong et al., 2008, "Generation, affinity maturation, and characterization of a human anti-human NKG2D monoclonal antibody with dual antagonistic and agonistic activity," Journal of Molecular Biology 384 (5): 1143-1156.
Lewis et al., 2014, "Generation of bispecific IgG antibodies by structure-based design of an orthogonal Fab interface", Nat. Biotechnol., 32(2):198-198.
Lin et al. (2011) "Improved affinity of a chicken single-chain antibody to avian infectious bronchitis virus by site-directed mutagenesis of complementarity-determining region H3," African Journal of Biotechnology 10(79):18294-18302.
Lin et al., 2014, "CD4(+) NKG2D(+) T cells induce NKG2D down-regulation in natural killer cells in CD86-RAE-1ε transgenic mice", Immunology, 141(3):401-415.
Liu et al., 2017, "Fc engineering for Developing Therapeutic Bispecific Antibodies and Novel Scaffolds," Frontiers in Immunology 8, 38: 1-15.
Lloyd et al. (2009) "Modelling the human immune response: performance of a 1011 human antibody repertoire against a broad panel of therapeutically relevant antigens," Protein Engineering, Design and Selection 22(3):159-168.
Long et al. (2013) "Controlling NK Cell Responses: Integration of Signals for Activation and Inhibition," Annu Rev Immunol. 2013 ; 31: 10.1146/annurev-immunol-020711-075005.
Lund et al. (1996) "Multiple interactions of IgG with its core oligosaccharide can modulate recognition by complement and human Fc gamma receptor I and influence the synthesis of its oligosaccharide chains," J. Immunol 157:4963-4969.
MacCallum et al. (1996) "Antibody-antigen Interactions: Contact Analysis and Binding Site Topography, " J. Mol. Biol. 262:732-745.
Madlener et al., 2010, "A Bispecific Protein Targeting the NKG2D Receptor on Natural Killer Cells: In Vitro and In Vivo activity of ULBP2-CEA, " Blood 116(21):2095.
Maeda et al. (2015) "New antibody modification technology and its application to antibody drugs," Farumashia 51(5):424-428.
Maeda Y. et al. (1997) "Engineering of Functional Chimeric Protein G-Vargula Luciferase" Analytical biochemistry, 249(2):147-152.
Mariuzza et al. (1987) "The Structural Basis of Antigen-Antibody Recognition," Ann. Rev. Biophys. Chem. 16:139:59.
May S. K. S. et al., 2013, SGN-CD33A: a novel CD33-targeting antibody-drug conjugate using a pyrrolobenzodiazepine dimer is active in models of drugresistant AML. Blood, vol. 122, No. 8, pp. 1455-1463.
McCarthy et al. (2001) "Altering the fine specificity of an anti-Legionella single chain antibody by a single amino acid insertion," Journal of Immunological Methods 251:137-149.
McWilliams et al. (2015) "Targeting the Tumor Evasion Interaction of NKG2A and Its Ligand HLA-E Increases Natural-Killer Cell Activity in Chronic Lymphocytic Leukemia," Blood 126 (23):1289.
Mimoto et al., 2014, "Crystal structure of a novel asymmetrically engineered Fc variant with improved affinity for FcγRs", Mol. Immunol., 58(1):132-138.
Morris (1996) "Epitope Mapping of Protein Antigens by Competition ELISA," The Protein Protocols Handbook, Totowa, NJ, Humana Press, 595-600.
Morvan et al. (2016). "NK cells and cancer: you can teach innate cells new tricks" Nat Rev Cancer, 16(1):7-19.
Muda et al., 2011, "Therapeutic assessment of SEED: a new engineered antibody platform designed to generate mono- and bispecific antibodies", Protein Eng. Des. Sel., 24(5):447-454.
Myers et al. (2021) "Exploring the NK cell platform for cancer immunotherapy," Nature Reviews Clinical Oncology 18(2):85-100.
Nagasaki et al., 2013, "Interleukin-6 released by colon cancer-associated fibroblasts is critical for tumour angiogenesis: anti-interleukin-6 receptor antibody suppressed angiogenesis and inhibited tumour-stroma interaction", British Journal of Cancer, 110(2):469-478.
Nie et al. (2020) "Biology drives the discovery of bispecific antibodies as innovative therapeutics," Antibody Therapeutics 3(1):18-62.
Notice of Opposition for Colombia Patent Application No. NC2020/0010345 dated Dec. 16, 2020.
Padlan et al. (1989) "Structure of an antibody-antigen complex: Crystal structure of the HyHEL-10 Fab-lysozyme complex," Pro. Natl. Acad. Sci. USA 86:5938-5942.
Paul et al. (1993) "Fundamental Immunology," (textbook) 292-295.
Petricevic et al. (2013) "Trastuzumab mediates antibody-dependent cell-mediated cytotoxicity and phagocytosis to the same extent in both adjuvant and metastatic HER2/neu breast cancer patients," Journal of Translational Medicine 11 (307).
Portolano et al., 1993, "Lack of promiscuity in autoantigen-specific H and L chain combinations as revealed by human H and L chain 'roulette'," J. Immunol. 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," Cancer Research 4 pages.
Raab et al. (2014) "Fc-Optimized NKG2D-Fc Constructs Induce NK Cell Antibody-Dependent Cellular Cytotoxicity Against Breast Cancer Cells Independently of HER2/neu Expression Status," Journal of Immunology 193(8): 4261-72.
Roda-Navarro et al. (2020) "Understanding the Spatial Topology of Artificial Immunological Synapses Assembled in T Cell-Redirecting Strategies: A Major Issue in Cancer Immunotherapy," Frontiers in Cell and Developmental Biology 7:1-5.
Roitt I., Brostoff J., Male D. (1998) Immunology, 5th Edition. p. 150.
Romee et al. (2013) "NK cell CD16 surface expression and function is regulated by a disintegrin and metalloprotease-17 (ADAM17)," Blood 121(18): 3599-608.
Rothe et al., 2013, "The Bispecific Immunoligand ULBP2-aCEA Redirects Natural Killer Cells to Tumor Cells and Reveals Potent Anti-Tumor Activity Against Colon Carcinoma," Int. J. Cancer 134(12):2829-2840.
Rudikoff et al. (1982) "Single amino acid substitution altering antigen-binding specificity," Pro. Natl. Acad. Sci USA 79:1979-1983.
Safdari Y. et al. (2013) "Antibody humanization methods-a review and update" Biotechnology and Genetic Engineering Reviews, 29(2):175-186.
Schroeder et al. (2010) "Structure and Function of Immunoglobulins," J Allergy Clin Immunol 125:S41-S52.
Schuster et al. (2015) "Immunotherapy with the trifunctional anti-CD20 x anti-CD3 antibody FBTA05 (Lymphomun) in paediatric high-risk patients with recurrent CD20-positive B cell malignancies," British Journal of Haematology 169 (1):90-102.
Shen J. et al. (2006) "Single variable domain-IgG fusion: a novel recombinant approach to Fc domain-containing bispecific antibodies" Journal of Biological Chemistry, 281(16):10706-10714.
Shum et al. (2002) "Conservation and Variation in Human and Common Chimpanzee CD94 and NKG2 Genes, " The Journal of Immunology 168:240-252.
Smits et al., 2016, "Designing multivalent proteins based on natural killer cell receptors and their ligands as immunotherapy for cancer", Expert Opinion on Biological Therapy, 16(9):1105-1112.
Spear et al., 2013, "NKG2D ligands as therapeutic targets", Cancer Immunology, 13(8): 14 pages.
Stamova et al. (2011) "Simultaneous engagement of the activatory receptors NKG2D and CD3 for retargeting of effector cells to CD33-positive malignant cells, " Leukemia 25:1053-1056.
Steigerwald et al., 2009, "Human lgG1 antibodies antagonizing activating receptor NKG2D on natural killer cells," mAbs 1(2): 115-127.
Stein et al. (2012) "Natural Killer (NK)- and T-Cell Engaging Antibody-Derived Therapeutics," Antibodies 1:88-123.
Steinbacher et al., 2014, "An Fc-optimized NKG2D-immunoglobulin G fusion protein for induction of natural killer cell reactivity against leukemia," International Journal of Cancer 136(5):1073-1084.

(56) References Cited

OTHER PUBLICATIONS

Strong, 2002, "Asymmetric ligand recognition by the activating natural killer cell receptor NKG2D, a symmetric homodimer," Molecular Immunology 38 (14):1029-1037.
Tay et al., 2016, "TriKEs and BiKEs join CARs on the cancer immunotherapy highway", Human Vaccines and Immunotherapeutics, 12(11):2790-2796.
Teplyakov A. et al. (2014) "Antibody modeling assessment II. Structures and models" Proteins: Structure, Function, and Bioinformatics, 82(8):1563-1582.
Torres M et al. (2008) "The immunoglobulin constant region contributes to affinity and specificity" Trends in immunology, 29(2):91-97.
Vajdos et al. (2002) "Comprehensive Functional Maps of the Antigen-binding Site of an Anti-ErbB2 Antibody Obtained with Shotgun Scanning Mutagenesis," J. Mol. Biol. 320:415-428.
Vaks et al., 2018, "Design Principles for Bispecific lgGs, Opportunities and Pitfalls of Artificial Disulfide Bonds," Antibodies 7(3): 1-28.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," Clin Cancer Res, 22(14):3440-50.
Von Strandmann, 2006, "A novel bispecific protein (ULBP2-BB4) targeting the NKG2D receptor on natural killer (NK) cells and CD138 activates NK cells and has potent antitumor activity against human multiple myeloma in vitro and in vivo," Blood 107(5): 1955-1962.
Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.
Wang et al. (2018) "IgG Fc engineering to modulate antibody effector functions," Protein Cell 9(1):63-73.
Wang et al., 2016, "A bispecific protein rG7S-MICA recruits natural killer cells and enhances NKG2D-mediated immunosurveillance against hepatocellular carcinoma," Cancer Letters 372:166-178.
Weiss-Steider et al. (2011) "Expression of Mica, Micb and NKG2D in human leukemic myelomonocytic and cervical cancer cells," Journal of Experimental & Clinical Cancer Research 30 (1):37.
Wranik et al., 2012, "LUZ-Y, a novel platform for the mammalian cell production of full-length IgG-bispecific antibodies", J. Biol. Chem., 287:43331-43339.
Written Opinion for International Application No. PCT/US2019/017330 dated Jun. 11, 2019.
Written Opinion for International Application No. PCT/US2019/018751 dated Jul. 1, 2019.
Wu et al. (1999) "Humanization of a Murine Monoclonal Antibody by Simultaneous Optimization of Framework and CDR Residues," J. Mol. Biol. 294:151-162.
Xu et al. (2014) "Production of bispecific antibodies in "knobs-into-holes" using a cell-free expression system," mAbs 7(1)231-242.
Xu et al., 2019, A VEGFR2-MICA bispecific antibody activates tumor-infiltrating lymphocytes and exhibits potent anti-tumor efficacy in mice, Cancer Immunology Immunotherapy, 68(9): 1429-1441.
Yao et al., 2019, "A VEGFR2-MICA bispecific antibody activates tumor-infiltrating lymphocytes and exhibits potent anti-tumor efficacy in mice," Cancer Immunology Immunotherapy, Springer, Berlin/Heidelberg 68 (9):1429-1441.
Yeap et al., 2016, "CD16 is indispensable for antibodydependent cellular cytotoxicity by human monocytes," Scientific Reports 6:34310.
Young et al., 1995, "Thermal stabilization of a single-chain Fv antibody fragment by introduction of a disulphide bond," FEBS Letters 377 (2): 135-139.
Zhang et al., "Bispecific antibody-mediated redirection of NKG2D-CAR natural killer cells facilitates dual targeting and enhances antitumor activity." Journal for immunotherapy of cancer 9.10 (2021).
Affimed, Affimed Enters Into Collaboration With Merck To Evaluate AFM13 in Combination With . . . Retreived <URL:https://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.
Akbar et al., 2021, "A compact vocabulary of paratope-epitope interactions enables predictability of antibody-antigen binding," *Cell Reports*, 34:108856 21 pages.
Altshuler et al., 2010, "Generation of Recombinant Antibodies and Means for Increasing Their Affinity," Biochemistry (Moscow), 75(13):1584-1605.
Berenbaum, 1977, "Synergy, additivism and antagonism in immunosuppression," Clin. Exp. Immunol., 28:1-18.
Berenbaum, 1989, "What is Synergy?" Pharmacological Reviews, 41:93-141.
Boltz, 2011, "Bi-specific Aptamers mediating Tumour Cell Lysis," Dissertation, M.Sc. Molekulare Biotechnologie, Technische Universität Darmstadt, pp. 1-133.
Bost et al., 1988, "Antibodies Against a Peptide Sequence Within the HIV Envelope Protein Crossreacts with Human Interleukin-2," Immunological Investigations, 17(6&7): 577-586.
Bowen et al., 2016, "Revisiting the Immunoglobulin Intramolecular Signaling Hypothesis," *Trends Immunol.*, 37(11):721-723.
Branca et al., 2018, "Nature Biotechnology's Academic Spinouts of 2017," Nature Biotechnology, 36(4): 297-306.
Brown, et al., 1996, "Tolerance of single, but not multiple, amino acid replacements in antibody VH CDR 2: a means of minimizing B cell wastage from somatic hypermutation?," Journal of Immunology, 156: 3285-3291.
Bruhns et al., 2009, "Specificity and affinity of human FCg receptors and their polymorphic variants for human IgG subclasses," *Blood*, 113(16):3716-3724.
Casset et al., 2003, "A peptide mimetic of an anti-CD4 monoclonal antibody by rational design," Biochemical and Biophysical Research Communications, 307:198-205.
Chan et al., 2010, "Therapeutic antibodies for autoimmunity and inflammation," Nature Reviews 10:301-316.
Choi et al., 2015, "Crystal structures of immunoglobulin Fc heterodimers reveal the molecular basis for heterodimer formation," Molecular Immunology 65(2):377-83.
Co et al., 1993, "Genetically engineered deglycosylation of the variable domain increases the affinity of an anti-CD33 monoclonal antibody," Molecular Immunology, 30(15):1361-1367.
Cunningham et al., 1969, "Subgroups of Amino Acid Sequences in the Variable Regions of Immunoglobulin Heavy Chains," Proc Natl Acad Sci USA 64(3):997-1003.
Dahlberg et al., 2015, "Natural Killer Cell-Based Therapies Targeting Cancer: Possible Strategies to Gain and sustain Anti-Tumor Activity" Frontiers In Immunology 6(Article 605): 19 pages.
Davis et al., 2010, "SEEDbodies: Fusion Proteins Based on Strand-Exchange Engineered Domain (Seed) CH3 Heterodimers in an Fc Analogue Platform for Asymmetric Binders or Immunofusions and Bispecific Antibodies," Protein Eng Des Sel 23(4):195-202.
El-Amine et al., 2002, "In vivo induction of tolerance by an Ig peptide is not affected by the deletion of FcR or a mutated IgG Fc fragment," *International Immunology*, 14(7):761-766.
Feng et al., 2011, "Design, Expression and Characterization of a Soluble Single-Chain Functional Human Neonatal Fc Receptor," Protein Expr Purif 79(1):66-71.
Germain et al., 2008, "Redirecting NK cells mediated tumor cell lysis by a new recombinant bifunctional protein," *Protein Engineering, Design & Selection*, 21(11):665-672.
Goel et al., 2004, "Plasticity Within the Antigen-Combining Site May Manifest as Molecular Mimicry in the Humoral Immune Response," Journal of Immunology, 173:7358-7367.

(56) References Cited

OTHER PUBLICATIONS

Gunasekaran et al., 2010, "Enhancing Antibody Fc Heterodimer Formation through Electrostatic Steering Effects: Applications to Bispecific Molecules and Monovalent IgG," J Biol Chem 285(25):19637-46.
Hasegawa et al., 2017, "Single amino acid substitution in LC-CDR1 induces Russell body phenotype that attenuates cellular protein synthesis through elF2a phosphorylation and thereby downregulates IgG secretion despite operational secretory pathway traffic," MABS, 9(5):854-873.
Holliger et al., 2005, "Engineered antibody fragments and the rise of single domains," Nat Biotechnol 23(9): 1126-36.
Janeway et al., 1997, "Immunology Third Edition," Garland Publishing, Inc. Ch. 3, Structure of the Antibody Molecule and Immunoglobulin Genes, 3:1-11.
Jonnalagadda et al., 2015, "Chimeric Antigen Receptors With Mutated IgG4 Fc Spacer Avoid Fc Receptor Binding and Improve T Cell Persistence and Antitumor Efficacy," Molecular Therapy, 23(4):757-768.
Kanyavuz et al., 2019, "Breaking the Law: Unconventional Strategies for Antibody Diversification," Nature Review, 19:355-368.
Kaur et al., 2015, "Applications of In Vitro- In Vivo Correlations in Generic Drug Development: Case Studies," The AAPS Journal, 17(4):1035-1039; doi: 10.1208/s12248-015-9765-1.
Kellner et al., 2013, "Promoting natural killer cell functions by recombinant immunoligands mimicking an induced self phenotype", OncoImmunology, 2(6):e24481.
Kjellev et al., 2007, "Inhibition of NKG2D receptor function by antibody therapy attenuates transfer-induced colitis in SCID mice," Eur. J. Immunol. , 37:1397-1406.
Klein et al., 2012, "Progress in overcoming the chain association issue in bispecific; heterodimeric IgG antibodies," MaBs 4(6):653-663.
Kranz et al., 1981, "Restricted reassociation of heavy and light chains from hapten-specific monoclonal antibodies." Proceedings of the National Academy of Sciences, 78.9: 5807-5811.
Krupka, et al., 2014, "CD33 target validation and sustained depletion of AML blasts in long-term cultures by the bispecific T-cell-engaging antibody AMG 330," Blood, 123(3): 356-365.
Lamminmaki et al., "Crystal structure of a recombinant anti-estradiol Fab fragment in complex with 17B-estradiol." Journal of Biological Chemistry, 276.39 (2001): 36687-36694.
Lippow et al., 2007, "Computational design of antibody-affinity improvement beyond in vivo maturation," Nature Biotechnology, 25(10):1171-1176.
Lo et al., 2021 "Conformational epitope matching and prediction based on protein surface spiral features," BMC Genomics, 22(Suppl 2):116 16 pages.
Mandelboim et al., 1999, "Human CD16 as a lysis receptor mediating direct natural killer cell cytotoxicity," PNAS USA, 96(10):5640-5644; doi: 10.1073/pnas.96.10.5640.
Marks et al., 2020, "How repertoire data are changing antibody science," J. Biol. Chem., 295(29):9823-9837.
Merchant et al., 1998, "An efficient route to human bispecific IgG," Nature Biotechnology 16, 677-681 doi : 10.1038/nbt0798-677.
Miller et al., 2003, "Design, Construction, and in Vitro Analyses of Multivalent Antibodies," J Immunol 170(9):4854-61.
Moore et al., 2011, "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.
Muller et al., 2015, "Trastuzumab emtansine (T-DM1) renders HER2+ breast cancer highly susceptible to CTLA-4/PD-1 blockade," Sci. Transl. Med., 7(315):1-14.
Muntasell et al., 2017, "Targeting NK-cell checkpoints for cancer immunotherapy," Current Opinion in Immunology 45:73-81.
Pakula et al., 1989, "Genetic analysis of protein stability and function." Annual review of genetics 23.1: 289-310.
Parsons et al., 2016, "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089- 1096.
Piche-Nicholas et al., 2018, "Changes in complementarity-determining regions significantly alter IgG binding to the neonatal Fc receptor (FcRn) and pharmacokinetics, " mAbs 10(1): 81-94.
Rabia et al., 2018, "Understanding and overcoming trade-offs between antibody affinity, specificity, stability and solubility" Biochem Eng J., 137:365-374.
Raulet, 2003, "Roles of the NKG2D immunoreceptor and its ligands," Nature: Reviews Immunology, 3:781-790; doi: 10.1038/nri1199.
Ridgway et al., 1996, "'Knobs-into-Holes' engineering of antibody Ch3 domains for heavy chain heterodimerization," Protein Engineering 9(7):617-21.
Roell et al., 2017, "An Introduction to Terminology and Methoodology of Chemical Synergy—Perspectives from Across Disciplines," Frontiers in Pharmacology: Cancer Molecular Targets and Therapeutics, 8:1-11.
Rosano et al., 2014, "Recombinant protein expression in Escherichia coli: advances and challenges" Frontiers in Microbiology, 5(172):17 pages.
Roskopf, et al., 2016, "Dual-targeting triplebody 33-3-19 mediates selective lyssi of biphenotypic CD19+ CD33+ leukemia cells," Oncotarget, 7(6): 22579-22589.
Sazinsky et al., 2008, "Aglycosylated immunoglobulin $G_1$ variants productively engage activating Fc receptors," Proceedings of the National Academy of Sciences, 105(51)20167-20172.
Singer et al., 1998, "Genes and Genomes," Moscow, "Mir" 1:63-64.
Strop et al., 2012, "Generating Bispecific Human IgG1 and IgG2 Antibodies from Any Antibody Pair," J Mol Biol 420:204-19.
Sulea et al., 2018, "Application of Assisted Design of Antibody and Protein Therapeutics (ADAPT) improves efficacy of a Clostridium difficile toxin A single-domain antibody," 8:2260, 11 pages.
Sutherland et al., 2012, "SGN-CD33A: A Novel CD 33 Directed Antibody-Drug Conjugate, Utilizing Pyrrolobenzodiazepine Dimers, Demonstrates Preclinical Antitumor Activity Against Multi-Drug Resistant Human AML," Blood, 120(21):3589.
Tallarida, 2000, "Drug Synergism and Dose Effect Analysis," Ed. Chapman & Hall pp. 1-71.
Thakur et al., 2018, "Bispecific antibody based therapeutics: Strengths and challenges," Blood Review, 32:339-347.
Vajda et al., 2021, "Progress toward improved understanding of antibody maturation," Current Opinion in Structural Biology, 67:226-231.
Von Kreudenstein et al., 2013, "Improving Biophysical Properties of a Bispecific Antibody Scaffold to Aid Developability: Quality by Molecular Design, " mAbs 5(5):646-54.
Von Kreudenstein et al., 2014, "Protein Engineering and the Use of Molecular Modeling and Simulation: The Case of Heterodimeric Fe Engineering, " Methods 65(1):77-94.
Ward et al., 1989, "Binding activities of a epertoire of single immunoglobulin variable domains secreted from Escherichia coli," Nature, 341:544-546.
Wark et al., 2006, "Latest technologies for the enhancement of antibody affinity", Advanced Drug Delivery Reviews, 58(5-6):657-670.
Wensveen et al., 2018, "NKG2D: A master regulator of immune cell responsiveness," Frontiers in Immunology, 9:441.
Wikipedia: "Trifunctional antibody Feb. 1, 2018",, Jan. 2, 2018 (Jan. 2, 2018), pp. 1-4, XP093016568, Retrieved from the Internet: URL:https://en.wikipedia.org/w/index.php?title=Trifunctional antibody8 oldid=818265015.
Written Opinion for International Application No. PCT/US2018/017470 dated Apr. 24, 2018.
Xie et al., 2005, "A new format of bispecific antibody: highly efficient heterodimerization, expression and tumor cell lysis," J Immunol Methods 296(1):95-101.
Yan et al., 2014, "Construction of a synthetic phage-displayed Nanobody library with CDR3 regions randomized by trinucleotide cassettes for diagnostic applications." Journal of Translational Medicine, 12.1 : 1-12.

(56) References Cited

OTHER PUBLICATIONS

Bogen et al., 2021, "Design of a Trispecific Checkpoint Inhibitor and Natural Killer Cell Engager Based on a 2 + 1 Common Light Chain Antibody Architecture," Frontiers in Immunology 12:16 pages.
Briney et al., 2019, "Commonality despite exceptional diversity in the baseline human antibody repertoire," Nature 566:393 (19 pages).
Dasgupta et al., 2005, "Inhibition of NK Cell Activity through TGF-b1 by Down-Regulation of NKG2D in a Murine Model of Head and Neck Cancer," J Immunol 175(8):5541-5550.
Demaria et al., 2021, "Natural killer cell engagers in cancer immunotherapy: Next generation of immuno-oncology treatments," Eur. J. Immunol. 51:1934-1942.
Feng et al., 2020, "NKG2D-Fc fusion protein promotes antitumor immunity through the depletion of immunosuppressive cells," Cancer Immunol. Immunother. 69(10):2147-2155.
Giuliani et al., 2017, "Activation of NK cells and disruption of PD-L1/PD-1 axis: two different ways for lenalidomide to block myeloma progression," Oncotarget 8(14):24031-24044.
Katano et al., 2015, "Predominant Development of Mature and Functional Human NK Cells in a Novel Human IL-2-Producing Transgenic NOG Mouse" J. Immunol. 194(7):3513-3525.
Khan et al., 2014, "Adjustable Locks and Flexible Keys: Plasticity of Epitope-Paratope Interactions in Germline Antibodies," J. Immunol 192:5398-5405.
Miller et al., 2018, "Annual Review of Cancer Biology Natural Killer Cells in Cancer Immunotherapy," Annu. Rev. Cancer Biol. 8(3):77-103.
Miller et al., 2019, "Natural Killer Cells in Cancer Immunotherapy," Ann. Rev. Cancer Biol. 3:77-103.
Poosaria et al., 2017, "Computational de novo Design of Antibodies binding to a Peptide with High Affinity," 114(6):1331-1342.
Spiess et al., 2015, "Alternative molecular formats and therapeutic applications for bispecific antibodies, " Molecular Immunology 67:95-106.
Walsh et al., 1996, "The Philippine cynomolgus monkey (*Macaca fasicularis*) provides a new nonhuman primate model of tuberculosis that resembles human disease." Nat Med 2, 430-436 (Abstract).
Watanabe et al., 2014, NKG2D functions as an activating receptor on natural killer cells in the common marmoset (*Callithrix jacchus*), Int. Immunol., 26(11): 597-606.
Whalen et al., 2023, "Engaging natural killer cells for cancer therapy via NKG2D, CD16A and other receptors," 15(1) 15 pages.
Xie et al., 2015, "VEGFR2 targeted antibody fused with MICA stimultes NKG2D mediated immunosurveillance and exhibits potent anti-tumor activity against breast cancer," Oncotarget 7(13):16455-16471.
Yang et al., 2016, "Bispecific Antibodies as a Development Platform for New Concepts and Treatment Strategies" Int. J. Mol. Sci. 18(48) 21 pages.
U.S. Appl. No. 16/483,330, filed Aug. 2, 2019.
U.S. Appl. No. 16/483,572, filed Aug. 5, 2019.
U.S. Appl. No. 16/486,921, filed Aug. 19, 2019.
U.S. Appl. No. 16/967,216, filed Aug. 4, 2020.
U.S. Appl. No. 16/967,218, filed Aug. 4, 2020.
U.S. Appl. No. 16/971,098, filed Aug. 19, 2020.
U.S. Appl. No. 17/058,335, filed Nov. 24, 2020.
U.S. Appl. No. 17/686,238, filed Mar. 3, 2022.
U.S. Appl. No. 17/736,031, filed May 3, 2022.
U.S. Appl. No. 18/149,965, filed Jan. 4, 2023.
U.S. Appl. No. 18/150,040, filed Jan. 4, 2023.
U.S. Appl. No. 18/482,629, filed Oct. 6, 2023.
U.S. Appl. No. 18/501,413, filed Nov. 3, 2023.
U.S. Appl. No. 18/501,419, filed Nov. 3, 2023.
U.S. Appl. No. 18/501,427, filed Nov. 3, 2023.
Absolute Antibody, 2023, Anti-NKG2D [ADI-27749 (A49)] Standard Size Ab03079-3.0, 1 page.
Bartlett et al., 2007, "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S).
Hilpert et al., 2012, "Comprehensive analysis of NKG2D ligand expression and release in leukemia: implications for NKG2D-mediated NK cell responses, " J. Immunol., 189(3):1360-1371.
Kim et al., 1995 "Evidence That the Hinge Region Plays a Role in Maintaining Serum Levels of the Murine IgG1 Molecule," Molecular Immunology 32(7):467-475.
Mendoza Rincón, 2014, "The NKG2D receptor in the border of immune surveillance and carcinogenesis," Publicación Científica en Ciencias Biomédicas 2(21):37-43. (English Abstract).
Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.
Watzl et al., 2010, "Signal Transduction During Activation and Inhibition of Natural Killer Cells", Curr Protoc Immunol., 90(1):11. 9B1-11.9B.17.
Wu et al., 2011, "Lenalidomide enhances antibody-dependent cellular cytotoxicity of solid tumor cells in vitro: influence of host immune and tumor markers," Cancer Immunology, Immunotherapy, Springer, 60(1): 61-73.
Yang et al., 2017, "Enhancing NK cell-mediated cytotoxicity to cisplatin-resistant lung cancer cells via MEK/Erk signaling inhibition," Nature Scientific Reports, 7:7958 (13 pages).
Doppalapudi et al., 2010, "Chemical generation of bispecific antibodies," PNAS, 107(52):22611-22616.
Farumashia, 2015, Journal of the Pharmaceutical Society of Japan, 51(5), pp. 424-428.
Panka et al., 1988, "Variable region framework differences result in decreased or increased affinity of variant anti-digoxin antibodies," Proc. Natl Acad Sci USA, May 1988; 85(9):3080-4.
Schmitz et al., 2001, "Pharmacogenomics: implications for laboratory medicine," Clinica Chimica Acta 308:43-53.
Sondermann et al., 2000, "The 3.2-Å crystal structure of the human IgG1 Fc fragment-FcγRIII complex," Nature, 406(6793):267-273.
Vidarsson et al., 2014, "IgG subclasses and allotypes: from structure to effector functions, " Front. Immunol. 5:520.
Wiernik et al., 2013, "Targeting Natural Killer Cells to Acute Myeloid Leukemia In Vitro with a CD1633 Bispecific Killer Cell Engager and ADAM17 Inhibition," Clin. Cancer Research, 19(14):3844-3855.
Zhou et al., 1995, "Characterization of human homologue of 4-1BB and its ligand," Immunology Letters 45:67-73.

* cited by examiner

```
Features:

Query   0    DMNFWLQDESVTVQEGLCVLVPCTFFHPIPYVQKISPVHGVWFREGAIISRD    70
             D  +RVRLQDESVTVQEGLCVLVPCTFFHPAPY+ +NSPVHGVWFREGAIVSLD
Sbjct   0    DPIRVRLQDESVTVQEGLCVLVPCTFFHPAPYHTRNSPVHGVWFREGAIVSLD    80

Query   71   SPVATNKLDQEVQEETQGRFRLLGQPSRNWCSLSIVDARRRDNGSYFFRMERGSTKYSYK   130
             SPVATNKLDQEVQEETQGRFRLLGQPSRNWCSLSIVDARRRDNGSYFFRME+GSTKYSYK
Sbjct   90   SPVATNKLDQEVQEETQGRFRLLGQPSRNWCSLSIVDARRRDNGSYFFRMEKGSTKYSYK   149

Query   131  PDLSVHVTDLTHRPKLLIPGTLEPGHSKNLTCSVPNACEQGTPPIFSWLSAAPTSLGR   190
             PDLSVHVTDLTHRP+LLIPGL L+P+HSKNLTCSVP+ACE+GTPPIFSW +AAPTSLG+
Sbjct   150  PDLSVHVTDLTHRPDLLIPGALDPDHSKNLTCSVPWACEKGTPPIFSWMKAAPTSLGN   209

Query   191  TTHSSVLIITPRPQDMGTNLTCQVKIAGAGVTTERTIQLNMTYVPDMTTQLFPDGSGK   250
             TTHSSVLIITPRPQDHGTNLTCQVK+ GAGVTTERTIQLNM+Y +VP+MT IF DGSGK
Sbjct   210  TTHSSVLIITPRPQDHGTNLTCQVKIPGAGVTTERTIQLNMSYASXNHRTDIFLGDGSGK   269

Query   251  VFTRAGVVHGAIGGAGVTALLALCLCLIFFIVKTHRRKAARTAVGRNDTHPTTGSAPKH   310
             VF RAG VH GA+GGAGVT LLALCLCLIFF+VKTHRRKAARTAVG+ DTHP TG S KH
Sbjct   270  VFVQGAIGGAGVTVLLALCLCLIFFTVKTHRRKAARTAVGRIDTHPATGPTSSKH   325

Query   311  QKKSKLHGPTETSCSGAAPTVEMDEELHYASLNFHGMNPSKDTSTEYSEVRTQ   (SEQ ID NO:598)
             QKKSKLHG TETS CSG   TVEMDEELHYASLNFHGMNPS+DTSTEYSEVRTQ
Sbjct   326  QKKSKLHGATETSGCSGTTLTVEMDEELHYASLNFHGMNPSEDTSTEYSEVRTQ   (SEQ ID NO:599)
```

FIG. 2

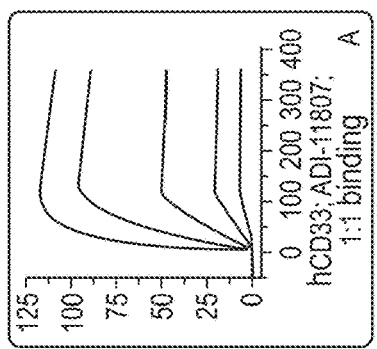
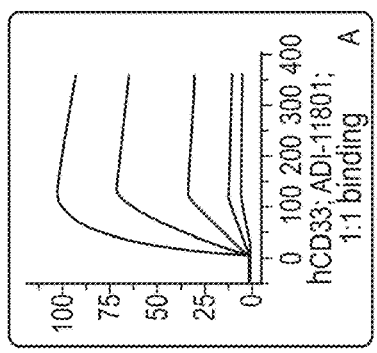
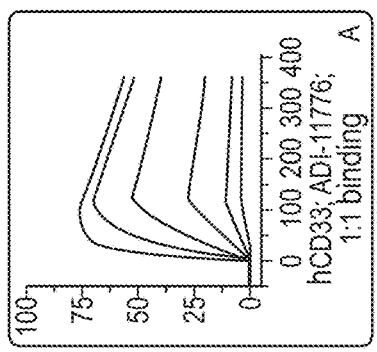
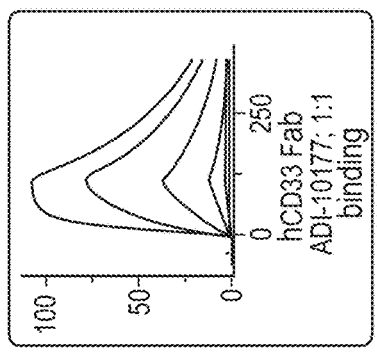
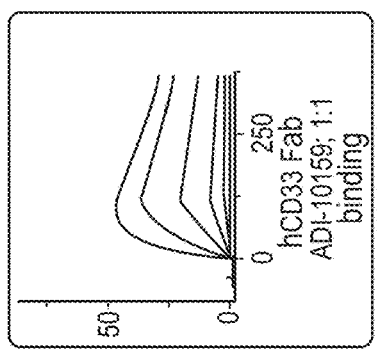
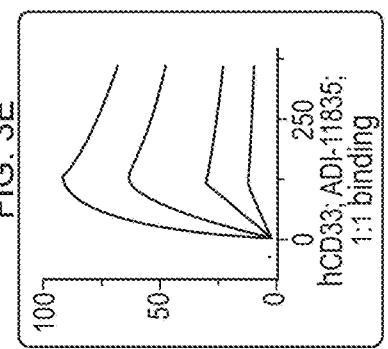
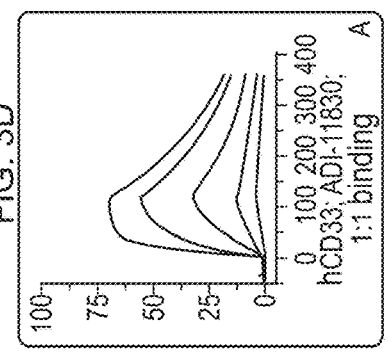
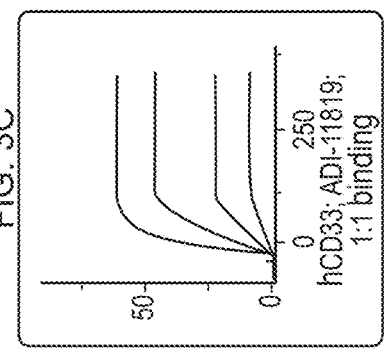
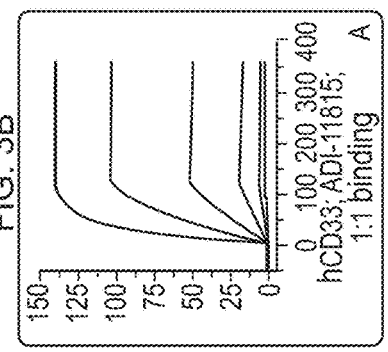
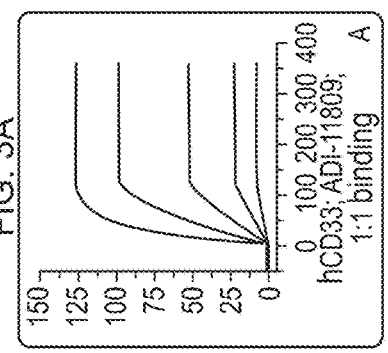
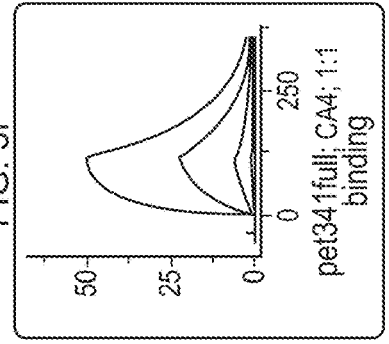

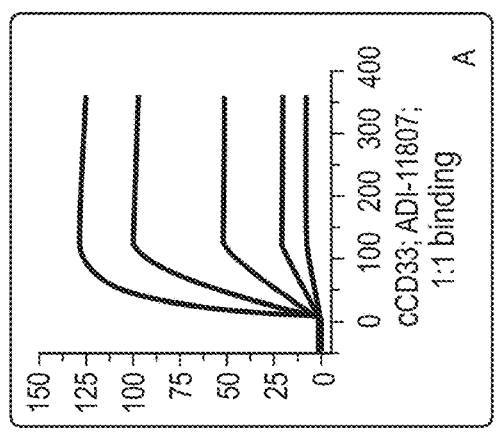
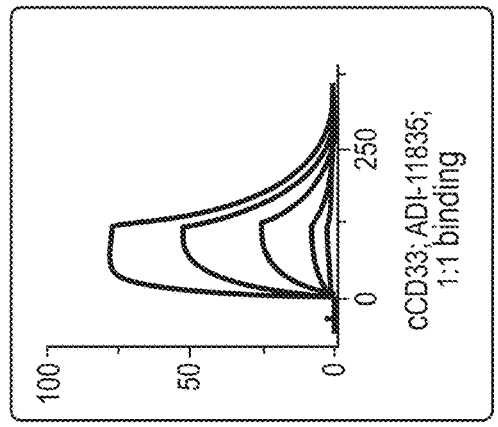
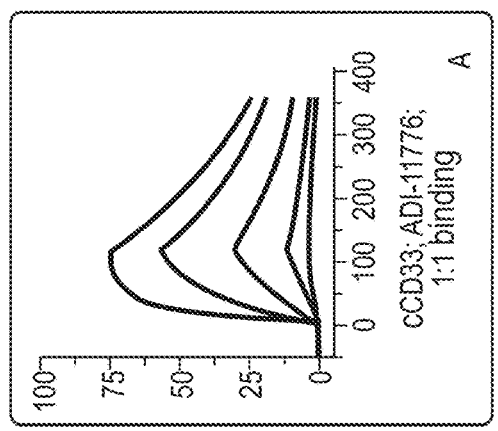
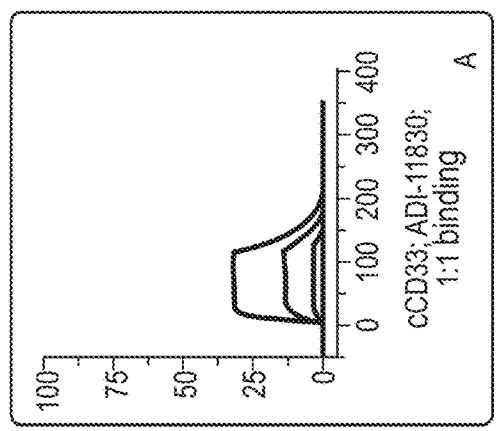
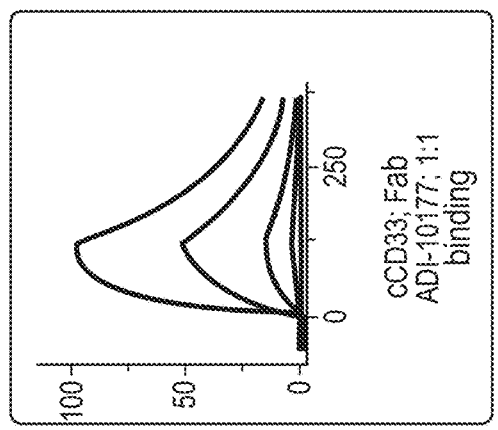
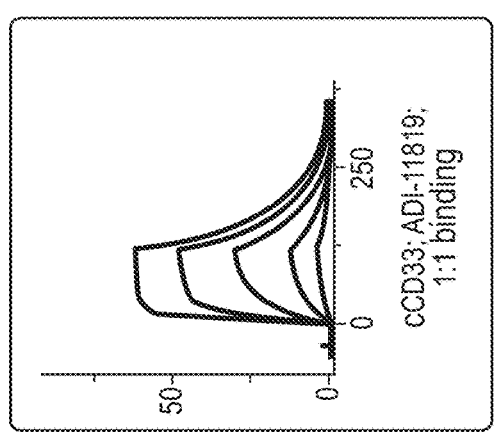
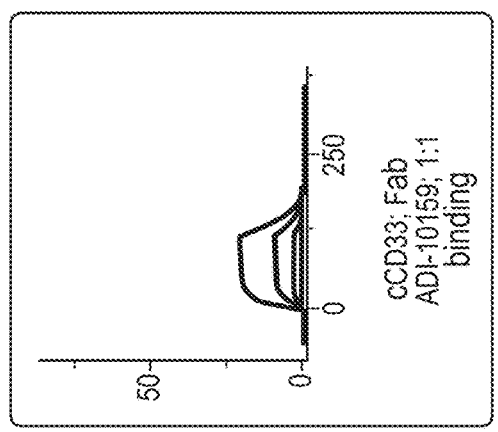
FIG. 4A  FIG. 4B  FIG. 4C  FIG. 4D
FIG. 4E  FIG. 4F  FIG. 4G  FIG. 4H

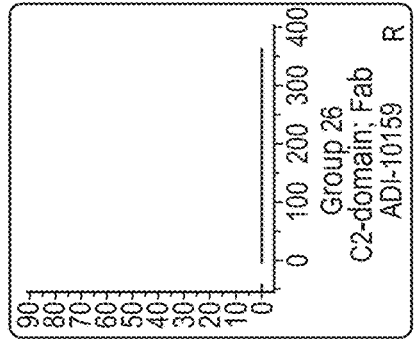
FIG. 5K
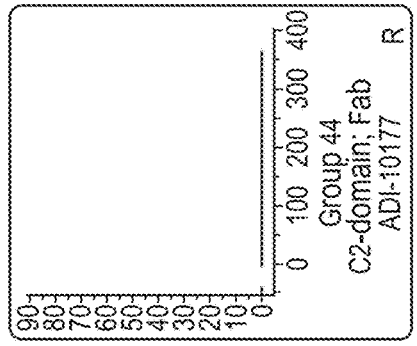
FIG. 5L
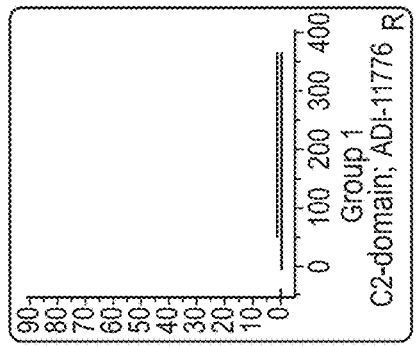
FIG. 5M
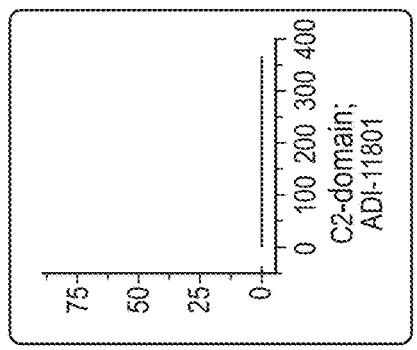
FIG. 5N
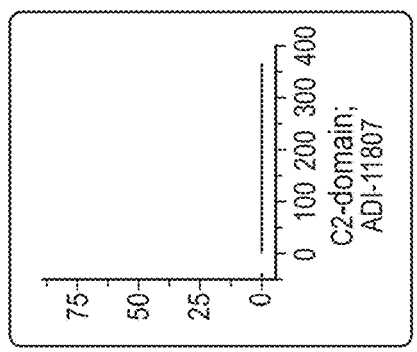
FIG. 5O
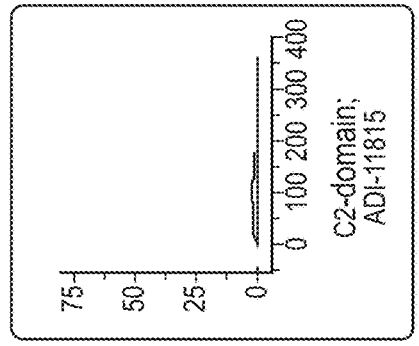
FIG. 5P
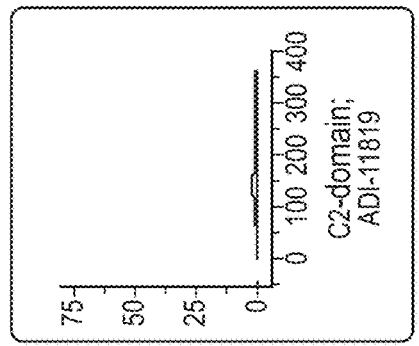
FIG. 5Q
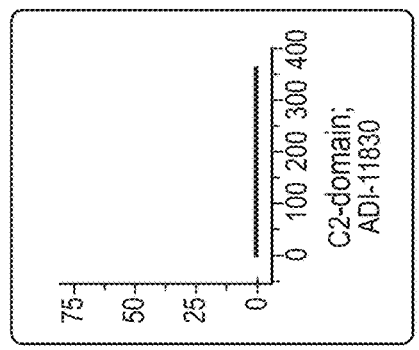
FIG. 5R
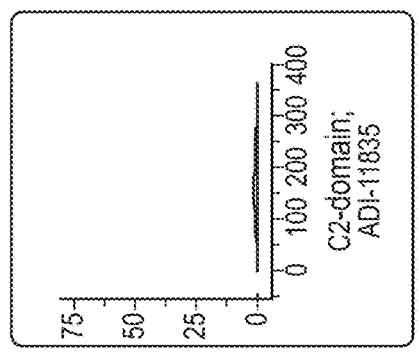
FIG. 5S
FIG. 5T FIG. 39
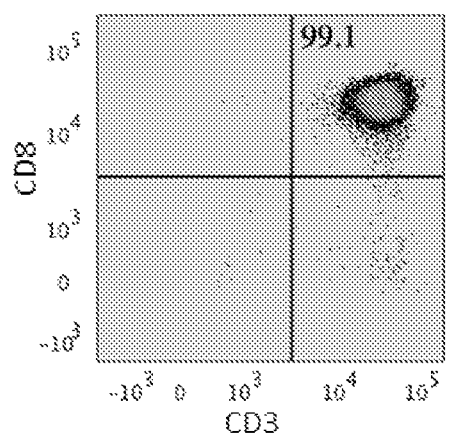
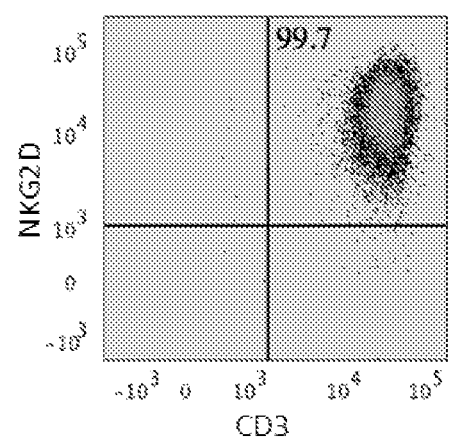
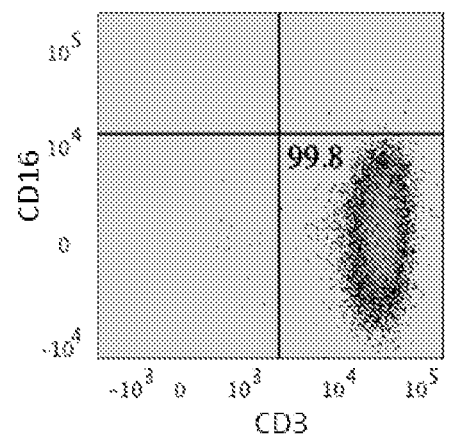

NK cells

CD8$^+$ T cells

CD4$^+$ T cells

B cells

Monocytes

F3' format

SEQUENCE LISTING

<160> NUMBER OF SEQ ID NOS: 599

<210> SEQ ID NO 1
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Gly Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

<210> SEQ ID NO 2
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Phe Pro Thr
                85                  90                  95

Phe Gly Gly Gly Thr Lys Val Glu Ile Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
            100                 105                 110

Met Val Thr Val Ser Ser
            115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Glu Ser Tyr Pro Leu
                85                  90                  95

Thr Phe Gly Gly Gly Thr Lys Val Glu Ile Lys
            100                 105

<210> SEQ ID NO 5
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Thr Met Ser Trp Val Arg Gln Ala Pro Gly Lys Gly Leu Glu Trp Val
        35                  40                  45

Ser Ala Ile Val Gly Ser Gly Glu Ser Thr Tyr Phe Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
            115                 120                 125

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Asp Leu Pro Thr
                 85                  90                  95

Phe Gly Gly Gly Thr Lys Val Glu Ile Lys
            100                 105

<210> SEQ ID NO 7
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Asp Tyr
             20                  25                  30

Tyr Met His Trp Val Arg Gln Ala Pro Gly Gln Gly Leu Glu Trp Met
         35                  40                  45

Gly Met Ile Asn Pro Ser Trp Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ala Asp Gly Phe Val Gly Glu Arg Tyr Phe Asp Leu
            100                 105                 110

```
Trp Gly Arg Gly Thr Leu Val Thr Val Ser Ser
        115                 120
```

<210> SEQ ID NO 8
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Val Ala Leu Pro Ile Thr Phe Gly Gly Gly Thr Lys Val Glu Ile Lys
            100                 105                 110
```

<210> SEQ ID NO 9
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Trp Met Ser Trp Val Arg Gln Ala Pro Gly Lys Gly Leu Glu Trp Val
        35                  40                  45

Ala Thr Ile Lys Gln Asp Gly Ser Glu Lys Ser Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
            100                 105                 110

Met Val Thr Val Ser Ser
        115
```

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Gly Gly Thr Lys Val Glu Ile Lys
            100                 105

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Ser Tyr
            20                  25                  30

Trp Met Ser Trp Val Arg Gln Ala Pro Gly Lys Gly Leu Glu Trp Val
        35                  40                  45

Ala Thr Ile Lys Arg Asp Gly Ser Glu Lys Gly Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
            100                 105                 110

Met Val Thr Val Ser Ser
        115

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45
```

```
Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Gly Gly Thr Lys Val Glu Ile Lys
                100                 105

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Thr Tyr
                20                  25                  30

Tyr Met His Trp Val Arg Gln Ala Pro Gly Gln Gly Leu Glu Trp Met
            35                  40                  45

Gly Ile Ile Asn Pro Ser Arg Gly Ser Thr Val Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Asp Asp Glu Asp Met Asp Val Trp Gly Lys
                100                 105                 110

Gly Thr Thr Val Thr Val Ser Ser
            115                 120

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Tyr Pro Leu
                85                  90                  95

Thr Phe Gly Gly Gly Thr Lys Val Glu Ile Lys
                100                 105
```

```
<210> SEQ ID NO 15
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Ser Ser Glu Gly Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

<210> SEQ ID NO 16
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Gln Met Thr Gln Ser Pro Ser Thr Leu Ser Ala Ser Val Gly
1               5                   10                  15

Asp Arg Val Thr Ile Thr Cys Arg Ala Ser Asn Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Thr Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Gly Gly Thr Lys Val Glu Ile Lys
            100                 105

<210> SEQ ID NO 17
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
```

```
                1               5                   10                  15
Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Asn Thr Asp Gly Ser Glu Val Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
                100                 105                 110

Trp Gly Gln Gly Thr Leu Val Thr Val Ser Ser
            115                 120
```

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Tyr Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Lys Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Gly Gly Thr Lys Val Glu Ile Lys
            100                 105
```

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
                20                  25                  30

Asp Tyr Tyr Trp Gly Trp Ile Arg Gln Pro Pro Gly Lys Gly Leu Glu
            35                  40                  45

Trp Ile Gly Ser Ile Gly Tyr Ser Gly Thr Tyr Tyr Asn Pro Ser Leu
        50                  55                  60

Lys Ser Arg Val Thr Ile Ser Val Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                    85                  90                  95
Ala Arg Glu Thr Ala His Asp Val His Gly Met Asp Val Trp Gly Gln
                100                 105                 110
Gly Thr Thr Val Thr Val Ser Ser
        115                 120

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Leu Thr Gln Ser Pro Ala Thr Leu Ser Leu Ser Pro Gly
1               5                   10                  15
Glu Arg Ala Thr Leu Ser Cys Arg Ala Ser His Ser Val Tyr Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Tyr Asp Asn Leu Pro Thr
                85                  90                  95
Phe Gly Gly Gly Thr Lys Val Glu Ile Lys
            100                 105

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Thr Phe Ser Ser Tyr Gly Met Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Ile Lys Gln Asp Gly Ser Glu Lys Tyr Tyr Val Asp Ser Val Lys
1               5                   10                  15
Gly

<210> SEQ ID NO 23
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 23

Ala Arg Glu Gly Gly Pro Tyr Tyr Asp Ser Ser Gly Tyr Phe Val Tyr
1               5                   10                  15

Tyr Gly Met Asp Val
            20

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ala Ser Gln Ser Ile Ser Ser Trp Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asp Ala Ser Ser Leu Glu Ser
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Tyr Glu Ser Phe Pro Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Thr Phe Ser Ser Tyr Trp Met Ser
1               5

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Ile Lys Gln Asp Gly Ser Glu Lys Tyr Tyr Val Asp Ser Val Lys
```

```
1               5                   10                  15

Gly

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Pro Leu Asn Ala Gly Glu Leu Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Ser Gln Ser Ile Ser Ser Trp Leu Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ala Ser Ser Leu Glu Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Leu Glu Ser Tyr Pro Leu Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Thr Phe Ser Lys Tyr Thr Met Ser
1               5

<210> SEQ ID NO 34
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 34

Ala Ile Val Gly Ser Gly Glu Ser Thr Tyr Phe Ala Asp Ser Val Lys
1               5                   10                  15

Gly

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Arg Glu Gly Gly Pro Tyr Tyr Asp Ser Ser Gly Tyr Phe Val Tyr
1               5                   10                  15

Tyr Gly Met Asp Val
            20

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Ser Gln Ser Ile Ser Ser Trp Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Ala Ser Ser Leu Glu Ser
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gln Tyr Asp Asp Leu Pro Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 39

Tyr Thr Phe Ser Asp Tyr Tyr Met His
1               5

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Met Ile Asn Pro Ser Trp Gly Ser Thr Ser Tyr Ala Gln Lys Phe Gln
1               5                   10                  15

Gly

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Arg Glu Ala Ala Asp Gly Phe Val Gly Glu Arg Tyr Phe Asp Leu
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Ser Gln Ser Leu Leu Tyr Ser Asn Gly Tyr Asn Tyr Leu Asp
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Gly Ser Asn Arg Ala Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Gln Asp Val Ala Leu Pro Ile Thr
1               5

<210> SEQ ID NO 45
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Thr Phe Gly Ser Tyr Trp Met Ser
1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ile Lys Gln Asp Gly Ser Glu Lys Ser Tyr Val Asp Ser Val Lys
1               5                   10                  15

Gly

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Pro Leu Asn Ala Gly Glu Leu Asp Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Ala Ser Gln Ser Ile Ser Ser Trp Leu Ala
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Glu Ala Ser Ser Leu Glu Ser
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 50

Gln Gln Ser Gln Ser Tyr Pro Pro Ile Thr
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Thr Phe Pro Ser Tyr Trp Met Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Ile Lys Arg Asp Gly Ser Glu Lys Gly Tyr Val Asp Ser Val Lys
1               5                   10                  15

Gly

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Pro Leu Asn Ala Gly Glu Leu Asp Val
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Ser Ile Ser Ser Trp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Glu Ala Ser Ser Leu Glu Ser
1               5

<210> SEQ ID NO 56
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Gln Ser Gln Ser Tyr Pro Pro Ile Thr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Thr Phe Gly Thr Tyr Tyr Met His
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Ile Asn Pro Ser Arg Gly Ser Thr Val Tyr Ala Gln Lys Phe Gln
1               5                   10                  15

Gly

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Arg Gly Ala Gly Tyr Asp Asp Glu Asp Met Asp Val
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Ala Ser Gln Gly Ile Asp Ser Trp Leu Ala
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 61

Ala Ala Ser Ser Leu Gln Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Gln Ala His Ser Tyr Pro Leu Thr
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Thr Phe Ser Ser Tyr Ala Met Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Ile Ser Ser Ser Ser Glu Gly Ile Tyr Tyr Ala Asp Ser Val Lys
1               5                   10                  15

Gly

<210> SEQ ID NO 65
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Arg Glu Gly Gly Pro Tyr Tyr Asp Ser Ser Gly Tyr Phe Val Tyr
1               5                   10                  15

Tyr Gly Met Asp Val
            20

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Ala Ser Asn Ser Ile Ser Ser Trp Leu Ala
1               5                   10
```

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Ala Ser Ser Thr Lys Ser
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Tyr Asp Asp Leu Pro Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Phe Thr Phe Ser Ser Tyr Trp Met Ser
1               5

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asn Ile Asn Thr Asp Gly Ser Glu Val Tyr Tyr Val Asp Ser Val Lys
1               5                   10                  15

Gly

<210> SEQ ID NO 71
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ala Arg Asp Val Gly Pro Gly Ile Ala Tyr Gln Gly His Phe Asp Tyr
1               5                   10                  15

<210> SEQ ID NO 72
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 72

Arg Ala Ser Gln Val Ile Tyr Ser Tyr Leu Asn
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Ala Ser Ser Leu Lys Ser
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Gln Val Tyr Asp Thr Pro Leu Thr
1               5

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Ile Ser Ser Thr Asp Tyr Tyr Trp Gly
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Ile Gly Tyr Ser Gly Thr Tyr Tyr Asn Pro Ser Leu Lys Ser
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Arg Glu Thr Ala His Asp Val His Gly Met Asp Val
1               5                   10
```

```
<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Ala Ser His Ser Val Tyr Ser Tyr Leu Ala
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Asp Ala Ser Asn Arg Ala Thr
1               5

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Tyr Asp Asn Leu Pro Thr
1               5

<210> SEQ ID NO 81
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 82
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 83
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
```

```
            20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 85
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
        115                 120

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
```

```
                    85                  90                  95

Thr Phe Gly Gly Gly Thr Lys Val Glu Ile Lys
                100                 105

<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser
        115                 120

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Ser Phe Pro Arg
                85                  90                  95

Thr Phe Gly Gly Gly Thr Lys Val Glu Ile Lys
                100                 105

<210> SEQ ID NO 89
<211> LENGTH: 125
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 91
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: VARIANT
<222> LOCATION: (102)..(102)
<223> OTHER INFORMATION: Met, Leu, Ile, Val, Gln, or Phe

<400> SEQUENCE: 91

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
                20                  25                  30
Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Xaa Gly Ala Ala Ala Gly Trp Phe Asp Pro Trp
            100                 105                 110

Gly Gln Gly Thr Leu Val Thr Val Ser Ser
            115                 120
```

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (6)..(6)
<223> OTHER INFORMATION: Met, Leu, Ile, Val, Gln, or Phe

<400> SEQUENCE: 92

```
Ala Arg Gly Ala Pro Xaa Gly Ala Ala Ala Gly Trp Phe Asp Pro
1               5                   10                  15
```

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

```
Tyr Thr Phe Thr Ser Tyr Tyr Met His
1               5
```

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

```
Ile Ile Asn Pro Ser Gly Gly Ser Thr Ser Tyr Ala Gln Lys Phe Gln
1               5                   10                  15

Gly
```

<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Ala Arg Gly Ala Pro Asn Tyr Gly Asp Thr Thr His Asp Tyr Tyr Tyr
1               5                   10                  15

Met Asp Val

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Gln Ser Val Ser Ser Asn Leu Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Ala Ser Thr Arg Ala Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gln Gln Tyr Asp Asp Trp Pro Phe Thr
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Tyr Thr Phe Thr Gly Tyr Tyr Met His
1               5

<210> SEQ ID NO 100
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Trp Ile Asn Pro Asn Ser Gly Gly Thr Asn Tyr Ala Gln Lys Phe Gln
1               5                   10                  15

Gly

<210> SEQ ID NO 101
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg Asp Thr Gly Glu Tyr Tyr Asp Thr Asp Asp His Gly Met Asp
1               5                   10                  15
Val

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ala Ser Gln Ser Val Ser Ser Asn Leu Ala
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ala Ser Thr Arg Ala Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gln Gln Asp Asp Tyr Trp Pro Pro Thr
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Phe Thr Phe Ser Ser Tyr Ala Met Ser
1               5

<210> SEQ ID NO 106
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 106

Ala Ile Ser Gly Ser Gly Gly Ser Thr Tyr Tyr Ala Asp Ser Val Lys
1               5                   10                  15
Gly

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Lys Asp Gly Gly Tyr Tyr Asp Ser Gly Ala Gly Asp Tyr
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Ser Gln Gly Ile Asp Ser Trp Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Ala Ser Ser Leu Gln Ser
1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gln Gln Gly Val Ser Tyr Pro Arg Thr
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Phe Thr Phe Ser Ser Tyr Ser Met Asn
1               5

<210> SEQ ID NO 112
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ile Ser Ser Ser Ser Ser Tyr Ile Tyr Tyr Ala Asp Ser Val Lys
1               5                   10                  15

Gly

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Arg Gly Ala Pro Met Gly Ala Ala Ala Gly Trp Phe Asp Pro
1               5                   10                  15

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Gly Ile Ser Ser Trp Leu Ala
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Ala Ala Ser Ser Leu Gln Ser
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Gln Gly Val Ser Phe Pro Arg Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 117

Tyr Thr Phe Thr Ser Tyr Tyr Met His
1               5

<210> SEQ ID NO 118
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Ile Asn Pro Ser Gly Gly Ser Thr Ser Tyr Ala Gln Lys Phe Gln
1               5                   10                  15
Gly

<210> SEQ ID NO 119
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ala Arg Glu Gly Ala Gly Phe Ala Tyr Gly Met Asp Tyr Tyr Tyr Met
1               5                   10                  15
Asp Val

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ala Ser Gln Ser Val Ser Ser Tyr Leu Ala
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Asp Ala Ser Asn Arg Ala Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gln Gln Ser Asp Asn Trp Pro Phe Thr
1               5
```

<210> SEQ ID NO 123
<211> LENGTH: 13
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: VARIANT
<222> LOCATION: (4)..(4)
<223> OTHER INFORMATION: Met, Leu, Ile, Val, Gln, or Phe

<400> SEQUENCE: 123

Gly Ala Pro Xaa Gly Ala Ala Ala Gly Trp Phe Asp Pro
1               5                   10

<210> SEQ ID NO 124
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Ser Phe Ser Gly Tyr Tyr Trp Ser
1               5

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Ile Asp His Ser Gly Ser Thr Asn Tyr Asn Pro Ser Leu Lys Ser
1               5                   10                  15

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ala Arg Ala Arg Gly Pro Trp Ser Phe Asp Pro
1               5                   10

<210> SEQ ID NO 129
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110
```

```
Val Thr Val Ser Ser
        115

<210> SEQ ID NO 130
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 131
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 132
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 132

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 133
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 134
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Asn Ser Tyr Tyr Thr
                85                  90                  95

Phe Gly Gly Gly Thr Lys Val Glu Ile Lys
                100                 105

<210> SEQ ID NO 135
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
        115

<210> SEQ ID NO 136
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
                100                 105

<210> SEQ ID NO 137
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115

<210> SEQ ID NO 138
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105

<210> SEQ ID NO 139
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Gln Gln Trp Gly Ala Gly Leu Leu Lys Pro Ser Glu

-continued

```
             1               5                  10                 15
            Thr Leu Ser Leu Thr Cys Ala Val Tyr Gly Gly Ser Phe Ser Gly Tyr
                        20                  25                  30

Tyr Trp Ser Trp Ile Arg Gln Pro Pro Gly Lys Gly Leu Glu Trp Ile
                        35                  40                  45

Gly Glu Ile Asp His Ser Gly Ser Thr Asn Tyr Asn Pro Ser Leu Lys
                        50                  55                  60

Ser Arg Val Thr Ile Ser Val Asp Thr Ser Lys Asn Gln Phe Ser Leu
             65                  70                  75                  80

Lys Leu Ser Ser Val Thr Ala Ala Asp Thr Ala Val Tyr Tyr Cys Ala
                        85                  90                  95

Arg Ala Arg Gly Pro Trp Ser Phe Asp Pro Trp Gly Gln Gly Thr Leu
                        100                 105                 110

Val Thr Val Ser Ser
                        115
```

<210> SEQ ID NO 140
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

```
Asp Ile Gln Met Thr Gln Ser Pro Ser Thr Leu Ser Ala Ser Val Gly
1               5                  10                 15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
            85                  90                  95

Thr Phe Gly Gly Gly Thr Lys Val Glu Ile Lys
            100                 105
```

<210> SEQ ID NO 141
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95

Arg Ala Arg Gly Pro Trp Ser Phe Asp Pro Trp Gly Gln Gly Thr Leu
                100                 105                 110

Val Thr Val Ser Ser
        115

<210> SEQ ID NO 142
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Lys Glu Val Pro Trp
                85                  90                  95

Thr Phe Gly Gln Gly Thr Lys Val Glu Ile Lys
                100                 105

<210> SEQ ID NO 143
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
                100                 105                 110

Val Thr Val Ser Ser
        115
```

```
<210> SEQ ID NO 144
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 145
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 146
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 147
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Val Gln Leu Gln Gln Trp Gly Ala Gly Leu Leu Lys Pro Ser Glu
1               5                  10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 148
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Asp Ile Gln Met Thr Gln Ser Pro Ser Thr Leu Ser Ala Ser Val Gly
1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
 65                  70                  75                  80
```

```
Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 149
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 150
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105

<210> SEQ ID NO 151
<211> LENGTH: 117
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 151

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 152
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105

<210> SEQ ID NO 153
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 154
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
                85                  90                  95

Phe Gly Gly Gly Thr Lys Val Glu Ile Lys
            100                 105

<210> SEQ ID NO 155
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

```
Arg Ala Arg Gly Pro Trp Ser Phe Asp Pro Trp Gly Gln Gly Thr Leu
            100                 105                 110

Val Thr Val Ser Ser
        115

<210> SEQ ID NO 156
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 157
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 158
<211> LENGTH: 106
<212> TYPE: PRT
<213> ORGANISM: Artificial Sequence
<220> FEATURE:
```

<223> OTHER INFORMATION: Description of Artificial Sequence: Synthetic
     polypeptide

<400> SEQUENCE: 158

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 159
<211> LENGTH: 117
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 159

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 160
<211> LENGTH: 106
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 160

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile

```
                35                  40                  45
Tyr Lys Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gln Ser Tyr Pro Thr
                 85                  90                  95

Phe Gly Gly Gly Thr Lys Val Glu Ile Lys
            100                 105

<210> SEQ ID NO 161
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asp His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 162
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
             20                  25                  30

Leu Ala Trp Tyr Gln Gln Lys Pro Gly Lys Ala Pro Lys Leu Leu Ile
         35                  40                  45

Tyr Lys Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr His Ser Phe Pro Thr
                 85                  90                  95

Phe Gly Gly Gly Thr Lys Val Glu Ile Lys
```

<210> SEQ ID NO 163
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 164
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105

<210> SEQ ID NO 165
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115
```

<210> SEQ ID NO 166
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Thr Phe Ile Thr
                85                  90                  95

Phe Gly Gly Gly Thr Lys Val Glu Ile Lys
            100                 105
```

<210> SEQ ID NO 167
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Ser Ser Ile Arg His Ala Tyr Tyr Tyr Gly Met
            100                 105                 110

Asp Val Trp Gly Gln Gly Thr Thr Val Thr Val Ser Ser
        115                 120                 125

<210> SEQ ID NO 168
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Ile Thr Phe Gly Gly Gly Thr Lys Val Glu Ile
            100                 105                 110

Lys

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Thr Phe Ser Ser Tyr Ala Ile Ser
  1               5

<210> SEQ ID NO 170
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Ile Ile Pro Ile Phe Gly Thr Ala Asn Tyr Ala Gln Lys Phe Gln
  1               5                  10                  15

Gly

<210> SEQ ID NO 171
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Arg Gly Asp Ser Ser Ile Arg His Ala Tyr Tyr Tyr Gly Met
1               5                   10                  15

Asp Val

<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Lys Ser Ser Gln Ser Val Leu Tyr Ser Ser Asn Asn Lys Asn Tyr Leu
1               5                   10                  15

Ala

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Trp Ala Ser Thr Arg Glu Ser
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Gln Tyr Tyr Ser Thr Pro Ile Thr
1               5

<210> SEQ ID NO 175
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
```

```
                50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 176
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Arg Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Asp Thr Trp Pro Pro
                 85                  90                  95

Thr Phe Gly Gly Gly Thr Lys Val Glu Ile Lys
            100                 105

<210> SEQ ID NO 177
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Ser Ile Ser Ser Ser Ser Tyr Tyr Trp Gly
 1               5                  10

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Ile Tyr Tyr Ser Gly Ser Thr Tyr Tyr Asn Pro Ser Leu Lys Ser
 1               5                  10                  15

<210> SEQ ID NO 179
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 179

Ala Arg Gly Ser Asp Arg Phe His Pro Tyr Phe Asp Tyr
1               5                   10

<210> SEQ ID NO 180
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ala Ser Gln Ser Val Ser Arg Tyr Leu Ala
1               5                   10

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Tyr Trp Met Ser
1               5

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Pro Leu Asn Ala Gly Glu Leu Asp Val
1               5                   10

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Lys Tyr Thr Met Ser
1               5

<210> SEQ ID NO 184
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Glu Gly Gly Pro Tyr Tyr Asp Ser Ser Gly Tyr Phe Val Tyr Tyr Gly
1               5                   10                  15
```

Met Asp Val

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Lys Ala Ser Ser Leu Glu
1               5

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Gly Gly Gly Ser Gly Gly Gly Ser Gly Gly Gly Gly Ser Gly
1               5                   10                  15

Gly Gly Gly Ser
            20

<210> SEQ ID NO 187
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Gly Ser Tyr
145                 150                 155                 160

Trp Met Ser Trp Val Arg Gln Ala Pro Gly Lys Cys Leu Glu Trp Val
                165                 170                 175

Ala Thr Ile Lys Gln Asp Gly Ser Glu Lys Ser Tyr Val Asp Ser Val
            180                 185                 190

Lys Gly Arg Phe Thr Ile Ser Arg Asp Asn Ala Lys Asn Ser Leu Tyr
            195                 200                 205

Leu Gln Met Asn Ser Leu Arg Ala Glu Asp Thr Ala Val Tyr Tyr Cys
        210                 215                 220

Ala Arg Pro Leu Asn Ala Gly Glu Leu Asp Val Trp Gly Gln Gly Thr
225                 230                 235                 240

Met Val Thr Val Ser Ala Ser Asp Lys Thr His Thr Cys Pro Pro
            245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
            290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Arg Val Tyr Thr Leu Pro Pro Cys Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Val Ser Asp Gly Ser Phe
            420                 425                 430

Thr Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
        450                 455                 460

Thr Gln Lys Ser Leu Ser Leu Ser Pro Gly
465                 470

<210> SEQ ID NO 188
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro

```
                 65                  70                  75                  80
Asp Asp Phe Ala Thr Tyr Tyr Cys Gln Gln Ser Gln Ser Tyr Pro Pro
                 85                  90                  95

Ile Thr Phe Gly Cys Gly Thr Lys Val Glu Ile Lys Gly Gly Gly Gly
                100                 105                 110

Ser Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
            130                 135                 140

Ser Leu Arg Leu Ser Cys Ala Ala Ser Gly Phe Thr Phe Gly Ser Tyr
145                 150                 155                 160

Trp Met Ser Trp Val Arg Gln Ala Pro Gly Lys Cys Leu Glu Trp Val
                165                 170                 175

Ala Thr Ile Lys Gln Asp Gly Ser Glu Lys Ser Tyr Val Asp Ser Val
                180                 185                 190

Lys Gly Arg Phe Thr Ile Ser Arg Asp Asn Ala Lys Asn Ser Leu Tyr
                195                 200                 205

Leu Gln Met Asn Ser Leu Arg Ala Glu Asp Thr Ala Val Tyr Tyr Cys
                210                 215                 220

Ala Arg Pro Leu Asn Ala Gly Glu Leu Asp Val Trp Gly Gln Gly Thr
225                 230                 235                 240

Met Val Thr Val Ser Ser
                245

<210> SEQ ID NO 189
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Glu Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 190
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 191
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
        115                 120

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Tyr Ser Met Asn
1               5

<210> SEQ ID NO 193

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Ala Pro Met Gly Ala Ala Ala Gly Trp Phe Asp Pro
1               5                   10

<210> SEQ ID NO 194
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Arg Gly Ala Pro Ile Gly Ala Ala Ala Gly Trp Phe Asp Pro
1               5                   10                  15

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Ala Pro Ile Gly Ala Ala Ala Gly Trp Phe Asp Pro
1               5                   10

<210> SEQ ID NO 196
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr

```
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Val Glu Pro Lys Ser
210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
His Glu Asp Pro Glu Val Lys Phe Asn Trp Tyr Val Asp Gly Val Glu
                275                 280                 285
Val His Asn Ala Lys Thr Lys Pro Arg Glu Glu Gln Tyr Asn Ser Thr
                290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
                340                 345                 350
Val Cys Thr Leu Pro Pro Ser Arg Asp Glu Leu Thr Glu Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Leu
                435                 440                 445
Ser Pro Gly
    450

<210> SEQ ID NO 197
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
                35                  40                  45
```

```
Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Cys Gly Thr Lys Val Glu Ile Lys Gly Gly Gly Gly Ser Gly
                100                 105                 110

Gly Gly Gly Ser Gly Gly Gly Gly Ser Gly Gly Gly Gly Ser Glu Val
            115                 120                 125

Gln Leu Leu Glu Ser Gly Gly Gly Leu Val Gln Pro Gly Gly Ser Leu
130                 135                 140

Arg Leu Ser Cys Ala Ala Ser Gly Phe Thr Phe Ser Lys Tyr Thr Met
145                 150                 155                 160

Ser Trp Val Arg Gln Ala Pro Gly Lys Cys Leu Glu Trp Val Ser Ala
                165                 170                 175

Ile Val Gly Ser Gly Glu Ser Thr Tyr Phe Ala Asp Ser Val Lys Gly
                180                 185                 190

Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Ala Arg
    210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
    275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
                340                 345                 350

Lys Glu Tyr Lys Cys Lys Val Ser Asn Lys Ala Leu Pro Ala Pro Ile
                355                 360                 365

Glu Lys Thr Ile Ser Lys Ala Lys Gly Gln Pro Arg Glu Pro Arg Val
    370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Val Ser Asp Gly Ser Phe Thr Leu Tyr Ser Lys Leu Thr Val
            435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
```

<210> SEQ ID NO 198
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Glu Val
        115                 120                 125

Gln Leu Leu Glu Ser Gly Gly Gly Leu Val Gln Pro Gly Gly Ser Leu
130                 135                 140

Arg Leu Ser Cys Ala Ala Ser Gly Phe Thr Phe Ser Lys Tyr Thr Met
145                 150                 155                 160

Ser Trp Val Arg Gln Ala Pro Gly Lys Cys Leu Glu Trp Val Ser Ala
                165                 170                 175

Ile Val Gly Ser Gly Glu Ser Thr Tyr Phe Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser
                245                 250

<210> SEQ ID NO 199
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

-continued

Trp Met Ser Trp Val Arg Gln Ala Pro Gly Lys Gly Leu Glu Trp Val
         35                  40                  45

Ala Thr Ile Lys Gln Asp Gly Ser Glu Lys Ser Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Pro Leu Asn Ala Gly Glu Leu Asp Val Trp Gly Gln Gly Thr
                100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Leu Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

```
<210> SEQ ID NO 200
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 201
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Trp Met Ser Trp Val Arg Gln Ala Pro Gly Lys Gly Leu Glu Trp Val
        35                  40                  45

Ala Thr Ile Lys Gln Asp Gly Ser Glu Lys Ser Tyr Val Asp Ser Val
50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
            100                 105                 110

Met Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 202
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

```
Gln Val Gln Leu Val Gln Ser Gly Ala Glu Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asp Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Glu Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 203
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 204
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

-continued

```
Tyr Glu Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ser Gln Ser Tyr Pro Pro
                 85                  90                  95

Ile Thr Phe Gly Cys Gly Thr Lys Val Glu Ile Lys Gly Gly Gly Gly
                100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Gln Pro Gly Gly
        130                 135                 140

Ser Leu Arg Leu Ser Cys Ala Ala Ser Gly Phe Thr Phe Gly Ser Tyr
145                 150                 155                 160

Trp Met Ser Trp Val Arg Gln Ala Pro Gly Lys Cys Leu Glu Trp Val
                165                 170                 175

Ala Thr Ile Lys Gln Asp Gly Ser Glu Lys Ser Tyr Val Asp Ser Val
                180                 185                 190

Lys Gly Arg Phe Thr Ile Ser Arg Asp Asn Ala Lys Asn Ser Leu Tyr
                195                 200                 205

Leu Gln Met Asn Ser Leu Arg Ala Glu Asp Thr Ala Val Tyr Tyr Cys
        210                 215                 220

Ala Arg Pro Leu Asn Ala Gly Glu Leu Asp Val Trp Gly Gln Gly Thr
225                 230                 235                 240

Met Val Thr Val Ser Ser Ala Ser Asp Lys Thr His Thr Cys Pro Pro
                245                 250                 255

Cys Pro Ala Pro Glu Ala Ala Gly Gly Pro Ser Val Phe Leu Phe Pro
                260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
                340                 345                 350

Asn Lys Ala Leu Gly Ala Pro Ile Glu Lys Thr Ile Ser Lys Ala Lys
                355                 360                 365

Gly Gln Pro Arg Glu Pro Arg Val Tyr Thr Leu Pro Pro Cys Arg Asp
        370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Val Ser Asp Gly Ser Phe
                420                 425                 430

Thr Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly
```

```
465                 470
```

<210> SEQ ID NO 205
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
            340                 345                 350
```

```
Val Cys Thr Leu Pro Pro Ser Arg Asp Glu Leu Thr Glu Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
        450

<210> SEQ ID NO 206
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Phe Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Gly Ser Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Phe Ser Ser Tyr Gly Met
145                 150                 155                 160

Ser Trp Val Arg Gln Ala Pro Gly Lys Cys Leu Glu Trp Val Ala Asn
                165                 170                 175

Ile Lys Gln Asp Gly Ser Glu Lys Tyr Tyr Val Asp Ser Val Lys Gly
            180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Val Tyr Tyr Cys Ala Arg
    210                 215                 220

Glu Gly Gly Pro Tyr Tyr Asp Ser Ser Gly Tyr Phe Val Tyr Gly
225                 230                 235                 240

Met Asp Val Trp Gly Gln Gly Thr Thr Val Thr Val Ser Ser
                245                 250
```

<210> SEQ ID NO 207
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Cys Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Asp Ile Gln Met Thr Gln Ser Pro Ser Thr Leu Ser
145                 150                 155                 160

Ala Ser Val Gly Asp Arg Val Thr Ile Thr Cys Arg Ala Ser Gln Ser
                165                 170                 175

Ile Ser Ser Trp Leu Ala Trp Tyr Gln Gln Lys Pro Gly Lys Ala Pro
            180                 185                 190

Lys Leu Leu Ile Tyr Asp Ala Ser Ser Leu Glu Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Asp Asp Phe Ala Thr Tyr Tyr Cys Gln Gln Tyr Glu
225                 230                 235                 240

Ser Phe Pro Thr Phe Gly Cys Gly Thr Lys Val Glu Ile Lys
                245                 250

<210> SEQ ID NO 208
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

```
Tyr Glu Ala Ser Ser Leu Glu Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Leu Glu Ser Tyr Pro Leu
                 85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Gly Ser Gly Gly Gly Gly Ser Glu
            115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Lys Gln Asp Gly Ser Glu Lys Tyr Tyr Val Asp Ser Val Lys
                180                 185                 190

Gly Arg Phe Thr Ile Ser Arg Asp Asn Ala Lys Asn Ser Leu Tyr Leu
    195                 200                 205

Gln Met Asn Ser Leu Arg Ala Glu Asp Thr Ala Val Tyr Tyr Cys Ala
    210                 215                 220

Arg Pro Leu Asn Ala Gly Glu Leu Asp Val Trp Gly Gln Gly Thr Met
225                 230                 235                 240

Val Thr Val Ser Ser
                245

<210> SEQ ID NO 209
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Trp Met Ser Trp Val Arg Gln Ala Pro Gly Lys Cys Leu Glu Trp Val
             35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Pro Leu Asn Ala Gly Glu Leu Asp Val Trp Gly Gln Gly Thr
            100                 105                 110

Met Val Thr Val Ser Ser Gly Gly Gly Gly Ser Gly Gly Gly Gly Ser
            115                 120                 125

Gly Gly Gly Gly Ser Gly Gly Gly Gly Ser Asp Ile Gln Met Thr Gln
    130                 135                 140

Ser Pro Ser Thr Leu Ser Ala Ser Val Gly Asp Arg Val Thr Ile Thr
```

```
            145                 150                 155                 160
Cys Arg Ala Ser Gln Ser Ile Ser Ser Trp Leu Ala Trp Tyr Gln Gln
                165                 170                 175

Lys Pro Gly Lys Ala Pro Lys Leu Leu Ile Tyr Glu Ala Ser Ser Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Leu Glu Ser Tyr Pro Leu Thr Phe Gly Cys Gly Thr
225                 230                 235                 240

Lys Val Glu Ile Lys
                245

<210> SEQ ID NO 210
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Thr Met Ser Trp Val Arg Gln Ala Pro Gly Lys Cys Leu Glu Trp Val
        35                  40                  45

Ser Ala Ile Val Gly Ser Gly Glu Ser Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Asp Ile Gln Met Thr Gln Ser Pro Ser Thr Leu Ser
145                 150                 155                 160

Ala Ser Val Gly Asp Arg Val Thr Ile Thr Cys Arg Ala Ser Gln Ser
                165                 170                 175

Ile Ser Ser Trp Leu Ala Trp Tyr Gln Gln Lys Pro Gly Lys Ala Pro
            180                 185                 190

Lys Leu Leu Ile Tyr Lys Ala Ser Ser Leu Glu Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Asp Asp Phe Ala Thr Tyr Tyr Cys Gln Gln Tyr Asp
225                 230                 235                 240

Asp Leu Pro Thr Phe Gly Cys Gly Thr Lys Val Glu Ile Lys
                245                 250
```

<210> SEQ ID NO 211
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Val Ala Leu Pro Ile Thr Phe Gly Cys Gly Thr Lys Val Glu Ile Lys
            100                 105                 110

Gly Gly Gly Gly Ser Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Ser Asp Tyr Tyr Met His Trp Val Arg Gln Ala Pro Gly Gln Cys
                165                 170                 175

Leu Glu Trp Met Gly Met Ile Asn Pro Ser Trp Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Glu Ala Ala Asp Gly Phe Val Gly Glu Arg
225                 230                 235                 240

Tyr Phe Asp Leu Trp Gly Arg Gly Thr Leu Val Thr Val Ser Ser
                245                 250                 255

<210> SEQ ID NO 212
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Tyr Met His Trp Val Arg Gln Ala Pro Gly Gln Cys Leu Glu Trp Met
        35                  40                  45

Gly Met Ile Asn Pro Ser Trp Gly Ser Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Ala Asp Gly Phe Val Gly Glu Arg Tyr Phe Asp Leu
                100                 105                 110

Trp Gly Arg Gly Thr Leu Val Thr Val Ser Ser Gly Gly Gly Gly Ser
            115                 120                 125

Gly Gly Gly Gly Ser Gly Gly Gly Ser Gly Gly Gly Gly Ser Asp
        130                 135                 140

Ile Val Met Thr Gln Ser Pro Leu Ser Leu Pro Val Thr Pro Gly Glu
145                 150                 155                 160

Pro Ala Ser Ile Ser Cys Arg Ser Ser Gln Ser Leu Leu Tyr Ser Asn
                165                 170                 175

Gly Tyr Asn Tyr Leu Asp Trp Tyr Leu Gln Lys Pro Gly Gln Ser Pro
            180                 185                 190

Gln Leu Leu Ile Tyr Leu Gly Ser Asn Arg Ala Ser Gly Val Pro Asp
        195                 200                 205

Arg Phe Ser Gly Ser Gly Ser Gly Thr Asp Phe Thr Leu Lys Ile Ser
    210                 215                 220

Arg Val Glu Ala Glu Asp Val Gly Val Tyr Tyr Cys Met Gln Asp Val
225                 230                 235                 240

Ala Leu Pro Ile Thr Phe Gly Cys Gly Thr Lys Val Glu Ile Lys
                245                 250                 255

<210> SEQ ID NO 213
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Trp Met Ser Trp Val Arg Gln Ala Pro Gly Lys Cys Leu Glu Trp Val
        35                  40                  45

Ala Thr Ile Lys Gln Asp Gly Ser Glu Lys Ser Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
                100                 105                 110

Met Val Thr Val Ser Ser Gly Gly Gly Ser Gly Gly Gly Gly Ser
            115                 120                 125

Gly Gly Gly Gly Ser Gly Gly Gly Gly Ser Asp Ile Gln Met Thr Gln
        130                 135                 140

Ser Pro Ser Thr Leu Ser Ala Ser Val Gly Asp Arg Val Thr Ile Thr
145                 150                 155                 160

```
Cys Arg Ala Ser Gln Ser Ile Ser Ser Trp Leu Ala Trp Tyr Gln Gln
            165                 170                 175

Lys Pro Gly Lys Ala Pro Lys Leu Leu Ile Tyr Glu Ala Ser Ser Leu
        180                 185                 190

Glu Ser Gly Val Pro Ser Arg Phe Ser Gly Ser Gly Ser Gly Thr Glu
    195                 200                 205

Phe Thr Leu Thr Ile Ser Ser Leu Gln Pro Asp Asp Phe Ala Thr Tyr
210                 215                 220

Tyr Cys Gln Gln Ser Gln Ser Tyr Pro Pro Ile Thr Phe Gly Cys Gly
225                 230                 235                 240

Thr Lys Val Glu Ile Lys
            245

<210> SEQ ID NO 214
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Leu Val Gln Pro Gly Gly
    130                 135                 140

Ser Leu Arg Leu Ser Cys Ala Ala Ser Gly Phe Thr Phe Pro Ser Tyr
145                 150                 155                 160

Trp Met Ser Trp Val Arg Gln Ala Pro Gly Lys Cys Leu Glu Trp Val
            165                 170                 175

Ala Thr Ile Lys Arg Asp Gly Ser Glu Lys Gly Tyr Val Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Pro Leu Asn Ala Gly Glu Leu Asp Val Trp Gly Gln Gly Thr
225                 230                 235                 240

Met Val Thr Val Ser Ser
            245
```

```
<210> SEQ ID NO 215
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Ser Tyr
            20                  25                  30

Trp Met Ser Trp Val Arg Gln Ala Pro Gly Lys Cys Leu Glu Trp Val
        35                  40                  45

Ala Thr Ile Lys Arg Asp Gly Ser Glu Lys Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Gly Gly Gly Ser Asp Ile Gln Met Thr Gln
    130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Ser Trp Leu Ala Trp Tyr Gln Gln
                165                 170                 175

Lys Pro Gly Lys Ala Pro Lys Leu Leu Ile Tyr Glu Ala Ser Ser Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Ser Gln Ser Tyr Pro Pro Ile Thr Phe Gly Cys Gly
225                 230                 235                 240

Thr Lys Val Glu Ile Lys
                245

<210> SEQ ID NO 216
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                50              55              60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Ser Tyr Pro Leu
                     85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Ser Gly Gly Gly Gly Ser Gln
            115                 120                 125

Val Gln Leu Val Gln Ser Gly Ala Glu Val Lys Lys Pro Gly Ala Ser
            130                 135                 140

Val Lys Val Ser Cys Lys Ala Ser Gly Tyr Thr Phe Gly Thr Tyr Tyr
145                 150                 155                 160

Met His Trp Val Arg Gln Ala Pro Gly Gln Cys Leu Glu Trp Met Gly
                165                 170                 175

Ile Ile Asn Pro Ser Arg Gly Ser Thr Val Tyr Ala Gln Lys Phe Gln
                180                 185                 190

Gly Arg Val Thr Met Thr Arg Asp Thr Ser Thr Ser Thr Val Tyr Met
                195                 200                 205

Glu Leu Ser Ser Leu Arg Ser Glu Asp Thr Ala Val Tyr Tyr Cys Ala
            210                 215                 220

Arg Gly Ala Gly Tyr Asp Asp Glu Asp Met Asp Val Trp Gly Lys Gly
225                 230                 235                 240

Thr Thr Val Thr Val Ser Ser
                245

<210> SEQ ID NO 217
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Gly Thr Tyr
                20                  25                  30

Tyr Met His Trp Val Arg Gln Ala Pro Gly Gln Cys Leu Glu Trp Met
            35                  40                  45

Gly Ile Ile Asn Pro Ser Arg Gly Ser Thr Val Tyr Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ala Gly Tyr Asp Asp Glu Asp Met Asp Val Trp Gly Lys
            100                 105                 110

Gly Thr Thr Val Thr Val Ser Ser Gly Gly Gly Gly Ser Gly Gly Gly
        115                 120                 125

Gly Ser Gly Gly Gly Ser Gly Gly Gly Gly Ser Asp Ile Gln Met
    130                 135                 140

Thr Gln Ser Pro Ser Ser Val Ser Ala Ser Val Gly Asp Arg Val Thr
145                 150                 155                 160
```

```
Ile Thr Cys Arg Ala Ser Gln Gly Ile Asp Ser Trp Leu Ala Trp Tyr
            165                 170                 175

Gln Gln Lys Pro Gly Lys Ala Pro Lys Leu Leu Ile Tyr Ala Ala Ser
        180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
        210                 215                 220

Thr Tyr Tyr Cys Gln Gln Ala His Ser Tyr Pro Leu Thr Phe Gly Cys
225                 230                 235                 240

Gly Thr Lys Val Glu Ile Lys
                245

<210> SEQ ID NO 218
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asp Ile Gln Met Thr Gln Ser Pro Ser Thr Leu Ser Ala Ser Val Gly
1               5                   10                  15

Asp Arg Val Thr Ile Thr Cys Arg Ala Ser Asn Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Thr Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Gly Ser Glu Val
        115                 120                 125

Gln Leu Val Glu Ser Gly Gly Gly Leu Val Lys Pro Gly Gly Ser Leu
    130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Cys Leu Glu Trp Val Ser Ser
                165                 170                 175

Ile Ser Ser Ser Glu Gly Ile Tyr Tyr Ala Asp Ser Val Lys Gly
            180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Val Tyr Tyr Cys Ala Arg
    210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser
                245                 250

<210> SEQ ID NO 219
```

```
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ser Ile Ser Ser Ser Ser Glu Gly Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Gly Ser Gly Gly Gly Gly Ser Gly
    130                 135                 140

Gly Gly Ser Asp Ile Gln Met Thr Gln Ser Pro Ser Thr Leu Ser
145                 150                 155                 160

Ala Ser Val Gly Asp Arg Val Thr Ile Thr Cys Arg Ala Ser Asn Ser
                165                 170                 175

Ile Ser Ser Trp Leu Ala Trp Tyr Gln Gln Lys Pro Gly Lys Ala Pro
            180                 185                 190

Lys Leu Leu Ile Tyr Glu Ala Ser Ser Thr Lys Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Asp Asp Phe Ala Thr Tyr Tyr Cys Gln Gln Tyr Asp
225                 230                 235                 240

Asp Leu Pro Thr Phe Gly Cys Gly Thr Lys Val Glu Ile Lys
                245                 250

<210> SEQ ID NO 220
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Tyr Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Lys Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
            115                 120                 125

Val Gln Leu Val Glu Ser Gly Gly Leu Val Gln Pro Gly Gly Ser
130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Asn Thr Asp Gly Ser Glu Val Tyr Tyr Val Asp Ser Val Lys
                180                 185                 190

Gly Arg Phe Thr Ile Ser Arg Asp Asn Ala Lys Asn Ser Leu Tyr Leu
            195                 200                 205

Gln Met Asn Ser Leu Arg Ala Glu Asp Thr Ala Val Tyr Tyr Cys Ala
        210                 215                 220

Arg Asp Val Gly Pro Gly Ile Ala Tyr Gln Gly His Phe Asp Tyr Trp
225                 230                 235                 240

Gly Gln Gly Thr Leu Val Thr Val Ser Ser
                245                 250

<210> SEQ ID NO 221
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Thr Asp Gly Ser Glu Val Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Asp
            130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Val Ile Tyr Ser Tyr Leu

```
                    165                 170                 175

Asn Trp Tyr Gln Gln Lys Pro Gly Lys Ala Pro Lys Leu Leu Ile Tyr
            180                 185                 190

Ala Ala Ser Ser Leu Lys Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Val Tyr Asp Thr Pro Leu Thr
225                 230                 235                 240

Phe Gly Cys Gly Thr Lys Val Glu Ile Lys
                245                 250

<210> SEQ ID NO 222
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Ile Val Leu Thr Gln Ser Pro Ala Thr Leu Ser Leu Ser Pro Gly
1               5                   10                  15

Glu Arg Ala Thr Leu Ser Cys Arg Ala Ser His Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Asn Leu Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Gln Leu
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ser Ser Thr Asp Tyr
145                 150                 155                 160

Tyr Trp Gly Trp Ile Arg Gln Pro Pro Gly Lys Cys Leu Glu Trp Ile
                165                 170                 175

Gly Ser Ile Gly Tyr Ser Gly Thr Tyr Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Glu Thr Ala His Asp Val His Gly Met Asp Val Trp Gly Gln Gly Thr
225                 230                 235                 240

Thr Val Thr Val Ser Ser
                245

<210> SEQ ID NO 223
<211> LENGTH: 246
```

<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 223

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Asp Tyr Tyr Trp Gly Trp Ile Arg Gln Pro Pro Gly Lys Cys Leu Glu
        35                  40                  45

Trp Ile Gly Ser Ile Gly Tyr Ser Gly Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Glu Thr Ala His Asp Val His Gly Met Asp Val Trp Gly Gln
        100                 105                 110

Gly Thr Thr Val Thr Val Ser Ser Gly Gly Gly Ser Gly Gly Gly
            115                 120                 125

Gly Ser Gly Gly Gly Ser Gly Gly Gly Ser Glu Ile Val Leu
    130                 135                 140

Thr Gln Ser Pro Ala Thr Leu Ser Leu Ser Pro Gly Glu Arg Ala Thr
145                 150                 155                 160

Leu Ser Cys Arg Ala Ser His Ser Val Tyr Ser Tyr Leu Ala Trp Tyr
            165                 170                 175

Gln Gln Lys Pro Gly Gln Ala Pro Arg Leu Leu Ile Tyr Asp Ala Ser
        180                 185                 190

Asn Arg Ala Thr Gly Ile Pro Ala Arg Phe Ser Gly Ser Gly Ser Gly
    195                 200                 205

Thr Asp Phe Thr Leu Thr Ile Ser Ser Leu Glu Pro Glu Asp Phe Ala
    210                 215                 220

Val Tyr Tyr Cys Gln Gln Tyr Asp Asn Leu Pro Thr Phe Gly Cys Gly
225                 230                 235                 240

Thr Lys Val Glu Ile Lys
            245

<210> SEQ ID NO 224
<211> LENGTH: 482
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 224

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

-continued

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Glu Ser Phe Pro Thr
                 85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Glu Val
        115                 120                 125

Gln Leu Val Glu Ser Gly Gly Leu Val Gln Pro Gly Gly Ser Leu
    130                 135                 140

Arg Leu Ser Cys Ala Ala Ser Gly Phe Thr Phe Ser Ser Tyr Gly Met
145                 150                 155                 160

Ser Trp Val Arg Gln Ala Pro Gly Lys Cys Leu Glu Trp Val Ala Asn
                165                 170                 175

Ile Lys Gln Asp Gly Ser Glu Lys Tyr Tyr Val Asp Ser Val Lys Gly
                180                 185                 190

Arg Phe Thr Ile Ser Arg Asp Asn Ala Lys Asn Ser Leu Tyr Leu Gln
            195                 200                 205

Met Asn Ser Leu Arg Ala Glu Asp Thr Ala Val Tyr Tyr Cys Ala Arg
    210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Arg Val
    370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Val Ser Asp Gly Ser Phe Thr Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly
```

<210> SEQ ID NO 225
<211> LENGTH: 482
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 225

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Cys Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Asp Ile Gln Met Thr Gln Ser Pro Ser Thr Leu Ser
145                 150                 155                 160

Ala Ser Val Gly Asp Arg Val Thr Ile Thr Cys Arg Ala Ser Gln Ser
                165                 170                 175

Ile Ser Ser Trp Leu Ala Trp Tyr Gln Gln Lys Pro Gly Lys Ala Pro
            180                 185                 190

Lys Leu Leu Ile Tyr Asp Ala Ser Ser Leu Glu Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Asp Asp Phe Ala Thr Tyr Tyr Cys Gln Gln Tyr Glu
225                 230                 235                 240

Ser Phe Pro Thr Phe Gly Cys Gly Thr Lys Val Glu Ile Lys Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
```

```
                355                 360                 365
Glu Lys Thr Ile Ser Lys Ala Lys Gly Gln Pro Arg Glu Pro Arg Val
370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
                420                 425                 430

Val Leu Val Ser Asp Gly Ser Phe Thr Leu Tyr Ser Lys Leu Thr Val
                435                 440                 445

Asp Lys Ser Arg Trp Gln Gln Gly Asn Val Phe Ser Cys Ser Val Met
                450                 455                 460

His Glu Ala Leu His Asn His Tyr Thr Gln Lys Ser Leu Ser Leu Ser
465                 470                 475                 480

Pro Gly

<210> SEQ ID NO 226
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Glu Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Glu Ser Tyr Pro Leu
                85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Gly Ser Gly Gly Gly Gly Ser Glu
            115                 120                 125

Val Gln Leu Val Glu Ser Gly Gly Gly Leu Val Gln Pro Gly Gly Ser
        130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Lys Gln Asp Gly Ser Glu Lys Tyr Tyr Val Asp Ser Val Lys
                180                 185                 190

Gly Arg Phe Thr Ile Ser Arg Asp Asn Ala Lys Asn Ser Leu Tyr Leu
            195                 200                 205

Gln Met Asn Ser Leu Arg Ala Glu Asp Thr Ala Val Tyr Tyr Cys Ala
        210                 215                 220

Arg Pro Leu Asn Ala Gly Glu Leu Asp Val Trp Gly Gln Gly Thr Met
```

225                 230                 235                 240
Val Thr Val Ser Ser Ala Ser Asp Lys Thr His Thr Cys Pro Pro Cys
                245                 250                 255

Pro Ala Pro Glu Leu Leu Gly Gly Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
                290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Arg Val Tyr Thr Leu Pro Pro Cys Arg Asp Glu
                370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Val Ser Asp Gly Ser Phe Thr
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
                450                 455                 460

Gln Lys Ser Leu Ser Leu Ser Pro Gly
465                 470

<210> SEQ ID NO 227
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Cys Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Leu Asn Ala Gly Glu Leu Asp Val Trp Gly Gln Gly Thr
                100                 105                 110

Met Val Thr Val Ser Ser Gly Gly Gly Gly Ser Gly Gly Gly Gly Ser
115                 120                 125

Gly Gly Gly Gly Ser Gly Gly Gly Ser Asp Ile Gln Met Thr Gln
130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Ser Trp Leu Ala Trp Tyr Gln Gln
                165                 170                 175

Lys Pro Gly Lys Ala Pro Lys Leu Leu Ile Tyr Glu Ala Ser Ser Leu
            180                 185                 190

Glu Ser Gly Val Pro Ser Arg Phe Ser Gly Ser Gly Ser Gly Thr Glu
        195                 200                 205

Phe Thr Leu Thr Ile Ser Ser Leu Gln Pro Asp Asp Phe Ala Thr Tyr
    210                 215                 220

Tyr Cys Gln Gln Leu Glu Ser Tyr Pro Leu Thr Phe Gly Cys Gly Thr
225                 230                 235                 240

Lys Val Glu Ile Lys Ala Ser Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Arg Val Tyr Thr Leu Pro Pro Cys Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Val Ser Asp Gly Ser Phe Thr
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470

<210> SEQ ID NO 228
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Thr Met Ser Trp Val Arg Gln Ala Pro Gly Lys Cys Leu Glu Trp Val
        35                  40                  45

Ser Ala Ile Val Gly Ser Gly Glu Ser Thr Tyr Phe Ala Asp Ser Val
    50                  55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gly
        130                 135                 140

Gly Gly Gly Ser Asp Ile Gln Met Thr Gln Ser Pro Ser Thr Leu Ser
145                 150                 155                 160

Ala Ser Val Gly Asp Arg Val Thr Ile Thr Cys Arg Ala Ser Gln Ser
                165                 170                 175

Ile Ser Ser Trp Leu Ala Trp Tyr Gln Gln Lys Pro Gly Lys Ala Pro
            180                 185                 190

Lys Leu Leu Ile Tyr Lys Ala Ser Ser Leu Glu Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Asp Asp Phe Ala Thr Tyr Tyr Cys Gln Gln Tyr Asp
225                 230                 235                 240

Asp Leu Pro Thr Phe Gly Cys Gly Thr Lys Val Glu Ile Lys Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Arg Val
    370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
            405                 410                 415
```

Trp Glu Ser Asn Gly Gln Pro Glu Asn Asn Tyr Lys Thr Thr Pro Pro
                    420                 425                 430

Val Leu Val Ser Asp Gly Ser Phe Thr Leu Tyr Ser Lys Leu Thr Val
            435                 440                 445

Asp Lys Ser Arg Trp Gln Gln Gly Asn Val Phe Ser Cys Ser Val Met
        450                 455                 460

His Glu Ala Leu His Asn His Tyr Thr Gln Lys Ser Leu Ser Leu Ser
465                 470                 475                 480

Pro Gly

<210> SEQ ID NO 229
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Val Ala Leu Pro Ile Thr Phe Gly Cys Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Gln Val Gln Leu Val Gln Ser Gly Ala Glu Val Lys
    130                 135                 140

Lys Pro Gly Ala Ser Val Lys Val Ser Cys Lys Ala Ser Gly Tyr Thr
145                 150                 155                 160

Phe Ser Asp Tyr Tyr Met His Trp Val Arg Gln Ala Pro Gly Gln Cys
                165                 170                 175

Leu Glu Trp Met Gly Met Ile Asn Pro Ser Trp Gly Ser Thr Ser Tyr
            180                 185                 190

Ala Gln Lys Phe Gln Gly Arg Val Thr Met Thr Arg Asp Thr Ser Thr
        195                 200                 205

Ser Thr Val Tyr Met Glu Leu Ser Ser Leu Arg Ser Glu Asp Thr Ala
    210                 215                 220

Val Tyr Tyr Cys Ala Arg Glu Ala Ala Asp Gly Phe Val Gly Glu Arg
225                 230                 235                 240

Tyr Phe Asp Leu Trp Gly Arg Gly Thr Leu Val Thr Val Ser Ser Ala
                245                 250                 255

Ser Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
        275                 280                 285

```
Met Ile Ser Arg Thr Pro Glu Val Thr Cys Val Val Val Asp Val Ser
    290                 295                 300
His Glu Asp Pro Glu Val Lys Phe Asn Trp Tyr Val Asp Gly Val Glu
305                 310                 315                 320
Val His Asn Ala Lys Thr Lys Pro Arg Glu Glu Gln Tyr Asn Ser Thr
                325                 330                 335
Tyr Arg Val Val Ser Val Leu Thr Val Leu His Gln Asp Trp Leu Asn
                340                 345                 350
Gly Lys Glu Tyr Lys Cys Lys Val Ser Asn Lys Ala Leu Pro Ala Pro
                355                 360                 365
Ile Glu Lys Thr Ile Ser Lys Ala Lys Gly Gln Pro Arg Glu Pro Arg
370                 375                 380
Val Tyr Thr Leu Pro Pro Cys Arg Asp Glu Leu Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
                420                 425                 430
Pro Val Leu Val Ser Asp Gly Ser Phe Thr Leu Tyr Ser Lys Leu Thr
                435                 440                 445
Val Asp Lys Ser Arg Trp Gln Gln Gly Asn Val Phe Ser Cys Ser Val
450                 455                 460
Met His Glu Ala Leu His Asn His Tyr Thr Gln Lys Ser Leu Ser Leu
465                 470                 475                 480

Ser Pro Gly

<210> SEQ ID NO 230
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ser Asp Tyr
                20                  25                  30
Tyr Met His Trp Val Arg Gln Ala Pro Gly Gln Cys Leu Glu Trp Met
            35                  40                  45
Gly Met Ile Asn Pro Ser Trp Gly Ser Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Glu Ala Ala Asp Gly Phe Val Gly Glu Arg Tyr Phe Asp Leu
                100                 105                 110
Trp Gly Arg Gly Thr Leu Val Thr Val Ser Ser Gly Gly Gly Gly Ser
            115                 120                 125
Gly Gly Gly Gly Ser Gly Gly Gly Ser Gly Gly Gly Ser Asp
        130                 135                 140
Ile Val Met Thr Gln Ser Pro Leu Ser Leu Pro Val Thr Pro Gly Glu
145                 150                 155                 160
```

Pro Ala Ser Ile Ser Cys Arg Ser Ser Gln Ser Leu Leu Tyr Ser Asn
                165                 170                 175
Gly Tyr Asn Tyr Leu Asp Trp Tyr Leu Gln Lys Pro Gly Gln Ser Pro
            180                 185                 190
Gln Leu Leu Ile Tyr Leu Gly Ser Asn Arg Ala Ser Gly Val Pro Asp
        195                 200                 205
Arg Phe Ser Gly Ser Gly Ser Gly Thr Asp Phe Thr Leu Lys Ile Ser
    210                 215                 220
Arg Val Glu Ala Glu Asp Val Gly Val Tyr Tyr Cys Met Gln Asp Val
225                 230                 235                 240
Ala Leu Pro Ile Thr Phe Gly Cys Gly Thr Lys Val Glu Ile Lys Ala
                245                 250                 255
Ser Asp Lys Thr His Thr Cys Pro Pro Cys Pro Ala Pro Glu Leu Leu
            260                 265                 270
Gly Gly Pro Ser Val Phe Leu Phe Pro Pro Lys Pro Lys Asp Thr Leu
        275                 280                 285
Met Ile Ser Arg Thr Pro Glu Val Thr Cys Val Val Val Asp Val Ser
    290                 295                 300
His Glu Asp Pro Glu Val Lys Phe Asn Trp Tyr Val Asp Gly Val Glu
305                 310                 315                 320
Val His Asn Ala Lys Thr Lys Pro Arg Glu Glu Gln Tyr Asn Ser Thr
                325                 330                 335
Tyr Arg Val Val Ser Val Leu Thr Val Leu His Gln Asp Trp Leu Asn
            340                 345                 350
Gly Lys Glu Tyr Lys Cys Lys Val Ser Asn Lys Ala Leu Pro Ala Pro
        355                 360                 365
Ile Glu Lys Thr Ile Ser Lys Ala Lys Gly Gln Pro Arg Glu Pro Arg
    370                 375                 380
Val Tyr Thr Leu Pro Pro Cys Arg Asp Glu Leu Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
            420                 425                 430
Pro Val Leu Val Ser Asp Gly Ser Phe Thr Leu Tyr Ser Lys Leu Thr
        435                 440                 445
Val Asp Lys Ser Arg Trp Gln Gln Gly Asn Val Phe Ser Cys Ser Val
    450                 455                 460
Met His Glu Ala Leu His Asn His Tyr Thr Gln Lys Ser Leu Ser Leu
465                 470                 475                 480
Ser Pro Gly

<210> SEQ ID NO 231
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Gly Ser Tyr
            20                  25                  30

```
Trp Met Ser Trp Val Arg Gln Ala Pro Gly Lys Cys Leu Glu Trp Val
         35                  40                  45
Ala Thr Ile Lys Gln Asp Gly Ser Glu Lys Ser Tyr Val Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Pro Leu Asn Ala Gly Glu Leu Asp Val Trp Gly Gln Gly Thr
             100                 105                 110
Met Val Thr Val Ser Ser Gly Gly Gly Gly Ser Gly Gly Gly Gly Ser
             115                 120                 125
Gly Gly Gly Gly Ser Gly Gly Gly Ser Asp Ile Gln Met Thr Gln
             130                 135                 140
Ser Pro Ser Thr Leu Ser Ala Ser Val Gly Asp Arg Val Thr Ile Thr
145                 150                 155                 160
Cys Arg Ala Ser Gln Ser Ile Ser Ser Trp Leu Ala Trp Tyr Gln Gln
                 165                 170                 175
Lys Pro Gly Lys Ala Pro Lys Leu Leu Ile Tyr Glu Ala Ser Ser Leu
             180                 185                 190
Glu Ser Gly Val Pro Ser Arg Phe Ser Gly Ser Gly Ser Gly Thr Glu
             195                 200                 205
Phe Thr Leu Thr Ile Ser Ser Leu Gln Pro Asp Asp Phe Ala Thr Tyr
             210                 215                 220
Tyr Cys Gln Gln Ser Gln Ser Tyr Pro Pro Ile Thr Phe Gly Cys Gly
225                 230                 235                 240
Thr Lys Val Glu Ile Lys Ala Ser Asp Lys Thr His Thr Cys Pro Pro
                 245                 250                 255
Cys Pro Ala Pro Glu Leu Leu Gly Gly Pro Ser Val Phe Leu Phe Pro
             260                 265                 270
Pro Lys Pro Lys Asp Thr Leu Met Ile Ser Arg Thr Pro Glu Val Thr
             275                 280                 285
Cys Val Val Val Asp Val Ser His Glu Asp Pro Glu Val Lys Phe Asn
             290                 295                 300
Trp Tyr Val Asp Gly Val Glu Val His Asn Ala Lys Thr Lys Pro Arg
305                 310                 315                 320
Glu Glu Gln Tyr Asn Ser Thr Tyr Arg Val Val Ser Val Leu Thr Val
                 325                 330                 335
Leu His Gln Asp Trp Leu Asn Gly Lys Glu Tyr Lys Cys Lys Val Ser
             340                 345                 350
Asn Lys Ala Leu Pro Ala Pro Ile Glu Lys Thr Ile Ser Lys Ala Lys
             355                 360                 365
Gly Gln Pro Arg Glu Pro Arg Val Tyr Thr Leu Pro Pro Cys Arg Asp
             370                 375                 380
Glu Leu Thr Lys Asn Gln Val Ser Leu Thr Cys Leu Val Lys Gly Phe
385                 390                 395                 400
Tyr Pro Ser Asp Ile Ala Val Glu Trp Glu Ser Asn Gly Gln Pro Glu
                 405                 410                 415
Asn Asn Tyr Lys Thr Thr Pro Pro Val Leu Val Ser Asp Gly Ser Phe
             420                 425                 430
Thr Leu Tyr Ser Lys Leu Thr Val Asp Lys Ser Arg Trp Gln Gln Gly
             435                 440                 445
Asn Val Phe Ser Cys Ser Val Met His Glu Ala Leu His Asn His Tyr
```

```
                450                 455                 460
Thr Gln Lys Ser Leu Ser Leu Ser Pro Gly
465                 470

<210> SEQ ID NO 232
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Cys Gly Thr Lys Val Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Gly Leu Val Gln Pro Gly Gly
130                 135                 140

Ser Leu Arg Leu Ser Cys Ala Ala Ser Gly Phe Thr Phe Pro Ser Tyr
145                 150                 155                 160

Trp Met Ser Trp Val Arg Gln Ala Pro Gly Lys Cys Leu Glu Trp Val
                165                 170                 175

Ala Thr Ile Lys Arg Asp Gly Ser Glu Lys Gly Tyr Val Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Pro Leu Asn Ala Gly Glu Leu Asp Val Trp Gly Gln Gly Thr
225                 230                 235                 240

Met Val Thr Val Ser Ser Ala Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335
```

```
Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Arg Val Tyr Thr Leu Pro Pro Cys Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Val Ser Asp Gly Ser Phe
            420                 425                 430

Thr Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly
465                 470

<210> SEQ ID NO 233
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Ser Tyr
            20                  25                  30

Trp Met Ser Trp Val Arg Gln Ala Pro Gly Lys Cys Leu Glu Trp Val
        35                  40                  45

Ala Thr Ile Lys Arg Asp Gly Ser Glu Lys Gly Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Pro Leu Asn Ala Gly Glu Leu Asp Val Trp Gly Gln Gly Thr
        100                 105                 110

Met Val Thr Val Ser Ser Gly Gly Gly Gly Ser Gly Gly Gly Gly Ser
    115                 120                 125

Gly Gly Gly Gly Ser Gly Gly Gly Ser Asp Ile Gln Met Thr Gln
    130                 135                 140

Ser Pro Ser Thr Leu Ser Ala Ser Val Gly Asp Arg Val Thr Ile Thr
145                 150                 155                 160

Cys Arg Ala Ser Gln Ser Ile Ser Ser Trp Leu Ala Trp Tyr Gln Gln
            165                 170                 175

Lys Pro Gly Lys Ala Pro Lys Leu Leu Ile Tyr Glu Ala Ser Ser Leu
        180                 185                 190

Glu Ser Gly Val Pro Ser Arg Phe Ser Gly Ser Gly Ser Gly Thr Glu
    195                 200                 205

Phe Thr Leu Thr Ile Ser Ser Leu Gln Pro Asp Asp Phe Ala Thr Tyr
    210                 215                 220
```

Tyr Cys Gln Gln Ser Gln Ser Tyr Pro Pro Ile Thr Phe Gly Cys Gly
225                 230                 235                 240

Thr Lys Val Glu Ile Lys Ala Ser Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Arg Val Tyr Thr Leu Pro Pro Cys Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Val Ser Asp Gly Ser Phe
            420                 425                 430

Thr Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly
465                 470

<210> SEQ ID NO 234
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Tyr Pro Leu
                85                  90                  95

Thr Phe Gly Cys Gly Thr Lys Val Glu Ile Lys Gly Gly Gly Gly Ser

```
                100             105             110
Gly Gly Gly Gly Ser Gly Gly Gly Ser Gly Gly Gly Ser Gln
            115             120             125

Val Gln Leu Val Gln Ser Gly Ala Glu Val Lys Lys Pro Gly Ala Ser
    130             135             140

Val Lys Val Ser Cys Lys Ala Ser Gly Tyr Thr Phe Gly Thr Tyr Tyr
145             150             155             160

Met His Trp Val Arg Gln Ala Pro Gly Gln Cys Leu Glu Trp Met Gly
                165             170             175

Ile Ile Asn Pro Ser Arg Gly Ser Thr Val Tyr Ala Gln Lys Phe Gln
            180             185             190

Gly Arg Val Thr Met Thr Arg Asp Thr Ser Thr Ser Thr Val Tyr Met
        195             200             205

Glu Leu Ser Ser Leu Arg Ser Glu Asp Thr Ala Val Tyr Tyr Cys Ala
    210             215             220

Arg Gly Ala Gly Tyr Asp Asp Glu Asp Met Asp Val Trp Gly Lys Gly
225             230             235             240

Thr Thr Val Thr Val Ser Ser Ala Ser Asp Lys Thr His Thr Cys Pro
            245             250             255

Pro Cys Pro Ala Pro Glu Leu Leu Gly Gly Pro Ser Val Phe Leu Phe
        260             265             270

Pro Pro Lys Pro Lys Asp Thr Leu Met Ile Ser Arg Thr Pro Glu Val
    275             280             285

Thr Cys Val Val Val Asp Val Ser His Glu Asp Pro Glu Val Lys Phe
    290             295             300

Asn Trp Tyr Val Asp Gly Val Glu Val His Asn Ala Lys Thr Lys Pro
305             310             315             320

Arg Glu Glu Gln Tyr Asn Ser Thr Tyr Arg Val Val Ser Val Leu Thr
                325             330             335

Val Leu His Gln Asp Trp Leu Asn Gly Lys Glu Tyr Lys Cys Lys Val
            340             345             350

Ser Asn Lys Ala Leu Pro Ala Pro Ile Glu Lys Thr Ile Ser Lys Ala
        355             360             365

Lys Gly Gln Pro Arg Glu Pro Arg Val Tyr Thr Leu Pro Pro Cys Arg
    370             375             380

Asp Glu Leu Thr Lys Asn Gln Val Ser Leu Thr Cys Leu Val Lys Gly
385             390             395             400

Phe Tyr Pro Ser Asp Ile Ala Val Glu Trp Glu Ser Asn Gly Gln Pro
                405             410             415

Glu Asn Asn Tyr Lys Thr Thr Pro Pro Val Leu Val Ser Asp Gly Ser
            420             425             430

Phe Thr Leu Tyr Ser Lys Leu Thr Val Asp Lys Ser Arg Trp Gln Gln
        435             440             445

Gly Asn Val Phe Ser Cys Ser Val Met His Glu Ala Leu His Asn His
    450             455             460

Tyr Thr Gln Lys Ser Leu Ser Leu Ser Pro Gly
465             470             475
```

<210> SEQ ID NO 235
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Thr Tyr
            20                  25                  30

Tyr Met His Trp Val Arg Gln Ala Pro Gly Gln Cys Leu Glu Trp Met
        35                  40                  45

Gly Ile Ile Asn Pro Ser Arg Gly Ser Thr Val Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Asp Asp Glu Asp Met Asp Val Trp Gly Lys
            100                 105                 110

Gly Thr Thr Val Thr Val Ser Ser Gly Gly Gly Ser Gly Gly Gly
            115                 120                 125

Gly Ser Gly Gly Gly Ser Gly Gly Gly Ser Asp Ile Gln Met
        130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Asp Ser Trp Leu Ala Trp Tyr
            165                 170                 175

Gln Gln Lys Pro Gly Lys Ala Pro Lys Leu Leu Ile Tyr Ala Ala Ser
        180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
210                 215                 220

Thr Tyr Tyr Cys Gln Gln Ala His Ser Tyr Pro Leu Thr Phe Gly Cys
225                 230                 235                 240

Gly Thr Lys Val Glu Ile Lys Ala Ser Asp Lys Thr His Thr Cys Pro
            245                 250                 255

Pro Cys Pro Ala Pro Glu Leu Leu Gly Gly Pro Ser Val Phe Leu Phe
        260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Arg Val Tyr Thr Leu Pro Pro Cys Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro

```
                    405                 410                 415
Glu Asn Asn Tyr Lys Thr Thr Pro Val Leu Val Ser Asp Gly Ser
                420                 425                 430

Phe Thr Leu Tyr Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly
465                 470                 475

<210> SEQ ID NO 236
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Asp Ile Gln Met Thr Gln Ser Pro Ser Thr Leu Ser Ala Ser Val Gly
1               5                   10                  15

Asp Arg Val Thr Ile Thr Cys Arg Ala Ser Asn Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Thr Lys Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Glu Val
        115                 120                 125

Gln Leu Val Glu Ser Gly Gly Gly Leu Val Lys Pro Gly Gly Ser Leu
    130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Cys Leu Glu Trp Val Ser Ser
                165                 170                 175

Ile Ser Ser Ser Ser Glu Gly Ile Tyr Tyr Ala Asp Ser Val Lys Gly
            180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Val Tyr Tyr Cys Ala Arg
    210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285
```

```
Ile Ser Arg Thr Pro Glu Val Thr Cys Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Arg Val
370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Val Ser Asp Gly Ser Phe Thr Leu Tyr Ser Lys Leu Thr Val
        435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly

<210> SEQ ID NO 237
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ser Ile Ser Ser Ser Glu Gly Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Pro Tyr Tyr Asp Ser Ser Gly Tyr Phe Val Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Ser Gly Gly Gly Gly Ser Gly
    130                 135                 140

Gly Gly Gly Ser Asp Ile Gln Met Thr Gln Ser Pro Ser Thr Leu Ser
145                 150                 155                 160
```

Ala Ser Val Gly Asp Arg Val Thr Ile Thr Cys Arg Ala Ser Asn Ser
            165                 170                 175

Ile Ser Ser Trp Leu Ala Trp Tyr Gln Gln Lys Pro Gly Lys Ala Pro
        180                 185                 190

Lys Leu Leu Ile Tyr Glu Ala Ser Ser Thr Lys Ser Gly Val Pro Ser
    195                 200                 205

Arg Phe Ser Gly Ser Gly Ser Gly Thr Glu Phe Thr Leu Thr Ile Ser
210                 215                 220

Ser Leu Gln Pro Asp Asp Phe Ala Thr Tyr Tyr Cys Gln Gln Tyr Asp
225                 230                 235                 240

Asp Leu Pro Thr Phe Gly Cys Gly Thr Lys Val Glu Ile Lys Ala Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Arg Val
    370                 375                 380

Tyr Thr Leu Pro Pro Cys Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Val Ser Asp Gly Ser Phe Thr Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly

<210> SEQ ID NO 238
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Tyr Ser Tyr
            20                  25                  30

-continued

```
Leu Asn Trp Tyr Gln Gln Lys Pro Gly Lys Ala Pro Lys Leu Leu Ile
            35                  40                  45
Tyr Ala Ala Ser Ser Leu Lys Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Val Tyr Asp Thr Pro Leu
                85                  90                  95
Thr Phe Gly Cys Gly Thr Lys Val Glu Ile Lys Gly Gly Gly Gly Ser
            100                 105                 110
Gly Gly Gly Gly Ser Gly Gly Gly Ser Gly Gly Gly Gly Ser Glu
            115                 120                 125
Val Gln Leu Val Glu Ser Gly Gly Leu Val Gln Pro Gly Gly Ser
130                 135                 140
Leu Arg Leu Ser Cys Ala Ala Ser Gly Phe Thr Phe Ser Ser Tyr Trp
145                 150                 155                 160
Met Ser Trp Val Arg Gln Ala Pro Gly Lys Cys Leu Glu Trp Val Ala
            165                 170                 175
Asn Ile Asn Thr Asp Gly Ser Glu Val Tyr Tyr Val Asp Ser Val Lys
            180                 185                 190
Gly Arg Phe Thr Ile Ser Arg Asp Asn Ala Lys Asn Ser Leu Tyr Leu
            195                 200                 205
Gln Met Asn Ser Leu Arg Ala Glu Asp Thr Ala Val Tyr Tyr Cys Ala
            210                 215                 220
Arg Asp Val Gly Pro Gly Ile Ala Tyr Gln Gly His Phe Asp Tyr Trp
225                 230                 235                 240
Gly Gln Gly Thr Leu Val Thr Val Ser Ser Ala Ser Asp Lys Thr His
            245                 250                 255
Thr Cys Pro Pro Cys Pro Ala Pro Glu Leu Leu Gly Gly Pro Ser Val
            260                 265                 270
Phe Leu Phe Pro Pro Lys Pro Lys Asp Thr Leu Met Ile Ser Arg Thr
            275                 280                 285
Pro Glu Val Thr Cys Val Val Val Asp Val Ser His Glu Asp Pro Glu
            290                 295                 300
Val Lys Phe Asn Trp Tyr Val Asp Gly Val Glu Val His Asn Ala Lys
305                 310                 315                 320
Thr Lys Pro Arg Glu Glu Gln Tyr Asn Ser Thr Tyr Arg Val Val Ser
            325                 330                 335
Val Leu Thr Val Leu His Gln Asp Trp Leu Asn Gly Lys Glu Tyr Lys
            340                 345                 350
Cys Lys Val Ser Asn Lys Ala Leu Pro Ala Pro Ile Glu Lys Thr Ile
            355                 360                 365
Ser Lys Ala Lys Gly Gln Pro Arg Glu Pro Arg Val Tyr Thr Leu Pro
370                 375                 380
Pro Cys Arg Asp Glu Leu Thr Lys Asn Gln Val Ser Leu Thr Cys Leu
385                 390                 395                 400
Val Lys Gly Phe Tyr Pro Ser Asp Ile Ala Val Glu Trp Glu Ser Asn
            405                 410                 415
Gly Gln Pro Glu Asn Asn Tyr Lys Thr Thr Pro Val Leu Val Ser
            420                 425                 430
Asp Gly Ser Phe Thr Leu Tyr Ser Lys Leu Thr Val Asp Lys Ser Arg
            435                 440                 445
Trp Gln Gln Gly Asn Val Phe Ser Cys Ser Val Met His Glu Ala Leu
```

His Asn His Tyr Thr Gln Lys Ser Leu Ser Leu Ser Pro Gly
465                 470                 475

<210> SEQ ID NO 239
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Thr Asp Gly Ser Glu Val Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Val Ile Tyr Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Lys Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Val Tyr Asp Thr Pro Leu Thr
225                 230                 235                 240

Phe Gly Cys Gly Thr Lys Val Glu Ile Lys Ala Ser Asp Lys Thr His
                245                 250                 255

Thr Cys Pro Pro Cys Pro Ala Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Arg Val Tyr Thr Leu Pro
    370                 375                 380

Pro Cys Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Val Ser
            420                 425                 430

Asp Gly Ser Phe Thr Leu Tyr Ser Lys Leu Thr Val Asp Lys Ser Arg
            435                 440                 445

Trp Gln Gln Gly Asn Val Phe Ser Cys Ser Val Met His Glu Ala Leu
            450                 455                 460

His Asn His Tyr Thr Gln Lys Ser Leu Ser Leu Ser Pro Gly
465                 470                 475

<210> SEQ ID NO 240
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Ile Val Leu Thr Gln Ser Pro Ala Thr Leu Ser Leu Ser Pro Gly
1               5                   10                  15

Glu Arg Ala Thr Leu Ser Cys Arg Ala Ser His Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Asn Leu Pro Thr
                85                  90                  95

Phe Gly Cys Gly Thr Lys Val Glu Ile Lys Gly Gly Gly Gly Ser Gly
            100                 105                 110

Gly Gly Gly Ser Gly Gly Gly Ser Gly Gly Gly Ser Gln Leu
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ser Ser Thr Asp Tyr
145                 150                 155                 160

Tyr Trp Gly Trp Ile Arg Gln Pro Pro Gly Lys Cys Leu Glu Trp Ile
                165                 170                 175

Gly Ser Ile Gly Tyr Ser Gly Thr Tyr Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

-continued

Glu Thr Ala His Asp Val His Gly Met Asp Val Trp Gly Gln Gly Thr
225                 230                 235                 240

Thr Val Thr Val Ser Ser Ala Ser Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
        340                 345                 350

Asn Lys Ala Leu Pro Ala Pro Ile Glu Lys Thr Ile Ser Lys Ala Lys
    355                 360                 365

Gly Gln Pro Arg Glu Pro Arg Val Tyr Thr Leu Pro Pro Cys Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Val Ser Asp Gly Ser Phe
        420                 425                 430

Thr Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
450                 455                 460

Thr Gln Lys Ser Leu Ser Leu Ser Pro Gly
465                 470

<210> SEQ ID NO 241
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Asp Tyr Tyr Trp Gly Trp Ile Arg Gln Pro Pro Gly Lys Cys Leu Glu
        35                  40                  45

Trp Ile Gly Ser Ile Gly Tyr Ser Gly Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Thr Ala His Asp Val His Gly Met Asp Val Trp Gly Gln

```
            100                 105                 110
Gly Thr Thr Val Thr Val Ser Ser Gly Gly Gly Ser Gly Gly Gly
            115                 120                 125

Gly Ser Gly Gly Gly Ser Gly Gly Gly Ser Glu Ile Val Leu
        130                 135             140

Thr Gln Ser Pro Ala Thr Leu Ser Leu Ser Pro Gly Glu Arg Ala Thr
145                 150                 155                 160

Leu Ser Cys Arg Ala Ser His Ser Val Tyr Ser Tyr Leu Ala Trp Tyr
                165                 170                 175

Gln Gln Lys Pro Gly Gln Ala Pro Arg Leu Leu Ile Tyr Asp Ala Ser
            180                 185                 190

Asn Arg Ala Thr Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
210                 215                 220

Val Tyr Tyr Cys Gln Gln Tyr Asp Asn Leu Pro Thr Phe Gly Cys Gly
225                 230                 235                 240

Thr Lys Val Glu Ile Lys Ala Ser Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Arg Val Tyr Thr Leu Pro Pro Cys Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Val Ser Asp Gly Ser Phe
            420                 425                 430

Thr Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
450                 455                 460

Thr Gln Lys Ser Leu Ser Leu Ser Pro Gly
465                 470
```

<210> SEQ ID NO 242
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 242

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Ser Gln Ser Tyr Pro Pro
                85                  90                  95

Ile Thr Phe Gly Cys Gly Thr Lys Val Glu Ile Lys Gly Gly Gly Gly
            100                 105                 110

Ser Gly Gly Gly Gly Ser Gly Gly Gly Ser Gly Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Gly Ser Tyr
145                 150                 155                 160

Trp Met Ser Trp Val Arg Gln Ala Pro Gly Lys Cys Leu Glu Trp Val
                165                 170                 175

Ala Thr Ile Lys Gln Asp Gly Ser Glu Lys Ser Tyr Val Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Pro Leu Asn Ala Gly Glu Leu Asp Val Trp Gly Gln Gly Thr
225                 230                 235                 240

Met Val Thr Val Ser Ser Ala Ser Thr Lys Gly Pro Ser Val Phe Pro
                245                 250                 255

Leu Ala Pro Ser Ser Lys Ser Thr Ser Gly Gly Thr Ala Ala Leu Gly
            260                 265                 270

Cys Leu Val Lys Asp Tyr Phe Pro Glu Pro Val Thr Val Ser Trp Asn
        275                 280                 285

Ser Gly Ala Leu Thr Ser Gly Val His Thr Phe Pro Ala Val Leu Gln
    290                 295                 300

Ser Ser Gly Leu Tyr Ser Leu Ser Ser Val Val Thr Val Pro Ser Ser
305                 310                 315                 320

Ser Leu Gly Thr Gln Thr Tyr Ile Cys Asn Val Asn His Lys Pro Ser
                325                 330                 335

Asn Thr Lys Val Asp Lys Lys Val Glu Pro Lys Ser Cys Asp Lys Thr
            340                 345                 350

His Thr Cys Pro Pro Cys Pro Ala Pro Glu Leu Leu Gly Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
```

```
                    405                 410                 415
Lys Thr Lys Pro Arg Glu Glu Gln Tyr Asn Ser Thr Tyr Arg Val Val
            420                 425                 430

Ser Val Leu Thr Val Leu His Gln Asp Trp Leu Asn Gly Lys Glu Tyr
            435                 440                 445

Lys Cys Lys Val Ser Asn Lys Ala Leu Pro Ala Pro Ile Glu Lys Thr
            450                 455                 460

Ile Ser Lys Ala Lys Gly Gln Pro Arg Glu Pro Gln Val Cys Thr Leu
465                 470                 475                 480

Pro Pro Ser Arg Asp Glu Leu Thr Glu Asn Gln Val Ser Leu Thr Cys
            485                 490                 495

Leu Val Lys Gly Phe Tyr Pro Ser Asp Ile Ala Val Glu Trp Glu Ser
            500                 505                 510

Asn Gly Gln Pro Glu Asn Asn Tyr Lys Thr Thr Pro Pro Val Leu Asp
            515                 520                 525

Ser Asp Gly Ser Phe Phe Leu Tyr Ser Trp Leu Thr Val Asp Lys Ser
            530                 535                 540

Arg Trp Gln Gln Gly Asn Val Phe Ser Cys Ser Val Met His Glu Ala
545                 550                 555                 560

Leu His Asn His Tyr Thr Gln Lys Ser Leu Ser Leu Ser Pro Gly
            565                 570                 575
```

<210> SEQ ID NO 243
<211> LENGTH: 583
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Asp Leu Pro Thr
            85                  90                  95

Phe Gly Cys Gly Thr Lys Val Glu Ile Lys Gly Gly Gly Gly Ser Gly
            100                 105                 110

Gly Gly Gly Ser Gly Gly Gly Gly Ser Gly Gly Gly Gly Ser Glu Val
            115                 120                 125

Gln Leu Leu Glu Ser Gly Gly Gly Leu Val Gln Pro Gly Gly Ser Leu
            130                 135                 140

Arg Leu Ser Cys Ala Ala Ser Gly Phe Thr Phe Ser Lys Tyr Thr Met
145                 150                 155                 160

Ser Trp Val Arg Gln Ala Pro Gly Lys Cys Leu Glu Trp Val Ser Ala
            165                 170                 175

Ile Val Gly Ser Gly Glu Ser Thr Tyr Phe Ala Asp Ser Val Lys Gly
            180                 185                 190
```

Arg Phe Thr Ile Ser Arg Asp Asn Ser Lys Asn Thr Leu Tyr Leu Gln
            195                 200                 205

Met Asn Ser Leu Arg Ala Glu Asp Thr Ala Val Tyr Tyr Cys Ala Arg
210                 215                 220

Glu Gly Gly Pro Tyr Tyr Asp Ser Ser Gly Tyr Phe Val Tyr Tyr Gly
225                 230                 235                 240

Met Asp Val Trp Gly Gln Gly Thr Thr Val Thr Val Ser Ser Ala Ser
                245                 250                 255

Thr Lys Gly Pro Ser Val Phe Pro Leu Ala Pro Ser Ser Lys Ser Thr
            260                 265                 270

Ser Gly Gly Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Gln Thr Tyr Ile
                325                 330                 335

Cys Asn Val Asn His Lys Pro Ser Asn Thr Lys Val Asp Lys Lys Val
            340                 345                 350

Glu Pro Lys Ser Cys Asp Lys Thr His Thr Cys Pro Pro Cys Pro Ala
        355                 360                 365

Pro Glu Leu Leu Gly Gly Pro Ser Val Phe Leu Phe Pro Pro Lys Pro
370                 375                 380

Lys Asp Thr Leu Met Ile Ser Arg Thr Pro Glu Val Thr Cys Val Val
385                 390                 395                 400

Val Asp Val Ser His Glu Asp Pro Glu Val Lys Phe Asn Trp Tyr Val
                405                 410                 415

Asp Gly Val Glu Val His Asn Ala Lys Thr Lys Pro Arg Glu Glu Gln
            420                 425                 430

Tyr Asn Ser Thr Tyr Arg Val Val Ser Val Leu Thr Val Leu His Gln
        435                 440                 445

Asp Trp Leu Asn Gly Lys Glu Tyr Lys Cys Lys Val Ser Asn Lys Ala
450                 455                 460

Leu Pro Ala Pro Ile Glu Lys Thr Ile Ser Lys Ala Lys Gly Gln Pro
465                 470                 475                 480

Arg Glu Pro Gln Val Cys Thr Leu Pro Pro Ser Arg Asp Glu Leu Thr
                485                 490                 495

Glu Asn Gln Val Ser Leu Thr Cys Leu Val Lys Gly Phe Tyr Pro Ser
            500                 505                 510

Asp Ile Ala Val Glu Trp Glu Ser Asn Gly Gln Pro Glu Asn Asn Tyr
        515                 520                 525

Lys Thr Thr Pro Pro Val Leu Asp Ser Asp Gly Ser Phe Phe Leu Tyr
530                 535                 540

Ser Trp Leu Thr Val Asp Lys Ser Arg Trp Gln Gln Gly Asn Val Phe
545                 550                 555                 560

Ser Cys Ser Val Met His Glu Ala Leu His Asn His Tyr Thr Gln Lys
                565                 570                 575

Ser Leu Ser Leu Ser Pro Gly
            580

<210> SEQ ID NO 244
<211> LENGTH: 347
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 244

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser Ala Ser Asp Lys Thr His
        115                 120                 125

Thr Cys Pro Pro Cys Pro Ala Pro Glu Leu Leu Gly Gly Pro Ser Val
130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Arg Val Tyr Thr Leu Pro
                245                 250                 255

Pro Cys Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Val Ser
290                 295                 300

Asp Gly Ser Phe Thr Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu
            340                 345

<210> SEQ ID NO 245
<211> LENGTH: 347
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 245

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser Ala Ser Asp Lys Thr His
        115                 120                 125

Thr Cys Pro Pro Cys Pro Ala Pro Glu Leu Leu Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser His Glu Asp Pro Glu
                165                 170                 175

Val Lys Phe Asn Trp Tyr Val Asp Gly Val Glu Val His Asn Ala Lys
            180                 185                 190

Thr Lys Pro Arg Glu Glu Gln Tyr Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Ala Leu Pro Ala Pro Ile Glu Lys Thr Ile
225                 230                 235                 240

Ser Lys Ala Lys Gly Gln Pro Arg Glu Pro Arg Val Tyr Thr Leu Pro
                245                 250                 255

Pro Cys Arg Asp Glu Leu Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Val Ser
    290                 295                 300

Asp Gly Ser Phe Thr Leu Tyr Ser Lys Leu Thr Val Asp Lys Ser Arg
305                 310                 315                 320

Trp Gln Gln Gly Asn Val Phe Ser Cys Ser Val Met His Glu Ala Leu
                325                 330                 335

His Asn His Tyr Thr Gln Lys Ser Leu Ser Leu
            340                 345
```

<210> SEQ ID NO 246
<211> LENGTH: 762
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 246

```
gacatccaga tgacccagag ccccagcacc ctgagcgcca gcgtgggcga cagggtgacc      60
atcacctgca gggccagcca gagcatcagc agctggctgg cctggtacca gcagaagccc     120
ggcaaggccc ccaagctgct gatctacgac gccagcagcc tggagagcgg cgtgcccagc     180
aggttcagcg gcagcggcag cggcaccgag ttcaccctga ccatcagcag cctgcagccc     240
gacgacttcg ccacctacta ctgccagcag tacgagagct cccccacctt cggctgcggc     300
accaaggtgg agatcaaggg cggcggcggc agcggcggcg gcggcagcgg cggcggcggc     360
agcggcggcg gcggcagcga ggtgcagctg gtggagagcg gcggcggcct ggtgcagccc     420
ggcggcagcc tgaggctgag ctgcgccgcc agcggcttca ccttcagcag ctacggcatg     480
agctgggtga ggcaggcccc cggcaagtgc ctggagtggg tggccaacat caagcaggac     540
ggcagcgaga agtactacgt ggacagcgtg aagggcaggt tcaccatcag cagggacaac     600
gccaagaaca gcctgtacct gcagatgaac agcctgaggg ccgaggacac cgccgtgtac     660
tactgcgcca gggagggcgg ccccctactac gacagcagcg gctacttcgt gtactacggc     720
atggacgtgt ggggccaggg caccaccgtg accgtgagca gc                        762
```

<210> SEQ ID NO 247
<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 247

```
gaggtgcagc tggtggagag cggcggcggc ctggtgcagc ccggcggcag cctgaggctg      60
agctgcgccg ccagcggctt caccttcagc agctacggca tgagctgggt gaggcaggcc     120
cccggcaagt gcctggagtg gtggccaac atcaagcagg acggcagcga gaagtactac      180
gtggacagcg tgaagggcag gttcaccatc agcagggaca acgccaagaa cagcctgtac     240
ctgcagatga acagcctgag ggccgaggac accgccgtgt actactgcgc cagggagggc     300 ggccccctact acgacagcag cggctacttc gtgtactacg gcatggacgt gtggggccag     360
ggcaccaccg tgaccgtgag cagcggcggc ggcggcagcg gcggcggcgg cagcggcggc     420
ggcggcagcg gcggcggcgg cagcgacatc cagatgaccc agagcccag caccctgagc     480 gccagcgtgg gcgacagggt gaccatcacc tgcagggcca gcagcatcag cagctggctg     540
gcctggtacc agcagaaacc cggcaaggcc cccaagctgc tgatctacga cgccagcagc     600
agcctggaga gcggcgtgcc cagcaggttc agcggcagcg gcagcggcac cgagttcacc     660
ctgaccatca gcagcctgca gcccgacgac ttcgccacct actactgcca gcagtacgag     720 agcttccccca ccttcggctg cggcaccaag gtggagatca ag                        762
```

<210> SEQ ID NO 248
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 248

```
gacatccaga tgacccagag ccccagcacc ctgagcgcca gcgtgggcga cagggtgacc      60
```

| | | |
|---|---|---|
| atcacctgca gggccagcca gagcatcagc agctggctgg cctggtacca gcagaagccc | | 120 |
| ggcaaggccc ccaagctgct gatctacgag gccagcagcc tggagagcgg cgtgcccagc | | 180 |
| aggttcagcg gcagcggcag cggcaccgag ttcaccctga ccatcagcag cctgcagccc | | 240 |
| gacgacttcg ccacctacta ctgccagcag ctggagagct accccctgac cttcggctgc | | 300 |
| ggcaccaagg tggagatcaa gggcggcggc ggcagcggcg gcggcggcag cggcggcggc | | 360 |
| ggcagcggcg gcggcggcag cgaggtgcag ctggtggaga gcggcggcgg cctggtgcag | | 420 |
| cccggcggca gcctgaggct gagctgcgcc gccagcggct tcaccttcag cagctactgg | | 480 |
| atgagctggg tgaggcaggc ccccggcaag tgcctggagt gggtggccaa catcaagcag | | 540 |
| gacggcagcg agaagtacta cgtggacagc gtgaagggca ggttcaccat cagcagggac | | 600 |
| aacgccaaga cagcctgta cctgcagatg aacagcctga ggccgagga caccgccgtg | | 660 |
| tactactgcg ccaggcccct gaacgccggc gagctggacg tgtggggcca gggcaccatg | | 720 |
| gtgaccgtga gcagc | | 735 |

<210> SEQ ID NO 249
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249

| | | |
|---|---|---|
| gaggtgcagc tggtggagag cggcggcggc ctggtgcagc ccggcggcag cctgaggctg | | 60 |
| agctgcgccg ccagcggctt caccttcagc agctactgga tgagctgggt gaggcaggcc | | 120 |
| cccggcaagt gcctggagtg ggtggccaac atcaagcagg acggcagcga gaagtactac | | 180 |
| gtggacagcg tgaagggcag gttcaccatc agcagggaca acgccaagaa cagcctgtac | | 240 |
| ctgcagatga acagcctgag gccgaggac accgccgtgt actactgcgc caggcccctg | | 300 |
| aacgccggcg agctggacgt gtggggccag ggcaccatgt gaccgtgag cagcggcggc | | 360 |
| ggcggcagcg gcggcggcgg cagcggcggc ggcggcagcg gcggcggcgg cagcgacatc | | 420 |
| cagatgaccc agagccccag caccctgagc gccagcgtgg gcgacagggt gaccatcacc | | 480 |
| tgcagggcca gcagagcat cagcagctgg ctggcctggt accagcagaa gcccggcaag | | 540 |
| gcccccaagc tgctgatcta cgaggccagc agcctggaga gcggcgtgcc cagcaggttc | | 600 |
| agcggcagcg gcagcggcac cgagttcacc ctgaccatca gcagcctgca gcccgacgac | | 660 |
| ttcgccacct actactgcca gcagctggag agctaccccc tgaccttcgg ctgcggcacc | | 720 |
| aaggtggaga tcaag | | 735 |

<210> SEQ ID NO 250
<211> LENGTH: 762
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 250

| | | |
|---|---|---|
| gacatccaga tgacccagag ccccagcacc ctgagcgcca gcgtgggcga cagggtgacc | | 60 |
| atcacctgca gggccagcca gagcatcagc agctggctgg cctggtacca gcagaagccc | | 120 |
| ggcaaggccc ccaagctgct gatctacaag gccagcagcc tggagagcgg cgtgcccagc | | 180 |
| aggttcagcg gcagcggcag cggcaccgag ttcaccctga ccatcagcag cctgcagccc | | 240 |

```
gacgacttcg ccacctacta ctgccagcag tacgacgacc tgcccacctt cggctgcggc    300
accaaggtgg agatcaaggg cggcggcggc agcggcggcg gcggcagcgg cggcggcggc    360
agcggcggcg gcggcagcga ggtgcagctg ctggagagcg gcggcggcct ggtgcagccc    420
ggcggcagcc tgaggctgag ctgcgccgcc agcggcttca ccttcagcaa gtacaccatg    480
agctgggtga ggcaggcccc cggcaagtgc ctggagtggg tgagcgccat cgtgggcagc    540
ggcgagagca cctacttcgc cgacagcgtg aagggcaggt tcaccatcag cagggacaac    600
agcaagaaca ccctgtacct gcagatgaac agcctgaggg ccgaggacac cgccgtgtac    660
tactgcgcca gggagggcgg ccctactac gacagcagcg gctacttcgt gtactacggc    720
atggacgtgt ggggccaggg caccaccgtg accgtgagca gc                       762
```

```
<210> SEQ ID NO 251
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 251
```

```
gaggtgcagc tgctggagag cggcggcggc ctggtgcagc ccggcggcag cctgaggctg     60
agctgcgccg ccagcggctt caccttcagc aagtacacca tgagctgggt gaggcaggcc    120
cccggcaagt gcctggagtg ggtgagcgcc atcgtgggca gcggcgagag cacctacttc    180
gccgacagcg tgaagggcag gttcaccatc agcagggaca cagcaagaa cacccctgtac    240 ctgcagatga acagcctgag ggccgaggac accgccgtgt actactgcgc cagggagggc    300
ggcccctact acgacagcag cggctacttc gtgtactacg gcatggacgt gtggggccag    360
ggcaccaccg tgaccgtgag cagcggcggc ggcggcagcg gcggcggcgg cagcggcggc    420
ggcggcagcg gcggcggcgg cagcgacatc cagatgaccc agagcccag cccctgagc     480 gccagcgtgg gcgacagggt gaccatcacc tgcagggcca gcagcat cagcagctgg     540 ctggcctggt accagcagaa gcccggcaag gcccccaagc tgctgatcta caaggccagc    600
agcctggaga gcggcgtgcc cagcaggttc agcggcagcg gcagcggcac cgagttcacc    660
ctgaccatca gcagcctgca gcccgacgac ttcgccacct actactgcca gcagtacgac    720
gacctgccca ccttcggctg cggcaccaag gtggagatca ag                       762
```

```
<210> SEQ ID NO 252
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
```

```
gacatcgtga tgacccagag cccctgagc ctgcccgtga ccccggcga gccgccagc       60 atcagctgca ggagcagcca gagcctgctg tacagcaacg gctacaacta cctggactgg    120
tacctgcaga agcccggcca gagccccag ctgctgatct acctgggcag caacagggcc    180
agcggcgtgc ccgacaggtt cagcggcagc ggcagcggca ccgacttcac cctgaagatc    240
agcagggtgg aggccgagga cgtgggcgtg tactactgca tgcaggacgt ggccctgccc    300
atcaccttcg gctgcggcac caaggtggag atcaagggcg gcggcggcag cggcggcggc    360
```

| | |
|---|---|
| ggcagcggcg gcggcggcag cggcggcggc ggcagccagg tgcagctggt gcagagcggc | 420 |
| gccgaggtga agaagcccgg cgccagcgtg aaggtgagct gcaaggccag cggctacacc | 480 |
| ttcagcgact actacatgca ctgggtgagg caggcccccg gccagtgcct ggagtggatg | 540 |
| ggcatgatca accccagctg gggcagcacc agctacgccc agaagttcca gggcagggtg | 600 |
| accatgacca gggacaccag caccagcacc gtgtacatgg agctgagcag cctgaggagc | 660 |
| gaggacaccg ccgtgtacta ctgcgccagg gaggccgccg acggcttcgt gggcgagagg | 720 |
| tacttcgacc tgtggggcag ggcaccctg gtgaccgtga gcagc | 765 |

<210> SEQ ID NO 253
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 253

| | |
|---|---|
| caggtgcagc tggtgcagag cggcgccgag gtgaagaagc ccggcgccag cgtgaaggtg | 60 |
| agctgcaagg ccagcggcta caccttcagc gactactaca tgcactgggt gaggcaggcc | 120 |
| cccggccagt gcctggagtg gatgggcatg atcaaccca gctggggcag caccagctac | 180 |
| gcccagaagt tccagggcag ggtgaccatg accagggaca ccagcaccag caccgtgtac | 240 |
| atggagctga gcagcctgag gagcgaggac accgccgtgt actactgcgc cagggaggcc | 300 |
| gccgacggct tcgtgggcga gaggtacttc gacctgtggg gcaggggcac cctggtgacc | 360 |
| gtgagcagcg cggcggcgg cagcggcggc ggcggcagcg cggcggcgg cagcggcggc | 420 |
| ggcggcagcg acatcgtgat gacccagagc cccctgagcc tgcccgtgac ccccggcgag | 480 |
| cccgccagca tcagctgcag gagcagccag agcctgctgt acagcaacgg ctacaactac | 540 |
| ctggactggt acctgcagaa gcccggccag agccccagc tgctgatcta cctgggcagc | 600 |
| aacagggcca gcggcgtgcc cgacaggttc agcggcagcg gcagcggcac cgacttcacc | 660 |
| ctgaagatca gcagggtgga ggccgaggac gtgggcgtgt actactgcat gcaggacgtg | 720 |
| gccctgccca tcaccttcgg ctgcggcacc aaggtggaga tcaag | 765 |

<210> SEQ ID NO 254
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 254

| | |
|---|---|
| gacatccaga tgacccagag ccccagcacc ctgagcgcca gcgtgggcga cagggtgacc | 60 |
| atcacctgca gggccagcca gagcatcagc agctggctgg cctggtacca gcagaagccc | 120 |
| ggcaaggccc ccaagctgct gatctacgag gccagcagcc tggagagcgg cgtgcccagc | 180 |
| aggttcagcg gcagcggcag cggcaccgag ttcaccctga ccatcagcag cctgcagccc | 240 |
| gacgacttcg ccacctacta ctgccagcag agccagagct acccccccat caccttcggc | 300 |
| tgcggcacca aggtggagat caagggcggc ggcggcagcg gcggcggcgg cagcggcggc | 360 |
| ggcggcagcg gcggcggcgg cagcgaggtg cagctggtgg agagcggcgg cggcctggtg | 420 |
| cagcccggcg gcagcctgag gctgagctgc gccgccagcg gcttcacctt cggcagctac | 480 |
| tggatgagct gggtgaggca ggccccggc aagtgcctgg agtgggtggc caccatcaag | 540 |

```
caggacggca gcgagaagag ctacgtggac agcgtgaagg gcaggttcac catcagcagg    600
gacaacgcca agaacagcct gtacctgcag atgaacagcc tgagggccga ggacaccgcc    660
gtgtactact gcgccaggcc cctgaacgcc ggcgagctgg acgtgtgggg ccagggcacc    720
atggtgaccg tgagcagc                                                  738
```

<210> SEQ ID NO 255
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 255

```
gaggtgcagc tggtggagag cggcggcggc ctggtgcagc ccggcggcag cctgaggctg     60
agctgcgccg ccagcggctt caccttcggc agctactgga tgagctgggt gaggcaggcc    120
cccggcaagt gcctggagtg ggtggccacc atcaagcagg acggcagcga aagagctac    180 gtggacagcg tgaagggcag gttcaccatc agcaggaca cgccaagaa cagcctgtac    240 ctgcagatga cagcctgag ggccgaggac accgccgtgt actactgcgc caggcccctg    300
aacgccggcg agctggacgt gtggggccag ggcaccatgg tgaccgtgag cagcggcggc    360
ggcggcagcg gcggcggcgg cagcggcggc ggcggcagcg gcggcggcgg cagcgacatc    420
cagatgaccc agagccccag caccctgagc gccagcgtgg gcgacagggt gaccatcacc    480
tgcagggcca gcagagcat cagcagctgg ctggcctggt accagcagaa gcccggcaag    540
gcccccaagc tgctgatcta cgaggccagc agcctggaga gcggcgtgcc cagcaggttc    600
agcggcagcg gcagcggcac cgagttcacc ctgaccatca gcagcctgca gcccgacgac    660
ttcgccacct actactgcca gcagagccag agctaccccc ccatcacctt cggctgcggc    720
accaaggtgg agatcaag                                                  738
```

<210> SEQ ID NO 256
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256

```
gacatccaga tgacccagag ccccagcacc ctgagcgcca gcgtgggcga cagggtgacc     60
atcacctgca gggccagcca gagcatcagc agctggctgg cctggtacca gcagaagccc    120
ggcaaggccc ccaagctgct gatctacgag gccagcagcc tggagagcgg cgtgcccagc    180
aggttcagcg gcagcggcag cggcaccgag ttcaccctga ccatcagcag cctgcagccc    240
gacgacttcg ccacctacta ctgccagcag agccagagct accccccccat cacccttcggc    300 tgcggcacca aggtggagat caagggcggc ggcggcagcg gcggcggcgg cagcggcggc    360
ggcggcagcg gcggcggcgg cagcgaggtg cagctggtgg agagcggcgg cggcctggtg    420
cagcccggcg gcagcctgag gctgagctgc gccgccagcg gcttcacctt ccccagctac    480
tggatgagct gggtgaggca ggcccccggc aagtgcctgg agtgggtggc caccatcaag    540
agggacggca gcgagaaggg ctacgtggac agcgtgaagg gcaggttcac catcagcagg    600
gacaacgcca agaacagcct gtacctgcag atgaacagcc tgagggccga ggacaccgcc    660
```

```
gtgtactact gcgccaggcc cctgaacgcc ggcgagctgg acgtgtgggg ccagggcacc    720
atggtgaccg tgagcagc                                                  738

<210> SEQ ID NO 257
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 257
gaggtgcagc tggtggagag cggcggcggc ctggtgcagc ccggcggcag cctgaggctg     60
agctgcgccg ccagcggctt caccttcccc agctactgga tgagctgggt gaggcaggcc    120
cccggcaagt gcctggagtg ggtggccacc atcaagaggg acggcagcga aagggctac     180 gtggacagcg tgaagggcag gttcaccatc agcagggaca cgccaagaa cagcctgtac    240 ctgcagatga acagcctgag ggccgaggac accgccgtgt actactgcgc caggcccctg    300
aacgccggcg agctggacgt gtggggccag ggcaccatgg tgaccgtgag cagcgccggc    360
ggcggcagcg gcggcggcgg cagcggcggc ggcggcagcg gcggcggcgg cagcgacatc    420
cagatgaccc agagccccag caccctgagc gccagcgtgg gcgacagggt gaccatcacc    480
tgcagggcca gcagagcat cagcagctgg ctggcctggt accagcagaa gcccggcaag    540
gcccccaagc tgctgatcta cgaggccagc agcctggaga gcggcgtgcc cagcaggttc    600
agcggcagcg gcagcggcac cgagttcacc ctgaccatca gcagcctgca gcccgacgac    660
ttcgccacct actactgcca gcagagccag agctacccc catcaccttt cggctgcggc    720
accaaggtgg agatcaag                                                  738

<210> SEQ ID NO 258
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
gacatccaga tgacccagag ccccagcagc gtgagcgcca gcgtgggcga cagggtgacc     60
atcacctgca gggccagcca gggcatcgac agctggctgg cctggtacca gcagaagccc    120
ggcaaggccc ccaagctgct gatctacgcc gccagcagcc tgcagagcgg cgtgcccagc    180
aggttcagcg gcagcggcag cggcaccgac ttcaccctga ccatcagcag cctgcagccc    240
gaggacttcg ccacctacta ctgccagcag gcccacagct accccctgac cttcggctgc    300
ggcaccaagg tggagatcaa gggcggcggc ggcagcggcg gcggcggcag cggcggcggc    360
ggcagcggcg gcggcggcag ccaggtgcag ctggtgcaga gcggcgccga ggtgaagaag    420
cccggcgcca gcgtgaaggt gagctgcaag gccagcggct acaccttcgg cacctactac    480
atgcactggg tgaggcaggc ccccggccag tgcctggagt ggatgggcat catcaacccc    540 agcagggca gcaccgtgta cgcccagaag ttccagggca gggtgaccat gaccagggac    600
accagcacca gcaccgtgta catggagctg agcagcctga ggagcgagga caccgccgtg    660
tactactgcg ccaggggcgc cggctacgac gacgaggaca tggacgtgtg gggcaagggc    720
accaccgtga ccgtgagcag c                                              741
```

-continued

```
<210> SEQ ID NO 259
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 259
caggtgcagc tggtgcagag cggcgccgag gtgaagaagc ccggcgccag cgtgaaggtg     60
agctgcaagg ccagcggcta caccttcggc acctactaca tgcactgggt gaggcaggcc    120
cccggccagt gcctggagtg gatgggcatc atcaaccccc agcggggcag caccgtgtac    180
gcccagaagt tccagggcag ggtgaccatg accagggaca ccagcaccag caccgtgtac    240
atggagctga gcagcctgag gagcgaggac accgccgtgt actactgcgc caggggcgcc    300
ggctacgacg acgaggacat ggacgtgtgg ggcaagggcc caccgtgac cgtgagcagc     360 ggcggcggcg gcagcggcgg cggcggcagc ggcggcggcg gcagcggcgg cggcggcagc    420
gacatccaga tgacccagag ccccagcagc gtgagcgcca gcgtgggcga cagggtgacc    480
atcacctgca gggccagcca gggcatcgac agctggctgg cctggtacca gcagaagccc    540
ggcaaggccc ccaagctgct gatctacgcc gccagcagcc tgcagagcgg cgtgcccagc    600
aggttcagcg gcagcggcag cggcaccgac ttcaccctga ccatcagcag cctgcagccc    660
gaggacttcg ccacctacta ctgccagcag gcccacagct accccctgac cttcggctgc    720
ggcaccaagg tggagatcaa g                                              741

<210> SEQ ID NO 260
<211> LENGTH: 762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
gacatccaga tgacccagag ccccagcacc ctgagcgcca gcgtgggcga cagggtgacc     60
atcacctgca gggccagcaa cagcatcagc agctggctgg cctggtacca gcagaagccc    120
ggcaaggccc ccaagctgct gatctacgag gccagcagca ccaagagcgg cgtgcccagc    180
aggttcagcg gcagcggcag cggcaccgag ttcaccctga ccatcagcag cctgcagccc    240
gacgacttcg ccacctacta ctgccagcag tacgacgacc tgcccacctt cggctgcggc    300
accaaggtgg agatcaaggg cggcggcggc agcggcggcg gcggcagcgg cggcggcggc    360
agcggcggcg gcggcagcga ggtgcagctg gtggagagcg gcggcggcct ggtgaagccc    420
ggcggcagcc tgaggctgag ctgcgccgcc agcggcttca ccttcagcag ctacgccatg    480
agctgggtga ggcaggcccc cggcaagtgc ctggagtggg tgagcagcat cagcagcagc    540
agcgagggca tctactacgc cgacagcgtg aagggcaggt tcaccatcag cagggacaac    600
gccaagaaca gcctgtacct gcagatgaac agcctgaggg ccgaggacac cgccgtgtac    660
tactgcgcca ggggagggcgg cccctactac gacagcagcg gctacttcgt gtactacggc    720
atggacgtgt ggggccaggg caccaccgtg accgtgagca gc                       762

<210> SEQ ID NO 261
<211> LENGTH: 762
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 261

```
gaggtgcagc tggtggagag cggcggcggc ctggtgaagc ccggcggcag cctgaggctg      60
agctgcgccg ccagcggctt caccttcagc agctacgcca tgagctgggt gaggcaggcc     120
cccggcaagt gcctggagtg ggtgagcagc atcagcagca gcagcgaggg catctactac     180
gccgacagcg tgaagggcag gttcaccatc agcagggaca cgccaagaa cagcctgtac      240
ctgcagatga acagcctgag ggccgaggac accgccgtgt actactgcgc cagggagggc     300
ggcccctact acgacagcag cggctacttc gtgtactacg gcatggacgt gtggggccag     360
ggcaccaccg tgaccgtgag cagcggcggc ggcggcagcg gcggcggcgg cagcggcggc     420
ggcggcagcg gcggcggcgg cagcgacatc cagatgaccc agagcccag cccctgagc       480
gccagcgtgg gcgacagggt gaccatcacc tgcagggcca gcaacagcat cagcagctgg     540
ctggcctggt accagcagaa gcccggcaag gcccccaagc tgctgatcta cgaggccagc     600
agcaccaaga gcggcgtgcc cagcaggttc agcggcagcg gcagcggcac cgagttcacc     660
ctgaccatca gcagcctgca gcccgacgac ttcgccacct actactgcca gcagtacgac     720
gacctgccca ccttcggctg cggcaccaag gtggagatca ag                         762
```

<210> SEQ ID NO 262
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 262

```
gacatccaga tgacccagag ccccagcagc ctgagcgcca gcgtgggcga cagggtgacc      60
atcacctgca gggccagcca ggtgatctac agctacctga actggtacca gcagaagccc     120
ggcaaggccc ccaagctgct gatctacgcc gccagcagcc tgaagagcgg cgtgcccagc     180
aggttcagcg gcagcggcag cggcaccgac ttcaccctga ccatcagcag cctgcagccc     240
gaggacttcg ccacctacta ctgccagcag gtgtacgaca cccccctgac cttcggctgc     300
ggcaccaagg tggagatcaa gggcggcggc ggcagcggcg gcggcggcag cggcggcggc     360
ggcagcggcg gcggcggcag cgaggtgcag ctggtggaga gcggcggcgg cctggtgcag     420
cccggcggca gcctgaggct gagctgcgcc gccagcggct tcaccttcag cagctactgg     480
atgagctggg tgaggcaggc ccccggcaag tgcctggagt gggtggccaa catcaacacc     540
gacggcagcg aggtgtacta cgtggacagc gtgaagggca ggttcaccat cagcagggac     600
aacgccaaga acagcctgta cctgcagatg aacagcctga ggccgagga caccgccgtg     660
tactactgcg ccagggacgt gggccccggc atcgcctacc agggccactt cgactactgg     720
ggccagggca ccctggtgac cgtgagcagc                                        750
```

<210> SEQ ID NO 263
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 263

```
gaggtgcagc tggtggagag cggcggcggc ctggtgcagc ccggcggcag cctgaggctg    60
agctgcgccg ccagcggctt caccttcagc agctactgga tgagctgggt gaggcaggcc   120
cccggcaagt gcctggagtg ggtggccaac atcaacaccg acggcagcga ggtgtactac   180
gtggacagcg tgaagggcag gttcaccatc agcagggaca cgccaagaa cagcctgtac    240 ctgcagatga acagcctgag ggccgaggac accgccgtgt actactgcgc cagggacgtg   300
ggccccggca tcgcctacca gggccacttc gactactggg gccagggcac cctggtgacc   360
gtgagcagcg cggcggcgg cagcggcggc ggcgcagcg cggcggcgg cagcggcggc     420 ggcggcagcg acatccagat gacccagagc cccagcagcc tgagcgccag cgtgggcgac   480
agggtgacca tcacctgcag ggccagccag gtgatctaca gctacctgaa ctggtaccag   540
cagaagcccg gcaaggcccc caagctgctg atctacgccg ccagcagcct gaagagcggc   600
gtgcccagca ggttcagcgg cagcggcagc ggcaccgact cacccctgac catcagcagc   660
ctgcagcccg aggacttcgc cacctactac tgccagcagg tgtacgacac ccccctgacc   720
ttcggctgcg gcaccaaggt ggagatcaag                                    750
```

<210> SEQ ID NO 264
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 264

```
gagatcgtgc tgacccagag ccccgccacc ctgagcctga gccccggcga gagggccacc    60
ctgagctgca gggccagcca cagcgtgtac agctacctgg cctggtacca gcagaagccc   120
ggccaggccc ccaggctgct gatctacgac gccagcaaca gggccaccgg catccccgcc   180
aggttcagcg gcagcggcag cggcaccgac ttcaccctga ccatcagcag cctggagccc   240
gaggacttcg ccgtgtacta ctgccagcag tacgacaacc tgcccacctt cggctgcggc   300
accaaggtgg agatcaaggg cggcggcggc agcggcggcg gcggcagcgg cggcggcggc   360
agcggcggcg gcggcagcca gctgcagctg caggagagcg gccccggcct ggtgaagccc   420
agcgagaccc tgagcctgac ctgcaccgtg agcggcggca gcatcagcag caccgactac   480
tactggggct ggatcaggca gcccccggc aagtgcctgg agtggatcgg cagcatcggc   540
tacagcggca cctactacaa ccccagcctg aagagcaggg tgaccatcag cgtggacacc   600
agcaagaacc agttcagcct gaagctgagc agcgtgaccg ccgccgacac cgccgtgtac   660
tactgcgcca gggagaccgc ccacgacgtg cacggcatgg acgtgtgggg ccagggcacc   720
accgtgaccg tgagcagc                                                 738
```

<210> SEQ ID NO 265
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 265

```
cagctgcagc tgcaggagag cggccccggc ctggtgaagc ccagcgagac cctgagcctg    60
acctgcaccg tgagcggcgg cagcatcagc agcaccgact actactgggg ctggatcagg   120 cagcccccg gcaagtgcct ggagtggatc ggcagcatcg gctacagcgg cacctactac   180
```

```
aaccccagcc tgaagagcag ggtgaccatc agcgtggaca ccagcaagaa ccagttcagc      240
ctgaagctga gcagcgtgac cgccgccgac accgccgtgt actactgcgc cagggagacc      300
gcccacgacg tgcacggcat ggacgtgtgg ggccagggca ccaccgtgac cgtgagcagc      360
ggcggcggcg gcagcggcgg cggcggcagc ggcggcggcg gcagcggcgg cggcggcagc      420
gagatcgtgc tgacccagag ccccgccacc ctgagcctga gccccggcga gagggccacc      480
ctgagctgca gggccagcca gagcgtgtac agctacctgg cctggtacca gcagaagccc      540
ggccaggccc ccaggctgct gatctacgac gccagcaaca gggccaccgg catccccgcc      600
aggttcagcg gcagcggcag cggcaccgac ttcaccctga ccatcagcag cctggagccc      660
gaggacttcg ccgtgtacta ctgccagcag tacgacaacc tgcccacctt cggctgcggc      720
accaaggtgg agatcaag                                                   738
```

<210> SEQ ID NO 266
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ala Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ala Tyr Tyr Asp Ser Ser Gly Phe Lys Val Asn Tyr
            100                 105                 110

Gly Met Asp Val Trp Gly Gln Gly Thr Thr Val Thr Val Ser Ser
        115                 120                 125

<210> SEQ ID NO 267
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ser Ser Ser Pro
                85                  90                  95

Pro Thr Phe Gly Gly Gly Thr Lys Val Glu Ile Lys
            100                 105

<210> SEQ ID NO 268
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly His Ser Ser Ser Tyr Tyr Asp His Ala Phe Asp Ile
            100                 105                 110

Trp Gly Gln Gly Thr Met Val Thr Val Ser Ser
        115                 120

<210> SEQ ID NO 269
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln His Ser Ser Ala Pro
                85                  90                  95

Pro Thr Phe Gly Gly Gly Thr Lys Val Glu Ile Lys
            100                 105

<210> SEQ ID NO 270
<211> LENGTH: 123

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Ser Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Gly Val Tyr Ser Thr Ile Glu Thr Tyr Gly Met Asp Val
            100                 105                 110

Trp Gly Gln Gly Thr Thr Val Thr Val Ser Ser
        115                 120

<210> SEQ ID NO 271
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Val Tyr Pro Pro
                85                  90                  95

Thr Phe Gly Gly Gly Thr Lys Val Glu Ile Lys
            100                 105

<210> SEQ ID NO 272
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
                    20                  25                  30

Tyr Trp Ser Trp Ile Arg Gln Pro Pro Gly Lys Gly Leu Glu Trp Ile
                35                  40                  45

Gly Glu Ile Asp His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Gly Ile His Gly Leu Arg Tyr Phe Asp Leu Trp Gly Arg Gly
            100                 105                 110

Thr Leu Val Thr Val Ser Ser
            115

<210> SEQ ID NO 273
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Asp His Asn Phe Pro Tyr
                85                  90                  95

Thr Phe Gly Gly Gly Thr Lys Val Glu Ile Lys
            100                 105

<210> SEQ ID NO 274
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

-continued

```
                    85                  90                  95

Ala Arg Glu Ala Asn Tyr Tyr Gly Asn Val Gly Asp Asp Tyr Trp Gly
                100                 105                 110

Gln Gly Thr Leu Val Thr Val Ser Ser
            115                 120

<210> SEQ ID NO 275
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Tyr Val Thr Pro Ile
                85                  90                  95

Thr Phe Gly Gly Gly Thr Lys Val Glu Ile Lys
            100                 105

<210> SEQ ID NO 276
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Asp Ser Trp Tyr His Ala Phe Asp Ile Trp Gly
                100                 105                 110

Gln Gly Thr Met Val Thr Val Ser Ser
            115                 120

<210> SEQ ID NO 277
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 277

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Leu Ser Leu Pro Leu
                85                  90                  95

Thr Phe Gly Gly Gly Thr Lys Val Glu Ile Lys
            100                 105

<210> SEQ ID NO 278
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 278

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Leu Asp Tyr Ser Tyr Asn Tyr Gly Met Asp Val
            100                 105                 110

Trp Gly Gln Gly Thr Thr Val Thr Val Ser Ser
        115                 120

<210> SEQ ID NO 279
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 279

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

```
Leu Asn Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ala Pro Phe
                85                  90                  95

Thr Phe Gly Gly Gly Thr Lys Val Glu Ile Lys
            100                 105

<210> SEQ ID NO 280
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Pro Pro Trp Phe Gly Phe Ser Tyr Phe Asp Leu Trp Gly
            100                 105                 110

Arg Gly Thr Leu Val Thr Val Ser Ser
        115                 120

<210> SEQ ID NO 281
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Asp Asn Tyr Pro Pro
                85                  90                  95
```

Thr Phe Gly Gly Gly Thr Lys Val Glu Ile Lys
            100                 105

<210> SEQ ID NO 282
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser
        115                 120

<210> SEQ ID NO 283
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Gly Gly Thr Lys Val Glu Ile Lys
            100                 105

<210> SEQ ID NO 284
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Thr Ala His Asp Val His Gly Met Asp Val Trp Gly
            100                 105                 110

Gln Gly Thr Thr Val Thr Val Ser Ser
        115                 120

<210> SEQ ID NO 285
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 285

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Asn Leu Pro Thr
                85                  90                  95

Phe Gly Gly Gly Thr Lys Val Glu Ile Lys
            100                 105

<210> SEQ ID NO 286
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

-continued

```
Gly Ser Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Val Gly Tyr Gly Trp Tyr Thr Lys Ile Ala Phe Asp Ile
            100                 105                 110

Trp Gly Gln Gly Thr Met Val Thr Val Ser Ser
            115                 120

<210> SEQ ID NO 287
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 287

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Lys Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Ser Asn His Pro Ser
                 85                  90                  95

Thr Phe Gly Gly Gly Thr Lys Val Glu Ile Lys
            100                 105

<210> SEQ ID NO 288
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Ser Gly Gly Ser Thr Thr Tyr Ala Gln Lys Phe
    50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ala Ala Asp Gly Phe Val Gly Glu Arg Tyr Phe Asp Leu
            100                 105                 110
```

```
Trp Gly Arg Gly Thr Leu Val Thr Val Ser Ser
        115                 120
```

<210> SEQ ID NO 289
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gly Val Pro Leu Thr Phe Gly Gly Gly Thr Lys Val Glu Ile Lys
            100                 105                 110
```

<210> SEQ ID NO 290
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
            20                  25                  30

Tyr Met His Trp Val Arg Gln Ala Pro Gly Gln Gly Leu Glu Trp Met
        35                  40                  45

Gly Met Ile Asn Pro Tyr Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Ala Asp Gly Phe Val Gly Glu Arg Tyr Phe Asp Leu
            100                 105                 110

Trp Gly Arg Gly Thr Leu Val Thr Val Ser Ser
        115                 120
```

<210> SEQ ID NO 291
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 291

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Tyr Tyr Cys Met Gln Asp
                85                  90                  95

Val Ala Leu Pro Ile Thr Phe Gly Gly Gly Thr Lys Val Glu Ile Lys
            100                 105                 110

<210> SEQ ID NO 292
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Ile Tyr
            20                  25                  30

Tyr Met His Trp Val Arg Gln Ala Pro Gly Gln Gly Leu Glu Trp Met
        35                  40                  45

Gly Ile Ile Asn Pro Ser Ser Gly Ser Thr Val Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Asp Asp Glu Asp Met Asp Val Trp Gly Lys
            100                 105                 110

Gly Thr Thr Val Thr Val Ser Ser
        115                 120

<210> SEQ ID NO 293
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala His Ser Tyr Pro Leu
                 85                  90                  95

Thr Phe Gly Gly Gly Thr Lys Val Glu Ile Lys
            100                 105

<210> SEQ ID NO 294
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Gly Gly Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Ala Asn Tyr Tyr Gly Asn Val Gly Asp Asp Tyr Trp Gly
            100                 105                 110

Gln Gly Thr Leu Val Thr Val Ser Ser
        115                 120

<210> SEQ ID NO 295
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Phe His Val Pro Ile
                 85                  90                  95

Thr Phe Gly Gly Gly Thr Lys Val Glu Ile Lys
            100                 105
```

```
<210> SEQ ID NO 296
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Gly Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Val Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asn Tyr Tyr Gly Asn Val Gly Asp Asp Tyr Trp Gly
            100                 105                 110

Gln Gly Thr Leu Val Thr Val Ser Ser
        115                 120

<210> SEQ ID NO 297
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Thr Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe His Val Pro Ile
                85                  90                  95

Thr Phe Gly Gly Gly Thr Lys Val Glu Ile Lys
            100                 105

<210> SEQ ID NO 298
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Val Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser
        115                 120

<210> SEQ ID NO 299
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Arg Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Gly Gly Thr Lys Val Glu Ile Lys
            100                 105

<210> SEQ ID NO 300
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Tyr Met His Trp Val Arg Gln Ala Pro Gly Gln Gly Leu Glu Trp Met
        35                  40                  45

Gly Trp Ile Asn Pro Phe Ser Gly Gly Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

```
Met Glu Leu Ser Ser Leu Arg Ser Glu Asp Thr Ala Val Tyr Tyr Cys
                85                  90                  95

Ala Arg Asp Val Gly Ser Ser Ala Tyr Tyr Met Asp Val Trp Gly
            100                 105                 110

Lys Gly Thr Thr Val Thr Val Ser Ser
        115                 120

<210> SEQ ID NO 301
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Asp Ile Gln Met Thr Gln Ser Pro Ser Ser Val Ser Ala Ser Val Gly
1               5                   10                  15

Asp Arg Val Thr Ile Thr Cys Glu Ala Ser Lys Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asp Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe Leu Phe Pro Pro
                85                  90                  95

Thr Phe Gly Gly Gly Thr Lys Val Glu Ile Lys
            100                 105

<210> SEQ ID NO 302
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ser Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Ala Tyr Gly Asp Tyr Lys Gly Gly Val Asp Tyr Trp
            100                 105                 110

Gly Gln Gly Thr Leu Val Thr Val Ser Ser
        115                 120

<210> SEQ ID NO 303
```

<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Asp Ser Pro Pro
                85                  90                  95

Pro Thr Phe Gly Gly Gly Thr Lys Val Glu Ile Lys
            100                 105

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ser Tyr Ala Met Ser
1               5

<210> SEQ ID NO 305
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ala Ile Ser Ala Ser Gly Gly Ser Thr Tyr Tyr Ala Asp Ser Val Lys
1               5                   10                  15

Gly

<210> SEQ ID NO 306
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Pro Arg Ala Tyr Tyr Asp Ser Ser Gly Phe Lys Val Asn Tyr Gly Met
1               5                   10                  15

Asp Val

<210> SEQ ID NO 307
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Ala Ser Gln Ser Val Ser Ser Ser Phe Leu Ala
1               5                   10

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gly Ala Ser Ser Arg Ala Thr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln Gln Ala Ser Ser Ser Pro Pro Thr
1               5

<210> SEQ ID NO 310
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Tyr Ala Met Ser
1               5

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Ile Ser Gly Ser Gly Gly Ser Thr Tyr Tyr Ala Asp Ser Val Lys
1               5                   10                  15

Gly

<210> SEQ ID NO 312
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312
```

```
Glu Gly His Ser Ser Ser Tyr Tyr Asp His Ala Phe Asp Ile
1               5                   10
```

```
<210> SEQ ID NO 313
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Arg Ala Ser Gln Ser Val Ser Ser Asp Tyr Leu Ala
1               5                   10
```

```
<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Ala Ser Ser Arg Ala Thr
1               5
```

```
<210> SEQ ID NO 315
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Gln His Ser Ser Ala Pro Pro Thr
1               5
```

```
<210> SEQ ID NO 316
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ser Tyr Tyr Trp Ser
1               5
```

```
<210> SEQ ID NO 317
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Ser Ile Tyr Tyr Ser Gly Ser Thr Asn Tyr Asn Pro Ser Leu Lys Ser
1               5                   10                  15
```

```
<210> SEQ ID NO 318
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 318

Val Gly Gly Val Tyr Ser Thr Ile Glu Thr Tyr Gly Met Asp Val
1               5                   10                  15

<210> SEQ ID NO 319
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Arg Ala Ser Gln Ser Val Ser Ser Asn Leu Ala
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gly Ala Ser Thr Arg Ala Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln Tyr Thr Val Tyr Pro Pro Thr
1               5

<210> SEQ ID NO 322
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gly Tyr Tyr Trp Ser
1               5

<210> SEQ ID NO 323
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Ile Asp His Ser Gly Ser Thr Asn Tyr Asn Pro Ser Leu Lys Ser
1               5                   10                  15
```

<210> SEQ ID NO 324
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Gly Ile His Gly Leu Arg Tyr Phe Asp Leu
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Arg Ala Ser Gln Ser Val Ser Ser Tyr Leu Ala
1               5                   10

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Asp Ala Ser Asn Arg Ala Thr
1               5

<210> SEQ ID NO 327
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Gln Gln Asp His Asn Phe Pro Tyr Thr
1               5

<210> SEQ ID NO 328
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ser Tyr Trp Met Ser
1               5

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 329

Asn Ile Asn Gln Asp Gly Ser Glu Lys Tyr Tyr Val Asp Ser Val Lys
1               5                   10                  15

Gly

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Glu Ala Asn Tyr Tyr Gly Asn Val Gly Asp Asp Tyr
1               5                   10

<210> SEQ ID NO 331
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Arg Ala Ser Gln Ser Ile Ser Ser Tyr Leu Asn
1               5                   10

<210> SEQ ID NO 332
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Ala Ser Ser Leu Gln Ser
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Gln Gln Tyr Val Thr Pro Ile Thr
1               5

<210> SEQ ID NO 334
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Ser Tyr Trp Met Ser
1               5

<210> SEQ ID NO 335
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asn Ile Asn Gln Asp Gly Ser Glu Lys Tyr Tyr Val Asp Ser Val Lys
1               5                   10                  15
Gly

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Glu Gly Gly Asp Ser Trp Tyr His Ala Phe Asp Ile
1               5                   10

<210> SEQ ID NO 337
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Ala Ser Gln Gly Ile Ser Ser Trp Leu Ala
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ala Ala Ser Asn Leu Gln Ser
1               5

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Gln Lys Leu Ser Leu Pro Leu Thr
1               5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 340

Ser Gly Gly Tyr Tyr Trp Ser
1               5

<210> SEQ ID NO 341
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ser Ile Tyr Tyr Ser Gly Ser Thr Tyr Tyr Asn Pro Ser Leu Lys Ser
1               5                   10                  15

<210> SEQ ID NO 342
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Arg Leu Asp Tyr Ser Tyr Asn Tyr Gly Met Asp Val
1               5                   10

<210> SEQ ID NO 343
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Arg Ala Ser Gln Ser Ile Ser Ser Tyr Leu Asn
1               5                   10

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Gly Ala Ser Ser Leu Gln Ser
1               5

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Gln Val Tyr Ser Ala Pro Phe Thr
1               5

<210> SEQ ID NO 346
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 346

Ser Gly Tyr Tyr Trp Gly
1               5

<210> SEQ ID NO 347
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ser Ile Tyr His Ser Gly Ser Thr Asn Tyr Asn Pro Ser Leu Lys Ser
1               5                   10                  15

<210> SEQ ID NO 348
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Leu Pro Pro Trp Phe Gly Phe Ser Tyr Phe Asp Leu
1               5                   10

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Arg Ala Ser Gln Ser Val Ser Ser Tyr Leu Ala
1               5                   10

<210> SEQ ID NO 350
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asp Ala Ser Asn Arg Ala Thr
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Gln Gln Val Asp Asn Tyr Pro Pro Thr
1               5
```

<210> SEQ ID NO 352
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ser Tyr Trp Met Ser
1               5

<210> SEQ ID NO 353
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asn Ile Lys Gln Asp Gly Ser Glu Lys Tyr Tyr Val Asp Ser Val Lys
1               5                   10                  15

Gly

<210> SEQ ID NO 354
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Val Gly Pro Gly Ile Ala Tyr Gln Gly His Phe Asp Tyr
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Arg Ala Ser Gln Ser Ile Ser Ser Tyr Leu Asn
1               5                   10

<210> SEQ ID NO 356
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Ala Ser Ser Leu Gln Ser
1               5

<210> SEQ ID NO 357
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 357

Gln Gln Val Tyr Asp Thr Pro Leu Thr
1               5

<210> SEQ ID NO 358
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ser Ser Ser Tyr Tyr Trp Gly
1               5

<210> SEQ ID NO 359
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ser Ile Tyr Tyr Ser Gly Ser Thr Tyr Tyr Asn Pro Ser Leu Lys Ser
1               5                   10                  15

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Glu Thr Ala His Asp Val His Gly Met Asp Val
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Arg Ala Ser Gln Ser Val Ser Ser Tyr Leu Ala
1               5                   10

<210> SEQ ID NO 362
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Asp Ala Ser Asn Arg Ala Thr
1               5

```
<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gln Gln Tyr Asp Asn Leu Pro Thr
1               5

<210> SEQ ID NO 364
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ser Tyr Ala Ile Ser
1               5

<210> SEQ ID NO 365
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ser Ile Ile Pro Ile Phe Gly Thr Ala Asn Tyr Ala Gln Lys Phe Gln
1               5                   10                  15

Gly

<210> SEQ ID NO 366
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Glu Val Gly Tyr Gly Trp Tyr Thr Lys Ile Ala Phe Asp Ile
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Arg Ala Ser Gln Ser Val Ser Ser Tyr Leu Ala
1               5                   10

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 368

Asp Ala Ser Lys Arg Ala Thr
1               5

<210> SEQ ID NO 369
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Gln Gln Ser Ser Asn His Pro Ser Thr
1               5

<210> SEQ ID NO 370
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Ser Tyr Tyr Met His
1               5

<210> SEQ ID NO 371
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ile Ile Asn Pro Ser Gly Gly Ser Thr Thr Tyr Ala Gln Lys Phe Gln
1               5                   10                  15

Gly

<210> SEQ ID NO 372
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Glu Ala Ala Asp Gly Phe Val Gly Glu Arg Tyr Phe Asp Leu
1               5                   10

<210> SEQ ID NO 373
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Arg Ser Ser Gln Ser Leu Leu His Ser Asn Gly Tyr Asn Tyr Leu Asp
1               5                   10                  15
```

```
<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Leu Gly Ser Asn Arg Ala Ser
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Met Gln Ala Leu Gly Val Pro Leu Thr
1               5

<210> SEQ ID NO 376
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Gly Tyr Tyr Met His
1               5

<210> SEQ ID NO 377
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Met Ile Asn Pro Tyr Gly Gly Ser Thr Arg Tyr Ala Gln Lys Phe Gln
1               5                   10                  15

Gly

<210> SEQ ID NO 378
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Glu Ala Ala Asp Gly Phe Val Gly Glu Arg Tyr Phe Asp Leu
1               5                   10

<210> SEQ ID NO 379
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 379

Arg Ser Ser Gln Ser Leu Leu Tyr Ser Asn Gly Tyr Asn Tyr Leu Asp
1               5                   10                  15

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Leu Gly Ser Asn Arg Ala Ser
1               5

<210> SEQ ID NO 381
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Met Gln Asp Val Ala Leu Pro Ile Thr
1               5

<210> SEQ ID NO 382
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ile Tyr Tyr Met His
1               5

<210> SEQ ID NO 383
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ile Ile Asn Pro Ser Ser Gly Ser Thr Val Tyr Ala Gln Lys Phe Gln
1               5                   10                  15

Gly

<210> SEQ ID NO 384
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gly Ala Gly Tyr Asp Asp Glu Asp Met Asp Val
1               5                   10
```

<210> SEQ ID NO 385
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Arg Ala Ser Gln Gly Ile Asp Ser Trp Leu Ala
1               5                   10

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Ala Ser Ser Leu Gln Ser
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Gln Ala His Ser Tyr Pro Leu Thr
1               5

<210> SEQ ID NO 388
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gly Tyr Trp Met Ser
1               5

<210> SEQ ID NO 389
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Asn Ile Asn Gln Asp Gly Ser Glu Glu Tyr Tyr Val Asp Ser Val Lys
1               5                   10                  15

Gly

<210> SEQ ID NO 390
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 390

Glu Ala Asn Tyr Tyr Gly Asn Val Gly Asp Asp Tyr
1               5                   10

<210> SEQ ID NO 391
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Arg Ala Ser Gln Ser Ile Tyr Asn Tyr Leu Asn
1               5                   10

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Ala Ala Ser Asn Leu His Ser
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gln Gln Ala Phe His Val Pro Ile Thr
1               5

<210> SEQ ID NO 394
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Gly Tyr Trp Met Ser
1               5

<210> SEQ ID NO 395
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Asn Ile Asn Gln Asp Gly Ser Glu Val Tyr Tyr Val Asp Ser Val Lys
1               5                   10                  15

Gly
```

```
<210> SEQ ID NO 396
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Glu Ala Asn Tyr Tyr Gly Asn Val Gly Asp Asp Tyr
1               5                   10

<210> SEQ ID NO 397
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Arg Ala Ser Gln Ser Ile Tyr Asn Tyr Leu Asn
1               5                   10

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Ala Ala Ser Ser Thr Gln Ser
1               5

<210> SEQ ID NO 399
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gln Gln Ala Phe His Val Pro Ile Thr
1               5

<210> SEQ ID NO 400
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ser Tyr Trp Met Ser
1               5

<210> SEQ ID NO 401
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401
```

Asn Ile Asn Gln Asp Gly Ser Glu Val Tyr Tyr Val Asp Ser Val Lys
1               5                   10                  15

Gly

<210> SEQ ID NO 402
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 402

Asp Val Gly Pro Gly Ile Ala Tyr Gln Gly His Phe Asp Tyr
1               5                   10

<210> SEQ ID NO 403
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Arg Ala Ser Gln Ser Ile Tyr Tyr Tyr Leu Asn
1               5                   10

<210> SEQ ID NO 404
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Ala Ala Ser Ser Arg Gln Ser
1               5

<210> SEQ ID NO 405
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Gln Gln Val Tyr Asp Thr Pro Leu Thr
1               5

<210> SEQ ID NO 406
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Asn Tyr Tyr Met His
1               5

<210> SEQ ID NO 407
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Trp Ile Asn Pro Phe Ser Gly Gly Thr Arg Tyr Ala Gln Lys Phe Gln
1               5                   10                  15
Gly

<210> SEQ ID NO 408
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Asp Val Gly Ser Ser Ala Tyr Tyr Tyr Met Asp Val
1               5                   10

<210> SEQ ID NO 409
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Glu Ala Ser Lys Gly Ile Ser Ser Trp Leu Ala
1               5                   10

<210> SEQ ID NO 410
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Ala Ala Ser Asp Leu Gln Ser
1               5

<210> SEQ ID NO 411
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Gln Gln Ala Phe Leu Phe Pro Pro Thr
1               5

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412
```

```
Ser Tyr Trp Ile Gly
1               5

<210> SEQ ID NO 413
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Ser Ile Tyr Pro Gly Asp Ser Asp Thr Arg Tyr Ser Pro Ser Phe Gln
1               5                   10                  15

Gly

<210> SEQ ID NO 414
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Glu Leu Ala Tyr Gly Asp Tyr Lys Gly Gly Val Asp Tyr
1               5                   10

<210> SEQ ID NO 415
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Arg Ala Ser Gln Ser Val Ser Ser Ser Phe Leu Ala
1               5                   10

<210> SEQ ID NO 416
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Ala Ser Ser Arg Ala Thr
1               5

<210> SEQ ID NO 417
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Gln Gln Leu Asp Ser Pro Pro Thr
1               5

<210> SEQ ID NO 418
<211> LENGTH: 117
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Val Ala Asp Tyr Ala Gln Lys Phe
    50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser
        115

<210> SEQ ID NO 419
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Gln Gly Thr Lys Leu Glu Ile Lys
            100                 105

<210> SEQ ID NO 420
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr

```
                    20                  25                  30

Asn Met His Trp Val Arg Gln Ala Pro Gly Gln Gly Leu Glu Trp Ile
        35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser
            115

<210> SEQ ID NO 421
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Gln Gly Thr Lys Val Glu Ile Lys
            100                 105                 110

<210> SEQ ID NO 422
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Asp Tyr Ala Ile Ser
1               5

<210> SEQ ID NO 423
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Arg Ile Ile Pro Ile Leu Gly Val Ala Asp Tyr Ala Gln Lys Phe Gln
1               5                   10                  15
```

Gly

<210> SEQ ID NO 424
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Asn Trp Ala Asp Ala Phe Asp Ile
1               5

<210> SEQ ID NO 425
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Arg Ala Ser Gln Gly Ile Ser Ser Val Leu Ala
1               5                   10

<210> SEQ ID NO 426
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Asp Ala Ser Ser Leu Glu Ser
1               5

<210> SEQ ID NO 427
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Gln Gln Phe Asp Ser Ser Ile Thr
1               5

<210> SEQ ID NO 428
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Asp Tyr Asn Met His
1               5

<210> SEQ ID NO 429
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 429

Tyr Ile Tyr Pro Tyr Asn Gly Gly Thr Gly Tyr Asn Gln Lys Phe Lys
1               5                   10                  15

Ser

<210> SEQ ID NO 430
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly Arg Pro Ala Met Asp Tyr
1               5

<210> SEQ ID NO 431
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Arg Ala Ser Glu Ser Val Asp Asn Tyr Gly Ile Ser Phe Met Asn
1               5                   10                  15

<210> SEQ ID NO 432
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Ala Ser Asn Gln Gly Ser
1               5

<210> SEQ ID NO 433
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Gln Gln Ser Lys Glu Val Pro Trp Thr
1               5

<210> SEQ ID NO 434
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Ser Tyr Gly Met Ser
1               5
```

```
<210> SEQ ID NO 435
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Glu Gly Gly Pro Tyr Tyr Asp Ser Ser Gly Tyr Phe Val Tyr Tyr Gly
1               5                   10                  15

Met Asp Val

<210> SEQ ID NO 436
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Pro Leu Asn Ala Gly Glu Leu Asp Val
1               5

<210> SEQ ID NO 437
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Asp Tyr Tyr Met His
1               5

<210> SEQ ID NO 438
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Glu Ala Ala Asp Gly Phe Val Gly Glu Arg Tyr Phe Asp Leu
1               5                   10

<210> SEQ ID NO 439
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Pro Leu Asn Ala Gly Glu Leu Asp Val
1               5

<210> SEQ ID NO 440
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 440

Thr Tyr Tyr Met His
1               5

<210> SEQ ID NO 441
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Gly Ala Gly Tyr Asp Asp Glu Asp Met Asp Val
1               5                   10

<210> SEQ ID NO 442
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Ser Tyr Ala Met Ser
1               5

<210> SEQ ID NO 443
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Glu Gly Gly Pro Tyr Tyr Asp Ser Ser Gly Tyr Phe Val Tyr Gly
1               5                   10                  15

Met Asp Val

<210> SEQ ID NO 444
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Asp Val Gly Pro Gly Ile Ala Tyr Gln Gly His Phe Asp Tyr
1               5                   10

<210> SEQ ID NO 445
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Ser Thr Asp Tyr Tyr Trp Gly
1               5
```

<210> SEQ ID NO 446
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 446

Glu Thr Ala His Asp Val His Gly Met Asp Val
1               5                   10

<210> SEQ ID NO 447
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ser Ser Ser Pro
                85                  90                  95

Pro Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Leu Glu Ser Gly Gly Gly Leu Val Gln Pro Gly Gly
    130                 135                 140

Ser Leu Arg Leu Ser Cys Ala Ala Ser Gly Phe Thr Phe Ser Ser Tyr
145                 150                 155                 160

Ala Met Ser Trp Val Arg Gln Ala Pro Gly Lys Cys Leu Glu Trp Val
                165                 170                 175

Ser Ala Ile Ser Ala Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Pro Arg Ala Tyr Tyr Asp Ser Ser Gly Phe Lys Val Asn Tyr
225                 230                 235                 240

Gly Met Asp Val Trp Gly Gln Gly Thr Thr Val Thr Val Ser Ser
                245                 250                 255

<210> SEQ ID NO 448
<211> LENGTH: 255
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 448

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Ala Ile Ser Ala Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Arg Ala Tyr Tyr Asp Ser Ser Gly Phe Lys Val Asn Tyr
            100                 105                 110

Gly Met Asp Val Trp Gly Gln Gly Thr Thr Val Thr Val Ser Ser Gly
        115                 120                 125

Gly Gly Gly Ser Gly Gly Gly Gly Ser Gly Gly Gly Gly Ser Gly Gly
    130                 135                 140

Gly Gly Ser Glu Ile Val Leu Thr Gln Ser Pro Gly Thr Leu Ser Leu
145                 150                 155                 160

Ser Pro Gly Glu Arg Ala Thr Leu Ser Cys Arg Ala Ser Gln Ser Val
                165                 170                 175

Ser Ser Ser Phe Leu Ala Trp Tyr Gln Gln Lys Pro Gly Gln Ala Pro
            180                 185                 190

Arg Leu Leu Ile Tyr Gly Ala Ser Ser Arg Ala Thr Gly Ile Pro Asp
        195                 200                 205

Arg Phe Ser Gly Ser Gly Ser Gly Thr Asp Phe Thr Leu Thr Ile Ser
    210                 215                 220

Arg Leu Glu Pro Glu Asp Phe Ala Val Tyr Tyr Cys Gln Gln Ala Ser
225                 230                 235                 240

Ser Ser Pro Pro Thr Phe Gly Cys Gly Thr Lys Val Glu Ile Lys
                245                 250                 255

<210> SEQ ID NO 449
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

Pro Glu Asp Phe Ala Val Tyr Tyr Cys Gln Gln His Ser Ser Ala Pro
                85                  90                  95

Pro Thr Phe Gly Cys Gly Thr Lys Val Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Leu Glu Ser Gly Gly Gly Leu Val Gln Pro Gly Gly
    130                 135                 140

Ser Leu Arg Leu Ser Cys Ala Ala Ser Gly Phe Thr Phe Ser Ser Tyr
145                 150                 155                 160

Ala Met Ser Trp Val Arg Gln Ala Pro Gly Lys Cys Leu Glu Trp Val
                165                 170                 175

Ser Gly Ile Ser Gly Ser Gly Gly Ser Thr Tyr Tyr Ala Asp Ser Val
            180                 185                 190

Lys Gly Arg Phe Thr Ile Ser Arg Asp Asn Ser Lys Asn Thr Leu Tyr
            195                 200                 205

Leu Gln Met Asn Ser Leu Arg Ala Glu Asp Thr Ala Val Tyr Tyr Cys
        210                 215                 220

Ala Arg Glu Gly His Ser Ser Ser Tyr Tyr Asp His Ala Phe Asp Ile
225                 230                 235                 240

Trp Gly Gln Gly Thr Met Val Thr Val Ser Ser
                245                 250

<210> SEQ ID NO 450
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Cys Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly His Ser Ser Ser Tyr Tyr Asp His Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Ser Gly Gly Gly Gly Ser Glu
    130                 135                 140

Ile Val Leu Thr Gln Ser Pro Gly Thr Leu Ser Leu Ser Pro Gly Glu
145                 150                 155                 160

Arg Ala Thr Leu Ser Cys Arg Ala Ser Gln Ser Val Ser Ser Asp Tyr
                165                 170                 175

Leu Ala Trp Tyr Gln Gln Lys Pro Gly Gln Ala Pro Arg Leu Leu Ile

```
              180                 185                 190
Tyr Gly Ala Ser Ser Arg Ala Thr Gly Ile Pro Asp Arg Phe Ser Gly
            195                 200                 205

Ser Gly Ser Gly Thr Asp Phe Thr Leu Thr Ile Ser Arg Leu Glu Pro
            210                 215                 220

Glu Asp Phe Ala Val Tyr Tyr Cys Gln Gln His Ser Ser Ala Pro Pro
225                 230                 235                 240

Thr Phe Gly Cys Gly Thr Lys Val Glu Ile Lys
            245                 250

<210> SEQ ID NO 451
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Thr Val Tyr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Gly Ser Ile Ser Ser Tyr Tyr
145                 150                 155                 160

Trp Ser Trp Ile Arg Gln Pro Pro Gly Lys Cys Leu Glu Trp Ile Gly
                165                 170                 175

Ser Ile Tyr Tyr Ser Gly Ser Thr Asn Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Val Gly Gly Val Tyr Ser Thr Ile Glu Thr Tyr Gly Met Asp Val Trp
225                 230                 235                 240

Gly Gln Gly Thr Thr Val Thr Val Ser Ser
                245                 250

<210> SEQ ID NO 452
<211> LENGTH: 250
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 452

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Cys Leu Glu Trp Ile
        35                  40                  45

Gly Ser Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Gly Gly Val Tyr Ser Thr Ile Glu Thr Tyr Gly Met Asp Val
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Gly Ser Gly Gly Gly Gly Ser Glu
    130                 135                 140

Ile Val Met Thr Gln Ser Pro Ala Thr Leu Ser Val Ser Pro Gly Glu
145                 150                 155                 160

Arg Ala Thr Leu Ser Cys Arg Ala Ser Gln Ser Val Ser Ser Asn Leu
                165                 170                 175

Ala Trp Tyr Gln Gln Lys Pro Gly Gln Ala Pro Arg Leu Leu Ile Tyr
            180                 185                 190

Gly Ala Ser Thr Arg Ala Thr Gly Ile Pro Ala Arg Phe Ser Gly Ser
        195                 200                 205

Gly Ser Gly Thr Glu Phe Thr Leu Thr Ile Ser Ser Leu Gln Ser Glu
    210                 215                 220

Asp Phe Ala Val Tyr Tyr Cys Gln Gln Tyr Thr Val Tyr Pro Pro Thr
225                 230                 235                 240

Phe Gly Cys Gly Thr Lys Val Glu Ile Lys
                245                 250
```

<210> SEQ ID NO 453
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Phe Ala Val Tyr Tyr Cys Gln Gln Asp His Asn Phe Pro Tyr
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Ser Gln
            115                 120                 125

Val Gln Leu Gln Gln Trp Gly Ala Gly Leu Leu Lys Pro Ser Glu Thr
    130                 135                 140

Leu Ser Leu Thr Cys Ala Val Tyr Gly Gly Ser Phe Ser Gly Tyr Tyr
145                 150                 155                 160

Trp Ser Trp Ile Arg Gln Pro Pro Gly Lys Cys Leu Glu Trp Ile Gly
                165                 170                 175

Glu Ile Asp His Ser Gly Ser Thr Asn Tyr Asn Pro Ser Leu Lys Ser
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ala Arg
    210                 215                 220

Gln Gly Ile His Gly Leu Arg Tyr Phe Asp Leu Trp Gly Arg Gly Thr
225                 230                 235                 240

Leu Val Thr Val Ser Ser
                245

<210> SEQ ID NO 454
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Cys Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Gly Ile His Gly Leu Arg Tyr Phe Asp Leu Trp Gly Arg Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Glu Ile Val Met Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ser Ser Tyr Leu Ala Trp Tyr Gln
                165                 170                 175

Gln Lys Pro Gly Gln Ala Pro Arg Leu Leu Ile Tyr Asp Ala Ser Asn
            180                 185                 190
```

```
Arg Ala Thr Gly Ile Pro Ala Arg Phe Ser Gly Ser Gly Ser Gly Thr
            195                 200                 205

Asp Phe Thr Leu Thr Ile Ser Ser Leu Glu Pro Glu Asp Phe Ala Val
        210                 215                 220

Tyr Tyr Cys Gln Gln Asp His Asn Phe Pro Tyr Thr Phe Gly Cys Gly
225                 230                 235                 240

Thr Lys Val Glu Ile Lys
            245

<210> SEQ ID NO 455
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gln Tyr Val Thr Pro Ile
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Asn Gln Asp Gly Ser Glu Lys Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Glu Ala Asn Tyr Tyr Gly Asn Val Gly Asp Tyr Trp Gly Gln
225                 230                 235                 240

Gly Thr Leu Val Thr Val Ser Ser
            245

<210> SEQ ID NO 456
<211> LENGTH: 248
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 456

Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asn Tyr Tyr Gly Asn Val Gly Asp Asp Tyr Trp Gly
            100                 105                 110

Gln Gly Thr Leu Val Thr Val Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Ser Ser Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220

Ala Thr Tyr Tyr Cys Gln Gln Gln Tyr Val Thr Pro Ile Thr Phe Gly
225                 230                 235                 240

Cys Gly Thr Lys Val Glu Ile Lys
                245

<210> SEQ ID NO 457
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Leu Ser Leu Pro Leu

```
                        85                  90                  95
Thr Phe Gly Cys Gly Thr Lys Val Glu Ile Lys Gly Gly Gly Ser
                    100                 105                 110

Gly Gly Gly Gly Ser Gly Gly Gly Ser Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Asn Gln Asp Gly Ser Glu Lys Tyr Tyr Val Asp Ser Val Lys
                180                 185                 190

Gly Arg Phe Thr Ile Ser Arg Asp Asn Ala Lys Asn Ser Leu Tyr Leu
                195                 200                 205

Gln Met Asn Ser Leu Arg Ala Glu Asp Thr Ala Val Tyr Tyr Cys Ala
        210                 215                 220

Arg Glu Gly Gly Asp Ser Trp Tyr His Ala Phe Asp Ile Trp Gly Gln
225                 230                 235                 240

Gly Thr Met Val Thr Val Ser Ser
                245

<210> SEQ ID NO 458
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Asp Ser Trp Tyr His Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Arg Ala Ser Gln Gly Ile Ser Ser Trp Leu Ala Trp
                165                 170                 175

Tyr Gln Gln Lys Pro Gly Lys Ala Pro Lys Leu Leu Ile Tyr Ala Ala
                180                 185                 190
```

```
Ser Asn Leu Gln Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
        210                 215                 220

Ala Thr Tyr Tyr Cys Gln Gln Lys Leu Ser Leu Pro Leu Thr Phe Gly
225                 230                 235                 240

Cys Gly Thr Lys Val Glu Ile Lys
                245

<210> SEQ ID NO 459
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ala Pro Phe
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Gln Glu Ser Gly Pro Gly Leu Val Lys Pro Ser Gln Thr
130                 135                 140

Leu Ser Leu Thr Cys Thr Val Ser Gly Gly Ser Ile Ser Ser Gly Gly
145                 150                 155                 160

Tyr Tyr Trp Ser Trp Ile Arg Gln His Pro Gly Lys Cys Leu Glu Trp
                165                 170                 175

Ile Gly Ser Ile Tyr Tyr Ser Gly Ser Thr Tyr Tyr Asn Pro Ser Leu
            180                 185                 190

Lys Ser Arg Val Thr Ile Ser Val Asp Thr Ser Lys Asn Gln Phe Ser
        195                 200                 205

Leu Lys Leu Ser Ser Val Thr Ala Ala Asp Thr Ala Val Tyr Tyr Cys
    210                 215                 220

Ala Arg Asp Arg Leu Asp Tyr Ser Tyr Asn Tyr Gly Met Asp Val Trp
225                 230                 235                 240

Gly Gln Gly Thr Thr Val Thr Val Ser Ser
                245                 250

<210> SEQ ID NO 460
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 460

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Cys Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Leu Asp Tyr Ser Tyr Asn Tyr Gly Met Asp Val
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Gly Gly Gly Gly Ser Asp
130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Gly Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Val Tyr Ser Ala Pro Phe Thr
225                 230                 235                 240

Phe Gly Cys Gly Thr Lys Val Glu Ile Lys
                245                 250

<210> SEQ ID NO 461
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Val Asp Asn Tyr Pro Pro
                85                  90                  95
```

```
Thr Phe Gly Cys Gly Thr Lys Val Glu Ile Lys Gly Gly Gly Ser
                100                 105                 110

Gly Gly Gly Gly Ser Gly Gly Gly Ser Gly Gly Gly Gly Ser Gln
            115                 120                 125

Val Gln Leu Gln Glu Ser Gly Pro Gly Leu Val Lys Pro Ser Glu Thr
130                 135                 140

Leu Ser Leu Thr Cys Ala Val Ser Gly Tyr Ser Ile Ser Ser Gly Tyr
145                 150                 155                 160

Tyr Trp Gly Trp Ile Arg Gln Pro Pro Gly Lys Cys Leu Glu Trp Ile
                165                 170                 175

Gly Ser Ile Tyr His Ser Gly Ser Thr Asn Tyr Asn Pro Ser Leu Lys
                180                 185                 190

Ser Arg Val Thr Ile Ser Val Asp Thr Ser Lys Asn Gln Phe Ser Leu
                195                 200                 205

Lys Leu Ser Ser Val Thr Ala Ala Asp Thr Ala Val Tyr Tyr Cys Ala
210                 215                 220

Arg Leu Pro Pro Trp Phe Gly Phe Ser Tyr Phe Asp Leu Trp Gly Arg
225                 230                 235                 240

Gly Thr Leu Val Thr Val Ser Ser
                245

<210> SEQ ID NO 462
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Cys Leu Glu Trp
        35                  40                  45

Ile Gly Ser Ile Tyr His Ser Gly Ser Thr Asn Tyr Asn Pro Ser Leu
50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Pro Pro Trp Phe Gly Phe Ser Tyr Phe Asp Leu Trp Gly
            100                 105                 110

Arg Gly Thr Leu Val Thr Val Ser Ser Gly Gly Gly Ser Gly Gly Gly
        115                 120                 125

Gly Gly Ser Gly Gly Gly Ser Gly Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
```

```
                195                 200                 205
Gly Thr Asp Phe Thr Leu Thr Ile Ser Ser Leu Glu Pro Glu Asp Phe
    210                 215                 220

Ala Val Tyr Tyr Cys Gln Gln Val Asp Asn Tyr Pro Pro Thr Phe Gly
225                 230                 235                 240

Cys Gly Thr Lys Val Glu Ile Lys
                245

<210> SEQ ID NO 463
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Lys Gln Asp Gly Ser Glu Lys Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Asp Val Gly Pro Gly Ile Ala Tyr Gln Gly His Phe Asp Tyr Trp
225                 230                 235                 240

Gly Gln Gly Thr Leu Val Thr Val Ser Ser
                245                 250

<210> SEQ ID NO 464
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 464

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Val Tyr Asp Thr Pro Leu Thr
225                 230                 235                 240

Phe Gly Cys Gly Thr Lys Val Glu Ile Lys
                245                 250

<210> SEQ ID NO 465
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Asn Leu Pro Thr
                85                  90                  95

```
Phe Gly Cys Gly Thr Lys Val Glu Ile Lys Gly Gly Gly Ser Gly
                100                 105                 110

Gly Gly Gly Ser Gly Gly Gly Ser Gly Gly Gly Ser Gln Leu
            115                 120                 125

Gln Leu Gln Glu Ser Gly Pro Gly Leu Val Lys Pro Ser Glu Thr Leu
130                 135                 140

Ser Leu Thr Cys Thr Val Ser Gly Gly Ser Ile Ser Ser Ser Tyr
145                 150                 155                 160

Tyr Trp Gly Trp Ile Arg Gln Pro Pro Gly Lys Cys Leu Glu Trp Ile
                165                 170                 175

Gly Ser Ile Tyr Tyr Ser Gly Ser Thr Tyr Tyr Asn Pro Ser Leu Lys
                180                 185                 190

Ser Arg Val Thr Ile Ser Val Asp Thr Ser Lys Asn Gln Phe Ser Leu
            195                 200                 205

Lys Leu Ser Ser Val Thr Ala Ala Asp Thr Ala Val Tyr Tyr Cys Ala
210                 215                 220

Arg Glu Thr Ala His Asp Val His Gly Met Asp Val Trp Gly Gln Gly
225                 230                 235                 240

Thr Thr Val Thr Val Ser Ser
                245
```

<210> SEQ ID NO 466
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Cys Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Thr Ala His Asp Val His Gly Met Asp Val Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Gly Gly Gly Ser Glu Ile Val
    130                 135                 140

Leu Thr Gln Ser Pro Ala Thr Leu Ser Leu Ser Pro Gly Glu Arg Ala
145                 150                 155                 160

Thr Leu Ser Cys Arg Ala Ser Gln Ser Val Ser Ser Tyr Leu Ala Trp
                165                 170                 175

Tyr Gln Gln Lys Pro Gly Gln Ala Pro Arg Leu Leu Ile Tyr Asp Ala
            180                 185                 190

Ser Asn Arg Ala Thr Gly Ile Pro Ala Arg Phe Ser Gly Ser Gly Ser
        195                 200                 205
```

Gly Thr Asp Phe Thr Leu Thr Ile Ser Ser Leu Glu Pro Glu Asp Phe
            210                 215                 220

Ala Val Tyr Tyr Cys Gln Gln Tyr Asp Asn Leu Pro Thr Phe Gly Cys
225                 230                 235                 240

Gly Thr Lys Val Glu Ile Lys
            245

<210> SEQ ID NO 467
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn His Pro Ser
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln
        115                 120                 125

Val Gln Leu Val Gln Ser Gly Ala Glu Val Lys Lys Pro Gly Ser Ser
    130                 135                 140

Val Lys Val Ser Cys Lys Ala Ser Gly Gly Thr Phe Ser Ser Tyr Ala
145                 150                 155                 160

Ile Ser Trp Val Arg Gln Ala Pro Gly Gln Cys Leu Glu Trp Met Gly
                165                 170                 175

Ser Ile Ile Pro Ile Phe Gly Thr Ala Asn Tyr Ala Gln Lys Phe Gln
            180                 185                 190

Gly Arg Val Thr Ile Thr Ala Asp Glu Ser Thr Ser Thr Ala Tyr Met
        195                 200                 205

Glu Leu Ser Ser Leu Arg Ser Glu Asp Thr Ala Val Tyr Tyr Cys Ala
    210                 215                 220

Arg Glu Val Gly Tyr Gly Trp Tyr Thr Lys Ile Ala Phe Asp Ile Trp
225                 230                 235                 240

Gly Gln Gly Thr Met Val Thr Val Ser Ser
                245                 250

<210> SEQ ID NO 468
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Gln Val Gln Leu Val Gln Ser Gly Ala Glu Val Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Cys Leu Glu Trp Met
            35                  40                  45

Gly Ser Ile Ile Pro Ile Phe Gly Thr Ala Asn Tyr Ala Gln Lys Phe
50                      55                  60

Gln Gly Arg Val Thr Ile Thr Ala Asp Glu Ser Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Glu Val Gly Tyr Gly Trp Tyr Thr Lys Ile Ala Phe Asp Ile
            100                 105                 110

Trp Gly Gln Gly Thr Met Val Thr Val Ser Ser Gly Gly Gly Gly Ser
            115                 120                 125

Gly Gly Gly Gly Ser Gly Gly Gly Ser Gly Gly Gly Gly Ser Glu
            130                 135                 140

Ile Val Leu Thr Gln Ser Pro Ala Thr Leu Ser Leu Ser Pro Gly Glu
145                 150                 155                 160

Arg Ala Thr Leu Ser Cys Arg Ala Ser Gln Ser Val Ser Ser Tyr Leu
                165                 170                 175

Ala Trp Tyr Gln Gln Lys Pro Gly Gln Ala Pro Arg Leu Leu Ile Tyr
            180                 185                 190

Asp Ala Ser Lys Arg Ala Thr Gly Ile Pro Ala Arg Phe Ser Gly Ser
            195                 200                 205

Gly Ser Gly Thr Asp Phe Thr Leu Thr Ile Ser Ser Leu Glu Pro Glu
            210                 215                 220

Asp Phe Ala Val Tyr Tyr Cys Gln Gln Ser Ser Asn His Pro Ser Thr
225                 230                 235                 240

Phe Gly Cys Gly Thr Lys Val Glu Ile Lys
            245                 250

<210> SEQ ID NO 469
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                      60

Asp Arg Phe Ser Gly Ser Gly Ser Gly Thr Asp Phe Thr Leu Lys Ile
65                  70                      75                  80

Ser Arg Val Glu Ala Glu Asp Val Gly Val Tyr Tyr Cys Met Gln Ala
                85                  90                  95

Leu Gly Val Pro Leu Thr Phe Gly Cys Gly Thr Lys Val Glu Ile Lys

```
                100                 105                 110
Gly Gly Gly Gly Ser Gly Gly Gly Ser Gly Gly Gly Ser Gly
            115                 120                 125

Gly Gly Gly Ser Gln Val Gln Leu Val Gln Ser Gly Ala Glu Val Lys
            130                 135                 140

Lys Pro Gly Ala Ser Val Lys Val Ser Cys Lys Ala Ser Gly Tyr Thr
145                 150                 155                 160

Phe Thr Ser Tyr Tyr Met His Trp Val Arg Gln Ala Pro Gly Gln Cys
                165                 170                 175

Leu Glu Trp Met Gly Ile Ile Asn Pro Ser Gly Gly Ser Thr Thr Tyr
            180                 185                 190

Ala Gln Lys Phe Gln Gly Arg Val Thr Met Thr Arg Asp Thr Ser Thr
            195                 200                 205

Ser Thr Val Tyr Met Glu Leu Ser Ser Leu Arg Ser Glu Asp Thr Ala
210                 215                 220

Val Tyr Tyr Cys Ala Arg Glu Ala Ala Asp Gly Phe Val Gly Glu Arg
225                 230                 235                 240

Tyr Phe Asp Leu Trp Gly Arg Gly Thr Leu Val Thr Val Ser Ser
                245                 250                 255

<210> SEQ ID NO 470
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Cys Leu Glu Trp Met
        35                  40                  45

Gly Ile Ile Asn Pro Ser Gly Gly Ser Thr Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Ala Asp Gly Phe Val Gly Glu Arg Tyr Phe Asp Leu
            100                 105                 110

Trp Gly Arg Gly Thr Leu Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Val Met Thr Gln Ser Pro Leu Ser Leu Pro Val Thr Pro Gly Glu
145                 150                 155                 160

Pro Ala Ser Ile Ser Cys Arg Ser Ser Gln Ser Leu Leu His Ser Asn
                165                 170                 175

Gly Tyr Asn Tyr Leu Asp Trp Tyr Leu Gln Lys Pro Gly Gln Ser Pro
            180                 185                 190

Gln Leu Leu Ile Tyr Leu Gly Ser Asn Arg Ala Ser Gly Val Pro Asp
        195                 200                 205
```

```
Arg Phe Ser Gly Ser Gly Ser Gly Thr Asp Phe Thr Leu Lys Ile Ser
    210                 215                 220
Arg Val Glu Ala Glu Asp Val Gly Val Tyr Tyr Cys Met Gln Ala Leu
225                 230                 235                 240
Gly Val Pro Leu Thr Phe Gly Cys Gly Thr Lys Val Glu Ile Lys
                245                 250                 255

<210> SEQ ID NO 471
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Leu Tyr Ser
                20                  25                  30
Asn Gly Tyr Asn Tyr Leu Asp Trp Tyr Leu Gln Lys Pro Gly Gln Ser
            35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Asp
                85                  90                  95
Val Ala Leu Pro Ile Thr Phe Gly Cys Gly Thr Lys Val Glu Ile Lys
                100                 105                 110
Gly Gly Gly Gly Ser Gly Gly Gly Ser Gly Gly Gly Gly Ser Gly
                115                 120                 125
Gly Gly Gly Ser Gln Val Gln Leu Val Gln Ser Gly Ala Glu Val Lys
            130                 135                 140
Lys Pro Gly Ala Ser Val Lys Val Ser Cys Lys Ala Ser Gly Tyr Thr
145                 150                 155                 160
Phe Ser Gly Tyr Tyr Met His Trp Val Arg Gln Ala Pro Gly Gln Cys
                165                 170                 175
Leu Glu Trp Met Gly Met Ile Asn Pro Tyr Gly Gly Ser Thr Arg Tyr
                180                 185                 190
Ala Gln Lys Phe Gln Gly Arg Val Thr Met Thr Arg Asp Thr Ser Thr
            195                 200                 205
Ser Thr Val Tyr Met Glu Leu Ser Ser Leu Arg Ser Glu Asp Thr Ala
    210                 215                 220
Val Tyr Tyr Cys Ala Arg Glu Ala Ala Asp Gly Phe Val Gly Glu Arg
225                 230                 235                 240
Tyr Phe Asp Leu Trp Gly Arg Gly Thr Leu Val Thr Val Ser Ser
                245                 250                 255

<210> SEQ ID NO 472
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Gly Tyr
            20                  25                  30

Tyr Met His Trp Val Arg Gln Ala Pro Gly Gln Cys Leu Glu Trp Met
        35                  40                  45

Gly Met Ile Asn Pro Tyr Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Ala Asp Gly Phe Val Gly Glu Arg Tyr Phe Asp Leu
            100                 105                 110

Trp Gly Arg Gly Thr Leu Val Thr Val Ser Ser Gly Gly Gly Gly Ser
            115                 120                 125

Gly Gly Gly Gly Ser Gly Gly Ser Gly Gly Gly Gly Ser Gly Gly Asp Ser Asp
            130                 135                 140

Ile Val Met Thr Gln Ser Pro Leu Ser Leu Pro Val Thr Pro Gly Glu
145                 150                 155                 160

Pro Ala Ser Ile Ser Cys Arg Ser Ser Gln Ser Leu Leu Tyr Ser Asn
            165                 170                 175

Gly Tyr Asn Tyr Leu Asp Trp Tyr Leu Gln Lys Pro Gly Gln Ser Pro
            180                 185                 190

Gln Leu Leu Ile Tyr Leu Gly Ser Asn Arg Ala Ser Gly Val Pro Asp
            195                 200                 205

Arg Phe Ser Gly Ser Gly Ser Gly Thr Asp Phe Thr Leu Lys Ile Ser
    210                 215                 220

Arg Val Glu Ala Glu Asp Val Gly Val Tyr Tyr Cys Met Gln Asp Val
225                 230                 235                 240

Ala Leu Pro Ile Thr Phe Gly Cys Gly Thr Lys Val Glu Ile Lys
            245                 250                 255

<210> SEQ ID NO 473
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Ser Tyr Pro Leu
                85                  90                  95

Thr Phe Gly Cys Gly Thr Lys Val Glu Ile Lys Gly Gly Gly Gly Ser
            100                 105                 110

```
Gly Gly Gly Gly Ser Gly Gly Gly Ser Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Glu Ile Tyr Tyr
145                 150                 155                 160

Met His Trp Val Arg Gln Ala Pro Gly Gln Cys Leu Glu Trp Met Gly
                165                 170                 175

Ile Ile Asn Pro Ser Ser Gly Ser Thr Val Tyr Ala Gln Lys Phe Gln
                180                 185                 190

Gly Arg Val Thr Met Thr Arg Asp Thr Ser Thr Ser Thr Val Tyr Met
                195                 200                 205

Glu Leu Ser Ser Leu Arg Ser Glu Asp Thr Ala Val Tyr Tyr Cys Ala
                210                 215                 220

Arg Gly Ala Gly Tyr Asp Asp Glu Asp Met Asp Val Trp Gly Lys Gly
225                 230                 235                 240

Thr Thr Val Thr Val Ser Ser
                245

<210> SEQ ID NO 474
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Ile Tyr
                20                  25                  30

Tyr Met His Trp Val Arg Gln Ala Pro Gly Gln Cys Leu Glu Trp Met
            35                  40                  45

Gly Ile Ile Asn Pro Ser Ser Gly Ser Thr Val Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Gly Tyr Asp Asp Glu Asp Met Asp Val Trp Gly Lys
                100                 105                 110

Gly Thr Thr Val Thr Val Ser Ser Gly Gly Gly Gly Ser Gly Gly Gly
            115                 120                 125

Gly Ser Gly Gly Gly Gly Ser Gly Gly Gly Gly Ser Asp Ile Gln Met
    130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Asp Ser Trp Leu Ala Trp Tyr
                165                 170                 175

Gln Gln Lys Pro Gly Lys Ala Pro Lys Leu Leu Ile Tyr Ala Ala Ser
                180                 185                 190

Ser Leu Gln Ser Gly Val Pro Ser Arg Phe Ser Gly Ser Gly Ser Gly
            195                 200                 205

Thr Asp Phe Thr Leu Thr Ile Ser Ser Leu Gln Pro Glu Asp Phe Ala
```

```
                    210                 215                 220
Thr Tyr Tyr Cys Gln Gln Ala His Ser Tyr Pro Leu Thr Phe Gly Cys
225                 230                 235                 240

Gly Thr Lys Val Glu Ile Lys
                245

<210> SEQ ID NO 475
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Asn Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Phe His Val Pro Ile
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Thr Phe Gly Gly Tyr Trp
145                 150                 155                 160

Met Ser Trp Val Arg Gln Ala Pro Gly Lys Cys Leu Glu Trp Val Ala
                165                 170                 175

Asn Ile Asn Gln Asp Gly Ser Glu Glu Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
210                 215                 220

Arg Glu Ala Asn Tyr Tyr Gly Asn Val Gly Asp Asp Tyr Trp Gly Gln
225                 230                 235                 240

Gly Thr Leu Val Thr Val Ser Ser
                245

<210> SEQ ID NO 476
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Thr Phe Gly Gly Tyr
            20                  25                  30

Trp Met Ser Trp Val Arg Gln Ala Pro Gly Lys Cys Leu Glu Trp Val
            35                  40                  45

Ala Asn Ile Asn Gln Asp Gly Ser Glu Glu Tyr Tyr Val Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Ala Asn Tyr Tyr Gly Asn Val Gly Asp Asp Tyr Trp Gly
            100                 105                 110

Gln Gly Thr Leu Val Thr Val Ser Ser Gly Gly Gly Ser Gly Gly Gly
            115                 120                 125

Gly Gly Ser Gly Gly Gly Gly Ser Gly Gly Gly Gly Ser Asp Ile Gln
            130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Tyr Asn Tyr Leu Asn Trp
                165                 170                 175

Tyr Gln Gln Lys Pro Gly Lys Ala Pro Lys Leu Leu Ile Tyr Ala Ala
            180                 185                 190

Ser Asn Leu His Ser Gly Val Pro Ser Arg Phe Ser Gly Ser Gly Ser
            195                 200                 205

Gly Thr Asp Phe Thr Leu Thr Ile Ser Ser Leu Gln Pro Glu Asp Phe
            210                 215                 220

Ala Thr Tyr Tyr Cys Gln Gln Ala Phe His Val Pro Ile Thr Phe Gly
225                 230                 235                 240

Cys Gly Thr Lys Val Glu Ile Lys
                245

<210> SEQ ID NO 477
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Tyr Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Thr Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Phe His Val Pro Ile
                85                  90                  95

Thr Phe Gly Cys Gly Thr Lys Val Glu Ile Lys Gly Gly Gly Gly Ser
            100                 105                 110
```

```
Gly Gly Gly Gly Ser Gly Gly Gly Ser Gly Gly Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Thr Phe Pro Gly Tyr Trp
145                 150                 155                 160

Met Ser Trp Val Arg Gln Ala Pro Gly Lys Cys Leu Glu Trp Val Ala
                165                 170                 175

Asn Ile Asn Gln Asp Gly Ser Glu Val Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Glu Ala Asn Tyr Tyr Gly Asn Val Gly Asp Asp Tyr Trp Gly Gln
225                 230                 235                 240

Gly Thr Leu Val Thr Val Ser Ser
                245

<210> SEQ ID NO 478
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 478

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Pro Gly Tyr
            20                  25                  30

Trp Met Ser Trp Val Arg Gln Ala Pro Gly Lys Cys Leu Glu Trp Val
        35                  40                  45

Ala Asn Ile Asn Gln Asp Gly Ser Glu Val Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Asn Tyr Tyr Gly Asn Val Gly Asp Asp Tyr Trp Gly
            100                 105                 110

Gln Gly Thr Leu Val Thr Val Ser Ser Gly Gly Gly Ser Gly Gly Gly
        115                 120                 125

Gly Gly Ser Gly Gly Gly Ser Gly Gly Gly Ser Asp Ile Gln
    130                 135                 140

Met Thr Gln Ser Pro Ser Ser Leu Ser Ala Ser Val Gly Asp Arg Val
145                 150                 155                 160

Thr Ile Thr Cys Arg Ala Ser Gln Ser Ile Tyr Asn Tyr Leu Asn Trp
                165                 170                 175

Tyr Gln Gln Lys Pro Gly Lys Ala Pro Lys Leu Leu Ile Tyr Ala Ala
            180                 185                 190

Ser Ser Thr Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220
```

```
Ala Thr Tyr Tyr Cys Gln Gln Ala Phe His Val Pro Ile Thr Phe Gly
225                 230                 235                 240

Cys Gly Thr Lys Val Glu Ile Lys
                245

<210> SEQ ID NO 479
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Arg Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Asp Thr Pro Leu
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Thr Phe Ser Ser Tyr Trp
145                 150                 155                 160

Met Ser Trp Val Arg Gln Ala Pro Gly Lys Cys Leu Glu Trp Val Ala
                165                 170                 175

Asn Ile Asn Gln Asp Gly Ser Glu Val Tyr Tyr Val Asp Ser Val Lys
            180                 185                 190

Gly Arg Phe Thr Ile Ser Arg Asp Asn Ala Lys Asn Ser Leu Tyr Leu
        195                 200                 205

Gln Met Asn Ser Leu Arg Ala Glu Asp Thr Ala Val Tyr Tyr Cys Ala
    210                 215                 220

Arg Asp Val Gly Pro Gly Ile Ala Tyr Gln Gly His Phe Asp Tyr Trp
225                 230                 235                 240

Gly Gln Gly Thr Leu Val Thr Val Ser Ser
                245                 250

<210> SEQ ID NO 480
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Cys Leu Glu Trp Val
        35                  40                  45

Ala Asn Ile Asn Gln Asp Gly Ser Glu Val Tyr Tyr Val Asp Ser Val
 50                  55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
                85                  90                  95

Ala Arg Asp Val Gly Pro Gly Ile Ala Tyr Gln Gly His Phe Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Gly Gly Gly Gly Ser Asp
            130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Tyr Tyr Tyr Leu
            165                 170                 175

Asn Trp Tyr Gln Gln Lys Pro Gly Lys Ala Pro Lys Leu Leu Ile Tyr
            180                 185                 190

Ala Ala Ser Ser Arg Gln Ser Gly Val Pro Ser Arg Phe Ser Gly Ser
            195                 200                 205

Gly Ser Gly Thr Asp Phe Thr Leu Thr Ile Ser Ser Leu Gln Pro Glu
            210                 215                 220

Asp Phe Ala Thr Tyr Tyr Cys Gln Gln Val Tyr Asp Thr Pro Leu Thr
225                 230                 235                 240

Phe Gly Cys Gly Thr Lys Val Glu Ile Lys
            245                 250

<210> SEQ ID NO 481
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Asp Ile Gln Met Thr Gln Ser Pro Ser Ser Val Ser Ala Ser Val Gly
1               5                   10                  15

Asp Arg Val Thr Ile Thr Cys Glu Ala Ser Lys Gly Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Asp Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                   70                  75                  80

Glu Asp Phe Ala Thr Tyr Tyr Cys Gln Gln Ala Phe Leu Phe Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Gln

```
                115                 120                 125
Val Gln Leu Val Gln Ser Gly Ala Glu Val Lys Lys Pro Gly Ala Ser
        130                 135                 140

Val Lys Val Ser Cys Lys Ala Ser Gly Tyr Thr Phe Ser Asn Tyr Tyr
145                 150                 155                 160

Met His Trp Val Arg Gln Ala Pro Gly Gln Cys Leu Glu Trp Met Gly
                165                 170                 175

Trp Ile Asn Pro Phe Ser Gly Gly Thr Arg Tyr Ala Gln Lys Phe Gln
            180                 185                 190

Gly Arg Val Thr Met Thr Arg Asp Thr Ser Thr Ser Thr Val Tyr Met
        195                 200                 205

Glu Leu Ser Ser Leu Arg Ser Glu Asp Thr Ala Val Tyr Tyr Cys Ala
        210                 215                 220

Arg Asp Val Gly Ser Ser Ala Tyr Tyr Tyr Met Asp Val Trp Gly Lys
225                 230                 235                 240

Gly Thr Thr Val Thr Val Ser Ser
                245

<210> SEQ ID NO 482
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 482

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Tyr Met His Trp Val Arg Gln Ala Pro Gly Gln Cys Leu Glu Trp Met
        35                  40                  45

Gly Trp Ile Asn Pro Phe Ser Gly Gly Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Val Gly Ser Ser Ala Tyr Tyr Tyr Met Asp Val Trp Gly
            100                 105                 110

Lys Gly Thr Thr Val Thr Val Ser Gly Gly Gly Gly Ser Gly Gly
            115                 120                 125

Gly Gly Ser Gly Gly Gly Gly Ser Gly Gly Gly Gly Ser Asp Ile Gln
        130                 135                 140

Met Thr Gln Ser Pro Ser Ser Val Ser Ala Ser Val Gly Asp Arg Val
145                 150                 155                 160

Thr Ile Thr Cys Glu Ala Ser Lys Gly Ile Ser Ser Trp Leu Ala Trp
                165                 170                 175

Tyr Gln Gln Lys Pro Gly Lys Ala Pro Lys Leu Leu Ile Tyr Ala Ala
            180                 185                 190

Ser Asp Leu Gln Ser Gly Val Pro Ser Arg Phe Ser Gly Ser Gly Ser
        195                 200                 205

Gly Thr Asp Phe Thr Leu Thr Ile Ser Ser Leu Gln Pro Glu Asp Phe
    210                 215                 220
```

Ala Thr Tyr Tyr Cys Gln Gln Ala Phe Leu Phe Pro Pro Thr Phe Gly
225                 230                 235                 240

Cys Gly Thr Lys Val Glu Ile Lys
                245

<210> SEQ ID NO 483
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Asp Ser Pro Pro
                85                  90                  95

Pro Thr Phe Gly Cys Gly Thr Lys Val Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Gln Ser Gly Ala Glu Val Lys Lys Pro Gly Glu
    130                 135                 140

Ser Leu Lys Ile Ser Cys Lys Gly Ser Gly Tyr Ser Phe Thr Ser Tyr
145                 150                 155                 160

Trp Ile Gly Trp Val Arg Gln Met Pro Gly Lys Cys Leu Glu Trp Met
                165                 170                 175

Gly Ser Ile Tyr Pro Gly Asp Ser Asp Thr Arg Tyr Ser Pro Ser Phe
            180                 185                 190

Gln Gly Gln Val Thr Ile Ser Ala Asp Lys Ser Ile Ser Thr Ala Tyr
        195                 200                 205

Leu Gln Trp Ser Ser Leu Lys Ala Ser Asp Thr Ala Met Tyr Tyr Cys
    210                 215                 220

Ala Arg Glu Leu Ala Tyr Gly Asp Tyr Lys Gly Gly Val Asp Tyr Trp
225                 230                 235                 240

Gly Gln Gly Thr Leu Val Thr Val Ser Ser
                245                 250

<210> SEQ ID NO 484
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Glu Val Gln Leu Val Gln Ser Gly Ala Glu Val Lys Lys Pro Gly Glu
1               5                   10                  15

```
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Cys Leu Glu Trp Met
        35                  40                  45

Gly Ser Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Glu Leu Ala Tyr Gly Asp Tyr Lys Gly Gly Val Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Gly Gly Ser Glu Ile
    130                 135                 140

Val Leu Thr Gln Ser Pro Gly Thr Leu Ser Leu Ser Pro Gly Glu Arg
145                 150                 155                 160

Ala Thr Leu Ser Cys Arg Ala Ser Gln Ser Val Ser Ser Ser Phe Leu
                165                 170                 175

Ala Trp Tyr Gln Gln Lys Pro Gly Gln Ala Pro Arg Leu Leu Ile Tyr
            180                 185                 190

Gly Ala Ser Ser Arg Ala Thr Gly Ile Pro Asp Arg Phe Ser Gly Ser
        195                 200                 205

Gly Ser Gly Thr Asp Phe Thr Leu Thr Ile Ser Arg Leu Glu Pro Glu
    210                 215                 220

Asp Phe Ala Val Tyr Tyr Cys Gln Gln Leu Asp Ser Pro Pro Pro Thr
225                 230                 235                 240

Phe Gly Cys Gly Thr Lys Val Glu Ile Lys
                245                 250

<210> SEQ ID NO 485
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Val
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asp Ser Ser Ile Thr
                85                  90                  95

Phe Gly Cys Gly Thr Lys Leu Glu Ile Lys Gly Gly Gly Gly Ser Gly
            100                 105                 110

Gly Gly Gly Ser Gly Gly Gly Gly Ser Gly Gly Gly Gly Ser Gln Val
        115                 120                 125
```

Gln Leu Val Gln Ser Gly Ala Glu Val Lys Lys Pro Gly Ser Ser Val
            130                 135                 140

Lys Val Ser Cys Lys Ala Ser Gly Gly Thr Phe Ser Asp Tyr Ala Ile
145                 150                 155                 160

Ser Trp Val Arg Gln Ala Pro Gly Gln Cys Leu Glu Trp Met Gly Arg
                165                 170                 175

Ile Ile Pro Ile Leu Gly Val Ala Asp Tyr Ala Gln Lys Phe Gln Gly
                180                 185                 190

Arg Val Thr Ile Thr Ala Asp Lys Ser Thr Arg Thr Ala Tyr Met Glu
                195                 200                 205

Leu Ser Ser Leu Arg Ser Glu Asp Thr Ala Val Tyr Tyr Cys Ala Arg
    210                 215                 220

Asn Trp Ala Asp Ala Phe Asp Ile Trp Gly Gln Gly Thr Met Val Thr
225                 230                 235                 240

Val Ser Ser

<210> SEQ ID NO 486
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 486

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asp Tyr
                20                  25                  30

Ala Ile Ser Trp Val Arg Gln Ala Pro Gly Gln Cys Leu Glu Trp Met
            35                  40                  45

Gly Arg Ile Ile Pro Ile Leu Gly Val Ala Asp Tyr Ala Gln Lys Phe
        50                  55                  60

Gln Gly Arg Val Thr Ile Thr Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Ala Asp Ala Phe Asp Ile Trp Gly Gln Gly Thr Met
            100                 105                 110

Val Thr Val Ser Ser Gly Gly Gly Ser Gly Gly Gly Ser Gly
            115                 120                 125

Gly Gly Gly Ser Gly Gly Gly Ser Asp Ile Gln Leu Thr Gln Ser
        130                 135                 140

Pro Ser Ser Leu Ser Ala Ser Val Gly Asp Arg Val Thr Ile Thr Cys
145                 150                 155                 160

Arg Ala Ser Gln Gly Ile Ser Ser Val Leu Ala Trp Tyr Gln Gln Lys
                165                 170                 175

Pro Gly Lys Ala Pro Lys Leu Leu Ile Tyr Asp Ala Ser Ser Leu Glu
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Phe Asp Ser Ser Ile Thr Phe Gly Cys Gly Thr Lys Leu
225                 230                 235                 240

Glu Ile Lys

<210> SEQ ID NO 487
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Tyr
            20                  25                  30

Gly Ile Ser Phe Met Asn Trp Phe Gln Gln Lys Pro Gly Lys Ala Pro
        35                  40                  45

Lys Leu Leu Ile Tyr Ala Ala Ser Asn Gln Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Asp Asp Phe Ala Thr Tyr Tyr Cys Gln Gln Ser Lys
                85                  90                  95

Glu Val Pro Trp Thr Phe Gly Cys Gly Thr Lys Val Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Val Gln Ser Gly Ala Glu Val Lys Lys
    130                 135                 140

Pro Gly Ser Ser Val Lys Val Ser Cys Lys Ala Ser Gly Tyr Thr Phe
145                 150                 155                 160

Thr Asp Tyr Asn Met His Trp Val Arg Gln Ala Pro Gly Gln Cys Leu
                165                 170                 175

Glu Trp Ile Gly Tyr Ile Tyr Pro Tyr Asn Gly Gly Thr Gly Tyr Asn
            180                 185                 190

Gln Lys Phe Lys Ser Lys Ala Thr Ile Thr Ala Asp Glu Ser Thr Asn
        195                 200                 205

Thr Ala Tyr Met Glu Leu Ser Ser Leu Arg Ser Glu Asp Thr Ala Val
    210                 215                 220

Tyr Tyr Cys Ala Arg Gly Arg Pro Ala Met Asp Tyr Trp Gly Gln Gly
225                 230                 235                 240

Thr Leu Val Thr Val Ser Ser
                245

<210> SEQ ID NO 488
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Cys Leu Glu Trp Ile
            35                  40                  45

Gly Tyr Ile Tyr Pro Tyr Asn Gly Gly Thr Gly Tyr Asn Gln Lys Phe
    50                  55                  60

Lys Ser Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Arg Pro Ala Met Asp Tyr Trp Gly Gln Gly Thr Leu Val
            100                 105                 110

Thr Val Ser Ser Gly Gly Gly Gly Ser Gly Gly Gly Gly Ser Gly Gly
            115                 120                 125

Gly Gly Ser Gly Gly Gly Gly Ser Asp Ile Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Glu Ser Val Asp Asn Tyr Gly Ile Ser Phe Met Asn Trp Phe
                165                 170                 175

Gln Gln Lys Pro Gly Lys Ala Pro Lys Leu Leu Ile Tyr Ala Ala Ser
            180                 185                 190

Asn Gln Gly Ser Gly Val Pro Ser Arg Phe Ser Gly Ser Gly Ser Gly
        195                 200                 205

Thr Asp Phe Thr Leu Thr Ile Ser Ser Leu Gln Pro Asp Asp Phe Ala
    210                 215                 220

Thr Tyr Tyr Cys Gln Gln Ser Lys Glu Val Pro Trp Thr Phe Gly Cys
225                 230                 235                 240

Gly Thr Lys Val Glu Ile Lys
                245

<210> SEQ ID NO 489
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 489
gagatcgtgc tgacccagag ccccggcacc ctgagcctga gccccggcga gagggccacc      60
ctgagctgca gggccagcca gagcgtgagc agcagcttcc tggcctggta ccagcagaag     120
cccggccagg cccccaggct gctgatctac ggcgccagca gagggccac ggcatcccc      180 gacaggttca gcggcagcgg cagcggcacc gacttcaccc tgaccatcag caggctggag     240
cccgaggact tcgccgtgta ctactgccag caggccagca gcagcccccc caccttcggc     300
tgcggcacca aggtggagat caagggcggc ggcggcagcg gcggcggcgg cagcggcggc     360
ggcggcagcg gcggcggcgg cagcgaggtg cagctgctgg agagcggcgg cggcctggtg     420
cagcccggcg gcagcctgag gctgagctgc gccgccagcg gcttcacctt cagcagctac     480
gccatgagct gggtgaggca ggcccccggc aagtgcctgg agtgggtgag cgccatcagc     540
gccagcggcg gcagcaccta ctacgccgac agcgtgaagg gcaggttcac catcagcagg     600
gacaacagca agaacaccct gtacctgcag atgaacagcc tgagggccga ggacaccgcc     660
gtgtactact gcgccaggcc cagggcctac tacgacagca gcggcttcaa ggtgaactac     720
ggcatggacg tgtggggcca gggcaccacc gtgaccgtga gcagc                    765

<210> SEQ ID NO 490
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 490

```
gaggtgcagc tgctggagag cggcggcggc ctggtgcagc ccggcggcag cctgaggctg      60
agctgcgccg ccagcggctt caccttcagc agctacgcca tgagctgggt gaggcaggcc     120
cccggcaagt gcctggagtg ggtgagcgcc atcagcgcca gcggcggcag cacctactac     180
gccgacagcg tgaagggcag gttcaccatc agcagggaca cagcaagaa caccctgtac      240
ctgcagatga acagcctgag ggccgaggac accgccgtgt actactgcgc caggcccagg     300
gcctactacg acagcagcgg cttcaaggtg aactacggca tggacgtgtg gggccagggc     360
accaccgtga ccgtgagcag cggcggcggc ggcagcggcg gcggcggcag cggcggcggc     420
ggcagcggcg gcggcggcag cgagatcgtg ctgacccaga gccccggcac cctgagcctg     480
agccccggcg agagggccac cctgagctgc agggccagcc agagcgtgag cagcagcttc     540
ctggcctggt accagcagaa gcccggccag gcccccaggc tgctgatcta cggcgccagc     600
agcagggcca ccggcatccc cgacaggttc agcggcagcg gcagcggcac cgacttcacc     660
ctgaccatca gcaggctgga gcccgaggac ttcgccgtgt actactgcca gcaggccagc     720
agcagccccc ccaccttcgg ctgcggcacc aaggtggaga tcaag                     765
```

<210> SEQ ID NO 491
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 491

```
gagatcgtgc tgacccagag ccccggcacc ctgagcctga gccccggcga gagggccacc      60
ctgagctgca gggccagcca gagcgtgagc agcgactacc tggcctggta ccagcagaag     120
cccggccagg cccccaggct gctgatctac ggcgccagca gcagggccac cggcatcccc     180
gacaggttca gcggcagcgg cagcggcacc gacttcaccc tgaccatcag caggctggag     240
cccgaggact tcgccgtgta ctactgccag cagcacagca gcgccccccc caccttcggc     300
tgcggcacca aggtggagat caagggcggc ggcggcagcg gcggcggcgg cagcggcggc     360
ggcggcagcg gcggcggcgg cagcgaggtg cagctgctgg agagcggcgg cggcctggtg     420
cagcccggcg gcagcctgag gctgagctgc gccgccagcg gcttcacctt cagcagctac     480
gccatgagct gggtgaggca ggcccccggc aagtgcctgg agtgggtgag cggcatcagc     540
ggcagcggcg gcagcaccta ctacgccgac agcgtgaagg gcaggttcac catcagcagg     600
gacaacagca agaacaccct gtacctgcag atgaacagcc tgagggccga ggacaccgcc     660
gtgtactact gcgccaggga gggccacagc agcagctact acgaccacgc cttcgacatc     720
tggggccagg gcaccatggt gaccgtgagc agc                                  753
```

<210> SEQ ID NO 492
<211> LENGTH: 753
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 492
gaggtgcagc tgctggagag cggcggcggc ctggtgcagc ccggcggcag cctgaggctg      60
agctgcgccg ccagcggctt caccttcagc agctacgcca tgagctgggt gaggcaggcc     120
cccggcaagt gcctggagtg ggtgagcggc atcagcggca cggcggcag cacctactac     180 gccgacagcg tgaagggcag gttcaccatc agcagggaca acagcaagaa caccctgtac     240
ctgcagatga acagcctgag ggccgaggac accgccgtgt actactgcgc cagggagggc     300
cacagcagca gctactacga ccacgccttc gacatctggg gccagggcac catggtgacc     360
gtgagcagcg gcggcggcgg cagcggcggc ggcggcagcg gcggcggcgg cagcggcggc     420
ggcggcagcg agatcgtgct gacccagagc cccggcaccc tgagcctgag ccccggcgag     480
agggccaccc tgagctgcag ggccagccag agcgtgagca gcgactacct ggcctggtac     540
cagcagaagc ccgccaggc ccccaggctg ctgatctacg gcgccagcag cagggccacc     600
ggcatccccg acaggttcag cggcagcggc agcggcaccg acttcaccct gaccatcagc     660
aggctggagc ccgaggactt cgccgtgtac tactgccagc agcacagcag cgccccccc      720 accttcggct gcggcaccaa ggtggagatc aag                                  753

<210> SEQ ID NO 493
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 493
gagatcgtga tgacccagag ccccgccacc ctgagcgtga gccccggcga gagggccacc      60
ctgagctgca gggccagcca gagcgtgagc agcaacctgg cctggtacca gcagaagccc     120
ggccaggccc ccaggctgct gatctacggg ccagcacca gggccaccgg catccccgcc     180
aggttcagcg gcagcggcag cggcaccgag ttcccctga ccatcagcag cctgcagagc     240
gaggacttcg ccgtgtacta ctgccagcag tacaccgtgt acccccccac cttcggctgc     300
ggcaccaagg tggagatcaa gggcggcggc ggcagcggcg gcggcggcag cggcggcggc     360
ggcagcggcg gcggcggcag ccaggtgcag ctgcaggaga gcggccccgg cctggtgaag     420
cccagcgaga ccctgagcct gacctgcacc gtgagcggcg gcagcatcag cagctactac     480
tggagctgga tcaggcagcc ccccggcaag tgcctggagt ggatcggcag catctactac     540
agcggcagca ccaactacaa ccccagcctg aagagcaggg tgaccatcag cgtggacacc     600
agcaagaacc agttcagcct gaagctgagc agcgtgaccg ccgccgacac cgccgtgtac     660
tactgcgcca gggtgggcgg cgtgtacagc accatcgaga cctacggcat ggacgtgtgg     720
ggccagggca ccaccgtgac cgtgagcagc                                      750

<210> SEQ ID NO 494
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 494
```

```
caggtgcagc tgcaggagag cggccccggc ctggtgaagc ccagcgagac cctgagcctg    60
acctgcaccg tgagcggcgg cagcatcagc agctactact ggagctggat caggcagccc   120
cccggcaagt gcctggagtg gatcggcagc atctactaca gcggcagcac caactacaac   180
cccagcctga gagcagggt gaccatcagc gtggacacca gcaagaacca gttcagcctg   240
aagctgagca gcgtgaccgc cgccgacacc gccgtgtact actgcgccag ggtgggcggc   300
gtgtacagca ccatcgagac ctacggcatg gacgtgtggg gccagggcac caccgtgacc   360
gtgagcagcg cggcggcgg cagcggcggc ggcggcagcg cggcggcgg cagcggcggc   420
ggcggcagcg agatcgtgat gacccagagc cccgccaccc tgagcgtgag ccccggcgag   480
agggccaccc tgagctgcag ggccagccag agcgtgagca gcaacctggc ctggtaccag   540
cagaagcccg gccaggcccc caggctgctg atctacggcg ccagcaccag ggccaccggc   600
atccccgcca ggttcagcgg cagcggcagc ggcaccgagt tcaccctgac catcagcagc   660
ctgcagagcg aggacttcgc cgtgtactac tgccagcagt acaccgtgta ccccccccac   720
ttcggctgcg gcaccaaggt ggagatcaag                                    750

<210> SEQ ID NO 495
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 495
gagatcgtga tgacccagag ccccgccacc ctgagcctga gccccggcga gagggccacc    60
ctgagctgca gggccagcca gagcgtgagc agctacctgg cctggtacca gcagaagccc   120
ggccaggccc ccaggctgct gatctacgac gccagcaaca gggccaccgg catccccgcc   180
aggttcagcg gcagcggcag cggcaccgac ttcaccctga ccatcagcag cctggagccc   240
gaggacttcg ccgtgtacta ctgccagcag gaccacaact tcccctacac cttcggctgc   300
ggcaccaagg tggagatcaa gggcggcggc ggcagcggcg gcggcggcag cggcggcggc   360
ggcagcggcg gcggcggcag ccaggtgcag ctgcagcagt ggggcgccgg cctgctgaag   420
cccagcgaga ccctgagcct gacctgcgcc gtgtacggcg gcagcttcag cggctactac   480
tggagctgga tcaggcagcc ccccggcaag tgcctggagt ggatcggcga gatcgaccac   540
agcggcagca ccaactacaa ccccagcctg aagagcaggg tgaccatcag cgtggacacc   600
agcaagaacc agttcagcct gaagctgagc agcgtgaccg ccgccgacac cgccgtgtac   660
tactgcgcca gcagggcat ccacggcctg aggtacttcg acctgtgggg caggggcacc   720
ctggtgaccg tgagcagc                                                 738

<210> SEQ ID NO 496
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 496
caggtgcagc tgcagcagtg gggcgccggc ctgctgaagc ccagcgagac cctgagcctg    60
acctgcgccg tgtacggcgg cagcttcagc ggctactact ggagctggat caggcagccc   120
```

| | |
|---|---|
| cccggcaagt gcctggagtg gatcggcgag atcgaccaca gcggcagcac caactacaac | 180 |
| cccagcctga agagcagggt gaccatcagc gtggacacca gcaagaacca gttcagcctg | 240 |
| aagctgagca gcgtgaccgc cgccgacacc gccgtgtact actgcgccag cagggcatc | 300 |
| cacggcctga ggtacttcga cctgtggggc aggggcaccc tggtgaccgt gagcagcggc | 360 |
| ggcggcggca gcggcggcgg cggcagcggc ggcggcggca gcggcggcgg cggcagcgag | 420 |
| atcgtgatga cccagagccc cgccacccig agcctgagcc ccggcgagag ggccaccctg | 480 |
| agctgcaggg ccagccagag cgtgagcagc tacctggcct ggtaccagca gaagcccggc | 540 |
| caggcccca ggctgctgat ctacgacgcc agcaacaggg ccaccggcat ccccgccagg | 600 |
| ttcagcggca gcggcagcgg caccgacttc accctgacca tcagcagcct ggagcccgag | 660 |
| gacttcgccg tgtactactg ccagcaggac cacaacttcc cctacacctt cggctgcggc | 720 |
| accaaggtgg agatcaag | 738 |

<210> SEQ ID NO 497
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 497

| | |
|---|---|
| gacatccaga tgacccagag ccccagcagc ctgagcgcca gcgtgggcga cagggtgacc | 60 |
| atcacctgca gggccagcca gagcatcagc agctacctga actggtacca gcagaagccc | 120 |
| ggcaaggccc ccaagctgct gatctacgcc gccagcagcc tgcagagcgg cgtgcccagc | 180 |
| aggttcagcg gcagcggcag cggcaccgac ttcaccctga ccatcagcag cctgcagccc | 240 |
| gaggacttcg ccacctacta ctgccagcag cagtacgtga cccccatcac cttcggctgc | 300 |
| ggcaccaagg tggagatcaa gggcggcggc ggcagcggcg gcggcggcag cggcggcggc | 360 |
| ggcagcggcg gcggcggcag cgaggtgcag ctggtggaga gcggcggcgg cctggtgcag | 420 |
| cccggcggca gcctgaggct gagctgcgcc gccagcggct tcaccttcag cagctactgg | 480 |
| atgagctggg tgaggcaggc ccccggcaag tgcctggagt gggtggccaa catcaaccag | 540 |
| gacggcagcg agaagtacta cgtggacagc gtgaagggca ggttcaccat cagcagggac | 600 |
| aacgccaaga cagcctgta cctgcagatg aacagcctga ggccgagga caccgccgtg | 660 |
| tactactgcg ccagggaggc caactactac ggcaacgtgg cgacgacta ctggggccag | 720 |
| ggcaccctgg tgaccgtgag cagc | 744 |

<210> SEQ ID NO 498
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 498

| | |
|---|---|
| gaggtgcagc tggtggagag cggcggcggc ctggtgcagc ccggcggcag cctgaggctg | 60 |
| agctgcgccg ccagcggctt caccttcagc agctactgga tgagctgggt gaggcaggcc | 120 |
| cccggcaagt gcctggagtg ggtggccaac atcaaccagg acggcagcga gaagtactac | 180 |
| gtggacagcg tgaagggcag gttcaccatc agcagggaca acgccaagaa cagcctgtac | 240 |
| ctgcagatga acagcctgag gccgaggac accgccgtgt actactgcgc cagggaggcc | 300 |

```
aactactacg gcaacgtggg cgacgactac tggggccagg gcaccctggt gaccgtgagc    360
agcggcggcg gcggcagcgg cggcggcggc agcggcggcg gcggcagcgg cggcggcggc    420
agcgacatcc agatgaccca gagccccagc agcctgagcg ccagcgtggg cgacagggtg    480
accatcacct gcagggccag ccagagcatc agcagctacc tgaactggta ccagcagaag    540
cccggcaagg cccccaagct gctgatctac gccgccagca gcctgcagag cggcgtgccc    600
agcaggttca gcggcagcgg cagcggcacc gacttcaccc tgaccatcag cagcctgcag    660
cccgaggact cgccaccta ctactgccag cagcagtacg tgaccccat caccttcggc      720 tgcggcacca aggtggagat caag                                           744
```

<210> SEQ ID NO 499
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 499

```
gacatccaga tgacccagag ccccagcagc gtgagcgcca gcgtgggcga cagggtgacc    60
atcacctgca gggccagcca gggcatcagc agctggctgg cctggtacca gcagaagccc   120
ggcaaggccc ccaagctgct gatctacgcc gccagcaacc tgcagagcgg cgtgcccagc   180
aggttcagcg gcagcggcag cggcaccgac ttcaccctga ccatcagcag cctgcagccc   240
gaggacttcg ccacctacta ctgccagcag aagctgagcc tgcccctgac cttcggctgc   300
ggcaccaagg tggagatcaa gggcggcggc ggcagcggcg gcggcggcag cggcggcggc   360
ggcagcggcg gcggcggcag cgaggtgcag ctggtggaga gcggcggcgg cctggtgcag   420
cccggcggca gcctgaggct gagctgcgcc gccagcggct tcaccttcag cagctactgg   480
atgagctggg tgaggcaggc ccccggcaag tgcctggagt gggtggccaa catcaaccag   540
gacggcagcg agaagtacta cgtggacagc gtgaagggca ggttcaccat cagcagggac   600
aacgccaaga cagcctgta cctgcagatg aacagcctga ggccgagga caccgccgtg   660 tactactgcg ccagggaggg cggcgacagc tggtaccacg ccttcgacat ctggggccag   720
ggcaccatgg tgaccgtgag cagc                                           744
```

<210> SEQ ID NO 500
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 500

```
gaggtgcagc tggtggagag cggcggcggc ctggtgcagc ccggcggcag cctgaggctg    60
agctgcgccg ccagcggctt caccttcagc agctactgga tgagctgggt gaggcaggcc   120
cccggcaagt gcctggagtg ggtggccaac atcaaccagg acggcagcga gaagtactac   180
gtggacagcg tgaagggcag gttcaccatc agcagggaca acgccaagaa cagcctgtac   240
ctgcagatga acagcctgag ggccgaggac accgccgtgt actactgcgc caggagggc   300 ggcgacagct ggtaccacgc cttcgacatc tggggccagg gcaccatggt gaccgtgagc   360
agcggcggcg gcggcagcgg cggcggcggc agcggcggcg gcggcagcgg cggcggcggc   420
```

| | |
|---|---|
| agcgacatcc agatgaccca gagccccagc agcgtgagcg ccagcgtggg cgacagggtg | 480 |
| accatcacct gcagggccag ccagggcatc agcagctggc tggcctggta ccagcagaag | 540 |
| cccggcaagg cccccaagct gctgatctac gccgccagca acctgcagag cggcgtgccc | 600 |
| agcaggttca gcggcagcgg cagcggcacc gacttcaccc tgaccatcag cagcctgcag | 660 |
| cccgaggact cgccacccta ctactgccag cagaagctga gcctgcccct gaccttcggc | 720 |
| tgcggcacca aggtggagat caag | 744 |

```
<210> SEQ ID NO 501
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 501
```

| | |
|---|---|
| gacatccaga tgacccagag ccccagcagc ctgagcgcca gcgtgggcga cagggtgacc | 60 |
| atcacctgca gggccagcca gagcatcagc agctacctga actggtacca gcagaagccc | 120 |
| ggcaaggccc ccaagctgct gatctacggc gccagcagcc tgcagagcgg cgtgcccagc | 180 |
| aggttcagcg gcagcggcag cggcaccgac ttcaccctga ccatcagcag cctgcagccc | 240 |
| gaggacttcg ccacctacta ctgccagcag gtgtacagcg cccccttcac cttcggctgc | 300 |
| ggcaccaagg tggagatcaa gggcggcggc ggcagcggcg gcggcggcag cggcggcggc | 360 |
| ggcagcggcg gcggcggcag ccaggtgcag ctgcaggaga gcggcccggg cctggtgaag | 420 |
| cccagccaga ccctgagcct gacctgcacc gtgagcggcg gcagcatcag cagcggcggc | 480 |
| tactactgga gctggatcag gcagcacccc ggcaagtgcc tggagtggat cggcagcatc | 540 |
| tactacagcg gcagcaccta ctacaacccc agcctgaaga gcagggtgac catcagcgtg | 600 |
| gacaccagca gaaaccagtt cagcctgaag ctgagcagcg tgaccgccgc cgacaccgcc | 660 |
| gtgtactact gcgccaggga caggctggac tacagctaca ctacggcat ggacgtgtgg | 720 |
| ggccagggca ccaccgtgac cgtgagcagc | 750 |

```
<210> SEQ ID NO 502
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 502
```

| | |
|---|---|
| caggtgcagc tgcaggagag cggcccccggc ctggtgaagc ccagccagac cctgagcctg | 60 |
| acctgcaccg tgagcggcgg cagcatcagc agcggcggct actactggag ctggatcagg | 120 |
| cagcaccccg gcaagtgcct ggagtggatc ggcagcatct actacagcgg cagcacctac | 180 |
| tacaacccca gcctgaagag cagggtgacc atcagcgtgg acaccagcaa gaaccagttc | 240 |
| agcctgaagc tgagcagcgt gaccgccgcc gacaccgccg tgtactactg cgcccaggga c | 300 |
| aggctggact acagctacaa ctacggcatg gacgtgtggg gccagggcac caccgtgacc | 360 |
| gtgagcagcg gcggcggcgg cagcggcggc ggcggcagcg gcggcggcgg cagcggcggc | 420 |
| ggcggcagcg acatccagat gacccagagc cccagcagcc tgagcgccag cgtgggcgac | 480 |
| agggtgacca tcacctgcag ggccagccag agcatcagca gctacctgaa ctggtaccag | 540 |
| cagaagcccg gcaaggcccc caagctgctg atctacggcg ccagcagcct gcagagcggc | 600 |

```
gtgcccagca ggttcagcgg cagcggcagc ggcaccgact tcaccctgac catcagcagc    660
ctgcagcccg aggacttcgc cacctactac tgccagcagg tgtacagcgc ccccttcacc    720
ttcggctgcg gcaccaaggt ggagatcaag                                     750
```

<210> SEQ ID NO 503
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 503

```
gagatcgtgc tgacccagag ccccgccacc ctgagcctga gccccggcga gagggccacc     60
ctgagctgca gggccagcca gagcgtgagc agctacctgg cctggtacca gcagaagccc    120
ggccaggccc ccaggctgct gatctacgac gccagcaaca gggccaccgg catccccgcc    180
aggttcagcg gcagcggcag cggcaccgac ttcaccctga ccatcagcag cctggagccc    240
gaggacttcg ccgtgtacta ctgccagcag gtggacaact acccccccac cttcggctgc    300
ggcaccaagg tggagatcaa gggcggcggc ggcagcggcg gcggcggcag cggcggcggc    360
ggcagcggcg gcggcggcag ccaggtgcag ctgcaggaga gcggccccgg cctggtgaag    420
cccagcgaga ccctgagcct gacctgcgcc gtgagcggct acagcatcag cagcggctac    480
tactggggct ggatcaggca gccccccggc aagtgcctgg agtggatcgg cagcatctac    540
cacagcggca gcaccaacta caaccccagc ctgaagagcg ggtgaccat cagcgtggac    600 accagcaaga accagttcag cctgaagctg agcagcgtga ccgccgccga caccgccgtg    660
tactactgcg ccaggctgcc ccctggttc ggcttcagct acttcgacct gtggggcagg    720
ggcaccctgg tgaccgtgag cagc                                          744
```

<210> SEQ ID NO 504
<211> LENGTH: 744
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 504

```
caggtgcagc tgcaggagag cggccccggc ctggtgaagc ccagcgagac cctgagcctg     60
acctgcgccg tgagcggcta cagcatcagc agcggctact actggggctg gatcaggcag    120
ccccccggca agtgcctgga gtggatcggc agcatctacc acagcggcag caccaactac    180
aaccccagcc tgaagagcag ggtgaccatc agcgtggaca ccagcaagaa ccagttcagc    240
ctgaagctga gcagcgtgac cgccgccgac accgccgtgt actactgcgc caggctgccc    300 cctggttcg gcttcagcta cttcgacctg tggggcaggg gcaccctggt gaccgtgagc    360
agcggcggcg gcggcagcgg cggcggcggc agcggcggcg gcggcagcgg cggcggcggc    420
agcgagatcg tgctgaccca gagccccgcc accctgagcc tgagcccggg cgagagggcc    480
accctgagct gcagggccag ccagagcgtg agcagctacc tggcctggta ccagcagaag    540
cccggccagg cccccaggct gctgatctac gacgccagca cagggccac cggcatcccc    600 gccaggttca gcggcagcgg cagcggcacc gacttcaccc tgaccatcag cagcctggag    660
cccgaggact tcgccgtgta ctactgccag caggtggaca actaccccc caccttcggc    720
```
tgcggcacca aggtggagat caag                                              744

<210> SEQ ID NO 505
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 505
gacatccaga tgacccagag ccccagcagc ctgagcgcca gcgtgggcga cagggtgacc        60
atcacctgca gggccagcca gagcatcagc agctacctga actggtacca gcagaagccc       120
ggcaaggccc ccaagctgct gatctacgcc gccagcagcc tgcagagcgg cgtgcccagc       180
aggttcagcg gcagcggcag cggcaccgac ttcaccctga ccatcagcag cctgcagccc       240
gaggacttcg ccacctacta ctgccagcag gtgtacgaca ccccccctga cttcggctgc       300
ggcaccaagg tggagatcaa gggcggcggc ggcagcggcg gcggcggcag cggcggcggc       360
ggcagcggcg gcggcggcag cgaggtgcag ctggtggaga gcggcggcgg cctggtgcag       420
cccggcggca gcctgaggct gagctgcgcc gccagcggct tcaccttcag cagctactgg       480
atgagctggg tgaggcaggc ccccggcaag tgcctggagt gggtggccaa catcaagcag       540
gacggcagcg agaagtacta cgtggacagc gtgaagggcg ggttcaccat cagcagggac       600
aacgccaaga cagcctgta cctgcagatg aacagcctga gggccgagga caccgccgtg       660
tactactgcg ccagggacgt gggccccggc atcgcctacc agggccactt cgactactgg       720
ggccagggca ccctggtgac cgtgagcagc                                        750

<210> SEQ ID NO 506
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 506
gaggtgcagc tggtggagag cggcggcggc ctggtgcagc ccggcggcag cctgaggctg        60
agctgcgccg ccagcggctt caccttcagc agctactgga tgagctgggt gaggcaggcc       120
cccggcaagt gcctggagtg ggtggccaac atcaagcagg acggcagcga gaagtactac       180
gtggacagcg tgaagggcag gttcaccatc agcagggaca acgccaagaa cagcctgtac       240
ctgcagatga acagcctgag ggccgaggac accgccgtgt actactgcgc cagggacgtg       300
ggccccggca tcgcctacca gggccacttc gactactggg gccagggcac cctggtgacc       360
gtgagcagcg gcggcggcgg cagcggcggc ggcggcagcg gcggcggcgg cagcggcggc       420
ggcggcagcg acatccagat gacccagagc cccagcagcc tgagcgccag cgtgggcgac       480
agggtgacca tcacctgcag ggccagccag agcatcagca gctacctgaa ctggtaccag       540
cagaagcccg gcaaggcccc caagctgctg atctacgccg ccagcagcct gcagagcggc       600
gtgcccagca ggttcagcgg cagcggcagc ggcaccgact tcaccctgac catcagcagc       660
ctgcagcccg aggacttcgc cacctactac tgccagcagg tgtacgacac cccccctgacc      720
ttcggctgcg gcaccaaggt ggagatcaag                                        750

<210> SEQ ID NO 507
<211> LENGTH: 741

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 507

| | | | | | |
|---|---|---|---|---|---|
| gagatcgtgc | tgacccagag | ccccgccacc | ctgagcctga | gccccggcga | gagggccacc | 60 |
| ctgagctgca | gggccagcca | gagcgtgagc | agctacctgg | cctggtacca | gcagaagccc | 120 |
| ggccaggccc | ccaggctgct | gatctacgac | gccagcaaca | gggccaccgg | catccccgcc | 180 |
| aggttcagcg | gcagcggcag | cggcaccgac | ttcaccctga | ccatcagcag | cctggagccc | 240 |
| gaggacttcg | ccgtgtacta | ctgccagcag | tacgacaacc | tgcccacctt | cggctgcggc | 300 |
| accaaggtgg | agatcaaggg | cggcggcggc | agcggcggcg | gcggcagcgg | cggcggcggc | 360 |
| agcggcggcg | gcggcagcca | gctgcagctg | caggagagcg | gccccggcct | ggtgaagccc | 420 |
| agcgagaccc | tgagcctgac | ctgcaccgtg | agcggcggca | gcatcagcag | cagcagctac | 480 |
| tactggggct | ggatcaggca | gcccccggc | aagtgcctgg | agtggatcgg | cagcatctac | 540 |
| tacagcggca | gcacctacta | caaccccagc | ctgaagagca | gggtgaccat | cagcgtggac | 600 |
| accagcaaga | accagttcag | cctgaagctg | agcagcgtga | ccgccgccga | caccgccgtg | 660 |
| tactactgcg | ccagggagac | cgcccacgac | gtgcacggca | tggacgtgtg | gggccagggc | 720 |
| accaccgtga | ccgtgagcag | c | | | | 741 |

<210> SEQ ID NO 508
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 508

| | | | | | |
|---|---|---|---|---|---|
| cagctgcagc | tgcaggagag | cggccccggc | ctggtgaagc | ccagcgagac | cctgagcctg | 60 |
| acctgcaccg | tgagcggcgg | cagcatcagc | agcagcagct | actactgggg | ctggatcagg | 120 |
| cagccccccg | gcaagtgcct | ggagtggatc | ggcagcatct | actacagcgg | cagcacctac | 180 |
| tacaacccca | gcctgaagag | cagggtgacc | atcagcgtgg | acaccagcaa | gaaccagttc | 240 |
| agcctgaagc | tgagcagcgt | gaccgccgcc | gacaccgccg | tgtactactg | cgccagggag | 300 |
| accgcccacg | acgtgcacgg | catggacgtg | tggggccagg | gcaccaccgt | gaccgtgagc | 360 |
| agcggcggcg | gcggcagcgg | cggcggcggc | agcggcggcg | gcggcagcgg | cggcggcggc | 420 |
| agcgagatcg | tgctgaccca | gagccccgcc | accctgagcc | tgagccccgg | cgagagggcc | 480 |
| accctgagct | gcagggccag | ccagagcgtg | agcagctacc | tggcctggta | ccagcagaag | 540 |
| cccggccagg | cccccaggct | gctgatctac | gacgccagca | acagggccac | cggcatcccc | 600 |
| gccaggttca | gcggcagcgg | cagcggcacc | gacttcaccc | tgaccatcag | cagcctggag | 660 |
| cccgaggact | tcgccgtgta | ctactgccag | cagtacgaca | acctgcccac | cttcggctgc | 720 |
| ggcaccaagg | tggagatcaa | g | | | | 741 |

<210> SEQ ID NO 509
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 509

```
gagatcgtgc tgacccagag ccccgccacc ctgagcctga gccccggcga gagggccacc      60
ctgagctgca gggccagcca gagcgtgagc agctacctgg cctggtacca gcagaagccc     120
ggccaggccc ccaggctgct gatctacgac gccagcaaga gggccaccgg catccccgcc     180
aggttcagcg gcagcggcag cggcaccgac ttcaccctga ccatcagcag cctggagccc     240
gaggacttcg ccgtgtacta ctgccagcag agcagcaacc accccagcac cttcggctgc     300
ggcaccaagg tggagatcaa gggcggcggc ggcagcggcg gcggcggcag cggcggcggc     360
ggcagcggcg gcggcggcag ccaggtgcag ctggtgcaga gcggcgccga ggtgaagaag     420
cccggcagca gcgtgaaggt gagctgcaag gccagcggcg gcaccttcag cagctacgcc     480
atcagctggg tgaggcaggc ccccggccag tgcctggagt ggatgggcag catcatcccc     540
atcttcggca ccgccaacta cgcccagaag ttccagggca gggtgaccat caccgccgac     600
gagagcacca gcaccgccta catggagctg agcagcctga ggagcgagga caccgccgtg     660
tactactgcg ccagggaggt gggctacggc tggtacacca agatcgcctt cgacatctgg     720
ggccagggca ccatggtgac cgtgagcagc                                      750
```

<210> SEQ ID NO 510
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 510

```
caggtgcagc tggtgcagag cggcgccgag gtgaagaagc ccggcagcag cgtgaaggtg      60
agctgcaagg ccagcggcgg caccttcagc agctacgcca tcagctgggt gaggcaggcc     120
cccggccagt gcctggagtg gatgggcagc atcatcccca tcttcggcac cgccaactac     180
gcccagaagt tccagggcag ggtgaccatc accgccgacg agagcaccag caccgcctac     240
atggagctga gcagcctgag gagcgaggac accgccgtgt actactgcgc cagggaggtg     300
ggctacggct ggtacaccaa gatcgccttc gacatctggg gccagggcac catggtgacc     360
gtgagcagcg gcggcggcgg cagcggcggc ggcggcagcg gcggcggcgg cagcggcggc     420
ggcggcagcg agatcgtgct gacccagagc cccgccaccc tgagcctgag ccccggcgag     480
agggccaccc tgagctgcag ggccagccag agcgtgagca gctacctggc ctggtaccag     540
cagaagcccg gccaggcccc caggctgctg atctacgacg ccagcaagag ggccaccggc     600
atccccgcca ggttcagcgg cagcggcagc ggcaccgact tcaccctgac catcagcagc     660
ctggagcccg aggacttcgc cgtgtactac tgccagcaga gcagcaacca ccccagcacc     720
ttcggctgcg gcaccaaggt ggagatcaag                                      750
```

<210> SEQ ID NO 511
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 511

```
gacatcgtga tgacccagag ccccctgagc ctgccgtga cccccggcga gccgccagc        60
```

| | | |
|---|---|---|
| atcagctgca ggagcagcca gagcctgctg cacagcaacg gctacaacta cctggactgg | 120 | |
| tacctgcaga agcccggcca gagcccccag ctgctgatct acctgggcag caacagggcc | 180 | |
| agcggcgtgc ccgacaggtt cagcggcagc ggcagcggca ccgacttcac cctgaagatc | 240 | |
| agcagggtgg aggccgagga cgtgggcgtg tactactgca tgcaggccct gggcgtgccc | 300 | |
| ctgaccttcg gctgcggcac caaggtggag atcaagggcg gcggcggcag cggcggcggc | 360 | |
| ggcagcggcg gcggcggcag cggcggcggc ggcagccagg tgcagctggt gcagagcggc | 420 | |
| gccgaggtga agaagcccgg cgccagcgtg aaggtgagct gcaaggccag cggctacacc | 480 | |
| ttcaccagct actacatgca ctgggtgagg caggcccccg gccagtgcct ggagtggatg | 540 | |
| ggcatcatca accccagcgg cggcagcacc acctacgccc agaagttcca gggcagggtg | 600 | |
| accatgacca gggacaccag caccagcacc gtgtacatgg agctgagcag cctgaggagc | 660 | |
| gaggacaccg ccgtgtacta ctgcgccagg gaggccgccg acggcttcgt gggcgagagg | 720 | |
| tacttcgacc tgtggggcag ggcaccctg gtgaccgtga gcagc | 765 | |

<210> SEQ ID NO 512
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 512

| | | |
|---|---|---|
| caggtgcagc tggtgcagag cggcgccgag gtgaagaagc ccggcgccag cgtgaaggtg | 60 | |
| agctgcaagg ccagcggcta caccttcacc agctactaca tgcactgggt gaggcaggcc | 120 | |
| cccggccagt gcctggagtg gatgggcatc atcaacccca gcggcggcag caccacctac | 180 | |
| gcccagaagt tccagggcag ggtgaccatg accagggaca ccagcaccag caccgtgtac | 240 | |
| atggagctga gcagcctgag gagcgaggac accgccgtgt actactgcgc cagggaggcc | 300 | |
| gccgacggct tcgtgggcga ggtacttc gacctgtggg gcaggggcac cctggtgacc | 360 | |
| gtgagcagcg gcggcggcgg cagcggcggc ggcggcagcg gcggcggcgg cagcggcggc | 420 | |
| ggcggcagcg acatcgtgat gacccagagc cccctgagcc tgcccgtgac ccccggcgag | 480 | |
| cccgccagca tcagctgcag gagcagccag agcctgctgc acagcaacgg ctacaactac | 540 | |
| ctggactggt acctgcagaa gcccggccag agcccccagc tgctgatcta cctgggcagc | 600 | |
| aacagggcca gcggcgtgcc cgacaggttc agcggcagcg gcagcggcac cgacttcacc | 660 | |
| ctgaagatca gcagggtgga ggccgaggac gtgggcgtgt actactgcat gcaggccctg | 720 | |
| ggcgtgcccc tgaccttcgg ctgcggcacc aaggtggaga tcaag | 765 | |

<210> SEQ ID NO 513
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 513

| | | |
|---|---|---|
| gacatcgtga tgacccagag ccccctgagc ctgcccgtga ccccggcga gcccgccagc | 60 | |
| atcagctgca ggagcagcca gagcctgctg tacagcaacg gctacaacta cctggactgg | 120 | |
| tacctgcaga agcccggcca gagcccccag ctgctgatct acctgggcag caacagggcc | 180 | |
| agcggcgtgc ccgacaggtt cagcggcagc ggcagcggca ccgacttcac cctgaagatc | 240 | |

```
agcagggtgg aggccgagga cgtgggcgtg tactactgca tgcaggacgt ggccctgccc      300
atcaccttcg gctgcggcac caaggtggag atcaagggcg gcggcggcag cggcggcggc      360
ggcagcggcg gcggcggcag cggcggcggc ggcagccagg tgcagctggt gcagagcggc      420
gccgaggtga agaagcccgg cgccagcgtg aaggtgagct gcaaggccag cggctacacc      480
ttcagcggct actacatgca ctgggtgagg caggcccccg gccagtgcct ggagtggatg      540
ggcatgatca ccccctacgg cggcagcacc aggtacgccc agaagttcca gggcagggtg      600
accatgacca gggacaccag caccagcacc gtgtacatgg agctgagcag cctgaggagc      660
gaggacaccg ccgtgtacta ctgcgccagg gaggccgccg acggcttcgt gggcgagagg      720
tacttcgacc tgtggggcag gggcaccctg gtgaccgtga gcagc                      765
```

<210> SEQ ID NO 514
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 514

```
caggtgcagc tggtgcagag cggcgccgag gtgaagaagc ccggcgccag cgtgaaggtg       60
agctgcaagg ccagcggcta caccttcagc ggctactaca tgcactgggt gaggcaggcc      120
cccggccagt gcctggagtg gatgggcatg atcaacccct acggcggcag caccaggtac      180
gcccagaagt tccagggcag ggtgaccatg accagggaca ccagcaccag caccgtgtac      240
atggagctga gcagcctgag gagcgaggac accgccgtgt actactgcgc cagggaggcc      300
gccgacggct tcgtgggcga gaggtacttc gacctgtggg gcaggggcac cctggtgacc      360
gtgagcagcg cggcggcggc cagcggcggc ggcggcagcg gcggcggcgg cagcggcggc      420
ggcggcagca catcgtgat gacccagagc cccctgagcc tgcccgtgac ccccggcgag      480
cccgccagca tcagctgcag gagcagccag agcctgctgt acagcaacgg ctacaactac      540
ctggactggt acctgcagaa gcccggccag agcccccagc tgctgatcta cctgggcagc      600
aacagggcca gcggcgtgcc cgacaggttc agcggcagcg gcagcggcac cgacttcacc      660
ctgaagatca gcagggtgga ggccgaggac gtgggcgtgt actactgcat gcaggacgtg      720
gccctgccca tcaccttcgg ctgcggcacc aaggtggaga tcaag                      765
```

<210> SEQ ID NO 515
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 515

```
gacatccaga tgacccagag ccccagcagc gtgagcgcca gcgtgggcga cagggtgacc       60
atcacctgca gggccagcca gggcatcgac agctggctgg cctggtacca gcagaagccc      120
ggcaaggccc ccaagctgct gatctacgcc gccagcagcc tgcagagcgg cgtgcccagc      180
aggttcagcg gcagcggcag cggcaccgac ttcaccctga ccatcagcag cctgcagccc      240
gaggacttcg ccacctacta ctgccagcag gcccacagtc accccctgac cttcggctgc      300
ggcaccaagg tggagatcaa gggcggcggc ggcagcggcg gcggcggcag cggcggcggc      360
```

```
ggcagcggcg gcggcggcag ccaggtgcag ctggtgcaga gcggcgccga ggtgaagaag      420
cccggcgcca gcgtgaaggt gagctgcaag gccagcggct acaccttcga gatctactac      480
atgcactggg tgaggcaggc ccccggccag tgcctggagt ggatgggcat catcaacccc      540
agcagcggca gcaccgtgta cgcccagaag ttcagggca gggtgaccat gaccagggac       600
accagcacca gcaccgtgta catggagctg agcagcctga ggagcgagga caccgccgtg      660
tactactgcg ccaggggcgc cggctacgac gacgaggaca tggacgtgtg gggcaagggc      720
accaccgtga ccgtgagcag c                                                741
```

<210> SEQ ID NO 516
<211> LENGTH: 741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 516

```
caggtgcagc tggtgcagag cggcgccgag gtgaagaagc ccggcgccag cgtgaaggtg      60
agctgcaagg ccagcggcta caccttcgag atctactaca tgcactgggt gaggcaggcc    120
cccggccagt gcctggagtg gatgggcatc atcaaccca gcagcggcag caccgtgtac      180
gcccagaagt tcagggcag ggtgaccatg accaggggac ccagcaccag caccgtgtac       240
atggagctga gcagcctgag gagcgaggac accgccgtgt actactgcgc caggggcgcc    300
ggctacgacg acgaggacat ggacgtgtgg ggcaagggca ccaccgtgac cgtgagcagc    360
ggcggcggcg gcagcggcgg cggcggcagc ggcggcggcg gcagcggcgg cggcggcagc    420
gacatccaga tgacccagag ccccagcagc gtgagcgcca gcgtgggcga cagggtgacc     480
atcacctgca gggccagcca gggcatcgac agctggctgg cctggtacca gcagaagccc    540
ggcaaggccc ccaagctgct gatctacgcc gccagcagcc tgcagagcgg cgtgcccagc    600
aggttcagcg gcagcggcag cggcaccgac ttcaccctga ccatcagcag cctgcagccc    660
gaggacttcg ccacctacta ctgccagcag gcccacagct accccctgac cttcggctgc    720
ggcaccaagg tggagatcaa g                                               741
```

<210> SEQ ID NO 517
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 517

```
gacatccaga tgacccagag ccccagcagc ctgagcgcca gcgtgggcga cagggtgacc     60
atcacctgca gggccagcca gagcatctac aactacctga actggtacca gcagaagccc    120
ggcaaggccc ccaagctgct gatctacgcc gccagcaacc tgcacagcgg cgtgcccagc    180
aggttcagcg gcagcggcag cggcaccgac ttcaccctga ccatcagcag cctgcagccc    240
gaggacttcg ccacctacta ctgccagcag gccttccacg tgcccatcac cttcggctgc    300
ggcaccaagg tggagatcaa gggcggcggc ggcagcggcg gcggcggcag cggcggcggc    360
ggcagcggcg gcggcggcag cgaggtgcag ctggtggaga gcggcggcgg cctggtgcag    420
cccggcggca gcctgaggct gagctgcgcc gccagcggct tcaccttcgg cggctactgg    480
atgagctggg tgaggcaggc ccccggcaag tgcctggagt gggtggccaa catcaaccag    540
```

```
gacggcagcg aggagtacta cgtggacagc gtgaagggca ggttcaccat cagcagggac    600
aacgccaaga acagcctgta cctgcagatg aacagcctga ggccgagga caccgccgtg    660 tactactgcg ccagggaggc caactactac ggcaacgtgg cgacgacta ctggggccag    720 ggcaccctgg tgaccgtgag cagc                                          744
```

<210> SEQ ID NO 518
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 518

```
gaggtgcagc tggtggagag cggcggcggc ctggtgcagc ccggcggcag cctgaggctg     60
agctgcgccg ccagcggctt caccttcggc ggctactgga tgagctgggt gaggcaggcc    120
cccggcaagt gcctggagtg ggtggccaac atcaaccagg acggcagcga ggagtactac    180
gtggacagcg tgaagggcag gttcaccatc agcagggaca acgccaagaa cagcctgtac    240
ctgcagatga acagcctgag gccgaggac accgccgtgt actactgcgc cagggaggcc    300
aactactacg gcaacgtggg cgacgactac tggggccagg gcaccctggt gaccgtgagc    360
agcggcggcg gcggcagcgg cggcggcggc agcggcggcg gcggcagcgg cggcggcggc    420
agcgacatcc agatgaccca gagccccagc agcctgagcg ccagcgtggg cgacagggtg    480
accatcacct gcagggccag ccagagcatc tacaactacc tgaactggta ccagcagaag    540
cccggcaagg cccccaagct gctgatctac gccgccagca acctgcacag cggcgtgccc    600
agcaggttca gcggcagcgg cagcggcacc gacttcaccc tgaccatcag cagcctgcag    660
cccgaggact tcgccaccta ctactgccag caggccttcc acgtgccat caccttcggc    720 tgcggcacca aggtggagat caag                                          744
```

<210> SEQ ID NO 519
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 519

```
gacatccaga tgacccagag ccccagcagc ctgagcgcca gcgtgggcga cagggtgacc     60
atcacctgca gggccagcca gagcatctac aactacctga actggtacca gcagaagccc    120
ggcaaggccc ccaagctgct gatctacgcc gccagcagca acctgcacag cggcgtgccc    180
agcaggttca gcggcagcgg cagcggcacc gacttcaccc tgaccatcag cagcctgcag    240
cccgaggact tcgccaccta ctactgccag caggccttcc acgtgccat caccttcggc    300 tgcggcacca aggtggagat caagggcggc ggcggcagcg gcggcggcag cggcggcggc    360
ggcagcggcg gcggcggcag cgaggtgcag ctggtggaga gcggcggcgg cctggtgcag    420
cccggcggca gcctgaggct gagctgcgcc gccagcggct tcaccttccc cggctactgg    480
atgagctggg tgaggcaggc ccccggcaag tgcctggagt gggtggccaa catcaaccag    540
gacggcagcg aggtgtacta cgtggacagc gtgaagggca ggttcaccat cagcagggac    600
aacgccaaga acagcctgta cctgcagatg aacagcctga gggccgagga caccgccgtg    660
```

```
tactactgcg ccagggaggc caactactac ggcaacgtgg gcgacgacta ctggggccag    720
ggcaccctgg tgaccgtgag cagc                                          744
```

<210> SEQ ID NO 520
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 520

```
gaggtgcagc tggtggagag cggcggcggc ctggtgcagc ccggcggcag cctgaggctg    60
agctgcgccg ccagcggctt caccttcccc ggctactgga tgagctgggt gaggcaggcc    120
cccggcaagt gcctggagtg ggtggccaac atcaaccagg acggcagcga ggtgtactac    180
gtggacagcg tgaagggcag gttcaccatc agcagggaca acgccaagaa cagcctgtac    240
ctgcagatga acagcctgag ggccgaggac accgccgtgt actactgcgc cagggaggcc    300
aactactacg gcaacgtggg cgacgactac tggggccagg gcaccctggt gaccgtgagc    360
agcggcggcg gcggcagcgg cggcggcggc agcggcggcg gcggcagcgg cggcggcggc    420
agcgacatcc agatgaccca gagccccagc agcctgagcg ccagcgtggg cgacagggtg    480
accatcacct gcagggccag ccagagcatc tacaactacc tgaactggta ccagcagaag    540
cccggcaagg cccccaagct gctgatctac gccgccagca cacccagag cggcgtgccc    600 agcaggttca gcggcagcgg cagcggcacc gacttcaccc tgaccatcag cagcctgcag    660
cccgaggact tcgccaccta ctactgccag caggccttcc acgtgcccat caccttcggc    720
tgcggcacca aggtggagat caag                                          744
```

<210> SEQ ID NO 521
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 521

```
gacatccaga tgacccagag ccccagcagc ctgagcgcca gcgtgggcga cagggtgacc    60
atcacctgca gggccagcca gagcatctac tactacctga actggtacca gcagaagccc    120
ggcaaggccc ccaagctgct gatctacgcc gccagcagca gcagagcgg cgtgcccagc    180 aggttcagcg gcagcggcag cggcaccgac ttcaccctga ccatcagcag cctgcagccc    240
gaggacttcg ccacctacta ctgccagcag gtgtacgaca ccccctgac cttcggctgc    300 ggcaccaagg tggagatcaa gggcggcggc ggcagcggcg gcggcggcag cggcggcggc    360
ggcagcggcg gcggcggcag cgaggtgcag ctggtggaga gcggcggcgg cctggtgcag    420
cccggcggca gcctgaggct gagctgcgcc gccagcggct tcaccttcag cagctactgg    480
atgagctggg tgaggcaggc ccccggcaag tgcctggagt gggtggccaa catcaaccag    540
gacggcagcg aggtgtacta cgtggacagc gtgaagggca ggttcaccat cagcaggac    600 aacgccaaga acagcctgta cctgcagatg aacagcctga gggccgagga caccgccgtg    660
tactactgcg ccagggacgt gggccccggc atcgcctacc agggccactt cgactactgg    720
ggccagggca ccctggtgac cgtgagcagc                                    750
```

```
<210> SEQ ID NO 522
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 522
gaggtgcagc tggtggagag cggcggcggc ctggtgcagc ccggcggcag cctgaggctg      60
agctgcgccg ccagcggctt caccttcagc agctactgga tgagctgggt gaggcaggcc     120
cccggcaagt gcctggagtg ggtggccaac atcaaccagg acggcagcga ggtgtactac     180
gtggacagcg tgaagggcag gttcaccatc agcagggaca cgccaagaa cagcctgtac      240 ctgcagatga acagcctgag ggccgaggac accgccgtgt actactgcgc cagggacgtg     300
ggccccggca tcgcctacca gggccacttc gactactggg gccagggcac cctggtgacc     360
gtgagcagcg gcggcggcgg cagcggcggc ggcggcagcg gcggcggcgg cagcggcggc     420
ggcggcagcg acatccagat gacccagagc cccagcagcc tgagcgccag cgtgggcgac     480
agggtgacca tcacctgcag ggccagccag agcatctact actacctgaa ctggtaccag     540
cagaagcccg gcaaggcccc caagctgctg atctacgccg ccagcagcag gcagagcggc     600
gtgcccagca ggttcagcgg cagcggcagc ggcaccgact tcaccctgac catcagcagc     660
ctgcagcccg aggacttcgc cacctactac tgccagcagg tgtacgacac cccccctgacc    720 ttcggctgcg gcaccaaggt ggagatcaag                                      750

<210> SEQ ID NO 523
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 523
gacatccaga tgacccagag ccccagcagc gtgagcgcca gcgtgggcga cagggtgacc      60
atcacctgcg aggccagcaa gggcatcagc agctggctgg cctggtacca gcagaagccc     120
ggcaaggccc ccaagctgct gatctacgcc gccagcgacc tgcagagcgg cgtgcccagc     180
aggttcagcg gcagcggcag cggcaccgac ttcaccctga ccatcagcag cctgcagccc     240
gaggacttcg ccacctacta ctgccagcag gccttcctgt ccccccccac cttcggctgc     300
ggcaccaagg tggagatcaa gggcggcggc ggcagcggcg gcggcggcag cggcggcggc     360
ggcagcggcg gcggcggcag ccaggtgcag ctggtgcaga gcggcgccga ggtgaagaag     420
cccggcgcca gcgtgaaggt gagctgcaag gccagcggct acaccttcag caactactac     480
atgcactggg tgaggcaggc ccccggccag tgcctggagt ggatgggctg atcaaccccc     540
ttcagcggcg gcaccaggta cgcccagaag ttccagggca gggtgaccat gaccagggac     600
accagcacca gcaccgtgta catggagctg agcagcctga ggagcgagga caccgccgtg     660
tactactgcg ccagggacgt gggcagcagc gcctactact acatggacgt gtggggcaag     720
ggcaccaccg tgaccgtgag cagc                                            744

<210> SEQ ID NO 524
<211> LENGTH: 744
<212> TYPE: DNA
<213> ORGANISM: Artificial Sequence
<220> FEATURE:
```

<223> OTHER INFORMATION: Description of Artificial Sequence: Synthetic
polynucleotide

<400> SEQUENCE: 524

```
caggtgcagc tggtgcagag cggcgccgag gtgaagaagc ccggcgccag cgtgaaggtg    60
agctgcaagg ccagcggcta caccttcagc aactactaca tgcactgggt gaggcaggcc   120
cccggccagt gcctggagtg gatgggctgg atcaacccct tcagcggcgg caccaggtac   180
gcccagaagt tccagggcag ggtgaccatg accaggaca ccagcaccag caccgtgtac   240
atggagctga gcagcctgag gagcgaggac accgccgtgt actactgcgc cagggacgtg   300
ggcagcagcg cctactacta catggacgtg tggggcaagg gcaccaccgt gaccgtgagc   360
agcggcggcg gcggcagcgg cggcggcggc agcggcggcg gcggcagcgg cggcggcggc   420
agcgacatcc agatgaccca gagccccagc agcgtgagcg ccagcgtggg cgacagggtg   480
accatcacct gcgaggccag caagggcatc agcagctggc tggcctggta ccagcagaag   540
cccggcaagg cccccaagct gctgatctac gccgccagcg acctgcagag cggcgtgccc   600
agcaggttca gcggcagcgg cagcggcacc gacttcaccc tgaccatcag cagcctgcag   660
cccgaggact cgccaccta ctactgccag caggccttcc tgttcccccc caccttcggc   720
tgcggcacca aggtggagat caag                                          744
```

<210> SEQ ID NO 525
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 525

```
gagatcgtgc tgacccagag ccccggcacc ctgagcctga gccccggcga gagggccacc    60
ctgagctgca gggccagcca gagcgtgagc agcagcttcc tggcctggta ccagcagaag   120
cccggccagg cccccaggct gctgatctac ggcgccagca gagggccac cggcatcccc   180
gacaggttca gcggcagcgg cagcggcacc gacttcaccc tgaccatcag caggctggag   240
cccgaggact tcgccgtgta ctactgccag cagctggaca gcccccccc caccttcggc   300
tgcggcacca aggtggagat caagggcggc ggcggcagcg gcggcggcgg cagcggcggc   360
ggcggcagcg gcggcggcgg cagcgaggtg cagctggtgc agagcggcgc cgaggtgaag   420
aagcccggcg agagcctgaa gatcagctgc aagggcagcg gctacagctt caccagctac   480
tggatcggct gggtgaggca gatgcccggc aagtgcctgg agtggatggg cagcatctac   540
cccggcgaca gcgacaccag gtacagcccc agcttccagg gccaggtgac catcagcgcc   600
gacaagagca tcagcaccgc ctacctgcag tggagcagcc tgaaggccag cgacaccgcc   660
atgtactact gcgccaggga gctggcctac ggcgactaca agggcggcgt ggactactgg   720
ggccagggca cctggtgac cgtgagcagc                                     750
```

<210> SEQ ID NO 526
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 526

-continued

```
gaggtgcagc tggtgcagag cggcgccgag gtgaagaagc ccggcgagag cctgaagatc    60
agctgcaagg gcagcggcta cagcttcacc agctactgga tcggctgggt gaggcagatg   120
cccggcaagt gcctggagtg gatgggcagc atctaccccg gcgacagcga caccaggtac   180
agccccagct tccagggcca ggtgaccatc agcgccgaca gagcatcag caccgcctac    240 ctgcagtgga gcagcctgaa ggccagcgac accgccatgt actactgcgc cagggagctg   300
gcctacggcg actacaaggg cggcgtggac tactggggcc agggcaccct ggtgaccgtg   360
agcagcggcg gcggcggcag cggcggcggc ggcagcggcg gcggcggcag cggcggcggc   420
ggcagcgaga tcgtgctgac ccagagcccc ggcaccctga gcctgagccc cggcgagagg   480
gccaccctga gctgcagggc cagccagagc gtgagcagca gcttcctggc ctggtaccag   540
cagaagcccg gccaggcccc caggctgctg atctacggcg ccagcagcag ggccaccggc   600
atccccgaca ggttcagcgg cagcggcagc ggcaccgact caccctgac catcagcagg    660 ctggagcccg aggacttcgc cgtgtactac tgccagcagc tggacagccc ccccccacc   720 ttcggctgcg gcaccaaggt ggagatcaag                                    750
```

<210> SEQ ID NO 527
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (4)..(4)
<223> OTHER INFORMATION: Ala, Val, Leu, Ile, Pro, Phe, Trp, Gly, Ser,
      Thr, Cys, Asn, Gln, or Tyr

<400> SEQUENCE: 527

Gly Ala Pro Xaa Gly Ala Ala Ala Gly Trp Phe Asp Pro
1               5                   10

<210> SEQ ID NO 528
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Phe Thr Phe Ser Ser Tyr Ala Met Ser
1               5

<210> SEQ ID NO 529
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Ala Arg Pro Arg Ala Tyr Tyr Asp Ser Ser Gly Phe Lys Val Asn Tyr
1               5                   10                  15

Gly Met Asp Val
            20

<210> SEQ ID NO 530
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Phe Thr Phe Ser Ser Tyr Ala Met Ser
1               5

<210> SEQ ID NO 531
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Ala Arg Glu Gly His Ser Ser Ser Tyr Tyr Asp His Ala Phe Asp Ile
1               5                   10                  15

<210> SEQ ID NO 532
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

Gly Ser Ile Ser Ser Tyr Tyr Trp Ser
1               5

<210> SEQ ID NO 533
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ala Arg Val Gly Gly Val Tyr Ser Thr Ile Glu Thr Tyr Gly Met Asp
1               5                   10                  15

Val

<210> SEQ ID NO 534
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Gly Ser Phe Ser Gly Tyr Tyr Trp Ser
1               5

<210> SEQ ID NO 535
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535
```

Ala Arg Gln Gly Ile His Gly Leu Arg Tyr Phe Asp Leu
1               5                   10

<210> SEQ ID NO 536
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Phe Thr Phe Ser Ser Tyr Trp Met Ser
1               5

<210> SEQ ID NO 537
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Ala Arg Glu Ala Asn Tyr Tyr Gly Asn Val Gly Asp Asp Tyr
1               5                   10

<210> SEQ ID NO 538
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Phe Thr Phe Ser Ser Tyr Trp Met Ser
1               5

<210> SEQ ID NO 539
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Ala Arg Glu Gly Gly Asp Ser Trp Tyr His Ala Phe Asp Ile
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gly Ser Ile Ser Ser Gly Gly Tyr Tyr Trp Ser
1               5                   10

<210> SEQ ID NO 541
<211> LENGTH: 15
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 541

Ala Arg Asp Arg Leu Asp Tyr Ser Tyr Asn Tyr Gly Met Asp Val
1               5                   10                  15

<210> SEQ ID NO 542
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Tyr Ser Ile Ser Ser Gly Tyr Tyr Trp Gly
1               5                   10

<210> SEQ ID NO 543
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Ala Arg Leu Pro Pro Trp Phe Gly Phe Ser Tyr Phe Asp Leu
1               5                   10

<210> SEQ ID NO 544
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544

Phe Thr Phe Ser Ser Tyr Trp Met Ser
1               5

<210> SEQ ID NO 545
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Ala Arg Asp Val Gly Pro Gly Ile Ala Tyr Gln Gly His Phe Asp Tyr
1               5                   10                  15

<210> SEQ ID NO 546
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Gly Ser Ile Ser Ser Ser Ser Tyr Tyr Trp Gly
1               5                   10
```

```
<210> SEQ ID NO 547
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Ala Arg Glu Thr Ala His Asp Val His Gly Met Asp Val
1               5                   10

<210> SEQ ID NO 548
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Gly Thr Phe Ser Ser Tyr Ala Ile Ser
1               5

<210> SEQ ID NO 549
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Ala Arg Glu Val Gly Tyr Gly Trp Tyr Thr Lys Ile Ala Phe Asp Ile
1               5                   10                  15

<210> SEQ ID NO 550
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

Tyr Thr Phe Thr Ser Tyr Tyr Met His
1               5

<210> SEQ ID NO 551
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Ala Arg Glu Ala Ala Asp Gly Phe Val Gly Glu Arg Tyr Phe Asp Leu
1               5                   10                  15

<210> SEQ ID NO 552
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 552

Tyr Thr Phe Ser Gly Tyr Tyr Met His
1               5

<210> SEQ ID NO 553
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Ala Arg Glu Ala Ala Asp Gly Phe Val Gly Glu Arg Tyr Phe Asp Leu
1               5                   10                  15

<210> SEQ ID NO 554
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Tyr Thr Phe Glu Ile Tyr Tyr Met His
1               5

<210> SEQ ID NO 555
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Ala Arg Gly Ala Gly Tyr Asp Asp Glu Asp Met Asp Val
1               5                   10

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Phe Thr Phe Gly Gly Tyr Trp Met Ser
1               5

<210> SEQ ID NO 557
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Ala Arg Glu Ala Asn Tyr Tyr Gly Asn Val Gly Asp Asp Tyr
1               5                   10

<210> SEQ ID NO 558
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 558

Phe Thr Phe Pro Gly Tyr Trp Met Ser
1               5

<210> SEQ ID NO 559
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 559

Ala Arg Glu Ala Asn Tyr Tyr Gly Asn Val Gly Asp Asp Tyr
1               5                   10

<210> SEQ ID NO 560
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Phe Thr Phe Ser Ser Tyr Trp Met Ser
1               5

<210> SEQ ID NO 561
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ala Arg Asp Val Gly Pro Gly Ile Ala Tyr Gln Gly His Phe Asp Tyr
1               5                   10                  15

<210> SEQ ID NO 562
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Tyr Thr Phe Ser Asn Tyr Tyr Met His
1               5

<210> SEQ ID NO 563
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 563

Ala Arg Asp Val Gly Ser Ser Ala Tyr Tyr Tyr Met Asp Val
1               5                   10
```

```
<210> SEQ ID NO 564
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Tyr Ser Phe Thr Ser Tyr Trp Ile Gly
1               5

<210> SEQ ID NO 565
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Ala Arg Glu Leu Ala Tyr Gly Asp Tyr Lys Gly Gly Val Asp Tyr
1               5                   10                  15

<210> SEQ ID NO 566
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 566

Ser Tyr Tyr Met His
1               5

<210> SEQ ID NO 567
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Gly Ala Pro Asn Tyr Gly Asp Thr Thr His Asp Tyr Tyr Tyr Met Asp
1               5                   10                  15

Val

<210> SEQ ID NO 568
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 568

Gly Tyr Tyr Met His
1               5

<210> SEQ ID NO 569
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 569

Asp Thr Gly Glu Tyr Tyr Asp Thr Asp Asp His Gly Met Asp Val
1               5                   10                  15

<210> SEQ ID NO 570
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Ser Tyr Ala Met Ser
1               5

<210> SEQ ID NO 571
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Asp Gly Gly Tyr Tyr Asp Ser Gly Ala Gly Asp Tyr
1               5                   10

<210> SEQ ID NO 572
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Ser Tyr Tyr Met His
1               5

<210> SEQ ID NO 573
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Glu Gly Ala Gly Phe Ala Tyr Gly Met Asp Tyr Tyr Met Asp Val
1               5                   10                  15

<210> SEQ ID NO 574
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Tyr Tyr Trp Ser
1               5

```
<210> SEQ ID NO 575
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ala Arg Gly Pro Trp Ser Phe Asp Pro
1               5

<210> SEQ ID NO 576
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ser Tyr Ala Ile Ser
1               5

<210> SEQ ID NO 577
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Gly Asp Ser Ser Ile Arg His Ala Tyr Tyr Tyr Tyr Gly Met Asp Val
1               5                   10                  15

<210> SEQ ID NO 578
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Ser Ser Ser Tyr Tyr Trp Gly
1               5

<210> SEQ ID NO 579
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 579

Gly Ser Asp Arg Phe His Pro Tyr Phe Asp Tyr
1               5                   10

<210> SEQ ID NO 580
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580
```

```
Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Pro Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys
```

```
<210> SEQ ID NO 581
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Asp Ala Ser Asn Arg Ala Thr
1               5
```

```
<210> SEQ ID NO 582
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Gln Gln Phe Asp Thr Trp Pro Pro Thr
1               5
```

```
<210> SEQ ID NO 583
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 583

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 584
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 584

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 585
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 585

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120

<210> SEQ ID NO 586
<211> LENGTH: 122
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 586

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
            100                 105                 110

Gly Gln Gly Thr Leu Val Thr Val Ser Ser
        115                 120

<210> SEQ ID NO 587
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Ala Arg Gly Ala Pro Gln Gly Ala Ala Ala Gly Trp Phe Asp Pro
1               5                   10                  15

<210> SEQ ID NO 588
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Gly Ala Pro Gln Gly Ala Ala Ala Gly Trp Phe Asp Pro
1               5                   10

<210> SEQ ID NO 589
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 589

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

```
Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
            115                 120

<210> SEQ ID NO 590
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Ala Arg Gly Ala Pro Leu Gly Ala Ala Ala Gly Trp Phe Asp Pro
 1               5                  10                  15

<210> SEQ ID NO 591
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gly Ala Pro Leu Gly Ala Ala Ala Gly Trp Phe Asp Pro
 1               5                  10

<210> SEQ ID NO 592
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 592

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
            115                 120
```

```
<210> SEQ ID NO 593
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Ala Arg Gly Ala Pro Phe Gly Ala Ala Ala Gly Trp Phe Asp Pro
1               5                   10                  15

<210> SEQ ID NO 594
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Gly Ala Pro Phe Gly Ala Ala Ala Gly Trp Phe Asp Pro
1               5                   10

<210> SEQ ID NO 595
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Val Gly Ala Ala Ala Gly Trp Phe Asp Pro Trp
            100                 105                 110

Gly Gln Gly Thr Leu Val Thr Val Ser Ser
        115                 120

<210> SEQ ID NO 596
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 596

Ala Arg Gly Ala Pro Val Gly Ala Ala Ala Gly Trp Phe Asp Pro
1               5                   10                  15

<210> SEQ ID NO 597
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Gly Ala Pro Val Gly Ala Ala Gly Trp Phe Asp Pro
1               5                   10

<210> SEQ ID NO 598
<211> LENGTH: 347
<212> TYPE: PRT
<213> ORGANISM: Homo sapiens

<400> SEQUENCE: 598

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His Gly Ala Ile Gly Gly Ala Gly Val Thr Ala Leu Leu Ala Leu
                245                 250                 255

Cys Leu Cys Leu Ile Phe Phe Ile Val Lys Thr His Arg Arg Lys Ala
            260                 265                 270

Ala Arg Thr Ala Val Gly Arg Asn Asp Thr His Pro Thr Thr Gly Ser
        275                 280                 285

Ala Ser Pro Lys His Gln Lys Lys Ser Lys Leu His Gly Pro Thr Glu
    290                 295                 300

Thr Ser Ser Cys Ser Gly Ala Ala Pro Thr Val Glu Met Asp Glu Glu
305                 310                 315                 320
```

Leu His Tyr Ala Ser Leu Asn Phe His Gly Met Asn Pro Ser Lys Asp
            325                 330                 335

Thr Ser Thr Glu Tyr Ser Glu Val Arg Thr Gln
            340                 345

<210> SEQ ID NO 599
<211> LENGTH: 343
<212> TYPE: PRT
<213> ORGANISM: Macaca fascicularis

<400> SEQUENCE: 599

Asp Pro Arg Val Arg Leu Glu Val Gln Glu Ser Val Thr Val Gln Glu
1               5                   10                  15

Gly Leu Cys Val Leu Val Pro Cys Thr Phe Phe His Pro Val Pro Tyr
                20                  25                  30

His Thr Arg Asn Ser Pro Val His Gly Tyr Trp Phe Arg Glu Gly Ala
            35                  40                  45

Ile Val Ser Leu Asp Ser Pro Val Ala Thr Asn Lys Leu Asp Gln Glu
        50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Asp Asn
                85                  90                  95

Gly Ser Tyr Phe Phe Arg Met Glu Lys Gly Ser Thr Lys Tyr Ser Tyr
                100                 105                 110

Lys Ser Thr Gln Leu Ser Val His Val Thr Asp Leu Thr His Arg Pro
            115                 120                 125

Gln Ile Leu Ile Pro Gly Ala Leu Asp Pro Asp His Ser Lys Asn Leu
        130                 135                 140

Thr Cys Ser Val Pro Trp Ala Cys Glu Gln Gly Thr Pro Pro Ile Phe
145                 150                 155                 160

Ser Trp Met Ser Ala Ala Pro Thr Ser Leu Gly Leu Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Pro Gly Ala Gly Val Thr Thr Glu Arg
        195                 200                 205

Thr Ile Gln Leu Asn Val Ser Tyr Ala Ser Gln Asn Pro Arg Thr Asp
210                 215                 220

Ile Phe Leu Gly Asp Gly Ser Gly Lys Gln Gly Val Val Gln Gly Ala
225                 230                 235                 240

Ile Gly Gly Ala Gly Val Thr Val Leu Leu Ala Leu Cys Leu Cys Leu
                245                 250                 255

Ile Phe Phe Thr Val Lys Thr His Arg Arg Lys Ala Ala Arg Thr Ala
            260                 265                 270

Val Gly Arg Ile Asp Thr His Pro Ala Thr Gly Pro Thr Ser Ser Lys
        275                 280                 285

His Gln Lys Lys Ser Lys Leu His Gly Ala Thr Glu Thr Ser Gly Cys
        290                 295                 300

```
Ser Gly Thr Thr Leu Thr Val Glu Met Asp Glu Glu Leu His Tyr Ala
305                 310                 315                 320

Ser Leu Asn Phe His Gly Met Asn Pro Ser Glu Asp Thr Ser Thr Glu
                325                 330                 335

Tyr Ser Glu Val Arg Thr Gln
            340
```

MULTI-SPECIFIC BINDING PROTEINS THAT BIND CD33, NKG2D, AND CD16, AND METHODS OF USE

CROSS-REFERENCE TO RELATED APPLICATIONS

This application is a U.S. National Stage Application under 35 U.S.C. § 371 of International Patent Application No. PCT/US2019/018751, filed Feb. 20, 2019, which claims the benefit of and priority to U.S. Provisional Patent Application No. 62/632,756, filed Feb. 20, 2018 and U.S. Provisional Patent Application No. 62/677,137, filed May 28, 2018, the disclosure of each of which is incorporated by reference herein in its entirety for all purposes.

SEQUENCE LISTING

This application incorporates by reference in its entirety the Computer Readable Form (CRF) of a Sequence Listing in ASCII text format submitted via EFS-Web. The Sequence Listing text file submitted via EFS-Web is entitled "14247-430-999_Sequence_Listing.txt," was created on Jul. 27, 2020 and is 571,237 bytes in size.

FIELD OF THE INVENTION

The invention relates to multi-specific binding proteins that bind to CD33 (Siglec-3), and exhibit high potency and maximum lysis of target cells compared to anti-CD33 monoclonal antibodies.

BACKGROUND

Cancer continues to be a significant health problem despite the substantial research efforts and scientific advances reported in the literature for treating this disease. Some of the most frequently diagnosed cancers in adults include prostate cancer, breast cancer, and lung cancer. Hematological malignancies, though less frequent than solid cancers, have low survival rates. Current treatment options for these cancers are not effective for all patients and/or can have substantial adverse side effects. Other types of cancer also remain challenging to treat using existing therapeutic options.

Cancer immunotherapies are desirable because they are highly specific and can facilitate destruction of cancer cells using the patient's own immune system. Fusion proteins such as bi-specific T-cell engagers are cancer immunotherapies described in the literature that bind to tumor cells and T-cells to facilitate destruction of tumor cells. T cells are major effectors of the adaptive immune system that attack foreign cells as well as host cells that present mutant or mis-expressed peptides. Cells targeted by T cells may be virally-infected, such that they express foreign proteins, or malignant, where they might express mutant proteins. T cells recognize target cells via their T cell receptor (TCR) engaging intracellular peptides presented by major histocompatibility complex proteins on target cells. Individual T cells typically recognize target cells bearing specific MHC-peptide complexes, but novel agents have been developed that usurp and amplify this natural process for therapeutic benefit. Bi-specific T cell engagers link antigen binding site(s) of tumor-associated antigens to antigen binding site(s) of components of the TCR complex to redirect T cell activity towards desired target cells independent of native peptide-MHC recognition. For example, Blincyto is an FDA-approved T cell engager that targets CD19 on malignant B cells.

T cells can also be engineered to express chimeric antigen receptors (CAR) that endow it with target recognition capabilities of its CAR. CARs contain antigen binding site(s) to tumor associated antigens linked to T cell activation domains. These CAR-T cells can also be employed to target malignant cells, and some have been FDA-approved for use against B cell malignancies.

Antibodies that bind to certain tumor-associated antigens and to certain immune cells have been described in the literature. See, e.g., WO 2016/134371 and WO 2015/095412. Antibody-drug conjugates or immunocytokines using antigen binding sites targeting tumor associated antigens to deliver toxic agents or immune-modulatory cytokines to specific target cells.

Natural killer (NK) cells are a component of the innate immune system and make up approximately 15% of circulating lymphocytes. NK cells infiltrate virtually all tissues and were originally characterized by their ability to kill tumor cells effectively without the need for prior sensitization. Activated NK cells kill target cells by means similar to cytotoxic T cells—i.e., via cytolytic granules that contain perforin and granzymes as well as via death receptor pathways. Activated NK cells also secrete inflammatory cytokines such as IFN-gamma and chemokines that promote the recruitment of other leukocytes to the target tissue.

NK cells respond to signals through a variety of activating and inhibitory receptors on their surface. For example, when NK cells encounter healthy self-cells, their activity is inhibited through activation of the killer-cell immunoglobulin-like receptors (KIRs). Alternatively, when NK cells encounter foreign cells or cancer cells, they are activated via their activating receptors (e.g., NKG2D, NCRs, DNAM1). NK cells are also activated by the constant region of some immunoglobulins through CD16 receptors on their surface. The overall sensitivity of NK cells to activation depends on the sum of stimulatory and inhibitory signals.

CD33 is a member of the sialic acid-binding immunoglobulin-like lectins. As a transmembrane receptor mainly expressed on cells of myeloid lineage, CD33 modulates inflammatory and immune responses through a dampening effect on tyrosine kinase-driven signaling pathways. For example, CD33 was shown to constitutively suppress the production of pro-inflammatory cytokines such as IL-1β, TNF-α, and IL-8 by human monocytes.

CD33 is associated with hematopoietic cancers. It is broadly expressed in blasts of nearly all acute myeloid leukemia (AML). Furthermore, hematopoietic cancer stem and/or progenitor cells are found to be CD33$^+$, implying that CD33-directed therapy could potentially eradicate malignant stem and/or progenitor cells in such cases while sparing normal hematopoietic stem cells. In addition to its expression in AML, CD33 is found on other myeloid neoplasms (e.g., myelodysplastic syndromes and myeloproliferative neoplasms) and on subsets of B-cell and T-cell acute lymphoblastic leukemias (ALL)/lymphoblastic lymphomas. This expression pattern has led to the use of CD33-directed therapeutics in patients with malignancies including AML, myelodysplastic syndromes, chronic myelomonocytic leukemia, myeloid blast crisis of chronic myeloid leukemia, and ALLs.

SUMMARY OF THE INVENTION

The invention provides multi-specific binding proteins that bind to CD33 on a cancer cell and to the NKG2D receptor and CD16 receptor on natural killer cells. Such proteins can engage more than one kind of NK activating receptor, and may block the binding of natural ligands to NKG2D. In certain embodiments, the proteins can agonize NK cells in humans, and in other species such as rodents and cynomolgus monkeys. Various aspects and embodiments of the invention are described in further detail below.

In certain embodiments, the present invention provides a protein that includes a human CD33 antigen-binding site including a heavy chain variable domain, which includes an amino acid sequence at least 90% (e.g., 90%, 91%, 92%, 93%, 94%, 95%, 96%, 97%, 98%, 99%, or 100%) identical to the amino acid sequence of SEQ ID NO: 1, 3, 5, 7, 9, 11, 13, 15, 17, 19, 266, 268, 270, 272, 274, 276, 278, 280, 282, 284, 286, 288, 290, 292, 294, 296, 298, 300, or 302, and further comprises a second antigen binding site same or different from the antigen-binding site that binds to human CD33.

In certain embodiments, the present invention provides an antigen-binding site in a protein (e.g., a multi-specific binding protein) that binds to CD33 on a cancer cell, and the NKG2D receptor and CD16 receptor on natural killer cells to activate the natural killer cell. The binding protein (e.g., a multi-specific binding protein) is useful in the pharmaceutical compositions and therapeutic methods described herein. Binding of the protein including an antigen-binding site that binds to CD33, and to NKG2D receptor and CD16 receptor on natural killer cell enhances the activity of the natural killer cell toward destruction of a cancer cell. Binding of the protein including an antigen-binding site that binds to CD33 (e.g., a multi-specific binding protein) on a cancer cell brings the cancer cell into proximity to the natural killer cell, which facilitates direct and indirect destruction of the cancer cell by the natural killer cell. Further description of exemplary multi-specific binding proteins is provided below.

The first component of the multi-specific binding proteins of the present disclosure binds to CD33-expressing cells, which can include but are not limited to AML, myelodysplastic syndromes, chronic myelomonocytic leukemia, myeloid blast crisis of chronic myeloid leukemia, and ALLs.

The second component of the multi-specific binding proteins of the present disclosure binds to NKG2D receptor-expressing cells, which can include but are not limited to NK cells, γδ T cells and CD8⁺ αβ T cells. Upon NKG2D binding, the multi-specific binding proteins may block natural ligands, such as ULBP6 and MICA, from binding to NKG2D and activating NKG2D receptors. The NKG2D antigen binding site can include, for example:

(1) a heavy chain variable domain comprising an amino acid sequence at least 90% (e.g., 90%, 91%, 92%, 93%, 94%, 95%, 96%, 97%, 98%, 99%, or 100%) identical to SEQ ID NO:81 and a light chain variable domain comprising an amino acid sequence at least 90% (e.g., 90%, 91%, 92%, 93%, 94%, 95%, 96%, 97%, 98%, 99%, or 100%) identical to SEQ ID NO:82 [ADI-29379];

(2) a heavy chain variable domain comprising an amino acid sequence at least 90% (e.g., 90%, 91%, 92%, 93%, 94%, 95%, 96%, 97%, 98%, 99%, or 100%) identical to SEQ ID NO:83 and a light chain variable domain comprising an amino acid sequence at least 90% (e.g., 90%, 91%, 92%, 93%, 94%, 95%, 96%, 97%, 98%, 99%, or 100%) identical to SEQ ID NO:84 [ADI-29463];

(3) a heavy chain variable domain comprising an amino acid sequence at least 90% (e.g., 90%, 91%, 92%, 93%, 94%, 95%, 96%, 97%, 98%, 99%, or 100%) identical to SEQ ID NO:85 and a light chain variable domain comprising an amino acid sequence at least 90% (e.g., 90%, 91%, 92%, 93%, 94%, 95%, 96%, 97%, 98%, 99%, or 100%) identical to SEQ ID NO:86 [ADI-27744];

(4) a heavy chain variable domain comprising an amino acid sequence at least 90% (e.g., 90%, 91%, 92%, 93%, 94%, 95%, 96%, 97%, 98%, 99%, or 100%) identical to SEQ ID NO:87 and a light chain variable domain comprising an amino acid sequence at least 90% (e.g., 90%, 91%, 92%, 93%, 94%, 95%, 96%, 97%, 98%, 99%, or 100%) identical to SEQ ID NO:88 [ADI-27749];

(5) a heavy chain variable domain comprising an amino acid sequence at least 90% (e.g., 90%, 91%, 92%, 93%, 94%, 95%, 96%, 97%, 98%, 99%, or 100%) identical to SEQ ID NO:191 and a light chain variable domain comprising an amino acid sequence at least 90% (e.g., 90%, 91%, 92%, 93%, 94%, 95%, 96%, 97%, 98%, 99%, or 100%) identical to SEQ ID NO:88 [A49MI]; or (6) a heavy chain variable domain comprising an amino acid sequence at least 90% (e.g., 90%, 91%, 92%, 93%, 94%, 95%, 96%, 97%, 98%, 99%, or 100%) identical to SEQ ID NO:89 and a light chain variable domain comprising an amino acid sequence at least 90% (e.g., 90%, 91%, 92%, 93%, 94%, 95%, 96%, 97%, 98%, 99%, or 100%) identical to SEQ ID NO:90 [ADI-29378].

The third component for the multi-specific binding proteins of the present disclosure binds to cells expressing CD16, an Fc receptor on the surface of leukocytes including natural killer cells, macrophages, neutrophils, eosinophils, mast cells, and follicular dendritic cells.

In certain embodiments, any of the foregoing isolated antibodies has a KD of 1 nM or lower, 5 nM or lower, or 12 nM or lower for extracellular domain of human CD33, as measured by surface plasmon resonance (SPR) (e.g., using the Biacore™ method described in Example 1 infra) or by bio-layer interferometry (BLI) (e.g., using the Octet™ method described in Example 1 infra), and/or binds CD33 from a body fluid, tissue, and/or cell of a subject. In certain embodiments, any of the foregoing isolated antibodies has a $K_d$ (i.e., off-rate, also called $K_{off}$) equal to or lower than $1 \times 10^{-5}$, $1 \times 10^{-4}$, $1 \times 10^{-3}$, $5 \times 10^{-3}$, 0.01, 0.02, or 0.05 1/s, as measured by SPR (e.g., using the Biacore™ method described in Example 1 infra) or by BLI (e.g., using the Octet™ method described in Example 1 infra).

Some proteins of the present disclosure bind to NKG2D with a $K_D$ of 10 nM or weaker affinity.

In another aspect, the invention provides one or more isolated nucleic acids comprising sequences encoding an immunoglobulin heavy chain and/or immunoglobulin light chain variable region of any one of the foregoing antibodies. The invention provides one or more expression vectors that express the immunoglobulin heavy chain and/or immunoglobulin light chain variable region of any one of the foregoing antibodies. Similarly the invention provides host cells comprising one or more of the foregoing expression vectors and/or isolated nucleic acids.

Formulations including any of the proteins that include a CD33-binding domain described herein and methods of enhancing tumor cell death using these proteins and/or formulations are also provided.

In another aspect, the invention provides a method of treating a cancer, for example, a CD33-associated cancer, in a subject. The method comprises administering to the subject an effective amount of a protein containing any CD33-binding domain described herein, for example, a multi-specific protein containing a CD33 binding domain, an NKG2D-binding domain and a CD16-binding domain, to treat the cancer in the subject.

In another aspect, the invention provides a method of inhibiting cancer growth, for example, the growth of a CD33-associated cancer, in a subject. The method comprises exposing the subject to an effective amount of an antibody comprising any CD33-binding domain described herein, for example, a multi-specific protein containing an CD33-binding domain, an NKG2D-binding domain and a CD16-binding domain, to inhibit cancer growth in the subject.

Another aspect of the invention provides a method of treating cancer in a patient. The method comprises administering to a patient in need thereof a therapeutically effective amount of the multi-specific binding protein described herein. Exemplary cancers for treatment using the multi-specific binding proteins include, for example, wherein the cancer is selected from the group consisting of AML, myelodysplastic syndromes, chronic myelomonocytic leukemia, myeloid blast crisis of chronic myeloid leukemia, and ALLs.

Another aspect of the invention provides a protein comprising:
(a) a first antigen-binding site comprising an Fab fragment that binds NKG2D;
(b) a second antigen-binding site comprising a single-chain variable fragment (scFv) that binds CD33 comprising a heavy chain variable domain and a light chain variable domain; and
(c) an antibody Fc domain or a portion thereof sufficient to bind CD16, or a third antigen-binding site that binds CD16, wherein the scFv is linked to the antibody Fc domain or a portion thereof sufficient to bind CD16, or the third antigen-binding site that binds CD16, via a hinge comprising Ala-Ser or Gly-Ala-Ser.

In certain embodiments, the scFv is linked to the antibody Fc domain. In certain embodiments, the heavy chain variable domain of the scFv forms a disulfide bridge with the light chain variable domain of the scFv. In certain embodiments, the disulfide bridge is formed between C44 from the heavy chain variable domain and C100 from the light chain variable domain.

In certain embodiments, the scFv is linked to the antibody Fc domain, wherein the light chain variable domain of the scFv is positioned at the N-terminus of the heavy chain variable domain of the scFv, and is linked to the heavy chain variable domain of the scFv via a flexible linker (GlyGlyGlyGlySer)4 ((G4S)4), and the Fab is linked to the antibody Fc domain.

In certain embodiments, the present invention provides a protein as disclosed herein, wherein the heavy chain variable domain of the scFv is linked to the light chain variable domain of the scFv via a flexible linker. In certain embodiments, the flexible linker comprises (GlyGlyGlyGlySer)4 ((G4S)4).

In certain embodiments, the present invention provides a protein as disclosed herein, wherein the heavy chain variable domain of the scFv is positioned at the N-terminus or the C-terminus of the light chain variable domain of the scFv. In certain embodiments, the light chain variable domain of the scFv is positioned at the N-terminus of the heavy chain variable domain of the scFv.

In certain embodiments, the present invention provides a protein as disclosed herein, wherein the Fab fragment is linked to the antibody Fc domain or a portion thereof sufficient to bind CD16 or the third antigen-binding site that binds CD16. In certain embodiments, the heavy chain portion of the Fab fragment comprises a heavy chain variable domain and a CH1 domain, and wherein the heavy chain variable domain is linked to the CH1 domain. In certain embodiments, the Fab fragment is linked to the antibody Fc domain.

In certain embodiments, the first antigen-binding site that binds NKG2D comprises a heavy chain variable domain comprising complementarity-determining region 1 (CDR1), complementarity-determining region 2 (CDR2), and complementarity-determining region 3 (CDR3) sequences represented by the amino acid sequences of SEQ ID NOs:93, 94, and 95, respectively; and a light chain variable domain comprising CDR1, CDR2, and CDR3 sequences represented by the amino acid sequences of SEQ ID NOs:96, 97, and 98, respectively. In certain embodiments, the first antigen-binding site that binds NKG2D comprises a heavy chain variable domain comprising CDR1, CDR2, and CDR3 sequences represented by the amino acid sequences of SEQ ID NOs:99, 100, and 101, respectively; and a light chain variable domain comprising CDR1, CDR2, and CDR3 sequences represented by the amino acid sequences of SEQ ID NOs:102, 103, and 104, respectively. In certain embodiments, the first antigen-binding site that binds NKG2D comprises a heavy chain variable domain comprising CDR1, CDR2, and CDR3 sequences represented by the amino acid sequences of SEQ ID NOs:105, 106, and 107, respectively; and a light chain variable domain comprising CDR1, CDR2, and CDR3 sequences represented by the amino acid sequences of SEQ ID NOs:108, 109, and 110, respectively. In certain embodiments, the first antigen-binding site that binds NKG2D comprises a heavy chain variable domain comprising CDR1, CDR2, and CDR3 sequences represented by the amino acid sequences of SEQ ID NOs:192, 112, and 193, respectively; and a light chain variable domain comprising CDR1, CDR2, and CDR3 sequences represented by the amino acid sequences of SEQ ID NOs:114, 115, and 116, respectively. In certain embodiments, the first antigen-binding site that binds NKG2D comprises a heavy chain variable domain comprising CDR1, CDR2, and CDR3 sequences represented by the amino acid sequences of SEQ ID NOs:192, 112, and 195, respectively; and a light chain variable domain comprising CDR1, CDR2, and CDR3 sequences represented by the amino acid sequences of SEQ ID NOs:114, 115, and 116, respectively. In certain embodiments, the first antigen-binding site that binds NKG2D comprises a heavy chain variable domain comprising CDR1, CDR2, and CDR3 sequences represented by the amino acid sequences of SEQ ID NOs: 117, 118, and 119, respectively; and a light chain variable domain comprising CDR1, CDR2, and CDR3 sequences represented by the amino acid sequences of SEQ ID NOs: 120, 121, and 122, respectively.

In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:81 and a light chain variable domain comprising an amino acid sequence at least 90% (e.g., 91%, 92%, 93%, 94%, 95%, 96%, 97%, 98%, 99%, or 100%) identical to SEQ ID NO:82. In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:83 and a light chain variable domain comprising an amino acid sequence at least 90% (e.g., 91%, 92%, 93%, 94%, 95%, 96%, 97%, 98%, 99%, or 100%) identical to SEQ ID NO:84. In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:85 and a light chain variable domain comprising an amino acid sequence at least 90% (e.g., 91%, 92%, 93%, 94%, 95%, 96%, 97%, 98%, 99%, or 100%) identical to SEQ ID NO:86. In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:87 and a light chain variable domain comprising an amino acid sequence at least 90% (e.g., 91%, 92%, 93%, 94%, 95%, 96%, 97%, 98%, 99%, or 100%) identical to SEQ ID NO:88. In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:191 and a light chain variable domain comprising an amino acid sequence at least 90% (e.g., 91%, 92%, 93%, 94%, 95%, 96%, 97%, 98%, 99%, or 100%) identical to SEQ ID NO:88. In certain embodiments, the first antigen-binding site that binds NKG2D comprises a heavy chain variable domain comprising an amino acid sequence at least 90% (e.g., 91%, 92%, 93%, 94%, 95%, 96%, 97%, 98%, 99%, or 100%) identical to SEQ ID NO:89 and a light chain variable domain comprising an amino acid sequence at least 90% (e.g., 91%, 92%, 93%, 94%, 95%, 96%, 97%, 98%, 99%, or 100%) identical to SEQ ID NO:90.

In certain embodiments, the second antigen-binding site that binds CD33 comprises a heavy chain variable domain comprising CDR1, CDR2, and CDR3 sequences represented by the amino acid sequences of SEQ ID NOs:181, 46, and 182, respectively; and a light chain variable domain comprising CDR1, CDR2, and CDR3 sequences represented by the amino acid sequences of SEQ ID NOs:48, 49, and 50, respectively. In certain embodiments, the second antigen-binding site that binds CD33 comprises a heavy chain variable domain comprising CDR1, CDR2, and CDR3 sequences represented by the amino acid sequences of SEQ ID NOs:183, 34, and 184, respectively; and a light chain variable domain comprising CDR1, CDR2, and CDR3 sequences represented by the amino acid sequences of SEQ ID NOs:36, 185, and 38, respectively.

In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:9 and a light chain variable domain comprising an amino acid sequence at least 90% (e.g., 91%, 92%, 93%, 94%, 95%, 96%, 97%, 98%, 99%, or 100%) identical to SEQ ID NO:10. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:5 and a light chain variable domain comprising an amino acid sequence at least 90% (e.g., 91%, 92%, 93%, 94%, 95%, 96%, 97%, 98%, 99%, or 100%) identical to SEQ ID NO:6. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:1 and a light chain variable domain comprising an amino acid sequence at least 90% (e.g., 91%, 92%, 93%, 94%, 95%, 96%, 97%, 98%, 99%, or 100%) identical to SEQ ID NO:2. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:3 and a light chain variable domain comprising an amino acid sequence at least 90% (e.g., 91%, 92%, 93%, 94%, 95%, 96%, 97%, 98%, 99%, or 100%) identical to SEQ ID NO:4. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:7 and a light chain variable domain comprising an amino acid sequence at least 90% (e.g., 91%, 92%, 93%, 94%, 95%, 96%, 97%, 98%, 99%, or 100%) identical to SEQ ID NO:8. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:11 and a light chain variable domain comprising an amino acid sequence at least 90% (e.g., 91%, 92%, 93%, 94%, 95%, 96%, 97%, 98%, 99%, or 100%) identical to SEQ ID NO:12. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:13 and a light chain variable domain comprising an amino acid sequence at least 90% (e.g., 91%, 92%, 93%, 94%, 95%, 96%, 97%, 98%, 99%, or 100%) identical to SEQ ID NO:14. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:15 and a light chain variable domain comprising an amino acid sequence at least 90% (e.g., 91%, 92%, 93%, 94%, 95%, 96%, 97%, 98%, 99%, or 100%) identical to SEQ ID NO:16. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:17 and a light chain variable domain comprising an amino acid sequence at least 90% (e.g., 91%, 92%, 93%, 94%, 95%, 96%, 97%, 98%, 99%, or 100%) identical to SEQ ID NO:18. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:19 and a light chain variable domain comprising an amino acid sequence at least 90% (e.g., 91%, 92%, 93%, 94%, 95%, 96%, 97%, 98%, 99%, or 100%) identical to SEQ ID NO:20. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:266 and a light chain variable domain comprising an amino acid sequence at least 90% (e.g., 91%, 92%, 93%, 94%, 95%, 96%, 97%, 98%, 99%, or 100%) identical to SEQ ID NO:267. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:268 and a light chain variable domain comprising an amino acid sequence at least 90% (e.g., 91%, 92%, 93%, 94%, 95%, 96%, 97%, 98%, 99%, or 100%) identical to SEQ ID NO:269. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:270 and a light chain variable domain comprising an amino acid sequence at least 90% (e.g., 91%, 92%, 93%, 94%, 95%, 96%, 97%, 98%, 99%, or 100%) identical to SEQ ID NO:271. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:272 and a light chain variable domain comprising an amino acid sequence at least 90% (e.g., 91%, 92%, 93%, 94%, 95%, 96%, 97%, 98%, 99%, or 100%) identical to SEQ ID NO:273. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:274 and a light chain variable domain comprising an amino acid sequence at least 90% (e.g., 91%, 92%, 93%, 94%, 95%, 96%, 97%, 98%, 99%, or 100%) identical to SEQ ID NO:275. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:276 and a light chain variable domain comprising an amino acid sequence at least 90% (e.g., 91%, 92%, 93%, 94%, 95%, 96%, 97%, 98%, 99%, or 100%) identical to SEQ ID NO:277. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:278 and a light chain variable domain comprising an amino acid sequence at least 90% (e.g., 91%, 92%, 93%, 94%, 95%, 96%, 97%, 98%, 99%, or 100%) identical to SEQ ID NO:279. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:280 and a light chain variable domain comprising an amino acid sequence at least 90% (e.g., 91%, 92%, 93%, 94%, 95%, 96%, 97%, 98%, 99%, or 100%) identical to SEQ ID NO:281. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:282 and a light chain variable domain comprising an amino acid sequence at least 90% (e.g., 91%, 92%, 93%, 94%, 95%, 96%, 97%, 98%, 99%, or 100%) identical to SEQ ID NO:283. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:284 and a light chain variable domain comprising an amino acid sequence at least 90% (e.g., 91%, 92%, 93%, 94%, 95%, 96%, 97%, 98%, 99%, or 100%) identical to SEQ ID NO:285. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:286 and a light chain variable domain comprising an amino acid sequence at least 90% (e.g., 91%, 92%, 93%, 94%, 95%, 96%, 97%, 98%, 99%, or 100%) identical to SEQ ID NO:287. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:288 and a light chain variable domain comprising an amino acid sequence at least 90% (e.g., 91%, 92%, 93%, 94%, 95%, 96%, 97%, 98%, 99%, or 100%) identical to SEQ ID NO:289. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:290 and a light chain variable domain comprising an amino acid sequence at least 90% (e.g., 91%, 92%, 93%, 94%, 95%, 96%, 97%, 98%, 99%, or 100%) identical to SEQ ID NO:291. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:292 and a light chain variable domain comprising an amino acid sequence at least 90% (e.g., 91%, 92%, 93%, 94%, 95%, 96%, 97%, 98%, 99%, or 100%) identical to SEQ ID NO:293. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:294 and a light chain variable domain comprising an amino acid sequence at least 90% (e.g., 91%, 92%, 93%, 94%, 95%, 96%, 97%, 98%, 99%, or 100%) identical to SEQ ID NO:295. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:296 and a light chain variable domain comprising an amino acid sequence at least 90% (e.g., 91%, 92%, 93%, 94%, 95%, 96%, 97%, 98%, 99%, or 100%) identical to SEQ ID NO:297. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:298 and a light chain variable domain comprising an amino acid sequence at least 90% (e.g., 91%, 92%, 93%, 94%, 95%, 96%, 97%, 98%, 99%, or 100%) identical to SEQ ID NO:299. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:300 and a light chain variable domain comprising an amino acid sequence at least 90% (e.g., 91%, 92%, 93%, 94%, 95%, 96%, 97%, 98%, 99%, or 100%) identical to SEQ ID NO:301. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:302 and a light chain variable domain comprising an amino acid sequence at least 90% (e.g., 91%, 92%, 93%, 94%, 95%, 96%, 97%, 98%, 99%, or 100%) identical to SEQ ID NO:303. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:418 and a light chain variable domain comprising an amino acid sequence at least 90% (e.g., 91%, 92%, 93%, 94%, 95%, 96%, 97%, 98%, 99%, or 100%) identical to SEQ ID NO:419. In certain embodiments, the second antigen-binding site that binds CD33 comprises a heavy chain variable domain comprising an amino acid sequence at least 90% (e.g., 91%, 92%, 93%, 94%, 95%, 96%, 97%, 98%, 99%, or 100%) identical to SEQ ID NO:420 and a light chain variable domain comprising an amino acid sequence at least 90% (e.g., 91%, 92%, 93%, 94%, 95%, 96%, 97%, 98%, 99%, or 100%) identical to SEQ ID NO:421.

In certain embodiments, the present invention provides a protein disclosed herein comprising a sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, SEQ ID NO:484, SEQ ID NO:485, SEQ ID NO:486, SEQ ID NO:487, and SEQ ID NO:488.

In certain embodiments, the present invention provides a multi-specific binding protein disclosed herein comprising an scFv linked to an antibody Fc domain, wherein the scFv linked to the antibody Fc domain is represented by a sequence selected from SEQ ID NO:187, SEQ ID NO:197, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, and SEQ ID NO:243.

In certain embodiments, the present invention provides a protein disclosed herein comprising a sequence selected from SEQ ID NO:189, SEQ ID NO:196, SEQ ID NO:244, and SEQ ID NO:245.

In certain embodiments, the present invention provides a protein disclosed herein comprising a sequence at least 90% (e.g., 90%, 91%, 92%, 93%, 94%, 95%, 96%, 97%, 98%, 99%, or 100%) identical to an amino acid sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, and SEQ ID NO:484. In certain embodiments, the present invention provides a protein disclosed herein comprising a sequence at least 95% identical to an amino acid sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, and SEQ ID NO:484. In certain embodiments, the present invention provides a protein disclosed herein comprising a sequence at least 99% identical to an amino acid sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, and SEQ ID NO:484.

In certain embodiments, the present invention provides a protein disclosed herein comprising a sequence at least 90% (e.g., 90%, 91%, 92%, 93%, 94%, 95%, 96%, 97%, 98%, 99%, or 100%) identical to an amino acid sequence selected from SEQ ID NO:187, SEQ ID NO:197, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, and SEQ ID NO:243. In certain embodiments, the present invention provides a protein disclosed herein comprising a sequence at least 95% identical to an amino acid sequence selected from SEQ ID NO:187, SEQ ID NO:197, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, and SEQ ID NO:243. In certain embodiments, the present invention provides a protein disclosed herein comprising a sequence at least 99% identical to an amino acid sequence selected from SEQ ID NO:187, SEQ ID NO:197, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, and SEQ ID NO:243.

Another aspect of the present invention provides a formulation comprising a protein as disclosed herein, and a pharmaceutically acceptable carrier.

Another aspect of the present invention provides a method of treating a CD33-expressing cancer, the method comprising administering a therapeutically effective amount of a protein or formulation thereof disclosed herein to a subject in need thereof.

In certain embodiments, the cancer is selected from the group consisting of acute myeloid leukemia (AML), myelodysplastic syndrome (MDS), acute lymphoblastic leukemia (ALL), myeloproliferative neoplasms (MPNs), lymphoma, non-Hodgkin lymphomas, and classical Hodgkin lymphoma. In certain embodiments, the AML is selected from undifferentiated acute myeloblastic leukemia, acute myeloblastic leukemia with minimal maturation, acute myeloblastic leukemia with maturation, acute promyelocytic leukemia (APL), acute myelomonocytic leukemia, acute myelomonocytic leukemia with eosinophilia, acute monocytic leukemia, acute erythroid leukemia, acute megakaryoblastic leukemia (AMKL), acute basophilic leukemia, acute panmyelosis with fibrosis, and blastic plasmacytoid dendritic cell neoplasm (BPDCN). In certain embodiments, the AML is characterized by expression of CLL-1 on the AML leukemia stem cells (LSCs). In certain embodiments, the LSCs further express a membrane marker selected from CD34, CD38, CD123, TIM3, CD25, CD32, and CD96.

In certain embodiments, the AML is a minimal residual disease (MRD). In certain embodiments, the MRD is characterized by the presence or absence of a mutation selected from FLT3-ITD ((Fms-like tyrosine kinase 3)-internal tandem duplications (ITD)), NPM1 (Nucleophosmin 1), DNMT3A (DNA methyltransferase gene DNMT3A), and IDH (Isocitrate dehydrogenase 1 and 2 (IDH1 and IDH2)). In certain embodiments, the MDS is selected from MDS with multilineage dysplasia (MDS-MLD), MDS with single lineage dysplasia (MDS-SLD), MDS with ring sideroblasts (MDS-RS), MDS with excess blasts (MDS-EB), MDS with isolated del(5q), and MDS, unclassified (MDS-U). In certain embodiments, the MDS is a primary MDS or a secondary MDS.

In certain embodiments, the ALL is selected from B-cell acute lymphoblastic leukemia (B-ALL) and T-cell acute lymphoblastic leukemia (T-ALL). In certain embodiments, the MPN is selected from polycythaemia vera, essential thrombocythemia (ET), and myelofibrosis. In certain embodiments, the non-Hodgkin lymphoma is selected from B-cell lymphoma and T-cell lymphoma. In certain embodiments, the lymphoma is selected from chronic lymphocytic leukemia (CLL), lymphoblastic lymphoma (LPL), diffuse large B-cell lymphoma (DLBCL), Burkitt lymphoma (BL), primary mediastinal large B-cell lymphoma (PMBL), follicular lymphoma, mantle cell lymphoma, hairy cell leukemia, plasma cell myeloma (PCM) or multiple myeloma (MM), mature T/NK neoplasms, and histiocytic neoplasms.

These and other aspects and advantages of the invention are illustrated by the following figures, detailed description and claims.

DESCRIPTION OF THE DRAWINGS

The invention can be more completely understood with reference to the following drawings.

FIG. 2 shows an alignment of the primary sequences of full length human and cyno CD33 (SEQ ID NO:598 and SEQ ID NO:599, respectively). V domain is underlined in blue, C domain is underlined in green. Difference in sequences are framed in red.

FIGS. 3A-3K show SPR profiles of Fab fragments from CD33 monoclonal antibodies binding to human CD33 ECD measured by Biacore™ at 37° C. Each Fab fragment includes a CD33-binding clone described herein. FIG. 3A is a Biacore™ profile of ADI-10159; FIG. 3B is a Biacore™ profile of ADI-10177; FIG. 3C is a Biacore™ profile of ADI-11776; FIG. 3D is a Biacore™ profile of ADI-11801; FIG. 3E is a Biacore™ profile of ADI-11807; FIG. 3F is a Biacore™ profile of ADI-11809; FIG. 3G is a Biacore™ profile of ADI-11815; FIG. 3H is a Biacore™ profile of ADI-11819; FIG. 3I is a Biacore™ profile of ADI-11830; FIG. 3J is a Biacore Biacore™ profile of ADI-11835; and FIG. 3K is a Biacore™ profile of Fab fragment from Lintuzumab.

FIGS. 4A-4H show SPR profiles of Fab fragments from CD33 monoclonal antibodies binding to cyno CD33 ECD measured by Biacore™ at 37° C. Each Fab fragment includes a CD33-binding clone described herein. FIG. 4A is a Biacore™ profile of ADI-10159; FIG. 4B is a Biacore™ profile of ADI-10177; FIG. 4C is a Biacore™ profile of ADI-11776; FIG. 4D is a Biacore™ profile of ADI-11807; FIG. 4E is a Biacore™ profile of ADI-11809; FIG. 4F is a Biacore™ profile of ADI-11819; FIG. 4G is a Biacore™ profile of ADI-11830; and FIG. 4H is a Biacore™ profile of ADI-11835.

FIGS. 5A-5T show SPR profiles of FABs from CD33 monoclonal antibodies binding to V domain and C domain of human CD33 measured at 37° C. Each Fab fragment includes a CD33-binding clone described herein. FIGS. 5A-5J represent binding to the V-domain; FIGS. 5K-5T represent binding to the C domain. FIGS. 5A and 5K are Biacore™ profiles of ADI-10159; FIGS. 5B and 5L are Biacore™ profiles of ADI-10177; FIGS. 5C and 5M are Biacore™ profiles of ADI-11776; FIGS. 5D and 5N are Biacore™ profiles of ADI-11801; FIGS. 5E and 5O are Biacore™ profiles of ADI-11807; FIGS. 5F and 5P are Biacore™ profiles of ADI-11809; FIGS. 5G and 5Q are Biacore™ profiles of ADI-11815; FIGS. 5H and 5R are Biacore™ profiles of ADI-11819; FIGS. 5I and 5S are Biacore™ profiles of ADI-11830; and FIGS. 5J and 5T are Biacore™ profiles of ADI-11835.

FIG. 6A: Fab binding to human CD33 ECD; FIG. 6B: Fab binding to V domain; FIG. 6C: Fab binding to C domain: FIG. 6D: Fab binding to human CD33 having R69G.

FIG. 7A: human CD33 ECD; FIG. 7B: V domain; FIG. 7C: C domain: FIG. 7D: human CD33 having R69G.

FIG. 10A shows binding of CD33-targeting TriNKETs to human NKG2D recombinantly expressed on EL4 cells. FIG. 10B shows binding of CD33-targeting TriNKETs to human NKG2D expressed on KHYG-1 cells. For each TriNKET, signal fold-over-background (FOB) was similar on both EL4-hNKG2D cells and KHYG-1 cells, and the rank of binding was also maintain on both cell lines.

FIG. 30A is an exemplary representation of one form of a κλ-Body; FIG. 30B is an exemplary representation of another κλ-Body.

FIG. 39 is a series of flow cytograms showing the expression level of CD3, CD8, NKG2D, and CD16 on isolated primary CD8$^+$ T cells.

FIG. 42A shows CD33 expression on monocytes from four healthy donors (dark gray) and Molm-13 (light grey). The bottom five rows are signals from the cell samples stained with an anti-CD33 antibody; the top five rows are signals from the same samples stained with an isotype antibody. FIG. 42B shows CD33 expression on monocytes from the same donor before (light grey) and after (dark grey) negative selection for monocytes.

FIG. 43A represents the results from an experiment using NK cells from one donor, and FIG. 43B represents the results from another experiment using NK cells from a different donor.

DETAILED DESCRIPTION

Figure 1:
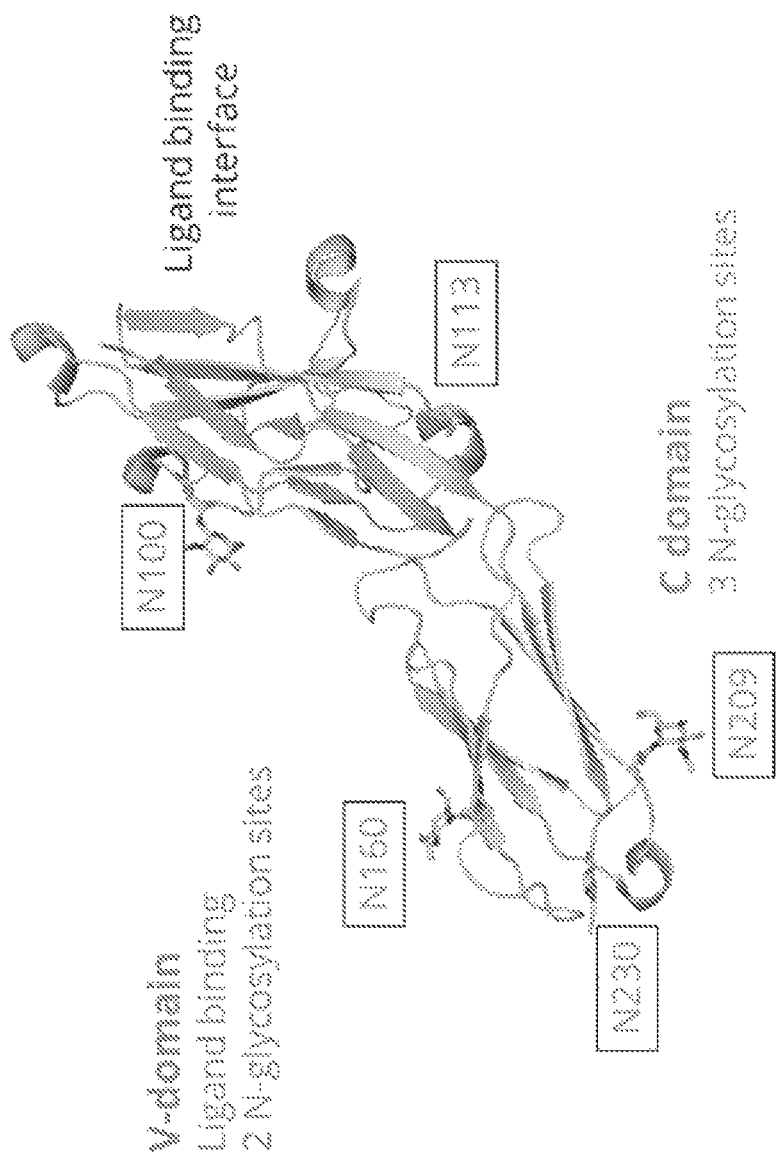
FIG. 1 shows a structural representation of the extracellular domain of human CD33 extracellular domain (ECD). CD33 ECD contains two prominent domains: distal V domain and membrane proximal C domain. Ligand binding interface is located on the V domain. Function of the C domain is unknown. ECD of CD33 is heavily glycosylated, with 2 N-linked glycosylation sites located in the V domain and 3 N-linked glycosylation sites located in the C domain. ECD of human CD33 contains several SNPs, with most prominent mutation R69G that is found in 42% patients. SNP R69G is in the V domain.

The invention provides multi-specific binding proteins that bind a CD33 on a cancer cell and the NKG2D receptor and CD16 receptor on natural killer cells to activate the natural killer cell, pharmaceutical compositions comprising such multi-specific binding proteins, and therapeutic methods using such multi-specific proteins and pharmaceutical compositions, including for the treatment of cancer. Various aspects of the invention are set forth below in sections; however, aspects of the invention described in one particular section are not to be limited to any particular section.

In one aspect, the invention provides a multi-specific binding protein comprising an antigen binding site that binds an epitope on an extracellular domain of human CD33 and/or Cynomolgus/Rhesus (cyno) CD33. In one aspect, the present invention provides an antigen binding site that recognizes and binds one or more conformational epitopes on the extracellular domain of human CD33 and/or Cynomolgus/Rhesus (cyno) CD33. In one aspect, the present invention provides an antigen binding site that recognizes and binds one or more conformational epitopes on the extracellular domain of human CD33 but does not recognize and/or bind one or more conformational epitopes on the extracellular domain of cyno CD33. In one aspect, the present invention provides an antigen binding site that binds to the R69G allele of human CD33. In one aspect, the present invention provides an antigen binding site that binds to wild-type human CD33 but not the R69G allele of human CD33. In one aspect, the present invention provides an antigen binding site that binds to an epitope on human CD33 that includes R69. In one aspect, the present invention provides an antigen binding site that binds to the S128N allele of human CD33. In one aspect, the present invention provides an antigen binding site that binds to wild-type human CD33 but not the S128N allele of human CD33. In one aspect, the present invention provides an antigen binding site that binds to an epitope on human CD33 that includes S128. In one aspect, the present invention provides an antigen binding site including a heavy chain variable domain, which binds to the extracellular domain in human CD33 and/or cyno CD33, irrespective of the glycosylation profile of the targeted CD33.

In certain embodiments the present invention provides a multi-specific binding protein comprising an antigen binding site, which binds to the extracellular domain in human CD33 and/or cyno CD33, such that the epitopes are unique compared to the epitopes targeted by one or more known anti-CD33 antibodies in the art. In certain embodiments, the present invention provides an antigen binding site, which binds to the extracellular domain in human CD33 and/or cyno CD33, and shows human or Cynomolgus/Rhesus (cyno) CD33 cross reactivity and high affinity binding to the target CD33.

To facilitate an understanding of the present invention, a number of terms and phrases are defined below.

The terms "a" and "an" as used herein mean "one or more" and include the plural unless the context is inappropriate.

As used herein, the term "antigen-binding site" refers to the part of the immunoglobulin molecule that participates in antigen binding. In human antibodies, the antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface, or in a recombinant polypeptide such as an scFv, using a peptide linker to connect the heavy chain variable domain to the light chain variable domain in a single polypeptide. All the amino acid positions in heavy or light chain variable regions disclosed herein are numbered according to Kabat numbering.

The CDRs of an antigen-binding site can be determined by the methods described in Kabat et al., J. Biol. Chem. 252, 6609-6616 (1977) and Kabat et al., Sequences of protein of immunological interest. (1991), Chothia et al., J. Mol. Biol. 196:901-917 (1987), and MacCallum et al., J. Mol. Biol. 262:732-745 (1996). The CDRs determined under these definitions typically include overlapping or subsets of amino acid residues when compared against each other. In certain embodiments, the term "CDR" is a CDR as defined by MacCallum et al., J. Mol. Biol. 262:732-745 (1996) and Martin A., Protein Sequence and Structure Analysis of Antibody Variable Domains, in Antibody Engineering, Kontermann and Dubel, eds., Chapter 31, pp. 422-439, Springer-Verlag, Berlin (2001). In certain embodiments, the term "CDR" is a CDR as defined by Kabat et al., J. Biol. Chem. 252, 6609-6616 (1977) and Kabat et al., Sequences of protein of immunological interest. (1991). In certain embodiments, heavy chain CDRs and light chain CDRs of an antibody are defined using different conventions. For example, in certain embodiments, the heavy chain CDRs are defined according to MacCallum (supra), and the light CDRs are defined according to Kabat (supra). CDRH1, CDRH2 and CDRH3 denote the heavy chain CDRs, and CDRL1, CDRL2 and CDRL3 denote the light chain CDRs.

As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably include humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Exemplary acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Exemplary bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Exemplary salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

Various features and aspects of the invention are discussed in more detail below.

I. Antigen-Binding Site

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:1, and an antibody light chain variable domain that includes an amino acid sequence at least 90% (e.g., at least 91%, 92%, 93%, 94%, 95%, 96%, 97%, 98%, 99%, or 100%) identical to SEQ ID NO:2. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:1, includes a CDR1 sequence represented by the amino acid sequence of SEQ ID NO:21, a CDR2 sequence represented by the amino acid sequence of SEQ ID NO:22, and a CDR3 sequence represented by the amino acid sequence of SEQ ID NO:23. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:1, includes a CDR1 sequence represented by the amino acid sequence of SEQ ID NO:434, a CDR2 sequence represented by the amino acid sequence of SEQ ID NO:22, and a CDR3 sequence represented by the amino acid sequence of SEQ ID NO:435. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:2, includes a CDR1 sequence represented by the amino acid sequence of SEQ ID NO:24, a CDR2 sequence represented by the amino acid sequence of SEQ ID NO:25, and a CDR3 sequence represented by the amino acid sequence of SEQ ID NO:26.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:3, and an antibody light chain variable domain that includes an amino acid sequence at least 90% (e.g., at least 91%, 92%, 93%, 94%, 95%, 96%, 97%, 98%, 99%, or 100%) identical to SEQ ID NO:4. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:3, includes a CDR1 sequence represented by the amino acid sequence of SEQ ID NO:27, a CDR2 sequence represented by the amino acid sequence of SEQ ID NO:28, and a CDR3 sequence represented by the amino acid sequence of SEQ ID NO:29. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:3, includes a CDR1 sequence represented by the amino acid sequence of SEQ ID NO:181, a CDR2 sequence represented by the amino acid sequence of SEQ ID NO:28, and a CDR3 sequence represented by the amino acid sequence of SEQ ID NO:436. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:4, includes a CDR1 sequence represented by the amino acid sequence of SEQ ID NO:30, a CDR2 sequence represented by the amino acid sequence of SEQ ID NO:31, and a CDR3 sequence represented by the amino acid sequence of SEQ ID NO:32.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:5, and an antibody light chain variable domain that includes an amino acid sequence at least 90% (e.g., at least 91%, 92%, 93%, 94%, 95%, 96%, 97%, 98%, 99%, or 100%) identical to SEQ ID NO:6. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:5, includes a CDR1 sequence represented by the amino acid sequence of SEQ ID NO:33, a CDR2 sequence represented by the amino acid sequence of SEQ ID NO:34, and a CDR3 sequence represented by the amino acid sequence of SEQ ID NO:35. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:5, includes a CDR1 sequence represented by the amino acid sequence of SEQ ID NO:183, a CDR2 sequence represented by the amino acid sequence of SEQ ID NO:34, and a CDR3 sequence represented by the amino acid sequence of SEQ ID NO:184. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:6, includes a CDR1 sequence represented by the amino acid sequence of SEQ ID NO:36, a CDR2 sequence represented by the amino acid sequence of SEQ ID NO:37, and a CDR3 sequence represented by the amino acid sequence of SEQ ID NO:38. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:6, includes a CDR1 sequence represented by the amino acid sequence of SEQ ID NO:36, a CDR2 sequence represented by the amino acid sequence of SEQ ID NO:185, and a CDR3 sequence represented by the amino acid sequence of SEQ ID NO:38. In certain embodiments, the antigen-binding site comprises an amino acid sequence at least 90% (e.g., at least 90%, 91%, 92%, 93%, 94%, 95%, 96%, 97%, 98%, 99%, or 100%) identical to SEQ ID NO:188. In certain embodiments, the antigen-binding site comprises an amino acid sequence at least 95% identical to SEQ ID NO:188. In certain embodiments, the antigen-binding site comprises an amino acid sequence at least 99% identical to SEQ ID NO:188. In certain embodiments, the antigen-binding site comprises the amino acid sequence of SEQ ID NO:188.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:7, and an antibody light chain variable domain that includes an amino acid sequence at least 90% (e.g., at least 91%, 92%, 93%, 94%, 95%, 96%, 97%, 98%, 99%, or 100%) identical to SEQ ID NO:8. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:7, includes a CDR1 sequence represented by the amino acid sequence of SEQ ID NO:39, a CDR2 sequence represented by the amino acid sequence of SEQ ID NO:40, and a CDR3 sequence represented by the amino acid sequence of SEQ ID NO:41. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:7, includes a CDR1 sequence represented by the amino acid sequence of SEQ ID NO:437, a CDR2 sequence represented by the amino acid sequence of SEQ ID NO:40, and a CDR3 sequence represented by the amino acid sequence of SEQ ID NO:438. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:8, includes a CDR1 sequence represented by the amino acid sequence of SEQ ID NO:42, a CDR2 sequence represented by the amino acid sequence of SEQ ID NO:43, and a CDR3 sequence represented by the amino acid sequence of SEQ ID NO:44.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:9, and an antibody light chain variable domain that includes an amino acid sequence at least 90% (e.g., at least 91%, 92%, 93%, 94%, 95%, 96%, 97%, 98%, 99%, or 100%) identical to SEQ ID NO:10. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:9, includes a CDR1 sequence represented by the amino acid sequence of SEQ ID NO:45, a CDR2 sequence represented by the amino acid sequence of SEQ ID NO:46, and a CDR3 sequence represented by the amino acid sequence of SEQ ID NO:47. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:9, includes a CDR1 sequence represented by the amino acid sequence of SEQ ID NO:181, a CDR2 sequence represented by the amino acid sequence of SEQ ID NO:46, and a CDR3 sequence represented by the amino acid sequence of SEQ ID NO:182. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:10, includes a CDR1 sequence represented by the amino acid sequence of SEQ ID NO:48, a CDR2 sequence represented by the amino acid sequence of SEQ ID NO:49, and a CDR3 sequence represented by the amino acid sequence of SEQ ID NO:50. In certain embodiments, the antigen-binding site comprises an amino acid sequence at least 90% (e.g., at least 91%, 92%, 93%, 94%, 95%, 96%, 97%, 98%, 99%, or 100%) identical to SEQ ID NO:198. In certain embodiments, the antigen-binding site comprises an amino acid sequence at least 95% identical to SEQ ID NO:198. In certain embodiments, the antigen-binding site comprises an amino acid sequence at least 99% identical to SEQ ID NO:198. In certain embodiments, the antigen-binding site comprises the amino acid sequence of SEQ ID NO:198.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:11, and an antibody light chain variable domain that includes an amino acid sequence at least 90% (e.g., at least 91%, 92%, 93%, 94%, 95%, 96%, 97%, 98%, 99%, or 100%) identical to SEQ ID NO:12. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:11, includes a CDR1 sequence represented by the amino acid sequence of SEQ ID NO:51, a CDR2 sequence represented by the amino acid sequence of SEQ ID NO:52, and a CDR3 sequence represented by the amino acid sequence of SEQ ID NO:53. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:11, includes a CDR1 sequence represented by the amino acid sequence of SEQ ID NO:181, a CDR2 sequence represented by the amino acid sequence of SEQ ID NO:52, and a CDR3 sequence represented by the amino acid sequence of SEQ ID NO:439. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:12, includes a CDR1 sequence represented by the amino acid sequence of SEQ ID NO:54, a CDR2 sequence represented by the amino acid sequence of SEQ ID NO:55, and a CDR3 sequence represented by the amino acid sequence of SEQ ID NO:56.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:13, and an antibody light chain variable domain that includes an amino acid sequence at least 90% (e.g., at least 91%, 92%, 93%, 94%, 95%, 96%, 97%, 98%, 99%, or 100%) identical to SEQ ID NO:14. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:13, includes a CDR1 sequence represented by the amino acid sequence of SEQ ID NO:57, a CDR2 sequence represented by the amino acid sequence of SEQ ID NO:58, and a CDR3 sequence represented by the amino acid sequence of SEQ ID NO:59. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:13, includes a CDR1 sequence represented by the amino acid sequence of SEQ ID NO:440, a CDR2 sequence represented by the amino acid sequence of SEQ ID NO:58, and a CDR3 sequence represented by the amino acid sequence of SEQ ID NO:441. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:14, includes a CDR1 sequence represented by the amino acid sequence of SEQ ID NO:60, a CDR2 sequence represented by the amino acid sequence of SEQ ID NO:61, and a CDR3 sequence represented by the amino acid sequence of SEQ ID NO:62.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:15, and an antibody light chain variable domain that includes an amino acid sequence at least 90% (e.g., at least 91%, 92%, 93%, 94%, 95%, 96%, 97%, 98%, 99%, or 100%) identical to SEQ ID NO:16. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:15, includes a CDR1 sequence represented by the amino acid sequence of SEQ ID NO:63, a CDR2 sequence represented by the amino acid sequence of SEQ ID NO:64, and a CDR3 sequence represented by the amino acid sequence of SEQ ID NO:65. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:15, includes a CDR1 sequence represented by the amino acid sequence of SEQ ID NO:442, a CDR2 sequence represented by the amino acid sequence of SEQ ID NO:64, and a CDR3 sequence represented by the amino acid sequence of SEQ ID NO:443. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:16, includes a CDR1 sequence represented by the amino acid sequence of SEQ ID NO:66, a CDR2 sequence represented by the amino acid sequence of SEQ ID NO:67, and a CDR3 sequence represented by the amino acid sequence of SEQ ID NO:68.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:17, and an antibody light chain variable domain that includes an amino acid sequence at least 90% (e.g., at least 91%, 92%, 93%, 94%, 95%, 96%, 97%, 98%, 99%, or 100%) identical to SEQ ID NO:18. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:17, includes a CDR1 sequence represented by the amino acid sequence of SEQ ID NO:69, a CDR2 sequence represented by the amino acid sequence of SEQ ID NO:70, and a CDR3 sequence represented by the amino acid sequence of SEQ ID NO:71. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:17, includes a CDR1 sequence represented by the amino acid sequence of SEQ ID NO:181, a CDR2 sequence represented by the amino acid sequence of SEQ ID NO:70, and a CDR3 sequence represented by the amino acid sequence of SEQ ID NO:444. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:18, includes a CDR1 sequence represented by the amino acid sequence of SEQ ID NO:72, a CDR2 sequence represented by the amino acid sequence of SEQ ID NO:73, and a CDR3 sequence represented by the amino acid sequence of SEQ ID NO:74.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:19, and an antibody light chain variable domain that includes an amino acid sequence at least 90% (e.g., at least 91%, 92%, 93%, 94%, 95%, 96%, 97%, 98%, 99%, or 100%) identical to SEQ ID NO:20. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:19, includes a CDR1 sequence represented by the amino acid sequence of SEQ ID NO:75, a CDR2 sequence represented by the amino acid sequence of SEQ ID NO:76, and a CDR3 sequence represented by the amino acid sequence of SEQ ID NO:77. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:19, includes a CDR1 sequence represented by the amino acid sequence of SEQ ID NO:445, a CDR2 sequence represented by the amino acid sequence of SEQ ID NO:76, and a CDR3 sequence represented by the amino acid sequence of SEQ ID NO:446. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:20, includes a CDR1 sequence represented by the amino acid sequence of SEQ ID NO:78, a CDR2 sequence represented by the amino acid sequence of SEQ ID NO:79, and a CDR3 sequence represented by the amino acid sequence of SEQ ID NO:80.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:266, and an antibody light chain variable domain that includes an amino acid sequence at least 90% (e.g., at least 91%, 92%, 93%, 94%, 95%, 96%, 97%, 98%, 99%, or 100%) identical to SEQ ID NO:267. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:266, includes a CDR1 sequence represented by the amino acid sequence of SEQ ID NO:304, a CDR2 sequence represented by the amino acid sequence of SEQ ID NO:305, and a CDR3 sequence represented by the amino acid sequence of SEQ ID NO:306. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:266, includes a CDR1 sequence represented by the amino acid sequence of SEQ ID NO:528, a CDR2 sequence represented by the amino acid sequence of SEQ ID NO:305, and a CDR3 sequence represented by the amino acid sequence of SEQ ID NO:529. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:267, includes a CDR1 sequence represented by the amino acid sequence of SEQ ID NO:307, a CDR2 sequence represented by the amino acid sequence of SEQ ID NO:308, and a CDR3 sequence represented by the amino acid sequence of SEQ ID NO:309.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:268, and an antibody light chain variable domain that includes an amino acid sequence at least 90% (e.g., at least 91%, 92%, 93%, 94%, 95%, 96%, 97%, 98%, 99%, or 100%) identical to SEQ ID NO:269. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:268, includes a CDR1 sequence represented by the amino acid sequence of SEQ ID NO:310, a CDR2 sequence represented by the amino acid sequence of SEQ ID NO:311, and a CDR3 sequence represented by the amino acid sequence of SEQ ID NO:312. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:268, includes a CDR1 sequence represented by the amino acid sequence of SEQ ID NO:530, a CDR2 sequence represented by the amino acid sequence of SEQ ID NO:311, and a CDR3 sequence represented by the amino acid sequence of SEQ ID NO:531. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:269, includes a CDR1 sequence represented by the amino acid sequence of SEQ ID NO:313, a CDR2 sequence represented by the amino acid sequence of SEQ ID NO:314, and a CDR3 sequence represented by the amino acid sequence of SEQ ID NO:315.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:270, and an antibody light chain variable domain that includes an amino acid sequence at least 90% (e.g., at least 91%, 92%, 93%, 94%, 95%, 96%, 97%, 98%, 99%, or 100%) identical to SEQ ID NO:271. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:270, includes a CDR1 sequence represented by the amino acid sequence of SEQ ID NO:316, a CDR2 sequence represented by the amino acid sequence of SEQ ID NO:317, and a CDR3 sequence represented by the amino acid sequence of SEQ ID NO:318. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:270, includes a CDR1 sequence represented by the amino acid sequence of SEQ ID NO:532, a CDR2 sequence represented by the amino acid sequence of SEQ ID NO:317, and a CDR3 sequence represented by the amino acid sequence of SEQ ID NO:533. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:271, includes a CDR1 sequence represented by the amino acid sequence of SEQ ID NO:319, a CDR2 sequence represented by the amino acid sequence of SEQ ID NO:320, and a CDR3 sequence represented by the amino acid sequence of SEQ ID NO:321.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:272, and an antibody light chain variable domain that includes an amino acid sequence at least 90% (e.g., at least 91%, 92%, 93%, 94%, 95%, 96%, 97%, 98%, 99%, or 100%) identical to SEQ ID NO:273. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:272, includes a CDR1 sequence represented by the amino acid sequence of SEQ ID NO:322, a CDR2 sequence represented by the amino acid sequence of SEQ ID NO:323, and a CDR3 sequence represented by the amino acid sequence of SEQ ID NO:324. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:272, includes a CDR1 sequence represented by the amino acid sequence of SEQ ID NO:534, a CDR2 sequence represented by the amino acid sequence of SEQ ID NO:323, and a CDR3 sequence represented by the amino acid sequence of SEQ ID NO:535. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:273, includes a CDR1 sequence represented by the amino acid sequence of SEQ ID NO:325, a CDR2 sequence represented by the amino acid sequence of SEQ ID NO:326, and a CDR3 sequence represented by the amino acid sequence of SEQ ID NO:327.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:274, and an antibody light chain variable domain that includes an amino acid sequence at least 90% (e.g., at least 91%, 92%, 93%, 94%, 95%, 96%, 97%, 98%, 99%, or 100%) identical to SEQ ID NO:275. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:274, includes a CDR1 sequence represented by the amino acid sequence of SEQ ID NO:328, a CDR2 sequence represented by the amino acid sequence of SEQ ID NO:329, and a CDR3 sequence represented by the amino acid sequence of SEQ ID NO:330. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:274, includes a CDR1 sequence represented by the amino acid sequence of SEQ ID NO:536, a CDR2 sequence represented by the amino acid sequence of SEQ ID NO:329, and a CDR3 sequence represented by the amino acid sequence of SEQ ID NO:537. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:275, includes a CDR1 sequence represented by the amino acid sequence of SEQ ID NO:331, a CDR2 sequence represented by the amino acid sequence of SEQ ID NO:332, and a CDR3 sequence represented by the amino acid sequence of SEQ ID NO:333.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:276, and an antibody light chain variable domain that includes an amino acid sequence at least 90% (e.g., at least 91%, 92%, 93%, 94%, 95%, 96%, 97%, 98%, 99%, or 100%) identical to SEQ ID NO:277. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:276, includes a CDR1 sequence represented by the amino acid sequence of SEQ ID NO:334, a CDR2 sequence represented by the amino acid sequence of SEQ ID NO:335, and a CDR3 sequence represented by the amino acid sequence of SEQ ID NO:336. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:276, includes a CDR1 sequence represented by the amino acid sequence of SEQ ID NO:538, a CDR2 sequence represented by the amino acid sequence of SEQ ID NO:335, and a CDR3 sequence represented by the amino acid sequence of SEQ ID NO:539. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:277, includes a CDR1 sequence represented by the amino acid sequence of SEQ ID NO:337, a CDR2 sequence represented by the amino acid sequence of SEQ ID NO:338, and a CDR3 sequence represented by the amino acid sequence of SEQ ID NO:339.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:278, and an antibody light chain variable domain that includes an amino acid sequence at least 90% (e.g., at least 91%, 92%, 93%, 94%, 95%, 96%, 97%, 98%, 99%, or 100%) identical to SEQ ID NO:279. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:278, includes a CDR1 sequence represented by the amino acid sequence of SEQ ID NO:340, a CDR2 sequence represented by the amino acid sequence of SEQ ID NO:341, and a CDR3 sequence represented by the amino acid sequence of SEQ ID NO:342. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:278, includes a CDR1 sequence represented by the amino acid sequence of SEQ ID NO:540, a CDR2 sequence represented by the amino acid sequence of SEQ ID NO:341, and a CDR3 sequence represented by the amino acid sequence of SEQ ID NO:541. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:279, includes a CDR1 sequence represented by the amino acid sequence of SEQ ID NO:343, a CDR2 sequence represented by the amino acid sequence of SEQ ID NO:344, and a CDR3 sequence represented by the amino acid sequence of SEQ ID NO:345.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:280, and an antibody light chain variable domain that includes an amino acid sequence at least 90% (e.g., at least 91%, 92%, 93%, 94%, 95%, 96%, 97%, 98%, 99%, or 100%) identical to SEQ ID NO:281. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:280, includes a CDR1 sequence represented by the amino acid sequence of SEQ ID NO:346, a CDR2 sequence represented by the amino acid sequence of SEQ ID NO:347, and a CDR3 sequence represented by the amino acid sequence of SEQ ID NO:348. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:280, includes a CDR1 sequence represented by the amino acid sequence of SEQ ID NO:542, a CDR2 sequence represented by the amino acid sequence of SEQ ID NO:347, and a CDR3 sequence represented by the amino acid sequence of SEQ ID NO:543. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:281, includes a CDR1 sequence represented by the amino acid sequence of SEQ ID NO:349, a CDR2 sequence represented by the amino acid sequence of SEQ ID NO:350, and a CDR3 sequence represented by the amino acid sequence of SEQ ID NO:351.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:282, and an antibody light chain variable domain that includes an amino acid sequence at least 90% (e.g., at least 91%, 92%, 93%, 94%, 95%, 96%, 97%, 98%, 99%, or 100%) identical to SEQ ID NO:283. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:282, includes a CDR1 sequence represented by the amino acid sequence of SEQ ID NO:352, a CDR2 sequence represented by the amino acid sequence of SEQ ID NO:353, and a CDR3 sequence represented by the amino acid sequence of SEQ ID NO:354. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:282, includes a CDR1 sequence represented by the amino acid sequence of SEQ ID NO:544, a CDR2 sequence represented by the amino acid sequence of SEQ ID NO:353, and a CDR3 sequence represented by the amino acid sequence of SEQ ID NO:545. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:283, includes a CDR1 sequence represented by the amino acid sequence of SEQ ID NO:355, a CDR2 sequence represented by the amino acid sequence of SEQ ID NO:356, and a CDR3 sequence represented by the amino acid sequence of SEQ ID NO:357.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:284, and an antibody light chain variable domain that includes an amino acid sequence at least 90% (e.g., at least 91%, 92%, 93%, 94%, 95%, 96%, 97%, 98%, 99%, or 100%) identical to SEQ ID NO:285. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:284, includes a CDR1 sequence represented by the amino acid sequence of SEQ ID NO:358, a CDR2 sequence represented by the amino acid sequence of SEQ ID NO:359, and a CDR3 sequence represented by the amino acid sequence of SEQ ID NO:360. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:284, includes a CDR1 sequence represented by the amino acid sequence of SEQ ID NO:546, a CDR2 sequence represented by the amino acid sequence of SEQ ID NO:359, and a CDR3 sequence represented by the amino acid sequence of SEQ ID NO:547. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:285, includes a CDR1 sequence represented by the amino acid sequence of SEQ ID NO:361, a CDR2 sequence represented by the amino acid sequence of SEQ ID NO:362, and a CDR3 sequence represented by the amino acid sequence of SEQ ID NO:363.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:286, and an antibody light chain variable domain that includes an amino acid sequence at least 90% (e.g., at least 91%, 92%, 93%, 94%, 95%, 96%, 97%, 98%, 99%, or 100%) identical to SEQ ID NO:287. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:286, includes a CDR1 sequence represented by the amino acid sequence of SEQ ID NO:364, a CDR2 sequence represented by the amino acid sequence of SEQ ID NO:365, and a CDR3 sequence represented by the amino acid sequence of SEQ ID NO:366. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:286, includes a CDR1 sequence represented by the amino acid sequence of SEQ ID NO:548, a CDR2 sequence represented by the amino acid sequence of SEQ ID NO:365, and a CDR3 sequence represented by the amino acid sequence of SEQ ID NO:549. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:287, includes a CDR1 sequence represented by the amino acid sequence of SEQ ID NO:367, a CDR2 sequence represented by the amino acid sequence of SEQ ID NO:368, and a CDR3 sequence represented by the amino acid sequence of SEQ ID NO:369.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:288, and an antibody light chain variable domain that includes an amino acid sequence at least 90% (e.g., at least 91%, 92%, 93%, 94%, 95%, 96%, 97%, 98%, 99%, or 100%) identical to SEQ ID NO:289. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:288, includes a CDR1 sequence represented by the amino acid sequence of SEQ ID NO:370, a CDR2 sequence represented by the amino acid sequence of SEQ ID NO:371, and a CDR3 sequence represented by the amino acid sequence of SEQ ID NO:372. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:288, includes a CDR1 sequence represented by the amino acid sequence of SEQ ID NO:550, a CDR2 sequence represented by the amino acid sequence of SEQ ID NO:371, and a CDR3 sequence represented by the amino acid sequence of SEQ ID NO:551. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:289, includes a CDR1 sequence represented by the amino acid sequence of SEQ ID NO:373, a CDR2 sequence represented by the amino acid sequence of SEQ ID NO:374, and a CDR3 sequence represented by the amino acid sequence of SEQ ID NO:375.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:290, and an antibody light chain variable domain that includes an amino acid sequence at least 90% (e.g., at least 91%, 92%, 93%, 94%, 95%, 96%, 97%, 98%, 99%, or 100%) identical to SEQ ID NO:291. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:290, includes a CDR1 sequence represented by the amino acid sequence of SEQ ID NO:376, a CDR2 sequence represented by the amino acid sequence of SEQ ID NO:377, and a CDR3 sequence represented by the amino acid sequence of SEQ ID NO:378. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:290, includes a CDR1 sequence represented by the amino acid sequence of SEQ ID NO:552, a CDR2 sequence represented by the amino acid sequence of SEQ ID NO:377, and a CDR3 sequence represented by the amino acid sequence of SEQ ID NO:553. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:291, includes a CDR1 sequence represented by the amino acid sequence of SEQ ID NO:379, a CDR2 sequence represented by the amino acid sequence of SEQ ID NO:380, and a CDR3 sequence represented by the amino acid sequence of SEQ ID NO:381.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:292, and an antibody light chain variable domain that includes an amino acid sequence at least 90% (e.g., at least 91%, 92%, 93%, 94%, 95%, 96%, 97%, 98%, 99%, or 100%) identical to SEQ ID NO:293. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:292, includes a CDR1 sequence represented by the amino acid sequence of SEQ ID NO:382, a CDR2 sequence represented by the amino acid sequence of SEQ ID NO:383, and a CDR3 sequence represented by the amino acid sequence of SEQ ID NO:384. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:292, includes a CDR1 sequence represented by the amino acid sequence of SEQ ID NO:554, a CDR2 sequence represented by the amino acid sequence of SEQ ID NO:383, and a CDR3 sequence represented by the amino acid sequence of SEQ ID NO:555. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:293, includes a CDR1 sequence represented by the amino acid sequence of SEQ ID NO:385, a CDR2 sequence represented by the amino acid sequence of SEQ ID NO:386, and a CDR3 sequence represented by the amino acid sequence of SEQ ID NO:387.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:294, and an antibody light chain variable domain that includes an amino acid sequence at least 90% (e.g., at least 91%, 92%, 93%, 94%, 95%, 96%, 97%, 98%, 99%, or 100%) identical to SEQ ID NO:295. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:294, includes a CDR1 sequence represented by the amino acid sequence of SEQ ID NO:388, a CDR2 sequence represented by the amino acid sequence of SEQ ID NO:389, and a CDR3 sequence represented by the amino acid sequence of SEQ ID NO:390. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:294, includes a CDR1 sequence represented by the amino acid sequence of SEQ ID NO:556, a CDR2 sequence represented by the amino acid sequence of SEQ ID NO:389, and a CDR3 sequence represented by the amino acid sequence of SEQ ID NO:557. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:295, includes a CDR1 sequence represented by the amino acid sequence of SEQ ID NO:391, a CDR2 sequence represented by the amino acid sequence of SEQ ID NO:392, and a CDR3 sequence represented by the amino acid sequence of SEQ ID NO:393.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:296, and an antibody light chain variable domain that includes an amino acid sequence at least 90% (e.g., at least 91%, 92%, 93%, 94%, 95%, 96%, 97%, 98%, 99%, or 100%) identical to SEQ ID NO:297. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:296, includes a CDR1 sequence represented by the amino acid sequence of SEQ ID NO:394, a CDR2 sequence represented by the amino acid sequence of SEQ ID NO:395, and a CDR3 sequence represented by the amino acid sequence of SEQ ID NO:396. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:296, includes a CDR1 sequence represented by the amino acid sequence of SEQ ID NO:558, a CDR2 sequence represented by the amino acid sequence of SEQ ID NO:395, and a CDR3 sequence represented by the amino acid sequence of SEQ ID NO:559. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:297, includes a CDR1 sequence represented by the amino acid sequence of SEQ ID NO:397, a CDR2 sequence represented by the amino acid sequence of SEQ ID NO:398, and a CDR3 sequence represented by the amino acid sequence of SEQ ID NO:399.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:298, and an antibody light chain variable domain that includes an amino acid sequence at least 90% (e.g., at least 91%, 92%, 93%, 94%, 95%, 96%, 97%, 98%, 99%, or 100%) identical to SEQ ID NO:299. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:298, includes a CDR1 sequence represented by the amino acid sequence of SEQ ID NO:400, a CDR2 sequence represented by the amino acid sequence of SEQ ID NO:401, and a CDR3 sequence represented by the amino acid sequence of SEQ ID NO:402. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:298, includes a CDR1 sequence represented by the amino acid sequence of SEQ ID NO:560, a CDR2 sequence represented by the amino acid sequence of SEQ ID NO:401, and a CDR3 sequence represented by the amino acid sequence of SEQ ID NO:561. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:299, includes a CDR1 sequence represented by the amino acid sequence of SEQ ID NO:403, a CDR2 sequence represented by the amino acid sequence of SEQ ID NO:404, and a CDR3 sequence represented by the amino acid sequence of SEQ ID NO:405.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:300, and an antibody light chain variable domain that includes an amino acid sequence at least 90% (e.g., at least 91%, 92%, 93%, 94%, 95%, 96%, 97%, 98%, 99%, or 100%) identical to SEQ ID NO:301. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:300, includes a CDR1 sequence represented by the amino acid sequence of SEQ ID NO:406, a CDR2 sequence represented by the amino acid sequence of SEQ ID NO:407, and a CDR3 sequence represented by the amino acid sequence of SEQ ID NO:408. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:300, includes a CDR1 sequence represented by the amino acid sequence of SEQ ID NO:562, a CDR2 sequence represented by the amino acid sequence of SEQ ID NO:407, and a CDR3 sequence represented by the amino acid sequence of SEQ ID NO:563. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:301, includes a CDR1 sequence represented by the amino acid sequence of SEQ ID NO:409, a CDR2 sequence represented by the amino acid sequence of SEQ ID NO:410, and a CDR3 sequence represented by the amino acid sequence of SEQ ID NO:411.

In certain embodiments, the present invention provides an antigen-binding site that includes an antibody heavy chain variable domain that includes an amino acid sequence at least 90% (e.g., at least 91%, 92%, 93%, 94%, 95%, 96%, 97%, 98%, 99%, or 100%) identical to the amino acid sequence of SEQ ID NO:302, and an antibody light chain variable domain that includes an amino acid sequence at least 90% (e.g., at least 91%, 92%, 93%, 94%, 95%, 96%, 97%, 98%, 99%, or 100%) identical to SEQ ID NO:303. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:302, includes a CDR1 sequence represented by the amino acid sequence of SEQ ID NO:412, a CDR2 sequence represented by the amino acid sequence of SEQ ID NO:413, and a CDR3 sequence represented by the amino acid sequence of SEQ ID NO:414. In certain embodiments, an antigen-binding site that includes an antibody heavy chain variable domain with an amino acid sequence at least 90% (e.g., at least 91%, 92%, 93%, 94%, 95%, 96%, 97%, 98%, 99%, or 100%) identical to the amino acid sequence of SEQ ID NO:302, includes a CDR1 sequence represented by the amino acid sequence of SEQ ID NO:564, a CDR2 sequence represented by the amino acid sequence of SEQ ID NO:413, and a CDR3 sequence represented by the amino acid sequence of SEQ ID NO:565. In certain embodiments, an antigen-binding site that includes an antibody light chain variable domain with an amino acid sequence at least 90% (e.g., at least 91%, 92%, 93%, 94%, 95%, 96%, 97%, 98%, 99%, or 100%) identical to the amino acid sequence of SEQ ID NO:303, includes a CDR1 sequence represented by the amino acid sequence of SEQ ID NO:415, a CDR2 sequence represented by the amino acid sequence of SEQ ID NO:416, and a CDR3 sequence represented by the amino acid sequence of SEQ ID NO:417.

In each of the foregoing embodiments, it is contemplated herein that immunoglobulin heavy chain variable region sequences and/or light chain variable region sequences that together bind CD33 may contain amino acid alterations (e.g., at least 1, 2, 3, 4, 5, or 10 amino acid substitutions, deletions, or additions) in the framework regions of the heavy and/or light chain variable regions without affecting their ability to bind to CD33 significantly.

Table 1 lists peptide sequences of heavy chain variable domains and light chain variable domains that, in combination (either as a Fab fragment or a single-chain variable fragment (scFv)), can bind to CD33. Unless indicated otherwise, the CDR sequences provided in Table 1 are determined under Kabat. The CD33-binding domains can vary in their binding affinity to CD33. Table 1 also lists scFv forms of the CD33-binding heavy and light chain variable domains. The exemplary nucleic acid sequences listed in Table 1 are predicted possible nucleic acid sequences that the listed corresponding peptide sequences originated from, and were generated using EMBL-EBI's Protein Sequence Back-translation program.

TABLE 1

| | VH | VL |
|---|---|---|
| ADI-10159 [Ab1] (G59) | EVQLVESGGGLVQPGGSLRLSC AASGFTFSSYGMSWVRQAPGKG LEWVANIKQDGSEKYYVDSVKG RFTISRDNAKNSLYLQMNSLRA EDTAVYYCAREGGPYYDSSGYF VYYGMDVWGQGTTVTVSS [SEQ ID NO: 1] | DIQMTQSPSTLSASVGDRVTITCR ASQSISSWLAWYQQKPGKAPKLLI YDASSLESGVPSRFSGSGSGTEFT LTISSLQPDDFATYYCQQYESFPT FGGGTKVEIK[SEQ ID NO: 2] |
| | CDR1: FTFSSYGMS[SEQ ID NO: 21](non-Kabat) or SYGMS[SEQ ID NO: 434] | CDR1: RASQSISSWLA[SEQ ID NO: 24] |
| | CDR2: NIKQDGSEKYYVDSVK G[SEQ ID NO: 22] | CDR2: DASSLES[SEQ ID NO: 25] |
| | CDR3: AREGGPYYDSSGYFVY YGMDV[SEQ ID NO: 23] (non-Kabat) or EGGPYYD SSGYFVYYGMDV[SEQ ID NO: 435] | CDR3: QQYESFPT[SEQ ID NO: 26] |
| scFv of Ab1 | DIQMTQSPSTLSASVGDRVTITCRASQSISSWLAWYQQKPGKAPKL LIYDASSLESGVPSRFSGSGSGTEFTLTISSLQPDDFATYYCQQYE SFPTFGCGTKVEIKGGGGSGGGGSGGGGSGGGGSEVQLVESGGGLV QPGGSLRLSCAASGFTFSSYGMSWVRQAPGKCLEWVANIKQDGSEK YYVDSVKGRFTISRDNAKNSLYLQMNSLRAEDTAVYYCAREGGPYY DSSGYFVYYGMDVWGQGTTVTVSS[SEQ ID NO: 206] | |
| | EVQLVESGGGLVQPGGSLRLSCAASGFTFSSYGMSWVRQAPGKCLE WVANIKQDGSEKYYVDSVKGRFTISRDNAKNSLYLQMNSLRAEDTA VYYCAREGGPYYDSSGYFVYYGMDVWGQGTTVTVSSGGGGSGGG GSGGGGSGGGGSDIQMTQSPSTLSASVGDRVTITCRASQSISSWLA WYQQKPGKAPKLLIYDASSLESGVPSRFSGSGSGTEFTLTISSLQP DDFATYYCQQYESFPTFGCGTKVEIK[SEQ ID NO: 207] | |
| Exemplary nucleotide sequence of Ab1 scFv | GACATCCAGMTGACCCAGAGCCCCAGCACCCTGAGcGcCAGCGT GGGCGACAGGGTGACCATCACCTGCAGGGCCAGCCAGAGCATCA GCAGCTGGCTGGCCTGGTACCAGCAGAAGCCCGGCAAGGCCCCC AAGCTGCTGATCTACGACGCCAGCAGCCTGGAGAGCGGCGTGCC CAGCAGGTTCAGCGGCAGCGGCAGCGGCACCGAGTTCACCCTGA CCATCAGCAGCCTGCAGCCCGACGACTCGCCACCTACTACTGCC AGCAGTACGAGAGCTTCCCCCACCTTCGGCTGCGGCACCAAGGTG GAGATCAAGGGCGGCGGCGGCAGCGGCGGCGGCGGCAGCGGCGG CGGCGGCAGCGGCGGCGGCGGCAGCGAGGTGCAGCTGGTGGAGA GCGGCGGCGGCCTGGTGCAGCCCGGCGGCAGCCTGAGGCTGAGC TGCGCCGCCAGCGGCTTCACCTTCAGCAGCTACGGCATGAGCTG GGTGAGGCAGGCCCCCGGCAAGTGccTGGAGTGGGTGGCCAACA TCAAGCAGGACGGCAGCGAGAAGTACTACGTGGACAGCGTGAAG GGCAGGTTCACCATCAGCAGGGACAACGCCAAGAACAGCCTGTA CCTGCAGATGAACAGCCTGAGGGCCGAGGACACCGCCGTGTACT ACTGCGCCAGGGGAGGGCGGCCCCTACTACGACAGCAGCGGCTAC TTCGTGTACTACGGCATGGACGTGTGGGGCCAGGGCACCACCGT GACCGTGAGCAGC[SEQ ID NO: 246] | |

TABLE 1-continued

| | VH | VL |
|---|---|---|
| | GAGGTGCAGCTGGTGGAGAGCGGCGGCGGCCTGGTGCAGCCCGG<br>CGGCAGCCTGAGGCTGAGCTGCGCCGCCAGCGGCTTCACCTTCA<br>GCAGCTACGGCATGAGCTGGGTGAGGCAGGCCCCCGGCAAGTGC<br>CTGGAGTGGGTGGCCAACATCAAGCAGGACGGCAGCGAGAAGTA<br>CTACGTGGACAGCGTGAAGGGCAGGTTCACCATCAGCAGGGACA<br>ACGCCAAGAACAGCCTGTACCTGCAGATGAACAGCCTGAGGGCC<br>GAGGACACCGCCGTGTACTACTGCGCCAGGGAGGGCGGCCCCTA<br>CTACGACAGCAGCGGCTACTTCGTGTACTACGGCATGGACGTGT<br>GGGGCCAGGGCACCACCGTGACCGTGAGCAGCGGCGGCGGCGGC<br>AGCGGCGGCGGCGGCAGCGGCGGCGGCGGCAGCGGCGGCGGCGG<br>CAGCGACATCCAGATGACCCAGAGCCCCAGCACCCTGAGCGCCA<br>GCGTGGGCGACAGGGTGACCATCACCTGCAGGGCCAGCCAGAGC<br>ATCAGCAGCTGGCTGGCCTGGTACCAGCAGAAGCCCGGCAAGGC<br>CCCCAAGCTGCTGATCTACGAGGCCAGCAGCCTGGAGAGCGGCG<br>TGCCCAGCAGGTTCAGCGGCAGCGGCAGCGGCACCGAGTTCACC<br>CTGACCATCAGCAGCCTGCAGCCCGACGACTTCGCCACCTACTA<br>CTGCCAGCAGTACGAGAGCTTCCCCACCTTCGGCTGCGGCACCA<br>AGGTGGAGATCAAG[SEQ ID NO: 247] | |
| ADI-<br>10177<br>[Ab2] | EVQLVESGGGLVQPGGSLRLSC<br>AASGFTFSSYWMSWVRQAPGKG<br>LEWVANIKQDGSEKYYVDSVKG<br>RFTISRDNAKNSLYLQMNSLRA<br>EDTAVYYCARPLNAGELDVWGQ<br>GTMVTVSS[SEQ ID NO: 3] | DIQMTQSPSTLSASVGDRVTITCR<br>ASQSISSWLAWYQQKPGKAPKLLI<br>YEASSLESGVPSRFSGSGSGTEFT<br>LTISSLQPDDFATYYCQQLESYPL<br>TFGGGTKVEIK[SEQ ID NO:<br>4] |
| | CDR1: FTFSSYWMS[SEQ ID<br>NO: 27](non-Kabat) or<br>SYWMS[SEQ ID NO: 181] | CDR1: RASQSISSWLA[SEQ ID<br>NO: 30] |
| | CDR2: NIKQDGSEKYYVDSVK<br>[GSEQ ID NO: 28] | CDR2: EASSLES[SEQ ID NO:<br>31] |
| | CDR3: ARPLNAGELDV[SEQ<br>ID NO: 29](non-Kabat)<br>or PLNAGELDV[SEQ ID<br>NO: 436] | CDR3: QQLESYPLT[SEQ ID<br>NO: 32] |
| scFv of<br>Ab2 | DIQMTQSPSTLSASVGDRVTITCRASQSISSWLAWYQQKPGKAPKL<br>LIYEASSLESGVPSRFSGSGSGTEFTLTISSLQPDDFATYYCQQLE<br>SYPLTFGCGTKVEIKGGGGSGGGGSGGGGSGGGGSEVQLVESGGG<br>LVQPGGSLRLSCAASGFTFSSYWMSWVRQAPGKCLEWVANIKQDGS<br>EKYYVDSVKGRFTISRDNAKNSLYLQMNSLRAEDTAVYYCARPLNA<br>GELDVWGQGTMVTVSS[SEQ ID NO: 208] | |
| | EVQLVESGGGLVQPGGSLRLSCAASGFTFSSYWMSWVRQAPGKCLE<br>WVANIKQDGSEKYYVDSVKGRFTISRDNAKNSLYLQMNSLRAEDTA<br>VYYCARPLNAGELDVWGQGTMVTVSSGGGGSGGGGSGGGGSGG<br>GGSDIQMTQSPSTLSASVGDRVTITCRASQSISSWLAWYQQKPGKA<br>PKLLIYEASSLESGVPSRFSGSGSGTEFTLTISSLQPDDFATYYCQ<br>QLESYPLTFGCGTKVEIK[SEQ ID NO: 209] | |
| Exemplary<br>nucleotide<br>sequence<br>of Ab2<br>scFv | GACATCCAGATGACCCAGAGCCCCAGCACCCTGAGCGCCAGCGT<br>GGGCGACAGGGTGACCATCACCTGCAGGGCCAGCCAGAGCATCA<br>GCAGCTGGCTGGCCTGGTACCAGCAGAAGCCCGGCAAGGCCCCC<br>AAGCTGCTGATCTACGAGGCCAGCAGCGGGAGAGCGGCGTGCCC<br>AGCAGGTTCAGCGGCAGCGGCAGCGGCACCGAGTTCACCCTGAC<br>CATCAGCAGCCTGCAGCCCGACGACTTCGCCACCTACTACTGCC<br>AGCAGCTGGAGAGCTACCCCCTGACCTTCGGCTGCGGCACCAAG<br>GTGGAGATCAAGGGCGGCGGCGGCAGCGGCGGCGGCGGCAGCGG<br>CGGCGGCGGCAGCGGCGGCGGCGGCAGCGAGGTGCAGCTGGTGG<br>AGAGCGGCGGCGGCCTGGTGCAGCCCGGCGGCAGCCTGAGGCTG<br>AGCTGCGCCGCCAGCGGCTTCACGTCAGCAGCTACTGGATGAGC<br>TGGGTGAGGCAGGCCCCCGGCAAGTGCCTGGAGTGGGTGGCCAA<br>CATCAAGCAGGACGGCAGCGAGAAGTACTACGTGGACAGCGTGA<br>AGGGCAGGTTCACCATCAGCAGGGACAACGCCAAGAACAGCCTG<br>TACCTGCAGATGAACAGCCTGAGGGCCGAGGACACCGCCGTGTA<br>CTACTGCGCCAGGCCCCTGAACGCCGGCGAGCTGGACGTGTGGG<br>GCCAGGGCACCATGGTGACCGTGAGCAGC[SEQ ID NO:<br>248] | |
| | GAGGTGCAGCTGGTGGAGAGCGGCGGCGGCGGGTGCAGCCCGGC<br>GGCAGCCTGAGGCTGAGCTGCGCCGCCAGCGGCTTCACGTCAGC<br>AGCTACTGGATGAGCTGGGTGAGGCAGGCCCCCGGCAAGTGCCT<br>GGAGTGGGTGGCCAACATTTCAAGCAGGACGGCAGCGAGAAGTA<br>CTACGTGGACAGCGTGAAGGGCAGGTTCACCATCAGCAGGGACA<br>ACGCCAAGAACAGCCTGTACCTGCAGATGAACAGCCTGAGGGCC | |

TABLE 1-continued

| | VH | VL |
|---|---|---|
| | GAGGACACCGCCGTGTACTACTGCGCCAGGCCCCTGAACGCCGC CGAGCTGGACGTGTGGGGCCAGGGCACCATGGTGACCGTGAGCA GCGGCGGCGGCGGCAGCGGCGGCGGCGGCAGCGGCGGCGGCGGC AGCGGCGGCGGCGGCAGCGACATCCAGATGACCCAGAGCCCCAG CACCCTGAGCGCCAGCGTGGGCGACAGGGTGACCATCACCTGCA GGGCCAGCCAGAGCATCAGCAGCTGGCTGGCCTGGTACCAGCAG AAGCCCGGCAAGGCCCCCAAGCTGCTGATCTACGAGGCCAGCAG CGGGAGAGCGGCGTGCCCAGCAGGTTCAGCGGCAGCGGCAGCGG CACCGAGTTCACCCTGACCATCAGCAGCCTGCAGCCCGACGACT TCGCCACCTACTACTGCCAGCAGCTGGAGCTACCCCCTGACC TTCGGCTGCGGCACCAAGGTGGAGATCAAG[SEQ ID NO: 249] | |
| ADI-11776 [Ab3] (H76) | EVQLLESGGGLVQPGGSLRLSC AASGFTFSKYTMSWVRQAPGKG LEWVSAIVGSGESTYFADSVKG RFTISRDNSKNTLYLQMNSLRA EDTAVYYCAREGGPYYDSSGYF VYYGMDVWGQGTTVTVSS [SEQ ID NO: 5] | DIQMTQSPSTLSASVGDRVTITCR ASQSISSWLAWYQQKPGKAPKLLI YKASSLESGVPSRFSGSGSGTEFT LTISSLQPDDFATYYCQQYDDLPT FGGGTKVEIK[SEQ ID NO: 6] |
| | CDR1: FTFSKYTMS[SEQ ID NO: 33](non-Kabat) or KYTMS[SEQ ID NO: 183] | CDR1: RASQSISSWLA[SEQ ID NO: 36] |
| | CDR2: AIVGSGESTYFADSVK G[SEQ ID NO: 34] | CDR2: KASSLES[SEQ ID NO: 37] or KASSLE[SEQ ID NO: 185](non-Kabat) |
| | CDR3: AREGGPYYDSSGYFVY YGMDV[SEQ ID NO: 35] (non-Kabat) or EGGPYYD SSGYFVYYGMDV[SEQ ID NO: 184] | CDR3: QQYDDLPT[SEQ ID NO: 38] |
| scFv of Ab3 | DIQMTQSPSTLSASVGDRVTITCRASQSISSWLAWYQQKPGKAPKL LIYKASSLESGVPSRFSGSGSGTEFTLTISSLQPDDFATYYCQQYD DLPTFG<u>C</u>GTKVEIKGGGGSGGGGSGGGGSGGGGSEVQLLESGGGLV QPGGSLRLSCAASGFTFSKYTMSWVRQAPGKCLEWVS<u>AIVGSGEST YFADSVKGRFTISRDNSKNTLYLQMNSLRAEDTAVYYCAREGGPYY DSSGYFVYYGMDV</u>WGQGTTVTVSS [SEQ ID NO: 198] EVQLLESGGGLVQPGGSLRLSCAASGFTFSKYTMSWVRQAPGK<u>C</u>LE WVSAIVGSGESTYFADSVKGRFTISRDNSKNTLYLQMNSLRAEDTAV YYCAREGGPYYDSSGYFVYYGMDVWGQGTTVTVSSGGGGSGGGG SGGGGSGGGGSDIQMTQSPSTLSASVGDRVTITCRASQSISSWLAW YQQKPGKAPKLLIYKASSLESGVPSRFSGSGSGTEFTLTISSLQPD DFATYYCQQYDDLPTFG<u>C</u>GTKVEIK[SEQ ID NO: 210] | |
| Exemplary nucleotide sequence of Ab3 scFv | GACATCCAGATGACCCAGAGCCCCAGCACCCTGAGCGCCAGCGT GGGCGACAGGGTGACCATCACCTGCAGGGCCAGCCAGAGCKFCA GCAGCTGGCTGGCCTGGTACCAGCAGAAGCCCGGCAAGGCCCCC AAGCTTGCTGATCTACAAGGCCAGCAGCCTGGAGAGCGGCGTGC CCAGCAGGTTCAGCGGCAGCGGCAGCGGCACCGAGTTCACCCTG ACCATCAGCAGCCTGCAGCCCGACGACTTCGCCACCTACTACTG CCAGCAGTFACGACGACCTTGCCCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGGTGCAGCTGCTG GAGAGCGGCGGCGGCCTGGTTGCAGCCCGGCGGCAGCCTGAGGC TGAGCTGCGCCGCCAGCGGCTTCACCTTCAGCAAGTACACCATG AGCTGGGTGAGGCAGGCCCCCGGCAAGTGCCTGGAGTGGGTGAG CGCCATCCTCCCCAGCGCCCAGACCACCTACTTCGCCGACAGCG TGAAGGGCAGGTTCACCATCAGCAGGGACAACAGCAAGAACACC CTGTACCTGCAGATGAACAGCCTGAGGGCCGAGGACACCGCCGT GTTACTACTGCGCCAGGGAGGGCGGCCCCTACTACGACAGCAGC GGCTACTTCGTGTACTACGGCATGGACGTGTGGGGCCAGGGCAC CACCGTGACCGTGAGCAGC[SEQ ID NO: 250] GAGGTGCAGCTGCTGGAGAGCGGCGGCGGCCTGGTGCAGCCCGG CGGCAGCCTGAGGCTGAGCTGCGCCGCCAGCGGCTTCACCTTCA GCAAGTACACCATGAGCTGGGTGAGGCAGGCCCCCGGCAAGTGC CTGGAGTGGGTGAGCGCCATCGTGGGCAGCGGCGAGAGCACCTA CTTCGCCGACAGCGTGAAGGGCAGGTTCACCATCAGCAGGGACA ACAGCAAGAACACCCTGTACCTGcAGATGAACAGCCTGAGGGCC GAGGACACCGCCGTGTACTACTGCGCCAGGGAGGGCGGCCCCTA CTACGACAGCAGCGGCTACTTCGTGTACTACGGCATGGACGTGT GGGGCCAGGGCACCACCGTGACCGTGAGCAGCGGCCTGCGCCGG CAGCGGCGGCGGCGGCAGCGGCGGCGGCGGCAGCGGCGGCGGCG | |

TABLE 1-continued

| | VH | VL |
|---|---|---|
| | GCAGCGACATCCAGATGACCCAGAGCCCCAGCACCTGAGCGCCA GCGTGGGCGACAGGGTGACCATCACCTGCAGGGCCAGCCAGAGC ATCAGCAGCTGGCTGGCCTGGTACCAGCAGAAGCCCGGCAAGGC CCCCAAGCTGCTGATCTACAAGGCCAGCAGccTGGAGAGCGGCG TGCCCAGCAGGTTCAGCGGCAGCGGCAGCGGCACCGAGTTCACC CTGACCATCAGCAGCCTGCAGCCCGACGACTTCGCCACCTACTA CTGCCAGCAGTACGACGACCTGCCCACCTTCGGCTGCGGCACCA AGGTGGAGATCAAG[SEQ ID NO: 251] | |
| ADI-11801 [Ab4] | QVQLVQSGAEVKKPGASVKVSC KASGYTFSDYYMHWVRQAPGQG LEWMGMINPSWGSTSYAQKFQG RVTMTRDTSTSTVYMELSSLRS EDTAVYYCAREAADGFVGERYF DLWGRGTLVTVSS[SEQ ID NO: 7] | DIVMTQSPLSLPVTPGEPASISCR SSQSLLYSNGYNYLDWYLQKPGQS PQLLIYLGSNRASGVPDRFSGSGS GTDFTLKISRVEAEDVGVYYCMQD VALPITFGGGTKVEIK[SEQ ID NO: 8] |
| | CDR1: YTFSDYYMH[SEQ ID NO: 39](non-Kabat) or DYYMH[SEQ ID NO: 437] | CDR1: RSSQSLLYSNGYNYLD [SEQ ID NO: 42] |
| | CDR2: MINPSWGSTSYAQKFQ G[SEQ ID NO: 40] | CDR2: LGSNRAS[SEQ ID NO: 43] |
| | CDR3: AREAADGFVGERYFDL [SEQ ID NO: 41](non-Kabat) or EAADGFVGERYF DL[SEQ ID NO: 438] | CDR3: MQDVALPIT[SEQ ID NO: 44] |
| scFv of Ab4 | DIVIVITQSPLSLPVTPGEPASISCRSSQSLLYSNGYNYLDWYLQK PGQSPQLLIYLGSNRASGVPDRFSGSGSGTDFTLKISRVEAEDGV YYCMQDVALPITFGCGTKVEIKGGGGSGGGGSGGGGSGGGGSQVQL VQSGAEVKKPGASVKVSCKASGYTFSDYYMHWVRQAPGQCLEWMGM INPSWGSTSYAQKFQGRVTMTRDTSTSTVYMELSSLRSEDTAVYYC AREAADGFVGERYFDLWGRGTLVTVSS[SEQ ID NO: 211] QVQLVQSGAEVKKPGASVKVSCKASGYTFSDYYMHWVRQAPGQCLE WMGMINPSWGSTSYAQKFQGRVTMTRDTSTSTVYMELSSLRSEDTA VYYCAREAADGFVGERYFDLWGRGTLVTVSSGGGGSGGGGSGG GGSGGGGSDIVMTQSPLSLPVTPGEPASISCRSSQSLLYSNGYNYL DWYLQKPGQSPQLLIYLGSNRASGVPDRFSGSGSGTDFTLKISRVE AEDVGVYYCMQDVALPITFGCGTKVEIK[SEQ ID NO: 212] | |
| Exemplary nucleotide sequence of Ab4 scFv | GACATCGTGATGACCCAGAGCCCCCTGAGCCTGCCCGTGACCCC CGGCGAGCCCGCCAGCATCAGCTGCAGGAGCAGCCAGAGCCTGC TGTACAGCAACGGCTACAACTACCTGGACTGGTACCTGCAGAAG CCCGGCCAGAGCCCCCAGGTGCTGATCTACCTGGGCAGCAACAG GGCCAGCGGCGTGCCCGACAGGTTCAGCGGCAGCGGCAGCGGCA CCGAGTTCACCCTGAAGATCAGCAGGGTGGAGGCCGAGGACGTGG GCGTGTACTACTGCATGCAGGACGTGGCCCTGCCCATCACCTTC GGCTGCGGCACCAAGGTGGAGATCAAGGGCGGCGGCGGCAGCGG CGGCGGCGGCAGCGGCGGCGGCGGCAGCGGCGGCGGCGGCAGCC AGGTGCAGCTGGTGCAGAGCGGCGCCGAGGTGAAGAAGCCCGGC GCCAGCGTGAAGGTGAGCTGCAAGGCCAGCGGCTACACCTTCAG CGACTACTACATGCACTGGGTGAGGCAGGCCCCCGGCCAGTGCC TGGAGTGGATGGGCATGATCAACCCCAGCTGGGGCAGCACCAGC TACGCCCAGAAGTTCCAGGGCACTGGTGACCATGACCAGGGACA CCAGCACCAGCACCGTGTACATGGAGCTGAGCAGCCTGAGGAGC GAGGACACCGCCGTGTACTACTGCGCCAGGGAGGCCGCCGACGG CTTCGTGGGCGAGAGGTACTTCGACCTGTGGGGCAGGGGCACCC TGGTGACCGTGAGCAGC[SEQ ID NO: 252] CAGGTGCAGCTGGTGCAGAGCGGCGCCGAGGTGAAGAAGCCCGG CGCCAGCGTGAAGGTGAGCTGCAAGGCCAGCGGCTACACCTTCA GCGACTACTACATGCACTGGGTGAGGCAGGCCCCCGGCCAGTGC CTGGAGTGGATGGGCATGATCAACCCCAGCTGGGGCAGCACCAG CTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGAGGCCGCCGACGG CTTCGTGGGCGAGAGGTACTTCGACCTGTGGGGCAGGGGCACCC TGGTGACCGTGAGCAGCGGCGGCGGCGGCAGCGGCGGCGGCGGC AGCGGCGGCGGCGGCAGCGGCGGCGGCGGCAGCGACATCGTGAT GACCCAGAGCCCCCTGAGCCTGCCCGTGACCCCCGGCGAGCCCG CCAGCATCAGCTGCAGGAGCAGCCAGAGCCTGCTGTACAGCAAC GGCTACAACTACGGGACTGGTACCGGCAGAAGCCCGGCCAGAGCC | |

TABLE 1-continued

| | VH | VL |
|---|---|---|
| | CCCAGCTGCTGATCTACCTGGGCAGCAACAGGGCCAGCGGCGTG<br>CCCGACAGGTTCAGCGGCAGCGGCAGCGGCACCGACTTCACCCT<br>GAAGATCAGCAGGGTGGAGGCCGAGGACGTGGCGTGTACTACT<br>GCATGCAGGACGTGGCCCTGCCCATCACGTCGGCTGCGGCACCA<br>AGGTGGAGATCAAG[SEQ ID NO: 253] | |
| ADI-11807<br>[Ab5]<br>(I07) | EVQLVESGGGLVQPGGSLRLSC<br>AASGFTFGSYWMSWVRQAPGKG<br>LEWVATIKQDGSEKSYVDSVKG<br>RFTISRDNAKNSLYLQMNSLRA<br>EDTAVYYCARPLNAGELDVWGQ<br>GTMVTVSS[SEQ ID NO: 9] | DIQMTQSPSTLSASVGDRVTITCR<br>ASQSISSWLAWYQQKPGKAPKLLI<br>YEASSLESGVPSRFSGSGSGTEFT<br>LTISSLQPDDFATYYCQQSQSYPP<br>ITFGGGTKVEIK[SEQ ID<br>NO: 10] |
| | CDR1: FTFGSYWMS[SEQ ID<br>NO: 45](non-Kabat) or<br>SYWMS [SEQ ID NO: 181] | CDR1: RASQSISSWLA[SEQ ID<br>NO: 48] |
| | CDR2: TIKQDGSEKSYVDSVK<br>G[SEQ ID NO: 46] | CDR2: EASSLES[SEQ ID NO:<br>49] |
| | CDR3: ARPLNAGELDV[SEQ<br>ID NO: 47](non-Kabat)<br>or RPLNAGELDV[SEQ ID<br>NO: 182] | CDR3: QQSQSYPPIT[SEQ ID<br>NO: 50] |
| scFv of<br>Ab5 | 107scFv<br>DIQMTQSPSTLSASVGDRVTITCRASQSISSWLAWYQQKPGKAPKL<br>LIYEASSLESGVPSRFSGSGSGTEFTLTISSLQPDDFATYYCQQSQ<br>SYPPITFGCGTKVEIKGGGGSGGGGSGGGGSGGGGSEVQLVESGGG<br>LVQPGGSLRLSCAASGFTFGSYWMSWVRQAPGKCLEWVATIKQDGS<br>EKSYVDSVKGRFTISRDNAKNSLYLQMNSLRAEDTAVYYCARPLNA<br>GELDVWGQGTMVTVSS[SEQ ID NO: 188]<br><br>EVQLVESGGGLVQPGGSLRLSCAASGFTFGSYWMSWVRQAPGKCLE<br>WVATIKQDGSEKSYVDSVKGRFTISRDNAKNSLYLQMNSLRAEDTA<br>VYYCARPLNAGELDVWGQGTMVTVSSGGGGSGGGGSGGGGSGG<br>GGSDIQMTQSPSTLSASVGDRVTITCRASQSISSWLAWYQQKGKA<br>PKLLIYEASSLESGVPSRFSGSGSGTEFTLTISSLQPDDFATYYCQ<br>QSQSYPPITFGCGTKVEIK[SEQ ID NO: 213] | |
| Exemplary<br>nucleotide<br>sequence<br>of Ab5<br>scFv | GACATCCAGATGACCCAGAGCCCCAGCACCCTGAGCGCCAGCGT<br>GGGCGACAGGGTGACCATCACCTGCAGGGCCAGCCAGAGCATCA<br>GCAGCTGGCTGGCCTGGTACCAGCAGAAGCCCGGCAAGGCCCCC<br>AAGCTGCTGATCTACGAGGCCAGCAGCCTGGAGAGCGGCGTGCC<br>CAGCAGGTTCAGCGGCAGCGGCAGCGGCACCGAGTTCACCCTGA<br>CCATCAGCAGCCTGCAGCCCGACGACTTCGCCACCTACTACTGC<br>CAGCAGAGCCAGAGCTACCCCCCCATCACCTTCGGCTGCGGCAC<br>CAAGGTGGAGATCAAGGGCGGCGGCGGCAGCGGCGGCGGCGGCA<br>GCGGCGGCGGCGGCAGCGGCGGCGGCGGCAGCGAGGTGCAGCTG<br>GTGGAGAGCGGCGGCGGCCTGGTGCAGCCCGGCGGCAGCCTGAG<br>GCTGAGCTGCGCCGCCAGCGGCTTCACCTTCGGCAGCTACTGGA<br>TGAGCTGGGTGAGGCAGGCCCCCGGCAAGTGCCTGGAGTGGGTG<br>GCCACCATCAAGCAGGACGGCAGCGAGAAGAGCTACGTGGACAG<br>CGTGAAGGGCAGGTTCACCATCAGCAGGGACAACGCCAAGAACA<br>GCCTGTACCTGCAGATGAACAGCCTGAGGGCCGAGGACACCGCC<br>GTGTACTACTGCGCCAGGCCCCTGAACGCCGGCGAGCTGGACGT<br>GTGGGGCCAGGGCACCATGGTGACCGTGAGCAGC[SEQ ID<br>NO: 254]<br><br>GAGGTGCAGCTGGTGGAGAGCGGCGGCGGCCTGGTGCAGCCCGG<br>CGGCAGCCTGAGGCTGAGCTGCGCCGCCAGCGGCTTCACCTTCG<br>GCAGCTACTGGATGAGCTGGGTGAGGCAGGCCCCCGGCAAGTGC<br>CTGGAGTGGGTGGCCACCATCAAGCAGGACGGCAGCGAGAAGAG<br>CTACGTGGACAGCGTGAAGGGCAGGTTCACCATCAGCAGGGACA<br>ACGCCAAGAACAGCCTGTACCTGCAGATGAACAGCCTGAGGGCC<br>GAGGACACCGCCGTGTACTACTGCGCCAGGCCCCTGAACGCCGG<br>CGAGCTGGACGTGTGGGGCCAGGGCACCATGGTGACCGTGAGCA<br>GCGGCGGCGGCGGCAGCGGCGGCGGCGGCAGCGGCGGCGGCGGC<br>AGCGGCGGCGGCGGCAGCGACATCCAGATGACCCAGAGCCCCAG<br>CACCCTGAGCGCCAGCGTGGGCGACAGGGTGACCATCACCTGCA<br>GGGCCAGCCAGAGCATCAGCAGCTGGCTGGCCTGGTACCAGCAG<br>AAGCCCGGCAAGGCCCCCAAGCTGCTGATCTACGAGGCCAGCAG<br>CCTGGAGAGCGGCGTGCCCAGCAGGTTCAGCGGCAGCGGCAGCG<br>GCACCGAGTTCACCCTGACCATCAGCAGCCTGCAGCCCGACGAC<br>TTCGCCACCTACTACTGCCAGCAGAGCCAGAGCTACCCCCCCAT<br>CACCTTCGGCTGCGGCACCAAGGTGGAGATCAAG[SEQ ID<br>NO: 255] | |

TABLE 1-continued

| | VH | VL |
|---|---|---|
| ADI-11809 [Ab6] | EVQLVESGGGLVQPGGSLRLSC AASGFTFPSYWMSWVRQAPGKG LEWVATIKRDGSEKGYVDSVKG RFTISRDNAKNSLYLQMNSLRA EDTAVYYCARPLNAGELDVWGQ GTMVTVSS[SEQ ID NO: 11] | DIQMTQSPSTLSASVGDRVTITCR ASQSISSWLAWYQQKPGKAPKLLI YEASSLESGVPSRFSGSGSGTEFT LTISSLQPDDFATYYCQQSQSYPP ITFGGGTKVEIK[SEQ ID NO: 12] |
| | CDR1: FTFPSYWMS[SEQ ID NO: 51](non-Kabat) or SYWMS[SEQ ID NO: 181] | CDR1: RASQSISSWLA[SEQ ID NO: 54] |
| | CDR2: TIKRDGSEKGYVDSVK G[SEQ ID NO: 52] | CDR2: EASSLES[SEQ ID NO: 55] |
| | CDR3: ARPLNAGELDV[SEQ ID NO: 53](non-Kabat) or PLNAGELDV[SEQ ID NO: 439] | CDR3: QQSQSYPPIT[SEQ ID NO: 56] |
| scFv of Ab6 | DIQMTQSPSTLSASVGDRVTITCRASQSISSWLAWYQQKPGKAPKL LIYEASSLESGVPSRFSGSGSGTEFTLTISSLQPDDFATYYCQQSQ SYPPITFGCGTKVEIKGGGGSGGGGSGGGGSGGGGSEVQLVESGGG LVQPGGSLRLSCAASGFTFPSYWMSWVRQAPGKCLEWVATIKRDGS EKGYVDSVKGRFTISRDNAKNSLYLQMNSLRAEDTAVYYCARPLNA GELDVWGQGTMVTVSS[SEQ ID NO: 214] | |
| | EVQLVESGGGLVQPGGSLRLSCAASGFTFPSYWMSWVRQAPGKCLE WVATIKRDGSEKGYVDSVKGRFTISRDNAKNSLYLQMNSLRAEDTA VYYCARPLNAGELDVWGQGTMVTVSSGGGGSGGGGSGGGGSGG GGSDIQMTQSPSTLSASVGDRVTITCRASQSISSWLAWYQQKPGKA PKLLIYEASSLESGVPSRFSGSGSGTEFTLTISSLQPDDFATYYCQ QSQSYPPITFGCGTKVEIK[SEQ ID NO: 215] | |
| Exemplary nucleotide sequence of Ab6 scFv | GACATCCAGATGACCCAGAGCCCCAGCACCCTGAGCGCCAGCGT GGGCGACAGGGTGACCATCACCTGCAGGGCCAGCCAGAGCATCA GCAGCTGGCTGGCrGGTACCAGCAGAAGCCCGGCAAGGCCCCC AAGCTGCTGATCTACGAGGCCAGCAGCCTGGAGAGCGGCGTGCC CAGCAGGTTCAGCGGCAGCGGCAGCGGCACCGAGTTCACCCTGA CCATCAGCAGCCTGCAGCCCGACGACTTCGCCACCTACTACTGC CAGCAGAGCCAGAGCTACCCCCCCATCACCTTCGGCTGCGGCAC CAAGGTGGAGATCAAGGGCGGCGGCGGCAGCGGCGGCGGCGGCA GCGGCGGCGGCGGCAGCGGCGGCGGCGGCAGCGAGGTGCAGCTG GTGGAGAGCGGCGGCGGCCTGGTGCAGCCCGGCGGCAGCCTGAG GCTGAGCTGCGCCGCCAGCGGCTTCACCTTCCCCAGCTACTGGA TGAGCTGGGTGAGGCAGGCCCCCGGCAAGTGCCTGGAGTGGGTG GCCACCATCAAGAGGGACGGCAGCGAGAAGGGCTACGTGGACAG CGTGAAGGGCAGGTTCACCATCAGCAGGGACAACGCCAAGAACA GCCTGTACCTGCAGATGAACAGCCTGAGGGCCGAGGACACCGCC GTGTACTACTGCGCCAGGCCCCTGAACGCCGGCGAGCTGGACGT GTGGGGCCAGGGCACCATGGTGACCGTGAGCAGC[SEQ ID NO: 256] | |
| | GAGGTGCAGCTGGTGGAGAGCGGCGGCGGCCTGGTGCAGCCCGG CGGCAGCCTGAGGCTGAGCTGCGCCGCCAGCGGCTTCACCTTCC CCAGCTACTGGATGAGCTGGGTGAGGCAGGCCCCCGGCAAGTGC CTGGAGTGGGTGGCCACCATCAAGAGGGACGGCAGCGAGAAGGG CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGCCCCTGAACGCCGG CGAGCTGGACGTGTGGGGCCAGGGCACCATGGTGACCGTGAGCA GCGGCGGCGGCGGCAGCGGCGGCGGCGGCAGCGGCGGCGGCGGC AGCGGCGGCGGCGGCAGCGACATCCAGATGACCCAGAGCCCCAG CACCCTGAGCGCCAGCGTGGGCGACAGGGTGACCATCACCTGCA GGGCCAGCCAGAGCATCAGCAGCTGGCTGGCCTGGTACCAGCAG AAGCCCGGCAAGGCCCCCAAGCTGCTGATCTACGAGGCCAGCAG CCTGGAGAGCGGCGTGCCCAGCAGGTTCAGCGGCAGCGGCAGCG GCACCGAGTTCACCCTGACCATCAGCAGCCTGCAGCCCGACGAC TTCGCCACCTACTACTGCCAGCAGAGCCAGAGCTACCCCCCCAT CACCTTCGGCTGCGGCACCAAGGTGGAGATCAAG[SEQ ID NO: 257] | |

TABLE 1-continued

| | VH | VL |
|---|---|---|
| ADI-11815 [Ab7] | QVQLVQSGAEVKKPGASVKVSC KASGYTFGTYYMHWVRQAPGQG LEWMGIINPSRGSTVYAQKFQG RVTMTRDTSTSTVYMELSSLRS EDTAVYYCARGAGYDDEDMDVW GKGTTVTVSS[SEQ ID NO: 13] | DIQMTQSPSSVSASVGDRVTITC RASQGIDSWLAWYQQKPGKAPKL LIYAASSLQSGVPSRFSGSGSGT DFTLTISSLQPEDFATYYCQQAH SYPLTFGGGTKVEIK[SEQ ID NO: 14] |
| | CDR1: YTFGTYYMH[SEQ ID NO: 57](non-Kabat) or TYYMH [SEQ ID NO: 440] | CDR1: RASQGIDSWLA[SEQ ID NO: 60] |
| | CDR2: IINPSRGSTVYAQKFQ G[SEQ ID NO: 58] | CDR2: AASSLQS[SEQ ID NO: 61] |
| | CDR3: ARGAGYDDEDMDV [SEQ ID NO: 59](non-Kabat) or GAGYDDEDMDV [SEQ ID NO: 441] | CDR3: QQAHSYPLT[SEQ ID NO: 62] |
| scFv of Ab7 | DIQMTQSPSSVSASVGDRVTITCRASQGIDSWLAWYQQKPGKAPKL LIYAASSLQSGVPSRFSGSGSGTDFTLTISSLQPEDFATYYCQQAH SYPLTFGCGTKVEIKGGGGSGGGGSGGGGSGGGGSQVQLVQSGAEV KKPGASVKVSCKASGYTFGTYYMHWVRQAPGQCLEWMGIINPSRGS TVYAQKFQGRVTMTRDTSTSTVYMELSSLRSEDTAVYYCARGAGYD DEDMDVWGKGTTVTVSS[SEQ ID NO: 216] | |
| | QVQLVQSGAEVKKPGASVKVSCKASGYTFGTYYMHWVRQAPGQC LEWMGIINPSRGSTVYAQKFQGRVTMTRDTSTSTVYMELSSLRS EDTAVYYCARGAGYDDEDMDVWGKGTTVTVSSGGGGSGGGGSGGGG SGGGGSDIQMTQSPSSVSASVGDRVTITCRASQGIDSWLAWYQQ KPGKAPKLLIYAASSLQSGVPSRFSGSGSGTDFTLTISSLQPED FATYYCQQAHSYPLTFGCGTKVEIK[SEQ ID NO: 217] | |
| Exemplary nucleotide sequence of Ab7 scFv | GACATCCAGATGACCCAGAGCCCCAGCAGCGTGAGCGCCAGCGT GGGCGACAGGGTGACCATCACCni CAGGGCCAGCCAGGGCATCG ACAGCTGGCTGGCCTGGTACCAGCAGAAGCCCGGCAAGGCCCCC AAGCTGCTGATCTACGCCGCCAGCAGCCTGCAGAGCGGCGTGCC CAGGCAGGTTCAGCGGCAGCGGCAGCGGCACCGACTTCACCCTGA CCATCAGCAGCCTGCAGCCCGAGGACTTCGCCACCTACTACTGC CAGCAGGCCCACAGCTACCCCCTGACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGGTG CAGAGCGGCGCCGAGGTGAAGAAGCCCGGCCTCCAGCGTGAAGG TGAGCTGCAAGGCCAGCGGCTACACCTTCGGCACCTACTACATG CACTGGGTGAGGCAGGCCCCCGGCCAGTGCCTGGAGTGGATGGG CATCATCAACCCCAGCAGGGGCAGCACCGTGTACGCCCAGAAGT TCCAGGGCAGGGTGACCATGACCAGGGACACCAGCACCAGCACC GTGTACATGGAGCTGAGCAGCCTGAGGAGCGAGGACACCGCCGT GTACTACTGCGCCAGGGGCGCCGGCTACGACGACGAGGACATGG ACGTGTGGGGCAAGGGCACCACCGTGACCGTGAGCAGC[SEQ ID NO: 258] | |
| | CAGGTGCAGCTGGTGCAGAGCGGCGCCGAGGTGAAGAAGCCCGG CGCCAGCGTGAAGGTGAGCTGCAAGGCCAGCGGCTACACCTTCG GCACCTACTACATGCACTGGGTGAGGCAGGCCCCCGGCCAGTGC CTGGAGTGGATGGGCATCATCAACCCCAGCAGGGGCAGCACCGT GTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGGCGCCGGCTACGA CGACGAGGACATGGACGTGTGGGGCAAGGGCACCACCGTGACCG TGAGCAGCGGCGGCGGCGGCAGCGGCGGCGGCGGCAGCGGCGGC GGCGGCAGCGGCGGCGGCGGCAGCGACATCCAGATGACCCAGAG CCCCAGCAGCGTGAGCGCCAGCGTGGGCGACAGGGTGACCATCA CCTGCAGGGCCAGCCAGGGCATCGACAGCTGGCTGGCCTGGTAC CAGCAGAAGCCCGGCAAGGCCCCCAAGCTGCTGATCTACGCCGC CAGCAGCCTGCAGAGCGGCGTGCCCAGCAGGTTCAGCGGCAGCG GCAGCGGCACCGACTTCACCCTGACCATCAGCAGCCTGCAGCCC GAGGACTTCGCCACCTACTACTGCCAGCAGGCCCACAGCTACCC CCTGACCTTCGGCTGCGGCACCAAGGTGGAGATCAAG[SEQ ID NO: 259] | |

TABLE 1-continued

| | VH | VL |
|---|---|---|
| ADI-11819 [Ab8] | EVQLVESGGGLVKPGGSLRLSC AASGFTFSSYAMSWVRQAPGKG LEWVSSISSSSEGIYYADSVKG RFTISRDNAKNSLYLQMNSLRA EDTAVYYCAREGGPYYDSSGYF VYYGMDVWGQGTTVTVSS [SEQ ID NO: 15]<br><br>CDR1: FTFSSYAMS[SEQ ID NO: 63](non-Kabat) or SYAMS [SEQ ID NO: 442]<br><br>CDR2: SISSSSEGIYYADSVK G[SEQ ID NO: 64]<br><br>CDR3: AREGGPYYDSSGYFVY YGMDV[SEQ ID NO: 65] (non-Kabat) or EGGPYYD SSGYFVYYGMDV[SEQ ID NO: 443] | DIQMTQSPSTLSASVGDRVTITCR ASNSISSWLAWYQQKPGKAPKLLI YEASSTKSGVPSRFSGSGSGTEFT LTISSLQPDDFATYYCQQYDDLPT FGGGTKVEIK[SEQ ID NO: 16]<br><br>CDR1: RASNSISSWLA[SEQ ID NO: 66]<br><br>CDR2: EASSTKS[SEQ ID NO: 67]<br><br>CDR3: QQYDDLPT[SEQ ID NO: 68] |
| scFv of Ab8 | DIQMTQSPSTLSASVGDRVTITCRASNSISSWLAWYQQKPGKAPKL LIYEASSTKSGVPSRFSGSGSGTEFTLTISSLQPDDFATYYCQQYD DLPTFGCGTKVEIKGGGGSGGGGSGGGGSGGGGSEVQLVESGGGLV KPGGSLRLSCAASGFTFSSYAMSWVRQAPGKCLEWVSSISSSSEGI YYADSVKGRFTISRDNAKNSLYLQMNSLRAEDTAVYYCAREGGPYY DSSGYFVYYGMDVWGQGTTVTVSS[SEQ ID NO: 218]<br><br>EVQLVESGGGLVKPGGSLRLSCAASGFTFSSYAMSWVRQAPGKCLE WVSSISSSSEGIYYADSVKGRFTISRDNAKNSLYLQMNSLRAEDTA VYYCAREGGPYYDSSGYFVYYGMDVWGQGTTVTVSSGGGGSGGGG SGGGGSGGGGSDIQMTQSPSTLSASVGDRVTITCRASNSISSWLAW YQQKPGKAPKLLIYEASSTKSGVPSRFSGSGSGTEFTLTISSLQPD DFATYYCQQYDDLPTFGCGTKVEIK[SEQ ID NO: 219] | |
| Exemplary nucleotide sequence of Ab8 scFv | GACATCCAGATGACCCAGAGCCCCAGCACCCTGAGCGCCAGCGT GGGCGACAGGGTGACCATCACCTGCAGGGCCAGCAACAGCATCA GCAGCTGGCTGGCCTGGTACCAGCAGAAGCCCGGCAAGGCCCCC AAGCTGCTGATCTACGAGGCCAGCAGCACCAAGAGCGGCGTGCC CAGCAGGTTCAGCGGCAGCGGCAGCGGCACCGAGTTCACCCTGA CCATCAGCAGCCTGCAGCCCGACGACTTCGCCACCTACTACTGC CAGCAGTACGACGACCTGCCCACCTTCGGCTGCGGCACCAAGGT GGAGATCAAGGGCGGCGGCGGCAGCGGCGGCGGCGGCAGCGGCG GCGGCGGCAGCGGCGGCGGCGGCAGCGAGGTGCAGCTGGTGGAG AGCGGCGGCGGCCTGGTAAGCCCGGCGGCAGCCTGAGGCTGAG CTGCGCCGCCAGCGGCTTCACCTTCAGCAGCTACGCCATGAGCT GGGTGAGGCAGGCCCCCGGCAAGTGCCTGGAGTGGGTGAGCAGC ATCAGCAGCAGCAGCGAGGGCATCTACTACGCCGACAGCGTGAA GGGCAGGTTCACCATCAGGAGGGACAACGCCAAGAACAGCCTGT ACCTGCAGATGAACAGCCTGAGGGCCGAGGACACCGCCGTGTAC TACTGCGCCAGGGAGGGCGCGCCCTACTACG\CAGCAGCGGCTA CTTCGTGTACTACGGCATGGACGTGTGGGGCCAGGGCACCACCG TGACCGTGAGCAGC[SEQ ID NO: 260]<br><br>GAGGTGCAGCTGGTGGAGAGCGGCGGCGGCCTGGTGAAGCCCGG CGGCAGCCTGAGGCTGAGCTGCGCCGCCAGCGGCTTCACCTCAG CAGCTACGCCATGAGCTGGGTGAGGCAGGCCCCCGGCAAGTGCC TGGAGTGGGTGAGCAGCATCAGCAGCAGCAGCGAGGGCATCTAC TACGCCGACAGCGTGAAGGGCAGGTTCACCATCAGCAGGGACAA CGCCAAGAACAGCCTGTACCTGCAGATGAACAGCCTGAGGGCC AGGACACCGCCGTGTACTACTGCGCCAGGGAGGGCGGCCCCTAC TACGACAGCAGCGGCTACTTCGTGTACTACGGCATGGACGTGTG GGGCCAGGGCACCACCGTGACCGTGAGCAGCGGCGGCGGCGGCA GCGGCGGCGGCGGCAGCGGCGGCGGCGGCAGCGGCGGCGCCGGC AGCGACATCCAGATGACCCAGAGCCCCAGCACCCTGAGCGCCAG CGTGGGCGACAGGGTGACCATCACCTGCAGGGCCAGCAACAGCA TCAGCAGCTGGCTGGCCTGGTACCAGCAGAAGCCCGGCAAGGCC CCCAAGCTGCTGATCTACGAGGCCAGCAGCACCAAGAGCGGCGT GCCCAGCAGGTTCAGCGGCAGCGGCAGCGGCACCGAGTTCACCC TGACCATCAGCAGCCTGCAGCCCGACGACTTCGCCACCTACTAC TGCCAGCAGTACGACGACCTGCCCACCTTCGGCTGCGGCACCAA GGTGGAGATCAAG[SEQ ID NO: 261] | |

TABLE 1-continued

| | VH | VL |
|---|---|---|
| ADI-11830 [Ab9] | EVQLVESGGGLVQPGGSLRLSC AASGFTFSSYWMSWVRQAPGKG LEWVANINTDGSEVYYVDSVKG RFTISRDNAKNSLYLQMNSLRA EDTAVYYCARDVGPGIAYQGHF DYWGQGTLVTVSS[SEQ ID NO: 17] | DIQMTQSPSSLSASVGDRVTITCR ASQVIYSYLNWYQQKPGKAPKLLI YAASSLKSGVPSRFSGSGSGTDFT LTISSLQPEDFATYYCQQVYDTPL TFGGGTKVEIK[SEQ ID NO: 18] |
| | CDR1: FTFSSYWMS[SEQ ID NO: 69](non-Kabat) or SYWMS[SEQ ID NO: 181] | CDR1: RASQVIYSYLN[SEQ ID NO: 72] |
| | CDR2: NINTDGSEVYYVDSVK G[SEQ ID NO: 70] | CDR2: AASSLKS[SEQ ID NO: 73] |
| | CDR3: ARDVGPGIAYQGHFDY [SEQ ID NO: 71](non-Kabat) or DVGPGIAYQGHF DY[SEQ ID NO: 444] | CDR3: QQVYDTPLT[SEQ ID NO: 74] |
| scFv of Ab9 | DIQMTQSPSSLSASVGDRVTITCRASQVIYSYLNWYQQKPGKAPKL LIYAASSLKSGVPSRFSGSGSGTDFTLTISSLQPEDFATYYCQQVY DTPLTFGCGTKVEIKGGGGSGGGGSGGGGSGGGGSEVQLVESGGGL VQPGGSLRLSCAASGFTFSSYWMSWVRQAPGKCLEWVANINTDGSE VYYVDSVKGRFTISRDNAKNSLYLQMNSLRAEDTAVYYCARDVGPG IAYQGHFDYWGQGTLVTVSS[SEQ ID NO: 220] | |
| | EVQLVESGGGLVQPGGSLRLSCAASGFTFSSYWMSWVRQAPGKCLE WVANINTDGSEVYYVDSVKGRFTISRDNAKNSLYLQMNSLRAEDTA VYYCARDVGPGIAYQGHFDYWGQGTLVTVSSGGGGSGGGGSGGG GSGGGGSDIQMTQSPSSLSASVGDRVTITCRASQVIYSYLNWYQQK PGKAPKLLIYAASSLKSGVPSRFSGSGSGTDFTLTISSLQPEDFAT YYCQQVYDTPLTFGCGTKVEIK[SEQ ID NO: 221] | |
| Exemplary nucleotide sequence of Ab9 scFv | GACATCCAGATGACCCAGAGCCCCAGCAGCCTGAGCGCCAGCGT GGGCGACAGGGTGACCATCACCTGCAGGGCCAGCCAGGTGATCT ACAGCTACCTGAACTGGTACCAGCAGAAGCCCGGCAAGGCCCCC AAGCTGCTGATCTACGCCGCCAGCAGCCTGAAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGTGTACGACACCCCCCTGACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCGAGGTGCAGCTGGTG GAGAGCGGCGGCGGCCTGGTGCAGCCCGGCGGCAGCCTGAGGCT GAGCTGCGCCGCCAGCGGCTTCACCTTCAGCAGCTACTGGATGA GCTGGGTGAGGCAGGCCCCCGGCAAGTGCCTGGAGTGGGTGGCC AACATCAACACCGACGGCAGCGAGGTGTACTACGTGGACAGCGT GAAGGGCAGGTTCACCATCAGCAGGGACAACGCCAAGAACAGCC TGTACCTGCAGATGAACAGCCTGAGGGCCGAGGACACCGCCGTG TACTACTGCGCCAGGGACGTGGGCCCCGGCATCGCCTACCAGGG CCACTTCGACTACTGGGGCCAGGGCACCCTGGTGACCGTGAGCA GC[SEQ ID NO: 262] | |
| | GAGGTGCAGCTGGTGGAGAGCGGCGGCGGCCTGGTGCAGCCCGG CGGCAGCCTGAGGCTGAGCTGCGCCGCCAGCGGCTTCACCTTCA GCAGCTACTGGATGAGCTGGGTGAGGCAGGCCCCCGGCAAGTGC CTGGAGTGGGTGGCCAACATCAACACCGACGGCAGCGAGGTGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGACGTGGGCCCCGG CATCGCCTACCAGGGCCACTTCGACTACTGGGGCCAGGGCACCC TGGTGACCGTGAGCAGCGGCGGCGGCGGCAGCGGCGGCGGCGGC AGCGGCGGCGGCGGCAGCGGCGGCGGCGGCAGCGACATCCAGAT GACCCAGAGCCCCAGCAGCCTGAGCGCCACCGTGGGCGACAGGG TGACCATCACCTGCAGGGCCAGCCAGGTGATCTACAGCTACCTG AACTGGTACCAGCAGAAGCCCGGCAAGGCCCCCAAGCTGCTGAT CTACGCCGCCAGCAGCCTGAAGAGCGGCGTGCCCAGCAGGTTCA GCGGCAGCGGCAGCGGCACCGACTTCACCCTGACCATCAGCAGC CTGCAGCCCGAGGACTTCGCCACCTACTACTGCCAGCAGGTGTA CGACACCCCCCTGACCTTCGGCTGCGGCACCAAGGTGGAGATCA AG[SEQ ID NO: 263] | |

TABLE 1-continued

| | VH | VL |
|---|---|---|
| ADI-11835 [Ab10] (135) | QLQLQESGPGLVKPSETLSLTC TVSGGSISSTDYYWGWIRQPPG KGLEWIGSIGYSGTYYNPSLKS RVTISVDTSKNQFSLKLSSVTA ADTAVYYCARETAHDVHGMDVW GQGTTVTVSS[SEQ ID NO: 19] | EIVLTQSPATLSLSPGERATLSCR ASHSVYSYLAWYQQKPGQAPRLLI YDASNRATGIPARFSGSGSGTDFT LTISSLEPEDFAVYYCQQYDNLPT FGGGTKVEIK[SEQ ID NO: 20] |
| | CDR1: GSISSTDYYWG[SEQ ID NO: 75](non-Kabat) or STDYYWG[SEQ ID NO: 445] | CDR1: RASHSVYSYLA[SEQ ID NO: 78] |
| | CDR2: SIGYSGTYYNPSLKS [SEQ ID NO: 76] | CDR2: DASNRAT[SEQ ID NO: 79] |
| | CDR3: ARETAHDVHGMDV [SEQ ID NO: 77](non-Kabat) or ETAHDVHGMDV [SEQ ID NO: 446] | CDR3: QQYDNLPT[SEQ ID NO: 80] |
| scFv of Ab10 | EIVLTQSPATLSLSPGERATLSCRASHSVYSYLAWYQQKPGQAPRL LIYDASNRATGIPARFSGSGSGTDFTLTISSLEPEDFAVYYCQQYD NLPTFGCGTKVEIKGGGGSGGGGSGGGGSGGGGSQLQLQESGPGLV KPSETLSLTCTVSGGSISSTDYYWGWIRQPPGKCLEWIGSIGYSGT YYNPSLKSRVTISVDTSKNQFSLKLSSVTAADTAVYYCARETAHDV HGMDVWGQGTTVTVSS[SEQ ID NO: 222] | |
| | QLQLQESGPGLVKPSETLSLTCTVSGGSISSTDYYWGWIRQPPGKC LEWIGSIGYSGTYYNPSLKSRVTISVDTSKNQFSLKLSSVTAADTA VYYCARETAHDVHGMDVWGQGTTVTVSSGGGGSGGGGSGGGGSGGGG SEIVLTQSPATLSLSPGERATLSCRASHSVYSYLAWYQQKPGQAPR LLIYDASNRATGIPARFSGSGSGTDFTLTISSLEPEDFAVYYCQQY DNLPTFGCGTKVEIK[SEQ ID NO: 223] | |
| Exemplary nucleotide sequence of Ab10 scFv | GAGATCGTGCTGACCCAGAGCCCCGCCACCCTGAGCCTGAGCCC CGGCGAGAGGGCCACCCTGAGCTGCAGGGCCAGCCACAGCGTGT ACAGCTACCTGGCCTGGTACCAGCAGAAGCCCGGCCAGGCCCCC AGGCTGCTGATCTACGACGCCAGCAACAGGGCCACCGGCATCCC CGCCAGGTTCAGCGGCAGCGGCAGCGGCACCGACTTCACCCTGA CCATCAGCAGCCTGGAGCCCGAGGACTTCGCCGTGTACTACTGC CAGCAGTACGACAACCTGCCCACCTTCGGCTGCGGCACCAAGGT GGAGATCAAGGGCGGCGGCGGCAGCGGCGGCGGCGGCAGCGGCG GCGGCGGCAGCGGCGGCGGCGGCAGCCAGCTGCAGCTGCAGGAG AGCGGCCCCGGCCTGGTGAAGCCCAGCGAGACCCTGAGCCTGAC CTGCACCGTGAGCGGCGGCAGCATCAGCAGCACCGACTACTACT GGGGCTGGATCAGGCAGCCCCCCGGCAAGTGCCTGGAGTGGATC GGCAGCATCGGCTACAGCGGCACCTACTACAACCCCAGCCTGAA GAGCAGGGTGACCATCAGCGTGGACACCAGCAAGAACCAGTTCA GCCTGAAGCTGAGCAGCGTGACCGCCGCCGACACCGCCGTGTAC TACTGCGCCAGGGAGACCGCCCACGACGTGCACGGCATGGACGT GTGGGGCCAGGGCACCACCGTGACCGTGAGCAGC[SEQ ID NO: 264] | |
| | CAGGTGCAGCTGCAGGAGAGCGGCCCCGGCCTGGTGAAGCCCAG CGAGACCCTGAGCCTGACcrGcACCGTGAGCGGCGGCAGCATCA GCAGCACCGACTACTACTGGGGCTGGATCAGGCAGCCCCCCGGC AAGTGCCTGGAGTGGATCGGCAGCATCGGCTACAGCGGCACCTA CTACAACCCCAGCCTGAAGAGCAGGGTGACCATCAGCGTGGACA CCAGCAAGAACCAGTTCAGCCTGAAGCTGAGCAGCGTGACCGCC GCCGACACCGCCGTGTACTACTGcGCCAGGGAGACCGCCCACGA CGTGCACGGCATGGACGTGTGGGGCCAGGGCACCACCGTGACCG TGAGCAGCGGCGGCGGCGGCAGCGGCGGCGGCGGCAGCGGCGGC GGCGGCAGCGGCGGCGGCAGCGAGATCGTGCTGACCCAGAGC CCCGCCACCCTGAGCCTGAGCCCCGGCGAGAGGGCCACCCTGA GCTGCAGGGCCAGCCACAGCGTGTACAGCTACCTGGCCTGGTAC CAGCAGAAGCCCGGCCAGGCCCCCAGGCTGCTGATCTACGACGC CAGCAACAGGGCCACCGGCATCCCCGCCAGGTTCAGCGGCAGCG GCAGCGGCACCGACTTCACCCTGACCATCAGCAGCCTGGAGCCC GAGGACTTCGCCGTGTACTACTGCCAGCAGTACGACAACCTGCC CACCTTCGGCTGCGGCACCAAGGTGGAGATCAAG[SEQ ID NO: 265] | |

TABLE 1-continued

| | VH | VL |
|---|---|---|
| ADI-10154 [Ab11] | EVQLLESGGGLVQPGGSLRLSCAASGFTFSSYAMSWVRQAPGKGLEWVSAISASGGSTYYADSVKGRFTISRDNSKNTLYLQMNSLRAEDTAVYYCARPRAYYDSSGFKVNYGMDVWGQGTTVTVSS[SEQ ID NO: 266]<br><br>CDR1: SYAMS[SEQ ID NO: 304] or FTFSSYAMS [SEQ ID NO: 528](non-Kabat)<br><br>CDR2: AISASGGSTYYADSVKG[SEQ ID NO: 305]<br><br>CDR3: PRAYYDSSGFKVNYGMDV[SEQ ID NO: 306] or ARPRAYYDSSGFKVNYGMDV [SEQ ID NO: 529](non-Kabat) | EIVLTQSPGTLSLSPGERATLSCRASQSVSSSFLAWYQQKPGQAPRLLIYGASSRATGIPDRFSGSGSGTDFTLTISRLEPEDFAVYYCQQASSSPPTFGGGTKVEIK[SEQ ID NO: 267]<br><br>CDR1: RASQSVSSSFLA[SEQ ID NO: 307]<br><br>CDR2: GASSRAT[SEQ ID NO: 308]<br><br>CDR3: QQASSSPPT[SEQ ID NO: 309] |
| scFv of Ab11 | EIVLTQSPGTLSLSPGERATLSCRASQSVSSSFLAWYQQKPGQAPRLLIYGASSRATGIPDRFSGSGSGTDFTLTISRLEPEDFAVYYCQQASSSPPTFGCGTKVEIKGGGGSGGGGSGGGGSGGGGSEVQLLESGGGLVQPGGSLRLSCAASGFTFSSYAMSWVRQAPGKCLEWVSAISASGGSTYYADSVKGRFTISRDNSKNTLYLQMNSLRAEDTAVYYCARPRAYYDSSGFKVNYGMDVWGQGTTVTVSS[SEQ ID NO: 447]<br><br>EVQLLESGGGLVQPGGSLRLSCAASGFTFSSYAMSWVRQAPGKCLEWVSAISASGGSTYYADSVKGRFTISRDNSKNTLYLQMNSLRAEDTAVYYCARPRAYYDSSGFKVNYGMDVWGQGTTVTVSSGGGGSGGGGSGGGGSGGGGSEIVLTQSPGTLSLSPGERATLSCRASQSVSSSFLAWYQQKPGQAPRLLIYGASSRATGIPDRFSGSGSGTDFTLTISRLEPEDFAVYYCQQASSSPPTFGCGTKVEIK[SEQ ID NO: 448] | |
| Exemplary nucleotide sequence of Ab11 scFv | GAGATCGTGCTGACCCAGAGCCCCGGCACCCTGAGCCTGAGCCCCGGCGAGAGGGCCACCCTGAGCTGCAGGGCCAGCCAGAGCGTGAGCAGCAGCTTCCTGGCCTGGTACCAGCAGAAGCCCGGCCAGGCCCCCAGGCTGCTGATCTACGGCGCCAGCAGCAGGGCCACCGGCATCCCCGACAGGTTCAGCGGCAGCGGCAGCGGCACCGACTTCACCCTGACCATCAGCAGGCTGGAGCCCGAGGACTTCGCCGTGTACTACTGCCAGCAGGCCAGCAGCAGCCCCCCCACGTTCGGTGCGGCACCAAGGTGGAGATCAAGGGCGGCGGCGGCAGCGGCGGCGGCGGCAGCGGCGGCGGCGGCAGCGGCGGCGGCGGCAGCGAGGTGCAGCTGCTGGAGAGCGGCGGCGGCCTGGTGCAGCCCGGCGGCAGCCTGAGGCTGAGCTGCGCCGCCAGCGGCTTCACCTTCAGCAGCTACGCCATGAGCTGGGTGAGGCAGGCCCCCGGCAAGTGCCTGGAGTGGGTGAGCGCCATCAGCGCCAGCGGCGGCAGCACCTACTACGCCGACAGCGTGAAGGGCAGGTTCACCATCAGCAGGGACAACAGCAAGAACACCCTGTACCTGCAGATGAACAGCCTGAGGGCCGAGGACACCGCCGTGTACTACTGCGCCAGGCCCAGGGCCTACTACGACAGCAGCGGCTTCAAGGTGAACTACGGCATGGACGTGTGGGGCCAGGGCACCACCGTGACCGTGAGCAGC[SEQ ID NO: 489]<br><br>GAGGTGCAGCTGCTGGAGAGCGGCGGCGGCCTGGTGCAGCCCGGCGGCAGCCTGAGGCTGAGCTGCGCCGCCAGCGGCTTCACCTTCAGCAGCTACGCCATGAGCTGGGTGAGGCAGGCCCCCGGCAAGTGCCTGGAGTGGGTGAGCGCCATCAGCGCCAGCGGCGGCAGCACCTACTACGCCGACAGCGTGAAGGGCAGGTTCACCATCAGCAGGGACAACAGCAAGAACACCCTGTACCTGCAGATGAACAGCCTGAGGGCCGAGGACACCGCCGTGTACTACTGCGCCAGGCCCAGGGCCTACTACGACAGCAGCGGCTTCAAGGTGAACTACGGCATGGACGTGTGGGGCCAGGGCACCACCGTGACCGTGAGCAGCGGCGGCGGCGGCAGCGGCGGCGGCGGCAGCGGCGGCGGCGGCAGCGGCGGCGGCGGCAGCGAGATCGTGCTGACCCAGAGCCCCGGCACCCTGAGCCTGAGCCCCGGCGAGAGGGCCACCCTGAGCTGCAGGGCCAGCCAGAGCGTGAGCAGCAGCTTCCTGGCCTGGTACCAGCAGAAGCCCGGCCAGGCCCCCAGGCTGCTGATCTACGGCGCCAGCAGCAGGGCCACCGGCATCCCCGACAGGTTCAGCGGCAGCGGCAGCGGCACCGACTTCACCCTGACCATCAGCAGGCTGGAGCCCGAGGACTTCGCCGTGTACTACTGCCAGCAGGCCAGCAGCAGCCCCCCCACCTTCGGCTGCGGCACCAAGGTGGAGATCAAG[SEQ ID NO: 490] | |

TABLE 1-continued

| | VH | VL |
|---|---|---|
| ADI-10155 [Ab12] | EVQLLESGGGLVQPGGSLRLSC AASGFTFSSYAMSWVRQAPGKG LEWVSGISGSGGSTYYADSVKG RFTISRDNSKNTLYLQMNSLRA EDTAVYYCAREGHSSSYYDHAF DIWGQGTMVTVSS[SEQ ID NO: 268] | EIVLTQSPGTLSLSPGERATLSCR ASQSVSSDYLAWYQQKPGQAPRLL IYGASSRATGIPDRFSGSGSGTDF TLTISRLEPEDFAVYYCQQHSSAP PTFGGGTKVEIK[SEQ ID NO: 269] |
| | CDR1: SYAMS[SEQ ID NO: 310] or FTFSSYAMS[SEQ ID NO: 530](non-Kabat) | CDR1: RASQSVSSDYLA[SEQ ID NO: 313] |
| | CDR2: GISGSGGSTYYADSVK G[SEQ ID NO: 311] | CDR2: GASSRAT[SEQ ID NO: 314] |
| | CDR3: EGHSSSYYDHAFDI [SEQ ID NO: 312] or AREGHSSSYYDHAFDI[SEQ ID NO: 531](non-Kabat) | CDR3: QQHSSAPPT[SEQ ID NO: 315] |
| scFy of Ab12 | EIVLTQSPGTLSLSPGERATLSCRASQSVSSDYLAWYQQKPGQAPR LLIYGASSRATGIPDRFSGSGSGTDFTLTISRLEPEDFAVYYCQQH SSAPPTFGCGTKVEIKGGGGSGGGGSGGGGSGGGGSEVQLLESGGG LVQPGGSLRLSCAASGFTFSSYAMSWVRQAPGKCLEWVSGISGSGG STYYADSVKGRFTISRDNSKNTLYLQMNSLRAEDTAVYYCAREGHS SSYYDHAFDIWGQGTMVTVSS[SEQ ID NO: 449]<br><br>EVQLLESGGGLVQPGGSLRLSCAASGFTFSSYAMSWVRQAPGKCLE WVSGISGSGGSTYYADSVKGRFTISRDNSKNTLYLQMNSLRAEDTA VYYCAREGHSSSYYDHAFDIWGQGTMVTVSSGGGGSGGGGSGGG GSGGGSEIVLTQSPGTLSLSPGERATLSCRASQSVSSDYLAWYQQ KPGQAPRLLIYGASSRATGIPDRFSGSGSGTDFTLTISRLEPEDFA VYYCQQHSSAPPTFGCGTKVEIK[SEQ ID NO: 450] | |
| Exemplary nucleotide sequence of Ab12 scFy | GAGATCGTGCTGACCCAGAGCCCCGGCACCCTGAGCCTGAGCCC CGGCGAGAGGGCCACCCTGAGCTGCAGGGCCAGCCAGAGCGTGA GCAGCGACTACCTGGCCTGGTACCAGCAGAAGCCCGGCCAGGCC CCCAGGCTGCTGATCTACGGCGCCAGCAGCAGGGCCACCGGCAT CCCCGACAGGTTCAGCGGCAGCGGCAGCGGCACCGACTTCACCC TGACCATCAGCAGGCTGGAGCCCGAGGACTTCGCCGTGTACTAC TGCCAGCAGCACAGCAGCGCCCCCCCCACGTCGGCTGCGGCACC AAGGTGGAGATCAAGGGCGGCGGCGGCAGCGGCGGCGGCGGCAG CGGCGGCGGCGGCAGCGGCGGCGGCGGCAGCGAGGTGCAGCTGC TGGAGAGCGGCGGCGGCCTGGTGCAGCCCGGCGGCAGCCTGAGG CTGAGCTGCGCCGCCAGCGGCTTCACCTTCAGCAGCTACGCCAT GAGCTGGGTGAGGCAGGCCCCCGGCAAGTGCCTGGAGTGGGTGA GCGGCATCAGCGGCAGCGGCAGCACCTACTATCCCCACAGC GTGAAGGGCAGGTTCACCATCAGCAGGGACAACAGCAAGAACAC CCTGTACCTGCAGATGAACAGCCTGAGGGCCGAGGACACCGCCG TGTACTACTGCGCCAGGGAGGGCCACAGCAGCAGCTACTACGAC CACGCCTTCGACATCTGGGGCCAGGGCACCATGGTGACCGTGAG CAGC[SEQ ID NO: 491]<br><br>GAGGTGCAGCTGCTGGAGAGCGGCGGCGGCCTGGTGCAGCCCGG CGGCAGCCTGAGGCTGAGCTGCGCCGCCAGCGGCTTCACCTTCA GCAGCTACGCCATGAGCTGGGTGAGGCAGGCCCCCGGCAAGTGC CTGGAGTGGGTGAGCGGCATCAGCGGCAGCGGCGGCAGCACCTA CTACGCCGACAGCGTGAAGGGCAGGTTCACCATCAGCAGGGACA ACAGCAAGAACACCCTGTACCTGCAGATGAACAGCCTGAGGGCC GAGGACACCGCCGTGTACTACTGCGCCAGGGAGGGCCACAGCAG CAGCTACTACGACCACGCCTTCGACATCTGGGGCCAGGGCACCA TGGTGACCGTGAGCAGCGGCGGCGGCGGCAGCGGCGGCGGCGGC AGCGGCGGCGGCGGCAGCGGCGGCGGCAGCGAGATCGTGCT GACCCAGAGCCCCGGCACCCTGAGCCTGAGCCCCGGCGAGAGGG CCACCCTGAGCTGCAGGGCCAGCCAGAGCGTGAGCAGCGACTAC CTGGCCTGGTACCAGCAGAAGCCCGGCCAGGCCCCCAGGCTGCT GATCTACGGCGCCAGCAGCAGGGCCACCGGCATCCCCGACAGGT TCAGCGGCAGCGGCAGCGGCACCGACTTCACCCTGACCATCAGC AGGCTGGAGCCCGAGGACTTCGCCGTGTACTACTGCCAGCAGCA CAGCAGCGCCCCCCCCACCTTCGGCTGCGGCACCAAGGTGGAGA TCAAG[SEQ ID NO: 492] | |

TABLE 1-continued

| | VH | VL |
|---|---|---|
| ADI-10157 [Ab13] | QVQLQESGPGLVKPSETLSLTCTVSGGSISSYYWSWIRQPPGKGLEWIGSIYYSGSTNYNPSLKSRVTISVDTSKNQFSLKLSSVTAADTAVYYCARVGGVYSTIETYGMDVWGQGTTVTVSS[SEQ ID NO: 270] | EIVMTQSPATLSVSPGERATLSCRASQSVSSNLAWYQQKPGQAPRLLIYGASTRATGIPARFSGSGSGTEFTLTISSLQSEDFAVYYCQQYTVYPPTFGGGTKVEIK[SEQ ID NO: 271] |
| | CDR1: SYWS[SEQ ID NO: 316] or GSISSYYWS[SEQ ID NO: 532](non-Kabat) | CDR1: RASQSVSSNLA[SEQ ID NO: 319] |
| | CDR2: SIYYSGSTNYNPSLKS[SEQ ID NO: 317] | CDR2: GASTRAT[SEQ ID NO: 320] |
| | CDR3: VGGVYSTIETYGMDV[SEQ ID NO: 318] or ARVGGVYSTIETYGMDV[SEQ ID NO: 533](non-Kabat) | CDR3: QQYTVYPPT[SEQ ID NO: 321] |
| scFv of Ab13 | EIVMTQSPATLSVSPGERATLSCRASQSVSSNLAWYQQKPGQAPRLLIYGASTRATGIPARFSGSGSGTEFTLTISSLQSEDFAVYYCQQYTVYPPTFGCGTKVEIKGGGGSGGGGSGGGGSGGGGSQVQLQESGPGLVKPSETLSLTCTVSGGSISSYYWSWIRQPPGKCLEWIGSIYYSGSTNYNPSLKSRVTISVDTSKNQFSLKLSSVTAADTAVYYCARVGGVYSTIETYGMDVWGQGTTVTVSS[SEQ ID NO: 451] | |
| | QVQLQESGPGLVKPSETLSLTCTVSGGSISSYYWSWIRQPPGKCLEWIGSIYYSGSTNYNPSLKSRVTISVDTSKNQFSLKLSSVTAADTAVYYCARVGGVYSTIETYGMDVWGQGTTVTVSSGGGGSGGGGSGGGGSGGGGSEIVMTQSPATLSVSPGERATLSCRASQSVSSNLAWYQQKPGQAPRLLIYGASTRATGIPARFSGSGSGTEFTLTISSLQSEDFAVYYCQQYTVYPPTFGCGTKVEIK[SEQ ID NO: 452] | |
| Exemplary nucleotide sequence of Ab13 scFv | GAGATCGTGATGACCCAGAGCCCCGCCACCCTGAGCGTGAGCCCCGGCGAGAGGGCCACCCTGAGCTGCAGGGCCAGCCAGAGCGTGAGCAGCAACCTGGCCTGGTACCAGCAGAAGCCCGGCCAGGCCCCCAGGCTGCTGATCTACGGCGCCAGCACCAGGGCCACCGGCATCCCCGCCAGGTTCAGCGGCAGCGGCAGCGGCACCGAGTTCACCCTGACCATCAGCAGCCTGCAGAGCGAGGACTTCGCCGTGTACTACTGCCAGCAGTACACCGTGTACCCCCCCACCTTCGGCTGCGGCACCAAGGTGGAGATCAAGGGCGGCGGCGGCAGCGGCGGCGGCGGCAGCGGCGGCGGCGGCAGCGGCGGCGGCGGCAGCCAGGTGCAGCTGCAGGAGAGCGGCCCCGGCCTGGTGAAGCCCAGCGAGACCCTGAGCCTGACCTGCACCGTGAGCGGCGGCAGCATCAGCAGCTACTAGGGAGCTGGATCAGGCAGCCCCCCGGCAAGTGCCTGAGTGGATCGGCAGCATCTACTACAGCGGCAGCACCAACTACAACCCCAGCCTGAAGAGCAGGGTGACCATCAGCGTGGACACCAGCAAGAACCAGTTCAGCCTGAAGCTGAGCAGCGTGACCGCCGCCGACACCGCCGTGTACTACTGCGCCCAGGGTGGGCGGCGTGTACAGCACCATCGAGACCTACGGCATGGACGTGTGGGGCCAGGGCACCACCGTGACCGTGAGCAGC[SEQ ID NO: 493] | |
| | CAGGTGCAGCTGCAGGAGAGCGGCCCCGGCCTGGTGAAGCCCAGCGAGACCCTGAGCCTGACCTGCACCGTGAGCGGCGGCAGCATCAGCAGCTACTAGGGAGCTGGATCAGGCAGCCCCCCGGCAAGTGCCTGGAGTGGATCGGCAGCATCTACTACAGCGGCAGCACCAACTACAACCCCAGCCTGAAGAGCAGGGTGACCATCAGCGTGGACACCAGCAAGAACCAGTTCAGCCTGAAGCTGAGCAGCGTGACCGCCGCCGACACCGCCGTMACTACTGCGCCCAGGGTGGGCGGCGTGTACAGCACCATCGAGACCTACGGCATGGACGTGTGGGGCCAGGGCACCACCGTGACCGTGAGCAGCGGCGGCGGCGGCAGCGGCGGCGGCGGCAGCGGCGGCGGCGGCAGCGGCGGCGGCGGCAGCGAGATCGTGATGACCCAGAGCCCCGCCACCCTGAGCGTGAGCCCCGGCGAGAGGGCCACCCTGAGCTGCAGGGCCAGCCAGAGCGTGAGCAGCAACCTGGCCTGGTACCAGCAGAAGCCCGGCCAGGCCCCCAGGCTGCTGATCTACGGCGCCAGCACCAGGGCCACCGGCATCCCCGCCAGGTTCAGCGGCAGCGGCAGCGGCACCGAGTTCACCCTGACCATCAGCAGCCTGCAGAGCGAGGACTTCGCCGTGTACTACTGCCAGCAGTACACCGTGTACCCCCCCACCTTCGGCTGCGGCACCAAGGTGGAGATCAAG[SEQ ID NO: 494] | |

TABLE 1-continued

| | VH | VL |
|---|---|---|
| ADI-10158 [Ab14] | QVQLQQWGAGLLKPSETLSLTC AVYGGSFSGYYWSWIRQPPGKG LEWIGEIDHSGSTNYNPSLKSR VTISVDTKNQFSLKLSSVTAA DTAVYYCARQGIHGLRYFDLWG RGTLVTVSS[SEQ ID NO: 272] | EIVMTQSPATLSLSPGERATLSCR ASQSVSSYLAWYQQKPGQAPRLLI YDASNRATGIPARFSGSGSGTDFT LTISSLEPEDFAVYYCQQDHNFPY TFGGGTKVEIK[SEQ ID NO: 273] |
| | CDR1: GYYWS[SEQ ID NO: 322] or GSFSGYYWS[SEQ ID NO: 534](non-Kabat) | CDR1: RASQSVSSYLA[SEQ ID NO: 325] |
| | CDR2: EIDHSGSTNYNPSLKS [SEQ ID NO: 323] | CDR2: DASNRAT[SEQ ID NO: 326] |
| | CDR3: QGIHGLRYFDL[SEQ ID NO: 324] or ARQGIHG LRYFDL[SEQ ID NO: 535] (non-Kabat) | CDR3: QQDHNFPYT[SEQ ID NO: 327] |
| scFv of Ab14 | EIVMTQSPATLSLSPGERATLSC<u>RASQSVSSYLA</u>WYQQKPGQAPRL LIY<u>DASNRAT</u>GIPARF SGSGSGTDFTLTISSLEPEDFAVYYC<u>QQD HNFPYT</u>FG<u>C</u>GTKVEIKGGGGSGGGGSGGGGSGGGGSQVQLQQWGAG LLKPSETLSLTCAVYGGSFSGYYWSWIRQPPGKCLEWIGEIDHSGS TNYNPSLKSRVTISVDTKNQFSLKLSSVTAADTAVYYC<u>ARQGIHG LRYFDL</u>WGRGTLVTVSS[SEQ ID NO: 453] | |
| | QVQLQQWGAGLLKPSETLSLTCAVYGGSFSGYYWSWIRQPPGK<u>C</u>LE WIGEIDHSGSTNYNPSLKSRVTISVDTKN<u>Q</u>FSLKLSSVTAADTAV YYC<u>ARQGIHGLRYFDL</u>WGRGTLVTVSSGGGGSGGGGSGGGGSGGGG SEIVMTQSPATLSLSPGERATLSC<u>RASQSVSSYLA</u>WYQQKPGQAPR LLIY<u>DASNRAT</u>GIPARFSGSGSGTDFTLTISSLEPEDFAVYYC<u>QQD HNFPYT</u>FGCGTKVEIK[SEQ ID NO: 454] | |
| Exemplary nucleotide sequence of Ab14 scFv | GAGATCGTGATGACCCAGAGCCCCGCCACCCTGAGCCTGAGCCC CGGCGAGAGGGCCACCCTGAGCTGCAGGGCCAGCCAGAGCGTGA GCAGCTACCTGGCCTGGTACCAGCAGAAGCCCGGCCAGGCCCCC AGGCTGCTGATCTACGACGCCAGCAACAGGGCCACCGGCATCCC CGCCAGGTTCAGCGGCAGCGGCAGCGGCACCGACTTCACCcrGA CCATCAGCAGCCTGGAGCCCGAGGACTTCGCCGTGTACTACTGC CAGCAGGACCACAACTTCCCCTACACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGCAG CAGTGGGGCGCCGGCCTGCTGAAGCCCAGCGAGACCCTGAGCCT GACCTGCGCCGTGTACGGCGGCAGCTTCAGCGGCTACTACTGGA GCTGGATCAGGCAGCCCCCCGGCAAGTGCCTGGAGTGGATCGGC GAGATCGACCACAGCGGCAGCACCAACTACAACCCCAGCCTGAA GAGCAGGGTGACCATCAGCGTGGACACCAGCAAGAACCAGTTCA GCCTGAAGCTGAGCAGCGTGACCGCCGCCGACACCGCCGTGTAC TACTGCGCCAGGCAGGGCATCCACGGCCTGAGGTACTTCGACCT GTGGGGCAGGGGCACCCTGGTGACCGTGAGCAGC[SEQ ID NO: 495] | |
| | CAGGTGCAGCTGCAGCAGTGGGGCGCCGGCCTGTGAAGCCCAGC GAGACCCTGAGCCTGACCTGCGCCGTGTACGGCGGCAGCTTCAG CGGCTACTACTGGAGCTGGATCAGGCAGCCCCCCGGCAAGTGCC TGGAGTGGATCGGCGAGATCGACCACAGCGGCAGCACCAACTAC AACCCCAGCCTGAAGAGCAGGGTGACCATCAGCGTGGACACCAG CAAGAACCAGTTCAGCCTGAAGCTGAGCAGCGTGACCGCCGCCG ACACCGCCGTGTACTACTGCGCCAGGCAGGGCATCCACGGCCTG AGGTACTTCGACCTGTGGGGCAGGGGCACCCTGGTGACCGTGAG CAGCGGCGGCGGCGGCAGCGGCGGCGGCGGCAGCGGCGGCGGCG GCAGCGGCGGCGGCGGCAGCGAGATCGTGATGACCCAGAGCCCC GCCACCCTGAGCCTGAGCCCCGGCGAGAGGGCCACCCTGAGCTG CAGGGCCAGCCAGAGCGTGAGCAGCTACCTGGCCTGGTACCAGC AGAAGCCCGGCCAGGCCCCCAGGCTGCTGATCTACGACGCCAGC AACAGGGCCACCGGCATCCCCGCCAGGTTCAGCGGCAGCGGCAG CGGCACCGACTTCACCCTGACCATCAGCAGCCTGGAGCCCGAGG ACTTCGCCGTGTACTACTGCCAGCAGGACCACAAGTTCCCCTAC ACGFFCGGCTGCGGCACCAAGGTGGAGATCAAG[SEQ TD NO: 496] | |

TABLE 1-continued

| | VH | VL |
|---|---|---|
| ADI-10160 [Ab15] | EVQLVESGGGLVQPGGSLRLSC AASGFTFSSYWMSWVRQAPGKG LEWVANINQDGSEKYYVDSVKG RFTISRDNAKNSLYLQMNSLRA EDTAVYYCAREANYYGNVGDDY WGQGTLVTVSS[SEQ ID NO: 274] | DIQMTQSPSSLSASVGDRVTITCR ASQSISSYLNWYQQKPGKAPKLLI YAASSLQSGVPSRFSGSGSGTDFT LTISSLQPEDFATYYCQQQYVTPI TFGGGTKVEIK[SEQ ID NO: 275] |
| | CDR1: SYWMS[SEQ ID NO: 328] or FTFSSYWMS [SEQ ID NO: 536](non-Kabat) | CDR1: RASQSISSYLN[SEQ ID NO: 331] |
| | CDR2: NINQDGSEKYYVDSVK G[SEQ ID NO: 329] | CDR2: AASSLQS[SEQ ID NO: 332] |
| | CDR3: EANYYGNVGDDY[SEQ ID NO: 330] or AREANYY GNVGDDY[SEQ ID NO: 537](non-Kabat) | CDR3: QQQYVTPIT[SEQ ID NO: 333] |
| scFv of Ab15 | DIQMTQSPSSLSASVGDRVTITC<u>RASQSISSYLN</u>WYQQKPGKAPKL LIY<u>AASSLQS</u>GVPSRFSGSGSGTDFTLTISSLPEDFATYYC<u>QQQY VTPIT</u>FG<u>C</u>GTKVEIKGGGGSGGGGSGGGGSGGGGSEVQLVESGGGL VQPGGSLRLSCAASGFTFS<u>SYWMS</u>WVRQAPGKCLEWVA<u>NINQDGSE KYYVDSVKG</u>RFTISRDNAKNSLYLQMNSLRAEDTAVYYCAR<u>EANYY GNVGDDY</u>WGQGTLVTVSS[SEQ ID NO: 455] | |
| | EVQLVESGGGLVQPGGSLRLSCAASGFTFSSYWMSWVRQAPGK<u>C</u>LE WVANINQDGSEKYYVDSVKGRFTISRDNAKNSLYLQMNSLRAEDTA VYYCAREANYYGNVGDDYWGQGTLVTVSSGGGGSGGGGSGGGG SGGGGSDIQMTQSPSSLSASVGDRVTITC<u>RASQSISSYLN</u>WYQQKP GKAPKLLIY<u>AASSLQS</u>GVPSRFSGSGSGTDFTLTISSLPEDFATY YC<u>QQQYVTPIT</u>FG<u>C</u>GTKVEIK[SEQ ID NO: 456] | |
| Exemplary nucleotide sequence of Ab15 scFv | GACATCCAGATGACCCAGAGCCCCAGCAGCCTGAGCGCCAGCGT GGGCGACAGGGTGACCATCACCTGCAGGGCCAGCCAGAGCATCA GCAGCTACCTGAACTGGTACCAGCAGAAGCCCGGCAAGGCCCCC AAGCTGCTGATCTACGCCGCCAGCAGCCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGCAGTACGTGACCCCCATCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCGAGGTGCAGCTGGTG GAGAGCGGCGGCGGCCTGGTGCAGCCCGGCGGCAGCCTGAGGCT GAGCTGCGCCGCCAGCGGCTTCACGTCAGCAGCTACTGGATGAG CTGGGTGAGGCAGGCCCCCGGCAAGTGCCTGGAGTGGGTGGCCA ACATCAACCAGGACGGCAGCGAGAAGTACTACGTGGACAGCGTG AAGGGCAGGTTCACCATCAGCAGGGACAACGCCAAGAACAGCCT GTACCTGCAGATGAACAGCCTGAGGGCCGAGGACACCGCCGTGT ACTACTGCGCCAGGGAGGCCAACTACTACGGCAACGTGGGCGAC GACTACTGGGGCCAGGGCACCCTGGTGACCGTGAGCAGC[SEQ ID NO: 497] | |
| | GAGGTGCAGCTGGTGGAGAGCGGCGGCGGCCTGGTGCAGCCCGG CGGCAGCCTGAGGCTGAGCTGCGCCGCCAGCGGCTTCACCTTCA GCAGCTACTGGATGAGCTGGGTGAGGCAGGCCCCCGGCAAGTGC CTGGAGTGGGTGGCCAACATCAACCAGGACGGCAGCGAGAAGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGAGGCCAACTACTA CGGCAACGTGGGCGACGACTACTGGGGCCAGGGCACCCTGGTGA CCGTGAGCAGCGGCGGCGGCGGCAGCGGCGGCGGCGGCAGCGGC GGCGGCGGCAGCGGCGGCGGCGGCAGCGACATCCAGATGACCCA GAGCCCCAGCAGCCTGAGCGCCAGCGTGGGCGACAGGGTGACCA TCACCTGCAGGGCCAGCCAGAGCATCAGCAGCTACCTGAACTGG TACCAGCAGAAGCCCGGCAAGGCCCCCAAGCTGCTGATCTACGC CGCCAGCAGCCTGCAGAGCGGCGTGCCCAGCAGGTTCAGCGGCA GCGGCAGCGGCACCGACTTCACCCTGACCATCAGCAGCCTGCAG CCCGAGGACTTCGCCACCTACTACTGCCAGCAGCAGTACGTGAC CCCCATCACCTTCGGCTGCGGCACCAAGGTGGAGATCAAG[SEQ ID NO: 498] | |

TABLE 1-continued

| | VH | VL |
|---|---|---|
| ADI-10161 [Ab16] | EVQLVESGGGLVQPGGSLRLSC AASGFTFSSYWMSWVRQAPGKG LEWVANINQDGSEKYYVDSVKG RFTISRDNAKNSLYLQMNSLRA EDTAVYYCAREGGDSWYHAFDI WGQGTMVTVSS[SEQ ID NO: 276] | DIQMTQSPSSVSASVGDRVTITCR ASQGISSWLAWYQQKPGKAPKLLI YAASNLQSGVPSRFSGSGSGTDFT LTISSLQPEDFATYYCQQKLSLPL TFGGGTKVEIK[SEQ ID NO: 277] |
| | CDR1: SYWMS[SEQ ID NO: 334] or FTFSSYWMS[SEQ ID NO: 538](non-Kabat) | CDR1: RASQGISSWLA[SEQ ID NO: 337] |
| | CDR2: NINQDGSEKYYVDSVK G[SEQ ID NO: 335] | CDR2: AASNLQS[SEQ ID NO: 338] |
| | CDR3: EGGDSWYHAFDI[SEQ ID NO: 336] or AREGGDS WYHAFDI[SEQ ID NO: 539](non-Kabat) | CDR3: QQKLSLPLT[SEQ ID NO: 339] |
| scFv of Ab16 | DIQMTQSPSSVSASVGDRVTITC<u>R</u><u>ASQGISSWLA</u>WYQQKPGKAPKL LIY<u>AASNLQS</u>GVPSRFSGSGSGTDFTLTISSLQPEDFATYYC<u>QQKL SLPLT</u>FG<u>C</u>GTKVEIKGGGGSGGGGSGGGGSGGGGSEVQLVESGGGL VQPGGSLRLSCAASGFTFSSYWMSWVRQAPGK<u>C</u>LEWVA<u>NINQDGSE KYYVDSVKG</u>RFTISRDNAKNSLYLQMNSLRAEDTAVYYCAR<u>EGGDS WYHAFDI</u>WGQGTMVTVSS[SEQ ID NO: 457] | |
| | EVQLVESGGGLVQPGGSLRLSCAASGFTFSSYWMSWVRQAPGK<u>C</u>LE WVA<u>NINQDGSEKYYVDSVKG</u>RFTISRDNAKNSLYLQMNSLRAEDTA VYYCAR<u>EGGDSWYHAFDI</u>WGQGTMVTVSSGGGGSGGGGSGGGG SGGGGSDIQMTQSPSSVSASVGDRVTITC<u>RASQGISSWLA</u>WYQQKP GKAPKLLIY<u>AASNLQS</u>GVPSRFSGSGSGTDFTLTISSLQPEDFATY YC<u>QQKLSLPLT</u>FGCGTKVEIK[SEQ ID NO: 458] | |
| Exemplary nucleotide sequence of Ab16 scFv | GACATCCAGATGACCCAGAGCCCCAGCAGCGTGAGCGCCAGCGT GGGCGACAGGGTGACCATCACCTGCAGGGCCAGCCAGGGCATCA GCAGGTGGCTGGCCTGGTACCAGCAGAAGCCCGGCAAGGCCCCC AAGCTGCTGATCTACGCCGCCAGCAACCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGAAGCTGAGCGGCCCGGACCTTCGGCTGCGGCACCAAGG TGGAGATCAAGGGCGGCGGCGGCAGCGGCGGCGGCGGCAGCGGC GGCGGCGGCAGCGGCGGCGGCGGCAGCGAGGTGCAGCTGGTGGA GAGCGGCGGCGGCCTGGTGCAGCCCGGCGGCAGCCTGAGGCTGA GCTGCGCCGCCAGCGGCTTCACGTCAGCAGCTACTGGATGAGCT GCGTGAGGCAGGCCCCCGGCAAGTGCCTGGAGTGGGTGGCCAAC ATCAACCAGGACGGCAGCGAGAAGTACTACGTGGACAGCGTGAA GGGCAGGTTCACCATCAGCAGGGACAACGCCAAGAACAGCCTGT ACCTGCAGATGAACAGCCTGAGGGCCGAGGACACCGCCGTGTAC TACTGCGCCAGGGAGGGCGGCGACAGCTGGTACCACGCCTTCGA CATCTGGGGCCAGGGCACCATGGTGACCGTGAGCAGC[SEQ ID NO: 499] | |
| | GAGGTGCAGCTGGTGGAGAGCGGCGGCGGCCTGGTGCAGCCCGG CGGCAGCCTGAGGCTGAGCTGCGCCGCCAGCGGCTTCACCTTCA GCAGCTACTGGATGAGCTGGGTGAGGCAGGCCCCCGGCAAGTGC CTGGAGTGGGTGGCCAACATCAACCAGGACGGCAGCGAGAAGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGAGGGCGGCGACAG CTGGTACCACGCCTTCGACATCTGGGGCCAGGGCACCATGGTGA CCGTGAGCAGCGGCGGCGGCGGCAGCGGCGGCGGCGGCAGCGGC GGCGGCGGCAGCGGCGGCGGCGGCAGCGACATCCAGATGACCCA GAGCCCCAGCAGCGTGAGCGCCAGCGTGGGCGACAGGGTGACCA TCACCTGCAGGGCCAGCCAGGGCATCAGCAGCTGGCTGGCCTGG TACCAGCAGAAGCCCGGCAAGGCCCCCAAGCTGCTGATCTACGC CGCCAGCAACCTGCAGAGCGGCGTGCCCAGCAGGTTCAGCGGCA GCGGCAGCGGCACCGACTTCACCCTGACCATCAGCAGCCTGCAG CCCGAGGACTTCGCCACCTACTGCCAGCAAGCAGAAGCTGAGCC TGCCCCTGACCTTCGGCTGCGGCACCAAGGTGGAGATCAAG [SEQ ID NO: 500] | |

TABLE 1-continued

| | VH | VL |
|---|---|---|
| ADI-10163 [Ab17] | QVQLQESGPGLVKPSQTLSLTCT VSGGSISSGGYYWSWIRQHPGKG LEWIGSIYYSGSTYYNPSLKSRV TISVDTSKNQFSLKLSSVTAADT AVYYCARDRLDYSYNYGMDVWGQ GTTVTVSS[SEQ ID NO: 278] | DIQMTQSPSSLSASVGDRVTITCR ASQSISSYLNWYQQKPGKAPKLLI YGASSLQSGVPSRFSGSGSGTDFT LTISSLQPEDFATYYCQQVYSAPF TFGGGTKVEIK[SEQ ID NO: 279] |
| | CDR1: SGGYYWS[SEQ ID NO: 340]orGSISSGGYYWS [SEQ ID NO: 540](non-Kabat) | CDR1: RASQSISSYLN[SEQ ID NO: 343] |
| | CDR2: SIYYSGSTYYNPSLKS [SEQ ID NO: 341] | CDR2: GASSLQS[SEQ ID NO: 344] |
| | CDR3: DRLDYSYNYGMDV [SEQ ID NO: 342] or ARDRLDYSYNYGMDV[SEQ ID NO: 541](non-Kabat) | CDR3: QQVYSAPFT[SEQ ID NO: 345] |
| scFv of Ab17 | DIQMTQSPSSLSASVGDRVTITC<u>RASQSISSYLN</u>WYQQKPGKAPKL LIY<u>GASSLQS</u>GVPSRFSGSGSGTDFTLTISSLQPEDFATYYC<u>QQVY SAPFTFGC</u>GTKVEIKGGGGSGGGGSGGGGSGGGGSQVQLQESGPGL VKPSQTLSLTCTVSGGSIS<u>SGGYYWS</u>WIRQHPGKCLEWIGS<u>IYYSG STYYNPSLKS</u>RVTISVDTSK<u>NQFSLKL</u>SSVTAADTAVYYC<u>ARDRLD YSYNYGMDV</u>WGQGTTVTVSS[SEQ ID NO: 459] | |
| | QVQLQESGPGLVKPSQTLSLTCTVSGGSIS<u>SGGYYWS</u>WIRQHPGK<u>C</u> LEWIGSIYYSGSTYYNPSLKSRVTISVDTSK<u>NQFSLKL</u>SSVTAADT AVYYC<u>ARDRLDYSYNYGMDV</u>WGQGTTVTVSSGGGGSGGGGSGGGGS GGGGSDIQMTQSPSSLSASVGDRVTITC<u>RASQSISSYLN</u>WYQQKPG KAPKLLIY<u>GASSLQS</u>GVPSRFSGSGSGTDFTLTISSLQPEDFATYY C<u>QQVYSAPFTFGC</u>GTKVEIK[SEQ ID NO: 460] | |
| Exemplary nucleotide sequence of Ab17 scFv | GACATCCAGATGACCCAGAGCCCCAGCAGCCTGAGCGCCAGCGT GGGCGACAGGGTGACCATCACCTGCAGGGCCAGCCAGAGCATCA GCAGCTACCTGAACTGGTACCAGCAGAAGCCCGGCAAGGCCCCC AAGGTGCTGATCTACGGCGCCAGCAGCCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGTGTACAGCGCCCCCTTCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGCAG GAGAGCGGCCCCGGCGGGTGAAGCCCAGCCAGACCCTGAGCCTG ACCTGCACCGTGAGCGGCGGCAGCATCAGCAGCGGCGGCTACTA CTGGAGCTGGATCAGGCAGCACCCCGGCAAGTGCCTGGAGTGGA TCGGCAGCATCTACTACAGCGGCAGCACCTACTACAACCCCAGC CTGAAGAGCAGGGTGACCATCAGCGTGGACACCAGCAAGAACCA GTTCAGCCTGAAGCTGAGCAGCGTGACCGCCGCCGACACCGCCG TGTACTACTGCGCCAGGGACAGGCTGGACTACAGCTACAACTAC GGCATGGACGTGTGGGGCCAGGGCACCACCGTGACCGTGAGCAG C[SEQ ID NO: 501] | |
| | CAGGTGCAGCTGCAGGAGAGCGGCCCCGGCCTGGTGAAGCCCAG CCAGACCCTGAGCCTGACCTGCACCGTGAGCGGCGGCAGCATCA GCAGCGGCGGCTACTACTGGAGCTGGATCAGGCAGCACCCCGGC AAGTGCCTGGAGTGGATCGGCAGCATCTACTACAGCGGCAGCAC CTACTACAACCCCAGCCTGAAGAGCAGGGTGACCATCAGCGTGG ACACCAGCAAGAACCAGTTCAGCCTGAAGCTGAGCAGCGTGACC GCCGCCGACACCGCCGTGTACTACTGCGCCAGGGACAGGCTGGA CTACAGCTACAACTACGGCATGGACGTGTGGGGCCAGGGCACCA CCGTGACCGTGAGCAGCGGCGGCGGCGGCAGCGGCGGCGGCGGC AGCGGCGGCGGCGGCAGCGGCGGCGGCGGCAGCGACATCCAGAT GACCCAGAGCCCCAGCAGCCTGAGCGCCAGCGTGGGCGACAGGG TGACCATCACCTGCAGGGCCAGCCAGAGCATCAGCAGCTACCTG AACTGGTACCAGCAGAAGCCCGGCAAGGCCCCCAAGCTGCTGAT CTACGGCGCCAGCAGCCTGCAGAGCGGCGTGCCCAGGAGGTTCA GCGGCAGCGGCAGCGGCACCGACTTCACCCTGACCATCAGCAGC CTGCAGCCCGAGGACTTCGCCACCTACTACTGCCAGCAGGTGTA CAGCGCCCCCTTCACCTTCGGCTGCGGCACCAAGGTGGAGATCA AG[SEQ ID NO: 502] | |

TABLE 1-continued

| | VH | VL |
|---|---|---|
| ADI-10164 [Ab18] | QVQLQESGPGLVKPSETLSLTC AVSGYSISSGYYWGWIRQPPGK GLEWIGSIYHSGSTNYNPSLKS RVTISVDTSKNQFSLKLSSVTA ADTAVYYCARLPPWFGFSYFDL WGRGTLVTVSS[SEQ ID NO: 280] | EIVLTQSPATLSLSPGERATLSCR ASQSVSSYLAWYQQKPGQAPRLLI YDASNRATGIPARFSGSGSGTDFT LTISSLEPEDFAVYYCQQVDNYPP TFGGGTKVEIK[SEQ ID NO: 281] |
| | CDR1: SGYYWG[SEQ ID NO: 346] or YSISSGYYWG [SEQ ID NO: 542](non-Kabat) | CDR1: RASQSVSSYLA[SEQ ID NO: 349] |
| | CDR2: SIYHSGSTNYNPSLKS [SEQ ID NO: 347] | CDR2: DASNRAT[SEQ ID NO: 350] |
| | CDR3: LPPWFGFSYFDL[SEQ ID NO: 348]orARLPPWFGF SYFDL[SEQ ID NO: 543] (non-Kabat) | CDR3: QQVDNYPPT[SEQ ID NO: 351] |
| scFv of Ab18 | EIVLTQSPATLSLSPGERATLSCRASQSVSSYLAWYQQKPGQAPRL LIYDASNRATGIPARFSGSGSGTDFTLTISSLEPEDFAVYYCQQVD NYPPTFGCGTKVEIKGGGGSGGGGSGGGGSGGGGSQVQLQESGPGL VKPSETLSLTCAVSGYSISSGYYWGWIRQPPGKCLEWIGSIYHSGS TNYNPSLKSRVTISVDTSKNQFSLKLSSVTAADTAVYYCARLPPWF GFSYFDLWGRGTLVTVSS[SEQ ID NO: 461] | |
| | QVQLQESGPGLVKPSETLSLTCAVSGYSISSGYYWGWIRQPPGKCL EWIGSIYHSGSTNYNPSLKSRVTISVDTSKNQFSLKLSSVTAADTA VYYCARLPPWFGFSYFDLWGRGTLVTVSSGGGGSGGGGSGGGGSGGG GSEIVLTQSPATLSLSPGERATLSCRASQSVSSYLAWYQQKPGQAPR LLIYDASNRATGIPARFSGSGSGTDFTLTISSLEPEDFAVYYCQQV DNYPPTFGCGTKVEIK[SEQ ID NO: 462] | |
| Exemplary nucleotide sequence of Ab18 scFv | GAGATCGTGCTGACCCAGAGCCCCGCCACCCTGAGCCTGAGCCC CGGCGAGAGGGCCACCCTGAGCTGCAGGGCCAGCCAGAGCGTGA GCAGCTACCTGGCCTGGTACCAGCAGAAGCCCGGCCAGGCCCCC AGGCTGCTGATCTACGACGCCAGCAACAGGGCCACCGGCATCCC CGCCAGGTTCAGCGGCAGCGGCAGCGGCACCGACTTCACCCTGA CCATCAGCAGCCTGGAGCCCGAGGACTTCGCCGTGTACTACTGC CAGCAGGTGGACAACTACCCCCCCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGCAG GAGAGCGGCCCCGGCCTGGTGAAGCCCAGCGAGACCCTGAGCCT GACCTGCGCCGTGAGCGGCTACAGCATCAGCAGCGGCTACTACT GGGGCTGGATCAGGCAGCCCCCCGGCAAGTGCCTGGAGTGGATC GGCAGCATCTACCACAGCGGCAGCACCAACTACAACCCCAGCCT GAAGAGCAGGGTGACCATCAGCGTGGACACCAGCAAGAACCAGT TCAGCCTGAAGCTGAGCAGCGTGACCGCCGCCGACACCGCCGTG TACTACTGCGCCAGGCTGCCCCCCTGGTTCGGCTTCAGCTACTT CGACCTGTGGGGCAGGGGCACCCTGGTGACCGTGAGCAGC[SEQ ID NO: 503] | |
| | CAGGTGCAGCTGCAGGAGAGCGGCCCCGGCCTGGTGAAGCCCAG CGAGACCCTGAGCCTGACCTGCGCCGTGAGCGGCTACAGCATCA GCAGCGGCTACTACTGGGGCTGGATCAGGCAGCCCCCCGGCAAG TGCCTGGAGTGGATCGGCAGCATCTACCACAGCGGCAGCACCAA CTACAACCCCAGCCTGAAGAGCAGGGTGACCATCAGCGTGGACA CCAGCAAGAACCAGTTCAGCCTGAAGCTGAGCAGCGTGACCGCC GCCGACACCGCCGTGTACTACTGCGCCAGGCTGCCCCCCTGGTT CGGCTTCAGCTACTTCGACCTGTGGGGCAGGGGCACCCTGGTGA CCGTGAGCAGCGGCGGCGGCGGCAGCGGCGGCGGCGGCAGCGGC GGCGGCGGCAGCGGCGGCGGCGGCAGCGAGATCGTGCTGACCCA GAGCCCCGCCACCCTGAGCCTGAGCCCCGGCGAGAGGGCCACCC TGAGCTGCAGGGCCAGCCAGAGCGTGAGCAGCTACCTGGCCTGG TACCAGCAGAAGCCCGGCCAGGCCCCCAGGCTGCTGATCTACGA CGCCAGCAACAGGGCCACCGGCATCCCCGCCAGGTTCAGCGGCA GCGGCAGCGGCACCGACTTCACCCTGACCATCAGCAGCCTGGAG CCCGAGGACTTCGCCGTGTACTACTGCCAGCAGGTGGACAACTA CCCCCCCACCTTCGGCTGCGGCACCAAGGTGGAGATCAAG[SEQ ID NO: 504] | |

TABLE 1-continued

| | VH | VL |
|---|---|---|
| ADI-10165 [Ab19] | EVQLVESGGGLVQPGGSLRLSC AASGFTFSSYWMSWVRQAPGKG LEWVANIKQDGSEKYYVDSVKG RFTISRDNAKNSLYLQMNSLRA EDTAVYYCARDVGPGIAYQGHF DYWGQGTLVTVSS[SEQ ID NO: 282]<br><br>CDR1: SYWMS[SEQ ID NO: 352] or FTFSSYWMS[SEQ ID NO: 544](non-Kabat)<br><br>CDR2: NIKQDGSEKYYVDSVKG [SEQ ID NO: 353]<br><br>CDR3: DVGPGIAYQGHFDY [SEQ ID NO: 354] or ARDVGPGIAYQGHFDY[SEQ ID NO: 545](non-Kabat) | DIQMTQSPSSLSASVGDRVTITCR ASQSISSYLNWYQQKPGKAPKLLI YAASSLQSGVPSRFSGSGSGTDFT LTISSLQPEDFATYYCQQVYDTPL TFGGGTKVEIK[SEQ ID NO: 283]<br><br>CDR1: RASQSISSYLN[SEQ ID NO: 355]<br><br>CDR2: AASSLQS[SEQ ID NO: 356]<br><br>CDR3: QQVYDTPLT[SEQ ID NO: 357] |
| scFv of Ab19 | DIQMTQSPSSLSASVGDRVTITCRASQSISSYLNWYQQKPGKAPKL LIYAASSLQSGVPSRFSGSGSGTDFTLTISSLQPEDFATYYCQQVY DTPLTFGCGTKVEIKGGGGSGGGGSGGGGSGGGGSEVQLVESGGGL VQPGGSLRLSCAASGFTFSSYWMSWVRQAPGKCLEWVANIKQDGSE KYYVDSVKGRFTISRDNAKNSLYLQMNSLRAEDTAVYYCARDVGPG IAYQGHFDYWGQGTLVTVSS[SEQ ID NO: 463]<br><br>EVQLVESGGGLVQPGGSLRLSCAASGFTFSSYWMSWVRQAPGKCLE WVANIKQDGSEKYYVDSVKGRFTISRDNAKNSLYLQMNSLRAEDTA VYYCARDVGPGIAYQGHFDYWGQGTLVTVSSGGGGSGGGGSGGG GSGGGGSDIQMTQSPSSLSASVGDRVTITCRASQSISSYLNWYQQK PGKAPKLLIYAASSLQSGVPSRFSGSGSGTDFTLTISSLQPEDFAT YYCQQVYDTPLTFGCGTKVEIK[SEQ ID NO: 464] | |
| Exemplary nucleotide sequence of Ab19 scFv | GACATCCAGATGACCCAGAGCCCCAGCAGCCTGAGCGCCAGCGT GGGCGACAGGGTGACCATCACCTGCAGGGCCAGCCAGAGCATCA GCAGCTACCTGAACTGGTACCAGCAGAAGCCCGGCAAGGCCCCC AAGCTGCTGATCTACGCCGCCAGCAGCCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGTGTACGACACCCCCCTGACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCGAGGTGCAGCTGGTG GAGAGCGGCGGCGGCCTGGTGCAGCCCGGCGUTAGCCTGAGGCT GAGCTGCGCCGCCAGCGGCTTCACCTTCAGCAGCTACTGGATGA GCTGGGTGAGGCAGGCCCCCGGCAAGTGCCTGGAGTGGGTGGCC AACATCAAGCAGGACGGCAGCGAGAAGTACTACGTGGACAGCGT GAAGGGCAGGTTCACCATCAGCAGGGACAACGCCAAGAACAGCG TGTACCTGCAGATGAACAGCCTGAGGGCCGAGGACACCGCCGTG TACTACTGCGCCAGGGACGTGGGCCCCGGCATCGCCTACCAGGG CCACTTCGACTACTGGGGCCAGGGCACCCTGGTGACCGTGAGCA GC[SEQ ID NO: 505]<br><br>GAGGTGCAGCTGGTGGAGAGCGGCGGCGGCCTGGTGCAGCCCGG CGGCAGCCTGAGGCTGAGCTGCGCCGCCAGCGGCTTCACCTTCA GCAGCTACTGGATGAGCTGGGTGAGGCAGGCCCCCGGCAAGTGC CTGGAGTGGGTGGCCAACATCAAGCAGGACGGCAGCGAGAAGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGACGTGGGCCCCGG CATCGCCTACCAGGGCCACTTCGACTACTGGGGCCAGGGCACCC TGGTGACCGTGAGCAGCGGCGGCGGCGGCAGCGGCGGCGGCGGC AGCGGCGGCGGCGGCAGCGGCGGCGGCGGCAGCGACATCCAGAT GACCCAGAGCCCCAGCAGCCTGAGCGCCAGCGTGGGCGACAGGG TGACCATCACCTGCAGGGCCAGCCAGAGCATCAGCAGCTACCTG AACTGGTACCAGCAGAAGCCCGGCAAGGCCCCCAAGCTGCTGAT CTACGCCGCCAGCAGCCTGCAGAGCGGCGTGCCCAGCAGGTTCA GCGGCAGCGGCAGCGGCACCGACTTCACCCTGACCATCAGCAGC CTGCAGCCCGAGGACTTCGCCACCTACTACTGCCAGCAGGTGTA CGACACCCCCCTGACCTTCGGCTGCGGCACCAAGGTGGAGATCA AG[SEQ ID NO: 506] | |

TABLE 1-continued

| | VH | VL |
|---|---|---|
| ADI-10167 [Ab20] | QLQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCARETAHDVHGMDVWGQGTTVTVSS[SEQ ID NO: 284] | EIVLTQSPATLSLSPGERATLSCRASQSVSSYLAWYQQKPGQAPRLLIYDASNRATGIPARFSGSGSGTDFTLTISSLEPEDFAVYYCQQYDNLPTFGGGTKVEIK[SEQ ID NO: 285] |
| | CDR1: SSSYYWG[SEQ ID NO: 358]orGSISSSSYYWG [SEQ ID NO: 546](non-Kabat) | CDR1: RASQSVSSYLA[SEQ ID NO: 361] |
| | CDR2: SIYYSGSTYYNPSLKS[SEQ ID NO: 359] | CDR2: DASNRAT[SEQ ID NO: 362] |
| | CDR3: ETAHDVHGMDV[SEQ ID NO: 360] or ARETAHDVHGMDV[SEQ ID NO: 547](non-Kabat) | CDR3: QQYDNLPT[SEQ ID NO: 363] |
| scFv of Ab20 | EIVLTQSPATLSLSPGERATLSCRASQSVSSYLAWYQQKPGQAPRLLIYDASNRATGIPARFSGSGSGTDFTLTISSLEPEDFAVYYCQQYDNLPTFG*C*GTKVEIKGGGGSGGGGSGGGGSGGGGSQLQLQESGPGLVKPSETLSLTCTVSGGSISSSSYYWGWIRQPPGK*C*LEWIGSIYYSGSTYYNPSLKSRVTISVDTSKNQFSLKLSSVTAADTAVYYCARETAHDVHGMDVWGQGTTVTVSS[SEQ ID NO: 465] | |
| | QLQLQESGPGLVKPSETLSLTCTVSGGSISSSSYYWGWIRQPPGK*C*LEWIGSIYYSGSTYYNPSLKSRVTISVDTSKNQFSLKLSSVTAADTAVYYCARETAHDVHGMDVWGQGTTVTVSSGGGGSGGGGSGGGGSGGGGSEIVLTQSPATLSLSPGERATLSCRASQSVSSYLAWYQQKPGQAPRLLIYDASNRATGIPARFSGSGSGTDFTLTISSLEPEDFAVYYCQQYDNLPTFGCGTKVEIK[SEQ ID NO: 466] | |
| Exemplary nucleotide sequence of Ab20 scFv | GAGATCGTGCTGACCCAGAGCCCCGCCACCCTGAGCCTGAGCCCCGGCGAGAGGGCCACCCTGAGCTGCAGGGCCAGCCAGAGCGTGAGCAGCTACCTGGCCTGGTACCAGCAGAAGCCCGGCCAGGCCCCCAGGCTGCTGATCTACGACGCCAGCAACAGGGCCACCGGCATCCCCGCCAGGTTTCAGCGGCAGCGGCAGCGGCACCGAGTCACCCTGACCATCAGCAGCCTGGAGCCCGAGGACTTCGCCGTGTACTACTGCCAGCAGTACGACAACCTGCCCACCTTCGGCTGCGGCACCAAGGTGGAGATCAAGGGCGGCGGCGGCAGCGGCGGCGGCGGCAGCGGCGGCGGCGGCAGCGGCGGCGGCGGCAGCCAGCTGCAGGAGAGCGGCCCCGGCCTGGTGAAGCCCAGCGAGACCCTGAGCCTGACCTGCACCGTGAGCGGCGGCAGCATCAGCAGCAGCAGCTACTACTGGGGCTGGATCAGGCAGCCCCCCGGCAAGTGCCTGGAGTGGATCGGCAGCATCTACTACAGCGGCAGCACCTACTATAACCCCAGCCTGAAGAGCAGGGTGACCATCAGCGTGGACACCAGCAAGAACCAGTTCAGCCTGAAGCTGAGCAGCGTGACCGCCGCCGACACCGCCGTGTACTACTGCGCCAGGGAGACCGCCCACGACGTGCACGGCATGGACGTGTGGGGCCAGGGCACCACCGTGACCGTGAGCAGC[SEQ ID NO: 507] | |
| | CAGCTGCAGCTGCAGGAGAGCGGCCCCGGCCTGGTGAAGCCCAGCGAGACCCTGAGCCTGACCTGCACCGTGAGCGGCGGCAGCATCAGCAGCAGCAGCTACTACTGGGGCTGGATCAGGCAGCCCCCCGGCAAGTGCCTGGAGTGGATCGGCAGCATCTACTACAGCGGCAGCACCTACTACAACCCCAGCCTGAAGAGCAGGGTGACCATCAGCGTGGACACCAGCAAGAACCAGTTCAGCCTGAAGCTGAGCAGCGTGACCGCCGCCGACACCGCCGTGTACTACTGCGCCAGGGAGACCGCCCACGACGTGCACGGCATGGACGTGTGGGGCCAGGGCACCACCGTGACCGTGAGCAGCGGCGGCGGCGGCAGCGGCGGCGGCGGCAGCGGCGGCGGCGGCAGCGGCGGCGGCGGCAGCGAGATCGTGCTGACCCAGAGCCCCGCCACCCTGAGCCTGAGCCCCGGCGAGAGGGCCACCCTGAGCTGCAGGGCCAGCCAGAGCGTGAGCAGCTACCTGGCCTGGTACCAGCAGAAGCCCGGCCAGGCCCCCAGGCTGCTGATCTACGACGCCAGCAACAGGGCCACCGGCATCCCCGCCAGGTTCAGCGGCAGCGGCAGCGGCACCGACTTCACCCTGACCATCAGCAGCCTGGAGCCCGAGGACTTCGCCGTGTACTACTGCCAGCAGTACGACAACCTGCCCACCTTCGGCTGCGGCACCAAGGTGGAGATCAAG[SEQ ID NO: 508] | |

TABLE 1-continued

| | VH | VL |
|---|---|---|
| ADI-10168 [Ab21] | QVQLVQSGAEVKKPGSSVKVSC KASGGTFSSYAISWVRQAPGQG LEWMGSIIPIFGTANYAQKFQG RVTITADESTSTAYMELSSLRS EDTAVYYCAREVGYGWYTKIAF DIWGQGTMVTVSS[SEQ ID NO: 286] | EIVLTQSPATLSLSPGERATLSCR ASQSVSSYLAWYQQKPGQAPRLLI YDASKRATGIPARFSGSGSGTDFT LTISSLEPEDFAVYYCQQSSNHPS TFGGGTKVEIK[SEQ ID NO: 287] |
| | CDR1: SYAIS[SEQ ID NO: 364] or GTFSSYAIS[SEQ ID NO: 548] (non-Kabat) | CDR1: RASQSVSSYLA[SEQ ID NO: 367] |
| | CDR2: SIIPIFGTANYAQKFQ G[SEQ ID NO: 365] | CDR2: DASKRAT[SEQ ID NO: 368] |
| | CDR3: EVGYGWYTKIAFDI [SEQ ID NO: 366] or AREVGYGWYTKIAFDI[SEQ ID NO: 549](non-Kabat) | CDR3: QQSSNHPST[SEQ ID NO: 369] |
| scFv of Ab21 | EIVLTQSPATLSLSPGERATLSCRASQSVSSYLAWYQQKPGQAPRL LIYDASKRATGIPARFSGSGSGTDFTLTISSLEPEDFAVYYCQQSS NHPSTFGCGTKVEIKGGGGSGGGGSGGGGSGGGGSQVQLVQSGAEV KKPGSSVKVSCKASGGTFSSYAISWVRQAPGQCLEWMGSIIPIFGT ANYAQKFQGRVTITADESTSTAYMELSSLRSEDTAVYYCAREVGYG WYTKIAFDIWGQGTMVTVSS[SEQ ID NO: 467] | |
| | QVQLVQSGAEVKKPGSSVKVSCKASGGTFSSYAISWVRQAPGQCLE WMGSIIPIFGTANYAQKFQGRVTITADESTSTAYMELSSLRSEDTA VYYCAREVGYGWYTKIAFDIWGQGTMVTVSSGGGGSGGGGSGGGGS GGGGSEIVLTQSPATLSLSPGERATLSCRASQSVSSYLAWYQQKPG QAPRLLIYDASKRATGIPARFSGSGSGTDFTLTISSLEPEDFAVYY CQQSSNHPSTFGCGTKVEIK[SEQ ID NO: 468] | |
| Exemplary nucleotide sequence of Ab21 scFv | GAGATCGTGCTGACCCAGAGCCCCGCCACCCTGAGCCTGAGCCC CGGCGAGAGGGCCACCCTGAGCTGCAGGGCCAGCCAGAGCGTGA GCAGCTACCTGGCCTGGTACCAGCAGAAGCCCGGCCAGGCCCCC AGGCTGCTGATCTACGACGCCAGCAAGAGGGCCACCGGCATCCC CGCCAGGTTCAGCGGCAGCGGCAGCGGCACCGACTTCACCCTGA CCATCAGCAGCCTGGAGCCCGAGGACTTCGCCGTGTACTACTGC CAGCAGAGCAGCAACCACCCCAGCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGGTG CAGAGCGGCGCCGAGGTGAAGAAGCCCGGCAGCAGCGTGAAGGT GAGCTGCAAGGCCAGCGGCGGCACCTTCAGCAGCTACGCCATCA GCTGGGTGAGGCAGGCCCCCGGCCAGTGCCTGGAGTGGATGGGC AGCATCATCCCCATCTTCGGCACCGCCAACTACGCCCAGAAGTT CCAGGGCAGGGTGACCATCACCGCCGACGAGAGCACCAGCACCG CCTACATGGAGCTGAGCAGCCTGAGGAGCGAGGACACCGCCGTG TACTACTGCGCCAGGGAGGTGGGCTACGGCTGGTACACCAAGAT CGCCTTCGACATCTGGGGCCAGGGCACCATGGTGACCGTGAGCA GC[SEQ ID NO: 509] | |
| | CAGGTGCAGCTGGTGCAGAGCGGCGCCGAGGTGAAGAAGCCCGG CAGCAGCGTGAAGGTGAGCTGCAAGGCCAGCGGCGGCACCTTCA GCAGCTACGCCATCAGCTGGGTGAGGCAGGCCCCCGGCCAGTGC CTGGAGTGGATGGGCAGCATCATCCCCATCTTCGGCACCGCCAA CTACGCCCAGAAGTTCCAGGGCAGGGTGACCATCACCGCCGACG AGAGCACCAGCACCGCCTACATGGAGCTGAGCAGCCTGAGGAGC GAGGACACCGCCGTGTACTACTGCGCCAGGGAGGTGGGCTACGG CTGGTACACCAAGATCGCCTTCGACATCTGGGGCCAGGGCACCA TGGTGACCGTGAGCAGCGGCGGCGGCGGCAGCGGCGGCGGCGGC AGCGGCGGCGGCGGCAGCGGCGGCGGCGGCAGCGAGATCGTGCT GACCCAGAGCCCCGCCACCCTGAGCCTGAGCCCCGGCGAGAGGG CCACCCTGAGCTGCAGGGCCAGCCAGAGCGTGAGCAGCTACCTG GCCTGGTACCAGCAGAAGCCCGGCCAGGCCCCCAGGCTGCTGAT CTACGACGCCAGCAAGAGGGCCACCGGCATCCCCGCCAGGTTCA GCGGCAGCGGCAGCGGCACCGACTTCACCCTGACCATCAGCAGC CTGGAGCCCGAGGACTTCGCCGTGTACTACTGCCAGCAGAGCAG CAACCACCCCAGCACCTTCGGCTGCGGCACCAAGGTGGAGATCA AG[SEQ ID NO: 510] | |

TABLE 1-continued

| | VH | VL |
|---|---|---|
| ADI-10173 [Ab22] | QVQLVQSGAEVKKPGASVKVSC KASGYTFTSYYMHWVRQAPGQG LEWMGIINPSGGSTTYAQKFQG RVTMTRDTSTSTVYMELSSLRS EDTAVYYCAREAADGFVGERYF DLWGRGTLVTVSS[SEQ ID NO: 288] | DIVMTQSPLSLPVTPGEPASISCR SSQSLLHSNGYNYLDWYLQKPGQS PQLLIYLGSNRASGVPDRFSGSGS GTDFTLKISRVEAEDVGVYYCMQA LGVPLTFGGGTKVEIK[SEQ ID NO: 289] |
| | CDR1: SYYMH[SEQ ID NO: 370] or YTFTSYYMH[SEQ ID NO: 550] (non-Kabat) | CDR1: RSSQSLLHSNGYNYLD [SEQ ID NO: 373] |
| | CDR2: IINPSGGSTTYAQKFQ G[SEQ ID NO: 371] | CDR2: LGSNRAS[SEQ ID NO: 374] |
| | CDR3: EAADGFVGERYFDL [SEQ ID NO: 372] or AREAADGFVGERYFDL[SEQ ID NO: 551](non-Kabat) | CDR3: MQALGVPLT[SEQ ID NO: 375] |
| scFv of Ab22 | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQALGVPLTFGCGTKVEIKGGGGSGGGGSGGGGSGGGGSQVQLVQ SGAEVKKPGASVKVSCKASGYTFTSYYMHWVRQAPGQCLEWMGIIN PSGGSTTYAQKFQGRVTMTRDTSTSTVYMELSSLRSEDTAVYYCAR EAADGFVGERYFDLWGRGTLVTVSS[SEQ ID NO: 469] | |
| | QVQLVQSGAEVKKPGASVKVSCKASGYTFTSYYMHWVRQAPGQCLE WMGIINPSGGSTTYAQKFQGRVTMTRDTSTSTVYMELSSLRSEDTA VYYCAREAADGFVGERYFDLWGRGTLVTVSSGGGGSGGGGSGGG GSGGGGSDIVMTQSPLSLPVTPGEPASISCRSSQSLLHSNGYNYLD WYLQKPGQSPQLLIYLGSNRASGVPDRFSGSGSGTDFTLKISRVEA EDVGVYYCMQALGVPLTFGCGTKVEIK[SEQ ID NO: 470] | |
| Exemplary nucleotide sequence of Ab22 scFv | GACATCGTGATGACCCAGAGCCCCCTGAGCCTGCCCGTGACCCC CGGCGAGCCCGCCAGCATCAGCTGCAGGAGCAGCCAGAGCCTGC TGCACAGCAACGGCTACAACTACCTGGACTGGTACCTGCAGAAG CCCGGCCAGAGCCCCCAGCTGCTGATCTACCTGGGCAGCAACAG GGCCAGCGGCGTGCCCGACAGGTTCAGCGGCAGCGGCAGCGGCA CCGACTTCACCCTGAAGATCAGCAGGGTGGAGGCCGAGGACGTG GGCGTGTACTACTGCATGCAGGCCCTGGGCGTGCCCCTGACCTT CGGCTGCGGCACCAAGGTGGAGATCAAGGGCGGCGGCGGCAGCG GCGGCGGCGGCAGCGGCGGCGGCGGCAGCGGCGGCGGCGGCAGC CAGGTGCAGCTGGTGCAGAGCGGCGCCGAGGTGAAGAAGCCCGG CGCCAGCGTGAAGGTGAGCTGCAAGGCCAGCGGCTACACCTTCA CCAGCTACTACATGCACTGGGTGAGGCAGGCCCCCGGCCAGTGC CTGGAGTGGATGGGCATCATCAACCCCAGCGGCGGCAGCACCAC CTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGAGGCCGCCGACGG CTTCGTGGGCGAGAGGTACTTCGACCTGTGGGGCAGGGGCACCC TGGTGACCGTGAGCAGC[SEQ ID NO: 511] | |
| | CAGGTGCAGCTGGTGCAGAGCGGCGCCGAGGTGAAGAAGCCCGG CGCCAGCGTGAAGGTGAGCTGCAAGGCCAGCGGCTACACCTTCA CCAGCTACTACATGCACTGGGTGAGGCAGGCCCCCGGCCAGTGC CTGGAGTGGATGGGCATCATCAACCCCAGCGGCGGCAGCACCAC CTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGAGGCCGCCGACGG CTTCGTGGGCGAGAGGTACTTCGACCTGTGGGGCAGGGGCACCC TGGTGACCGTGAGCAGCGGCGGCGGCGGCAGCGGCGGCGGCGGC AGCGGCGGCGGCGGCAGCGGCGGCGGCGGCAGCGACATCGTGAT GACCCAGAGCCCCCTGAGCCTGCCCGTGACCCCCGGCGAGCCCG CCAGCATCAGCTGCAGGAGCAGCCAGAGCCTGCTGCACAGCAAC GGCTACAACTACCTGGACTGGTACCTGCAGAAGCCCGGCCAGAG CCCCCAGCTGCTGATCTACCTGGGCAGCAACAGGGCCAGCGGCG TGCCCGACAGGTTCAGCGGCAGCGGCAGCGGCACCGACTTCACC CTGAAGATCAGCAGGGTGGAGGCCGAGGACGTGGGCGTGTACTA CTGCATGCAGGCCCTGGGCGTGCCCCTGACCTTCGGCTGCGGCA CCAAGGTGGAGATCAAG[SEQ ID NO: 512] | |

TABLE 1-continued

| | VH | VL |
|---|---|---|
| ADI-11802 [Ab23] | QVQLVQSGAEVKKPGASVKVSC KASGYTFSGYYMHWVRQAPGQG LEWMGMINPYGGSTRYAQKFQG RVTMTRDTSTSTVYMELSSLRS EDTAVYYCAREAADGFVGERYF DLWGRGTLVTVSS[SEQ ID NO: 290] | DIVMTQSPLSLPVTPGEPASISCR SSQSLLYSNGYNYLDWYLQKPGQS PQLLIYLGSNRASGVPDRFSGSGS GTDFTLKISRVEAEDVGVYYCMQD VALPITGGGTKVEIK[SEQ ID NO: 291] |
| | CDR1: GYYMH[SEQ ID NO: 376] or YTFSGYYMH[SEQ ID NO: 552](non-Kabat) | CDR1: RSSQSLLYSNGYNYLD [SEQ ID NO: 379] |
| | CDR2: MINPYGGSTRYAQKFQ G[SEQ ID NO: 377] | CDR2: LGSNRAS[SEQ ID NO: 380] |
| | CDR3: EAADGFVGERYFDL [SEQ ID NO: 378] or AREAADGFVGERYFDL[SEQ ID NO: 553](non-Kabat) | CDR3: MQDVALPIT[SEQ ID NO: 381] |
| scFv of Ab23 | DIVMTQSPLSLPVTPGEPASISCRSSQSLLYSNGYNYLDWYLQKPG QSPQLLIYLGSNRASGVPDRFSGSGSGTDFTLKISRVEAEDVGVYY CMQDVALPITFGCGTKVEIKGGGGSGGGGSGGGGSGGGGSQVQLVQ SGAEVKKPGASVKVSCKASGYTFSGYYMHWVRQAPGQCLEWMGMIN PYGGSTRYAQKFQGRVTMTRDTSTSTVYMELSSLRSEDTAVYYCAR EAADGFVGERYFDLWGRGTLVTVSS[SEQ ID NO: 471] | |
| | QVQLVQSGAEVKKPGASVKVSCKASGYTFSGYYMHWVRQAPGQCLE WMGMINPYGGSTRYAQKFQGRVTMTRDTSTSTVYMELSSLRSEDTA VYYCAREAADGFVGERYFDLWGRGTLVTVSSGGGGSGGGGSGG GGSGGGGSDIVMTQSPLSLPVTPGEPASISCRSSQSLLYSNGYNYL DWYLQKPGQSPQLLIYLGSNRASGVPDRFSGSGSGTDFTLKISRVE AEDVGVYYCMQDVALPITFGCGTKVEIK[SEQ ID NO: 472] | |
| Exemplary nucleotide sequence of Ab23 scFv | GACATCGTGATGACCCAGAGCCCCCTGAGCCTGCCCGTGACCCC CGGCGAGCCCGCCAGCATCAGGTGCAGGAGCAGCCAGAGCCTGC TGTACAGCAACGGCTACAACTACCTGGACTGGTACCTGCAGAAG CCCGGCCAGAGCCCCCAGCTGCTGATCTACCTGGGCAGCAACAG GGCCAGCGGCGTGCCCGACAGGTTCAGCGGCAGCGGCAGCGGCA CCGACTTCACCCTGAAGATCAGCAGGGTGGAGGCCGAGGACGTG GGCGTGTACTACTGCATGCAGGACGTGGCCCTGCCCATCACGTC GGCTGCGGCACCAAGGTGGAGATCAAGGGCGGCGGCGGCAGCGG CGGCGGCGGCAGCGGCGGCGGCGGCAGCGGCGGCGGCGGCAGCC AGGTGCAGCTGGTGCAGAGCGGCGCCGAGGTGAAGAAGCCCGGC GCCAGCGTGAAGGTGAGCTGCAAGGCCAGCGGCTACACCTTCAG CGGCTACTACATGCACTGGGTGAGGCAGGCCCCCGGCCAGTGCC TGGAGTGGATGGGCATGATCAACCCCTACGGCGGCAGCACCAGG TACGCCCAGAAGTTCCAGGGCAGGGTGACCATGACCAGGGACAC CAGCACCAGCACCGTGTACATGGAGCTGAGCAGCCTGAGGAGCG AGGACACCGCCGTGTACTACTGCGCCAGGGAGGCCGCCGACGGC TTCGTGGGCGAGAGGTACTTCGACCTGTGGGGCAGGGGCACCCT GGTGACCGTGAGCAGC[SEQ ID NO: 513] | |
| | CAGGTGCAGCTGGTGCAGAGCGGCGCCGAGGTGAAGAAGCCCGG CGCCAGCGTGAAGGTGAGCTGCAAGGCCAGCGGCTACACCGTCAG CGGCTACTACATGCACTGGGTGAGGCAGGCCCCCGGCCAGTGCC TGGAGTGGATGGGCATGATCAACCCCTACGGCGGCAGCACCAGG TACGCCCAGAAGTTCCAGGGCAGGGTGACCATGACCAGGGACAC CAGCACCAGCACCGTGTACATGGAGCTGAGCAGCCTGAGGAGCG AGGACACCGCCGTGTACTACTGCGCCAGGGAGGCCGCCGACGGC TTCGTGGGCGAGAGGTACTTCGACCTGTGGGGCAGGGGCACCCT GGTGACCGTGAGCAGCGGCGGCGGCGGCAGCGGCGGCGGCGGCA GCGGCGGCGGCGGCAGCGGCGGCGGCGGCAGCGACATCGTGATG ACCCAGAGCCCCCTGAGCCTGCCCGTGACCCCCGGCGAGCCCGC CAGCATCAGGTGCAGGAGCAGCCAGAGCCTGCTGTACAGCAACG GCTACAACTACCTGGACTGGTACCTGCAGAAGCCCGGCCAGAGC CCCCAGCTGCTGATCTACCTGGGCAGCAACAGGGCCAGCGGCGT GCCCGACAGGTTCAGCGGCAGCGGCAGCGGCACCGACTTCACCC TGAAGATCAGCAGGGTGGAGGCCGAGGACGTGGGCGTGTACTAC TGCATGCAGGACGTGGCCCTGCCCATCACCTTCGGCTGCGGCAC CAAGGTGGAGATCAAG[SEQ ID NO: 514] | |

TABLE 1-continued

| | VH | VL |
|---|---|---|
| ADI-11812 [Ab24] | QVQLVQSGAEVKKPGASVKVSC KASGYTFEIYYMHWVRQAPGQG LEWMGIINPSSGSTVYAQKFQG RVTMTRDTSTSTVYMELSSLRS EDTAVYYCARGAGYDDEDMDVW GKGTTVTVSS[SEQ ID NO: 292] | DIQMTQSPSSVSASVGDRVTITCR ASQGIDSWLAWYQQKPGKAPKLLI YAASSLQSGVPSRFSGSGSGTDFT LTISSLQPEDFATYYCQQAHSYPL TFGGGTKVEIK[SEQ ID NO: 293] |
| | CDR1: IYYMH[SEQ ID NO: 382] or YTFEIYYMH[SEQ ID NO: 554](non-Kabat) | CDR1: RASQGIDSWLA[SEQ ID NO: 385] |
| | CDR2: IINPSSGSTVYAQKFQ G[SEQ ID NO: 383] | CDR2: AASSLQS[SEQ ID NO: 386] |
| | CDR3: GAGYDDEDMDV[SEQ ID NO: 384] or ARGAGYD DEDMDV[SEQ ID NO: 555] (non-Kabat) | CDR3: QQAHSYPLT[SEQ ID NO: 387] |
| scFv of Ab24 | DIQMTQSPSSVSASVGDRVTITC<u>RASQGIDSWLA</u>WYQQKPGKAPKL LIY<u>AASSLQS</u>GVPSRFSGSGSGTDFTLTISSLQPEDFATYYC<u>QQAH SYPLTFG</u>CGTKVEIKGGGGSGGGGSGGGGSGGGGSQVQLVQSGAEV KKPGASVKVSCKASGYTFEIYYMHWVRQAPGQCLEWMGI<u>INPSSGS TVYAQKFQ</u>GRVTMTRDTSTSTVYMELSSLRSEDTAVYYCAR<u>GAGYD DEDMDV</u>WGKGTTVTVSS[SEQ ID NO: 473] | |
| | QVQLVQSGAEVKKPGASVKVSCKASGYTFEIYYMHWVRQAPGQCLE WMGIINPSSGSTVYAQKFQGRVTMTRDTSTSTVYMELSSLRSEDTA VYYCARGAGYDDEDMDVWGKGTTVTVSSGGGGSGGGGSGGGGS GGGGSDIQMTQSPSSVSASVGDRVTITC<u>RASQGIDSWLA</u>WYQQKPG KAPKLLIY<u>AASSLQS</u>GVPSRFSGSGSGTDFTLTISSLQPEDFATYY C<u>QQAHSYPLT</u>FGCGTKVEIK[SEQ ID NO: 474] | |
| Exemplary nucleotide sequence of Ab24 scFv | GACATCCAGATGACCCAGAGCCCCAGCAGCGTGAGCGCCAGCGT GGGCGACAGGGTGACCATCACCTGCAGGGCCAGCCAGGGCATCG ACAGCTGGCTGGCCTGGTACCAGCAGAAGCCCGGCAAGGCCCCC AAGCTGCTGATCTACGCCGCCAGCAGCCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGCCCACAGCTACCCCCTGACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGGTG CAGAGCCTGCGCCGAGGTGAAGAACTCCCGGCGCCAGCGTGAAG GTGAGCTGCAAGGCCAGCGGCTACACCTTCGAGATCTACTACAT GCACTGGGTGAGGCAGGCCCCCGGCCAGTGCCTGGAGTGGATGG GCATCATCAACCCCAGCAGCGGCAGCACCGTGTACGCCCAGAAG TTCCAGGGCAGGGTGACCATGACCAGGGACACCAGCACCAGCAC CGTGTACATGGAGCTGAGCAGCCTGAGGACTCGAGGACACCGCC GTGTACTACTGCGCCAGGGGCGCCGGCTACGACGACGAGGACAT GGACGTGTGGGGCAAGGGCACCACCGTGACCGTGAGCAGC[SEQ ID NO: 515] | |
| | CAGGTGCAGCTGGTGCAGAGCGGCGCCGAGGTGAAGAAGCCCGG CGCCAGCGTGAAGGTGAGCTGCAAGGCCAGCGGCTACACCTTCG AGATCTACTACATGCACTGGGTGAGGCAGGCCCCCGGCCAGTGC CTGGAGTGGATGGGCATCATCAACCCCAGCAGCGGCAGCACCGT GTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGGCGCCGGCTACGA CGACGAGGACATGGACGTGTGGGGCAAGGGCACCACCGTGACCG TGAGCAGCGGCGGCGGCAGCGGCGGCGGCGGCAGCGGCGGCGGC GGCAGCGGCGGCGGCGGCAGCGACATCCAGATGACCCAGAG CCCCAGCAGCGTGAGCGCCAGCGTGGGCGACAGGGTGACCATCA CCTGCAGGGCCAGCCAGGGCATCGACAGCTGGCTGGCCTGCTTA CCAGCAGAAGCCCGGCAAGGCCCCCAAGCTGCTGATCTACGCCG CCAGCAGCCTGCAGAGCGGCGTGCCCAGCAGGTTCAGCGGCAGC GGCAGCGGCACCGACTTCACCCTGACCATCAGCAGCCTGCAGCC CGAGGACTTCGCCACCTACTACTGCCAGCAGGCCCACAGCTACC CCCTGACCTTCGGCTGCGGCACCAAGGTGGAGATCAAG[SEQ ID NO: 516] | |

TABLE 1-continued

|  | VH | VL |
|---|---|---|
| ADI-11825 [Ab25] | EVQLVESGGGLVQPGGSLRLSC AASGFTFGGYWMSWVRQAPGKG LEWVANINQDGSEEYYVDSVKG RFTISRDNAKNSLYLQMNSLRA EDTAVYYCAREANYYGNVGDDY WGQGTLVTVSS[SEQ ID NO: 294] | DIQMTQSPSSLSASVGDRVTITCR ASQSIYNYLNWYQQKPGKAPKLLI YAASNLHSGVPSRFSGSGSGTDFT LTISSLQPEDFATYYCQQAFHVPI TFGGGTKVEIK[SEQ ID NO: 295] |
|  | CDR1: GYWMS[SEQ ID NO: 388] or FTFGGYWMS[SEQ ID NO: 556](non-Kabat) | CDR1: RASQSIYNYLN[SEQ ID NO: 391] |
|  | CDR2: NINQDGSEEYYVDSVK G[SEQ ID NO: 389] | CDR2: AASNLHS[SEQ ID NO: 392] |
|  | CDR3: EANYYGNVGDDY[SEQ ID NO: 390] or AREANYY GNVGDDY[SEQ ID NO: 557] (non-Kabat) | CDR3: QQAFHVPIT[SEQ ID NO: 393] |
| scFv of Ab25 | DIQMTQSPSSLSASVGDRVTITC<u>RASQSIYNYLN</u>WYQQKPGKAPKL LIY<u>AASNLHS</u>GVPSRFSGSGSGTDFTLTISSLQPEDFATYYC<u>QQAF HVPIT</u>FG<u>C</u>GTKVEIKGGGGSGGGGSGGGGSGGGGSEVQLVESGGGL VQPGGSLRLSCAASGFTFGGYWMSWVRQAPGK<u>C</u>LEWVAN<u>INQDGSE EYYVDSVK</u>GRFTISRDNAKNSLYLQMNSLRAEDTAVYYCAR<u>EANYY GNVGDDY</u>WGQGTLVTVSS[SEQ ID NO: 475] | |
|  | EVQLVESGGGLVQPGGSLRLSCAASGFTFGGYWMSWVRQAPGKCLE WVANINQDGSEEYYVDSVKGRFTISRDNAKNSLYLQMNSLRAEDTA VYYCAREANYYGNVGDDYWGQGTLVTVSSGGGGSGGGGSGGG GSGGGGSDIQMTQSPSSLSASVGDRVTITC<u>RASQSIYNYLN</u>WYQQK PGKAPKLLIY<u>AASNLHS</u>GVPSRFSGSGSGTDFTLTISSLQPEDFAT YYC<u>QQAFHVPIT</u>FGCGTKVEIK[SEQ ID NO: 476] | |
| Exemplary nucleotide sequence of Ab25 scFv | GACATCCAGATGACCCAGAGCCCCAGCAGCCTGAGCGCCAGCGT GGGCGACAGGGTGACCATCACCTGCAGGGCCAGCCAGAGCATCT ACAACTACCTGAACTGGTACCAGCAGAAGCCCGGCAAGGCCCCC AAGCTGCTGATCTACGCCGCCAGCAACCTGCACAGCGGCGTGCC CAGCAGGTTCAGCGGCAGCGGCAGCGGCACCGACTTCACCCTGA CCATCAGCAGCCTGCAGCCCGAGGACTCGCCACCTACTACTGCC AGCAGGCCTTCCACGTGCCCATCACCTTCGGCTGCGGCACCAAG GTGGAGATCAAGGGCGGCGGCGGCAGCGGCGGCGGCGGCAGCGG CGGCGGCGGCAGCGGCGGCGGCGGCAGCGAGGTGCAGCTGGTGG AGAGCGGCGGCGGCCTGGTGCAGCCCGGCGGCAGCCTGAGGCTG AGCTGCGCCGCCAGCGGCTTCACGTCGGCGGCTACTGGATGAGC TGGGTGAGGCAGGCCCCCGGCAAGTGCCTGGAGTGGGTGGCCAA CATCAACCAGGACGGCAGCGAGGAGTACTACGTGGACAGCGTGA AGGGCAGGTTCACCATCAGCAGGGACAACGCCAAGAACAGCCTG TACCTGCAGATGAACAGCCTGAGGGCCGAGGACACCGCCGTGTA CTACTGCGCCAGGGAGGCCAACTACTACGGCAACGTGGGCGACG ACTACTGGGGCCAGGGCACCCTGGTGACCGTGAGCAGC[SEQ ID NO: 517] | |
|  | GAGGTGCAGCTGGTGGAGAGCGGCGGCGGCCTGGTGCAGCCCGG CGGCAGCCTGAGGCTGAGCTGCGCCGCCAGCGGCTTCACCTTCG GCGGCTACTGGATGAGCTGGGTGAGGCAGGCCCCCGGCAAGTGC CTGGAGTGGGTGGCCAACATCAACCAGGACGGCAGCGAGGAGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGAGGCCAACTACTA CGGCAACGTGGGCGACGACTACTGGGGCCAGGGCACCCTGGTGA CCGTGAGCAGCGGCGGCGGCGGCAGCGGCGGCGGCGGCAGCGGC GGCGGCGGCAGCGGCGGCGGCGGCAGCGACATCCAGATGACCCA GAGCCCCAGCAGCCTGAGCGCCAGCGTGGGCGACAGGGTGACCA TCACCTGCAGGGCCAGCCAGAGCATCTACAACTACCTGAACTGG TACCAGCAGAAGCCCGGCAAGGCCCCCAAGCTGCTGATCTACGC CGCCAGCAACCTGCACAGCGGCGTGCCCAGCAGGTTCAGCGGCA GCGGCAGCGGCACCGACTTCACCCTGACCATCAGCAGCCTGCAG CCCGAGGACTTCGCCACCTACTACTGCCAGCAGGCCTTCCACGT GCCCATCACCTTCGGCTGCGGCACCAAGGTGGAGATCAAG[SEQ ID NO: 518] | |

TABLE 1-continued

| | VH | VL |
|---|---|---|
| ADI-11826 [Ab26] | EVQLVESGGGLVQPGGSLRLSC AASGFTFPGYWMSWVRQAPGKG LEWVANINQDGSEVYYVDSVKG RFTISRDNAKNSLYLQMNSLRA EDTAVYYCAREANYYGNVGDDY WGQGTLVTVSS[SEQ ID NO: 296] | DIQMTQSPSSLSASVGDRVTITCR ASQSIYNYLNWYQQKPGKAPKLLI YAASSTQSGVPSRFSGSGSGTDFT LTISSLQPEDFATYYCQQAFHVPI TFGGGTKVEIK[SEQ ID NO: 297] |
| | CDR1: GYWMS[SEQ ID NO: 394] or FTFPGYWMS[SEQ ID NO: 558] (non-Kabat) | CDR1: RASQSIYNYLN[SEQ ID NO: 397] |
| | CDR2: NINQDGSEVYYVDSVK G[SEQ ID NO: 395] | CDR2: AASSTQS[SEQ ID NO: 398] |
| | CDR3: EANYYGNVGDDY[SEQ ID NO: 396] or AREANYY GNVGDDY[SEQ ID NO: 559](non-Kabat) | CDR3: QQAFHVPIT[SEQ ID NO: 399] |
| scFv of Ab26 | DIQMTQSPSSLSASVGDRVTITCRASQSIYNYLNWYQQKPGKAPKL LIYAASSTQSGVPSRFSGSGSGTDFTLTISSLQPEDFATYYCQQAF HVPITFGCGTKVEIKGGGGSGGGGSGGGGSGGGGSEVQLVESGGGL VQPGGSLRLSCAASGFTFPGYWMSWVRQAPGKCLEWVANINQDGSE VYYVDSVKGRFTISRDNAKNSLYLQMNSLRAEDTAVYYCAREANYY GNVGDDYWGQGTLVTVSS[SEQ ID NO: 477] | |
| | EVQLVESGGGLVQPGGSLRLSCAASGFTFPGYWMSWVRQAPGKCLE WVANINQDGSEVYYVDSVKGRFTISRDNAKNSLYLQMNSLRAEDTA VYYCAREANYYGNVGDDYWGQGTLVTVSSGGGGSGGGGSGGGG SGGGGSDIQMTQSPSSLSASVGDRVTITCRASQSIYNYLNWYQQKP GKAPKLLIYAASSTQSGVPSRFSGSGSGTDFTLTISSLQPEDFATY YCQQAFHVPITFGCGTKVEIK[SEQ ID NO: 478] | |
| Exemplary nucleotide sequence of Ab26 scFv | GACATCCAGATGACCCAGAGCCCCAGCAGCCTGAGCGCCAGCGT GGGCGACAGGGTGACCATCACCTGCAGGGCCAGCCAGAGCATCT ACAACTACCTGAACTGGTACCAGCAGAAGCCCGGCAAGGCCCCC AAGCTGCTGATCTACGCCGCCAGCAGCACCCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGCCTTCCACGTGCCCATCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCGAGGTGCAGCTGGTG GAGAGCGGCGGCGGCCTGGTGCAGCCCGGCGGCAGCCTGAGGCT GAGCTGCGCCGCCAGCGGCTTCACCTTCCCCGGCTACTGGATGA GCTGGGTGAGGCAGGCCCCCGGCAAGTGCCTGGAGTGGGTGGCC AACATCAACCAGGACGGCAGCGAGGTGTACTACGTGGACAGCGT GAAGGGCAGGTTCACCATCAGCAGGGACAACGCCAAGAACAGCC TGTACCTGCAGATGAACAGCCTGAGGGCCGAGGACACCGCCGTG TACTACTGCGCCAGGGAGGCCAACTACTACGGCAACGTGGGCGA CGACTACTGGGGCCAGGGCACCCTGGTGACCGTGAGCAGC[SEQ ID NO: 519] | |
| | GAGGTGCAGCTGGTGGAGAGCGGCGGCGGCCTGGTGCAGCCCGG CGGCAGCCTGAGGCTGAGCTGCGCCGCCAGCGGCTTCACCTTCC CCGGCTACTGGATGAGCTGGGTGAGGCAGGCCCCCGGCAAGTGC CTGGAGTGGGTGGCCAACATCAACCAGGACGGCAGCGAGGTGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGAGGCCAACTACTA CGGCAACGTGGGCGACGACTACTGGGGCCAGGGCACCCTGGTGA CCGTGAGCAGCGGCGGCGGCGGCAGCGGCGGCGGCGGCAGCGGC GGCGGCGGCAGCGGCGGCGGCGGCAGCGACATCCAGATGACCCA GAGCCCCAGCAGCCTGAGCGCCAGCGTGGGCGACAGGGTGACCA TCACCTGCAGGGCCAGCCAGAGCATCTACAACTACCTGAACTGG TACCAGCAGAAGCCCGGCAAGGCCCCCAAGCTGCTGATCTACGC CGCCAGCAGCACCCAGAGCGGCGTGCCCAGCAGGTTCAGCGGCA GCGGCAGCGGCACCGACTTCACCCTGACCATCAGCAGCCTGCAG CCCGAGGACTTCGCCACCTACTACTGCCAGCAGGCCTTCCACGT GCCCATCACCTTCGGCTGCGGCACCAAGGTGGAGATCAAG[SEQ ID NO: 520] | |

TABLE 1-continued

| | VH | VL |
|---|---|---|
| ADI-11828 [Ab27] | EVQLVESGGGLVQPGGSLRLSC AASGFTFSSYWMSWVRQAPGKG LEWVANINQDGSEVYYVDSVKG RFTISRDNAKNSLYLQMNSLRA EDTAVYYCARDVGPGIAYQGHF DYWGQGTLVTVSS[SEQ ID NO: 298]<br><br>CDR1: SYWMS[SEQ ID NO: 400] or FTFSSYWMS[SEQ ID NO: 560](non-Kabat)<br><br>CDR2: NINQDGSEVYYVDSVKG[SEQ ID NO: 401]<br><br>CDR3: DVGPGIAYQGHFDY [SEQ ID NO: 402] or ARDVGPGIAYQGHFDY[SEQ ID NO: 561](non-Kabat) | DIQMTQSPSSLSASVGDRVTITCR ASQSIYYYLNWYQQKPGKAPKLLI YAASSRQSGVPSRFSGSGSGTDFT LTISSLQPEDFATYYCQQVYDTPL TFGGGTKVEIK[SEQ ID NO: 299]<br><br>CDR1: RASQSIYYYLN[SEQ ID NO: 403]<br><br>CDR2: AASSRQS[SEQ ID NO: 404]<br><br>CDR3: QQVYDTPLT[SEQ ID NO: 405] |
| scFv of Ab27 | DIQMTQSPSSLSASVGDRVTITC<u>RASQSIYYYLN</u>WYQQKPGKAPKL LIYA<u>ASSRQS</u>GVPSRFSGSGSGTDFTLTISSLQPEDFATYYC<u>QQVY DTPLT</u>FG<u>C</u>GTKVEIKGGGGSGGGGSGGGGSGGGGSEVQLVESGGGL VQPGGSLRLSCAASGFTFS<u>SYWMS</u>WVRQAPGK<u>C</u>LEWVA<u>NINQDGSE VYYVDSVKG</u>RFTISRDNA<u>K</u>NSLYLQMNSLRAEDTAVYYCARD<u>VGPG IAYQGHFDY</u>WGQGTLVTVSS[SEQ ID NO: 479]<br><br>EVQLVESGGGLVQPGGSLRLSCAASGFTFS<u>SYWMS</u>WVRQAPGK<u>C</u>LE WVA<u>NINQDGSEVYYVDSVKG</u>RFTISRDNA<u>K</u>NSLYLQMNSLRAEDTA VYYCARD<u>VGPGIAYQGHFDY</u>WGQGTLVTVSSGGGGSGGGGSGGG GSGGGGSDIQMTQSPSSLSASVGDRVTITC<u>RASQSIYYYLN</u>WYQQK PGKAPKLLIYA<u>ASSRQS</u>GVPSRFSGSGSGTDFTLTISSLQPEDFAT YYC<u>QQVYDTPLT</u>FGCGTKVEIK[SEQ ID NO: 480] | |
| Exemplary nucleotide sequence of Ab27 scFv | GACATCCAGATGACCCAGAGCCCCAGCAGCCTGAGCGCCAGCGT GGGCGACAGGGTGACCATCACCTGCAGGGCCAGCCAGAGCATCT ACTACTACCTGAACTGGTACCAGCAGAAGCCCGGCAAGGCCCCC AAGCTGCTGATCTACGCCGCCAGCAGCAGGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGTGTACGACACCCCCCTGACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCGAGGTGCAGCTGGTG GAGAGCGGCGGCGGCCTGGTGCAGCCCGGCGGCAGCCTGAGGCT GAGCTGCGCCGCCAGCGGCTTCACCTTCAGCAGCTACTGGATGA GCTGGGTGAGGCAGGCCCCCGGCAAGTGCCTGGAGTGGGTGGCC AACATCAACCAGGACGGCAGCGAGGTGTACTACGTGGACAGCGT GAAGGGCAGGTTCACCATCAGCAGGGACAACGCCAAGAACAGCC TGTACCTGCAGATGAACAGCCTGAGGGCCGAGGACACCGCCGTG TACTACTGCGCCAGGGACGTGGGCCCCGGCATCGCCTACCAGGG CCACTTCGACTAGGGGGCCAGGGCACCCTGGTGACCGTGAGCAG C[SEQ ID NO: 521]<br><br>GAGGTGCAGCTGGTGGAGAGCGGCGGCGGCCTGGTGCAGCCCGG CGGCAGCCTGAGGCTGAGCTGCGCCGCCAGCGGCTTCACCTTCA GCAGCTACTGGATGAGCTGGGTGAGGCAGGCCCCCGGCAAGTGC CTGGAGTGGGTGGCCAACATCAACCAGGACGGCAGCGAGGTGTA CTACGTGGACAGCGTGAAGGGCAGGTTCACCATCAGCAGGGACA ACGCCAAGAACAGCCTGTACCTGCAGATGAACAGCCTGAGGGCC GAGGACACCGCCGTGTACTACTGCGCCAGGGACGTGGGCCCCGG CATCGCCTACCAGGGCCACTTCGACTACTGGGGCCAGGGCACCC TGGTGACCGTGAGCAGCGGCGGCGGCGGCAGCGGCGGCGGCGGC AGCGGCGGCGGCGGCAGCGGCGGCGGCGGCAGCGACATCCAGAT GACCCAGAGCCCCAGCAGCCTGAGCGCCAGCGTGGGCGACAGGG TGACCATCACCTGCAGGGCCAGCCAGAGCATCTACTACTACCTG AACTGGTACCAGCAGAAGCCCGGCAAGGCCCCCAAGCTGCTGAT CTACGCCGCCAGCAGCAGGCAGAGCGGCGTGCCCAGCAGGTTCA GCGGCAGCGGCAGCGGCACCGACTTCACCCTGACCATCAGCAGC CTGCAGCCCGAGGACTTCGCCACCTACTACTGCCAGCAGGTGTA CGACACCCCCCTGACCTTCGGCTGCGGCACCAAGGTGGAGATCA AG[SEQ ID NO: 522] | |

TABLE 1-continued

| | VH | VL |
|---|---|---|
| ADI-11839 [Ab28] | QVQLVQSGAEVKKPGASVKVSC KASGYTFSNYYMHWVRQAPGQG LEWMGWINPFSGGTRYAQKFQG RVTMTRDTSTSTVYMELSSLRS EDTAVYYCARDVGSSAYYYMDV WGKGTTVTVSS[SEQ ID NO: 300] | DIQMTQSPSSVSASVGDRVTITCE ASKGISSWLAWYQQKPGKAPKLLI YAASDLQSGVPSRFSGSGSGTDFT LTISSLQPEDFATYYCQQAFLFPP TFGGGTKVEIK[SEQ ID NO: 301] |
| | CDR1: NYYMH[SEQ ID NO: 406] or YTFSNYYMH[SEQ ID NO: 562](non-Kabat) | CDR1: EASKGISSWLA[SEQ ID NO: 409] |
| | CDR2: WINPFSGGTRYAQKFQ G[SEQ ID NO: 407] | CDR2: AASDLQS[SEQ ID NO: 410] |
| | CDR3: DVGSSAYYYMDV[SEQ ID NO: 408] or ARDVGSS AYYYMDV[SEQ ID NO: 563](non-Kabat) | CDR3: QQAFLFPPT[SEQ ID NO: 411] |
| scFv of Ab28 | DIQMTQSPSSVSASVGDRVTITCEASKGISSWLAWYQQKPGKAPKL LIYAASDLQSGVPSRFSGSGSGTDFTLTISSLQPEDFATYYCQQAF LFPPTFGCGTKVEIKGGGGSGGGGSGGGGSGGGGSQVQLVQSGAEV KKPGASVKVSCKASGYTFSNYYMHWVRQAPGQCLEWMGWINPFSGG TRYAQKFQGRVTMTRDTSTSTVYMELSSLRSEDTAVYYCARDVGSS AYYYMDVWGKGTTVTVSS[SEQ ID NO: 481] | |
| | QVQLVQSGAEVKKPGASVKVSCKASGYTFSNYYMHWVRQAPGQCLE WMGWINPFSGGTRYAQKFQGRVTMTRDTSTSTVYMELSSLRSEDTA VYYCARDVGSSAYYYMDVWGKGTTVTVSSGGGGSGGGGSGGG GSGGGGSDIQMTQSPSSVSASVGDRVTITCEASKGISSWLAWYQQK PGKAPKLLIYAASDLQSGVPSRFSGSGSGTDFTLTISSLQPEDFAT YYCQQAFLFPPTFGCGTKVEIK[SEQ ID NO: 482] | |
| Exemplary nucleotide sequence of Ab28 scFv | GACATCCAGATGACCCAGAGCCCCAGCAGCGTGAGCGCCAGCGT GGGCGACAGGGTGACCATCACCTGCGAGGCCAGCAAGGGCATCA GCAGCTGGCTGGCCTGGTACCAGCAGAAGCCCGGCAAGGCCCCC AAGCTGCTGATCTACGCCGCCAGCGACCTGCAGAGCGGCGTGCC CAGCAGGTTCAGCGGCAGCGGCAGCGGCACCGACTTCACCCTGA CCATCAGCAGCCTGCAGCCCGAGGACTTCGCCACCTACTACTGC CAGCAGGCCTTCCTGTTCCCCCCCACCTTCGGCTGCGGCACCAA GGTGGAGATCAAGGGCGGCGGCGGCAGCGGCGGCGGCGGCAGCG GCGGCGGCGGCAGCGGCGGCGGCGGCAGCCAGGTGCAGCTGGTG CAGAGCGGCGCCGAGGTGAAGAAGCCCGGCGCCAGCGTGAAGGT GAGCTGCAAGGCCAGCGGCTACACCTTCAGCAACTACTACATGC ACTGGGTGAGGCAGGCCCCCGGCCAGTGCCTGGAGTGGATGGGC TGGATCAACCCCTTCAGCGGCGGCACCAGGTACGCCCAGAAGTT CCAGGGCAGGGTGACCATGACCAGGGACACCAGCACCAGCACCG TGTACATGGAGCTGAGCAGCCTGAGGAGCGAGGACACCGCCGTG TACTACTGCGCCAGGGACGTGGGCAaAGCGCCTACTACTACATG GACGTGTGGGGCAAGGGCACCACCGTGACCGTGAGCAGC[SEQ ID NO: 523] | |
| | CAGGTGCAGCTGGTGCAGAGCGGCGCCGAGGTGAAGAAGCCCGG CGCCAGCGTGAAGGTGAGCTGCAAGGCCAGCGGCTACACCTTCA GCAACTACTACATGCACTGGGTGAGGCAGGCCCCCGGCCAGTGC CTGGAGTGGATGGGCTGGATCAACCCCATCAGCGGCGGCACCAG GTACGCCCAGAAGTTCCAGGGCAGGGTGACCATGACCAGGGACA CCAGCACCAGCACCGTGTACATGGAGCTGAGCAGCCTGAGGAGC GAGGACACCGCCGTGTACTACTGCGCCAGGGACGTGGGCAGCAG CGCCTACTACTACATGGACGTGTGGGGCAAGGGCACCACCGTGA CCGTGAGCAGCGGCGGCGGCGGCAGCGGCGGCGGCGGCAGCGGC GGCGGCGGCAGCGGCGGCGGCGGCAGCGACATCCAGATGACCCA GAGCCCCAGCAGCGTGAGCGCCAGCGTGGGCGACAGGGTGACCA TCACCTGCGAGGCCAGCAAGGGCATCAGCAGCTGGCTGGCCTGG TACCAGCAGAAGCCCGGCAAGGCCCCCAAGCTGCTGATCTACGC CGCCAGCGACCTGCAGAGCGGCGTGCCCAGCAGGTTCAGCGGCA GCGGCAGCGGCACCGACTTCACCCTGACCATCAGCAGCCTGCAG CCCGAGGACTTCGCCACCTACTACTGCCAGCAGGCCTTCCTGTT CCCCCCCACCTTCGGCTGCGGCACCAAGGTGGAGATCAAG[SEQ ID NO: 524] | |

TABLE 1-continued

| | VH | VL |
|---|---|---|
| ADI-10152 [Ab29] | EVQLVQSGAEVKKPGESLKISC KGSGYSFTSYWIGWVRQMPGKG LEWMGSIYPGDSDTRYSPSFQG QVTISADKSISTAYLQWSSLKA SDTAMYYCARELAYGDYKGGVD YWGQGTLVTVSS[SEQ ID NO: 302]<br><br>CDR1: SYWIG[SEQ ID NO: 412] or YSFTSYWIG[SEQ ID NO: 564](non-Kabat)<br><br>CDR2: SIYPGDSDTRYSPSFQ G[SEQ ID NO: 413]<br><br>CDR3: ELAYGDYKGGVDY [SEQ ID NO: 414] or ARELAYGDYKGGVDY[SEQ ID NO: 565](non-Kabat) | EIVLTQSPGTLSLSPGERATLSCR ASQSVSSSFLAWYQQKPGQAPRLL IYGASSRATGIPDRFSGSGSGTDF TLTISRLEPEDFAVYYCQQLDSPP PTFGGGTKVEIK[SEQ ID NO: 303]<br><br>CDR1: RASQSVSSSFLA[SEQ ID NO: 415]<br><br>CDR2: GASSRAT[SEQ ID NO: 416]<br><br>CDR3: QQLDSPPPT[SEQ ID NO: 417] |
| scFv of Ab29 | EIVLTQSPGTLSLSPGERATLSCRASQSVSSSFLAWYQQKPGQAPR LLIYGASSRATGIPDRFSGSGSGTDFTLTISRLEPEDFAVYYCQQL DSPPPTFGCGTKVEIGGGGSGGGGSGGGGSGGGGSEVQLVQSGAE VKKPGESLKISCKGSGYSFTSYWIGWVRQMPGKCLEWMGSIYPGDS DTRYSPSFQGQVTISADKSISTAYLQWSSLKASDTAMYYCARELAY GDYKGGVDYWGQGTLVTVSS[SEQ ID NO: 483]<br><br>EVQLVQSGAEVKKPGESLKISCKGSGYSFTSYWIGWVRQMPGKCLE WMGSIYPGDSDTRYSPSFQGQVTISADKSISTAYLQWSSLKASDTA MYYCARELAYGDYKGGVDYWGQGTLVTVSSGGGGSGGGGSGGG SGGGGSEIVLTQSPGTLSLSPGERATLSCRASQSVSSSFLAWYQQK PGQAPRLLIYGASSRATGIPDRFSGSGSGTDFTLTISRLEPEDFAV YYCQQLDSPPPTFGCGTKVEIK[SEQ ID NO: 484] | |
| Exemplary nucleotide sequence of Ab29 scFv | GAGATCGTGCTGACCCAGAGCCCCGGCACCCTGAGCCTGAGCCC CGGCGAGAGGGCCACCCTGAGCTGCAGGGCCAGCCAGAGCGTGA GCAGCAGCTTCCTGGCCTGGTACCAGCAGAAGCCCGGCCAGGCC CCCAGGCTGCTGATCTACGGCGCCAGCAGCAGGGCCACCGGCAT CCCCGACAGGTTCAGCGGCAGCGGCAGCGGCACCGAGTCACCCT GACCATCAGCAGGCTGGAGCCCGAGGACTTCGCCGTGTACTACT GCCAGCAGCTGGACAGCCCCCCCCCCACCTTCGGCTGCGGCACC AAGGTGGAGATCAAGGGCGGCGGCGGCAGCGGCGGCGGCGGCAG CGGCGGCGGCGGCAGCGGCGGCGGCGGCAGCGAGGTGCAGCTGG TGCAGAGCGGCGCCGAGGTGAAGAAGCCCGGCGAGAGCCTGAAG ATCAGCTGCAAGGGCAGCGGCTACAGCTTCACCAGCTACTGGAT CGGCTGGGTGAGGCAGATGCCCGGCAAGTGCCTGGAGTGGATGG GCAGCATCTACCCCGGCGACAGCGACACCAGGTACAGCCCCAGC TTCCAGGGCCAGGTGACCATCAGCGCCGACAAGAGCATCAGCAC CGCCTACCTGCAGTGGAGCAGCCTGAAGGCCAGCGACACCGCCA TGTACTACTGCGCCAGGGAGCTGGCCTACGGCGACTACAAGGGC GGCGTGGACTACTGGGGCCAGGGCACCCTGGTTGACCGTGAGCA GC[SEQ ID NO: 525]<br><br>GAGGTGCAGCTGGTGCAGAGCGGCGCCGAGGTGAAGAAGCCCGG CGAGAGCCTGAAGATCAGCTGCAAGGGCAGCGGCTACAGCTTCA CCAGCTACTGGATCGGCTGGGTGAGGCAGATGCCCGGCAAGTGC CTGGAGTGGATGGGCAGCATCTACCCCGGCGACAGCGACACCAG GTACAGCCCCAGCTTCCAGGGCCAGGTGACCATCAGCGCCGACA AGAGCATCAGCACCGCCTACCTGCAGTGGAGCAGCCTGAAGGCC AGCGACACCGCCATGTACTACTGCGCCAGGGAGCTGGCCTACGG CGACTACAAGGGCGGCGTGGACTACTGGGGCCAGGGCACCGGGT GACCGTGAGCAGCGGCGGCGGCAGCGGCGGCGGCGGCAGCG GCGGCGGCGGCAGCGGCGGCGGCGGCAGCGAGATCGTGCTGACC CAGAGCCCCGGCACCCTGAGCCTGAGCCCCGGCGAGAGGGCCAC CCTGAGCTGCAGGGCCAGCCAGAGCGTGAGCAGCAGCTTCGGGC CTGGTACCAGCAGAAGCCCGGCCAGGCCCCCAGGCTGCTGATCT ACGGCGCCAGCAGCAGGGCCACCGGCATCCCCGACAGGTTCAGC GGCAGCGGCAGCGGCACCGACTTCACCCTGACCATCAGCAGGCT GGAGCCCGAGGACTTCGCCGTGTACTACTGCCAGCAGCTGGACA GCCCCCCCCCCACCTTCGGCTGCGGCACCAAGGTGGAGATCAAG [SEQ ID NO: 526] | |

TABLE 1-continued

| | VH | VL |
|---|---|---|
| Clone 280-31-01 (mut) of WO 2012045752 | QVQLVQSGAEVKKPGSSVKVSC KASGGTFSDYAISWVRQAPGQG LEWMGRIIPILGVADYAQKFQG RVTITADKSTRTAYMELSSLRS EDTAVYYCARNWADAFDIWGQG TMVTVSS[SEQ ID NO: 418]<br><br>CDR1: DYAIS[SEQ ID NO: 422]<br><br>CDR2: RIIPILGVADYAQKFQG [SEQ ID NO: 423]<br><br>CDR3: NWADAFDI[SEQ ID NO: 424] | DIQLTQSPSSLSASVGDRVTITCR ASQGISSVLAWYQQKPGKAPKLLI YDASSLESGVPSRFSGSGSGTDFT LTISSLQPEDFATYYCQQFDSSIT FGQGTKLEIK[SEQ ID NO: 419]<br><br>CDR1: RASQGISSVLA[SEQ ID NO: 425]<br><br>CDR2: DASSLES[SEQ ID NO: 426]<br><br>CDR3: QQFDSSIT[SEQ ID NO: 427] |
| scFv of clone 280-31-01 (mut) of WO 2012045752 | DIQLTQSPSSLSASVGDRVTITCRASQGISSVLAWYQQKPGKAPKL LIYDASSLESGVPSRFSGSGSGTDFTLTISSLQPEDFATYYCQQFD SSITFGCGTKLEIGGGGSGGGGSGGGGSGGGGSQVQLVQSGAEVK KPGSSVKVSCKASGGTFSDYAISWVRQAPGQCLEWMGRIIPILGVA DYAQKFQGRVTITADKSTRTAYMELSSLRSEDTAVYYCARNWADAF DIWGQGTMVTVSS[SEQ ID NO: 485]<br><br>QVQLVQSGAEVKKPGSSVKVSCKASGGTFSDYAISWVRQAPGQCLE WMGRIIPILGVADYAQKFQGRVTITADKSTRTAYMELSSLRSEDTA VYYCARNWADAFDIWGQGTMVTVSSGGGGSGGGGSGGGGSGGGG SDIQLTQSPSSLSASVGDRVTITCRASQGISSVLAWYQQKPGKAPK LLIYDASSLESGVPSRFSGSGSGTDFTLTISSLQPEDFATYYCQQF DSSITFGCGTKLEIK[SEQ ID NO: 486] | |
| lintuzumab | QVQLVQSGAEVKKPGSSVKVSC KASGYTFTDYNMHWVRQAPGQG LEWIGYIYPYNGGTGYNQKFKS KATITADESTNTAYMELSSLRS EDTAVYYCARGRPAMDYWGQGT LVTVSS[SEQ ID NO: 420]<br><br>CDR1: DYNMH[SEQ ID NO: 428]<br><br>CDR2: YIYPYNGGTGYNQKFK S[SEQ ID NO: 429]<br><br>CDR3: GRPAMDY[SEQ ID NO: 430] | DIQMTQSPSSLSASVGDRVTITCR ASESVDNYGISFMNWFQQKPGKAP KLLIYAASNQGSGVPSRFSGSGSG TDFTLTISSLQPDDFATYYCQQSK EVPWTFGQGTKVEIK[SEQ ID NO: 421]<br><br>CDR1: RASESVDNYGISFMN [SEQ ID NO: 431]<br><br>CDR2: AASNQGS[SEQ ID NO: 432]<br><br>CDR3: QQSKEVPWT[SEQ ID NO: 433] |
| scFv of lintuzumab | DIQMTQSPSSLSASVGDRVTITCRASESVDNYGISFMNWFQQKPGK APKLLIYAASNQGSGVPSRFSGSGSGTDFTLTISSLQPDDFATYYC QQSKEVPWTFGCGTKVEIKGGGGSGGGGSGGGGSGGGGSQVQLVQS GAEVKKPGSSVKVSCKASGYTFTDYNMHWVRQAPGQCLEWIGYIYP YNGGTGYNQKFKSKATITADESTNTAYMELSSLRSEDTAVYYCARG RPAMDWYGQGTLVTVSS[SEQ ID NO: 487]<br><br>QVQLVQSGAEVKKPGSSVKVSCKASGYTFTDYNMHWVRQAPGQCLE WIGYIYPYNGGTGYNQKFKSKATITADESTNTAYMELSSLRSEDTA VYYCARGRPAMDWGQGTLVTVSSGGGGSGGGGSGGGGSGGGG SDIQMTQSPSSLSASVGDRVTITCRASESVDNYGISFMNWFQQKPG KAPKLLIYAASNQGSGVPSRFSGSGSGTDFTLTISSLQPDDFATYY CQQSKEVPWTFGCGTKVEIK[SEQ ID NO: 488] | |

An Antigen Binding Site that Binds an Epitope on an Extracellular Domain of Human CD33 and/or Cynomolgus/Rhesus (Cyno) CD33

In one aspect, the invention provides an antigen binding site including a heavy chain variable domain that binds an epitope on an extracellular domain of human CD33 and/or Cynomolgus/Rhesus (cyno) CD33.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVQPGGSLRLSCAASGFTFSSYG-MSWVRQAPGKGLEWVANIKQDGS EKYYVDS-VKGRFTISRDNAKNSLYLQMNSLRAEDTAVYY-CAREGGPYYDSSGYFVY YGMDVWGQGTTVTVSS [SEQ ID NO:1]. In some embodiments, the antibody heavy chain variable domain is at least 95% identical to SEQ ID NO:1. In some embodiments, the heavy chain variable domain includes amino acid sequences FTFSSYGMS [SEQ ID NO:21] as the first complementarity-determining region 1 ("CDR1"), NIKQDGSEKYYVDSVKG [SEQ ID NO:22] as the second CDR ("CDR2"), and AREGGPYYDSSGYFVYYGMDV [SEQ ID NO:23] as the third CDR ("CDR3") of SEQ ID NO:1. In some embodiments, the heavy chain variable domain includes amino acid sequences SYGMS [SEQ ID NO:434] as the first complementarity-determining region 1 ("CDR1"), NIKQDGSEKYYVDSVKG [SEQ ID NO:22] as the second CDR ("CDR2"), and EGGPYYDSSGYFVYYGMDV [SEQ ID NO:435] as the third CDR ("CDR3") of SEQ ID NO:1. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:1 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:1 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASQSISSWLAWYQQKPGKAPKLLIYDASSLESGV PSRFSGSGSGTEFTLTISSLQPDDFATYYCQQYESFPTFGGGTKVEIK [SEQ ID NO:2]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:1 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:2, which includes amino acid sequences RASQSISSWLA [SEQ ID NO:24] as CDR1, DASSLES [SEQ ID NO:25] as CDR2, and QQYESFPT [SEQ ID NO:26] as CDR3 of SEQ ID NO:2.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVQPGGSLRLSCAASGFTFSSYWMSWVRQAPGKGLEWVANIKQDG SEKYYVDSVKGRFTISRDNAKNSLYLQMNSLRAEDTAVYYCARPLNAGELDVWGQ GTMVTVSS [SEQ ID NO:3]. In some embodiments, the antibody heavy chain variable domain is at least 95% identical to SEQ ID NO:3. In some embodiments, the heavy chain variable domain incorporates amino acid sequences FTFSSYWMS [SEQ ID NO:27] as CDR1, NIKQDGSEKYYVDSVKG [SEQ ID NO:28] as CDR2, and ARPLNAGELDV [SEQ ID NO:29] as CDR3 of SEQ ID NO:3. In some embodiments, the heavy chain variable domain incorporates amino acid sequences SYWMS [SEQ ID NO:181] as CDR1, NIKQDGSEKYYVDSVKG [SEQ ID NO:28] as CDR2, and PLNAGELDV [SEQ ID NO:436] as CDR3 of SEQ ID NO:3. In certain embodiments, the antibody heavy chain variable domain, which includes an amino acid sequence at least 90% (e.g., at least 91%, 92%, 93%, 94%, 95%, 96%, 97%, 98%, 99%, or 100%) identical to the amino acid sequence of SEQ ID NO:3, is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASQSISSWLAWYQQKPGKAPKLLIYEASSLESGV PSRFSGSGSGTEFTLTISSLQPDDFATYYCQQLESYPLTFGGGTKVEIK [SEQ ID NO:4]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:4, which includes amino acid sequences RASQSISSWLA [SEQ ID NO:30] as CDR1, EASSLES [SEQ ID NO:31] as CDR2, and QQLESYPLT [SEQ ID NO:32] as CDR3 of SEQ ID NO:4.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLLESGGGLVQPGGSLRLSCAASGFTFSKYTMSWVRQAPGKGLEWVSAIVGSGE STYFADSVKGRFTISRDNSKNTLYLQMNSLRAEDTAVYYCAREGGPYYDSSGYFVY YGMDVWGQGTTVTVSS [SEQ ID NO:5]. In some embodiments, the antibody heavy chain variable domain is at least 95% identical to SEQ ID NO:5. In some embodiments, the heavy chain variable domain incorporates amino acid sequences FTFSKYTMS [SEQ ID NO:33] as CDR1, AIVGSGESTYFADSVKG [SEQ ID NO:34] as CDR2, and AREGGPYYDSSGYFVYYGMDV [SEQ ID NO:35] as CDR3 of SEQ ID NO:5. In some embodiments, the heavy chain variable domain incorporates amino acid sequences KYTMS [SEQ ID NO:183] as CDR1, AIVGSGESTYFADSVKG [SEQ ID NO:34] as CDR2, and EGGPYYDSSGYFVYYGMDV [SEQ ID NO:184] as CDR3 of SEQ ID NO:5. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:5 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:5 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASQSISSWLAWYQQKPGKAPKLLIYKASSLESGV PSRFSGSGSGTEFTLTISSLQPDDFATYYCQQYDDLPTFGGGTKVEIK [SEQ ID NO:6]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:5 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:6, which includes amino acid sequences RASQSISSWLA [SEQ ID NO:36] as CDR1, KASSLES [SEQ ID NO:37] or KASSLE [SEQ ID NO:185] as CDR2, and QQYDDLPT [SEQ ID NO:38] as CDR3 of SEQ ID NO:6.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of QVQLVQSGAEVKKPGASVKVSCK-ASGYTFSDYYMHWVRQAPGQGLEWMGMINPSWGSTSYAQKFQGRVTMTRDTSTSTVYMELSSL-RSEDTAVYYCAREAADGFVGERYF DLWGRGTLV-TVSS [SEQ ID NO:7]. In some embodiments, the antibody heavy chain variable domain is at least 95% identical to SEQ ID NO:7. In some embodiments, the heavy chain variable domain incorporates amino acid sequences YTFSDYYMH [SEQ ID NO:39] as CDR1, MINPSWGSTSYAQKFQG [SEQ ID NO:40] as CDR2, and AREAADGFVGERYFDL [SEQ ID NO:41] as CDR3 of SEQ ID NO:7. In some embodiments, the heavy chain variable domain incorporates amino acid sequences DYYMH [SEQ ID NO:437] as CDR1, AIVGSGESTYFADSVKG [SEQ ID NO:34] as CDR2, and EAADGFVGERYFDL [SEQ ID NO:438] as CDR3 of SEQ ID NO:7. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:7 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., at least 91%, 92%, 93%, 94%, 95%, 96%, 97%, 98%, 99%, or 100%) identical to the amino acid sequence DIVMTQSPLSLPVTPGEPASISCRSSQSLLY-SNGYNYLDWYLQKPGQSPQLLIYLGSN RASGVP-DRFSGSGSGTDFTLKISRVEAEDVGVYYCMQDVAL-PITFGGGTKVEIK [SEQ ID NO:8]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:8, which includes amino acid sequences RSSQSLLYSNGYNYLD [SEQ ID NO:42] as CDR1, LGSNRAS [SEQ ID NO:43] as CDR2, and MQDVALPIT [SEQ ID NO:44] as CDR3 of SEQ ID NO:8.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVQPGGSLRLSCAASGFTFGSYWMS-WVRQAPGKGLEWVATIKQDG SEKSYVDSVKGRF-TISRDNAKNSLYLQMNSLRAEDTAVYYCARPLNAG-ELDVWGQ GTMVTVSS [SEQ ID NO:9]. In some embodiments, the antibody heavy chain variable domain is at least 95% identical to SEQ ID NO:9. In some embodiments, the heavy chain variable domain incorporates amino acid sequences FTFGSYWMS [SEQ ID NO:45] as CDR1, TIKQDGSEKSYVDSVKG [SEQ ID NO:46] as CDR2, and ARPLNAGELDV [SEQ ID NO:47] as CDR3 of SEQ ID NO:9. In some embodiments, the heavy chain variable domain incorporates amino acid sequences SYWMS [SEQ ID NO:181] as CDR1, TIKQDGSEKSYVDSVKG [SEQ ID NO:46] as CDR2, and RPLNAGELDV [SEQ ID NO:182] as CDR3 of SEQ ID NO:9. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:9 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:9 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASQSISS-WLAWYQQKPGKAPKLLIYEASSLESGV PSRFSGSG-SGTEFTLTISSLQPDDFATYYCQQSQSYPPITFGGG-TKVEIK [SEQ ID NO:10]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:9 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:10, which includes amino acid sequences RASQSISSWLA [SEQ ID NO:48] as CDR1, EASSLES [SEQ ID NO:49] as CDR2, and QQSQSYPPIT [SEQ ID NO:50] as CDR3 of SEQ ID NO:10.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVQPGGSLRLSCAASGFTFPSYW-MSWVRQAPGKGLEWVATIKRDGS EKGYVDSVK-GRFTISRDNAKNSLYLQMNSLRAEDTAVYYCAR-PLNAGELDVWGQG TMVTVSS [SEQ ID NO:11]. In some embodiments, the antibody heavy chain variable domain is at least 95% identical to SEQ ID NO:11. In some embodiments, the heavy chain variable domain incorporates amino acid sequences FTFPSYWMS [SEQ ID NO:51] as CDR1, TIKRDGSEKGYVDSVKG [SEQ ID NO:52] as CDR2, and ARPLNAGELDV [SEQ ID NO:53] as CDR3 of SEQ ID NO:11. In some embodiments, the heavy chain variable domain incorporates amino acid sequences SYWMS [SEQ ID NO:181] as CDR1, TIKRDGSEKGYVDSVKG [SEQ ID NO:52] as CDR2, and PLNAGELDV [SEQ ID NO:439] as CDR3 of SEQ ID NO:11. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:11 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASQSISSWLAWYQQKPGKAPKLLIYEASSLESGV PSRFSGSGSGTEFTLTISSLQPDDFATYYCQQSQSYPPITFGGGTKVEIK [SEQ ID NO:12]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:12, which includes amino acid sequences RASQSISSWLA [SEQ ID NO:54] as CDR1, EASSLES [SEQ ID NO:55] as CDR2, and QQSQSYPPIT [SEQ ID NO:56] as CDR3 of SEQ ID NO:12.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of QVQLVQSGAEVKKPGASVKVSCKASGYTFGTYYMHWVRQAPGQGLEWMGIINPSRGSTVYAQKFQGRVTMTRDTSTSTVYMELSSLRSEDTAVYYCARGAGYDDEDMDV WGKGTTVTVSS [SEQ ID NO:13]. In some embodiments, the antibody heavy chain variable domain is at least 95% identical to SEQ ID NO:13. In some embodiments, the heavy chain variable domain incorporates amino acid sequences YTFGTYYMH [SEQ ID NO:57] as CDR1, IINPSRGSTVYAQKFQG [SEQ ID NO:58] as CDR2, and ARGAGYDDEDMDV [SEQ ID NO:59] as CDR3 of SEQ ID NO:13. In some embodiments, the heavy chain variable domain incorporates amino acid sequences TYYMH [SEQ ID NO:440] as CDR1, TIKRDGSEKGYVDSVKG [SEQ ID NO:52] as CDR2, and GAGYDDEDMDV [SEQ ID NO:441] as CDR3 of SEQ ID NO:13. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:13 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSSVSASVGDRVTITCRASQGIDSWLAWYQQKPGKAPKLLIYAASSLQSG VPSRFSGSGSGTDFTLTISSLQPEDFATYYCQQAHSYPLTFGGGTKVEIK [SEQ ID NO:14]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:14, which includes amino acid sequences RASQGIDSWLA [SEQ ID NO:60] as CDR1, AASSLQS [SEQ ID NO:61] as CDR2, and QQAHSYPLT [SEQ ID NO:62] as CDR3 of SEQ ID NO:14.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVKPGGSLRLSCAASGFTFSSYAMSWVRQAPGKGLEWVSSISSSSEG IYYADSVKGRFTISRDNAKNSLYLQMNSLRAEDTAVYYCAREGGPYYDSSGYFVYY GMDVWGQGTTVTVSS [SEQ ID NO:15]. In some embodiments, the antibody heavy chain variable domain is at least 95% identical to SEQ ID NO:15. In some embodiments, the heavy chain variable domain incorporates amino acid sequences FTFSSYAMS [SEQ ID NO:63] as CDR1, SISSSSEGIYYADSVKG [SEQ ID NO:64] as CDR2, and AREGGPYYDSSGYFVYYGMDV [SEQ ID NO:65] as CDR3 of SEQ ID NO:15. In some embodiments, the heavy chain variable domain incorporates amino acid sequences SYAMS [SEQ ID NO:442] as CDR1, SISSSSEGIYYADSVKG [SEQ ID NO:64] as CDR2, and EGGPYYDSSGYFVYYGMDV [SEQ ID NO:443] as CDR3 of SEQ ID NO:15. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:15 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSTLSASVGDRVTITCRASNSISSWLAWYQQKPGKAPKLLIYEASSTKSGV PSRFSGSGSGTEFTLTISSLQPDDFATYYCQQYDDLPTFGGGTKVEIK [SEQ ID NO:16]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:16, which includes amino acid sequences RASNSISSWLA [SEQ ID NO:66] as CDR1, EASSTKS [SEQ ID NO:67] as CDR2, and QQYDDLPT [SEQ ID NO:68] as CDR3 of SEQ ID NO:16.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of EVQLVESGGGLVQPGGSLRLSCAASGFTFSSYWMSWVRQAPGKGLEWVANINTDG SEVYYVDSVKGRFTISRDNAKNSLYLQMNSLRAEDTAVYYCARDVGPGIAYQGHFD YWGQGTLVTVSS [SEQ ID NO:17]. In some embodiments, the antibody heavy chain variable domain is at least 95% identical to SEQ ID NO:17. In some embodiments, the heavy chain variable domain incorporates amino acid sequences FTFSSYWMS [SEQ ID NO:69] as CDR1, NINTDGSEVYYVDSVKG [SEQ ID NO:70] as CDR2, and ARDVGPGIAYQGHFDY [SEQ ID NO:71] as CDR3 of SEQ ID NO:17. In some embodiments, the heavy chain variable domain incorporates amino acid sequences SYWMS [SEQ ID NO:181] as CDR1, NINTDGSEVYYVDSVKG [SEQ ID NO:70] as CDR2, and DVGPGIAYQGHFDY [SEQ ID NO:444] as CDR3 of SEQ ID NO:17. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:17 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:17 can be paired with an antibody light chain variable domain at least 90% (e.g., at least 91%, 92%, 93%, 94%, 95%, 96%, 97%, 98%, 99%, or 100%) identical to the amino acid sequence DIQMTQSPSSLSASVGDRVTITCRASQVIYSYLNW-YQQKPGKAPKLLIYAASSLKSGV PSRFSGSGSG-TDFTLTISSLQPEDFATYYCQQVYDTPLTFGGGTK-VEIK [SEQ ID NO:18]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:17 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:18, which includes amino acid sequences RASQVIYSYLN [SEQ ID NO:72] as CDR1, AASSLKS [SEQ ID NO:73] as CDR2, and QQVYDTPLT [SEQ ID NO:74] as CDR3 of SEQ ID NO:18.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of QLQLQESGPGLVKPSETLSLTCTVSGGSISSTDY-YWGWIRQPPGKGLEWIGSIGYSGT YYNPSLKSR-VTISVDTSKNQFSLKLSSVTAADTAVYYCARE-TAHDVHGMDVWGQG TTVTVSS [SEQ ID NO:19]. In some embodiments, the antibody heavy chain variable domain is at least 95% identical to SEQ ID NO:19. In some embodiments, the heavy chain variable domain incorporates amino acid sequences GSISSTDYYWG [SEQ ID NO:75] as CDR1, SIGYSGTYYNPSLKS [SEQ ID NO:76] as CDR2, and ARETAHDVHGMDV [SEQ ID NO:77] as CDR3 of SEQ ID NO:19. In some embodiments, the heavy chain variable domain incorporates amino acid sequences STDYYWG [SEQ ID NO:445] as CDR1, SIGYSGTYYNPSLKS [SEQ ID NO:76] as CDR2, and ETAHDVHGMDV [SEQ ID NO:446] as CDR3 of SEQ ID NO:19. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:19 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:19 can be paired with an antibody light chain variable domain at least 90% (e.g., at least 91%, 92%, 93%, 94%, 95%, 96%, 97%, 98%, 99%, or 100%) identical to the amino acid sequence EIVLTQSPATLSLSPGERATLSCRASHSVYSYLAWYQ-QKPGQAPRLLIYDASNRATGI PARFSGSGSGTD-FTLTISSLEPEDFAVYYCQQYDNLPTFGGGTKVEIK [SEQ ID NO:20]. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:19 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:20, which includes amino acid sequences RASHSVYSYLA [SEQ ID NO:78] as CDR1, DASNRAT [SEQ ID NO:79] as CDR2, and QQYDNLPT [SEQ ID NO:80] as CDR3 of SEQ ID NO:20.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:266. In some embodiments, the antibody heavy chain variable domain is at least 95% identical to SEQ ID NO:266. In some embodiments, the heavy chain variable domain incorporates amino acid sequences SEQ ID NO:304 as CDR1, SEQ ID NO:305 as CDR2, and SEQ ID NO:306 as CDR3 of SEQ ID NO:266. In some embodiments, the heavy chain variable domain incorporates amino acid sequences SEQ ID NO:528 as CDR1, SEQ ID NO:305 as CDR2, and SEQ ID NO:529 as CDR3 of SEQ ID NO:266. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:266 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267, which includes amino acid sequences SEQ ID NO:307 as CDR1, SEQ ID NO:308 as CDR2, and SEQ ID NO:309 as CDR3 of SEQ ID NO:267.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:268. In some embodiments, the antibody heavy chain variable domain is at least 95% identical to SEQ ID NO:268. In some embodiments, the heavy chain variable domain incorporates amino acid sequences SEQ ID NO:310 as CDR1, SEQ ID NO:311 as CDR2, and SEQ ID NO:312 as CDR3 of SEQ ID NO:268. In some embodiments, the heavy chain variable domain incorporates amino acid sequences SEQ ID NO:530 as CDR1, SEQ ID NO:311 as CDR2, and SEQ ID NO:531 as CDR3 of SEQ ID NO:268. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:268 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269, which includes amino acid sequences SEQ ID NO:313 as CDR1, SEQ ID NO:314 as CDR2, and SEQ ID NO:315 as CDR3 of SEQ ID NO:269.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:270. In some embodiments, the antibody heavy chain variable domain is at least 95% identical to SEQ ID NO:270. In some embodiments, the heavy chain variable domain incorporates amino acid sequences SEQ ID NO:316 as CDR1, SEQ ID NO:317 as CDR2, and SEQ ID NO:318 as CDR3 of SEQ ID NO:270. In some embodiments, the heavy chain variable domain incorporates amino acid sequences SEQ ID NO:532 as CDR1, SEQ ID NO:317 as CDR2, and SEQ ID NO:533 as CDR3 of SEQ ID NO:270. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:270 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271, which includes amino acid sequences SEQ ID NO:319 as CDR1, SEQ ID NO:320 as CDR2, and SEQ ID NO:321 as CDR3 of SEQ ID NO:271.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:272. In some embodiments, the antibody heavy chain variable domain is at least 95% identical to SEQ ID NO:272. In some embodiments, the heavy chain variable domain incorporates amino acid sequences SEQ ID NO:322 as CDR1, SEQ ID NO:323 as CDR2, and SEQ ID NO:324 as CDR3 of SEQ ID NO:272. In some embodiments, the heavy chain variable domain incorporates amino acid sequences SEQ ID NO:534 as CDR1, SEQ ID NO:323 as CDR2, and SEQ ID NO:535 as CDR3 of SEQ ID NO:272. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:272 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273, which includes amino acid sequences SEQ ID NO:325 as CDR1, SEQ ID NO:326 as CDR2, and SEQ ID NO:327 as CDR3 of SEQ ID NO:273.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:274. In some embodiments, the antibody heavy chain variable domain is at least 95% identical to SEQ ID NO:274. In some embodiments, the heavy chain variable domain incorporates amino acid sequences SEQ ID NO:328 as CDR1, SEQ ID NO:329 as CDR2, and SEQ ID NO:330 as CDR3 of SEQ ID NO:274. In some embodiments, the heavy chain variable domain incorporates amino acid sequences SEQ ID NO:536 as CDR1, SEQ ID NO:329 as CDR2, and SEQ ID NO:537 as CDR3 of SEQ ID NO:274. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:274 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275, which includes amino acid sequences SEQ ID NO:331 as CDR1, SEQ ID NO:332 as CDR2, and SEQ ID NO:333 as CDR3 of SEQ ID NO:275.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:276. In some embodiments, the antibody heavy chain variable domain is at least 95% identical to SEQ ID NO:276. In some embodiments, the heavy chain variable domain incorporates amino acid sequences SEQ ID NO:334 as CDR1, SEQ ID NO:335 as CDR2, and SEQ ID NO:336 as CDR3 of SEQ ID NO:276. In some embodiments, the heavy chain variable domain incorporates amino acid sequences SEQ ID NO:538 as CDR1, SEQ ID NO:335 as CDR2, and SEQ ID NO:539 as CDR3 of SEQ ID NO:276. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:276 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:277. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:277, which includes amino acid sequences SEQ ID NO:337 as CDR1, SEQ ID NO:338 as CDR2, and SEQ ID NO:339 as CDR3 of SEQ ID NO:277.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:278. In some embodiments, the antibody heavy chain variable domain is at least 95% identical to SEQ ID NO:278. In some embodiments, the heavy chain variable domain incorporates amino acid sequences SEQ ID NO:340 as CDR1, SEQ ID NO:341 as CDR2, and SEQ ID NO:342 as CDR3 of SEQ ID NO:278. In some embodiments, the heavy chain variable domain incorporates amino acid sequences SEQ ID NO:540 as CDR1, SEQ ID NO:341 as CDR2, and SEQ ID NO:541 as CDR3 of SEQ ID NO:278. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:278 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279, which includes amino acid sequences SEQ ID NO:343 as CDR1, SEQ ID NO:344 as CDR2, and SEQ ID NO:345 as CDR3 of SEQ ID NO:279.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:280. In some embodiments, the antibody heavy chain variable domain is at least 95% identical to SEQ ID NO:280. In some embodiments, the heavy chain variable domain incorporates amino acid sequences SEQ ID NO:346 as CDR1, SEQ ID NO:347 as CDR2, and SEQ ID NO:348 as CDR3 of SEQ ID NO:280. In some embodiments, the heavy chain variable domain incorporates amino acid sequences SEQ ID NO:542 as CDR1, SEQ ID NO:347 as CDR2, and SEQ ID NO:543 as CDR3 of SEQ ID NO:280. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:280 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281, which includes amino acid sequences SEQ ID NO:349 as CDR1, SEQ ID NO:350 as CDR2, and SEQ ID NO:351 as CDR3 of SEQ ID NO:281.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:282. In some embodiments, the antibody heavy chain variable domain is at least 95% identical to SEQ ID NO:282. In some embodiments, the heavy chain variable domain incorporates amino acid sequences SEQ ID NO:352 as CDR1, SEQ ID NO:353 as CDR2, and SEQ ID NO:354 as CDR3 of SEQ ID NO:282.

In some embodiments, the heavy chain variable domain incorporates amino acid sequences SEQ ID NO:544 as CDR1, SEQ ID NO:353 as CDR2, and SEQ ID NO:545 as CDR3 of SEQ ID NO:282. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:282 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283, which includes amino acid sequences SEQ ID NO:355 as CDR1, SEQ ID NO:356 as CDR2, and SEQ ID NO:357 as CDR3 of SEQ ID NO:283.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:284. In some embodiments, the antibody heavy chain variable domain is at least 95% identical to SEQ ID NO:284. In some embodiments, the heavy chain variable domain incorporates amino acid sequences SEQ ID NO:358 as CDR1, SEQ ID NO:359 as CDR2, and SEQ ID NO:360 as CDR3 of SEQ ID NO:284. In some embodiments, the heavy chain variable domain incorporates amino acid sequences SEQ ID NO:546 as CDR1, SEQ ID NO:359 as CDR2, and SEQ ID NO:360 as CDR3 of SEQ ID NO:547. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:284 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285, which includes amino acid sequences SEQ ID NO:361 as CDR1, SEQ ID NO:362 as CDR2, and SEQ ID NO:363 as CDR3 of SEQ ID NO:285.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:286. In some embodiments, the antibody heavy chain variable domain is at least 95% identical to SEQ ID NO:286. In some embodiments, the heavy chain variable domain incorporates amino acid sequences SEQ ID NO:364 as CDR1, SEQ ID NO:365 as CDR2, and SEQ ID NO:366 as CDR3 of SEQ ID NO:286. In some embodiments, the heavy chain variable domain incorporates amino acid sequences SEQ ID NO:548 as CDR1, SEQ ID NO:365 as CDR2, and SEQ ID NO:549 as CDR3 of SEQ ID NO:286. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:286 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287, which includes amino acid sequences SEQ ID NO:367 as CDR1, SEQ ID NO:368 as CDR2, and SEQ ID NO:369 as CDR3 of SEQ ID NO:287.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:290. In some embodiments, the antibody heavy chain variable domain is at least 95% identical to SEQ ID NO:290. In some embodiments, the heavy chain variable domain incorporates amino acid sequences SEQ ID NO:376 as CDR1, SEQ ID NO:377 as CDR2, and SEQ ID NO:378 as CDR3 of SEQ ID NO:290. In some embodiments, the heavy chain variable domain incorporates amino acid sequences SEQ ID NO:552 as CDR1, SEQ ID NO:377 as CDR2, and SEQ ID NO:553 as CDR3 of SEQ ID NO:290. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:290 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291, which includes amino acid sequences SEQ ID NO:379 as CDR1, SEQ ID NO:380 as CDR2, and SEQ ID NO:381 as CDR3 of SEQ ID NO:291.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:292. In some embodiments, the antibody heavy chain variable domain is at least 95% identical to SEQ ID NO:292. In some embodiments, the heavy chain variable domain incorporates amino acid sequences SEQ ID NO:382 as CDR1, SEQ ID NO:383 as CDR2, and SEQ ID NO:384 as CDR3 of SEQ ID NO:292. In some embodiments, the heavy chain variable domain incorporates amino acid sequences SEQ ID NO:554 as CDR1, SEQ ID NO:383 as CDR2, and SEQ ID NO:555 as CDR3 of SEQ ID NO:292. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:292 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293, which includes amino acid sequences SEQ ID NO:385 as CDR1, SEQ ID NO:386 as CDR2, and SEQ ID NO:387 as CDR3 of SEQ ID NO:293.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:294. In some embodiments, the antibody heavy chain variable domain is at least 95% identical to SEQ ID NO:294. In some embodiments, the heavy chain variable domain incorporates amino acid sequences SEQ ID NO:388 as CDR1, SEQ ID NO:389 as CDR2, and SEQ ID NO:390 as CDR3 of SEQ ID NO:294. In some embodiments, the heavy chain variable domain incorporates amino acid sequences SEQ ID NO:556 as CDR1, SEQ ID NO:389 as CDR2, and SEQ ID NO:557 as CDR3 of SEQ ID NO:294. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:294 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295, which includes amino acid sequences SEQ ID NO:391 as CDR1, SEQ ID NO:392 as CDR2, and SEQ ID NO:393 as CDR3 of SEQ ID NO:295.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:296. In some embodiments, the antibody heavy chain variable domain is at least 95% identical to SEQ ID NO:296. In some embodiments, the heavy chain variable domain incorporates amino acid sequences SEQ ID NO:394 as CDR1, SEQ ID NO:395 as CDR2, and SEQ ID NO:396 as CDR3 of SEQ ID NO:296. In some embodiments, the heavy chain variable domain incorporates amino acid sequences SEQ ID NO:558 as CDR1, SEQ ID NO:395 as CDR2, and SEQ ID NO:559 as CDR3 of SEQ ID NO:296. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:296 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297, which includes amino acid sequences SEQ ID NO:397 as CDR1, SEQ ID NO:398 as CDR2, and SEQ ID NO:399 as CDR3 of SEQ ID NO:297.

In certain embodiments, the present invention provides an antigen binding site that binds an epitope on an extracellular domain of human CD33 and Cynomolgus/Rhesus (cyno) CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:298. In some embodiments, the antibody heavy chain variable domain is at least 95% identical to SEQ ID NO:298. In some embodiments, the heavy chain variable domain incorporates amino acid sequences SEQ ID NO:400 as CDR1, SEQ ID NO:401 as CDR2, and SEQ ID NO:402 as CDR3 of SEQ ID NO:298. In some embodiments, the heavy chain variable domain incorporates amino acid sequences SEQ ID NO:560 as CDR1, SEQ ID NO:401 as CDR2, and SEQ ID NO:561 as CDR3 of SEQ ID NO:298. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:298 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299, which includes amino acid sequences SEQ ID NO:403 as CDR1, SEQ ID NO:404 as CDR2, and SEQ ID NO:405 as CDR3 of SEQ ID NO:299.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:300. In some embodiments, the antibody heavy chain variable domain is at least 95% identical to SEQ ID NO:300. In some embodiments, the heavy chain variable domain incorporates amino acid sequences SEQ ID NO:406 as CDR1, SEQ ID NO:407 as CDR2, and SEQ ID NO:408 as CDR3 of SEQ ID NO:300. In some embodiments, the heavy chain variable domain incorporates amino acid sequences SEQ ID NO:562 as CDR1, SEQ ID NO:407 as CDR2, and SEQ ID NO:563 as CDR3 of SEQ ID NO:300. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:300 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301, which includes amino acid sequences SEQ ID NO:409 as CDR1, SEQ ID NO:410 as CDR2, and SEQ ID NO:411 as CDR3 of SEQ ID NO:301.

In certain embodiments, the present invention provides an antigen binding site that binds an epitope on an extracellular domain of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:302. In some embodiments, the antibody heavy chain variable domain is at least 95% identical to SEQ ID NO:302. In some embodiments, the heavy chain variable domain incorporates amino acid sequences SEQ ID NO:412 as CDR1, SEQ ID NO:413 as CDR2, and SEQ ID NO:414 as CDR3 of SEQ ID NO:302. In some embodiments, the heavy chain variable domain incorporates amino acid sequences SEQ ID NO:564 as CDR1, SEQ ID NO:413 as CDR2, and SEQ ID NO:565 as CDR3 of SEQ ID NO:302. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:302 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303, which includes amino acid sequences SEQ ID NO:415 as CDR1, SEQ ID NO:416 as CDR2, and SEQ ID NO:417 as CDR3 of SEQ ID NO:303.

An Antigen Binding Site that Recognizes and Binds a Conformational Epitope on an Extracellular Domain of the Human CD33 and/or the Cynomolgus/Rhesus (Cyno) CD33

In one aspect, the present invention provides an antigen binding site including a heavy chain variable domain that recognizes and binds one or more conformational epitopes on the extracellular domain of the human CD33 and/or the Cynomolgus/Rhesus (cyno) CD33.

In certain embodiments, the present invention provides an antigen binding site that recognizes and binds a conformational epitope partially located in the V domain of human CD33 extracellular domain; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLS-CAASGFTFSSYWMSWVRQAPGKGLEWVANIKQDG SEKYYVDSVKGRFTISRDNAKNSLYLQMNSLRAED-TAVYYCARPLNAGELDVWGQ GTMVTVSS [SEQ ID NO:3]. In some embodiments, the antibody heavy chain variable domain is at least 95% identical to SEQ ID NO:3. In some embodiments, the heavy chain variable domain incorporates amino acid sequences FTFSSYWMS [SEQ ID NO:27] as CDR1, NIKQDGSEKYYVDSVKG [SEQ ID NO:28] as CDR2, and ARPLNAGELDV [SEQ ID NO:29] as CDR3 of SEQ ID NO:3. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:3 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASQSISSWLAWYQQKPGK-APKLLIYEASSLESGV PSRFSGSGSGTEFTLTISSLQP-DDFATYYCQQLESYPLTFGGGTKVEIK [SEQ ID NO:4]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., 91%, 92%, 93%, 94%, 95%, 96%, 97%, 98%, 99%, or 100%) identical to the amino acid sequence of SEQ ID NO:4, which includes amino acid sequences RASQSISS-WLA [SEQ ID NO:30] as CDR1, EASSLES [SEQ ID NO:31] as CDR2, and QQLESYPLT [SEQ ID NO:32] as CDR3 of SEQ ID NO:4.

In certain embodiments, the present invention provides an antigen binding site that recognizes and binds a conformational epitope partially located in the V domain of the human CD33 extracellular domain; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLS-CAASGFTFPSYWMSWVRQAPGKGLEWVATIKRDGS EKGYVDSVKGRFTISRDNAKNSLYLQMNSLRAED-TAVYYCARPLNAGELDVWGQG TMVTVSS [SEQ ID NO:11]. In some embodiments, the antibody heavy chain variable domain is at least 95% identical to SEQ ID NO:11. In some embodiments, the heavy chain variable domain incorporates amino acid sequences FTFPSYWMS [SEQ ID NO:51] as CDR1, TIKRDGSEKGYVDSVKG [SEQ ID NO:52] as CDR2, and ARPLNAGELDV [SEQ ID NO:53] as CDR3 of SEQ ID NO:11. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:11 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASQSISSWLAWYQQKP-GKAPKLLIYEASSLESGV PSRFSGSGSGTEFTLTIS-SLQPDDFATYYCQQSQSYPPITFGGGTKVEIK [SEQ ID NO:12]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., 91%, 92%, 93%, 94%, 95%, 96%, 97%, 98%, 99%, or 100%) identical to the amino acid sequence of SEQ ID NO:12, which includes amino acid sequences RASQSISS-WLA [SEQ ID NO:54] as CDR1, EASSLES [SEQ ID NO:55] as CDR2, and QQSQSYPPIT [SEQ ID NO:56] as CDR3 of SEQ ID NO:12.

In certain embodiments, the present invention provides an antigen binding site that recognizes and binds a conformational epitope partially located in the V domain of the human CD33 extracellular domain; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVKPGGSLRLS-CAASGFTFSSYAMSWVRQAPGKGLEWVSSISSSSEG IYYADSVKGRFTISRDNAKNSLYLQMNSLRAED-TAVYYCAREGGPYYDSSGYFVYY GMDVWGQ-GTTVTVSS [SEQ ID NO:15]. In some embodiments, the antibody heavy chain variable domain is at least 95% identical to SEQ ID NO:15. In some embodiments, the heavy chain variable domain incorporates amino acid sequences FTFSSYAMS [SEQ ID NO:63] as CDR1, SIS-SSSEGIYYADSVKG [SEQ ID NO:64] as CDR2, and AREGGPYYDSSGYFVYYGMDV [SEQ ID NO:65] as CDR3 of SEQ ID NO:15. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:15 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASNSISSWLAWYQQKPG-KAPKLLIYEASSTKSGV PSRFSGSGSGTEFTLTISSLQ-PDDFATYYCQQYDDLPTFGGGTKVEIK [SEQ ID NO:16]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., 91%, 92%, 93%, 94%, 95%, 96%, 97%, 98%, 99%, or 100%) identical to the amino acid sequence of SEQ ID NO:16, which includes amino acid sequences RASNSISS-WLA [SEQ ID NO:66] as CDR1, EASSTKS [SEQ ID NO:67] as CDR2, and QQYDDLPT [SEQ ID NO:68] as CDR3 of SEQ ID NO:16.

In certain embodiments, the present invention provides an antigen binding site that recognizes and binds a conformational epitope partially located in the V domain of the human CD33 extracellular domain; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:270. In some embodiments, the antibody heavy chain variable domain is at least 95% identical to SEQ ID NO:270. In some embodiments, the heavy chain variable domain incorporates amino acid sequences SEQ ID NO:316 as CDR1, SEQ ID NO:317 as CDR2, and SEQ ID NO:318 as CDR3 of SEQ ID NO:270. In some embodiments, the heavy chain variable domain incorporates amino acid sequences SEQ ID NO:532 as CDR1, SEQ ID NO:317 as CDR2, and SEQ ID NO:533 as CDR3 of SEQ ID NO:270. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:270 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271, which includes amino acid sequences SEQ ID NO:319 as CDR1, SEQ ID NO:320 as CDR2, and SEQ ID NO:321 as CDR3 of SEQ ID NO:271.

In certain embodiments, the present invention provides an antigen binding site that recognizes and binds a conformational epitope partially located in the V domain of the human CD33 extracellular domain; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:272. In some embodiments, the antibody heavy chain variable domain is at least 95% identical to SEQ ID NO:272. In some embodiments, the heavy chain variable domain incorporates amino acid sequences SEQ ID NO:322 as CDR1, SEQ ID NO:323 as CDR2, and SEQ ID NO:324 as CDR3 of SEQ ID NO:272. In some embodiments, the heavy chain variable domain incorporates amino acid sequences SEQ ID NO:534 as CDR1, SEQ ID NO:323 as CDR2, and SEQ ID NO:535 as CDR3 of SEQ ID NO:272. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:272 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273, which includes amino acid sequences SEQ ID NO:325 as CDR1, SEQ ID NO:326 as CDR2, and SEQ ID NO:327 as CDR3 of SEQ ID NO:273.

In certain embodiments, the present invention provides an antigen binding site that recognizes and binds a conformational epitope partially located in the V domain of the human CD33 extracellular domain; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:280. In some embodiments, the antibody heavy chain variable domain is at least 95% identical to SEQ ID NO:280. In some embodiments, the heavy chain variable domain incorporates amino acid sequences SEQ ID NO:346 as CDR1, SEQ ID NO:347 as CDR2, and SEQ ID NO:348 as CDR3 of SEQ ID NO:280. In some embodiments, the heavy chain variable domain incorporates amino acid sequences SEQ ID NO:542 as CDR1, SEQ ID NO:347 as CDR2, and SEQ ID NO:543 as CDR3 of SEQ ID NO:280. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:280 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281, which includes amino acid sequences SEQ ID NO:349 as CDR1, SEQ ID NO:350 as CDR2, and SEQ ID NO:351 as CDR3 of SEQ ID NO:281.

An Antigen Binding Site that Recognizes and Binds a Conformational Epitope on an Extracellular Domain of the Human CD33 but not a Conformational Epitope on an Extracellular Domain of the Cynomolgus/Rhesus (Cyno) CD33

In one aspect, the present invention provides an antigen binding site that recognizes and binds one or more conformational epitopes on the extracellular domain of the human CD33 but does not recognize and/or bind one or more conformational epitopes on the extracellular domain of the cyno CD33.

In certain embodiments, the present invention provides an antigen binding site that recognizes and binds one or more conformational epitopes on the extracellular domain of the human CD33 but does not recognize and/or bind one or more conformational epitopes on the extracellular domain of the cyno CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCKASGYTFSDYYM-HWVRQAPGQGLEWMGMINPS WGSTSYAQKFQG-RVTMTRDTSTSTVYMELSSLRSEDTAVYYCAREAA-DGFVGERYF DLWGRGTLVTVSS [SEQ ID NO:7]. In some embodiments, the antibody heavy chain variable domain is at least 95% identical to SEQ ID NO:7. In some embodiments, the heavy chain variable domain incorporates amino acid sequences YTFSDYYMH [SEQ ID NO:39] as CDR1, MINPSWGSTSYAQKFQG [SEQ ID NO:40] as CDR2, and AREAADGFVGERYFDL [SEQ ID NO:41] as CDR3 of SEQ ID NO:7. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:7 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence DIVMTQSPLSLPVTPGEPASISCRSSQSLLYSNGY-NYLDWYLQKPGQSPQLLIYLGSN RASGVPDRFSGS-GSGTDFTLKISRVEAEDVGVYYCMQDVALPITFGGG-TKVEIK [SEQ ID NO:8]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence of SEQ ID NO:8, which includes amino acid sequences RSSQSLLYSNGYNYLD [SEQ ID NO:42] as CDR1, LGSNRAS [SEQ ID NO:43] as CDR2, and MQDVALPIT [SEQ ID NO:44] as CDR3 of SEQ ID NO:8.

In certain embodiments, the present invention provides an antigen binding site that recognizes and binds one or more conformational epitopes on the extracellular domain of the human CD33 but does not recognize and/or bind one or more conformational epitopes on the extracellular domain of the cyno CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCKASGYTFGTYYM-HWVRQAPGQGLEWMGIINPSR GSTVYAQKFQGRVT-MTRDTSTSTVYMELSSLRSEDTAVYYCARGAGYDD-EDMDV WGKGTTVTVSS [SEQ ID NO:13]. In some embodiments, the antibody heavy chain variable domain is at least 95% identical to SEQ ID NO:13. In some embodiments, the heavy chain variable domain incorporates amino acid sequences YTFGTYYMH [SEQ ID NO:57] as CDR1, IINPSRGSTVYAQKFQG [SEQ ID NO:58] as CDR2, and ARGAGYDDEDMDV [SEQ ID NO:59] as CDR3 of SEQ ID NO:13. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:13 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., 91%, 92%, 93%, 94%, 95%, 96%, 97%, 98%, 99%, or 100%) identical to the amino acid sequence DIQMTQSPSSVSASVGDRVTITCRASQGIDSWLAW-YQQKPGKAPKLLIYAASSLQSG VPSRFSGSGSG-TDFTLTISSLQPEDFATYYCQQAHSYPLTFGGGT-KVEIK [SEQ ID NO:14]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., 91%, 92%, 93%, 94%, 95%, 96%, 97%, 98%, 99%, or 100%) identical to the amino acid sequence of SEQ ID NO:14, which includes amino acid sequences RASQGIDSWLA [SEQ ID NO:60] as CDR1, AASSLQS [SEQ ID NO:61] as CDR2, and QQAHSYPLT [SEQ ID NO:62] as CDR3 of SEQ ID NO:14.

In certain embodiments, an antibody binding site that includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCK-ASGYTFGTYYMHWVRQAPGQGLEWMGIINPSR GSTVYAQKFQGRVTMTRDTSTSTVYMELSSLRSED-TAVYYCARGAGYDDEDMDV WGKGTTVTVSS [SEQ ID NO:13] binds to the full-length extracellular domain of human CD33, but does not bind human CD33 V domain or C domain individually, and does not cross-block binding to human CD33 with lintuzumab. In certain embodiments, an antibody binding site that includes a heavy chain variable domain including an amino acid sequence at least 90% (e.g., 91%, 92%, 93%, 94%, 95%, 96%, 97%, 98%, 99%, or 100%) identical to the amino acid sequence of SEQ ID NO:13, and is paired with an antibody light chain variable domain at least 90% (e.g., 91%, 92%, 93%, 94%, 95%, 96%, 97%, 98%, 99%, or 100%) identical to the amino acid sequence DIQMTQSPSSVSASVGDRVTITCRASQGID-SWLAWYQQKPGKAPKLLIYAASSLQSG VPSRFSGS-GSGTDFTLTISSLQPEDFATYYCQQAHSYPLTFGGG-TKVEIK [SEQ ID NO:14], binds to the full-length extracellular domain of human CD33, but does not bind human CD33 V domain or C domain individually, and does not cross-block binding to human CD33 with lintuzumab. In certain embodiments, an antibody binding site that includes a heavy chain variable domain including an amino acid sequence at least 90% (e.g., 91%, 92%, 93%, 94%, 95%, 96%, 97%, 98%, 99%, or 100%) identical to the amino acid sequence of SEQ ID NO:13, and is paired with an antibody light chain variable domain at least 90% (e.g., 91%, 92%, 93%, 94%, 95%, 96%, 97%, 98%, 99%, or 100%) identical to the amino acid sequence of SEQ ID NO:14, which includes amino acid sequences RASQGIDSWLA [SEQ ID NO:60] as CDR1, AASSLQS [SEQ ID NO:61] as CDR2, and QQAHSYPLT [SEQ ID NO:62] as CDR3 of SEQ ID NO:14, binds to the full-length extracellular domain of human CD33, but does not bind human CD33 V domain or C domain individually, and does not cross-block binding to human CD33 with lintuzumab.

An Antigen Binding Site that Binds to the R69G Allele of Human CD33

In one aspect, the present invention provides an antigen binding site that binds to the R69G allele of human CD33. In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLSCAASGFTFSSYG-MSWVRQAPGKGLEWVANIKQDGS EKYYVDSVK-GRFTISRDNAKNSLYLQMNSLRAEDTAVYYCAREG-GPYYDSSGYFVY YGMDVWGQGTTVTVSS [SEQ ID NO:1]. In some embodiments, the antibody heavy chain variable domain is at least 95% identical to SEQ ID NO:1. In some embodiments, the heavy chain variable domain includes amino acid sequences FTFSSYGMS [SEQ ID NO:21] as the first complementarity-determining region 1 ("CDR1"), NIKQDGSEKYYVDSVKG [SEQ ID NO:22] as the second CDR ("CDR2"), and AREGGPYYDSSGYFVYYGMDV [SEQ ID NO:23] as the third CDR ("CDR3") of SEQ ID NO:1. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:1 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:1 can be paired with an antibody light chain variable domain at least 90% (e.g., 91%, 92%, 93%, 94%, 95%, 96%, 97%, 98%, 99%, or 100%) identical to the amino acid sequence DIQMTQSPSTLSASVGDRVTITCRASQSISS-WLAWYQQKPGKAPKLLIYDASSLESGV PSRFSGS-GSGTEFTLTISSLQPDDFATYYCQQYESFPTFGG-GTKVEIK [SEQ ID NO:2]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:1 can be paired with an antibody light chain variable domain at least 90% (e.g., 91%, 92%, 93%, 94%, 95%, 96%, 97%, 98%, 99%, or 100%) identical to the amino acid sequence of SEQ ID NO:2, which includes amino acid sequences RASQSISSWLA [SEQ ID NO:24] as CDR1, DASSLES [SEQ ID NO:25] as CDR2, and QQYESFPT [SEQ ID NO:26] as CDR3 of SEQ ID NO:2.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLSCAASGFTFSSYW-MSWVRQAPGKGLEWVANIKQDG SEKYYVDSV-KGRFTISRDNAKNSLYLQMNSLRAEDTAVYYCAR-PLNAGELDVWGQ GTMVTVSS [SEQ ID NO:3]. In some embodiments, the antibody heavy chain variable domain is at least 95% identical to SEQ ID NO:3. In some embodiments, the heavy chain variable domain incorporates amino acid sequences FTFSSYWMS [SEQ ID NO:27] as CDR1, NIKQDGSEKYYVDSVKG [SEQ ID NO:28] as CDR2, and ARPLNAGELDV [SEQ ID NO:29] as CDR3 of SEQ ID NO:3. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:3 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., 91%, 92%, 93%, 94%, 95%, 96%, 97%, 98%, 99%, or 100%) identical to the amino acid sequence DIQMTQSPSTL-SASVGDRVTITCRASQSISSWLAWYQQKPGK-APKLLIYEASSLESGV PSRFSGSGSGTEFTLTISSL-QPDDFATYYCQQLESYPLTFGGGTKVEIK [SEQ ID NO:4]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:3 can be paired with an antibody light chain variable domain at least 90% (e.g., 91%, 92%, 93%, 94%, 95%, 96%, 97%, 98%, 99%, or 100%) identical to the amino acid sequence of SEQ ID NO:4, which includes amino acid sequences RASQSISS-WLA [SEQ ID NO:30] as CDR1, EASSLES [SEQ ID NO:31] as CDR2, and QQLESYPLT [SEQ ID NO:32] as CDR3 of SEQ ID NO:4.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLLESGGGLVQPGGSLRLSCAASGFTFSKY-TMSWVRQAPGKGLEWVSAIVGSGE STYFADSVK-GRFTISRDNSKNTLYLQMNSLRAEDTAVYYCAREGG-PYYDSSGYFVY YGMDVWGQGTTVTVSS [SEQ ID NO:5]. In some embodiments, the antibody heavy chain variable domain is at least 95% identical to SEQ ID NO:5. In some embodiments, the heavy chain variable domain incorporates amino acid sequences FTFSKYTMS [SEQ ID NO:33] as CDR1, AIVGSGESTYFADSVKG [SEQ ID NO:34] as CDR2, and AREGGPYYDSSGYFVYYGMDV [SEQ ID NO:35] as CDR3 of SEQ ID NO:5. In some embodiments, the heavy chain variable domain incorporates amino acid sequences KYTMS [SEQ ID NO:183] as CDR1, AIVGSGESTYFADSVKG [SEQ ID NO:34] as CDR2, and EGGPYYDSSGYFVYYGMDV [SEQ ID NO:184] as CDR3 of SEQ ID NO:5. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:5 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:5 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASQSISSWLAWYQQKPG-KAPKLLIYKASSLESGV PSRFSGSGSGTEFTLTISSL-QPDDFATYYCQQYDDLPTFGGGTKVEIK [SEQ ID NO:6]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:5 can be paired with an antibody light chain variable domain at least 90% (e.g., 91%, 92%, 93%, 94%, 95%, 96%, 97%, 98%, 99%, or 100%) identical to the amino acid sequence of SEQ ID NO:6, which includes amino acid sequences RASQSISS-WLA [SEQ ID NO:36] as CDR1, KASSLES [SEQ ID NO:37] or KASSLE [SEQ ID NO:185] as CDR2, and QQYDDLPT [SEQ ID NO:38] as CDR3 of SEQ ID NO:6.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLSCAASGFTFGSYWM-SWVRQAPGKGLEWVATIKQDG SEKSYVDSVKGRF-TISRDNAKNSLYLQMNSLRAEDTAVYYCAR-PLNAGELDVWGQ GTMVTVSS [SEQ ID NO:9]. In some embodiments, the antibody heavy chain variable domain is at least 95% identical to SEQ ID NO:9. In some embodiments, the heavy chain variable domain incorporates amino acid sequences FTFGSYWMS [SEQ ID NO:45] as CDR1, TIKQDGSEKSYVDSVKG [SEQ ID NO:46] as CDR2, and ARPLNAGELDV [SEQ ID NO:47] as CDR3 of SEQ ID NO:9. In some embodiments, the heavy chain variable domain incorporates amino acid sequences SYWMS [SEQ ID NO:181] as CDR1, TIKQDGSEKSYVDSVKG [SEQ ID NO:46] as CDR2, and RPLNAGELDV [SEQ ID NO:182] as CDR3 of SEQ ID NO:9. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:9 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:9 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASQSISSWLAWYQQKPG-KAPKLLIYEASSLESGV PSRFSGSGSGTEFTLTISS-LQPDDFATYYCQQSQSYPPITFGGGTKVEIK [SEQ ID NO:10]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:9 can be paired with an antibody light chain variable domain at least 90% (e.g., 91%, 92%, 93%, 94%, 95%, 96%, 97%, 98%, 99%, or 100%) identical to the amino acid sequence of SEQ ID NO:10, which includes amino acid sequences RASQSISS-WLA [SEQ ID NO:48] as CDR1, EASSLES [SEQ ID NO:49] as CDR2, and QQSQSYPPIT [SEQ ID NO:50] as CDR3 of SEQ ID NO:10.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLSCAASGFTFPSYWM-SWVRQAPGKGLEWVATIKRDGS EKGYVDSVKG-RFTISRDNAKNSLYLQMNSLRAEDTAVYYCAR-PLNAGELDVWGQG TMVTVSS [SEQ ID NO:11]. In some embodiments, the antibody heavy chain variable domain is at least 95% identical to SEQ ID NO:11. In some embodiments, the heavy chain variable domain incorporates amino acid sequences FTFPSYWMS [SEQ ID NO:51] as CDR1, TIKRDGSEKGYVDSVKG [SEQ ID NO:52] as CDR2, and ARPLNAGELDV [SEQ ID NO:53] as CDR3 of SEQ ID NO:11. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:11 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., 91%, 92%, 93%, 94%, 95%, 96%, 97%, 98%, 99%, or 100%) identical to the amino acid sequence DIQMTQSP-STLSASVGDRVTITCRASQSISSWLAWYQQK-PGKAPKLLIYEASSLESGV PSRFSGSGSGTEFTLTI-SSLQPDDFATYYCQQSQSYPPITFGGGTKVEIK [SEQ ID NO:12]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:11 can be paired with an antibody light chain variable domain at least 90% (e.g., 91%, 92%, 93%, 94%, 95%, 96%, 97%, 98%, 99%, or 100%) identical to the amino acid sequence of SEQ ID NO:12, which includes amino acid sequences RASQSISS-WLA [SEQ ID NO:54] as CDR1, EASSLES [SEQ ID NO:55] as CDR2, and QQSQSYPPIT [SEQ ID NO:56] as CDR3 of SEQ ID NO:12.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCKASGYTFGTYYM-HWVRQAPGQGLEWMGIINPSR GSTVYAQKFQGR-VTMTRDTSTSTVYMELSSLRSEDTAVYYCAR-GAGYDDEDMDV WGKGTTVTVSS [SEQ ID NO:13]. In some embodiments, the antibody heavy chain variable domain is at least 95% identical to SEQ ID NO:13. In some embodiments, the heavy chain variable domain incorporates amino acid sequences YTFGTYYMH [SEQ ID NO:57] as CDR1, IINPSRGSTVYAQKFQG [SEQ ID NO:58] as CDR2, and ARGAGYDDEDMDV [SEQ ID NO:59] as CDR3 of SEQ ID NO:13. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:13 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., 91%, 92%, 93%, 94%, 95%, 96%, 97%, 98%, 99%, or 100%) identical to the amino acid sequence DIQMTQSPSSVSASVGDRVTITCRASQGIDSWLAW-YQQKPGKAPKLLIYAASSLQSG VPSRFSGSGSGTD-FTLTISSLQPEDFATYYCQQAHSYPLTFGGGTKVEIK [SEQ ID NO:14]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:13 can be paired with an antibody light chain variable domain at least 90% (e.g., 91%, 92%, 93%, 94%, 95%, 96%, 97%, 98%, 99%, or 100%) identical to the amino acid sequence of SEQ ID NO:14, which includes amino acid sequences RASQGID-SWLA [SEQ ID NO:60] as CDR1, AASSLQS [SEQ ID NO:61] as CDR2, and QQAHSYPLT [SEQ ID NO:62] as CDR3 of SEQ ID NO:14.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVKPGGSLRLSCAASGFTFSSYAM-SWVRQAPGKGLEWVSSISSSSEG IYYADSVKGRF-TISRDNAKNSLYLQMNSLRAEDTAVYY-CAREGGPYYDSSGYFVYY GMDVWGQGTTVTVSS [SEQ ID NO:15]. In some embodiments, the antibody heavy chain variable domain is at least 95% identical to SEQ ID NO:15. In some embodiments, the heavy chain variable domain incorporates amino acid sequences FTFSSYAMS [SEQ ID NO:63] as CDR1, SISSSSEGIYYADSVKG [SEQ ID NO:64] as CDR2, and AREGGPYYDS-SGYFVYYGMDV [SEQ ID NO:65] as CDR3 of SEQ ID NO:15. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:15 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., 91%, 92%, 93%, 94%, 95%, 96%, 97%, 98%, 99%, or 100%) identical to the amino acid sequence DIQMTQSPSTL-SASVGDRVTITCRASNSISSWLAWYQQKPGKA-PKLLIYEASSTKSGV PSRFSGSGSGTEFTLTISSLQPD-DFATYYCQQYDDLPTFGGGTKVEIK [SEQ ID NO:16]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:15 can be paired with an antibody light chain variable domain at least 90% (e.g., 91%, 92%, 93%, 94%, 95%, 96%, 97%, 98%, 99%, or 100%) identical to the amino acid sequence of SEQ ID NO:16, which includes amino acid sequences RASNSISSWLA [SEQ ID NO:66] as CDR1, EASSTKS [SEQ ID NO:67] as CDR2, and QQYDDLPT [SEQ ID NO:68] as CDR3 of SEQ ID NO:16.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of EVQLVESGGGLVQPGGSLRLSCAASGFTFSSYW-MSWVRQAPGKGLEWVANINTDG SEVYYVDSVKG-RFTISRDNAKNSLYLQMNSLRAEDTAVYYCARDVG-PGIAYQGHFD YWGQGTLVTVSS [SEQ ID NO:17]. In some embodiments, the antibody heavy chain variable domain is at least 95% identical to SEQ ID NO:17. In some embodiments, the heavy chain variable domain incorporates amino acid sequences FTFSSYWMS [SEQ ID NO:69] as CDR1, NINTDGSEVYYVDSVKG [SEQ ID NO:70] as CDR2, and ARDVGPGIAYQGHFDY [SEQ ID NO:71] as CDR3 of SEQ ID NO:17. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:17 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:17 can be paired with an antibody light chain variable domain at least 90% (e.g., 91%, 92%, 93%, 94%, 95%, 96%, 97%, 98%, 99%, or 100%) identical to the amino acid sequence DIQMTQSPSSLSASVGDRVTITCRASQVIYSYLNWY-QQKPGKAPKLLIYAASSLKSGV PSRFSGSGSGT-DFTLTISSLQPEDFATYYCQQVYDTPLTFGGGTKVEIK [SEQ ID NO:18]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:17 can be paired with an antibody light chain variable domain at least 90% (e.g., 91%, 92%, 93%, 94%, 95%, 96%, 97%, 98%, 99%, or 100%) identical to the amino acid sequence of SEQ ID NO:18, which includes amino acid sequences RASQVIY-SYLN [SEQ ID NO:72] as CDR1, AASSLKS [SEQ ID NO:73] as CDR2, and QQVYDTPLT [SEQ ID NO:74] as CDR3 of SEQ ID NO:18.

In certain embodiments, the present invention provides an antigen binding site that binds to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QLQLQESGPGLVKPSETLSLTCTVSGGSISSTDYYWG-WIRQPPGKGLEWIGSIGYSGT YYNPSLKSRVTISVD-TSKNQFSLKLSSVTAADTAVYYCARETAHDVHGMD-VWGQG TTVTVSS [SEQ ID NO:19]. In some embodiments, the antibody heavy chain variable domain is at least 95% identical to SEQ ID NO:19. In some embodiments, the heavy chain variable domain incorporates amino acid sequences GSISSTDYYWG [SEQ ID NO:75] as CDR1, SIGYSGTYYNPSLKS [SEQ ID NO:76] as CDR2, and ARETAHDVHGMDV [SEQ ID NO:77] as CDR3 of SEQ ID NO:19. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:19 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:19 can be paired with an antibody light chain variable domain at least 90% (e.g., 91%, 92%, 93%, 94%, 95%, 96%, 97%, 98%, 99%, or 100%) identical to the amino acid sequence EIVLTQSPATLSLSPGERATLSCRASHSVYSYLAWYQ-QKPGQAPRLLIYDASNRATGI PARFSGSGSGTD-FTLTISSLEPEDFAVYYCQQYDNLPTFGGGTKVEIK [SEQ ID NO:20]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:19 can be paired with an antibody light chain variable domain at least 90% (e.g., 91%, 92%, 93%, 94%, 95%, 96%, 97%, 98%, 99%, or 100%) identical to the amino acid sequence of SEQ ID NO:20, which includes amino acid sequences RASHSVY-SYLA [SEQ ID NO:78] as CDR1, DASNRAT [SEQ ID NO:79] as CDR2, and QQYDNLPT [SEQ ID NO:80] as CDR3 of SEQ ID NO:20.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:266. In some embodiments, the antibody heavy chain variable domain is at least 95% identical to SEQ ID NO:266. In some embodiments, the heavy chain variable domain incorporates amino acid sequences SEQ ID NO:304 as CDR1, SEQ ID NO:305 as CDR2, and SEQ ID NO:306 as CDR3 of SEQ ID NO:266. In some embodiments, the heavy chain variable domain incorporates amino acid sequences SEQ ID NO:528 as CDR1, SEQ ID NO:305 as CDR2, and SEQ ID NO:529 as CDR3 of SEQ ID NO:266. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:266 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267, which includes amino acid sequences SEQ ID NO:307 as CDR1, SEQ ID NO:308 as CDR2, and SEQ ID NO:309 as CDR3 of SEQ ID NO:267.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:268. In some embodiments, the antibody heavy chain variable domain is at least 95% identical to SEQ ID NO:268. In some embodiments, the heavy chain variable domain incorporates amino acid sequences SEQ ID NO:310 as CDR1, SEQ ID NO:311 as CDR2, and SEQ ID NO:312 as CDR3 of SEQ ID NO:268. In some embodiments, the heavy chain variable domain incorporates amino acid sequences SEQ ID NO:530 as CDR1, SEQ ID NO:311 as CDR2, and SEQ ID NO:531 as CDR3 of SEQ ID NO:268. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:268 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269, which includes amino acid sequences SEQ ID NO:313 as CDR1, SEQ ID NO:314 as CDR2, and SEQ ID NO:315 as CDR3 of SEQ ID NO:269.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:270. In some embodiments, the antibody heavy chain variable domain is at least 95% identical to SEQ ID NO:270. In some embodiments, the heavy chain variable domain incorporates amino acid sequences SEQ ID NO:316 as CDR1, SEQ ID NO:317 as CDR2, and SEQ ID NO:318 as CDR3 of SEQ ID NO:270. In some embodiments, the heavy chain variable domain incorporates amino acid sequences SEQ ID NO:532 as CDR1, SEQ ID NO:317 as CDR2, and SEQ ID NO:533 as CDR3 of SEQ ID NO:270. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:270 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271, which includes amino acid sequences SEQ ID NO:319 as CDR1, SEQ ID NO:320 as CDR2, and SEQ ID NO:321 as CDR3 of SEQ ID NO:271.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:272. In some embodiments, the antibody heavy chain variable domain is at least 95% identical to SEQ ID NO:272. In some embodiments, the heavy chain variable domain incorporates amino acid sequences SEQ ID NO:322 as CDR1, SEQ ID NO:323 as CDR2, and SEQ ID NO:324 as CDR3 of SEQ ID NO:272. In some embodiments, the heavy chain variable domain incorporates amino acid sequences SEQ ID NO:534 as CDR1, SEQ ID NO:323 as CDR2, and SEQ ID NO:535 as CDR3 of SEQ ID NO:272. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:272 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273, which includes amino acid sequences SEQ ID NO:325 as CDR1, SEQ ID NO:326 as CDR2, and SEQ ID NO:327 as CDR3 of SEQ ID NO:273.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:274. In some embodiments, the antibody heavy chain variable domain is at least 95% identical to SEQ ID NO:274. In some embodiments, the heavy chain variable domain incorporates amino acid sequences SEQ ID NO:328 as CDR1, SEQ ID NO:329 as CDR2, and SEQ ID NO:330 as CDR3 of SEQ ID NO:274. In some embodiments, the heavy chain variable domain incorporates amino acid sequences SEQ ID NO:536 as CDR1, SEQ ID NO:329 as CDR2, and SEQ ID NO:537 as CDR3 of SEQ ID NO:274. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:274 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275, which includes amino acid sequences SEQ ID NO:331 as CDR1, SEQ ID NO:332 as CDR2, and SEQ ID NO:333 as CDR3 of SEQ ID NO:275.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:276. In some embodiments, the antibody heavy chain variable domain is at least 95% identical to SEQ ID NO:276. In some embodiments, the heavy chain variable domain incorporates amino acid sequences SEQ ID NO:334 as CDR1, SEQ ID NO:335 as CDR2, and SEQ ID NO:336 as CDR3 of SEQ ID NO:276. In some embodiments, the heavy chain variable domain incorporates amino acid sequences SEQ ID NO:538 as CDR1, SEQ ID NO:335 as CDR2, and SEQ ID NO:539 as CDR3 of SEQ ID NO:276. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:276 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:277. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:277, which includes amino acid sequences SEQ ID NO:337 as CDR1, SEQ ID NO:338 as CDR2, and SEQ ID NO:339 as CDR3 of SEQ ID NO:277.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:278. In some embodiments, the antibody heavy chain variable domain is at least 95% identical to SEQ ID NO:278. In some embodiments, the heavy chain variable domain incorporates amino acid sequences SEQ ID NO:340 as CDR1, SEQ ID NO:341 as CDR2, and SEQ ID NO:342 as CDR3 of SEQ ID NO:278. In some embodiments, the heavy chain variable domain incorporates amino acid sequences SEQ ID NO:540 as CDR1, SEQ ID NO:341 as CDR2, and SEQ ID NO:541 as CDR3 of SEQ ID NO:278.

In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:278 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279, which includes amino acid sequences SEQ ID NO:343 as CDR1, SEQ ID NO:344 as CDR2, and SEQ ID NO:345 as CDR3 of SEQ ID NO:279.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:280. In some embodiments, the antibody heavy chain variable domain is at least 95% identical to SEQ ID NO:280. In some embodiments, the heavy chain variable domain incorporates amino acid sequences SEQ ID NO:346 as CDR1, SEQ ID NO:347 as CDR2, and SEQ ID NO:348 as CDR3 of SEQ ID NO:280. In some embodiments, the heavy chain variable domain incorporates amino acid sequences SEQ ID NO:542 as CDR1, SEQ ID NO:347 as CDR2, and SEQ ID NO:543 as CDR3 of SEQ ID NO:280. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:280 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281, which includes amino acid sequences SEQ ID NO:349 as CDR1, SEQ ID NO:350 as CDR2, and SEQ ID NO:351 as CDR3 of SEQ ID NO:281.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:282. In some embodiments, the antibody heavy chain variable domain is at least 95% identical to SEQ ID NO:282. In some embodiments, the heavy chain variable domain incorporates amino acid sequences SEQ ID NO:352 as CDR1, SEQ ID NO:353 as CDR2, and SEQ ID NO:354 as CDR3 of SEQ ID NO:282. In some embodiments, the heavy chain variable domain incorporates amino acid sequences SEQ ID NO:544 as CDR1, SEQ ID NO:353 as CDR2, and SEQ ID NO:545 as CDR3 of SEQ ID NO:282. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:282 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283, which includes amino acid sequences SEQ ID NO:355 as CDR1, SEQ ID NO:356 as CDR2, and SEQ ID NO:357 as CDR3 of SEQ ID NO:283.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:284. In some embodiments, the antibody heavy chain variable domain is at least 95% identical to SEQ ID NO:284. In some embodiments, the heavy chain variable domain incorporates amino acid sequences SEQ ID NO:358 as CDR1, SEQ ID NO:359 as CDR2, and SEQ ID NO:360 as CDR3 of SEQ ID NO:284. In some embodiments, the heavy chain variable domain incorporates amino acid sequences SEQ ID NO:546 as CDR1, SEQ ID NO:359 as CDR2, and SEQ ID NO:360 as CDR3 of SEQ ID NO:547. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:284 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285, which includes amino acid sequences SEQ ID NO:361 as CDR1, SEQ ID NO:362 as CDR2, and SEQ ID NO:363 as CDR3 of SEQ ID NO:285.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:286. In some embodiments, the antibody heavy chain variable domain is at least 95% identical to SEQ ID NO:286. In some embodiments, the heavy chain variable domain incorporates amino acid sequences SEQ ID NO:364 as CDR1, SEQ ID NO:365 as CDR2, and SEQ ID NO:366 as CDR3 of SEQ ID NO:286. In some embodiments, the heavy chain variable domain incorporates amino acid sequences SEQ ID NO:548 as CDR1, SEQ ID NO:365 as CDR2, and SEQ ID NO:549 as CDR3 of SEQ ID NO:286. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:286 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287, which includes amino acid sequences SEQ ID NO:367 as CDR1, SEQ ID NO:368 as CDR2, and SEQ ID NO:369 as CDR3 of SEQ ID NO:287.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:292. In some embodiments, the antibody heavy chain variable domain is at least 95% identical to SEQ ID NO:292. In some embodiments, the heavy chain variable domain incorporates amino acid sequences SEQ ID NO:382 as CDR1, SEQ ID NO:383 as CDR2, and SEQ ID NO:384 as CDR3 of SEQ ID NO:292. In some embodiments, the heavy chain variable domain incorporates amino acid sequences SEQ ID NO:554 as CDR1, SEQ ID NO:383 as CDR2, and SEQ ID NO:555 as CDR3 of SEQ ID NO:292. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:292 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293, which includes amino acid sequences SEQ ID NO:385 as CDR1, SEQ ID NO:386 as CDR2, and SEQ ID NO:387 as CDR3 of SEQ ID NO:293.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:294. In some embodiments, the antibody heavy chain variable domain is at least 95% identical to SEQ ID NO:294. In some embodiments, the heavy chain variable domain incorporates amino acid sequences SEQ ID NO:388 as CDR1, SEQ ID NO:389 as CDR2, and SEQ ID NO:390 as CDR3 of SEQ ID NO:294. In some embodiments, the heavy chain variable domain incorporates amino acid sequences SEQ ID NO:556 as CDR1, SEQ ID NO:389 as CDR2, and SEQ ID NO:557 as CDR3 of SEQ ID NO:294. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:294 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295, which includes amino acid sequences SEQ ID NO:391 as CDR1, SEQ ID NO:392 as CDR2, and SEQ ID NO:393 as CDR3 of SEQ ID NO:295.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:296. In some embodiments, the antibody heavy chain variable domain is at least 95% identical to SEQ ID NO:296. In some embodiments, the heavy chain variable domain incorporates amino acid sequences SEQ ID NO:394 as CDR1, SEQ ID NO:395 as CDR2, and SEQ ID NO:396 as CDR3 of SEQ ID NO:296. In some embodiments, the heavy chain variable domain incorporates amino acid sequences SEQ ID NO:558 as CDR1, SEQ ID NO:395 as CDR2, and SEQ ID NO:559 as CDR3 of SEQ ID NO:296. In certain embodiments, the antibody heavy chain variable domain which includes an amino acid sequence at least 90%

(e.g., at least 91%, 92%, 93%, 94%, 95%, 96%, 97%, 98%, 99%, or 100%) identical to the amino acid sequence of SEQ ID NO:296 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297, which includes amino acid sequences SEQ ID NO:397 as CDR1, SEQ ID NO:398 as CDR2, and SEQ ID NO:399 as CDR3 of SEQ ID NO:297.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:298. In some embodiments, the antibody heavy chain variable domain is at least 95% identical to SEQ ID NO:298. In some embodiments, the heavy chain variable domain incorporates amino acid sequences SEQ ID NO:400 as CDR1, SEQ ID NO:401 as CDR2, and SEQ ID NO:402 as CDR3 of SEQ ID NO:298. In some embodiments, the heavy chain variable domain incorporates amino acid sequences SEQ ID NO:560 as CDR1, SEQ ID NO:401 as CDR2, and SEQ ID NO:561 as CDR3 of SEQ ID NO:298. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:298 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299, which includes amino acid sequences SEQ ID NO:403 as CDR1, SEQ ID NO:404 as CDR2, and SEQ ID NO:405 as CDR3 of SEQ ID NO:299.

In certain embodiments, the present invention provides an antigen binding site that binds to the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:302. In some embodiments, the antibody heavy chain variable domain is at least 95% identical to SEQ ID NO:302. In some embodiments, the heavy chain variable domain incorporates amino acid sequences SEQ ID NO:412 as CDR1, SEQ ID NO:413 as CDR2, and SEQ ID NO:414 as CDR3 of SEQ ID NO:302. In some embodiments, the heavy chain variable domain incorporates amino acid sequences SEQ ID NO:564 as CDR1, SEQ ID NO:413 as CDR2, and SEQ ID NO:565 as CDR3 of SEQ ID NO:302. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:302 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303, which includes amino acid sequences SEQ ID NO:415 as CDR1, SEQ ID NO:416 as CDR2, and SEQ ID NO:417 as CDR3 of SEQ ID NO:303.

An Antigen Binding Site that does not Bind to the R69G Allele of Human CD33

In one aspect, the present invention provides an antigen binding site including a heavy chain variable domain that binds wild-type human CD33, but not the R69G allele of human CD33. In certain embodiments, the present invention provides an antigen binding site that does not bind to the R69G allele of human CD33; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCK-ASGYTFSDYYMHWVRQAPGQGLEWMGMINPS WGSTSYAQKFQGRVTMTRDTSTSTVYMELSSLRS-EDTAVYYCAREAADGFVGERYF DLWGRGTLVTVSS [SEQ ID NO:7]. In some embodiments, the antibody heavy chain variable domain is at least 95% identical to SEQ ID NO:7. In some embodiments, the heavy chain variable domain incorporates amino acid sequences YTFSDYYMH [SEQ ID NO:39] as CDR1, MINPSWGSTSYAQKFQG [SEQ ID NO:40] as CDR2, and AREAADGFVGERYFDL [SEQ ID NO:41] as CDR3 of SEQ ID NO:7. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:7 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence DIVMTQSPLSLPVTPGEPASISCRSSQSLLY-SNGYNYLDWYLQKPGQSPQLLIYLGSN RASGVPD-RFSGSGSGTDFTLKISRVEAEDVGVYYCMQDVAL- PITFGGGTKVEIK [SEQ ID NO:8]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence of SEQ ID NO:8, which includes amino acid sequences RSSQSLLYSNGYNYLD [SEQ ID NO:42] as CDR1, LGSNRAS [SEQ ID NO:43] as CDR2, and MQDVALPIT [SEQ ID NO:44] as CDR3 of SEQ ID NO:8.

In certain embodiments, the present invention provides an antigen binding site that binds to wild-type human CD33 but not the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

In certain embodiments, the present invention provides an antigen binding site that binds to wild-type human CD33 but not the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:290. In some embodiments, the antibody heavy chain variable domain is at least 95% identical to SEQ ID NO:290. In some embodiments, the heavy chain variable domain incorporates amino acid sequences SEQ ID NO:376 as CDR1, SEQ ID NO:377 as CDR2, and SEQ ID NO:378 as CDR3 of SEQ ID NO:290. In some embodiments, the heavy chain variable domain incorporates amino acid sequences SEQ ID NO:552 as CDR1, SEQ ID NO:377 as CDR2, and SEQ ID NO:553 as CDR3 of SEQ ID NO:290. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:290 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291, which includes amino acid sequences SEQ ID NO:379 as CDR1, SEQ ID NO:380 as CDR2, and SEQ ID NO:381 as CDR3 of SEQ ID NO:291.

In certain embodiments, the present invention provides an antigen binding site that binds to wild-type human CD33 but not the R69G allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:300. In some embodiments, the antibody heavy chain variable domain is at least 95% identical to SEQ ID NO:300. In some embodiments, the heavy chain variable domain incorporates amino acid sequences SEQ ID NO:406 as CDR1, SEQ ID NO:407 as CDR2, and SEQ ID NO:408 as CDR3 of SEQ ID NO:300. In some embodiments, the heavy chain variable domain incorporates amino acid sequences SEQ ID NO:562 as CDR1, SEQ ID NO:407 as CDR2, and SEQ ID NO:563 as CDR3 of SEQ ID NO:300. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:300 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301, which includes amino acid sequences SEQ ID NO:409 as CDR1, SEQ ID NO:410 as CDR2, and SEQ ID NO:411 as CDR3 of SEQ ID NO:301.

An Antigen Binding Site that Binds to a Unique Epitope Including R69 on Human CD33

In one aspect, the present invention provides an antigen binding site including a heavy chain variable domain that binds to a unique epitope on human CD33 that includes R69. In certain embodiments, the present invention provides an antigen binding site that binds to a unique epitope on human CD33 that includes R69; the antigen binding site includes a heavy chain variable domain including an amino acid sequence at least 90% (e.g., 91%, 92%, 93%, 94%, 95%, 96%, 97%, 98%, 99%, or 100%) identical to the amino acid sequence of QVQLVQSGAEVKKPGASVKVSCK- ASGYTFSDYYMHWVRQAPGQGLEWMGMINPS WGSTSYAQKFQGRVTMTRDTSTSTVYMELSSLRS- EDTAVYYCAREAADGFVGERYF DLWGRGTLVTVSS [SEQ ID NO:7].

In some embodiments, the antibody heavy chain variable domain is at least 95% identical to SEQ ID NO:7. In some embodiments, the heavy chain variable domain incorporates amino acid sequences YTFSDYYMH [SEQ ID NO:39] as CDR1, MINPSWGSTSYAQKFQG [SEQ ID NO:40] as CDR2, and AREAADGFVGERYFDL [SEQ ID NO:41] as CDR3 of SEQ ID NO:7. In certain embodiments, the antibody heavy chain variable domain which includes an amino acid sequence at least 90% (e.g., 91%, 92%, 93%, 94%, 95%, 96%, 97%, 98%, 99%, or 100%) identical to the amino acid sequence of SEQ ID NO:7 is combined with a light chain variable domain to form an antigen-binding site capable of binding to CD33. For example, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence DIVMTQSPLSLPVTPGEPASISCRSSQSLLYSNGY- NYLDWYLQKPGQSPQLLIYLGSN RASGVPDRFSG- SGSGTDFTLKISRVEAEDVGVYYCMQDVALPITFG- GGTKVEIK [SEQ ID NO:8]. In certain embodiments, an antibody heavy chain variable domain at least 90% (e.g., 91%, 92%, 93%, 94%, 95%, 96%, 97%, 98%, 99%, or 100%) identical to the amino acid sequence of SEQ ID NO:7 can be paired with an antibody light chain variable domain at least 90% (e.g., 91%, 92%, 93%, 94%, 95%, 96%, 97%, 98%, 99%, or 100%) identical to the amino acid sequence of SEQ ID NO:8, which includes amino acid sequences RSSQSLLYSNGYNYLD [SEQ ID NO:42] as CDR1, LGSNRAS [SEQ ID NO:43] as CDR2, and MQDVALPIT [SEQ ID NO:44] as CDR3 of SEQ ID NO:8.

In certain embodiments, the present invention provides an antigen binding site that binds to a unique epitope on human CD33 that includes R69; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

In certain embodiments, the present invention provides an antigen binding site that binds to a unique epitope on human CD33 that includes R69; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:290. In some embodiments, the antibody heavy chain variable domain is at least 95% identical to SEQ ID NO:290. In some embodiments, the heavy chain variable domain incorporates amino acid sequences SEQ ID NO:376 as CDR1, SEQ ID NO:377 as CDR2, and SEQ ID NO:378 as CDR3 of SEQ ID NO:290. In some embodiments, the heavy chain variable domain incorporates amino acid sequences SEQ ID NO:552 as CDR1, SEQ ID NO:377 as CDR2, and SEQ ID NO:553 as CDR3 of SEQ ID NO:290. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:290 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291, which includes amino acid sequences SEQ ID NO:379 as CDR1, SEQ ID NO:380 as CDR2, and SEQ ID NO:381 as CDR3 of SEQ ID NO:291.

In certain embodiments, the present invention provides an antigen binding site that binds to a unique epitope on human CD33 that includes R69; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:300. In some embodiments, the antibody heavy chain variable domain is at least 95% identical to SEQ ID NO:300. In some embodiments, the heavy chain variable domain incorporates amino acid sequences SEQ ID NO:406 as CDR1, SEQ ID NO:407 as CDR2, and SEQ ID NO:408 as CDR3 of SEQ ID NO:300.

In some embodiments, the heavy chain variable domain incorporates amino acid sequences SEQ ID NO:562 as CDR1, SEQ ID NO:407 as CDR2, and SEQ ID NO:563 as CDR3 of SEQ ID NO:300. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:300 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301, which includes amino acid sequences SEQ ID NO:409 as CDR1, SEQ ID NO:410 as CDR2, and SEQ ID NO:411 as CDR3 of SEQ ID NO:301.

An Antigen Binding Site that Binds to the S128N Allele of Human CD33

In one aspect, the present invention provides an antigen binding site that binds to the S128N allele of human CD33.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:268. In some embodiments, the antibody heavy chain variable domain is at least 95% identical to SEQ ID NO:268. In some embodiments, the heavy chain variable domain incorporates amino acid sequences SEQ ID NO:310 as CDR1, SEQ ID NO:311 as CDR2, and SEQ ID NO:312 as CDR3 of SEQ ID NO:268. In some embodiments, the heavy chain variable domain incorporates amino acid sequences SEQ ID NO:530 as CDR1, SEQ ID NO:311 as CDR2, and SEQ ID NO:531 as CDR3 of SEQ ID NO:268. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:268 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:268 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:269, which includes amino acid sequences SEQ ID NO:313 as CDR1, SEQ ID NO:314 as CDR2, and SEQ ID NO:315 as CDR3 of SEQ ID NO:269.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:274. In some embodiments, the antibody heavy chain variable domain is at least 95% identical to SEQ ID NO:274. In some embodiments, the heavy chain variable domain incorporates amino acid sequences SEQ ID NO:328 as CDR1, SEQ ID NO:329 as CDR2, and SEQ ID NO:330 as CDR3 of SEQ ID NO:274. In some embodiments, the heavy chain variable domain incorporates amino acid sequences SEQ ID NO:536 as CDR1, SEQ ID NO:329 as CDR2, and SEQ ID NO:537 as CDR3 of SEQ ID NO:274. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:274 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:274 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:275, which includes amino acid sequences SEQ ID NO:331 as CDR1, SEQ ID NO:332 as CDR2, and SEQ ID NO:333 as CDR3 of SEQ ID NO:275.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:276. In some embodiments, the antibody heavy chain variable domain is at least 95% identical to SEQ ID NO:276. In some embodiments, the heavy chain variable domain incorporates amino acid sequences SEQ ID NO:334 as CDR1, SEQ ID NO:335 as CDR2, and SEQ ID NO:336 as CDR3 of SEQ ID NO:276. In some embodiments, the heavy chain variable domain incorporates amino acid sequences SEQ ID NO:538 as CDR1, SEQ ID NO:335 as CDR2, and SEQ ID NO:539 as CDR3 of SEQ ID NO:276. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:276 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%)

identical to the amino acid sequence of SEQ ID NO:277. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:276 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:277, which includes amino acid sequences SEQ ID NO:337 as CDR1, SEQ ID NO:338 as CDR2, and SEQ ID NO:339 as CDR3 of SEQ ID NO:277.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:292. In some embodiments, the antibody heavy chain variable domain is at least 95% identical to SEQ ID NO:292. In some embodiments, the heavy chain variable domain incorporates amino acid sequences SEQ ID NO:382 as CDR1, SEQ ID NO:383 as CDR2, and SEQ ID NO:384 as CDR3 of SEQ ID NO:292. In some embodiments, the heavy chain variable domain incorporates amino acid sequences SEQ ID NO:554 as CDR1, SEQ ID NO:383 as CDR2, and SEQ ID NO:555 as CDR3 of SEQ ID NO:292. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:292 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:292 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:293, which includes amino acid sequences SEQ ID NO:385 as CDR1, SEQ ID NO:386 as CDR2, and SEQ ID NO:387 as CDR3 of SEQ ID NO:293.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:294. In some embodiments, the antibody heavy chain variable domain is at least 95% identical to SEQ ID NO:294. In some embodiments, the heavy chain variable domain incorporates amino acid sequences SEQ ID NO:388 as CDR1, SEQ ID NO:389 as CDR2, and SEQ ID NO:390 as CDR3 of SEQ ID NO:294. In some embodiments, the heavy chain variable domain incorporates amino acid sequences SEQ ID NO:556 as CDR1, SEQ ID NO:389 as CDR2, and SEQ ID NO:557 as CDR3 of SEQ ID NO:294. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:294 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:294 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:295, which includes amino acid sequences SEQ ID NO:391 as CDR1, SEQ ID NO:392 as CDR2, and SEQ ID NO:393 as CDR3 of SEQ ID NO:295.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:296. In some embodiments, the antibody heavy chain variable domain is at least 95% identical to SEQ ID NO:296. In some embodiments, the heavy chain variable domain incorporates amino acid sequences SEQ ID NO:394 as CDR1, SEQ ID NO:395 as CDR2, and SEQ ID NO:396 as CDR3 of SEQ ID NO:296. In some embodiments, the heavy chain variable domain incorporates amino acid sequences SEQ ID NO:558 as CDR1, SEQ ID NO:395 as CDR2, and SEQ ID NO:559 as CDR3 of SEQ ID NO:296. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:296 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:296 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:297, which includes amino acid sequences SEQ ID NO:397 as CDR1, SEQ ID NO:398 as CDR2, and SEQ ID NO:399 as CDR3 of SEQ ID NO:297.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:298. In some embodiments, the antibody heavy chain variable domain is at least 95% identical to SEQ ID NO:298. In some embodiments, the heavy chain variable domain incorporates amino acid sequences SEQ ID NO:400 as CDR1, SEQ ID NO:401 as CDR2, and SEQ ID NO:402 as CDR3 of SEQ ID NO:298. In some embodiments, the heavy chain variable domain incorporates amino acid sequences SEQ ID NO:560 as CDR1, SEQ ID NO:401 as CDR2, and SEQ ID NO:561 as CDR3 of SEQ ID NO:298. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:298 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:298 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:299, which includes amino acid sequences SEQ ID NO:403 as CDR1, SEQ ID NO:404 as CDR2, and SEQ ID NO:405 as CDR3 of SEQ ID NO:299.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:290. In some embodiments, the antibody heavy chain variable domain is at least 95% identical to SEQ ID NO:290. In some embodiments, the heavy chain variable domain incorporates amino acid sequences SEQ ID NO:376 as CDR1, SEQ ID NO:377 as CDR2, and SEQ ID NO:378 as CDR3 of SEQ ID NO:290. In some embodiments, the heavy chain variable domain incorporates amino acid sequences SEQ ID NO:552 as CDR1, SEQ ID NO:377 as CDR2, and SEQ ID NO:553 as CDR3 of SEQ ID NO:290. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:290 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:290 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:291, which includes amino acid sequences SEQ ID NO:379 as CDR1, SEQ ID NO:380 as CDR2, and SEQ ID NO:381 as CDR3 of SEQ ID NO:291.

In certain embodiments, the present invention provides an antigen binding site that binds to the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:300. In some embodiments, the antibody heavy chain variable domain is at least 95% identical to SEQ ID NO:300. In some embodiments, the heavy chain variable domain incorporates amino acid sequences SEQ ID NO:406 as CDR1, SEQ ID NO:407 as CDR2, and SEQ ID NO:408 as CDR3 of SEQ ID NO:300. In some embodiments, the heavy chain variable domain incorporates amino acid sequences SEQ ID NO:562 as CDR1, SEQ ID NO:407 as CDR2, and SEQ ID NO:563 as CDR3 of SEQ ID NO:300. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:300 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:300 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:301, which includes amino acid sequences SEQ ID NO:409 as CDR1, SEQ ID NO:410 as CDR2, and SEQ ID NO:411 as CDR3 of SEQ ID NO:301.

An Antigen Binding Site that does not Bind to the S128N Allele of Human CD33

In one aspect, the present invention provides an antigen binding site including a heavy chain variable domain that binds to wild-type human CD33 but not the S128N allele of human CD33.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:302. In some embodiments, the antibody heavy chain variable domain is at least 95% identical to SEQ ID NO:302. In some embodiments, the heavy chain variable domain incorporates amino acid sequences SEQ ID NO:412 as CDR1, SEQ ID NO:413 as CDR2, and SEQ ID NO:414 as CDR3 of SEQ ID NO:302. In some embodiments, the heavy chain variable domain incorporates amino acid sequences SEQ ID NO:564 as CDR1, SEQ ID NO:413 as CDR2, and SEQ ID NO:565 as CDR3 of SEQ ID NO:302. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:302 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303, which includes amino acid sequences SEQ ID NO:415 as CDR1, SEQ ID NO:416 as CDR2, and SEQ ID NO:417 as CDR3 of SEQ ID NO:303.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:266. In some embodiments, the antibody heavy chain variable domain is at least 95% identical to SEQ ID NO:266. In some embodiments, the heavy chain variable domain incorporates amino acid sequences SEQ ID NO:304 as CDR1, SEQ ID NO:305 as CDR2, and SEQ ID NO:306 as CDR3 of SEQ ID NO:266. In some embodiments, the heavy chain variable domain incorporates amino acid sequences SEQ ID NO:528 as CDR1, SEQ ID NO:305 as CDR2, and SEQ ID NO:529 as CDR3 of SEQ ID NO:266. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:266 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267, which includes amino acid sequences SEQ ID NO:307 as CDR1, SEQ ID NO:308 as CDR2, and SEQ ID NO:309 as CDR3 of SEQ ID NO:267.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:270. In some embodiments, the antibody heavy chain variable domain is at least 95% identical to SEQ ID NO:270. In some embodiments, the heavy chain variable domain incorporates amino acid sequences SEQ ID NO:316 as CDR1, SEQ ID NO:317 as CDR2, and SEQ ID NO:318 as CDR3 of SEQ ID NO:270. In some embodiments, the heavy chain variable domain incorporates amino acid sequences SEQ ID NO:532 as CDR1, SEQ ID NO:317 as CDR2, and SEQ ID NO:533 as CDR3 of SEQ ID NO:270. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:270 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271, which includes amino acid sequences SEQ ID NO:319 as CDR1, SEQ ID NO:320 as CDR2, and SEQ ID NO:321 as CDR3 of SEQ ID NO:271.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:272. In some embodiments, the antibody heavy chain variable domain is at least 95% identical to SEQ ID NO:272. In some embodiments, the heavy chain variable domain incorporates amino acid sequences SEQ ID NO:322 as CDR1, SEQ ID NO:323 as CDR2, and SEQ ID NO:324 as CDR3 of SEQ ID NO:272. In some embodiments, the heavy chain variable domain incorporates amino acid sequences SEQ ID NO:534 as CDR1, SEQ ID NO:323 as CDR2, and SEQ ID NO:535 as CDR3 of SEQ ID NO:272. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:272 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273, which includes amino acid sequences SEQ ID NO:325 as CDR1, SEQ ID NO:326 as CDR2, and SEQ ID NO:327 as CDR3 of SEQ ID NO:273.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:278. In some embodiments, the antibody heavy chain variable domain is at least 95% identical to SEQ ID NO:278. In some embodiments, the heavy chain variable domain incorporates amino acid sequences SEQ ID NO:340 as CDR1, SEQ ID NO:341 as CDR2, and SEQ ID NO:342 as CDR3 of SEQ ID NO:278. In some embodiments, the heavy chain variable domain incorporates amino acid sequences SEQ ID NO:540 as CDR1, SEQ ID NO:341 as CDR2, and SEQ ID NO:541 as CDR3 of SEQ ID NO:278. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:278 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279, which includes amino acid sequences SEQ ID NO:343 as CDR1, SEQ ID NO:344 as CDR2, and SEQ ID NO:345 as CDR3 of SEQ ID NO:279.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:280. In some embodiments, the antibody heavy chain variable domain is at least 95% identical to SEQ ID NO:280. In some embodiments, the heavy chain variable domain incorporates amino acid sequences SEQ ID NO:346 as CDR1, SEQ ID NO:347 as CDR2, and SEQ ID NO:348 as CDR3 of SEQ ID NO:280. In some embodiments, the heavy chain variable domain incorporates amino acid sequences SEQ ID NO:542 as CDR1, SEQ ID NO:347 as CDR2, and SEQ ID NO:543 as CDR3 of SEQ ID NO:280. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:280 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281, which includes amino acid sequences SEQ ID NO:349 as CDR1, SEQ ID NO:350 as CDR2, and SEQ ID NO:351 as CDR3 of SEQ ID NO:281.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:282. In some embodiments, the antibody heavy chain variable domain is at least 95% identical to SEQ ID NO:282. In some embodiments, the heavy chain variable domain incorporates amino acid sequences SEQ ID NO:352 as CDR1, SEQ ID NO:353 as CDR2, and SEQ ID NO:354 as CDR3 of SEQ ID NO:282. In some embodiments, the heavy chain variable domain incorporates amino acid sequences SEQ ID NO:544 as CDR1, SEQ ID NO:353 as CDR2, and SEQ ID NO:545 as CDR3 of SEQ ID NO:282. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:282 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283. In certain embodiments, an antibody heavy chain variable domain at least 90% (e.g., at least 91%, 92%, 93%, 94%, 95%, 96%, 9'7%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283, which includes amino acid sequences SEQ ID NO:355 as CDR1, SEQ ID NO:356 as CDR2, and SEQ ID NO:357 as CDR3 of SEQ ID NO:283.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:284. In some embodiments, the antibody heavy chain variable domain is at least 95% identical to SEQ ID NO:284. In some embodiments, the heavy chain variable domain incorporates amino acid sequences SEQ ID NO:358 as CDR1, SEQ ID NO:359 as CDR2, and SEQ ID NO:360 as CDR3 of SEQ ID NO:284. In some embodiments, the heavy chain variable domain incorporates amino acid sequences SEQ ID NO:546 as CDR1, SEQ ID NO:359 as CDR2, and SEQ ID NO:360 as CDR3 of SEQ ID NO:547. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:284 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285, which includes amino acid sequences SEQ ID NO:361 as CDR1, SEQ ID NO:362 as CDR2, and SEQ ID NO:363 as CDR3 of SEQ ID NO:285.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:286. In some embodiments, the antibody heavy chain variable domain is at least 95% identical to SEQ ID NO:286. In some embodiments, the heavy chain variable domain incorporates amino acid sequences SEQ ID NO:364 as CDR1, SEQ ID NO:365 as CDR2, and SEQ ID NO:366 as CDR3 of SEQ ID NO:286. In some embodiments, the heavy chain variable domain incorporates amino acid sequences SEQ ID NO:548 as CDR1, SEQ ID NO:365 as CDR2, and SEQ ID NO:549 as CDR3 of SEQ ID NO:286. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:286 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287, which includes amino acid sequences SEQ ID NO:367 as CDR1, SEQ ID NO:368 as CDR2, and SEQ ID NO:369 as CDR3 of SEQ ID NO:287.

In certain embodiments, the present invention provides an antigen binding site that binds to wild-type human CD33 but not the S128N allele of human CD33; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

An Antigen Binding Site that Binds to a Unique Epitope Including S128 on Human CD33

In one aspect, the present invention provides an antigen binding site including a heavy chain variable domain that binds to a unique epitope on human CD33 that includes S128.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:302. In some embodiments, the antibody heavy chain variable domain is at least 95% identical to SEQ ID NO:302. In some embodiments, the heavy chain variable domain incorporates amino acid sequences SEQ ID NO:412 as CDR1, SEQ ID NO:413 as CDR2, and SEQ ID NO:414 as CDR3 of SEQ ID NO:302. In some embodiments, the heavy chain variable domain incorporates amino acid sequences SEQ ID NO:564 as CDR1, SEQ ID NO:413 as CDR2, and SEQ ID NO:565 as CDR3 of SEQ ID NO:302. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:302 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:302 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:303, which includes amino acid sequences SEQ ID NO:415 as CDR1, SEQ ID NO:416 as CDR2, and SEQ ID NO:417 as CDR3 of SEQ ID NO:303.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:266. In some embodiments, the antibody heavy chain variable domain is at least 95% identical to SEQ ID NO:266. In some embodiments, the heavy chain variable domain incorporates amino acid sequences SEQ ID NO:304 as CDR1, SEQ ID NO:305 as CDR2, and SEQ ID NO:306 as CDR3 of SEQ ID NO:266. In some embodiments, the heavy chain variable domain incorporates amino acid sequences SEQ ID NO:528 as CDR1, SEQ ID NO:305 as CDR2, and SEQ ID NO:529 as CDR3 of SEQ ID NO:266. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:266 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:266 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:267, which includes amino acid sequences SEQ ID NO:307 as CDR1, SEQ ID NO:308 as CDR2, and SEQ ID NO:309 as CDR3 of SEQ ID NO:267.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:270. In some embodiments, the antibody heavy chain variable domain is at least 95% identical to SEQ ID NO:270. In some embodiments, the heavy chain variable domain incorporates amino acid sequences SEQ ID NO:316 as CDR1, SEQ ID NO:317 as CDR2, and SEQ ID NO:318 as CDR3 of SEQ ID NO:270. In some embodiments, the heavy chain variable domain incorporates amino acid sequences SEQ ID NO:532 as CDR1, SEQ ID NO:317 as CDR2, and SEQ ID NO:533 as CDR3 of SEQ ID NO:270. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:270 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:270 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:271, which includes amino acid sequences SEQ ID NO:319 as CDR1, SEQ ID NO:320 as CDR2, and SEQ ID NO:321 as CDR3 of SEQ ID NO:271.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:272. In some embodiments, the antibody heavy chain variable domain is at least 95% identical to SEQ ID NO:272. In some embodiments, the heavy chain variable domain incorporates amino acid sequences SEQ ID NO:322 as CDR1, SEQ ID NO:323 as CDR2, and SEQ ID NO:324 as CDR3 of SEQ ID NO:272. In some embodiments, the heavy chain variable domain incorporates amino acid sequences SEQ ID NO:534 as CDR1, SEQ ID NO:323 as CDR2, and SEQ ID NO:535 as CDR3 of SEQ ID NO:272. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:272 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:272 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:273, which includes amino acid sequences SEQ ID NO:325 as CDR1, SEQ ID NO:326 as CDR2, and SEQ ID NO:327 as CDR3 of SEQ ID NO:273.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:278. In some embodiments, the antibody heavy chain variable domain is at least 95% identical to SEQ ID NO:278. In some embodiments, the heavy chain variable domain incorporates amino acid sequences SEQ ID NO:340 as CDR1, SEQ ID NO:341 as CDR2, and SEQ ID NO:342 as CDR3 of SEQ ID NO:278. In some embodiments, the heavy chain variable domain incorporates amino acid sequences SEQ ID NO:540 as CDR1, SEQ ID NO:341 as CDR2, and SEQ ID NO:541 as CDR3 of SEQ ID NO:278. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:278 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279, which includes amino acid sequences SEQ ID NO:343 as CDR1, SEQ ID NO:344 as CDR2, and SEQ ID NO:345 as CDR3 of SEQ ID NO:279.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:280. In some embodiments, the antibody heavy chain variable domain is at least 95% identical to SEQ ID NO:280. In some embodiments, the heavy chain variable domain incorporates amino acid sequences SEQ ID NO:346 as CDR1, SEQ ID NO:347 as CDR2, and SEQ ID NO:348 as CDR3 of SEQ ID NO:280. In some embodiments, the heavy chain variable domain incorporates amino acid sequences SEQ ID NO:542 as CDR1, SEQ ID NO:347 as CDR2, and SEQ ID NO:543 as CDR3 of SEQ ID NO:280. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:280 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:280 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:281, which includes amino acid sequences SEQ ID NO:349 as CDR1, SEQ ID NO:350 as CDR2, and SEQ ID NO:351 as CDR3 of SEQ ID NO:281.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:282. In some embodiments, the antibody heavy chain variable domain is at least 95% identical to SEQ ID NO:282. In some embodiments, the heavy chain variable domain incorporates amino acid sequences SEQ ID NO:352 as CDR1, SEQ ID NO:353 as CDR2, and SEQ ID NO:354 as CDR3 of SEQ ID NO:282. In some embodiments, the heavy chain variable domain incorporates amino acid sequences SEQ ID NO:544 as CDR1, SEQ ID NO:353 as CDR2, and SEQ ID NO:545 as CDR3 of SEQ ID NO:282. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:282 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283, which includes amino acid sequences SEQ ID NO:355 as CDR1, SEQ ID NO:356 as CDR2, and SEQ ID NO:357 as CDR3 of SEQ ID NO:283.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:284. In some embodiments, the antibody heavy chain variable domain is at least 95% identical to SEQ ID NO:284. In some embodiments, the heavy chain variable domain incorporates amino acid sequences SEQ ID NO:358 as CDR1, SEQ ID NO:359 as CDR2, and SEQ ID NO:360 as CDR3 of SEQ ID NO:284. In some embodiments, the heavy chain variable domain incorporates amino acid sequences SEQ ID NO:546 as CDR1, SEQ ID NO:359 as CDR2, and SEQ ID NO:360 as CDR3 of SEQ ID NO:547. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:284 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285, which includes amino acid sequences SEQ ID NO:361 as CDR1, SEQ ID NO:362 as CDR2, and SEQ ID NO:363 as CDR3 of SEQ ID NO:285.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:286. In some embodiments, the antibody heavy chain variable domain is at least 95% identical to SEQ ID NO:286. In some embodiments, the heavy chain variable domain incorporates amino acid sequences SEQ ID NO:364 as CDR1, SEQ ID NO:365 as CDR2, and SEQ ID NO:366 as CDR3 of SEQ ID NO:286. In some embodiments, the heavy chain variable domain incorporates amino acid sequences SEQ ID NO:548 as CDR1, SEQ ID NO:365 as CDR2, and SEQ ID NO:549 as CDR3 of SEQ ID NO:286. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:286 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:286 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:287, which includes amino acid sequences SEQ ID NO:367 as CDR1, SEQ ID NO:368 as CDR2, and SEQ ID NO:369 as CDR3 of SEQ ID NO:287.

In certain embodiments, the present invention provides an antigen binding site that binds to a unique epitope on human CD33 that includes S128; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

An Antigen Binding Site Binds to the V Domain of Human CD33 in a Glycosylation Sensitive Manner In one aspect, the present invention provides an antigen binding site including a heavy chain variable domain that binds to the V domain of human CD33 in a glycosylation sensitive manner, e.g., binds to the V domain of CD33 only when the V domain is deglycosylated.

In certain embodiments, the present invention provides an antigen binding site that binds an epitope in the V domain of human CD33 only when the V domain is deglycosylated; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:278. In some embodiments, the antibody heavy chain variable domain is at least 95% identical to SEQ ID NO:278. In some embodiments, the heavy chain variable domain incorporates amino acid sequences SEQ ID NO:340 as CDR1, SEQ ID NO:341 as CDR2, and SEQ ID NO:342 as CDR3 of SEQ ID NO:278. In some embodiments, the heavy chain variable domain incorporates amino acid sequences SEQ ID NO:540 as CDR1, SEQ ID NO:341 as CDR2, and SEQ ID NO:541 as CDR3 of SEQ ID NO:278. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:278 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:278 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:279, which includes amino acid sequences SEQ ID NO:343 as CDR1, SEQ ID NO:344 as CDR2, and SEQ ID NO:345 as CDR3 of SEQ ID NO:279.

In certain embodiments, the present invention provides an antigen binding site that binds an epitope in the V domain of human CD33 only when the V domain is deglycosylated; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:282. In some embodiments, the antibody heavy chain variable domain is at least 95% identical to SEQ ID NO:282. In some embodiments, the heavy chain variable domain incorporates amino acid sequences SEQ ID NO:352 as CDR1, SEQ ID NO:353 as CDR2, and SEQ ID NO:354 as CDR3 of SEQ ID NO:282. In some embodiments, the heavy chain variable domain incorporates amino acid sequences SEQ ID NO:544 as CDR1, SEQ ID NO:353 as CDR2, and SEQ ID NO:545 as CDR3 of SEQ ID NO:282. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:282 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:282 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:283, which includes amino acid sequences SEQ ID NO:355 as CDR1, SEQ ID NO:356 as CDR2, and SEQ ID NO:357 as CDR3 of SEQ ID NO:283.

In certain embodiments, the present invention provides an antigen binding site that binds an epitope in the V domain of human CD33 only when the V domain is deglycosylated; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:284. In some embodiments, the antibody heavy chain variable domain is at least 95% identical to SEQ ID NO:284. In some embodiments, the heavy chain variable domain incorporates amino acid sequences SEQ ID NO:358 as CDR1, SEQ ID NO:359 as CDR2, and SEQ ID NO:360 as CDR3 of SEQ ID NO:284. In some embodiments, the heavy chain variable domain incorporates amino acid sequences SEQ ID NO:546 as CDR1, SEQ ID NO:359 as CDR2, and SEQ ID NO:360 as CDR3 of SEQ ID NO:547. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:284 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:284 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:285, which includes amino acid sequences SEQ ID NO:361 as CDR1, SEQ ID NO:362 as CDR2, and SEQ ID NO:363 as CDR3 of SEQ ID NO:285.

In certain embodiments, the present invention provides an antigen binding site that binds an epitope in the V domain of human CD33 only when the V domain is deglycosylated; the antigen binding site includes a heavy chain variable domain including an amino acid sequence at least 90% (e.g., at least 91%, 92%, 93%, 94%, 95%, 96%, 97%, 98%, 99%, or 100%) identical to the amino acid sequence of SEQ ID NO:288. In some embodiments, the antibody heavy chain variable domain is at least 95% identical to SEQ ID NO:288. In some embodiments, the heavy chain variable domain incorporates amino acid sequences SEQ ID NO:370 as CDR1, SEQ ID NO:371 as CDR2, and SEQ ID NO:372 as CDR3 of SEQ ID NO:288. In some embodiments, the heavy chain variable domain incorporates amino acid sequences SEQ ID NO:550 as CDR1, SEQ ID NO:371 as CDR2, and SEQ ID NO:551 as CDR3 of SEQ ID NO:288. In certain embodiments, the antibody heavy chain variable domain which includes an amino acid sequence at least 90% (e.g., at least 91%, 92%, 93%, 94%, 95%, 96%, 97%, 98%, 99%, or 100%) identical to the amino acid sequence of SEQ ID NO:288 is combined with a light chain variable domain to form an antigen-binding site capable of binding to CD33. For example, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289. In certain embodiments, an antibody heavy chain variable domain at least 90% (e.g., at least 91%, 92%, 93%, 94%, 95%, 96%, 97%, 98%, 99%, or 100%) identical to the amino acid sequence of SEQ ID NO:288 can be paired with an antibody light chain variable domain at least 90% (e.g., at least 91%, 92%, 93%, 94%, 95%, 96%, 97%, 98%, 99%, or 100%) identical to the amino acid sequence of SEQ ID NO:289, which includes amino acid sequences SEQ ID NO:373 as CDR1, SEQ ID NO:374 as CDR2, and SEQ ID NO:375 as CDR3 of SEQ ID NO:289.

An Antigen Binding Site that Binds to the Extracellular Domain in Human CD33 and/or Cyno CD33, Irrespective of the Glycosylation Profile of the Targeted CD33

In one aspect, the present invention provides an antigen binding site including a heavy chain variable domain which includes an amino acid sequence at least 90% (e.g., 90%, 91%, 92%, 93%, 94%, 95%, 96%, 97%, 98%, 99%, or 100%) identical to the amino acid sequence of SEQ ID NO: 1, 3, 5, 7, 9, 11, 13, 15, 17, 19, 266, 268, 270, 272, 274, 276, 278, 280, 282, 284, 286, 288, 290, 292, 294, 296, 298, 300, or 302, which binds to the extracellular domain in human CD33 irrespective of the glycosylation profile of the targeted CD33.

In certain embodiments, the present invention provides an antigen binding site including a heavy chain variable domain that binds to the extracellular domain in human CD33 and/or cyno CD33, such that the epitopes are unique compared to the epitopes targeted by one or more known anti-CD33 antibodies in the art. In certain embodiments, the present invention provides an antigen binding site including a heavy chain variable domain that binds to the extracellular domain in human CD33 and/or cyno CD33, which shows human or Cynomolgus/Rhesus (cyno) CD33 cross reactivity and high affinity binding to the target CD33.

A Second Antigen Binding Site Same or Different from the Antigen-Binding Site that Binds Human CD33

In certain embodiments, the present invention provides a protein that includes a human CD33 antigen-binding site including a heavy chain variable domain, which includes an amino acid sequence at least 90% (e.g., 90%, 91%, 92%, 93%, 94%, 95%, 96%, 97%, 98%, 99%, or 100%) identical to the amino acid sequence of SEQ ID NO: 1, 3, 5, 7, 9, 11, 13, 15, 17, 19, 266, 268, 270, 272, 274, 276, 278, 280, 282, 284, 286, 288, 290, 292, 294, 296, 298, 300, or 302, and further comprises a second antigen binding site same or different from the antigen-binding site that binds to human CD33.

Proteins with Antigen-Binding Sites

An antibody heavy chain variable domain of SEQ ID NOs: 1, 3, 5, 7, 9, 11, 13, 15, 17, 19, 266, 268, 270, 272, 274, 276, 278, 280, 282, 284, 286, 288, 290, 292, 294, 296, 298, 300, and/or 302 can optionally be coupled to an amino acid sequence at least 90% (e.g., 90%, 91%, 92%, 93%, 94%, 95%, 96%, 97%, 98%, 99%, or 100%) identical to an antibody constant region, such as an IgG constant region including hinge, CH2 and CH3 domains with or without a CH1 domain. In some embodiments, the amino acid sequence of the constant region is at least 90% (e.g., 90%, 91%, 92%, 93%, 94%, 95%, 96%, 97%, 98%, 99%, or 100%) identical to a human antibody constant region, such as an human IgG1 constant region, an IgG2 constant region, IgG3 constant region, or IgG4 constant region. In some other embodiments, the amino acid sequence of the constant region is at least 90% (e.g., 90%, 91%, 92%, 93%, 94%, 95%, 96%, 97%, 98%, 99%, or 100%) identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

II. Multi-Specific Binding Proteins

In certain embodiments, the present invention provides an antigen-binding site in a protein (e.g., a multi-specific binding protein) that binds to CD33 on a cancer cell, and the NKG2D receptor and CD16 receptor on natural killer cells to activate the natural killer cell. As used herein, the term "antibody" encompasses proteins (e.g., multi-specific binding proteins) that comprise one or more antigen-binding sites (e.g., an antigen-binding site that binds CD33), and is not limited to single-specific antibodies. In certain embodiments, the protein (e.g., multi-specific binding protein) or antibody is a trispecific antibody, also called Trispecific NK cell Engagement Therapy (TriNKET). The protein (e.g., a multi-specific binding protein) is useful in the pharmaceutical compositions and therapeutic methods described herein. Binding of the protein including an antigen-binding site that binds to CD33, and to NKG2D receptor and CD16 receptor on natural killer cell enhances the activity of the natural killer cell toward destruction of a cancer cell. Binding of the protein including an antigen-binding site that binds to CD33 (e.g., a multi-specific binding protein) on a cancer cell brings the cancer cell into proximity to the natural killer cell, which facilitates direct and indirect destruction of the cancer cell by the natural killer cell. Further description of exemplary multi-specific binding proteins is provided below.

In certain embodiments of the present disclosure, the first component of the multi-specific binding proteins binds to CD33-expressing cells, which can include but are not limited to AML, myelodysplastic syndromes, chronic myelomonocytic leukemia, myeloid blast crisis of chronic myeloid leukemia, and ALLs.

In certain embodiments of the present disclosure, the second component of the multi-specific binding proteins binds to NKG2D receptor-expressing cells, which can include but are not limited to NK cells, γδ T cells and CD8$^+$ αβ T cells. Upon NKG2D binding, the multi-specific binding proteins may block natural ligands, such as ULBP6 and MICA, from binding to NKG2D and activating NKG2D receptors.

In certain embodiments of the present disclosure, the third component for the multi-specific binding proteins binds to cells expressing CD16, an Fc receptor on the surface of leukocytes including natural killer cells, macrophages, neutrophils, eosinophils, mast cells, and follicular dendritic cells.

Another aspect of the present invention provides a protein comprising an antigen-binding site that binds NKG2D, the antigen-binding site comprising a heavy chain variable domain comprising:

CDR1 comprising the amino acid sequence of SYSMN [SEQ ID NO:192];

CDR2 comprising the amino acid sequence of SIS-SSSSYIYYADSVKG [SEQ ID NO:112]; and CDR3 comprising the amino acid sequence of GAPXGAAAGWFDP [SEQ ID NO:527], wherein X is A, V, L, I, P, F, W, G, S, T, C, N, Q, or Y; and a light chain variable domain comprising:

CDR1 comprising the amino acid sequence of RASQ-GISSWLA [SEQ ID NO:114],

CDR2 comprising the amino acid sequence of AASSLQS [SEQ ID NO:115], and

CDR3 comprising the amino acid sequence of QQGVSF-PRT [SEQ ID NO:116].

In certain embodiments, X is A, V, L, I, P, F, or W. In certain embodiments, X is V, L, or I. In certain embodiments, the amino acid sequence of CDR3 in the heavy chain variable domain comprises the sequence of SEQ ID NO:123. In certain embodiments, the amino acid sequence of CDR3 in the heavy chain variable domain comprises the sequence of SEQ ID NO:195, SEQ ID NO:588, SEQ ID NO:591, SEQ ID NO:594, or SEQ ID NO:597.

In certain embodiments, the antigen-binding site comprises a heavy chain variable domain comprising an amino acid sequence at least 90% (e.g., 91%, 92%, 93%, 94%, 95%, 96%, 97%, 98%, or 99%) identical to the amino acid sequence of SEQ ID NO:191; and a light chain variable domain comprising an amino acid sequence at least 90% (e.g., 91%, 92%, 93%, 94%, 95%, 96%, 97%, 98%, or 99%) identical to the amino acid sequence of SEQ ID NO:81. In certain embodiments, the antigen-binding site comprises a heavy chain variable domain comprising the amino acid sequence of SEQ ID NO:191; and a light chain variable domain comprising the amino acid sequence of SEQ ID NO:81.

In certain embodiments, the antigen-binding site that binds NKG2D is in the form of an Fab fragment. In certain embodiments, the antigen-binding site that binds NKG2D is in the form of an scFv.

In certain embodiments, the present invention provides a protein comprising (a) a first antigen-binding site comprising an Fab fragment that binds NKG2D as disclosed herein; (b) a second antigen-binding site comprising a single-chain variable fragment (scFv) that binds a tumor associated antigen (e.g., CD33); and (c) an antibody Fc domain or a portion thereof sufficient to bind CD16, or a third antigen-binding site that binds CD16.

The multi-specific binding proteins described herein can take various formats. For example, one format is a heterodimeric, multi-specific antibody which includes a first immunoglobulin heavy chain, a first immunoglobulin light chain, a second immunoglobulin heavy chain and a second immunoglobulin light chain. The first immunoglobulin heavy chain includes a first Fc (hinge-CH2-CH3) domain, a first heavy chain variable domain and optionally a first CH1 heavy chain constant domain. The first immunoglobulin light chain includes a first light chain variable domain and a first light chain constant domain. The first immunoglobulin light chain, together with the first immunoglobulin heavy chain, forms an antigen-binding site that binds CD33. The second immunoglobulin heavy chain comprises a second Fc (hinge-CH2-CH3) domain, a second heavy chain variable domain and optionally a second CH1 heavy chain constant domain. The second immunoglobulin light chain includes a second light chain variable domain and a second light chain constant domain. The second immunoglobulin light chain, together with the second immunoglobulin heavy chain, forms an antigen-binding site that binds NKG2D. The first Fc domain and second Fc domain together are able to bind to CD16.

Another exemplary format involves a heterodimeric, multi-specific antibody which includes a first immunoglobulin heavy chain, a second immunoglobulin heavy chain and an immunoglobulin light chain. The first immunoglobulin heavy chain includes a first Fc (hinge-CH2-CH3) domain fused via either a linker or an antibody hinge to a single-chain variable fragment (scFv) composed of a heavy variable domain and light chain variable domain which pair and bind CD33 or NKG2D. The second immunoglobulin heavy chain includes a second Fc (hinge-CH2-CH3) domain, a second heavy chain variable domain and optionally a CH1 heavy chain domain. The immunoglobulin light chain includes a light chain variable domain and a constant light chain domain. The second immunoglobulin heavy chain pairs with the immunoglobulin light chain and binds to NKG2D or CD33. The first Fc domain and the second Fc domain together are able to bind to CD16.

One or more additional binding motifs may be fused to the C-terminus of the constant region CH3 domain, optionally via a linker sequence. In certain embodiments, the antigen-binding site could be a single-chain or disulfide-stabilized variable region (scFv) or could form a tetravalent or trivalent molecule.

In some embodiments, the multi-specific binding protein is in the Triomab form, which is a trifunctional, bispecific antibody that maintains an IgG-like shape. This chimera consists of two half antibodies, each with one light and one heavy chain, that originate from two parental antibodies.

In some embodiments, the multi-specific binding protein is the KiH Common Light Chain (LC) form, which involves the knobs-into-holes (KIHs) technology. The KIH involves engineering $C_H3$ domains to create either a "knob" or a "hole" in each heavy chain to promote heterodimerization. The concept behind the "Knobs-into-Holes (KiH)" Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., T366S/L368A/Y407V$_{CH3B}$). The "hole" mutation was optimized by structured-guided phage library screening (Atwell S, Ridgway J B, Wells J A, Carter P., Stable heterodimers from remodeling the domain interface of a homodimer using a phage display library, *J. Mol. Biol.* (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426(9):1947-57; Mimoto F, Kadono S, Katada H, Igawa T, Kamikawa T, Hattori K. Crystal structure of a novel asymmetrically engineered Fc variant with improved affinity for FcgammaRs. *Mol. Immunol.* (2014) 58(1):132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

In some embodiments, the multi-specific binding protein is in the dual-variable domain immunoglobulin (DVD-Ig™) form, which combines the target binding domains of two monoclonal antibodies via flexible naturally occurring linkers, and yields a tetravalent IgG-like molecule.

In some embodiments, the multi-specific binding protein is in the Orthogonal Fab interface (Ortho-Fab) form. In the ortho-Fab IgG approach (Lewis S M, Wu X, Pustilnik A, Sereno A, Huang F, Rick H L, et al., Generation of bispecific IgG antibodies by structure-based design of an orthogonal Fab interface. *Nat. Biotechnol.* (2014) 32(2):191-8), structure-based regional design introduces complementary mutations at the LC and HC interface in only one Fab, without any changes being made to the other Fab.

In some embodiments, the multi-specific binding protein is in the 2-in-1 Ig format. In some embodiments, the multi-specific protein is in the ES form, which is a heterodimeric construct containing two different Fabs binding to targets 1 and target 2 fused to the Fc. Heterodimerization is ensured by electrostatic steering mutations in the Fc.

Figure 30A:
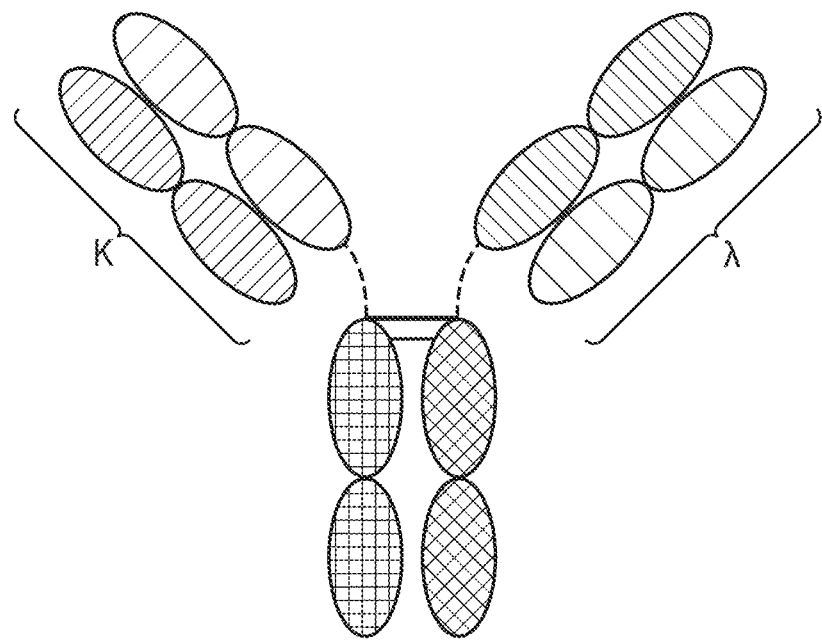
FIGS. 30A-30B represent TriNKETs in the κλ-Body forms, which are an heterodimeric constructs with two different Fabs fused to Fc stabilized by heterodimerization mutations: Fab1 targeting antigen 1 contains kappa LC, while second Fab targeting antigen 2 contains lambda LC.
Figure 30B:
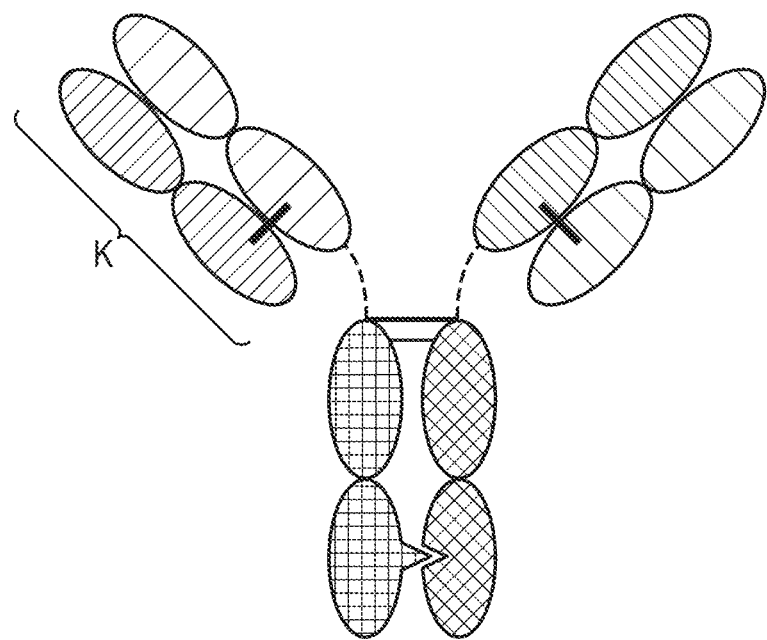
Figure 31:
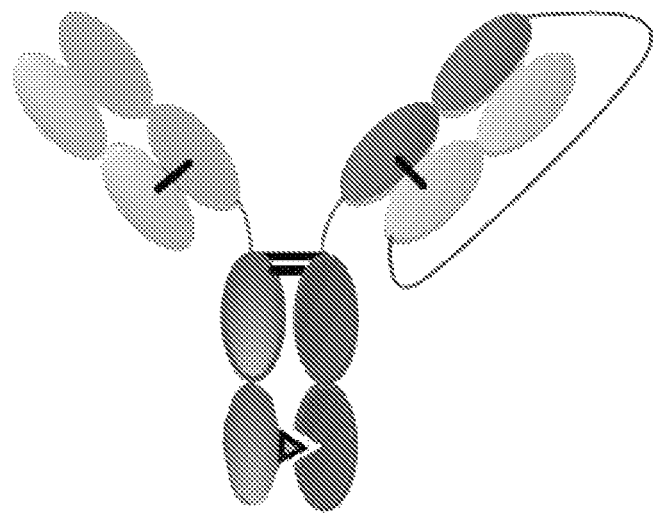
FIG. 31 is an Oasc-Fab heterodimeric construct that includes Fab binding to target 1 and scFab binding to target 2 fused to Fc. Heterodimerization is ensured by mutations in the Fc.
Figure 32:
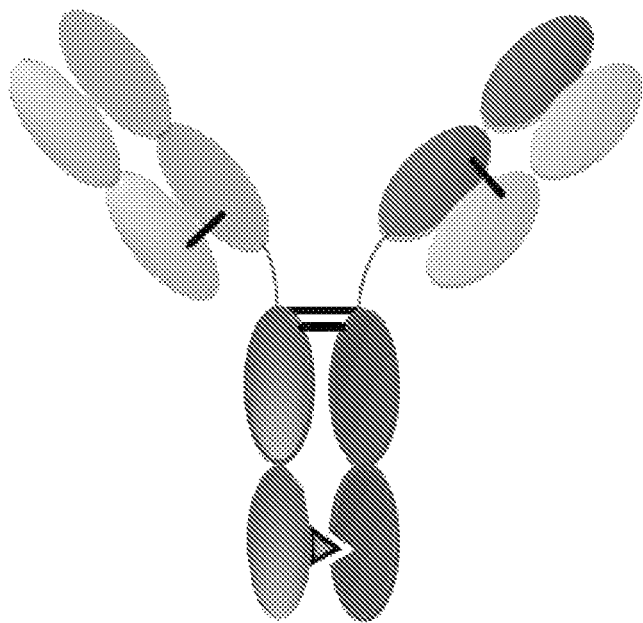
FIG. 32 is a DuetMab, which is an heterodimeric construct containing two different Fabs binding to antigens 1 and 2, and Fc stabilized by heterodimerization mutations. Fab 1 and 2 contain differential S-S bridges that ensure correct light chain (LC) and heavy chain (HC) pairing.
Figure 33:
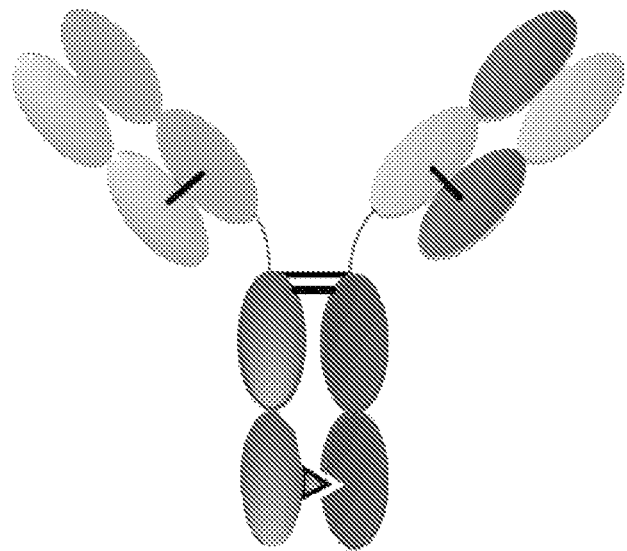
FIG. 33 is a CrossmAb, which is an heterodimeric construct with two different Fabs binding to targets 1 and 2 fused to Fc stabilized by heterodimerization. CL and CH1 domains and VH and VL domains are switched, e.g., CH1 is fused in-line with VL, while CL is fused in-line with VH.
Figure 34:
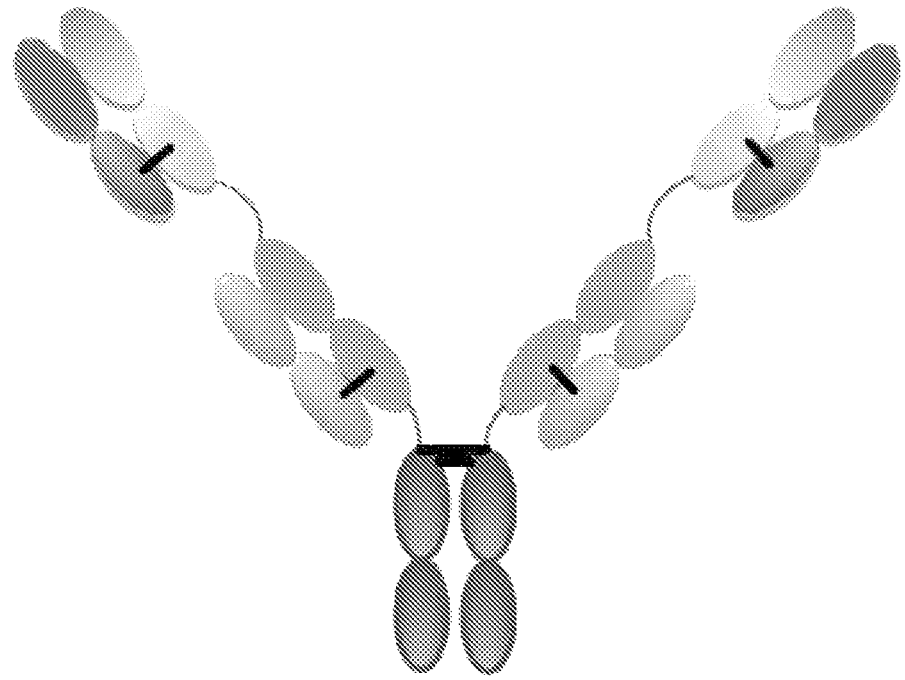
FIG. 34 is a Fit-Ig, which is a homodimeric constructs where Fab binding to antigen 2 is fused to the N terminus of HC of Fab that binds to antigen 1. The construct contains wild-type Fc.

In some embodiments, the multi-specific binding protein is in the κλ-Body form, which is an heterodimeric constructs with two different Fabs fused to Fc stabilized by heterodimerization mutations: Fab1 targeting antigen 1 contains kappa LC, while second Fab targeting antigen 2 contains lambda LC. FIG. 30A is an exemplary representation of one form of a κλ-Body; FIG. 30B is an exemplary representation of another κλ-Body.

In some embodiments, the multi-specific binding protein is in Fab Arm Exchange form (antibodies that exchange Fab arms by swapping a heavy chain and attached light chain (half-molecule) with a heavy-light chain pair from another molecule, which results in bispecific antibodies). In some embodiments, the multi-specific binding protein is in the SEED Body form. The strand-exchange engineered domain (SEED) platform was designed to generate asymmetric and bispecific antibody-like molecules, a capability that expands therapeutic applications of natural antibodies. This protein engineered platform is based on exchanging structurally related sequences of immunoglobulin within the conserved CH3 domains. The SEED design allows efficient generation of AG/GA heterodimers, while disfavoring homodimerization of AG and GA SEED CH3 domains. (Muda M. et al., Protein Eng. Des. Sel. (2011, 24(5):447-54)). In some embodiments, the multi-specific binding protein is in the LuZ-Y form, in which a leucine zipper is used to induce heterodimerization of two different HCs. (Wranik, B J. et al., J. Biol. Chem. (2012), 287:43331-9).

In some embodiments, the multi-specific binding protein is in the Cov-X-Body form. In bispecific CovX-Bodies, two different peptides are joined together using a branched azetidinone linker and fused to the scaffold antibody under mild conditions in a site-specific manner. Whereas the pharmacophores are responsible for functional activities, the antibody scaffold imparts long half-life and Ig-like distribution. The pharmacophores can be chemically optimized or replaced with other pharmacophores to generate optimized or unique bispecific antibodies. (Doppalapudi V R et al., PNAS (2010), 107(52); 22611-22616).

In some embodiments, the multi-specific binding protein is in an Oasc-Fab heterodimeric form that includes Fab binding to target 1, and scFab binding to target 2 fused to Fc. Heterodimerization is ensured by mutations in the Fc.

In some embodiments, the multi-specific binding protein is in a DuetMab form, which is an heterodimeric construct containing two different Fabs binding to antigens 1 and 2, and Fc stabilized by heterodimerization mutations. Fab1 and 2 contain differential S-S bridges that ensure correct LC and HC pairing.

In some embodiments, the multi-specific binding protein is in a CrossmAb form, which is an heterodimeric construct with two different Fabs binding to targets 1 and 2, fused to Fc stabilized by heterodimerization. CL and CH1 domains and VH and VL domains are switched, e.g., CH1 is fused in-line with VL, while CL is fused in-line with VH.

In some embodiments, the multi-specific binding protein is in a Fit-Ig form, which is a homodimeric constructs where Fab binding to antigen 2 is fused to the N terminus of HC of Fab that binds to antigen 1. The construct contains wild-type Fc.

Additional formats of the multi-specific binding proteins can be devised by combining various formats of CD33 binding-fragments described herein.

In certain embodiments of the present disclosure, the third component for the multi-specific binding proteins is an antibody constant region. In certain embodiments, each of the two immunoglobulin heavy chains of the antibody constant region includes a constant region with an amino acid sequence at least 90% (e.g., 90%, 91%, 92%, 93%, 94%, 95%, 96%, 97%, 98%, 99%, or 100%) identical to human IgG1 constant region. In certain embodiments, the amino acid sequence of one polypeptide chain of the antibody constant region differs from the amino acid sequence of an IgG1 constant region at one or more positions selected from the group consisting of Q347, Y349, L351, S354, E356, E357, K360, Q362, S364, T366, L368, K370, K392, T394, D399, S400, D401, F405, Y407, K409, T411 and K439; and the amino acid sequence of the other polypeptide chain of the antibody constant region differs from the amino acid sequence of an IgG1 constant region at one or more positions selected from the group consisting of Q347, Y349, L351, S354, E356, E357, S364, T366, L368, K370, N390, K392, T394, D399, D401, F405, Y407, K409, T411 and K439.

In certain embodiments of the present disclosure, the NKG2D-antigen binding site comprises:

(1) a heavy chain variable domain comprising an amino acid sequence at least 90% (e.g., 90%, 91%, 92%, 93%, 94%, 95%, 96%, 97%, 98%, 99%, or 100%) identical to SEQ ID NO:81 and a light chain variable domain comprising an amino acid sequence at least 90% (e.g., 90%, 91%, 92%, 93%, 94%, 95%, 96%, 97%, 98%, 99%, or 100%) identical to a SEQ ID NO:82 [ADI-29379];

(2) a heavy chain variable domain comprising an amino acid sequence at least 90% (e.g., 90%, 91%, 92%, 93%, 94%, 95%, 96%, 97%, 98%, 99%, or 100%) identical to SEQ ID NO:83 and a light chain variable domain comprising an amino acid sequence at least 90% (e.g., 90%, 91%, 92%, 93%, 94%, 95%, 96%, 97%, 98%, 99%, or 100%) identical to a SEQ ID NO:84 [ADI-29463];

(3) a heavy chain variable domain comprising an amino acid sequence at least 90% (e.g., 90%, 91%, 92%, 93%, 94%, 95%, 96%, 97%, 98%, 99%, or 100%) identical to SEQ ID NO:85 and a light chain variable domain comprising an amino acid sequence at least 90% (e.g., 90%, 91%, 92%, 93%, 94%, 95%, 96%, 97%, 98%, 99%, or 100%) identical to a SEQ ID NO:86 [ADI-27744];

(4) a heavy chain variable domain comprising an amino acid sequence at least 90% (e.g., 90%, 91%, 92%, 93%, 94%, 95%, 96%, 97%, 98%, 99%, or 100%) identical to SEQ ID NO:87 and a light chain variable domain comprising an amino acid sequence at least 90% (e.g., 90%, 91%, 92%, 93%, 94%, 95%, 96%, 97%, 98%, 99%, or 100%) identical to a SEQ ID NO:88 [ADI-27749];

(5) a heavy chain variable domain comprising an amino acid sequence at least 90% (e.g., 90%, 91%, 92%, 93%, 94%, 95%, 96%, 97%, 98%, 99%, or 100%) identical to SEQ ID NO:191 and a light chain variable domain comprising an amino acid sequence at least 90% (e.g., 90%, 91%, 92%, 93%, 94%, 95%, 96%, 97%, 98%, 99%, or 100%) identical to a SEQ ID NO:88 [A49MI]; or (6) a heavy chain variable domain comprising an amino acid sequence at least 90% (e.g., 90%, 91%, 92%, 93%, 94%, 95%, 96%, 97%, 98%, 99%, or 100%) identical to SEQ ID NO:89 and a light chain variable domain comprising an amino acid sequence at least 90% (e.g., 90%, 91%, 92%, 93%, 94%, 95%, 96%, 97%, 98%, 99%, or 100%) identical to a SEQ ID NO:90 [ADI-29378].

In certain embodiments of the present disclosure, the NKG2D-antigen binding site comprises:

(1) a heavy chain variable domain comprising an amino acid sequence at least 90% (e.g., 90%, 91%, 92%, 93%, 94%, 95%, 96%, 97%, 98%, 99%, or 100%) identical to SEQ ID NO:124 and a light chain variable domain comprising an amino acid sequence at least 90% (e.g., 90%, 91%, 92%, 93%, 94%, 95%, 96%, 97%, 98%, 99%, or 100%) identical to a SEQ ID NO:125 [ADI-27705];

(2) a heavy chain variable domain comprising an amino acid sequence at least 90% (e.g., 90%, 91%, 92%, 93%, 94%, 95%, 96%, 97%, 98%, 99%, or 100%) identical to SEQ ID NO:129 and a light chain variable domain comprising an amino acid sequence at least 90% (e.g., 90%, 91%, 92%, 93%, 94%, 95%, 96%, 97%, 98%, 99%, or 100%) identical to a SEQ ID NO:130 [ADI-27724];

(3) a heavy chain variable domain comprising an amino acid sequence at least 90% (e.g., 90%, 91%, 92%, 93%, 94%, 95%, 96%, 97%, 98%, 99%, or 100%) identical to SEQ ID NO:131 and a light chain variable domain comprising an amino acid sequence at least 90% (e.g., 90%, 91%, 92%, 93%, 94%, 95%, 96%, 97%, 98%, 99%, or 100%) identical to a SEQ ID NO:132 [ADI-27740];

(4) a heavy chain variable domain comprising an amino acid sequence at least 90% (e.g., 90%, 91%, 92%, 93%, 94%, 95%, 96%, 97%, 98%, 99%, or 100%) identical to SEQ ID NO:133 and a light chain variable domain comprising an amino acid sequence at least 90% (e.g., 90%, 91%, 92%, 93%, 94%, 95%, 96%, 97%, 98%, 99%, or 100%) identical to a SEQ ID NO:134 [ADI-27741];

(5) a heavy chain variable domain comprising an amino acid sequence at least 90% (e.g., 90%, 91%, 92%, 93%, 94%, 95%, 96%, 97%, 98%, 99%, or 100%) identical to SEQ ID NO:135 and a light chain variable domain comprising an amino acid sequence at least 90% (e.g., 90%, 91%, 92%, 93%, 94%, 95%, 96%, 97%, 98%, 99%, or 100%) identical to a SEQ ID NO:136 [ADI-27743];

(6) a heavy chain variable domain comprising an amino acid sequence at least 90% (e.g., 90%, 91%, 92%, 93%, 94%, 95%, 96%, 97%, 98%, 99%, or 100%) identical to SEQ ID NO:137 and a light chain variable domain comprising an amino acid sequence at least 90% (e.g., 90%, 91%, 92%, 93%, 94%, 95%, 96%, 97%, 98%, 99%, or 100%) identical to a SEQ ID NO:138 [ADI-28153];

(7) a heavy chain variable domain comprising an amino acid sequence at least 90% (e.g., 90%, 91%, 92%, 93%, 94%, 95%, 96%, 97%, 98%, 99%, or 100%) identical to SEQ ID NO:139 and a light chain variable domain comprising an amino acid sequence at least 90% (e.g., 90%, 91%, 92%, 93%, 94%, 95%, 96%, 97%, 98%, 99%, or 100%) identical to a SEQ ID NO:140 [ADI-28226 (C26)];

(8) a heavy chain variable domain comprising an amino acid sequence at least 90% (e.g., 90%, 91%, 92%, 93%, 94%, 95%, 96%, 97%, 98%, 99%, or 100%) identical to SEQ ID NO:141 and a light chain variable domain comprising an amino acid sequence at least 90% (e.g., 90%, 91%, 92%, 93%, 94%, 95%, 96%, 97%, 98%, 99%, or 100%) identical to a SEQ ID NO:142;

(9) a heavy chain variable domain comprising an amino acid sequence at least 90% (e.g., 90%, 91%, 92%, 93%, 94%, 95%, 96%, 97%, 98%, 99%, or 100%) identical to SEQ ID NO:143 and a light chain variable domain comprising an amino acid sequence at least 90% (e.g., 90%, 91%, 92%, 93%, 94%, 95%, 96%, 97%, 98%, 99%, or 100%) identical to a SEQ ID NO:144;

(10) a heavy chain variable domain comprising an amino acid sequence at least 90% (e.g., 90%, 91%, 92%, 93%, 94%, 95%, 96%, 97%, 98%, 99%, or 100%) identical to SEQ ID NO:145 and a light chain variable domain comprising an amino acid sequence at least 90% (e.g., 90%, 91%, 92%, 93%, 94%, 95%, 96%, 97%, 98%, 99%, or 100%) identical to a SEQ ID NO:146;

(11) a heavy chain variable domain comprising an amino acid sequence at least 90% (e.g., 90%, 91%, 92%, 93%, 94%, 95%, 96%, 97%, 98%, 99%, or 100%) identical to SEQ ID NO:147 and a light chain variable domain comprising an amino acid sequence at least 90% (e.g., 90%, 91%, 92%, 93%, 94%, 95%, 96%, 97%, 98%, 99%, or 100%) identical to a SEQ ID NO:148;

(12) a heavy chain variable domain comprising an amino acid sequence at least 90% (e.g., 90%, 91%, 92%, 93%, 94%, 95%, 96%, 97%, 98%, 99%, or 100%) identical to SEQ ID NO:149 and a light chain variable domain comprising an amino acid sequence at least 90% (e.g., 90%, 91%, 92%, 93%, 94%, 95%, 96%, 97%, 98%, 99%, or 100%) identical to a SEQ ID NO:150;

(13) a heavy chain variable domain comprising an amino acid sequence at least 90% (e.g., 90%, 91%, 92%, 93%, 94%, 95%, 96%, 97%, 98%, 99%, or 100%) identical to SEQ ID NO:151 and a light chain variable domain comprising an amino acid sequence at least 90% (e.g., 90%, 91%, 92%, 93%, 94%, 95%, 96%, 97%, 98%, 99%, or 100%) identical to a SEQ ID NO:152;

(14) a heavy chain variable domain comprising an amino acid sequence at least 90% (e.g., 90%, 91%, 92%, 93%, 94%, 95%, 96%, 97%, 98%, 99%, or 100%) identical to SEQ ID NO:153 and a light chain variable domain comprising an amino acid sequence at least 90% (e.g., 90%, 91%, 92%, 93%, 94%, 95%, 96%, 97%, 98%, 99%, or 100%) identical to a SEQ ID NO:154;

(15) a heavy chain variable domain comprising an amino acid sequence at least 90% (e.g., 90%, 91%, 92%, 93%, 94%, 95%, 96%, 97%, 98%, 99%, or 100%) identical to SEQ ID NO:155 and a light chain variable domain comprising an amino acid sequence at least 90% (e.g., 90%, 91%, 92%, 93%, 94%, 95%, 96%, 97%, 98%, 99%, or 100%) identical to a SEQ ID NO:156;

(16) a heavy chain variable domain comprising an amino acid sequence at least 90% (e.g., 90%, 91%, 92%, 93%, 94%, 95%, 96%, 97%, 98%, 99%, or 100%) identical to SEQ ID NO:157 and a light chain variable domain comprising an amino acid sequence at least 90% (e.g., 90%, 91%, 92%, 93%, 94%, 95%, 96%, 97%, 98%, 99%, or 100%) identical to a SEQ ID NO:158;

(17) a heavy chain variable domain comprising an amino acid sequence at least 90% (e.g., 90%, 91%, 92%, 93%, 94%, 95%, 96%, 97%, 98%, 99%, or 100%) identical to SEQ ID NO:159 and a light chain variable domain comprising an amino acid sequence at least 90% (e.g., 90%, 91%, 92%, 93%, 94%, 95%, 96%, 97%, 98%, 99%, or 100%) identical to a SEQ ID NO:160;

(18) a heavy chain variable domain comprising an amino acid sequence at least 90% (e.g., 90%, 91%, 92%, 93%, 94%, 95%, 96%, 97%, 98%, 99%, or 100%) identical to SEQ ID NO:161 and a light chain variable domain comprising an amino acid sequence at least 90% (e.g., 90%, 91%, 92%, 93%, 94%, 95%, 96%, 97%, 98%, 99%, or 100%) identical to a SEQ ID NO:162;

(19) a heavy chain variable domain comprising an amino acid sequence at least 90% (e.g., 90%, 91%, 92%, 93%, 94%, 95%, 96%, 97%, 98%, 99%, or 100%) identical to SEQ ID NO:163 and a light chain variable domain comprising an amino acid sequence at least 90% (e.g., 90%, 91%, 92%, 93%, 94%, 95%, 96%, 97%, 98%, 99%, or 100%) identical to a SEQ ID NO:164;

(20) a heavy chain variable domain comprising an amino acid sequence at least 90% (e.g., 90%, 91%, 92%, 93%, 94%, 95%, 96%, 97%, 98%, 99%, or 100%) identical to SEQ ID NO:165 and a light chain variable domain comprising an amino acid sequence at least 90% (e.g., 90%, 91%, 92%, 93%, 94%, 95%, 96%, 97%, 98%, 99%, or 100%) identical to a SEQ ID NO:166;

(21) a heavy chain variable domain comprising an amino acid sequence at least 90% (e.g., 90%, 91%, 92%, 93%, 94%, 95%, 96%, 97%, 98%, 99%, or 100%) identical to SEQ ID NO:167 and a light chain variable domain comprising an amino acid sequence at least 90% (e.g., 90%, 91%, 92%, 93%, 94%, 95%, 96%, 97%, 98%, 99%, or 100%) identical to a SEQ ID NO:168;

(22) a heavy chain variable domain comprising an amino acid sequence at least 90% (e.g., 90%, 91%, 92%, 93%, 94%, 95%, 96%, 97%, 98%, 99%, or 100%) identical to SEQ ID NO:175 and a light chain variable domain comprising an amino acid sequence at least 90% (e.g., 90%, 91%, 92%, 93%, 94%, 95%, 96%, 97%, 98%, 99%, or 100%) identical to a SEQ ID NO:176;

(23) a heavy chain variable domain comprising an amino acid sequence at least 90% (e.g., 90%, 91%, 92%, 93%, 94%, 95%, 96%, 97%, 98%, 99%, or 100%) identical to SEQ ID NO:583 and a light chain variable domain comprising an amino acid sequence at least 90% (e.g., 90%, 91%, 92%, 93%, 94%, 95%, 96%, 97%, 98%, 99%, or 100%) identical to a SEQ ID NO:584; or

(24) a heavy chain variable domain comprising an amino acid sequence at least 90% (e.g., 90%, 91%, 92%, 93%, 94%, 95%, 96%, 97%, 98%, 99%, or 100%) identical to SEQ ID NO:585 and a light chain variable domain comprising an amino acid sequence at least 90% (e.g., 90%, 91%, 92%, 93%, 94%, 95%, 96%, 97%, 98%, 99%, or 100%) identical to a SEQ ID NO:580.

Table 2 lists peptide sequences of heavy chain variable domains and light chain variable domains that, in combination, can bind to NKG2D. Unless indicated otherwise, the CDR sequences provided in Table 2 are determined under Kabat. The NKG2D-binding domains can vary in their binding affinity to NKG2D, nevertheless, they all activate human NKG2D and NK cells.

TABLE 2

| Clones | Heavy chain variable region amino acid sequence | Light chain variable region amino acid sequence |
| --- | --- | --- |
| ADI-29379 (E79) | QVQLVQSGAEVKKPGASVKVSCKAS GYTFTSYYMHWVRQAPGQGLEWMGI INPSGGSTSYAQKFQGRVTMTRDTSTS TVYMELSSLRSEDTAVYYCARGAPNY GDTTHDYYYMDVWGKGTTVTVSS [SEQ ID NO: 81] CDR1: YTFTSYYMH [SEQ ID NO: 93] (non-Kabat) or SYYMH [SEQ ID NO: 566] CDR2: IINPSGGSTSYAQKFQG [SEQ ID NO: 94] CDR3: ARGAPNYGDTTHDYYYMDV [SEQ ID NO: 95] (non-Kabat) or GAPNYGDTTHDYYYMDV [SEQ ID NO: 567] | EIVMTQSPATLSVSPGERATLS CRASQSVSSNLAWYQQKPGQA PRLLIYGASTRATGIPARFSGSG SGTEFTLTISSLQSEDFAVYYCQ QYDDWPFTFGGGTKVEIK [SEQ ID NO: 82] CDR1: RASQSVSSNLA [SEQ ID NO: 96] CDR2: GASTRAT [SEQ ID NO: 97] CDR3: QQYDDWPFT [SEQ ID NO: 98] |
| ADI-29463 (F63) | QVQLVQSGAEVKKPGASVKVSCKAS GYTFTGYYMHWVRQAPGQGLEWMG WINPNSGGTNYAQKFQGRVTMTRDT SISTAYMELSRLRSDDTAVYYCARDT GEYYDTDDHGMDVWGQGTTVTVSS [SEQ ID NO: 83] CDR1: YTFTGYYMH [SEQ ID NO: 99] (non-Kabat) or GYYMH [SEQ ID NO: 568] CDR2: WINPNSGGTNYAQKFQG [SEQ ID NO: 100] CDR3: ARDTGEYYDTDDHGMDV [SEQ ID NO: 101] (non-Kabat) or DTGEYYDTDDHGMDV [SEQ ID NO: 569] | EIVLTQSPGTLSLSPGERATLSC RASQSVSSNLAWYQQKPGQAP RLLIYGASTRATGIPARFSGSGS GTEFTLTISSLQSEDFAVYYCQ QDDYWPPTFGGGTKVEIK [SEQ ID NO: 84] CDR1: RASQSVSSNLA [SEQ ID NO: 102] CDR2: GASTRAT [SEQ ID NO: 103] CDR3: QQDDYWPPT [SEQ ID NO: 104] |
| ADI-27744 (A44) | EVQLLESGGGLVQPGGSLRLSCAASG FTFSSYAMSWVRQAPGKGLEWVSAIS GSGGSTYYADSVKGRFTISRDNSKNT LYLQMNSLRAEDTAVYYCAKDGGYY DSGAGDYWGQGTLVTVSS [SEQ ID NO: 85] CDR1: FTFSSYAMS [SEQ ID NO: 105] (non-Kabat) or SYAMS [SEQ ID NO: 570] CDR2: AISGSGGSTYYADSVKG [SEQ ID NO: 106] | DIQMTQSPSSVSASVGDRVTIT CRASQGIDSWLAWYQQKPGK APKLLIYAASSLQSGVPSRFSGS GSGTDFTLTISSLQPEDFATYYC QQGVSYPRTFGGGTKVEIK [SEQ ID NO: 86] CDR1: RASQGIDSWLA [SEQ ID NO: 108] CDR2: AASSLQS [SEQ ID NO: 109] |

TABLE 2-continued

| Clones | Heavy chain variable region amino acid sequence | Light chain variable region amino acid sequence |
|---|---|---|
| | CDR3: AKDGGYYDSGAGDY [SEQ ID NO: 107] (non-Kabat) or DGGYYDSGAGDY [SEQ ID NO: 571] | CDR3: QQGVSYPRT [SEQ ID NO: 110] |
| ADI-27749 (A49) | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPMGA AAGWFDPWGQGTLVTVSS [SEQ ID NO: 87] CDR1: FTFSSYSMN [SEQ ID NO: 111] or SYSMN [SEQ ID NO: 192] CDR2: SISSSSSYIYYADSVKG [SEQ ID NO: 112] CDR3: (non-Kabat) ARGAPMGAAAGWFDP [SEQ ID NO: 113] or GAPMGAAAGWFDP [SEQ ID NO: 193] | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK [SEQ ID NO: 88] CDR1: RASQGISSWLA [SEQ ID NO: 114] CDR2: AASSLQS [SEQ ID NO: 115] CDR3: QQGVSFPRT [SEQ ID NO: 116] |
| A49MI | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAP<u>I</u>GA AAGWFDPWGQGTLVTVSS [SEQ ID NO: 191] CDR1: (non-Kabat) FTFSSYSMN [SEQ ID NO: 111] or SYSMN [SEQ ID NO: 192] CDR2: SISSSSSYIYYADSVKG [SEQ ID NO: 112] CDR3: (non-Kabat) ARGAP<u>I</u>GAAAGWFDP [SEQ ID NO: 194] or GAP<u>I</u>GAAAGWFDP [SEQ ID NO: 195] | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK [SEQ ID NO: 88] CDR1: RASQGISSWLA [SEQ ID NO: 114] CDR2: AASSLQS [SEQ ID NO: 115] CDR3: QQGVSFPRT [SEQ ID NO: 116] |
| A49MQ | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAP<u>Q</u>GA AAGWFDPWGQGTLVTVSS (SEQ ID NO: 586) CDR1 (non-Kabat) (SEQ ID NO: 111)- FTFSSYSMN or CDR1 (SEQ ID NO: 192)- SYSMN CDR2 (SEQ ID NO: 112)- SISSSSSYIYYADSVKG CDR3 (non-Kabat) (SEQ ID NO: 587)- ARGAPQGAAAGWFDP or CDR3 (SEQ ID NO: 588)-GAPQGAAAGWFDP | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK (SEQ ID NO: 88) CDR1 (SEQ ID NO: 114)- RASQGISSWLA CDR2 (SEQ ID NO: 115)- AASSLQS CDR3 (SEQ ID NO: 116)- QQGVSFPRT |
| A49ML | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAP<u>L</u>GA AAGWFDPWGQGTLVTVSS (SEQ ID NO: 589) CDR1 (non-Kabat) (SEQ ID NO: 111)- FTFSSYSMN or CDR1 (SEQ ID NO: 192)- SYSMN CDR2 (SEQ ID NO: 112)- SISSSSSYIYYADSVKG CDR3 (non-Kabat) (SEQ ID NO: 590)- ARGAPLGAAAGWFDP or CDR3 (SEQ ID NO: 591)-GAPLGAAAGWFDP | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK (SEQ ID NO: 88) CDR1 (SEQ ID NO: 114)- RASQGISSWLA CDR2 (SEQ ID NO: 115)- AASSLQS CDR3 (SEQ ID NO: 116)- QQGVSFPRT |

TABLE 2-continued

| Clones | Heavy chain variable region amino acid sequence | Light chain variable region amino acid sequence |
|---|---|---|
| A49MF | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPFGA AAGWFDPWGQGTLVTVSS (SEQ ID NO: 592) CDR1 (non-Kabat) (SEQ ID NO: 111)- FTFSSYSMN or CDR1 (SEQ ID NO: 192)- SYSMN CDR2 (SEQ ID NO: 112)- SISSSSSYIYYADSVKG CDR3 (non-Kabat) (SEQ ID NO: 593)- ARGAPFGAAAGWFDP or CDR3 (SEQ ID NO: 594)-GAPFGAAAGWFDP | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK [SEQ ID NO: 88] CDR1: RASQGISSWLA [SEQ ID NO: 114] CDR2: AASSLQS [SEQ ID NO: 115] CDR3: QQGVSFPRT [SEQ ID NO: 116] |
| A49MV | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPVGA AAGWFDPWGQGTLVTVSS (SEQ ID NO: 595) CDR1 (non-Kabat) (SEQ ID NO: 111)- FTFSSYSMN or CDR1 (SEQ ID NO: 192)- SYSMN CDR2 (SEQ ID NO: 112)- SISSSSSYIYYADSVKG CDR3 (non-Kabat) (SEQ ID NO: 596)- ARGAPVGAAAGWFDP or CDR3 (SEQ ID NO: 597)-GAPVGAAAGWFDP | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK [SEQ ID NO: 88] CDR1: RASQGISSWLA [SEQ ID NO: 114] CDR2: AASSLQS [SEQ ID NO: 115] CDR3: QQGVSFPRT [SEQ ID NO: 116] |
| A49-consensus | EVQLVESGGGLVKPGGSLRLSCAASG FTFSSYSMNWVRQAPGKGLEWVSSIS SSSSYIYYADSVKGRFTISRDNAKNSL YLQMNSLRAEDTAVYYCARGAPXGA AAGWFDPWGQGTLVTVSS, wherein X is M, L, I, V, Q, or F (SEQ ID NO: 91) CDR1 (non-Kabat) (SEQ ID NO: 111)- FTFSSYSMN or CDR1 (SEQ ID NO: 192)- SYSMN CDR2 (SEQ ID NO: 112)- SISSSSSYIYYADSVKG CDR3 (non-Kabat) (SEQ ID NO: 92)- ARGAPXGAAAGWFDP or CDR3 (SEQ ID NO: 123)-GAPXGAAAGWFDP, wherein X is M, L, I, V, Q, or F | DIQMTQSPSSVSASVGDRVTIT CRASQGISSWLAWYQQKPGKA PKLLIYAASSLQSGVPSRFSGSG SGTDFTLTISSLQPEDFATYYCQ QGVSFPRTFGGGTKVEIK [SEQ ID NO: 88] CDR1: RASQGISSWLA [SEQ ID NO: 114] CDR2: AASSLQS [SEQ ID NO: 115] CDR3: QQGVSFPRT [SEQ ID NO: 116] |
| ADI-29378 (E78) | QVQLVQSGAEVKKPGASVKVSCKAS GYTFTSYYMEIWVRQAPGQGLEWMGI INPSGGSTSYAQKFQGRVTMTRDTSTS TVYMELSSLRSEDTAVYYCAREGAGF AYGMDYYYMDVWGKGTTVTVSS [SEQ ID NO: 89] CDR1: YTFTSYYMH [SEQ ID NO: 117] (non-Kabat) or SYYMH [SEQ ID NO: 572] CDR2: IINPSGGSTSYAQKFQG [SEQ ID NO: 118] CDR3: AREGAGFAYGMDYYYMDV [SEQ ID NO: 119] (non-Kabat) or EGAGFAYGMDYYYMDV [SEQ ID NO: 573] | EIVLTQSPATLSLSPGERATLSC RASQSVSSYLAWYQQKPGQAP RLLIYDASNRATGIPARFSGSGS GTDFTLTISSLEPEDFAVYYCQ QSDNWPFTFGGGTKVEIK [SEQ ID NO: 90] CDR1: RASQSVSSYLA [SEQ ID NO: 120] CDR2: DASNRAT [SEQ ID NO: 121] CDR3: QQSDNWPFT [SEQ ID NO: 122] |
| ADI-27705 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 124] CDR1: GSFSGYYWS [SEQ ID NO: 126] (non-Kabat) or GYYWS [SEQ ID NO: 574] CDR2: EIDHSGSTNYNPSLKS [SEQ ID NO: 127] CDR3: ARARGPWSFDP [SEQ ID NO: 128] (non-Kabat) or ARGPWSFDP [SEQ ID NO: 575] | DIQMTQSPSTLSASVGDRVTIT CRASQSISSWLAWYQQKPGKA PKLLIYKASSLESGVPSRFSGSG SGTEFTLTISSLQPDDFATYYCQ QYNSYPITFGGGTKVEIK [SEQ ID NO: 125] |

TABLE 2-continued

| Clones | Heavy chain variable region amino acid sequence | Light chain variable region amino acid sequence |
| --- | --- | --- |
| ADI-27724 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 129] | EIVLTQSPGTLSLSPGERATLSC RASQSVSSSYLAWYQQKPGQA PRLLIYGASSRATGIPDRFSGSG SGTDFTLTISRLEPEDFAVYYC QQYGSSPITFGGGTKVEIK [SEQ ID NO: 130] |
| ADI-27740 (A40) | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 131] | DIQMTQSPSTLSASVGDRVTIT CRASQSIGSWLAWYQQKPGKA PKLLIYKASSLESGVPSRFSGSG SGTEFTLTISSLQPDDFATYYCQ QYHSFYTFGGGTKVEIK [SEQ ID NO: 132] |
| ADI-27741 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 133] | DIQMTQSPSTLSASVGDRVTIT CRASQSIGSWLAWYQQKPGKA PKLLIYKASSLESGVPSRFSGSG SGTEFTLTISSLQPDDFATYYCQ QSNSYYTFGGGTKVEIK [SEQ ID NO: 134] |
| ADI-27743 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 135] | DIQMTQSPSTLSASVGDRVTIT CRASQSISSWLAWYQQKPGKA PKLLIYKASSLESGVPSRFSGSG SGTEFTLTISSLQPDDFATYYCQ QYNSYPTFGGGTKVEIK [SEQ ID NO: 136] |
| ADI-28153 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWG FDPWGQGTLVTVSS [SEQ ID NO: 137] | ELQMTQSPSSLSASVGDRVTIT CRTSQSSSYLNWYQQKPGQA KLLIYWASTRESGVPDRFSGSG SGTDFTLTISSLQPEDSATYYCQ QSYDIPYTFGQGTKLEIK [SEQ ID NO: 138] |
| ADI-28226 (C26) | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 139] | DIQMTQSPSTLSASVGDRVTIT CRASQSISSWLAWYQQKPGKA PKLLIYKASSLESGVPSRFSGSG SGTEFTLTISSLQPDDFATYYCQ QYGSFPITFGGGTKVEIK [SEQ ID NO: 140] |
| ADI-28154 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 141] | DIQMTQSPSTLSASVGDRVTIT CRASQSISSWLAWYQQKPGKA PKLLIYKASSLESGVPSRFSGSG SGTDFTLTISSLQPDDFATYYC QQSKEVPWTFGQGTKVEIK [SEQ ID NO: 142] |
| ADI-29399 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 143] | DIQMTQSPSTLSASVGDRVTIT CRASQSISSWLAWYQQKPGKA PKLLIYKASSLESGVPSRFSGSG SGTEFTLTISSLQPDDFATYYCQ QYNSFPTFGGGTKVEIK [SEQ ID NO: 144] |
| ADI-29401 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 145] | DIQMTQSPSTLSASVGDRVTIT CRASQSIGSWLAWYQQKPGKA PKLLIYKASSLESGVPSRFSGSG SGTEFTLTISSLQPDDFATYYCQ QYDIYPTFGGGTKVEIK [SEQ ID NO: 146] |
| ADI-29403 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 147] | DIQMTQSPSTLSASVGDRVTIT CRASQSISSWLAWYQQKPGKA PKLLIYKASSLESGVPSRFSGSG SGTEFTLTISSLQPDDFATYYCQ QYDSYPTFGGGTKVEIK [SEQ ID NO: 148] |
| ADI-29405 | QVQLQQWGAGLLKPSETLSLTCAVY GGSFSGYYWSWIRQPPGKGLEWIGEI DHSGSTNYNPSLKSRVTISVDTSKNQF SLKLSSVTAADTAVYYCARARGPWSF DPWGQGTLVTVSS [SEQ ID NO: 149] | DIQMTQSPSTLSASVGDRVTIT CRASQSISSWLAWYQQKPGKA PKLLIYKASSLESGVPSRFSGSG SGTEFTLTISSLQPDDFATYYCQ QYGSFPTFGGGTKVEIK [SEQ ID NO: 150] |

TABLE 2-continued

| Clones | Heavy chain variable region amino acid sequence | Light chain variable region amino acid sequence |
|---|---|---|
| ADI-29407 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 151] | DIQMTQSPSTLSASVGDRVTITCRASQSISSWLAWYQQKPGKAPKLLIYKASSLESGVPSRFSGSGSGTEFTLTISSLQPDDFATYYCQQYQSFPTFGGGTKVEIK [SEQ ID NO: 152] |
| ADI-29419 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 153] | DIQMTQSPSTLSASVGDRVTITCRASQSISSWLAWYQQKPGKAPKLLIYKASSLESGVPSRFSGSGSGTEFTLTISSLQPDDFATYYCQQYSSFSTFGGGTKVEIK [SEQ ID NO: 154] |
| ADI-29421 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 155] | DIQMTQSPSTLSASVGDRVTITCRASQSISSWLAWYQQKPGKAPKLLIYKASSLESGVPSRFSGSGSGTEFTLTISSLQPDDFATYYCQQYESYSTFGGGTKVEIK [SEQ ID NO: 156] |
| ADI-29424 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 157] | DIQMTQSPSTLSASVGDRVTITCRASQSISSWLAWYQQKPGKAPKLLIYKASSLESGVPSRFSGSGSGTEFTLTISSLQPDDFATYYCQQYDSFITFGGGTKVEIK [SEQ ID NO: 158] |
| ADI-29425 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 159] | DIQMTQSPSTLSASVGDRVTITCRASQSISSWLAWYQQKPGKAPKLLIYKASSLESGVPSRFSGSGSGTEFTLTISSLQPDDFATYYCQQYQSYPTFGGGTKVEIK [SEQ ID NO: 160] |
| ADI-29426 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 161] | DIQMTQSPSTLSASVGDRVTITCRASQSIGSWLAWYQQKPGKAPKLLIYKASSLESGVPSRFSGSGSGTEFTLTISSLQPDDFATYYCQQYHSFPTFGGGTKVEIK [SEQ ID NO: 162] |
| ADI-29429 | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 163] | DIQMTQSPSTLSASVGDRVTITCRASQSIGSWLAWYQQKPGKAPKLLIYKASSLESGVPSRFSGSGSGTEFTLTISSLQPDDFATYYCQQYELYSYTFGGGTKVEIK [SEQ ID NO: 164] |
| ADI-29447 (F47) | QVQLQQWGAGLLKPSETLSLTCAVYGGSFSGYYWSWIRQPPGKGLEWIGEIDHSGSTNYNPSLKSRVTISVDTSKNQFSLKLSSVTAADTAVYYCARARGPWSFDPWGQGTLVTVSS [SEQ ID NO: 165] | DIQMTQSPSTLSASVGDRVTITCRASQSISSWLAWYQQKPGKAPKLLIYKASSLESGVPSRFSGSGSGTEFTLTISSLQPDDFATYYCQQYDTFITFGGGTKVEIK [SEQ ID NO: 166] |
| ADI-27727 | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARGDSSIRHAYYYYGMDVWGQGTTVTVSS [SEQ ID NO: 167]<br>CDR1: GTFSSYAIS [SEQ ID NO: 169] (non-Kabat) or SYAIS [SEQ ID NO: 576]<br>CDR2: GIIPIFGTANYAQKFQG [SEQ ID NO: 170]<br>CDR3: ARGDSSIRHAYYYYGMDV [SEQ ID NO: 171] (non-Kabat) or GDSSIRHAYYYYGMDV [SEQ ID NO: 577] | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPITFGGGTKVEIK [SEQ ID NO: 168]<br>CDR1: KSSQSVLYSSNNKNYLA [SEQ ID NO: 172]<br>CDR2: WASTRES [SEQ ID NO: 173]<br>CDR3: QQYYSTPIT [SEQ ID NO: 174] |

TABLE 2-continued

| Clones | Heavy chain variable region amino acid sequence | Light chain variable region amino acid sequence |
|---|---|---|
| ADI-<br>29443<br>(F43) | QLQLQESGPGLVKPSETLSLTCTVSGG<br>SISSSSYYWGWIRQPPGKGLEWIGSIY<br>YSGSTYYNPSLKSRVTISVDTSKNQFS<br>LKLSSVTAADTAVYYCARGSDRFHPY<br>FDYWGQGTLVTVSS<br>[SEQ ID NO: 175]<br>CDR1: GSISSSSYYWG<br>[SEQ ID NO: 177] (non-Kabat) or<br>SSSYYWG [SEQ ID NO: 578]<br>CDR2: SIYYSGSTYYNPSLKS<br>[SEQ ID NO: 178]<br>CDR3: ARGSDRFHPYFDY<br>[SEQ ID NO: 179] (non-Kabat) or<br>GSDRFHPYFDY [SEQ ID NO: 579] | EIVLTQSPATLSLSPGERATLSC<br>RASQSVSRYLAWYQQKPGQAP<br>RLLIYDASNRATGIPARFSGSGS<br>GTDFTLTISSLEPEDFAVYYCQ<br>QFDTWPPTFGGGTKVEIK<br>[SEQ ID NO: 176]<br>CDR1: RASQSVSRYLA<br>[SEQ ID NO: 180]<br>CDR2: DASNRAT<br>[SEQ ID NO: 581]<br>CDR3: QQFDTWPPT<br>[SEQ ID NO: 582] |
| ADI-<br>29404<br>(F04) | QVQLQQWGAGLLKPSETLSLTCAVY<br>GGSFSGYYWSWIRQPPGKGLEWIGEI<br>DHSGSTNYNPSLKSRVTISVDTSKNQF<br>SLKLSSVTAADTAVYYCARARGPWSF<br>DPWGQGTLVTVSS<br>[SEQ ID NO: 583] | DIQMTQSPSTLSASVGDRVTIT<br>CRASQSISSWLAWYQQKPGKA<br>PKLLIYKASSLESGVPSRFSGSG<br>SGTEFTLTISSLQPDDFATYYCE<br>QYDSYPTFGGGTKVEIK<br>[SEQ ID NO: 584] |
| ADI-<br>28200 | QVQLVQSGAEVKKPGSSVKVSCKAS<br>GGTFSSYAISWVRQAPGQGLEWMGGI<br>IPIFGTANYAQKFQGRVTITADESTST<br>AYMELSSLRSEDTAVYYCARRGRKAS<br>GSFYYYYGMDVWGQGTTVTVSS<br>[SEQ ID NO: 585] | DIVMTQSPDSLAVSLGERATIN<br>CESSQSLLNSGNQKNYLTWYQ<br>QKPGQPPKPLIYWASTRESGVP<br>DRFSGSGSGTDFTLTISSLQAED<br>VAVYYCQNDYSYPYTFGQGTK<br>LEIK<br>[SEQ ID NO: 580] |

The antibody molecule may have a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has effector function and can fix complement. In other embodiments the antibody does not recruit effector cells or fix complement. In another embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

In some embodiments, the antibody constant domain comprises a CH2 domain and a CH3 domain of an IgG antibody, for example, a human IgG1 antibody. In some embodiments, mutations are introduced in the antibody constant domain to enable heterodimerization with another antibody constant domain. For example, if the antibody constant domain is derived from the constant domain of a human IgG1, the antibody constant domain can comprise an amino acid sequence at least 90% (e.g., 90%, 91%, 92%, 93%, 94%, 95%, 96%, 97%, 98%, 99%, or 100%) identical to amino acids 234-332 of a human IgG1 antibody, and differs at one or more positions selected from the group consisting of Q347, Y349, L351, S354, E356, E357, K360, Q362, 5364, T366, L368, K370, N390, K392, T394, D399, S400, D401, F405, Y407, K409, T411, and K439. All the amino acid positions in an Fc domain or hinge region disclosed herein are numbered according to EU numbering.

The assembly of heterodimeric antibody heavy chains can be accomplished by expressing two different antibody heavy chain sequences in the same cell, which may lead to the assembly of homodimers of each antibody heavy chain as well as assembly of heterodimers. Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289, 934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 and incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% (e.g., 90%, 91%, 92%, 93%, 94%, 95%, 96%, 97%, 98%, 99%, or 100%) identical to an antibody constant region, such as an IgG constant region including hinge, CH2 and CH3 domains with or without CH1 domain. In some embodiments, the amino acid sequence of the constant region is at least 90% (e.g., 90%, 91%, 92%, 93%, 94%, 95%, 96%, 97%, 98%, 99%, or 100%) identical to a human antibody constant region, such as an human IgG1 constant region, an IgG2 constant region, IgG3 constant region, or IgG4 constant region. In some other embodiments, the amino acid sequence of the constant region is at least 90% (e.g., 90%, 91%, 92%, 93%, 94%, 95%, 96%, 97%, 98%, 99%, or 100%) identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the CK of a human IgG1 constant region may be at amino acid E123, F116, S176, V163, S174, and/or T164.

Alternatively, amino acid substitutions could be selected from the following sets of substitutions shown in Table 3.

TABLE 3

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 4.

TABLE 4

| | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following set of substitutions shown in Table 5.

TABLE 5

| | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 6.

TABLE 6

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F, K392D, K392E, K409F, K409W, T411D and T411E |

Alternatively, at least one amino acid substitutions could be selected from the following set of substitutions in Table 7, where the position(s) indicated in the First Polypeptide column is replaced by any known negatively-charged amino acid, and the position(s) indicated in the Second Polypeptide Column is replaced by any known positively-charged amino acid.

TABLE 7

| First Polypeptide | Second Polypeptide |
|---|---|
| K392, K370, K409, or K439 | D399, E356, or E357 |

Alternatively, at least one amino acid substitutions could be selected from the following set of in Table 8, where the position(s) indicated in the First Polypeptide column is replaced by any known positively-charged amino acid, and the position(s) indicated in the Second Polypeptide Column is replaced by any known negatively-charged amino acid.

TABLE 8

| First Polypeptide | Second Polypeptide |
|---|---|
| D399, E356, or E357 | K409, K439, K370, or K392 |

Alternatively, amino acid substitutions could be selected from the following set of in Table 9.

TABLE 9

| First Polypeptide | Second Polypeptide |
|---|---|
| T350V, L351Y, F405A, and Y407V | T350V, T366L, K392L, and T394W |

Alternatively, or in addition, the structural stability of heterodimeric heavy chains within the multi-specific binding proteins can be increased by introducing S354C on either of the first or second polypeptide chain, and Y349C on the opposing polypeptide chain, which forms an artificial disulfide bridge within the interface of the two polypeptides.

In certain embodiments of the present disclosure, the amino acid sequence of one polypeptide chain of the antibody constant region differs from the amino acid sequence of an IgG1 constant region at position T366, and wherein the amino acid sequence of the other polypeptide chain of the antibody constant region differs from the amino acid sequence of an IgG1 constant region at one or more positions selected from the group consisting of T366, L368 and Y407.

In certain embodiments of the present disclosure, the amino acid sequence of one polypeptide chain of the antibody constant region differs from the amino acid sequence of an IgG1 constant region at one or more positions selected from the group consisting of T366, L368 and Y407, and wherein the amino acid sequence of the other polypeptide chain of the antibody constant region differs from the amino acid sequence of an IgG1 constant region at position T366.

In certain embodiments of the present disclosure, the amino acid sequence of one polypeptide chain of the antibody constant region differs from the amino acid sequence of an IgG1 constant region at one or more positions selected from the group consisting of E357, K360, Q362, S364, L368, K370, T394, D401, F405, and T411 and wherein the amino acid sequence of the other polypeptide chain of the antibody constant region differs from the amino acid sequence of an IgG1 constant region at one or more positions selected from the group consisting of Y349, E357, S364, L368, K370, T394, D401, F405 and T411.

In certain embodiments of the present disclosure, the amino acid sequence of one polypeptide chain of the antibody constant region differs from the amino acid sequence of an IgG1 constant region at one or more positions selected from the group consisting of Y349, E357, S364, L368, K370, T394, D401, F405 and T411 and wherein the amino acid sequence of the other polypeptide chain of the antibody constant region differs from the amino acid sequence of an IgG1 constant region at one or more positions selected from the group consisting of E357, K360, Q362, S364, L368, K370, T394, D401, F405, and T411.

In certain embodiments of the present disclosure, the amino acid sequence of one polypeptide chain of the antibody constant region differs from the amino acid sequence of an IgG1 constant region at one or more positions selected from the group consisting of L351, D399, S400 and Y407 and wherein the amino acid sequence of the other polypeptide chain of the antibody constant region differs from the amino acid sequence of an IgG1 constant region at one or more positions selected from the group consisting of T366, N390, K392, K409 and T411.

In certain embodiments of the present disclosure, the amino acid sequence of one polypeptide chain of the antibody constant region differs from the amino acid sequence of an IgG1 constant region at one or more positions selected from the group consisting of T366, N390, K392, K409 and T411 and wherein the amino acid sequence of the other polypeptide chain of the antibody constant region differs from the amino acid sequence of an IgG1 constant region at one or more positions selected from the group consisting of L351, D399, S400 and Y407.

In certain embodiments of the present disclosure, the amino acid sequence of one polypeptide chain of the antibody constant region differs from the amino acid sequence of an IgG1 constant region at one or more positions selected from the group consisting of Q347, Y349, K360, and K409, and wherein the amino acid sequence of the other polypeptide chain of the antibody constant region differs from the amino acid sequence of an IgG1 constant region at one or more positions selected from the group consisting of Q347, E357, D399 and F405.

In certain embodiments of the present disclosure, the amino acid sequence of one polypeptide chain of the antibody constant region differs from the amino acid sequence of an IgG1 constant region at one or more positions selected from the group consisting of Q347, E357, D399 and F405, and wherein the amino acid sequence of the other polypeptide chain of the antibody constant region differs from the amino acid sequence of an IgG1 constant region at one or more positions selected from the group consisting of Y349, K360, Q347 and K409.

In certain embodiments of the present disclosure, the amino acid sequence of one polypeptide chain of the antibody constant region differs from the amino acid sequence of an IgG1 constant region at one or more positions selected from the group consisting of K370, K392, K409 and K439, and wherein the amino acid sequence of the other polypeptide chain of the antibody constant region differs from the amino acid sequence of an IgG1 constant region at one or more positions selected from the group consisting of D356, E357 and D399.

In certain embodiments of the present disclosure, the amino acid sequence of one polypeptide chain of the antibody constant region differs from the amino acid sequence of an IgG1 constant region at one or more positions selected from the group consisting of D356, E357 and D399, and wherein the amino acid sequence of the other polypeptide chain of the antibody constant region differs from the amino acid sequence of an IgG1 constant region at one or more positions selected from the group consisting of K370, K392, K409 and K439.

In certain embodiments of the present disclosure, the amino acid sequence of one polypeptide chain of the antibody constant region differs from the amino acid sequence of an IgG1 constant region at one or more positions selected from the group consisting of L351, E356, T366 and D399, and wherein the amino acid sequence of the other polypeptide chain of the antibody constant region differs from the amino acid sequence of an IgG1 constant region at one or more positions selected from the group consisting of Y349, L351, L368, K392 and K409.

In certain embodiments of the present disclosure, the amino acid sequence of one polypeptide chain of the antibody constant region differs from the amino acid sequence of an IgG1 constant region at one or more positions selected from the group consisting of Y349, L351, L368, K392 and K409, and wherein the amino acid sequence of the other polypeptide chain of the antibody constant region differs from the amino acid sequence of an IgG1 constant region at one or more positions selected from the group consisting of L351, E356, T366 and D399.

In certain embodiments of the present disclosure, the amino acid sequence of one polypeptide chain of the antibody constant region differs from the amino acid sequence of an IgG1 constant region by an S354C substitution and wherein the amino acid sequence of the other polypeptide chain of the antibody constant region differs from the amino acid sequence of an IgG1 constant region by a Y349C substitution.

In certain embodiments of the present disclosure, the amino acid sequence of one polypeptide chain of the antibody constant region differs from the amino acid sequence of an IgG1 constant region by a Y349C substitution and wherein the amino acid sequence of the other polypeptide chain of the antibody constant region differs from the amino acid sequence of an IgG1 constant region by an S354C substitution.

In certain embodiments of the present disclosure, the amino acid sequence of one polypeptide chain of the antibody constant region differs from the amino acid sequence of an IgG1 constant region by K360E and K409W substitutions and wherein the amino acid sequence of the other polypeptide chain of the antibody constant region differs from the amino acid sequence of an IgG1 constant region by Q347R, D399V and F405T substitutions.

In certain embodiments of the present disclosure, the amino acid sequence of one polypeptide chain of the antibody constant region differs from the amino acid sequence of an IgG1 constant region by 0347R, D399V and F405T substitutions and wherein the amino acid sequence of the other polypeptide chain of the antibody constant region differs from the amino acid sequence of an IgG1 constant region by K360E and K409W substitutions.

In certain embodiments of the present disclosure, the amino acid sequence of one polypeptide chain of the antibody constant region differs from the amino acid sequence of an IgG1 constant region by a T366W substitutions and wherein the amino acid sequence of the other polypeptide chain of the antibody constant region differs from the amino acid sequence of an IgG1 constant region by T366S, T368A, and Y407V substitutions.

In certain embodiments of the present disclosure, the amino acid sequence of one polypeptide chain of the antibody constant region differs from the amino acid sequence of an IgG1 constant region by T366S, T368A, and Y407V substitutions and wherein the amino acid sequence of the other polypeptide chain of the antibody constant region differs from the amino acid sequence of an IgG1 constant region by a T366W substitution.

In certain embodiments of the present disclosure, the amino acid sequence of one polypeptide chain of the antibody constant region differs from the amino acid sequence of an IgG1 constant region by T350V, L351Y, F405A, and Y407V substitutions and wherein the amino acid sequence of the other polypeptide chain of the antibody constant region differs from the amino acid sequence of an IgG1 constant region by T350V, T366L, K392L, and T394W substitutions.

In certain embodiments of the present disclosure, the amino acid sequence of one polypeptide chain of the anti-body constant region differs from the amino acid sequence of an IgG1 constant region by T350V, T366L, K392L, and T394W substitutions and wherein the amino acid sequence of the other polypeptide chain of the antibody constant region differs from the amino acid sequence of an IgG1 constant region by T350V, L351Y, F405A, and Y407V substitutions.

Listed below are examples of CD33-binding F3'-TriN-KETs comprising: a CD33-binding single-chain variable fragment (scFv) linked to an Fc domain via a hinge comprising Ala-Ser; and an NKG2D-binding Fab fragment ("A49," "A49MI, "A49MQ," "A49ML," "A49MF," or "A49MV") comprising a heavy chain portion comprising an heavy chain variable domain (SEQ ID NO:87 or SEQ ID NO:191) and a CH1 domain, and a light chain portion comprising a light chain variable domain (SEQ ID NO:88) and a light chain constant domain, wherein the heavy chain variable domain is connected to the CH1 domain, and the CH1 domain is connected to an Fc domain. The CDR sequences are underlined.

In each of the examples, the Fc domain linked to the CD33-binding scFv comprises Q347R, D399V, and F405T substitutions for forming a heterodimer with the Fc domain linked to the Fab comprising K360E and K409W substitutions. These substitutions in the Fc domains are bold-underlined in the sequences described below. Alternatively, in an exemplary embodiment, the Fc domain linked to the NKG2D-binding Fab fragment includes the mutations of Q347R, D399V, and F405T, and the Fc domain linked to the CD33-binding scFv comprises matching mutations K360E and K409W for forming a heterodimer.

Additionally, the Fc domain linked to the CD33-binding scFv comprises S354C substitution, and the Fc domain linked to the Fab comprises Y349C substitution, thereby stabilizing the interaction between the two Fc domains via a S-S bridge. These substitutions in the Fc domains are bold-italics-underlined in the sequences below.

Alternatively, in an exemplary embodiment, the Fc domain linked to the NKG2D-binding Fab fragment includes a S354C substitution in the CH3 domain, which forms a disulfide bond with a Y349C substitution on the Fc linked to the CD33-binding scFv.

A CD33-binding scFv of the present disclosure can include a heavy chain variable domain connected to a light chain variable domain with a $(G4S)_4$ linker. The scFv is linked to an Fc domain via a hinge comprising Ala-Ser (bolded-underlined). SEQ ID NOs:188, 198, and 206-223 are exemplary sequences of such CD33-binding scFv polypeptides. The $V_L$ and $V_H$ comprised within the scFv (e.g., SEQ ID NOs:188, 198 or 206-223) contain $100V_L$-$44V_H$ S-S bridge (resulting from G100C and G44C substitutions, respectively) (cysteine residues are in bold-italics-underlined in the sequences below). $(G4S)_4$ is the bold-underlined sequence GGGGSGGGGSGGGGSGGGGS [SEQ ID NO:186] in SEQ ID NOs:188, 198, and 206-243.

Exemplary sequences of CD33-binding scFvs linked to an Fc domain via a hinge comprising Ala-Ser are provided below.

```
Ab1 scFv (LC-HC)-Fc (Q347R, D399V, F405T, and S354C substitutions)
                                                              [SEQ ID NO: 224]
DIQMTQSPSTLSASVGDRVTITCRASQSISSWLAWYQQKPGKAPKLLIYDASSLESGV

PSRFSGSGSGTEFTLTISSLQPDDFATYYCQQYESFPTFGCGTKVEIKGGGGSGGGGS

GGGGSGGGGSEVQLVESGGGLVQPGGSLRLSCAASGFTFSSYGMSWVRQAPGKCL
```

EWVANIKQDGSEKYYVDSVKGRFTISRDNAKNSLYLQMNSLRAEDTAVYYCAREG

GPYYDSSGYFVYYGMDVWGQGTTVTVSSASDKTHTCPPCPAPELLGGPSVFLFPPKP

KDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPRVYTLPPCRDELT

KNQVSLTCLVKGFYPSDIAVEWESNGQPENNYKTTPPVLVSDGSFTLYSKLTVDKSR

WQQGNVFSCSVMHEALHNHYTQKSLSLSPG

Ab1 scFv (HC-LC)-Fc (Q347R, D399V, F405T, and S354C substitutions)
[SEQ ID NO: 225]
EVQLVESGGGLVQPGGSLRLSCAASGFTFSSYGMSWVRQAPGKCLEWVANIKQDGS

EKYYVDSVKGRFTISRDNAKNSLYLQMNSLRAEDTAVYYCAREGGPYYDSSGYFVY

YGMDVWGQGTTVTVSSGGGGSGGGGSGGGGSGGGGSDIQMTQSPSTLSASVGDR

VTITCRASQSISSWLAWYQQKPGKAPKLLIYDASSLESGVPSRFSGSGSGTEFTLTISS

LQPDDFATYYCQQYESFPTFGCGTKVEIKASDKTHTCPPCPAPELLGGPSVFLFPPKP

KDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPRVYTLPPCRDELT

KNQVSLTCLVKGFYPSDIAVEWESNGQPENNYKTTPPVLVSDGSFTLYSKLTVDKSR

WQQGNVFSCSVMHEALHNHYTQKSLSLSPG

Ab2 scFv (LC-HC)-Fc (Q347R, D399V, F405T, and S354C substitutions)
[SEQ ID NO: 226]
DIQMTQSPSTLSASVGDRVTITCRASQSISSWLAWYQQKPGKAPKLLIYEASSLESGV

PSRFSGSGSGTEFTLTISSLQPDDFATYYCQQLESYPLTFGCGTKVEIKGGGGSGGGG

SGGGGSGGGGSEVQLVESGGGLVQPGGSLRLSCAASGFTFSSYWMSWVRQAPGKC

LEWVANIKQDGSEKYYVDSVKGRFTISRDNAKNSLYLQMNSLRAEDTAVYYCARPL

NAGELDVWGQGTMVTVSSASDKTHTCPPCPAPELLGGPSVFLFPPKPKDTLMISRTP

EVTCVVVDVSHEDPEVKFNWYVDGVEVHNAKTKPREEQYNSTYRVVSVLTVLHQD

WLNGKEYKCKVSNKALPAPIEKTISKAKGQPREPRVYTLPPCRDELTKNQVSLTCLV

KGFYPSDIAVEWESNGQPENNYKTTPPVLVSDGSFTLYSKLTVDKSRWQQGNVFSCS

VMHEALHNHYTQKSLSLSPG

Ab2 scFv (HC-LC)-Fc (Q347R, D399V, F405T, and S354C substitutions)
[SEQ ID NO: 227]
EVQLVESGGGLVQPGGSLRLSCAASGFTFSSYWMSWVRQAPGKCLEWVANIKQDG

SEKYYVDSVKGRFTISRDNAKNSLYLQMNSLRAEDTAVYYCARPLNAGELDVWGQ

GTMVTVSSGGGGSGGGGSGGGGSGGGGSDIQMTQSPSTLSASVGDRVTITCRASQ

SISSWLAWYQQKPGKAPKLLIYEASSLESGVPSRFSGSGSGTEFTLTISSLQPDDFATY

YCQQLESYPLTFGCGTKVEIKASDKTHTCPPCPAPELLGGPSVFLFPPKPKDTLMISRT

PEVTCVVVDVSHEDPEVKFNWYVDGVEVHNAKTKPREEQYNSTYRVVSVLTVLHQ

DWLNGKEYKCKVSNKALPAPIEKTISKAKGQPREPRVYTLPPCRDELTKNQVSLTCL

VKGFYPSDIAVEWESNGQPENNYKTTPPVLVSDGSFTLYSKLTVDKSRWQQGNVFS

CSVMHEALHNHYTQKSLSLSPG

H76 scFv (LC-HC)-Fc (Q347R, D399V, F405T, and S354C substitutions)
[SEQ ID NO: 197]
DIQMTQSPSTLSASVGDRVTITC<u>RASQSISSWLA</u>WYQQKPGKAPKLLIY<u>KASSLESG</u>V PSRFSGSGSGTEFTLTISSLQPDDFATYYC<u>QQYDDLPT</u>FGCGTKVEIKGGGGSGGGG

SGGGGSGGGGSEVQLLESGGGLVQPGGSLRLSCAASGFTFS<u>KYTMS</u>WVRQAPGKC

LEWVS<u>AIVGSGESTYFADSVKG</u>RFTISRDNSKNTLYLQMNSLRAEDTAVYYCAR<u>EG</u>

-continued

GPYYDSSGYFVYYGMDVWGQGTTVTVSSASDKTHTCPPCPAPELLGGPSVFLFPPKP

KDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPRVYTLPPCRDELT

KNQVSLTCLVKGFYPSDIAVEWESNGQPENNYKTTPPVLVSDGSFTLYSKLTVDKSR

WQQGNVF SCSVMHEALHNHYTQKSLSLSPG

H76 scFv (HC-LC)-Fc (Q347R, D399V, F405T, and S354C substitutions)
[SEQ ID NO: 228]
EVQLLESGGGLVQPGGSLRLSCAASGFTFS<u>KYTMS</u>WVRQAPGKCLEWVS<u>AIVGSGE</u>

<u>STYFADSVKG</u>RFTISRDNSKNTLYLQMNSLRAEDTAVYYCAREG<u>GPYYDSSGYFVY</u>

<u>YGMDV</u>WGQGTTVTVSSGGGGSGGGGSGGGGSGGGGSDIQMTQSPSTLSASVGDR

VTITC<u>RASQSISSWLA</u>WYQQKPGKAPKLLIY<u>KASSLESG</u>VPSRFSGSGSGTEFTLTISS

LQPDDFATYYC<u>QQYDDLPTFG</u>CGTKVEIKASDKTHTCPPCPAPELLGGPSVFLFPPKP

KDTLMISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPRVYTLPPCRDELT

KNQVSLTCLVKGFYPSDIAVEWESNGQPENNYKTTPPVLVSDGSFTLYSKLTVDKSR

WQQGNVF SCSVMHEALHNHYTQKSLSLSPG

H76 scFc (LC-HC)-Fc (K360E, K409W, and Y349C substitutions)
[SEQ ID NO: 243]
DIQMTQSPSTLSASVGDRVTITC<u>RASQSISSWLA</u>WYQQKPGKAPKLLIY<u>KASSLESG</u>V PSRFSGSGSGTEFTLTISSLQPDDFATYYC<u>QQYDDLPTFG</u>CGTKVEIIGGGGSGGGG

SGGGGSGGGGSEVQLLESGGGLVQPGGSLRLSCAASGFTFS<u>KYTMS</u>WVRQAPGKC

LEWVS<u>AIVGSGESTYFADSVKG</u>RFTISRDNSKNTLYLQMNSLRAEDTAVYYCAREG

<u>GPYYDSSGYFVYYGMDV</u>WGQGTTVTVSSASTKGPSVFPLAPSSKSTSGGTAALGCL

VKDYFPEPVTVSWNSGALTSGVHTFPAVLQSSGLYSLSSVVTVPSSSLGTQTYICNVN

HKPSNTKVDKKVEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVLHQDWLN

GKEYKCKVSNKALPAPIEKTISKAKGQPREPQVCTLPPSRDELTENQVSLTCLVKGFY

PSDIAVEWESNGQPENNYKTTPPVLDSDGSFFLYSWLTVDKSRWQQGNVFSCSVMH

EALHNHYTQKSLSLSPG

Ab4 scFv (LC-HC)-Fc (Q347R, D399V, F405T, and S354C substitutions)
[SEQ ID NO: 229]
DIVMTQSPLSLPVTPGEPASISC<u>RSSQSLLYSNGYNYLD</u>WYLQKPGQSPQLLIY<u>LGSN</u>

<u>RAS</u>GVPDRFSGSGSGTDFTLKISRVEAEDVGVYYC<u>MQDVALPITFG</u>CGTKVEIKGGG

GSGGGGSGGGGSGGGGSQVQLVQSGAEVKKPGASVKVSCKASGYTFSDYYMHW

VRQAPGQCLEWMGMINPSWGSTSYAQKFQGRVTMTRDTSTSTVYMELSSLRSEDT

AVYYCAREAADGFVGERYFDLWGRGTLVTVSSASDKTHTCPPCPAPELLGGPSVFLF

PPKPKDTLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPRVYTLPPCRD

ELTKNQVSLTCLVKGFYPSDIAVEWESNGQPENNYKTTPPVLVSDGSFTLYSKLTVD

KSRWQQGNVFSCSVMHEALHNHYTQKSLSLSPG

Ab4 scFv (HC-LC)-Fc (Q347R, D399V, F405T, and S354C substitutions)
[SEQ ID NO: 230]
QVQLVQSGAEVKKPGASVKVSCKASGYTFSDYYMHWVRQAPGQCLEWMGMINPS

WGSTSYAQKFQGRVTMTRDTSTSTVYMELSSLRSEDTAVYYCAREAADGFVGERYF

-continued

DLWGRGTLVTVSSGGGGSGGGGSGGGGSGGGGSDIVMTQSPLSLPVTPGEPASISC

RSSQSLLYSNGYNYLDWYLQKPGQSPQLLIYLGSNRASGVPDRFSGSGSGTDFTLKIS

RVEAEDVGVYYCMQDVALPITFGCGTKVEIKASDKTHTCPPCPAPELLGGPSVFLFPP

KPKDTLMISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPRVYTLPPCRDEL

TKNQVSLTCLVKGFYPSDIAVEWESNGQPENNYKTTPPVLVSDGSFTLYSKLTVDKS

RWQQGNVFSCSVMHEALHNHYTQKSLSLSPG

I07 scFv (LC-HC)-Fc (Q347R, D399V, F405T, and S354C substitutions)
                                                          [SEQ ID NO: 187]
DIQMTQSPSTLSASVGDRVTITC<u>RASQSISSWLA</u>WYQQKPGKAPKLLIY<u>EASSLESGV</u>

PSRFSGSGSGTEFTLTISSLQPDDFATYYC<u>QQSQSYPPITF</u>GCGTKVEIKGGGGSGGG

GSGGGGSGGGGSEVQLVESGGGLVQPGGSLRLSCAASGFTFG<u>SYWMS</u>WVRQAPG

KCLEWVAT<u>IKQDGSEKSYVDSVKG</u>RFTISRDNAKNSLYLQMNSLRAEDTAVYYCAR

<u>PLNAGELDV</u>WGQGTMVTVSSASDKTHTCPPCPAPELLGGPSVFLFPPKPKDTLMISR

TPEVTCVVVDVSHEDPEVKFNWYVDGVEVHNAKTKPREEQYNSTYRVVSVLTVLH

QDWLNGKEYKCKVSNKALPAPIEKTISKAKGQPREPRVYTLPPCRDELTKNQVSLTC

LVKGFYPSDIAVEWESNGQPENNYKTTPPVLVSDGSFTLYSKLTVDKSRWQQGNVF

SCSVMHEALHNHYTQKSLSLSPG

I07 scFv (HC-LC)-Fc (Q347R, D399V, F405T, and S354C substitutions)
                                                          [SEQ ID NO: 231]
EVQLVESGGGLVQPGGSLRLSCAASGFTFG<u>SYWMS</u>WVRQAPGKCLEWVAT<u>IKQDG</u>

<u>SEKSYVDSVKG</u>RFTISRDNAKNSLYLQMNSLRAEDTAVYYCAR<u>PLNAGELDV</u>WGQ

GTMVTVSSGGGGSGGGGSGGGGSGGGGSDIQMTQSPSTLSASVGDRVTITC<u>RASQ</u>

<u>SISSWLA</u>WYQQKPGKAPKLLIY<u>EASSLESGV</u>PSRFSGSGSGTEFTLTISSLQPDDFATY

YC<u>QQSQSYPPITF</u>GCGTKVEIKASDKTHTCPPCPAPELLGGPSVFLFPPKPKDTLMISR

TPEVTCVVVDVSHEDPEVKFNWYVDGVEVHNAKTKPREEQYNSTYRVVSVLTVLH

QDWLNGKEYKCKVSNKALPAPIEKTISKAKGQPREPRVYTLPPCRDELTKNQVSLTC

LVKGFYPSDIAVEWESNGQPENNYKTTPPVLVSDGSFTLYSKLTVDKSRWQQGNVF

SCSVMHEALHNHYTQKSLSLSPG

I07 scFc (LC-HC)-Fc (K360E, K409W, and Y349C substitutions)
                                                          [SEQ ID NO: 242]
DIQMTQSPSTLSASVGDRVTITC<u>RASQSISSWLA</u>WYQQKPGKAPKLLIY<u>EASSLESGV</u>

PSRFSGSGSGTEFTLTISSLQPDDFATYYC<u>QQSQSYPPITF</u>GCGTKVEIKGSGGGGSGGGGS

GSGGGGSGGGGSEVQLVESGGGLVQPGGSLRLSCAASGFTFG<u>SYWMS</u>WVRQAPG

KCLEWVAT<u>IKQDGSEKSYVDSVKG</u>RFTISRDNAKNSLYLQMNSLRAEDTAVYYCAR

<u>PLNAGELDV</u>WGQGTMVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYKCKV

SNKALPAPIEKTISKAKGQPREPQVCTLPPSRDELTENQVSLTCLVKGFYPSDIAVEW

ESNGQPENNYKTTPPVLDSDGSFFLYSWLTVDKSRWQQGNVFSCSVMHEALHNHY

TQKSLSLSPG

Ab6 scFv (LC-HC)-Fc (Q347R, D399V, F405T, and S354C substitutions)
[SEQ ID NO: 232]
DIQMTQSPSTLSASVGDRVTITCRASQSISSWLAWYQQKPGKAPKLLIYEASSLESGV

PSRFSGSGSGTEFTLTISSLQPDDFATYYCQQSQSYPPITFCGTKVEIKGSGGGGSGGGGS

GSGGGGSGGGGSEVQLVESGGGLVQPGGSLRLSCAASGFTFPSYWMSWVRQAPGK

CLEWVATIKRDGSEKGYVDSVKGRFTISRDNAKNSLYLQMNSLRAEDTAVYYCARP

LNAGELDVWGQGTMVTVSSASDKTHTCPPCPAPELLGGPSVFLFPPKPKDTLMISRT

PEVTCVVVDVSHEDPEVKFNWYVDGVEVHNAKTKPREEQYNSTYRVVSVLTVLHQ

DWLNGKEYKCKVSNKALPAPIEKTISKAKGQPREPRVYTLPPCRDELTKNQVSLTCL

VKGFYPSDIAVEWESNGQPENNYKTTPPVLVSDGSFTLYSKLTVDKSRWQQGNVFS

CSVMHEALHNHYTQKSLSLSPG

Ab6 scFv (HC-LC)-Fc (Q347R, D399V, F405T, and S354C substitutions)
[SEQ ID NO: 233]
EVQLVESGGGLVQPGGSLRLSCAASGFTFPSYWMSWVRQAPGKCLEWVATIKRDGS

EKGYVDSVKGRFTISRDNAKNSLYLQMNSLRAEDTAVYYCARPLNAGELDVWGQG

TMVTVSSGGGGSGGGGSGGGGSGGGGSDIQMTQSPSTLSASVGDRVTITCRASQSI

SSWLAWYQQKPGKAPKLLIYEASSLESGVPSRFSGSGSGTEFTLTISSLQPDDFATYY

CQQSQSYPPITFCGTKVEIKASDKTHTCPPCPAPELLGGPSVFLFPPKPKDTLMISRTP

EVTCVVVDVSHEDPEVKFNWYVDGVEVHNAKTKPREEQYNSTYRVVSVLTVLHQD

WLNGKEYKCKVSNKALPAPIEKTISKAKGQPREPRVYTLPPCRDELTKNQVSLTCLV

KGFYPSDIAVEWESNGQPENNYKTTPPVLVSDGSFTLYSKLTVDKSRWQQGNVFSCS

VMHEALHNHYTQKSLSLSPG

Ab7 scFv (LC-HC)-Fc (Q347R, D399V, F405T, and S354C substitutions)
[SEQ ID NO: 234]
DIQMTQSPSSVSASVGDRVTITCRASQGIDSWLAWYQQKPGKAPKLLIYAASSLQSG

VPSRFSGSGSGTDFTLTISSLQPEDFATYYCQQAHSYPLTFCGTKVEIKGGGGSGG

GGSGGGGSGGGGSQVQLVQSGAEVKKPGASVKVSCKASGYTFGTYYMHWVRQA

PGQCLEWMGIINPSRGSTVYAQKFQGRVTMTRDTSTSTVYMELSSLRSEDTAVYYC

ARGAGYDDEDMDVWGKGTTVTVSSASDKTHTCPPCPAPELLGGPSVFLFPPKPKDT

LMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPRVYTLPPCRDELTKNQV

SLTCLVKGFYPSDIAVEWESNGQPENNYKTTPPVLVSDGSFTLYSKLTVDKSRWQQG

NVFSCSVMHEALHNHYTQKSLSLSPG

Ab7 scFv (HC-LC)-Fc (Q347R, D399V, F405T, and S354C substitutions)
[SEQ ID NO: 235]
QVQLVQSGAEVKKPGASVKVSCKASGYTFGTYYMHWVRQAPGQCLEWMGIINPSR

GSTVYAQKFQGRVTMTRDTSTSTVYMELSSLRSEDTAVYYCARGAGYDDEDMDV

WGKGTTVTVSSGGGGSGGGGSGGGGSGGGGSDIQMTQSPSSVSASVGDRVTITCR

ASQGIDSWLAWYQQKPGKAPKLLIYAASSLQSGVPSRFSGSGSGTDFTLTISSLQPED

FATYYCQQAHSYPLTFCGTKVEIKASDKTHTCPPCPAPELLGGPSVFLFPPKPKDTL

MISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPRVYTLPPCRDELTKNQVS

LTCLVKGFYPSDIAVEWESNGQPENNYKTTPPVLVSDGSFTLYSKLTVDKSRWQQG

NVFSCSVMHEALHNHYTQKSLSLSPG

-continued

Ab8 scFv (LC-HC)-Fc (Q347R, D399V, F405T, and S354C substitutions)
[SEQ ID NO: 236]
DIQMTQSPSTLSASVGDRVTITCRASNSISSWLAWYQQKPGKAPKLLIYEASSTKSGV
PSRFSGSGSGTEFTLTISSLQPDDFATYYCQQYDDLPTFGCGTKVEIKGGGGSGGGG
SGGGGSGGGGSEVQLVESGGGLVKPGGSLRLSCAASGFTFSSYAMSWVRQAPGKC
LEWVSSISSSSEGIYYADSVKGRFTISRDNAKNSLYLQMNSLRAEDTAVYYCAREGG
PYYDSSGYFVYYGMDVWGQGTTVTVSSASDKTHTCPPCPAPELLGGPSVFLFPPKPK
DTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPRVYTLPPCRDELTKN
QVSLTCLVKGFYPSDIAVEWESNGQPENNYKTTPPVLVSDGSFTLYSKLTVDKSRWQ
QGNVFSCSVMHEALHNHYTQKSLSLSPG Ab8 scFv (HC-LC)-Fc (Q347R, D399V, F405T, and S354C substitutions)
[SEQ ID NO: 237]
EVQLVESGGGLVKPGGSLRLSCAASGFTFSSYAMSWVRQAPGKCLEWVSSISSSSEGI
YYADSVKGRFTISRDNAKNSLYLQMNSLRAEDTAVYYCAREGGPYYDSSGYFVYY
GMDVWGQGTTVTVSSGGGGSGGGGSGGGGSGGGGSDIQMTQSPSTLSASVGDRV
TITCRASNSISSWLAWYQQKPGKAPKLLIYEASSTKSGVPSRFSGSGSGTEFTLTISSL
QPDDFATYYCQQYDDLPTFGCGTKVEIKASDKTHTCPPCPAPELLGGPSVFLFPPKPK
DTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPRVYTLPPCRDELTKN
QVSLTCLVKGFYPSDIAVEWESNGQPENNYKTTPPVLVSDGSFTLYSKLTVDKSRWQ
QGNVFSCSVMHEALHNHYTQKSLSLSPG Ab9 scFv (LC-HC)-Fc (Q347R, D399V, F405T, and S354C substitutions)
[SEQ ID NO: 238]
DIQMTQSPSSLSASVGDRVTITCRASQVIYSYLNWYQQKPGKAPKLLIYAASSLKSGV
PSRFSGSGSGTDFTLTISSLQPEDFATYYCQQVYDTPLTFGCGTKVEIKGGGGSGGG
GSGGGGSGGGGSEVQLVESGGGLVQPGGSLRLSCAASGFTFSSYWMSWVRQAPGK
CLEWVANINTDGSEVYYVDSVKGRFTISRDNAKNSLYLQMNSLRAEDTAVYYCARD
VGPGIAYQGHFDYWGQGTLVTVSSASDKTHTCPPCPAPELLGGPSVFLFPPKPKDTL
MISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPRVYTLPPCRDELTKNQVS
LTCLVKGFYPSDIAVEWESNGQPENNYKTTPPVLVSDGSFTLYSKLTVDKSRWQQG
NVFSCSVMHEALHNHYTQKSLSLSPG Ab9 scFv (HC-LC)-Fc (Q347R, D399V, F405T, and S354C substitutions)
[SEQ ID NO: 239]
EVQLVESGGGLVQPGGSLRLSCAASGFTFSSYWMSWVRQAPGKCLEWVANINTDGS
EVYYVDSVKGRFTISRDNAKNSLYLQMNSLRAEDTAVYYCARDVGPGIAYQGHFD
YWGQGTLVTVSSGGGGSGGGGSGGGGSGGGGSDIQMTQSPSSLSASVGDRVTITC
RASQVIYSYLNWYQQKPGKAPKLLIYAASSLKSGVPSRFSGSGSGTDFTLTISSLQPE
DFATYYCQQVYDTPLTFGCGTKVEIKASDKTHTCPPCPAPELLGGPSVFLFPPKPKDT
LMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPRVYTLPPCRDELTKNQV
SLTCLVKGFYPSDIAVEWESNGQPENNYKTTPPVLVSDGSFTLYSKLTVDKSRWQQG
NVFSCSVMHEALHNHYTQKSLSLSPG -continued Ab10 scFv (LC-HC)-Fc (Q347R, D399V, F405T, and S354C substitutions)
[SEQ ID NO: 240]
EIVLTQSPATLSLSPGERATLSCRASHSVYSYLAWYQQKPGQAPRLLIYDASNRATGI

PARFSGSGSGTDFTLTISSLEPEDFAVYYCQQYDNLPTFG_C_GTKVEI_K_GGGGSGGGG

SGGGGSGGGGSQLQLQESGPGLVKPSETLSLTCTVSGGSISSTDYYWGWIRQPPGK_C_

LEWIGSIGYSGTYYNPSLKSRVTISVDTSKNQFSLKLSSVTAADTAVYYCARETAHDV

HGMDVWGQGTTVTVSSASDKTHTCPPCPAPELLGGPSVFLFPPKPKDTLMISRTPEV

TCVVVDVSHEDPEVKFNWYVDGVEVHNAKTKPREEQYNSTYRVVSVLTVLHQDW

LNGKEYKCKVSNKALPAPIEKTISKAKGQPREPRVYTLPP_C_RDELTKNQVSLTCLVK

GFYPSDIAVEWESNGQPENNYKTTPPVL_V_SDGSF_T_LYSKLTVDKSRWQQGNVFSCSV

MHEALHNHYTQKSLSLSPG

Ab10 scFv (HC-LC)-Fc (Q347R, D399V, F405T, and S354C substitutions)
[SEQ ID NO: 241]
QLQLQESGPGLVKPSETLSLTCTVSGGSISSTDYYWGWIRQPPGK_C_LEWIGSIGYSGT

YYNPSLKSRVTISVDTSKNQFSLKLSSVTAADTAVYYCARETAHDVHGMDVWGQG

TTVTVSGGGGSGGGGSGGGGSGGGGSEIVLTQSPATLSLSPGERATLSCRASHSV

YSYLAWYQQKPGQAPRLLIYDASNRATGIPARFSGSGSGTDFTLTISSLEPEDFAVYY

CQQYDNLPTFG_C_GTKVEIKASDKTHTCPPCPAPELLGGPSVFLFPPKPKDTLMISRTPE

VTCVVVDVSHEDPEVKFNWYVDGVEVHNAKTKPREEQYNSTYRVVSVLTVLHQD

WLNGKEYKCKVSNKALPAPIEKTISKAKGQPREPRVYTLPP_C_RDELTKNQVSLTCLV

KGFYPSDIAVEWESNGQPENNYKTTPPVL_V_SDGSF_T_LYSKLTVDKSRWQQGNVFSCS

VMHEALHNHYTQKSLSLSPG

A TriNKET of the present disclosure is A49-F3'-TriNKET-I07, comprising a first polypeptide chain, named "I07 scFv-Fc," which comprises a CD33-binding scFv linked to an Fc domain via an Ala-Ser linker; a second polypeptide chain, named "A49 VH-CH1-Fc," which comprises an NKG2D-targeting heavy chain; and a third polypeptide chain, named "A49 VL-CL," which comprises an NKG2D-targeting light chain. The amino acid sequence of I07 scFv-Fc comprises:

I07 scFv (LC-HC)-Fc (Q347R, D399V, F405T, and S354C substitutions)
[SEQ ID NO: 187]
DIQMTQSPSTLSASVGDRVTITC_RASQSISSWLA_WYQQKPGKAPKLLIYE

_ASSLES_GVPSRFSGSGSGTEFTLTISSLQPDDFATYYC_QQSQSYPPIT_FG

_C_GTKVEI_K_GGGSGGGGSGGGGSGGGGSEVQLVESGGGLVQPGGSLRSC

AASGFTFGS_YWMS_WVRQAPGK_C_LEWVAT_IKQDGSEKSYVDSVKG_RFTISR

DNAKNSLYLQMNSLRAEDTAVYYCAR_PLNAGELDV_WGQGTMVTVSSASDK

THTCPPCPAPELLGGPSVFLFPPKPKDTLMISRTPEVTCVVVDVSHEDPE

VKFNWYVDGVEVHNAKTKPREEQYNSTYRVVSVLTVLHQDWLNGKEYKCK

VSNKALPAPIEKTISKAKGQPREPRVYTLPP_C_RDELTKNQVSLTCLVKGF

YPSDIAVEWESNGQPENNYKTTPPVL_V_SDGSF_T_LYSKLTVDKSRWQQGNV

FSCSVMHEALHNHYTQKSLSLSPG

The amino acid sequence of the scFv portion of I07 scFv-Fc comprises:

I07 scFv
[SEQ ID NO: 188]
DIQMTQSPSTLSASVGDRVTITC_RASQSISSWLA_WYQQKPGKAPKLLIYE

_ASSLES_GVPSRFSGSGSGTEFTLTISSLQPDDFATYYC_QQSQSYPPIT_FG

_C_GTKVEI_K_GGGSGGGGSGGGGSGGGGSEVQLVESGGGLVQPGGSLR

LSCAASGFTFGS_YWMS_WVRQAPGK_C_LEWVAT_IKQDGSEKSYVDSVKG_RF

TISRDNAKNSLYLQMNSLRAEDTAVYYCAR_PLNAGELDV_WGQGTMVTVSS

A49 VH-CH1-Fc comprises A49 VH [SEQ ID NO:87] linked to a CH1 domain and an Fc domain (including hinge, CH2, and CH3 domains). The amino acid sequence of A49 VH-CH1-Fc comprises:

A49 VH-CH1-Fc (K360E, K409W, and Y349C substitutions)
[SEQ ID NO: 189]
EVQLVESGGGLVKPGGSLRLSCAASGFTFS_SYSMN_WVRQAPGKGLEWVSS

_ISSSSSYIYYADSVKG_RFTISRDNAKNSLYLQMNSLRAEDTAVYYCARGA

_PMGAAAGWFDP_WGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

```
YNSTYRVVSVLTVLHQDWLNGKEYKCKVSNKALPAPIEKTISKAKGQPRE

PQVCTLPPSRDELTENQVSLTCLVKGFYPSDIAVEWESNGQPENNYKTTP

PVLDSDGSFFLYSWLTVDKSRWQQGNVFSCSVMHEALHNHYTQKSLSLSP

G

A49 VH-CH1-Fc (Q347R, D399V, F405T, and S354C
substitutions)
                                        [SEQ ID NO: 244]
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PMGAAAGWFDPWGQGTLVTVSSASDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

RVYTLPPCRDELTKNQVSLTCLVKGFYPSDIAVEWESNGQPENNYKTTPP

VLVSDGSFTLYSKLTVDKSRWQQGNVFSCSVMHEALHNHYTQKSLSL
```

A49 VL-CL comprises A49 VL [SEQ ID NO:88] linked to a light chain constant domain (CL). The amino acid sequence of A49 VL-CL comprises:

```
A49 VL-CL
                                        [SEQ ID NO: 190]
DIQMTQSPSSVSASVGDRVTITCRASQGISSWLAWYQQKPGKAPKLLIYA

ASSLQSGVPSRFSGSGSGTDFTLTISSLQPEDFATYYCQQGVSFPRTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

Another TriNKET of the present disclosure is A49MI-F3'-TriNKET-I07, comprising a first polypeptide chain, named "I07 scFv-Fc," as described above [SEQ ID NO:187]; a second polypeptide chain, named "A49MI VH-CH1-Fc," that comprises an NKG2D-targeting heavy chain with an Fc domain; and a third polypeptide chain, named "A49 VL-CL," as described above [SEQ ID NO:190]. A49MI-F3'-TriNKET-I07 is identical to A49-F3'-TriNKET-I07 except for a substitution of I for M in CDR3 of the NKG2D-targeting VH. This substitution is bold-italic (and underlined because it is part of a CDR) in the sequence below. A49MI VH-CH1-Fc comprises A49MI VH [SEQ ID NO:191] linked to a CH1 domain and an Fc domain (including hinge, CH2, and CH3 domains). The amino acid sequence of A49MI VH-CH1-Fc comprises:

```
A49MI VH-CH1-Fc (K360E, K409W, and Y349C
substitutions)
                                        [SEQ ID NO: 196]
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PIGAAAGWFDPWGQGTLVTVSSASTKGPSVFPLAPSSKSTSGGTAALGCL

VKDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVCTLPPSRDELTENQVSLTCLVKGFYPSDIAVEWESNGQPENNYKTTP

PVLDSDGSFFLYSWLTVDKSRWQQGNVFSCSVMHEALHNHYTQKSLSLSP

G

A49MI VH-CH1-Fc (Q347R, D399V, F405T, and S354C
substitutions)
                                        [SEQ ID NO: 245]
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PIGAAAGWFDPWGQGTLVTVSSASDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

RVYTLPPCRDELTKNQVSLTCLVKGFYPSDIAVEWESNGQPENNYKTTPP

VLVSDGSFTLYSKLTVDKSRWQQGNVFSCSVMHEALHNHYTQKSLSL
```

Another TriNKET of the present disclosure is A49-F3'-TriNKET-I07(si), comprising a first polypeptide chain, named "I07 scFv-Fc(si)," which comprises a CD33-binding scFv linked to a silent Fc domain via an Ala-Ser linker; a second polypeptide chain, named "A49 VH-CH1-Fc(si)," which comprises an NKG2D-targeting heavy chain with a silent Fc domain; and a third polypeptide chain, named "A49 VL-CL," as described above [SEQ ID NO: 190]. A49-F3'-TriNKET-I07(si) is identical to A49-F3'-TriNKET-I07 except for L234A, L235A, and P329A substitutions in both Fc domains. These substitutions are bold-italic in the two sequences below. The amino acid sequence of I07 scFv-Fc(si) comprises:

```
I07 scFv-Fc(si)
                                        [SEQ ID NO: 204]
DIQMTQSPSTLSASVGDRVTITCRASQSISSWLAWYQQKPGKAPKLLIYE

ASSLESGVPSRFSGSGSGTEFTLTISSLQPDDFATYYCQQSQSYPPITFG

CGTKVEIKGGGGSGGGGSGGGGSGGGGSEVQLVESGGGLVQPGGSLR

LSCAASGFTFGSYWMSWVRQAPGKCLEWVATIKQDGSEKSYVDSVKGRF

TISRDNAKNSLYLQMNSLRAEDTAVYYCARPLNAGELDVWGQGTMVTVSS

ASDKTHTCPPCPAPEAAGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALGAPIEKTISKAKGQPREPRVYTLPPCRDELTKNQVS

LTCLVKGFYPSDIAVEWESNGQPENNYKTTPPVLVSDGSFTLYSKLTV

DKSRWQQGNVFSCSVMHEALHNHYTQKSLSLSPG
```

The amino acid sequence of the scFv portion of I07 scFv-Fc(si) is identical to that of the scFv portion of I07 scFv-Fc as described above [SEQ ID NO:188].

The amino acid sequence of A49 VH-CH1-Fc(si) comprises:

```
A49 VH-CH1-Fc(si)
                                        [SEQ ID NO: 205]
EVQLVESGGGLVKPGGSLRLSCAASGFTFSSYSMNWVRQAPGKGLEWVSS

ISSSSSYIYYADSVKGRFTISRDNAKNSLYLQMNSLRAEDTAVYYCARGA

PMGAAAGWFDPWGQGTLVTVSSASTKGPSVFPLAPSSKSTSGGTAALGCL

VKDYFPEPVTVSWNSGALTSGVHTFPAVLQSSGLYSLSSVVTVPSSSLGT
```

-continued

QTYICNVNHKPSNTKVDKKVEPKSCDKTHTCPPCPAPEAAGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALGAPIEKTISKAKGQPRE

PQVCTLPPSRDELTENQVSLTCLVKGFYPSDIAVEWESNGQPENNYKTTP

PVLDSDGSFFLYSWLTVDKSRWQQGNVFSCSVMHEALHNHYTQKSLSLSP

G

Another TriNKET of the present disclosure is A49-F3'-TriNKET-H76, comprising a first polypeptide chain, named "H76 scFv-Fc," that comprises a CD33-binding scFv linked to an Fc domain via an Ala-Ser linker; a second polypeptide chain, named "A49 VH-CH1-Fc," as described above [SEQ ID NO:189]; and a third polypeptide chain, named "A49 VL-CL," as described above [SEQ ID NO:190]. The amino acid sequence of H76 scFv-Fc comprises:

H76 scFv-Fc
[SEQ ID NO: 197]
DIQMTQSPSTLSASVGDRVTITC<u>RASQSISSWLAWY</u>QQKPGKAPKLLIYK

ASSLESGVPSRFSGSGSGTEFTLTISSLQPDDFATYYC<u>QQYDDLPTF</u>GCG

TKVEIK<u>GGGGSGGGGSGGGGSGGGGS</u>EVQLLESGGGLVQPGGSLRLSCAA

SGFTFS<u>KYTMS</u>WVRQAPGKCLEWVS<u>AIVGSGESTYFADSVKG</u>RFTISRDN

SKNTLYLQMNSLRAEDTAVYYCAR<u>EGGPYYDSSGYFVYY</u>GMDVWGQGTTV

TVSSASDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWL

NGKEYKCKVSNKALPAPIEKTISKAKGQPREPRVYTLPPCRDELTKNQVS

LTCLVKGFYPSDIAVEWESNGQPENNYKTTPPVLVSDGSFTLYSKLTVDK

SRWQQGNVFSCSVMHEALHNHYTQKSLSLSPG

The amino acid sequence of the scFv portion of H76 scFv-Fc comprises:

H76 scFv
[SEQ ID NO: 198]
DIQMTQSPSTLSASVGDRVTITC<u>RASQSISSWLAWY</u>QQKPGKAPKLLIYK

ASSLESGVPSRFSGSGSGTEFTLTISSLQPDDFATYYC<u>QQYDDLPTF</u>GCG

TKVEIK<u>GGGGSGGGGSGGGGSGGGGS</u>EVQLLESGGGLVQPGGSLRLSCAA

SGFTFS<u>KYTMS</u>WVRQAPGKCLEWVS<u>AIVGSGESTYFADSVKG</u>RFTISRDN

SKNTLYLQMNSLRAEDTAVYYCAR<u>EGGPYYDSSGYFVYY</u>GMDVWGQGTTV

TVSS

In other embodiments of the present disclosure, the CD33-binding scFv of the multi-specific binding protein (e.g., TriNKET) comprises the heavy chain variable domain CDR1, CDR2, and CDR3, and light chain variable domain CDR1, CDR2, and CDR3, of any one of the antibodies provided in Table 1. In certain embodiments, the amino acid sequence of the heavy chain variable domain is identical to the VH sequence of an antibody in Table 1 except for a substitution of Cys at position 44, and the amino acid sequence of the light chain variable domain is identical to the VL sequence of the same antibody except for a substitution of Cys at position 100. In certain embodiments, the heavy chain variable domain is connected to the light chain variable domain with a (G4S)$_4$ linker. The heavy chain variable domain can be N-terminal to the light chain variable domain or C-terminal to the light chain variable domain. The scFv is linked to an Fc domain via a hinge comprising Ala-Ser.

The multi-specific binding proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the first immunoglobulin light chain can be cloned into a third expression vector; a fourth nucleic acid sequence encoding the second immunoglobulin light chain can be cloned into a fourth expression vector; the first, second, third and fourth expression vectors can be stably transfected together into host cells to produce the multimeric proteins.

To achieve the highest yield of the multi-specific binding proteins, different ratios of the first, second, third and fourth expression vectors can be explored to determine the optimal ratio for transfection into the host cells. After transfection, single clones can be isolated for cell bank generation using methods known in the art, such as limited dilution, ELISA, FACS, microscopy, or ClonePix®.

Clones can be cultured under conditions suitable for bio-reactor scale-up and maintained expression of the multi-specific protein. The multi-specific binding proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

In certain embodiments, the antibody binds CD33 with a $K_D$ of 20 nM, 15 nM, 10 nM, 9 nM, 8 nM, 7 nM, 6 nM, 5 nM, 4 nM, 3 nM, 2 nM, 1 nM or lower, as measured using standard binding assays, for example, surface plasmon resonance or bio-layer interferometry. In certain embodiments the antibody binds EBI3 from a body fluid, tissue and/or cell of a subject.

Competition assays for determining whether an antibody binds to the same epitope as, or competes for binding with a disclosed antibody, e.g., the Ab1 antibody, the Ab2 antibody, the Ab3 antibody, the Ab4 antibody, or the Ab5 antibody, are known in the art. Exemplary competition assays include immunoassays (e.g., ELISA assays, RIA assays), surface plasmon resonance (e.g., Biacore™ analysis), bio-layer interferometry, and flow cytometry.

Typically, a competition assay involves the use of an antigen (e.g., a human CD33 protein or fragment thereof) bound to a solid surface or expressed on a cell surface, a test CD33-binding antibody and a reference antibody. The reference antibody is labeled and the test antibody is unlabeled. Competitive inhibition is measured by determining the amount of labeled reference antibody bound to the solid surface or cells in the presence of the test antibody. Usually the test antibody is present in excess (e.g., 1×, 5×, 10×, 20× or 100×). Antibodies identified by competition assay (e.g., competing antibodies) include antibodies binding to the same epitope, or similar (e.g., overlapping) epitopes, as the reference antibody, and antibodies binding to an adjacent epitope sufficiently proximal to the epitope bound by the reference antibody for steric hindrance to occur.

A competition assay can be conducted in both directions to ensure that the presence of the label does not interfere or otherwise inhibit binding. For example, in the first direction the reference antibody is labeled and the test antibody is unlabeled, and in the second direction, the test antibody is labeled and the reference antibody is unlabeled.

A test antibody competes with the reference antibody for specific binding to the antigen if an excess of one antibody (e.g., 1×, 5×, 10×, 20× or 100×) inhibits binding of the other antibody, e.g., by at least 50%, 75%, 90%, 95% or 99% as measured in a competitive binding assay.

Two antibodies may be determined to bind to the same epitope if essentially all amino acid mutations in the antigen that reduce or eliminate binding of one antibody reduce or eliminate binding of the other. Two antibodies may be determined to bind to overlapping epitopes if only a subset of the amino acid mutations that reduce or eliminate binding of one antibody reduce or eliminate binding of the other.

The antibodies disclosed herein may be further optimized (e.g., affinity-matured) to improve biochemical characteristics including affinity and/or specificity, improve biophysical properties including aggregation, stability, precipitation and/or non-specific interactions, and/or to reduce immunogenicity. Affinity-maturation procedures are within ordinary skill in the art. For example, diversity can be introduced into an immunoglobulin heavy chain and/or an immunoglobulin light chain by DNA shuffling, chain shuffling, CDR shuffling, random mutagenesis and/or site-specific mutagenesis.

In certain embodiments, isolated human antibodies contain one or more somatic mutations. In these cases, antibodies can be modified to a human germline sequence to optimize the antibody (e.g., by a process referred to as germlining).

Generally, an optimized antibody has at least the same, or substantially the same, affinity for the antigen as the non-optimized (or parental) antibody from which it was derived. Preferably, an optimized antibody has a higher affinity for the antigen when compared to the parental antibody.

If the antibody is for use as a therapeutic, it can be conjugated to an effector agent such as a small molecule toxin or a radionuclide using standard in vitro conjugation chemistries. If the effector agent is a polypeptide, the antibody can be chemically conjugated to the effector or joined to the effector as a fusion protein. Construction of fusion proteins is within ordinary skill in the art.

The antibody can be conjugated to an effector moiety such as a small molecule toxin or a radionuclide using standard in vitro conjugation chemistries. If the effector moiety is a polypeptide, the antibody can be chemically conjugated to the effector or joined to the effector as a fusion protein. Construction of fusion proteins is within ordinary skill in the art.

In certain embodiments, the protein (e.g., multi-specific binding protein) of the present disclosure is not substantially internalized by a CD33-expressing cell. A low level of internalization may improve the pharmacokinetics of the protein, thereby reducing the dose required to engage CD33-expressing target cells with effector cells (e.g., NK cells). Internalization can be measured by any method known in the art, e.g., the methods described in Examples 5 and 10 of the present disclosure. For example, in certain embodiments, internalization of the protein (e.g., multi-specific binding protein) by EOL-1 cells is lower than 25%, 30%, 35%, 40%, 45%, or 50% after a two-hour incubation, as assessed by the methods disclosed herein. In certain embodiments, internalization of the protein (e.g., multi-specific binding protein) by EOL-1 cells is lower than 25%, 30%, 35%, 40%, 45%, or 50% after a 24-hour incubation, as assessed by the methods disclosed herein. In certain embodiments, internalization of the protein (e.g., multi-specific binding protein) by Molm-13 cells is lower than 25%, 30%, 35%, 40%, 45%, or 50% after a two-hour incubation, as assessed by the methods disclosed herein.

KHYG-1 cells express surface NKG2D, but do not express CD16. In certain embodiments, TriNKET mediated killings of Molm-13 and THP-1 cells are dependent upon NKG2D-mediated activation of the KHYG-1 effector cells. In certain embodiments, TriNKETs of the present disclosure mediate KHYG-1 effector cell killing of Molm-13 (FIG. 15A), EOL-1 (FIG. 16), and THP-1 (FIG. 17A) human AML target cell lines.

Figure 38A:
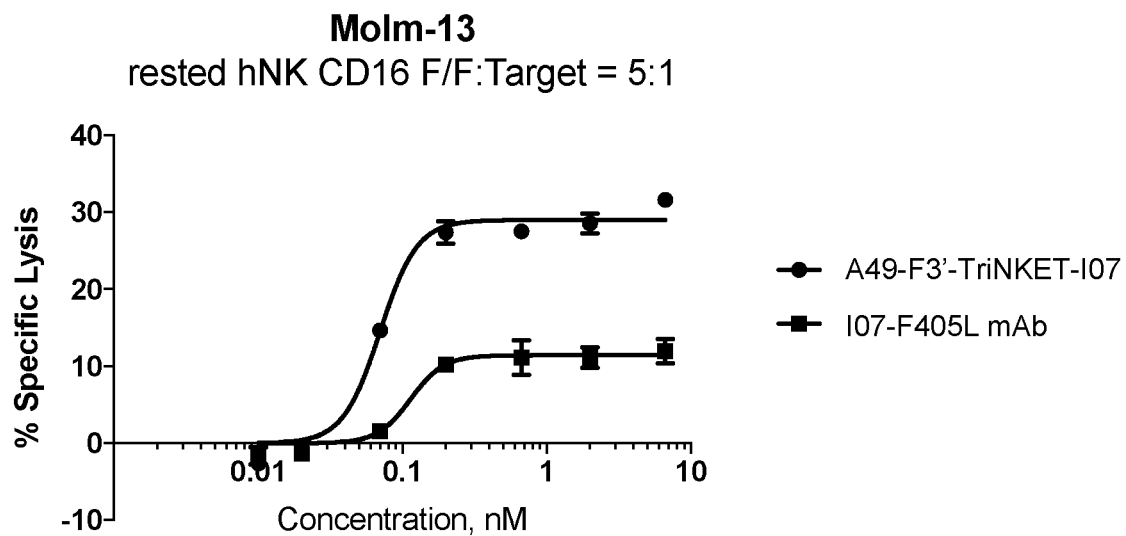
FIGS. 38A-38D are graphs showing specific lysis of Molm-13 (FIG. 38A), EOL-1 (FIG. 38B), and THP-1 (FIGS. 38C and 38D) human AML cells by rested human NK cells in the presence of A49-F3'-TriNKET-I07 and anti-CD33 monoclonal antibodies.

In certain embodiments, TriNKETs of the present disclosure mediate cytotoxicity of rested human NK cells against Molm-13 or THP-1 human AML cells. FIGS. 15B and 38A show that TriNKETs of the present disclosure mediate rested human NK cell killing of Molm-13 human AML cells. The rested human NK effector cell (E) to target cancer cell (T) ratio (E:T) was 10:1 in FIG. 15B and 5:1 in FIG. 38A. The E:T ratio may reflect differences in the maximal % lysis.

Figure 38B:
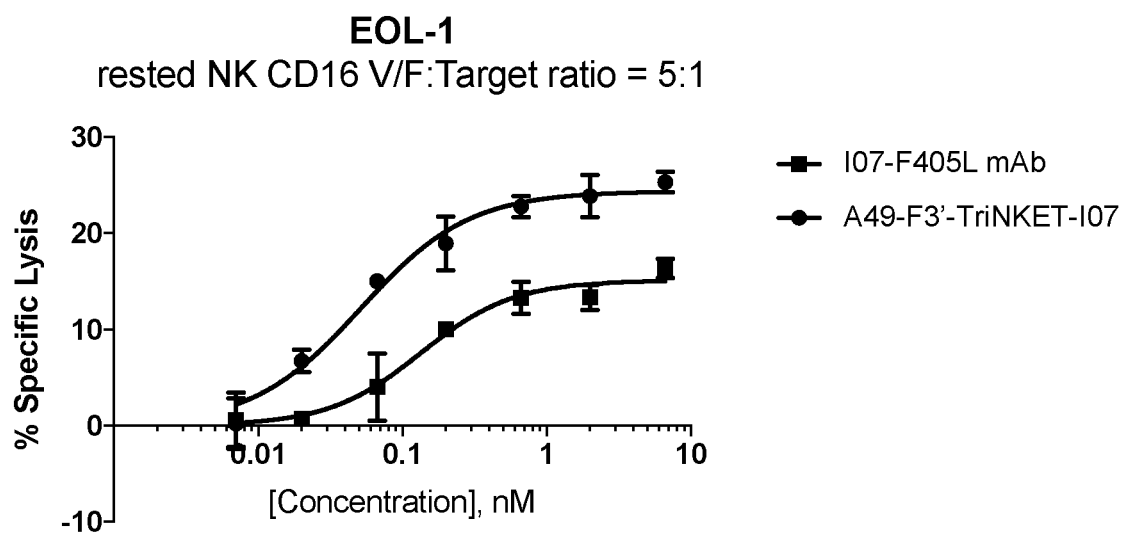
Figure 38C:
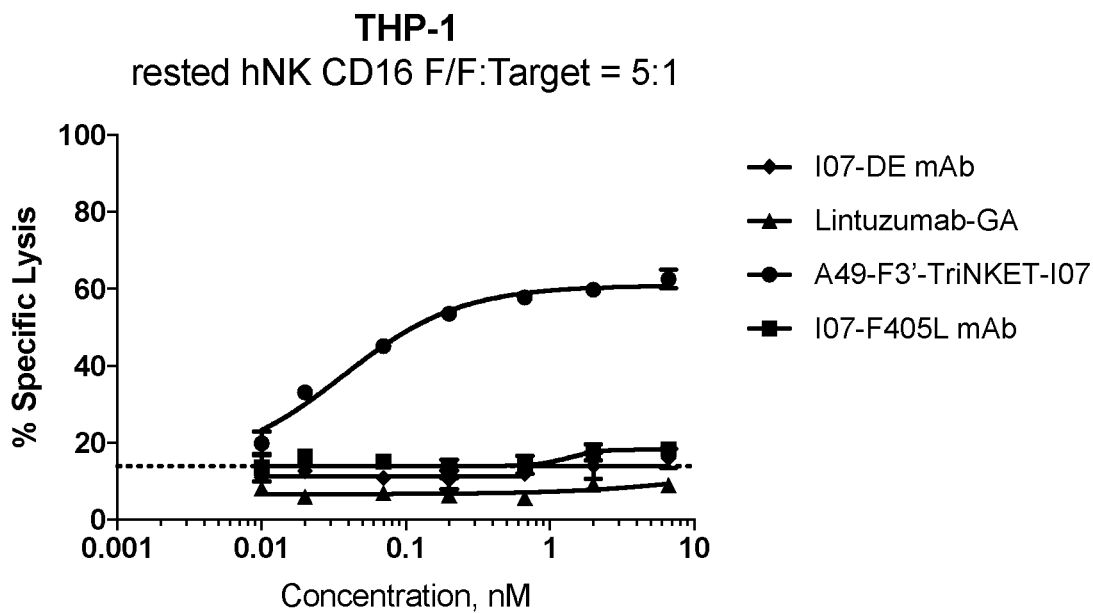
Figure 38D:
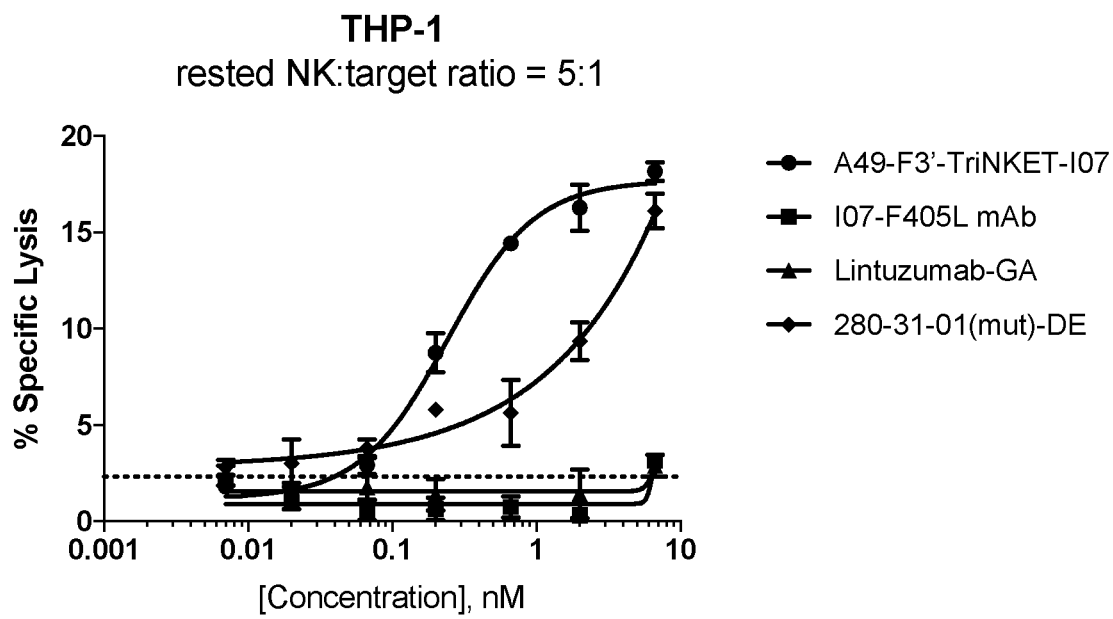

In certain embodiments, TriNKETs of the present disclosure mediate rested human NK cell killing of EOL-1 human AML cells. FIG. 38B shows that TriNKETs mediate rested human NK cell killing of EOL-1 cells at an E:T of 5:1. In certain embodiments, TriNKETs of the present disclosure mediate rested human NK cell killing of THP-1 target cells, which express the high-affinity FcγRI. FIGS. 17B, 38C, and 38D show that TriNKETs mediate rested human NK cell killing of THP-1 human AML cells using an E:T of 5:1.

Figure 40A:
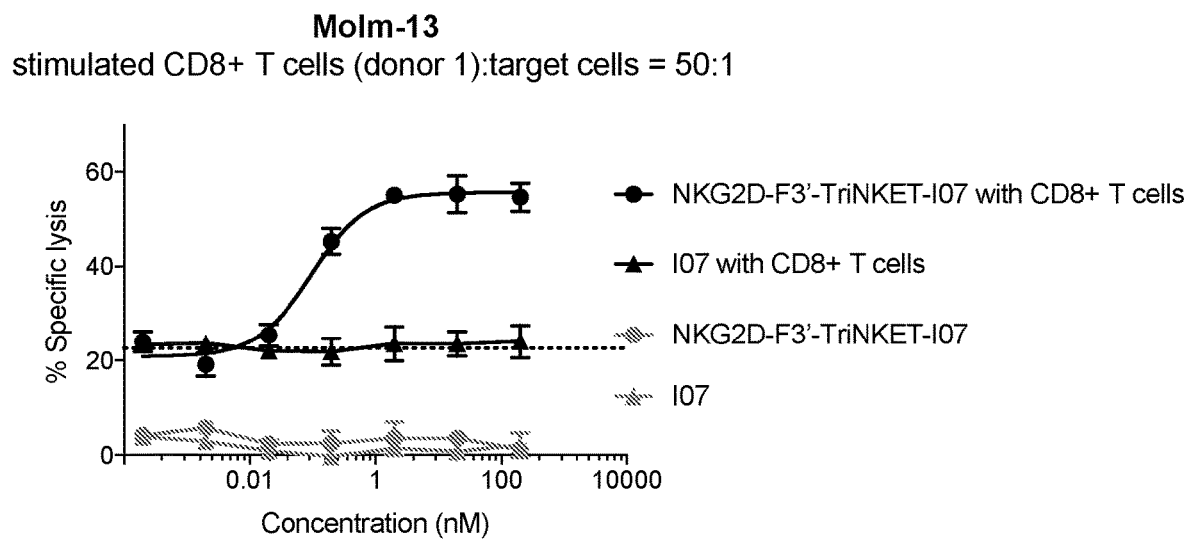
FIGS. 40A-40B are graphs showing specific lysis of Molm-13 cells by isolated primary CD8$^+$ T cells in the presence of A49-F3'-TriNKET-I07, A49-F3'-TriNKET-H76, a non-target TriNKET, or I07-F405L mAb (denoted as I07 in the figures). The primary CD8$^+$ T cells in FIG. 40A were isolated from PBMCs of donor 1, and the primary CD8$^+$ T cells in FIG. 40B were isolated from PBMCs of donor 2. The dotted lines indicate specific lysis of Molm-13 cells by CD8$^+$ T cells in the absence of TriNKET or antibody.
Figure 40B:
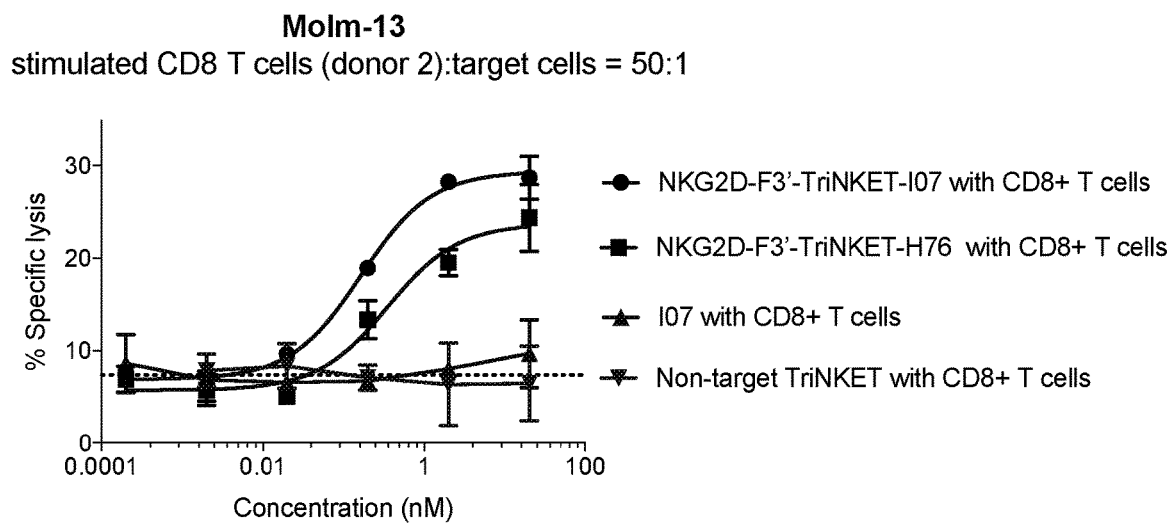
Figure 41A:
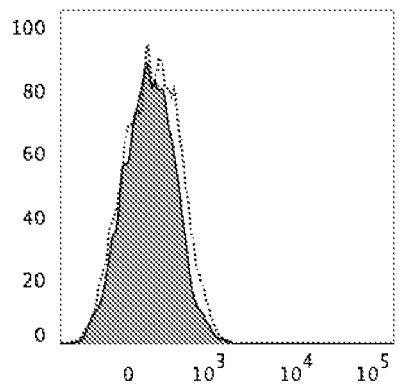
FIGS. 41A-41E are histograms showing the binding of A49-F3'-TriNKET-I07 to NK cells (FIG. 41A), CD8$^+$ T cells (FIG. 41B), CD4$^+$ T cells (FIG. 41C), B cells (FIG. 41D), and monocytes (FIG. 41E) in human whole blood. The dotted lines without fill represent binding of A49-F3'-TriNKET-I07 to the cells; the solid lines with fill represent binding of human IgG1 isotype control to the cells.
Figure 41B:
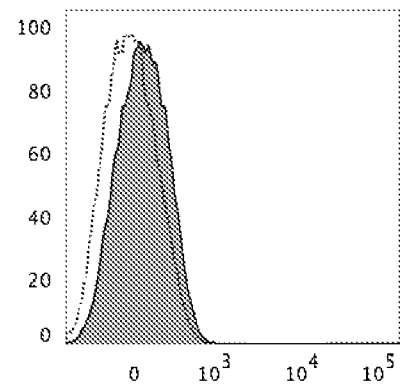
Figure 41C:
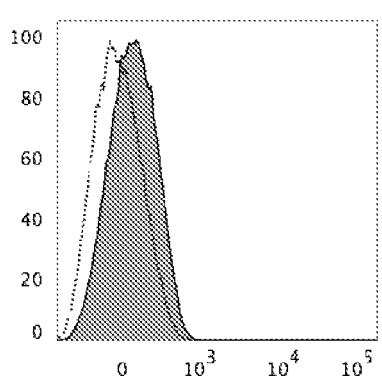
Figure 41D:
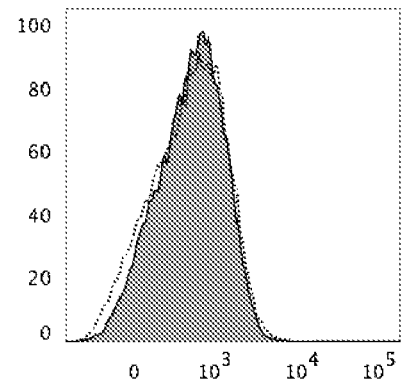
Figure 41E:
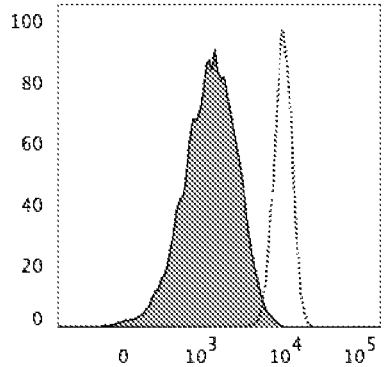

In certain embodiments, TriNKETs of the present disclosure mediate human CD8⁺ T cell killing of Molm-13 target cells. FIGS. 40A-40B show that TriNKETs mediate human CD8⁺ T cell killing of Molm-13 cells at an E:T of 50:1.

A Protein Comprising an Antigen-Binding Site that Competes with the CD33-Binding Sites Described Herein In one aspect, the present invention provides a protein that includes an antigen-binding site that competes with the CD33-binding sites described herein to bind to CD33. In certain embodiments, the present invention provides a protein that includes an antigen-binding site that competes for binding to human and cynomolgus CD33 with an antibody that includes an antibody heavy chain having the amino acid sequence of SEQ ID NO:1 and an antibody light chain having the amino acid sequence of SEQ ID NO:2.

In certain embodiments, the present invention provides a protein that includes an antigen-binding site that competes for binding to human and cynomolgus CD33 with an antibody that includes an antibody heavy chain having the amino acid sequence of SEQ ID NO:3 and an antibody light chain having the amino acid sequence of SEQ ID NO:4.

In certain embodiments, the present invention provides a protein that includes an antigen-binding site that competes for binding to human and cynomolgus CD33 with an antibody that includes an antibody heavy chain having the amino acid sequence of SEQ ID NO:5 and an antibody light chain having the amino acid sequence of SEQ ID NO:6.

In certain embodiments, the present invention provides a protein that includes an antigen-binding site that competes for binding to human and cynomolgus CD33 with an antibody that includes an antibody heavy chain having the amino acid sequence of SEQ ID NO:7 and an antibody light chain having the amino acid sequence of SEQ ID NO:8.

In certain embodiments, the present invention provides a protein that includes an antigen-binding site that competes for binding to human and cynomolgus CD33 with an antibody that includes an antibody heavy chain having the amino acid sequence of SEQ ID NO:9 and an antibody light chain having the amino acid sequence of SEQ ID NO:10.

In certain embodiments, the present invention provides a protein that includes an antigen-binding site that competes for binding to human and cynomolgus CD33 with an antibody that includes an antibody heavy chain having the amino acid sequence of SEQ ID NO:11 and an antibody light chain having the amino acid sequence of SEQ ID NO:12.

In certain embodiments, the present invention provides a protein that includes an antigen-binding site that competes for binding to human and cynomolgus CD33 with an antibody that includes an antibody heavy chain having the amino acid sequence of SEQ ID NO:13 and an antibody light chain having the amino acid sequence of SEQ ID NO:14.

In certain embodiments, the present invention provides a protein that includes an antigen-binding site that competes for binding to human and cynomolgus CD33 with an antibody that includes an antibody heavy chain having the amino acid sequence of SEQ ID NO:15 and an antibody light chain having the amino acid sequence of SEQ ID NO:16.

In certain embodiments, the present invention provides a protein that includes an antigen-binding site that competes for binding to human and cynomolgus CD33 with an antibody that includes an antibody heavy chain having the amino acid sequence of SEQ ID NO:17 and an antibody light chain having the amino acid sequence of SEQ ID NO:18.

In certain embodiments, the present invention provides a protein that includes an antigen-binding site that competes for binding to human and cynomolgus CD33 with an antibody that includes an antibody heavy chain having the amino acid sequence of SEQ ID NO:19 and an antibody light chain having the amino acid sequence of SEQ ID NO:20.

In some embodiments, an antigen-binding site of the protein that competes with the CD33-binding sites includes a heavy chain variable domain having an amino acid sequence at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:1 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:2. In some embodiments, an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:3 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:4.

In some embodiments, an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:5 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:6.

In some embodiments, an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:7 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:8.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:9 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:10.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:11 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:12.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:13 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:14.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:15 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:16.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:17 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:18.

In some embodiments an antigen-binding site of the protein that competes with the CD33-binding sites includes a heavy chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:19 and a light chain variable domain having an amino acid sequence at least at least 50% (e.g., 50%, 60%, 70%, 80%, 90%, 91%, 92%, 93%, 94%, 95%, 96%, 97%, 98%, 99%, or 100%) identical to the amino acid sequence of SEQ ID NO:20.

In certain embodiments, the present invention provides a protein that includes an antigen-binding site that competes for binding to human and cynomolgus CD33 with an antibody that includes an antigen-binding site that binds a tumor-associated antigen.

In certain embodiments, the present invention provides a protein that includes an antigen-binding site that competes for binding to human and cynomolgus CD33 with an antibody that includes an antibody constant region or a portion thereof capable of binding CD16.

CAR T Cells, CD33/CD3-Directed Bispecific T-Cell Engagers, Immunocytokines, Antibody-Drug Conjugates, and Immunotoxins Another aspect of the present disclosure provides a molecule or complex comprising an antigen-binding site that binds CD33 as disclosed herein. Exemplary molecules or complexes include but are not limited to chimeric antigen receptors (CARs), T-cell engagers (e.g., CD33/CD3-directed bispecific T-cell engagers), immunocytokines, antibody-drug conjugates, and immunotoxins.

Any antigen-binding site that binds CD33 as disclosed herein can be used, including but not limited to the antigen-binding site that binds CD33 as disclosed in Section I. Antigen-Binding Site. In certain embodiments, the amino acid sequence(s) of the antigen-binding site that binds CD33 are provided in Table 1. In certain embodiments, the antigen-binding site that binds CD33 is an scFv. In certain embodiments, the scFv comprises an amino acid sequence at least 90% (e.g., 90%, 91%, 92%, 93%, 94%, 95%, 96%, 97%, 98%, 99%, or 100%) identical to an amino acid sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, and SEQ ID NO:484. In certain embodiments, the scFv comprises an amino acid sequence selected from SEQ ID NO:188, SEQ ID NO:198, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:457, SEQ ID NO:458, SEQ ID NO:459, SEQ ID NO:460, SEQ ID NO:461, SEQ ID NO:462, SEQ ID NO:463, SEQ ID NO:464, SEQ ID NO:465, SEQ ID NO:466, SEQ ID NO:467, SEQ ID NO:468, SEQ ID NO:469, SEQ ID NO:470, SEQ ID NO:471, SEQ ID NO:472, SEQ ID NO:473, SEQ ID NO:474, SEQ ID NO:475, SEQ ID NO:476, SEQ ID NO:477, SEQ ID NO:478, SEQ ID NO:479, SEQ ID NO:480, SEQ ID NO:481, SEQ ID NO:482, SEQ ID NO:483, and SEQ ID NO:484.

In certain embodiments, the antigen-binding site that binds CD33 comprises a heavy chain variable domain comprising CDR1, CDR2, and CDR3 sequences represented by the amino acid sequences of SEQ ID NOs:181, 46, and 182, respectively; and a light chain variable domain comprising CDR1, CDR2, and CDR3 sequences represented by the amino acid sequences of SEQ ID NOs:48, 49, and 50, respectively. In certain embodiments, the antigen-binding site comprises a heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:9; and a light chain variable domain with an amino acid sequence at least 90% (e.g., 91%, 92%, 93%, 94%, 95%, 96%, 97%, 98%, 99%, or 100%) identical to the amino acid sequence of SEQ ID NO:10. In certain embodiments, the antigen-binding site comprises an scFv comprising an amino acid sequence at least 90% (e.g., 90%, 91%, 92%, 93%, 94%, 95%, 96%, 97%, 98%, 99%, or 100%) identical to SEQ ID NO:188.

In other embodiments of any one of the foregoing aspects in this subsection, the antigen-binding site that binds CD33 comprises a heavy chain variable domain comprising CDR1, CDR2, and CDR3 sequences represented by the amino acid sequences of SEQ ID NOs:183, 34, and 184, respectively; and a light chain variable domain comprising CDR1, CDR2, and CDR3 sequences represented by the amino acid sequences of SEQ ID NOs:36, 185, and 38, respectively. In certain embodiments, the antigen-binding site comprises a heavy chain variable domain with an amino acid sequence at least 90% (e.g., 91%, 92%, 93%, 94%, 95%, 96%, 97%, 98%, 99%, or 100%) identical to the amino acid sequence of SEQ ID NO:5; and a light chain variable domain with an amino acid sequence at least 90% (e.g., 91%, 92%, 93%, 94%, 95%, 96%, 97%, 98%, 99%, or 100%) identical to the amino acid sequence of SEQ ID NO:6. In certain embodiments, the antigen-binding site comprises an scFv comprising an amino acid sequence at least 90% (e.g., 90%, 91%, 92%, 93%, 94%, 95%, 96%, 97%, 98%, 99%, or 100%) identical to SEQ ID NO:198.

Chimeric Antigen Receptors (CARs)

In certain embodiments, the present disclosure provides a CD33-targeting CAR comprising an antigen-binding site that binds CD33 as disclosed herein (see, e.g., Table 1). The CD33-targeting CAR can comprise an Fab fragment or an scFv.

The term "chimeric antigen receptor" or alternatively a "CAR" refers to a recombinant polypeptide construct comprising at least an extracellular antigen binding domain, a transmembrane domain and an intracellular signaling domain comprising a functional signaling domain derived from a stimulatory molecule (also referred to herein as a "primary signaling domain").

Accordingly, in certain embodiments, the CAR comprises an extracellular antigen-binding site that binds CD33 as disclosed herein, a transmembrane domain, and an intracellular signaling domain comprising a primary signaling domain. In certain embodiments, the CAR further comprises one or more functional signaling domains derived from at least one costimulatory molecule (also referred to as a "costimulatory signaling domain").

In one embodiment, the CAR comprises a chimeric fusion protein comprising a CD33-binding domain (e.g., CD33-binding scFv domain) comprising a heavy chain variable domain and a light chain variable domain listed in Table 1 as an extracellular antigen binding domain, a transmembrane domain, and an intracellular signaling domain comprising a primary signaling domain. In one embodiment, the CAR comprises a chimeric fusion protein comprising a CD33-binding domain (e.g., CD33-binding scFv domain) comprising a heavy chain variable domain and a light chain variable domain listed in Table 1 as an extracellular antigen binding domain, a transmembrane domain and an intracellular signaling domain comprising a costimulatory signaling domain and a primary signaling domain. In one aspect, the CAR comprises a chimeric fusion protein comprising a CD33-binding domain (e.g., CD33-binding scFv domain) comprising a heavy chain variable domain and a light chain variable domain listed in Table 1 as an extracellular antigen binding domain, a transmembrane domain, and an intracellular signaling domain comprising two costimulatory signaling domains and a primary signaling domain. In one embodiment, the CAR comprises a chimeric fusion protein comprising a CD33-binding domain comprising a heavy chain variable domain and a light chain variable domain listed in Table 1 as an extracellular antigen binding domain, a transmembrane domain, and an intracellular signaling domain comprising at least two costimulatory signaling domains and a primary signaling domain.

With respect to the transmembrane domain, in various embodiments, the CAR is designed to comprise a transmembrane domain that is fused to the extracellular domain of the CAR. In one embodiment, the transmembrane domain is one that naturally is associated with one of the domains in the CAR. In some instances, the transmembrane domain can be selected or modified by amino acid substitution to avoid binding of such domains to the transmembrane domains of the same or different surface membrane proteins to minimize interactions with other members of the receptor complex. In another embodiment, the transmembrane domain is capable of homodimerization with another CAR on the CAR T cell surface. In another embodiment, the amino acid sequence of the transmembrane domain may be modified or substituted so as to minimize interactions with the binding domains of the native binding partner present in the same CAR T cell.

The transmembrane domain may be derived from any naturally occurring membrane-bound or transmembrane protein. In one embodiment, the transmembrane region is capable of signaling to the intracellular domain(s) whenever the CAR has bound to a target. In some embodiments, the transmembrane domain comprises the transmembrane region(s) of one or more proteins selected from the group consisting of TCR α chain, TCR β chain, TCR ζ chain, CD28, CD3ε, CD45, CD4, CD5, CD8, CD9, CD16, CD22, CD33, CD37, CD64, CD80, CD86, CD134, CD137, and CD154. In some embodiments, the transmembrane domain comprises the transmembrane region(s) of one or more proteins selected from the group consisting of KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7Rα, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, and NKG2C.

The extracellular CD33-binding domain (e.g., CD33-binding scFv domain) domain can be connected to the transmembrane domain by a hinge region. A variety of hinges can be employed, including but not limited to the human Ig (immunoglobulin) hinge (e.g., an IgG4 hinge, an IgD hinge), a Gly-Ser linker, a $(G_4S)_4$ linker, a KIR2DS2 hinge, and a CD8α hinge.

The intracellular signaling domain of the CAR disclosed herein is responsible for activation of at least one of the specialized functions of the immune cell (e.g., cytolytic activity or helper activity, including the secretion of cytokines, of a T cell) in which the CAR has been placed in. Thus, as used herein, the term "intracellular signaling domain" refers to the portion of a protein which transduces an effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular signaling domain of the CAR comprises a primary signaling domain (i.e., a functional signaling domain derived from a stimulatory molecule) and one or more costimulatory signaling domains (i.e., functional signaling domains derived from at least one costimulatory molecule).

As used herein, the term "stimulatory molecule" refers to a molecule expressed by an immune cell, e.g., a T cell, an NK cell, or a B cell, that provide the cytoplasmic signaling sequence(s) that regulate activation of the immune cell in a stimulatory way for at least some aspect of the immune cell signaling pathway. In one embodiment, the signal is a primary signal that is initiated by, for instance, binding of a TCR/CD3 complex with an MHC molecule loaded with a peptide, and which leads to mediation of a T cell response, including, but not limited to, proliferation, activation, differentiation, and the like.

Primary signaling domains that act in a stimulatory manner may contain signaling motifs which are known as immunoreceptor tyrosine-based activation motifs or ITAMs. Examples of ITAM containing cytoplasmic signaling sequences that are of particular use in the present disclosure include those derived from CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and DAP12. In one embodiment, the primary signaling domain in any one or more CARs disclosed herein comprises a cytoplasmic signaling sequence derived from CD3-zeta.

In some embodiments, the primary signaling domain is a functional signaling domain of TCR zeta, FcR gamma, FcR beta, CD3 gamma, CD3 delta, CD3 epsilon, CD5, CD22, CD79a, CD79b, CD66d, 4-1BB, and/or CD3-zeta. In an embodiment, the intracellular signaling domain comprises a functional signaling domain of CD3 zeta, common FcR gamma (FCER1G), Fc gamma RIIa, FcR beta (Fc Epsilon Rib), CD3 gamma, CD3 delta, CD3 epsilon, CD79a, CD79b, DAP10, and/or DAP12. In a particular embodiment, the primary signaling domain is a functional signaling domain of the zeta chain associated with the T cell receptor complex.

As used herein, the term "costimulatory molecule" refers to a cognate binding partner on a T cell that specifically binds with a costimulatory ligand, thereby mediating a costimulatory response by the T cell, such as, but not limited to, proliferation. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1, CD11a/CD18), CD2, CD7, CD258 (LIGHT), NKG2C, B7-H3, and a ligand that specifically binds with CD83, and the like. Further examples of such costimulatory molecules include CD5, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and a ligand that specifically binds with CD83. In some embodiments, the costimulatory signaling domain of the CAR is a functional signaling domain of a costimulatory molecule described herein, e.g., OX40, CD27, CD28, CD30, CD40, PD-1, CD2, CD7, CD258, NKG2C, B7-H3, a ligand that binds to CD83, ICAM-1, LFA-1 (CD11a/CD18), ICOS and 4-1BB (CD137), or any combination thereof.

As used herein, the term "signaling domain" refers to the functional portion of a protein which acts by transmitting information within the cell to regulate cellular activity via defined signaling pathways by generating second messengers or functioning as effectors by responding to such messengers.

The cytoplasmic signaling sequences within the cytoplasmic signaling portion of the CAR disclosed herein may be linked to each other in a random or specified order. Optionally, a short oligo- or polypeptide linker, for example, between 2 and 10 amino acids in length may form the linkage.

Another aspect of the present disclosure provides a nucleic acid encoding a CD33-targeting CAR disclosed herein. The nucleic acid is useful for expressing the CAR in an effector cell (e.g., T cell) by introducing the nucleic acid to the cell.

Exemplary nucleic acid sequences encoding the extracellular portions of the CARs are disclosed herein, e.g., as SEQ ID NOs:246-265. Modifications may be made in the sequence to create an equivalent or improved variant of the nucleic acid sequences, for example, by changing one or more of the codons according to the codon degeneracy table. A DNA codon degeneracy table is provided in Table 10.

TABLE 10

Amino Acid Codons

| Amino Acids | One letter code | Three letter code | Codons |
|---|---|---|---|
| Alanine | A | Ala | GCA GCC GCG GCU |
| Cysteine | C | Cys | UGC UGU |
| Aspartic acid | D | Asp | GAC GAU |
| Glutamic acid | E | Glu | GAA GAG |
| Phenylalanine | F | Phe | UUC UUU |
| Glycine | G | Gly | GGA GGC GGG GGU |
| Histidine | H | His | CAC CAU |
| Isoleucine | I | Iso | AUA AUC AUU |
| Lysine | K | Lys | AAA AAG |
| Leucine | L | Leu | UUA UUG CUA CUC CUG CUU |
| Methionine | M | Met | AUG |
| Asparagine | N | Asn | AAC AAU |
| Proline | P | Pro | CCA CCC CCG CCU |
| Glutamine | Q | Gln | CAA CAG |
| Arginine | R | Arg | AGA AGG CGA CGC CGG CGU |
| Serine | S | Ser | AGC AGU UCA UCC UCG UCU |
| Threonine | T | Thr | ACA ACC ACG ACU |
| Valine | V | Val | GUA GUC GUG GUU |
| Tryptophan | W | Trp | UGG |
| Tyrosine | Y | Tyr | UAC UAU |

In certain embodiments, the nucleic acid is a DNA molecule (e.g., a cDNA molecule). In certain embodiments, the nucleic acid further comprises an expression control sequence (e.g., promoter and/or enhancer) operably linked to the CAR coding sequence. In certain embodiments, the present disclosure provides a vector comprising the nucleic acid. The vector can be a viral vector (e.g., AAV vector, lentiviral vector, or adenoviral vector) or a non-viral vector (e.g., plasmid).

In certain embodiments, the nucleic acid is an RNA molecule (e.g., an mRNA molecule). A method for generating mRNA for use in transfection can involve in vitro transcription of a template with specially designed primers, followed by polyA addition, to produce an RNA construct containing 3' and 5' untranslated sequences, a 5' cap and/or Internal Ribosome Entry Site (IRES), the nucleic acid to be expressed, and a polyA tail, typically 50-2000 bases in length. The RNA molecule can be further modified to increase translational efficiency and/or stability, e.g., as disclosed in U.S. Pat. Nos. 8,278,036; 8,883,506, and 8,716,465. RNA molecules so produced can efficiently transfect different kinds of cells.

In one embodiment, the nucleic acid encodes an amino acid sequence comprising a signal peptide at the amino-terminus of the CAR. Such signal peptide can facilitate the cell surface localization of the CAR when it is expressed in an effector cell, and is cleaved from the CAR during cellular processing. In one embodiment, the nucleic acid encodes an amino acid sequence comprising a signal peptide at the N-terminus of the extracellular CD33-binding domain (e.g., CD33-binding scFv domain).

RNA or DNA can be introduced into target cells using any of a number of different methods, for instance, commercially available methods which include, but are not limited to, electroporation, cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001)).

Another aspect of the present disclosure provides an immune effector cell expressing the CD33-targeting CAR. Also provided is an immune effector cell comprising the nucleic acid encoding the CD33-targeting CAR. The immune effector cells include but are not limited to T cells and NK cells. In certain embodiments, the T cell is selected from a $CD8^+$ T cell, a $CD4^+$ T cell, and an NKT cell. The T cell or NK cell can be a primary cell or a cell line.

The immune effector cells can be obtained from a number of sources, including peripheral blood mononuclear cells, bone marrow, lymph node tissue, cord blood, thymus tissue, tissue from a site of infection, ascites, pleural effusion, spleen tissue, and tumors, by methods known in the art. The immune effector cells can also be differentiated in vitro from a pluripotent or multipotent cell (e.g., a hematopoietic stem cell). In some embodiments, the present disclosure provides a pluripotent or multipotent cell (e.g., a hematopoietic stem cell) expressing the CD33-targeting CAR or comprising a nucleic acid disclosed herein.

In certain embodiments, the immune effector cells are isolated and/or purified. For example, regulatory T cells can be removed from a T cell population using a CD25-binding ligand. Effector cells expressing a checkpoint protein (e.g., PD-1, LAG-3, or TIM-3) can be removed by similar methods. In certain embodiments, the effector cells are isolated by a positive selection step. For example, a population of T cells can be isolated by incubation with anti-CD3/anti-CD28-conjugated beads. Other cell surface markers, such as IFN-γ, TNF-α, IL-17A, IL-2, IL-3, IL-4, GM-CSF, IL-10, IL-13, granzyme B, and perforin, can also be used for positive selection.

Immune effector cells may be activated and expanded generally using methods known in the art, e.g., as described in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publications Nos. 2006/0121005 and 2016/0340406. For example, in certain embodiments, T cells can be expanded and/or activated by contact with an anti-CD3 antibody and an anti-CD28 antibody, under conditions appropriate for stimulating proliferation of the T cells. The cells can be expanded in culture for a period of several hours (e.g., about 2, 3, 4, 5, 6, 7, 8, 9, 10, 15, 18, 21 hours) to about 14 days (e.g., 1, 2, 3, 4, 5, 6, 7, 8, 9, 10, 11, 12, 13 or 14 days). In one embodiment, the cells are expanded for a period of 4 to 9 days. Multiple cycles of stimulation may be desirable for prolonged cell culture (e.g., culture for a period of 60 days or more). In certain embodiments, the cell culture comprises serum (e.g., fetal bovine or human serum), interleukin-2 (IL-2), insulin, IFN-γ, IL-4, IL-7, GM-CSF, IL-10, IL-12, IL-15, TGFβ, TNF-α, or a combination thereof. Other additives for the growth of cells known to the skilled person, e.g., surfactant, plasmanate, and reducing agents such as N-acetyl-cysteine and 2-mercaptoethanol, can also be included in the cell culture. In certain embodiments, the immune effector cell of the present disclosure is a cell obtained from in vitro expansion.

Further embodiments of the CD33-targeting CAR (e.g., regulatable CAR), nucleic acid encoding the CAR, and effector cells expressing the CAR or comprising the nucleic acid are provided in U.S. Pat. Nos. 7,446,190 and 9,181,527, U.S. Patent Application Publication Nos. 2016/0340406 and 2017/0049819, and International Patent Application Publication No. WO2018/140725.

CD33/CD3-Directed Bispecific T-Cell Engagers

In certain embodiments, the present disclosure provides a CD33/CD3-directed bispecific T-cell engager comprising an antigen-binding site that binds CD33 disclosed herein. In certain embodiments, the CD33/CD3-directed bispecific T-cell engager comprises an amino acid sequence at least 90% (e.g., 90%, 91%, 92%, 93%, 94%, 95%, 96%, 97%, 98%, 99%, or 100%) identical to SEQ ID NO:187. In certain embodiments, the CD33/CD3-directed bispecific T-cell engager comprises an amino acid sequence at least 90% (e.g., 90%, 91%, 92%, 93%, 94%, 95%, 96%, 97%, 98%, 99%, or 100%) identical to SEQ ID NO:197.

In certain embodiments, the CD33/CD3-directed bispecific T-cell engager further comprises an antigen-binding site that binds CD3. Exemplary antigen-binding sites that bind CD3 are disclosed in International Patent Application Publication Nos. WO2014/051433 and WO2017/097723.

Another aspect of the present disclosure provides a nucleic acid encoding at least one polypeptide of the CD33/CD3-directed bispecific T-cell engager, wherein the polypeptide comprises an antigen binding site that binds CD33. In certain embodiments, the nucleic acid further comprises a nucleotide sequence encoding a signal peptide that, when expressed, is at the N-terminus of one or more of the polypeptides of the CD33/CD3-directed bispecific T-cell engager. Also provided is a vector (e.g., a viral vector) comprising the nucleic acid, a producer cell comprising the nucleic acid or vector, and a producer cell expressing the CD33/CD3-directed bispecific T-cell engager.

Immunocytokines

In certain embodiments, the present disclosure provides an immunocytokine comprising an antigen-binding site that binds CD33 disclosed herein and a cytokine. Any cytokine (e.g., pro-inflammatory cytokines) known in the art can be used, including but not limited to IL-2, IL-4, IL-10, IL-12, IL-15, TNF, IFNα, IFNγ, and GM-CSF. More exemplary cytokines are disclosed in U.S. Pat. No. 9,567,399. In certain embodiments, the antigen-binding site is connected to the cytokine by chemical conjugation (e.g., covalent or noncovalent chemical conjugation). In certain embodiments, the antigen-binding site is connected to the cytokine by fusion of polypeptide. The immunocytokine can further comprise an Fc domain connected to the antigen-binding site that binds CD33. In certain embodiments, the immunocytokine comprises an amino acid sequence at least 90% (e.g., 90%, 91%, 92%, 93%, 94%, 95%, 96%, 97%, 98%, 99%, or 100%) identical to SEQ ID NO:187. In certain embodiments, the immunocytokine comprises an amino acid sequence at least 90% (e.g., 90%, 91%, 92%, 93%, 94%, 95%, 96%, 97%, 98%, 99%, or 100%) identical to SEQ ID NO:197. In certain embodiments, the cytokine is connected to the Fc domain directly or via a linker.

Another aspect of the present disclosure provides a nucleic acid encoding at least one polypeptide of the immunocytokine, wherein the polypeptide comprises an antigen binding site that binds CD33. In certain embodiments, the nucleic acid further comprises a nucleotide sequence encoding a signal peptide that, when expressed, is at the N-terminus of one or more of the polypeptides of the immunocytokine. Also provided is a vector (e.g., a viral vector) comprising the nucleic acid, a producer cell comprising the nucleic acid or vector, and a producer cell expressing the immunocytokine.

Antibody-Drug Conjugates

In certain embodiments, the present disclosure provides an antibody-drug conjugate comprising an antigen-binding site that binds CD33 disclosed herein and a cytotoxic drug moiety. Exemplary cytotoxic drug moieties are disclosed in International Patent Application Publication Nos. WO2014/160160 and WO2015/143382. In certain embodiments, the cytotoxic drug moiety is selected from auristatin, N-acetyl-γ calicheamicin, maytansinoid, pyrrolobenzodiazepine, and SN-38. The antigen-binding site can be connected to the cytotoxic drug moiety by chemical conjugation (e.g., covalent or noncovalent chemical conjugation). In certain embodiments, the antibody-drug conjugate further comprises an Fc domain connected to the antigen-binding site that binds CD33. In certain embodiments, the antibody-drug conjugate comprises an amino acid sequence at least 90% (e.g., 90%, 91%, 92%, 93%, 94%, 95%, 96%, 97%, 98%, 99%, or 100%) identical to SEQ ID NO:187. In certain embodiments, the antibody-drug conjugate comprises an amino acid sequence at least 90% (e.g., 90%, 91%, 92%, 93%, 94%, 95%, 96%, 97%, 98%, 99%, or 100%) identical to SEQ ID NO:197. In certain embodiments, the cytotoxic drug moiety is connected to the Fc domain directly or via a linker.

Immunotoxins

In certain embodiments, the present disclosure provides an immunotoxin comprising an antigen-binding site that binds CD33 disclosed herein and a cytotoxic peptide moiety. Any cytotoxic peptide moiety known in the art can be used, including but not limited to ricin, *Diphtheria* toxin, and *Pseudomonas* exotoxin A. More exemplary cytotoxic peptides are disclosed in International Patent Application Publication Nos. WO2012/154530 and WO2014/164680. In certain embodiments, the cytotoxic peptide moiety is connected to the protein by chemical conjugation (e.g., covalent or noncovalent chemical conjugation). In certain embodiments, the cytotoxic peptide moiety is connected to the protein by fusion of polypeptide. The immunotoxin can further comprise an Fc domain connected to the antigen-binding site that binds CD33. In certain embodiments, the immunotoxin comprises an amino acid sequence at least 90% (e.g., 90%, 91%, 92%, 93%, 94%, 95%, 96%, 97%, 98%, 99%, or 100%) identical to SEQ ID NO:187. In certain embodiments, the immunotoxin comprises an amino acid sequence at least 90% (e.g., 90%, 91%, 92%, 93%, 94%, 95%, 96%, 97%, 98%, 99%, or 100%) identical to SEQ ID NO:197. In certain embodiments, the cytotoxic peptide moiety is connected to the Fc domain directly or via a linker.

Another aspect of the present disclosure provides a nucleic acid encoding at least one polypeptide of the immunotoxin, wherein the polypeptide comprises an antigen binding site that binds CD33. In certain embodiments, the nucleic acid further comprises a nucleotide sequence encoding a signal peptide that, when expressed, is at the N-terminus of one or more of the polypeptides of the immunotoxin. Also provided is a vector (e.g., a viral vector) comprising the nucleic acid, a producer cell comprising the nucleic acid or vector, and a producer cell expressing the immunotoxin.

III. Therapeutic Compositions and Their Use

The invention provides methods for treating cancer using a multi-specific binding protein described herein and/or a pharmaceutical composition described herein. The methods may be used to treat a variety of cancers which express CD33 by administering to a patient in need thereof a therapeutically effective amount of a multi-specific binding protein described herein.

The therapeutic method can be characterized according to the cancer to be treated. For example, in certain embodiments, the cancers are AML, myelodysplastic syndromes, chronic myelomonocytic leukemia, myeloid blast crisis of chronic myeloid leukemia, and ALLs.

For example, in certain embodiments, the cancer is a solid tumor. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, bilary tract cancer, thyroid cancer, acral lentiginous melanoma, actinic keratoses, acute lymphocytic leukemia, acute myeloid leukemia, adenoid cycstic carcinoma, adenomas, adenosarcoma, adenosquamous carcinoma, anal canal cancer, anal cancer, anorectum cancer, astrocytic tumor, bartholin gland carcinoma, basal cell carcinoma, biliary cancer, bone cancer, bone marrow cancer, bronchial cancer, bronchial gland carcinoma, carcinoid, cholangiocarcinoma, chondosarcoma, choriod plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain other embodiments, the cancer is non-Hodgkin's lymphoma, such as a B-cell lymphoma or a T-cell lymphoma. In certain embodiments, the non-Hodgkin's lymphoma is a B-cell lymphoma, such as a diffuse large B-cell lymphoma, primary mediastinal B-cell lymphoma, follicular lymphoma, small lymphocytic lymphoma, mantle cell lymphoma, marginal zone B-cell lymphoma, extranodal marginal zone B-cell lymphoma, nodal marginal zone B-cell lymphoma, splenic marginal zone B-cell lymphoma, Burkitt lymphoma, lymphoplasmacytic lymphoma, hairy cell leukemia, or primary central nervous system (CNS) lymphoma. In certain other embodiments, the non-Hodgkin's lymphoma is a T-cell lymphoma, such as a precursor T-lymphoblastic lymphoma, peripheral T-cell lymphoma, cutaneous T-cell lymphoma, angioimmunoblastic T-cell lymphoma, extranodal natural killer/T-cell lymphoma, enteropathy type T-cell lymphoma, subcutaneous panniculitis-like T-cell lymphoma, anaplastic large cell lymphoma, or peripheral T-cell lymphoma.

The cancer to be treated can be characterized according to the presence of a particular antigen expressed on the surface of the cancer cell. In certain embodiments, the cancer cell can express one or more of the following in addition to CD33: CD2, CD19, CD20, CD30, CD38, CD40, CD52, CD70, EGFR/ERBB1, IGF1R, HER3/ERBB3, HER4/ERBB4, MUC1, TROP2, cMET, SLAMF7, PSCA, MICA, MICB, TRAILR1, TRAILR2, MAGE-A3, B7.1, B7.2, CTLA4, and PD1.

In embodiments of the present invention, the cancer to be treated is selected from acute myeloid leukemia (AML), myelodysplastic syndrome (MDS), acute lymphoblastic leukemia (ALL), myeloproliferative neoplasms (MPNs), lymphoma, non-Hodgkin lymphomas, and classical Hodgkin lymphoma.

In some embodiments of the present invention, the cancer to be treated is AML. In some embodiments of the present invention, the AML is selected from undifferentiated acute myeloblastic leukemia, acute myeloblastic leukemia with minimal maturation, acute myeloblastic leukemia with maturation, acute promyelocytic leukemia (APL), acute myelomonocytic leukemia, acute myelomonocytic leukemia with eosinophilia, acute monocytic leukemia, acute erythroid leukemia, acute megakaryoblastic leukemia (AMKL), acute basophilic leukemia, acute panmyelosis with fibrosis, and blastic plasmacytoid dendritic cell neoplasm (BPDCN). In some embodiments of the present invention, the AML is characterized by expression of CLL-1 on the AML leukemia stem cells (LSCs). In some embodiments of the present invention, the LSCs in an AML subject further express a membrane marker selected from CD34, CD38, CD123, TIM3, CD25, CD32, and CD96. In some embodiments of the present invention, the AML is characterized as a minimal residual disease (MRD). In some embodiments of the present invention, the MRD of AML is characterized by the presence or absence of a mutation selected from FLT3-ITD ((Fms-like tyrosine kinase 3)-internal tandem duplications (ITD)), NPM1 (Nucleophosmin 1), DNMT3A (DNA methyltransferase gene DNMT3A), and IDH (Isocitrate dehydrogenase 1 and 2 (IDH1 and IDH2)).

In certain embodiments of the present invention, the cancer is MDS selected from MDS with multilineage dysplasia (MDS-MLD), MDS with single lineage dysplasia (MDS-SLD), MDS with ring sideroblasts (MDS-RS), MDS with excess blasts (MDS-EB), MDS with isolated del(5q), and MDS, unclassified (MDS-U).

It is contemplated that the multi-specific binding proteins and/or pharmaceutical compositions of the present disclosure can be used to treat a variety of cancers, not limited to cancers in which the cancer cells express CD33. For example, in certain embodiments, the multi-specific binding proteins and/or pharmaceutical compositions disclosed herein can be used to treat cancers that are associated with CD33-expressing immune cells. CD33 is expressed on many myeloid lineages, and tumor-infiltrating myeloid cells (e.g., tumor-associated macrophages) may contribute to cancer progression and metastasis. Therefore, the methods disclosed herein may be used to treat a variety of cancers in which CD33 is expressed, whether on cancer cells or on immune cells.

In certain embodiments, the multi-specific binding proteins and/or pharmaceutical compositions of the present disclosure can be used to treat cancers that express an Fc receptor with a higher binding affinity to Fc (e.g., IgG1 Fc) than CD16. In certain embodiments, the Fc receptor is FcγRI. In certain embodiments, the Fc receptor is expressed on cancer cells and/or other cells in the tumor microenvironment.

In certain embodiments, the patient has effector cells (e.g., NK cells) that express a CD16 variant with V158F substitution. In certain embodiments, the patient has a single nucleotide polymorphism (SNP) in the CD16 gene that causes V158F substitution. In certain embodiments, the patient has such an SNP in only one allele. In certain embodiments, the patient has such an SNP or SNPs in both alleles.

IV. Combination Therapy

Another aspect of the invention provides for combination therapy. Multi-specific binding proteins described herein be used in combination with additional therapeutic agents to treat the cancer.

Exemplary therapeutic agents that may be used as part of a combination therapy in treating cancer, include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma, colony stimulating factor-1, colony stimulating factor-2, denileukin diftitox, interleukin-2, luteinizing hormone releasing factor and variations of the aforementioned agents that may exhibit differential binding to its cognate receptor, and increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T-lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma.

Yet other agents that may be used as part of a combination therapy in treating cancer are monoclonal antibody agents that target non-checkpoint targets (e.g., trastuzumab (HERCEPTIN®)) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxy-adenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

Proteins of the invention can also be used as an adjunct to surgical removal of the primary lesion.

The amount of multi-specific binding protein and additional therapeutic agent and the relative timing of administration may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. Further, for example, a multi-specific binding protein may be administered during a time when the additional therapeutic agent(s) exerts its prophylactic or therapeutic effect, or vice versa.

V. Pharmaceutical Compositions

The present disclosure also features pharmaceutical compositions that contain a therapeutically effective amount of a protein described herein. The composition can be formulated for use in a variety of drug delivery systems. One or more physiologically acceptable excipients or carriers can also be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

In one aspect, the present disclosure provides a formulation of a protein, which contains a CD33-binding site described herein, and a pharmaceutically acceptable carrier.

In certain embodiments, the pharmaceutical composition includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:1, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:2. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:3, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:4. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:5, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:6. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:7, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:8. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:9, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:10. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:11, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:12. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:13, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:14. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:15, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:16. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:17, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:18. In certain embodiments, the formulation includes a protein that includes an antigen-binding site with a heavy chain variable domain having an amino acid sequence at least 90% (e.g., 91%, 92%, 93%, 94%, 95%, 96%, 97%, 98%, 99%, or 100%) identical to the amino acid sequence of SEQ ID NO:19, and a light chain variable domain having an amino acid sequence at least 90% (e.g., 91%, 92%, 93%, 94%, 95%, 96%, 97%, 98%, 99%, or 100%) identical to the amino acid sequence of SEQ ID NO:20.

The composition can be formulated for use in a variety of drug delivery systems. One or more physiologically acceptable excipients or carriers can be included in the composition for proper formulation. Suitable formulations for use in the present disclosure are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990).

For example, this present disclosure could exist in an aqueous pharmaceutical formulation including a therapeutically effective amount of the protein in a buffered solution forming a formulation. Aqueous carriers can include sterile water for injection (SWFI), bacteriostatic water for injection (BWFI), a pH buffered solution (e.g. phosphate-buffered saline), sterile saline solution, Ringer's solution or dextrose solution. In certain embodiments, an aqueous formulation is prepared including the protein disclosed herein in a pH-buffered solution. The pH of the preparations typically will be between 3 and 11, more preferably between 5 and 9 or between 6 and 8, and most preferably between 7 and 8, such as 7 to 7.5. Ranges intermediate to the above recited pH's are also intended to be part of this disclosure. For example, ranges of values using a combination of any of the above recited values as upper and/or lower limits are intended to be included. Examples of buffers that will control the pH within this range include acetate (e.g., sodium acetate), succinate (such as sodium succinate), gluconate, histidine, citrate and other organic acid buffers. In certain embodiments, the buffer system includes citric acid monohydrate, sodium citrate, disodium phosphate dihydrate, and/or sodium dihydrogen phosphate dihydrate. In certain embodiments, the buffer system includes about 1.3 mg/mL of citric acid (e.g., 1.305 mg/mL), about 0.3 mg/mL of sodium citrate (e.g., 0.305 mg/mL), about 1.5 mg/mL of disodium phosphate dihydrate (e.g. 1.53 mg/mL), about 0.9 mg/mL of sodium dihydrogen phosphate dihydrate (e.g., 0.86), and about 6.2 mg/mL of sodium chloride (e.g., 6.165 mg/mL). In certain embodiments, the buffer system includes 1-1.5 mg/mL of citric acid, 0.25 to 0.5 mg/mL of sodium citrate, 1.25 to 1.75 mg/ml of disodium phosphate dihydrate, 0.7 to 1.1 mg/mL of sodium dihydrogen phosphate dihydrate, and 6.0 to 6.4 mg/mL of sodium chloride. The pH of the liquid formulation may be set by addition of a pharmaceutically acceptable acid and/or base. In certain embodiments, the pharmaceutically acceptable acid may be hydrochloric acid. In certain embodiments, the base may be sodium hydroxide.

In some embodiments, the formulation include an aqueous carrier, which is pharmaceutically acceptable (safe and non-toxic for administration to a human) and is useful for the preparation of a liquid formulation. Illustrative carriers include sterile water for injection (SWFI), bacteriostatic water for injection (BWFI), a pH buffered solution (e.g., phosphate-buffered saline), sterile saline solution, Ringer's solution or dextrose solution.

A polyol, which acts as a tonicifier and may stabilize the antibody, may also be included in the formulation. The polyol is added to the formulation in an amount which may vary with respect to the desired isotonicity of the formulation. In certain embodiments, the aqueous formulation may be isotonic. The amount of polyol added may also be altered with respect to the molecular weight of the polyol. For example, a lower amount of a monosaccharide (e.g., mannitol) may be added, compared to a disaccharide (such as trehalose). In certain embodiments, the polyol which may be used in the formulation as a tonicity agent is mannitol. In certain embodiments, the mannitol concentration may be about 5 to about 20 mg/mL. In certain embodiments, the concentration of mannitol may be about 7.5 to 15 mg/mL. In certain embodiments, the concentration of mannitol may be about 10-14 mg/mL. In certain embodiments, the concentration of mannitol may be about 12 mg/mL. In certain embodiments, the polyol sorbitol may be included in the formulation.

A detergent or surfactant may also be added to the formulation. Exemplary detergents include nonionic detergents such as polysorbates (e.g., polysorbates 20, 80 etc.) or poloxamers (e.g., poloxamer 188). The amount of detergent added is such that it reduces aggregation of the formulated antibody and/or minimizes the formation of particulates in the formulation and/or reduces adsorption. In certain embodiments, the formulation may include a surfactant which is a polysorbate. In certain embodiments, the formulation may contain the detergent polysorbate 80 or TWEEN®80. TWEEN®80 is a term used to describe polyoxyethylene (20) sorbitanmonooleate (see Fiedler, Lexikon der Hifsstoffe, Editio Cantor Verlag Aulendorf, 4th edi., 1996). In certain embodiments, the formulation may contain between about 0.1 mg/mL and about 10 mg/mL of polysorbate 80, or between about 0.5 mg/mL and about 5 mg/mL. In certain embodiments, about 0.1% polysorbate 80 may be added in the formulation.

In certain embodiments, the liquid formulation of the disclosure may be prepared as a 10 mg/mL concentration solution in combination with a sugar at stabilizing levels. In certain embodiments the liquid formulation may be prepared in an aqueous carrier. In certain embodiments, a stabilizer may be added in an amount no greater than that which may result in a viscosity undesirable or unsuitable for intravenous administration. In certain embodiments, the sugar may be disaccharides, e.g., sucrose. In certain embodiments, the liquid formulation may also include one or more of a buffering agent, a surfactant, and a preservative, which is added to the formulations herein to reduce bacterial action. The addition of a preservative may, for example, facilitate the production of a multi-use (multiple-dose) formulation.

In some embodiments, the present disclosure provides a formulation with an extended shelf life including the protein of the present disclosure, in combination with mannitol, citric acid monohydrate, sodium citrate, disodium phosphate dihydrate, sodium dihydrogen phosphate dihydrate, sodium chloride, polysorbate 80, water, and sodium hydroxide.

Deamidation is a common product variant of peptides and proteins that may occur during fermentation, harvest/cell clarification, purification, drug substance/drug product storage and during sample analysis. Deamidation is the loss of NH3 from a protein forming a succinimide intermediate that can undergo hydrolysis. The succinimide intermediate results in a 17 u mass decrease of the parent peptide. The subsequent hydrolysis results in an 18 u mass increase. Isolation of the succinimide intermediate is difficult due to instability under aqueous conditions. As such, deamidation is typically detectable as 1 u mass increase. Deamidation of an asparagine results in either aspartic or isoaspartic acid. The parameters affecting the rate of deamidation include pH, temperature, solvent dielectric constant, ionic strength, primary sequence, local polypeptide conformation and tertiary structure. The amino acid residues adjacent to Asn in the peptide chain affect deamidation rates. Gly and Ser following an Asn in protein sequences results in a higher susceptibility to deamidation. In certain embodiments, the liquid formulation of the present disclosure may be preserved under conditions of pH and humidity to prevent deamination of the protein product.

In some embodiment, the formulation is a lyophilized formulation. In certain embodiments, the formulation is freeze-dried (lyophilized) and contained in about 12-60 vials. In certain embodiments, the formulation is freeze-dried and 45 mg of the freeze-dried formulation may be contained in one vial. In certain embodiments, the about 40 mg—about 100 mg of freeze-dried formulation is contained in one vial. In certain embodiments, freeze dried formulation from 12, 27, or 45 vials are combined to obtained a therapeutic dose of the protein in the intravenous drug formulation. The formulation may be a liquid formulation. In some embodiments, a liquid formulation is stored as about 250 mg/vial to about 1000 mg/vial. In certain embodiments, the liquid formulation is stored as about 600 mg/vial. In certain embodiments, the liquid formulation is stored as about 250 mg/vial.

In some embodiments, the lyophilized formulation includes the proteins described herein and a lyoprotectant. The lyoprotectant may be sugar, e.g., disaccharides. In certain embodiments, the lyoprotectant may be sucrose or maltose. The lyophilized formulation may also include one or more of a buffering agent, a surfactant, a bulking agent, and/or a preservative. The amount of sucrose or maltose useful for stabilization of the lyophilized drug product may be in a weight ratio of at least 1:2 protein to sucrose or maltose. In certain embodiments, the protein to sucrose or maltose weight ratio may be of from 1:2 to 1:5.

In certain embodiments, the pH of the formulation, prior to lyophilization, may be set by addition of a pharmaceutically acceptable acid and/or base. In certain embodiments the pharmaceutically acceptable acid may be hydrochloric acid. In certain embodiments, the pharmaceutically acceptable base may be sodium hydroxide. Before lyophilization, the pH of the solution containing the protein of the present disclosure may be adjusted between 6 to 8. In certain embodiments, the pH range for the lyophilized drug product may be from 7 to 8.

In certain embodiments, a "bulking agent" may be added. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents.

In certain embodiments, the lyophilized protein product is constituted with an aqueous carrier. The aqueous carrier of interest herein is one which is pharmaceutically acceptable (e.g., safe and non-toxic for administration to a human) and is useful for the preparation of a liquid formulation, after lyophilization. Illustrative diluents include sterile water for injection (SWFI), bacteriostatic water for injection (BWFI), a pH buffered solution (e.g., phosphate-buffered saline), sterile saline solution, Ringer's solution or dextrose solution. In certain embodiments, the lyophilized drug product of the current disclosure is reconstituted with either Sterile Water for Injection, USP (SWFI) or 0.9% Sodium Chloride Injection, USP. During reconstitution, the lyophilized powder dissolves into a solution. In certain embodiments, the lyophilized protein product of the instant disclosure is constituted to about 4.5 mL water for injection and diluted with 0.9% saline solution (sodium chloride solution).

The protein compositions may be sterilized by conventional sterilization techniques, or may be sterile filtered. The resulting aqueous solutions may be packaged for use as-is, or lyophilized, the lyophilized preparation being combined with a sterile aqueous carrier prior to administration. The resulting compositions in solid form may be packaged in multiple single dose units, each containing a fixed amount of the above-mentioned agent or agents. The composition in solid form can also be packaged in a container for a flexible quantity.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The specific dose can be a uniform dose for each patient, for example, 50-5000 mg of protein. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can be adjusted as the progress of the disease is monitored. Blood levels of the targetable construct or complex in a patient can be measured to see if the dosage needs to be adjusted to reach or maintain an effective concentration. Pharmacogenomics may be used to determine which targetable constructs and/or complexes, and dosages thereof, are most likely to be effective for a given individual (Schmitz et al., *Clinica. Chimica. Acta.* 308: 43-53, 2001; Steimer et al., *Clinica. Chimica. Acta.* 308: 33-41, 2001).

In general, dosages based on body weight are from about 0.01 μg to about 100 mg per kg of body weight, such as about 0.01 μg to about 100 mg/kg of body weight, about 0.01 μg to about 50 mg/kg of body weight, about 0.01 μg to about 10 mg/kg of body weight, about 0.01 μg to about 1 mg/kg of body weight, about 0.01 μg to about 100 μg/kg of body weight, about 0.01 μg to about 50 μg/kg of body weight, about 0.01 μg to about 10 μg/kg of body weight, about 0.01 μg to about 1 μg/kg of body weight, about 0.01 μg to about 0.1 μg/kg of body weight, about 0.1 μg to about 100 mg/kg of body weight, about 0.1 μg to about 50 mg/kg of body weight, about 0.1 μg to about 10 mg/kg of body weight, about 0.1 μg to about 1 mg/kg of body weight, about 0.1 μg to about 100 μg/kg of body weight, about 0.1 μg to about 10

µg/kg of body weight, about 0.1 µg to about 1 µg/kg of body weight, about 1 µg to about 100 mg/kg of body weight, about 1 µg to about 50 mg/kg of body weight, about 1 µg to about 10 mg/kg of body weight, about 1 µg to about 1 mg/kg of body weight, about 1 µg to about 100 µg/kg of body weight, about 1 µg to about 50 µg/kg of body weight, about 1 µg to about 10 µg/kg of body weight, about 10 µg to about 100 mg/kg of body weight, about 10 µg to about 50 mg/kg of body weight, about 10 µg to about 10 mg/kg of body weight, about 10 µg to about 1 mg/kg of body weight, about 10 µg to about 100m/kg of body weight, about 10 µg to about 50 µg/kg of body weight, about 50 µg to about 100 mg/kg of body weight, about 50 µg to about 50 mg/kg of body weight, about 50 µg to about 10 mg/kg of body weight, about 50 µg to about 1 mg/kg of body weight, about 50 µg to about 100m/kg of body weight, about 100 µg to about 100 mg/kg of body weight, about 100 µg to about 50 mg/kg of body weight, about 100 µg to about 10 mg/kg of body weight, about 100 µg to about 1 mg/kg of body weight, about 1 mg to about 100 mg/kg of body weight, about 1 mg to about 50 mg/kg of body weight, about 1 mg to about 10 mg/kg of body weight, about 10 mg to about 100 mg/kg of body weight, about 10 mg to about 50 mg/kg of body weight, about 50 mg to about 100 mg/kg of body weight. Doses may be given once or more times daily, weekly, monthly or yearly, or even once every 2 to 20 years. Persons of ordinary skill in the art can easily estimate repetition rates for dosing based on measured residence times and concentrations of the targetable construct or complex in bodily fluids or tissues. Administration of the present invention could be intravenous, intraarterial, intraperitoneal, intramuscular, subcutaneous, intrapleural, intrathecal, intracavitary, by perfusion through a catheter or by direct intralesional injection. This may be administered once or more times daily, once or more times weekly, once or more times monthly, and once or more times annually.

The description above describes multiple aspects and embodiments of the invention. The patent application specifically contemplates all combinations and permutations of the aspects and embodiments.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

EXAMPLES

The following examples are merely illustrative and are not intended to limit the scope or content of the invention in any way.

Example 1. Kinetics and Affinity of Binding to Different Variants of CD33

Kinetics and affinity of a series of Fab fragments of anti-CD33 antibodies with different CD33 variants (human CD33 ECD, cyno CD33 ECD, V-domain of human CD33, C-domain or human CD33 and selected CD33 SNPs) were assessed by surface plasmon resonance using Biacore™ 8K instrument (GE Healthcare). Anti-Fab antibody was immobilized on a CM5 chip using standard amine coupling chemistry. CD33 FABs were captured on the anti-Fab chip at a density of ~100 RU. Solutions containing different concentrations of soluble monomeric CD33 or its domains were injected over the captured FABs and control surfaces at 30 µl/min at 37° C. Surfaces were regenerated between cycles by quick injection of 10 mM glycine, pH 1.8. To obtain kinetic rate constants double-referenced data were fit to a 1:1 interaction model using Biacore™ 8K Evaluation software (GE Healthcare). The equilibrium binding constant $K_D$ was determined by the ratio of binding rate constants $k_d/k_a$.

Octet™ Platform-Based Kinetic and Affinity Analysis

ForteBio affinity measurements were performed on an Octet™ HTX generally as described in Estep et al., High throughput solution-based measurement of antibody-antigen affinity and epitope binning. Mabs 5 (2), 270-278 (2013). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model. The results are shown in Table 11.

TABLE 11

Kinetic parameters of human CD33 binding to IgG antibodies measured by BLI.

| IgG ADI Name | $K_D$ (M) | $k_{on}$ (1/M/s) | $k_{off}$ (1/s) |
|---|---|---|---|
| ADI-10154 | 3.70E−09 | 2.46E+05 | 8.97E−04 |
| ADI-10155 | 5.30E−09 | 2.29E+05 | 1.21E−03 |
| ADI-10157 | 4.20E−09 | 7.99E+04 | 3.36E−04 |
| ADI-10158 | 2.60E−09 | 5.86E+05 | 1.55E−03 |
| ADI-10159 | 5.80E−10 | 3.48E+05 | 2.00E−04 |
| ADI-10160 | 5.10E−09 | 6.38E+05 | 3.25E−03 |
| ADI-10161 | 3.70E−09 | 5.87E+05 | 2.17E−03 |
| ADI-10163 | 6.80E−09 | 6.65E+05 | 4.53E−03 |
| ADI-10164 | 4.30E−09 | 3.44E+05 | 1.48E−03 |
| ADI-10165 | 4.00E−09 | 7.79E+05 | 3.11E−03 |
| ADI-10167 | 3.90E−09 | 1.00E+06 | 3.93E−03 |
| ADI-10168 | 1.00E−08 | 4.76E+05 | 4.78E−03 |
| ADI-10173 | 9.70E−09 | 3.24E+05 | 3.14E−03 |
| ADI-10177 | 3.60E−09 | 6.01E+05 | 2.14E−03 |
| ADI-11776 | 2.94E−10 | 6.79E+05 | 2.00E−04 |
| ADI-11801 | 4.57E−10 | 4.38E+05 | 2.00E−04 |
| ADI-11802 | 4.53E−10 | 4.41E+05 | 2.00E−04 |
| ADI-11807 | 3.07E−10 | 6.51E+05 | 2.00E−04 |
| ADI-11809 | 3.13E−10 | 6.38E+05 | 2.00E−04 |
| ADI-11812 | 1.91E−09 | 1.66E+05 | 3.15E−04 |
| ADI-11815 | 1.44E−09 | 1.59E+05 | 2.29E−04 |
| ADI-11819 | 2.43E−10 | 8.24E+05 | 2.00E−04 |
| ADI-11825 | 5.40E−10 | 6.96E+05 | 3.76E−04 |
| ADI-11826 | 3.93E−10 | 6.19E+05 | 2.43E−04 |
| ADI-11828 | 8.10E−10 | 6.58E+05 | 5.33E−04 |
| ADI-11830 | 1.20E−09 | 7.70E+05 | 9.23E−04 |
| ADI-11835 | 2.81E−10 | 8.44E+05 | 2.37E−04 |
| ADI-11839 | 2.45E−09 | 7.04E+05 | 1.72E−03 |
| Lintuzumab | 2.21E−09 | 4.31E+05 | 9.52E−04 |

Example 2. CD33 Antibodies Bind to Human CD33 with High Affinity and Cross-React with Cyno CD33

Despite rather high homology between human and cyno CD33 (87% in the ECD), most of commercially available anti-CD33 antibodies, e.g., lintuzumab, mylotarg, etc. lack cross-reactivity with cyno CD33. FIG. 2 shows alignment of full length human and cyno CD33 highlighting the differences in the primary sequence in the ECD domain.

Affinity of 29 Fab fragments binding to human and cyno CD33 ECD were assayed by Biacore™ analysis. Eight out of 29 antibodies show cross-reactivity with cyno CD33. Kinetic parameters of binding are given in Table 12. Data are compared to lintuzumab. Several antibodies show affinities >100 fold higher than lintuzumab.

Binding of the Fab fragments from CD33 monoclonal antibodies to the human CD33 extracellular domain (ECD) was measured by Biacore™ at 37° C. The Biacore™ profile of ADI-10159 is shown in FIG. 3A; the Biacore™ profile of ADI-10177 is shown in FIG. 3B; the Biacore™ profile of ADI-11776 is shown in FIG. 3C; the Biacore™ profile of ADI-11801 in FIG. 3D; the Biacore™ profile of ADI-11807 is shown in FIG. 3E; the Biacore™ profile of ADI-11809 is shown in FIG. 3F; the Biacore™ profile of ADI-11815 is shown in FIG. 3G; the Biacore™ profile of ADI-11819 FIG. 3H; the Biacore™ profile of ADI-11830 is shown in FIG. 3I; the Biacore™ profile of ADI-11835 is shown in FIG. 3J; and the Biacore™ profile of the Fab fragment from Lintuzumab is shown in FIG. FIG. 3K.

Binding of the Fab fragments from CD33 monoclonal antibodies to the cyno CD33 ECD was measured by Biacore™ at 37° C. The Biacore™ profile of ADI-10159 is shown in FIG. 4A; the Biacore™ profile of ADI-10177 in FIG. 4B; the Biacore™ profile of ADI-11776 is shown in FIG. 4C; the Biacore™ profile of ADI11807 is shown in FIG. 4D; the Biacore™ profile of ADI-11809 is shown in FIG. 4E; the Biacore™ profile of ADI-11819 is shown in FIG. 4F; the Biacore™ profile of ADI-11830 is shown in FIG. 4G; and the Biacore™ profile of ADI-11835 is shown in FIG. 4H.

Figure 5A:
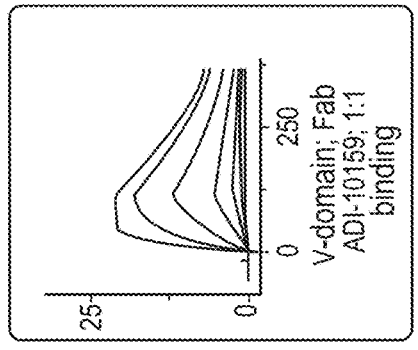
Figure 5B:
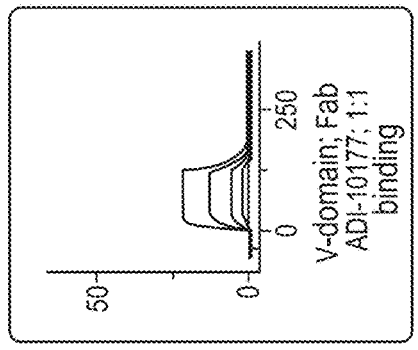
Figure 5C:
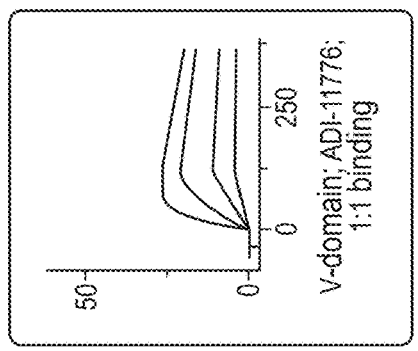
Figure 5D:
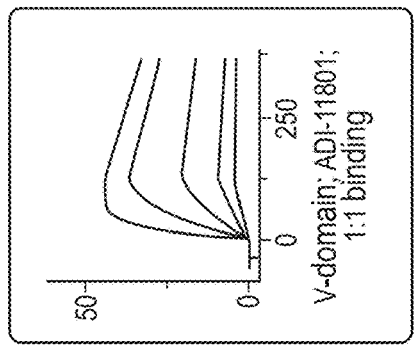
Figure 5E:
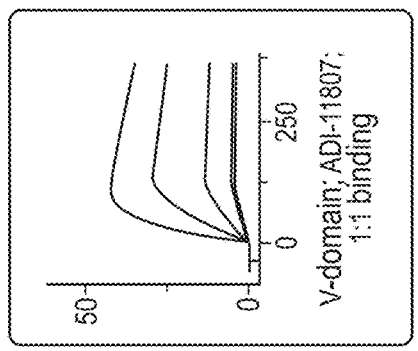
Figure 5F:
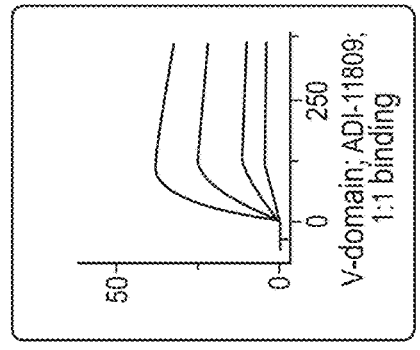
Figure 5G:
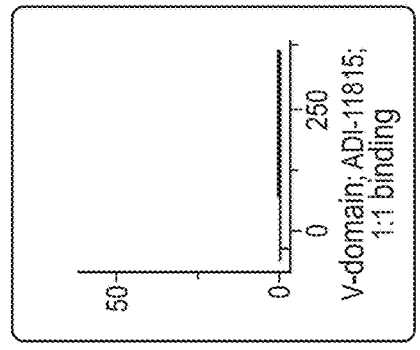
Figure 5H:
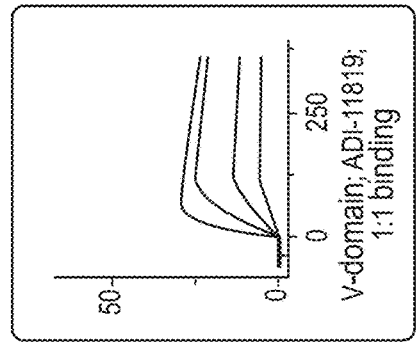
Figure 5I:
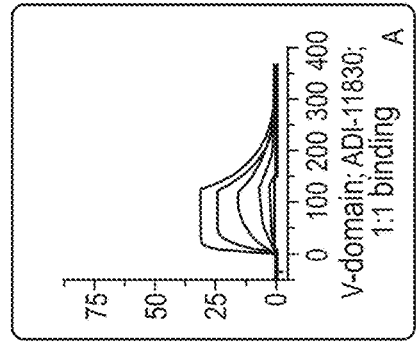
Figure 5J:
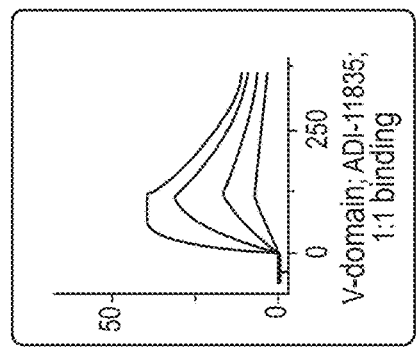
Figure 6A:
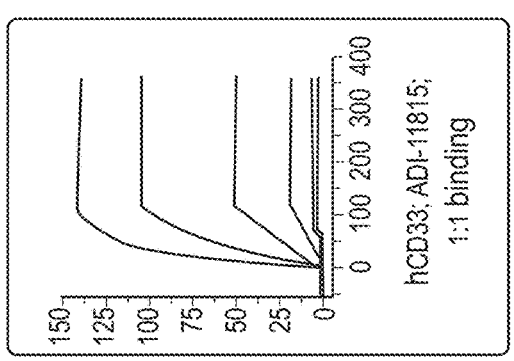
FIGS. 6A-6D show SPR profiles of an Fab that comprises ADI-11815 binding to different domains of human CD33 and human CD33 having an R69G point mutation.
Figure 6B:
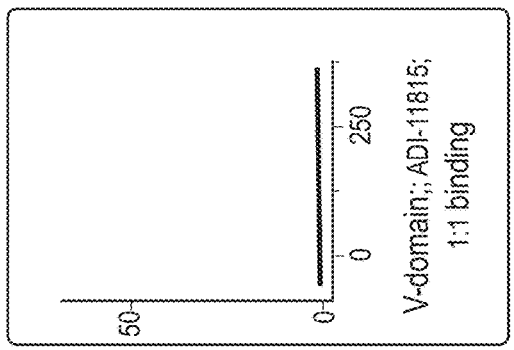
Figure 6C:
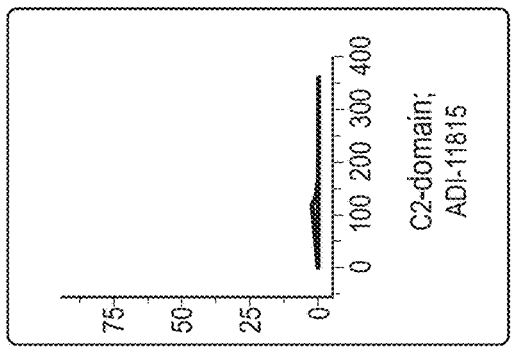
Figure 6D:
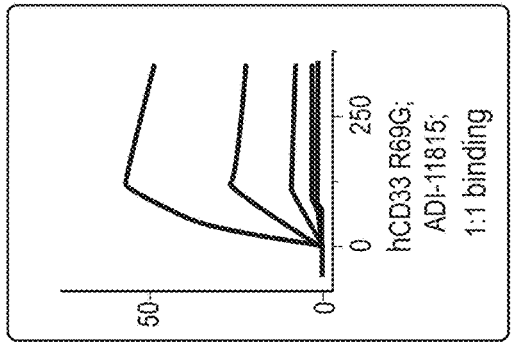
Figure 7A:
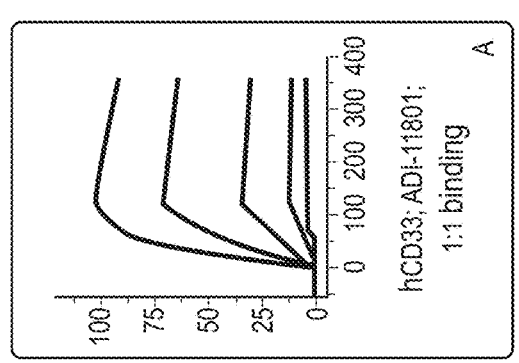
FIGS. 7A-7D show SPR profiles of a Fab that comprises ADI-11801 binding to different domains of human CD33 and human CD33 having an R69G point mutation.
Figure 7B:
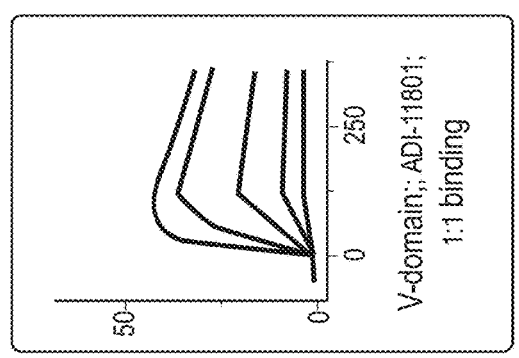
Figure 7C:
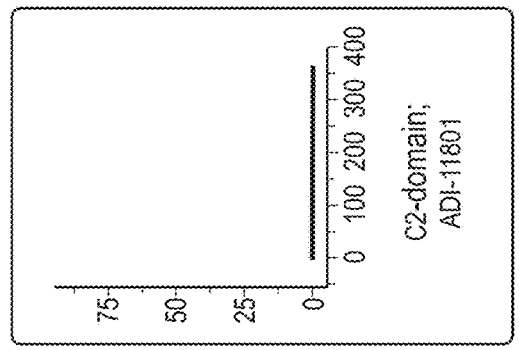
Figure 7D:
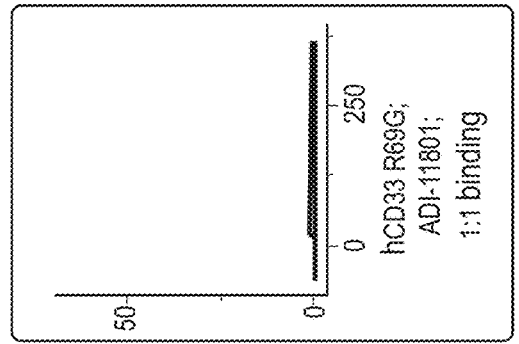

Binding of the Fab fragments from CD33 monoclonal antibodies to V domain and C domain of human CD33 was measured by Biacore™ at 37° C. FIGS. 5A-5J represent binding to the V-domain; panels K-T represent binding to the C domain. Both FIGS. 5A and 5K are Biacore™ profiles of ADI-10159; both FIGS. 5B and 5L are Biacore™ profiles of ADI-10177; both FIGS. 5C and 5M are Biacore™ profiles of ADI-11776; both FIGS. 5D and 5N are Biacore™ profiles of ADI-11801; both FIGS. 5E and 5O are Biacore™ profiles of ADI-11807; both FIGS. 5F and 5P are Biacore™ profiles of ADI-11809; both FIGS. 5G and 5Q are Biacore™ profiles of ADI-11815; both FIGS. 5H and 5R are Biacore™ profiles of ADI-11819; both FIGS. 5I and 5S are Biacore™ profiles of ADI-11830; and FIGS. 5J and 5T are Biacore™ profiles of ADI-11835.

TABLE 12

Kinetic parameters of human CD33 ECD and cyno CD33 ECD binding to Fabs measured by SPR at 37° C. No binding is defined as absence of signal at highest concentration of 100 nM.

| | Human CD33 | | | Cyno CD33 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| ADI-10159 | 4.29e5 | 1.95e−3 | 4.53 | 5.28e5 | 4.36e−2 | 74.9 |
| ADI-10177 | 5.58e5 | 6.36e−3 | 11.4 | 3.53e5 | 7.54e−3 | 21.4 |
| ADI-11776 | 1.6e6 | 1.24e−3 | 0.78 | 2.62e6 | 4.72e−3 | 1.81 |
| ADI-11807 | 1.14e6 | 3.32e−4 | 0.29 | 9.98e5 | 1.51e−4 | 0.15 |
| ADI-11809 | 1.02e6 | 1.23e−6 | 0.0012 | 1.06e6 | 1.26e−4 | 0.118 |
| ADI-11819 | 2.84e6 | 5.65e−5 | 0.02 | 3.82e6 | 1.90e−2 | 4.96 |
| ADI-11830 | 1.99e6 | 5.47e−3 | 2.75 | 1.34e6 | 3.64e−2 | 27.8 |

TABLE 12-continued

Kinetic parameters of human CD33 ECD and cyno CD33 ECD binding to Fabs measured by SPR at 37° C. No binding is defined as absence of signal at highest concentration of 100 nM.

| | Human CD33 | | | Cyno CD33 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| ADI-11835 | 2.6e6 | 1.43e−3 | 0.53 | 2.76e6 | 1.89e−2 | 6.86 |
| ADI-11815 | 3.39e5 | 7.91e−5 | 0.23 | | No binding | |
| ADI-11801 | 7.56e5 | 4.17e−4 | 0.55 | | No binding | |
| ADI-10152 | 2.46e5 | 9.14e−3 | 37.2 | | No binding | |
| ADI-10154 | 1.92e5 | 8.33e−3 | 43.4 | | No binding | |
| ADI-10155 | 1.70e5 | 6.85e−3 | 40.2 | | No binding | |
| ADI-10157 | 2.82e6 | 7.60e−3 | 2.69 | | No binding | |
| ADI-10158 | 4.75e5 | 1.49e−2 | 3.14 | | No binding | |
| ADI-10160 | 6.37e5 | 2.69e−2 | 42.2 | | No binding | |
| ADI-10161 | 5.74e5 | 1.18e−2 | 20.6 | | No binding | |
| ADI-10163 | 5.15e5 | 2.75e−2 | 53.5 | | No binding | |
| ADI-10164 | 3.19e5 | 1.01e−2 | 31.5 | | No binding | |
| ADI-10165 | 5.91e5 | 1.88e−2 | 31.8 | | No binding | |
| ADI-10167 | 1.25e6 | 3.07e−2 | 24.4 | | No binding | |
| ADI-10168 | 3.75e5 | 1.75e−2 | 46.6 | | No binding | |
| ADI-10173 | 2.12e5 | 1.25e−2 | 58.8 | | No binding | |
| ADI-11802 | 4.9e5 | 1.54e−3 | 3.14 | | No binding | |
| ADI-11812 | 3.96e5 | 4.86e−4 | 1.23 | | No binding | |
| ADI-11825 | 2.13e6 | 3.8e−3 | 1.78 | | No binding | |
| ADI-11826 | 1.76e6 | 4.63e−3 | 2.63 | | No binding | |
| ADI-11828 | 1.32e6 | 3.51e−3 | 2.67 | 1.03e6 | 5.48e−2 | 53.5 |
| ADI-11839 | 8.74e5 | 1.62e−2 | 18.6 | | No binding | |
| Lintuzumab | 7.35e5 | 1.22e−2 | 16.7 | | No binding | |

Mapping of Binding Interface to Individual Domains of CD33

The binding interface between the Fab fragment of each CD33 antibody to CD33 was mapped. FIGS. 5A-5T show binding of Fab fragments of different CD33 antibodies to individual domains of human CD33 (V domain and C domain). No binding to C domain was observed for any antibody tested. ADI-11815 did not bind to either V or C domain, suggesting that it requires a unique conformational epitope.

Table 13 shows a comparison between kinetics of binding to full ECD of human CD33 and a V domain. ADI-10159, ADI-11176, ADI-11807, ADI-11830, ADI-11835, ADI-11801, ADI-10155, ADI-11802, ADI-11825, ADI-11826, ADI-11828, and ADI-11839 show similar kinetics suggesting that the epitope for these antibodies are located entirely in the V domain. Reduced binding to V domain is observed for ADI-10177, ADI-11809 ADI-11819, ADI-10157, ADI-10158, and ADI-10164, suggesting that these antibodies bind to a conformational epitope, partially located in the V domain.

Kinetics of binding to the C domain of human CD33 was also measured with ADI-10152, ADI-10154, ADI-10155, ADI-10157, ADI-10158, ADI-10160, ADI-10161, ADI-10163, ADI-10164, ADI-10165, ADI-10167, ADI-10168, ADI-10173, ADI-11802, ADI-11812, ADI-11825, ADI-11826, ADI-11828, and ADI-11839. None of these antibodies bound the C domain of human CD33.

TABLE 13

Biacore™ analysis of FABs binding to recombinant full-length ECD and V domain of human CD33 performed at 37° C. Asterisk indicates antibodies that bind to a conformational epitope partially located in V domain.

| | Human CD33 V domain | | | Human CD33 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| ADI-10159 | 9.05e5 | 5.0e−3 | 5.56 | 4.29e5 | 1.95e−3 | 4.53 |
| ADI-10177* | 1.56e6 | 8.57e−2 | 54.8 | 5.58e5 | 6.36e−3 | 11.4 |
| ADI-11776 | 4.52e6 | 1.43e−2 | 0.33 | 1.6e6 | 1.24e−3 | 0.78 |
| ADI-11807 | 3.07e6 | 8.47e−4 | 0.28 | 1.14e6 | 3.32e−4 | 0.29 |
| ADI-11809* | 2.6e6 | 7.69e−4 | 0.3 | 1.02e6 | 1.23e−6 | 0.0012 |
| ADI-11819 | 6.75e6 | 9.16e−4 | 0.14 | 2.84e6 | 5.65e−5 | 0.02 |
| ADI-11830 | 6.67e6 | 2.99e−2 | 4.5 | 1.99e6 | 5.47e−3 | 2.75 |
| ADI-11835 | 7.6e6 | 8.68e−3 | 1.14 | 2.6e6 | 1.43e−3 | 0.53 |
| ADI-11815 | | No binding | | 3.39e5 | 7.91e−5 | 0.23 |
| ADI-11801 | 1.8e6 | 1.25e−3 | 0.69 | 7.56e5 | 4.17e−4 | 0.55 |
| ADI-10152 | 4.88e5 | 4.09e−2 | 100 | 2.46e5 | 9.14e−3 | 37.2 |
| ADI-10154 | 1.52e6 | 3.35e−1 | 220 | 1.92e5 | 8.33e−3 | 43.4 |
| ADI-10155 | 5.48e5 | 4.67e−2 | 85.2 | 1.70e5 | 6.85e−3 | 40.2 |
| ADI-10157* | 1.12e5 | 1.51e−2 | 134 | 2.82e6 | 7.60e−3 | 2.69 |
| ADI-10158* | 1.04e6 | 1.33e−1 | 127 | 4.75e5 | 1.49e−2 | 3.14 |
| ADI-10160 | 1.59e6 | 3.27e−1 | 206 | 6.37e5 | 2.69e−2 | 42.2 |
| ADI-10161 | 1.29e6 | 1.24e−1 | 95.8 | 5.74e5 | 1.18e−2 | 20.6 |

TABLE 13-continued

Biacore™ analysis of FABs binding to recombinant full-length ECD and V domain of human CD33 performed at 37° C. Asterisk indicates antibodies that bind to a conformational epitope partially located in V domain.

| Antibody | Human CD33 V domain | | | Human CD33 | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| ADI-10163 | | No binding | | 5.15e5 | 2.75e-2 | 53.5 |
| ADI-10164 | 1.29e6 | 3.7e-1 | 286 | 3.19e5 | 1.01e-2 | 31.5 |
| ADI-10165 | | No binding | | 5.91e5 | 1.88e-2 | 31.8 |
| ADI-10167 | | No binding | | 1.25e6 | 3.07e-2 | 24.4 |
| ADI-10168 | | No binding | | 3.75e5 | 1.75e-2 | 46.6 |
| ADI-10173 | | No binding | | 2.12e5 | 1.25e-2 | 58.8 |
| ADI-11802 | 1.34e6 | 4.35e-3 | 3.2 | 4.9e5 | 1.54e-3 | 3.14 |
| ADI-11812 | | No binding | | 3.96e5 | 4.86e-4 | 1.23 |
| ADI-11825 | 4.93e6 | 1.95e-2 | 3.95 | 2.13e6 | 3.8e-3 | 1.78 |
| ADI-11826 | 5.12e6 | 2.25e-3 | 4.38 | 1.76e6 | 4.63e-3 | 2.63 |
| ADI-11828 | 3.37e6 | 2.13e-2 | 6.3 | 1.32e6 | 3.51e-3 | 2.67 |
| ADI-11839 | 9.19e6 | 4.1e-1 | 44.6 | 8.74e5 | 1.62e-2 | 18.6 |

Antibodies Recognize CD33 Independent of its Glycosylation Status.

The ability of anti-CD33 antibodies to recognize glycosylated CD33 was assayed. Table 14 shows that antibodies recognize V domain independent of its glycosylation status. Human CD33 is heavily glycosylated with 2 glycosylation sites located in the V domain. Differences in the glycosylation level of CD33 in different cells have been reported in the literature. Glycosylation can potentially disturb antibody binding to the target. In some samples, the V domain was deglycosylated by PNGase before testing. De-glycosylation status was confirmed by a shift on SDS-PAGE and MS. All antibodies tested in Table 14 bound to deglycosylated V CD33 similarly to the fully glycosylated version except for ADI-10163, ADI-10165, ADI-10167, and ADI-10173.

TABLE 14

Biacore™ analysis of FABs binding to fully glycosylated vs deglycosylated V domain performed at 37° C.

| Antibody | Deglycosylated V domain | | | V domain | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| ADI-10159 | 9.78e5 | 1.2e-2 | 12.3 | 9.05e5 | 5.0e-3 | 5.56 |
| ADI-10177 | 1.88e6 | 7.01e-2 | 38.2 | 1.56e6 | 8.57e-2 | 54.8 |
| ADI-11776 | 4.85e6 | 1.36e-3 | 0.28 | 4.52e6 | 1.43e-2 | 0.33 |
| ADI-11807 | 3.9e6 | 7.45e-4 | 0.19 | 3.07e6 | 8.47e-4 | 0.28 |
| ADI-11809 | 3.4e6 | 7.11e-4 | 0.21 | 2.6e6 | 7.69e-4 | 0.3 |
| ADI-11819 | 9.15e6 | 1.03e-3 | 0.11 | 6.75e6 | 9.16e-4 | 0.14 |
| ADI-11830 | 6.8e6 | 2.69e-2 | 3.95 | 6.67e6 | 2.99e-2 | 4.5 |
| ADI-11835 | 7.94e6 | 7.79e-3 | 0.98 | 7.6e6 | 8.68e-3 | 1.14 |
| ADI-11801 | 2.1e6 | 1.15e-3 | 0.55 | 1.8e6 | 1.25e-3 | 0.69 |
| ADI-10152 | 1.05e5 | 7.7e-2 | 76.8 | 4.88e5 | 4.09e-2 | 100 |
| ADI-10154 | 3.13e6 | 6.55e-2 | 209 | 1.52e6 | 3.35e-1 | 220 |
| ADI-10155 | 1.25e6 | 1.32e-1 | 105 | 5.48e5 | 4.67e-2 | 85.2 |
| ADI-10157 | 4.11e5 | 2.61e-2 | 63.8 | 1.12e6 | 1.51e-2 | 134 |
| ADI-10158 | 2.63e6 | 2.31e-1 | 88.1 | 1.04e6 | 1.33e-1 | 127 |
| ADI-10160 | 1.7e6 | 2.25e-1 | 133 | 1.59e6 | 3.27e-1 | 206 |
| ADI-10161 | 2.29e6 | 1.96e-1 | 85.6 | 1.29e6 | 1.24e-1 | 95.8 |
| ADI-10163 | 1.68e6 | 2.56e-1 | 152 | | No binding | |
| ADI-10164 | 8.11e5 | 1.16e-1 | 143 | 1.29e6 | 3.7e-1 | 286 |
| ADI-10165 | 1.3e6 | 2.03e-1 | 156 | | No binding | |
| ADI-10167 | 1.66e6 | 1.28e-1 | 77.8 | | No binding | |
| ADI-10168 | | No binding | | | No binding | |
| ADI-10173 | 6.74e5 | 1.31e-1 | 200 | | No binding | |
| ADI-11802 | 1.57e6 | 4.17e-3 | 2.65 | 1.34e6 | 4.35e-3 | 3.2 |
| ADI-11812 | | No binding | | | No binding | |
| ADI-11825 | 5.78e6 | 1.8e-2 | 3.11 | 4.93e6 | 1.95e-2 | 3.95 |
| ADI-11826 | 5.37e6 | 1.98e-2 | 3.69 | 5.12e6 | 2.25e-3 | 4.38 |

TABLE 14-continued

Biacore™ analysis of FABs binding to fully glycosylated vs deglycosylated V domain performed at 37° C.

| Antibody | Deglycosylated V domain | | | V domain | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| ADI-11828 | 3.588e6 | 1.89e-2 | 4.87 | 3.37e6 | 2.13e-2 | 6.3 |
| ADI-11839 | 1.65e6 | 1.16e-1 | 70.3 | 9.19e6 | 4.1e-1 | 44.6 |

CD33 Antibodies Bind to the R69G SNP of CD33.

The ability of anti-CD33 antibodies to recognize the R69G mutation in CD33 was assayed. Although several SNPs have been described for CD33, R69G is particularly prominent, occurring in 39-42% of the population. Table 15 shows antibodies binding to human CD33 containing the R69G mutation.

TABLE 15

Biacore™ analysis of FABs binding to CD33 R69G.

| Antibody | Human CD33 R69G | | | Human CD33 | | |
|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) |
| ADI-10159 | 4.26e5 | 2.43e-3 | 5.68 | 4.29e5 | 1.95e-3 | 4.53 |
| ADI-10177 | 2.3e5 | 2.01e-3 | 87.4 | 5.58e5 | 6.36e-3 | 11.4 |
| ADI-11776 | 1.98e6 | 4.26e-4 | 0.22 | 1.6e6 | 1.24e-3 | 0.78 |
| ADI-11807 | 5.97e5 | 2.59e-4 | 0.43 | 1.14e6 | 3.32e-4 | 0.29 |
| ADI-11809 | 8.15e5 | 1.79e-4 | 0.22 | 1.02e6 | 1.23e-6 | 0.0012 |
| ADI-11819 | 2.78e6 | 2.44e-4 | 0.09 | 2.84e6 | 5.65e-5 | 0.02 |
| ADI-11830 | 2.27e6 | 6.63e-3 | 2.94 | 1.99e6 | 5.47e-3 | 2.75 |
| ADI-11835 | 3.07e6 | 2.05e-3 | 0.67 | 2.6e6 | 1.43e-3 | 0.53 |
| ADI-11815 | 3.00e5 | 1.3e-3 | 4.34 | 3.39e5 | 7.91e-5 | 0.23 |
| ADI-11801 | | No binding | | 7.56e5 | 4.17e-4 | 0.55 |
| ADI-10152 | 2.88e5 | 2.18e-2 | 75.8 | 2.46e5 | 9.14e-3 | 37.2 |
| ADI-10154 | 1.53e5 | 2.83e-2 | 186 | 1.92e5 | 8.33e-3 | 43.4 |
| ADI-10155 | 2.33e5 | 1.05e-2 | 45.0 | 1.70e5 | 6.85e-3 | 40.2 |
| ADI-10157 | 1.56e6 | 2.87e-2 | 17.8 | 2.82e6 | 7.60e-3 | 2.69 |
| ADI-10158 | 5.30e5 | 3.31e-2 | 62.3 | 4.75e5 | 1.49e-2 | 3.14 |
| ADI-10160 | 8.36e5 | 5.33e-2 | 63.7 | 6.37e5 | 2.69e-2 | 42.2 |
| ADI-10161 | 6.29e5 | 3.07e-2 | 48.9 | 5.74e5 | 1.18e-2 | 20.6 |
| ADI-10163 | 5.59e5 | 5.9e-2 | 106 | 5.15e5 | 2.75e-2 | 53.5 |
| ADI-10164 | 3.08e5 | 3.5e-2 | 113 | 3.19e5 | 1.01e-2 | 31.5 |
| ADI-10165 | 6.9e5 | 5.02e-2 | 72.7 | 5.91e5 | 1.88e-2 | 31.8 |

TABLE 15-continued

Biacore™ analysis of FABs binding to CD33 R69G.

| | Human CD33 R69G | | | Human CD33 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| ADI-10167 | 1.22e6 | 8.74e-2 | 71.6 | 1.25e6 | 3.07e-2 | 24.4 |
| ADI-10168 | 4.85e5 | 3.07e-2 | 63.5 | 3.75e5 | 1.75e-2 | 46.6 |
| ADI-10173 | No binding | | | 2.12e5 | 1.25e-2 | 58.8 |
| ADI-11802 | No binding | | | 4.9e5 | 1.54e-3 | 3.14 |
| ADI-11812 | 3.38e5 | 2.28e-3 | 6.74 | 3.96e5 | 4.86e-4 | 1.23 |
| ADI-11825 | 1.86e6 | 6.95e-3 | 3.74 | 2.13e6 | 3.8e-3 | 1.78 |
| ADI-11826 | 1.89e6 | 7.23e-3 | 3.83 | 1.76e6 | 4.63e-3 | 2.63 |
| ADI-11828 | 1.16e6 | 7.00e-3 | 6.03 | 1.32e6 | 3.51e-3 | 2.67 |
| ADI-11839 | No binding | | | 8.74e5 | 1.62e-2 | 18.6 |

CD33 Antibodies Bind to the S128N SNP of CD33

The ability of anti-CD33 antibodies to recognize the S128N mutation in CD33 was assayed. Table 16 shows antibodies binding to human CD33 containing the S128N mutation. The binding affinity of ADI-10152, ADI-10154, ADI-10157, ADI-10158, ADI-10163, ADI-10164, ADI-10165, ADI-10167, ADI-10168, and ADI-10173 to human CD33 was impaired by the S128N SNP.

TABLE 16

Biacore™ analysis of FABs binding to CD33 S128N.

| | Human CD33 S128N | | | Human CD33 | | |
|---|---|---|---|---|---|---|
| Antibody | $k_a$ (1/Ms) | $k_d$ (1/s) | $K_D$ (nM) | $k_a$ (1/Ms) | $k_d$ (1/s) | $K_D$ (nM) |
| ADI-10152 | 2.74e5 | 3.39e-2 | 124 | 2.46e5 | 9.14e-3 | 37.2 |
| ADI-10154 | 1.93e5 | 5.39e-2 | 279 | 1.92e5 | 8.33e-3 | 43.4 |
| ADI-10155 | 1.87e5 | 1.59e-2 | 85 | 1.70e5 | 6.85e-3 | 40.2 |
| ADI-10157 | 5.65e4 | 9.24e-3 | 163 | 2.82e6 | 7.60e-3 | 2.69 |
| ADI-10158 | 5.73e5 | 4.17e-2 | 72.8 | 4.75e5 | 1.49e-2 | 3.14 |
| ADI-10160 | 7.86e5 | 6.73e-2 | 85.7 | 6.37e5 | 2.69e-2 | 42.2 |
| ADI-10161 | 6.05e5 | 3.85e-2 | 63.6 | 5.74e5 | 1.18e-2 | 20.6 |
| ADI-10163 | 5.07e5 | 7.48e-2 | 147 | 5.15e5 | 2.75e-2 | 53.5 |
| ADI-10164 | 1.93e5 | 5.39e-2 | 279 | 3.19e5 | 1.01e-2 | 31.5 |
| ADI-10165 | 6.41e5 | 5.82e-2 | 90.7 | 5.91e5 | 1.88e-2 | 31.8 |
| ADI-10167 | 1.28e6 | 1.27e-1 | 98.6 | 1.25e6 | 3.07e-2 | 24.4 |
| ADI-10168 | 4.04e5 | 4.69e-2 | 116 | 3.75e5 | 1.75e-2 | 46.6 |
| ADI-10173 | 1.83e5 | 3.42e-2 | 187 | 2.12e5 | 1.25e-2 | 58.8 |
| ADI-11802 | 6.62e5 | 5.90e-4 | 0.809 | 4.9e5 | 1.54e-3 | 3.14 |
| ADI-11812 | 5.56e5 | 1.12e-3 | 2.01 | 3.96e5 | 4.86e-4 | 1.23 |
| ADI-11825 | 2.10e6 | 6.49e-3 | 3.09 | 2.13e6 | 3.8e-3 | 1.78 |
| ADI-11826 | 2.17e6 | 5.74e-3 | 2.65 | 1.76e6 | 4.63e-3 | 2.63 |
| ADI-11828 | 1.37e6 | 7.42e-3 | 5.41 | 1.32e6 | 3.51e-3 | 2.67 |
| ADI-11839 | 9.63e5 | 2.84e-2 | 29.5 | 8.74e5 | 1.62e-2 | 18.6 |

ADI-11815 Recognizes a Unique Conformational Epitope.

The binding epitope of the CD33-binding domain of ADI-11815 was assayed. FIG. 6 and Table 17 demonstrate that ADI-11815 has a unique conformational epitope. This antibody binds to the full-length ECD of human CD33, but not to individual domains and does not cross-block with lintuzumab.

TABLE 17

Kinetic parameters of ADI-11815 Fab binding to different domains and SNP R69G of human CD33.

| | hCD33 | | | V domain | | | C domain | | | hCD33 R69G SNP | | | Cross-blocking with lintuzumab |
|---|---|---|---|---|---|---|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) | |
| ADI-11815 | 3.39p5 | 7.91e-5 | 0.23 | No binding | | | No binding | | | 3.00e5 | 1.3e-3 | 4.34 | No |

ADI-11801 Binds to a Unique Epitope that Includes R69.

The binding epitope of CD33-binding domain including ADI-11815 was assayed. FIG. 7 and Table 18 demonstrate the epitope on CD33 that ADI-11801 recognize. Its binding to the human CD33 ECD is abrogated by R69G mutation.

TABLE 18

Kinetics of ADI-11801 Fab binding to different domains of CD33 and SNP R69G.

| | hCD33 | | | V domain | | | C domain | | | hCD33 R69G SNP | | | Cross-blocking with lintuzumab |
|---|---|---|---|---|---|---|---|---|---|---|---|---|---|
| | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) | $k_a$ (1/Ms) | $k_d$ (1/s) | $K_D$ (nM) | |
| AU-11801 | 7.5.6e5 | 4.17e-4 | 0.55 | 1.80e6 | 1.25e-3 | 0.69 | No binding | | | No binding | | | No |

Example 3: Assessment of TriNKET Binding to Cell Expressing Human NKG2D

The ability of TriNKETs that include an NKG2D-binding domain and a CD33-binding domain to bind to NKG2D was assayed. EL4 cells transduced with human NKG2D and human KHYG-1 cells were used to test binding to cell-expressed human NKG2D. TriNKETs were diluted to the top concentration, and then diluted serially. The mAb or TriNKET dilutions were used to stain cells, and binding of the TriNKET or mAb was detected using a fluorophore-conjugated anti-human IgG secondary antibody. Cells were analyzed by flow cytometry, binding MFI was normalized to secondary antibody controls to obtain fold over background values.

Figure 10A:
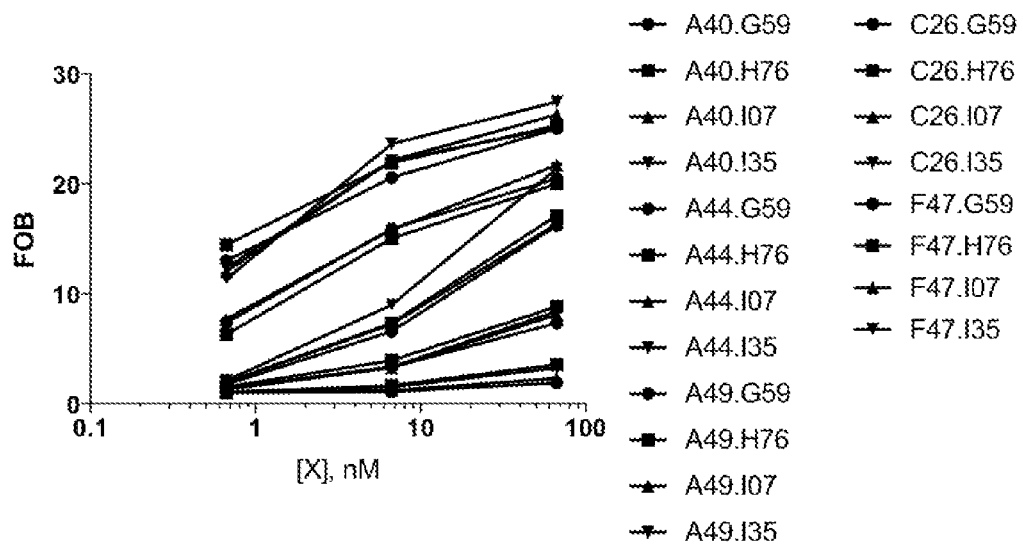
FIGS. 10A-10B show binding of CD33-targeting TriNKETs to human NKG2D expressed on EL4-hNKG2D and KHYG-1 cells.
Figure 10B:
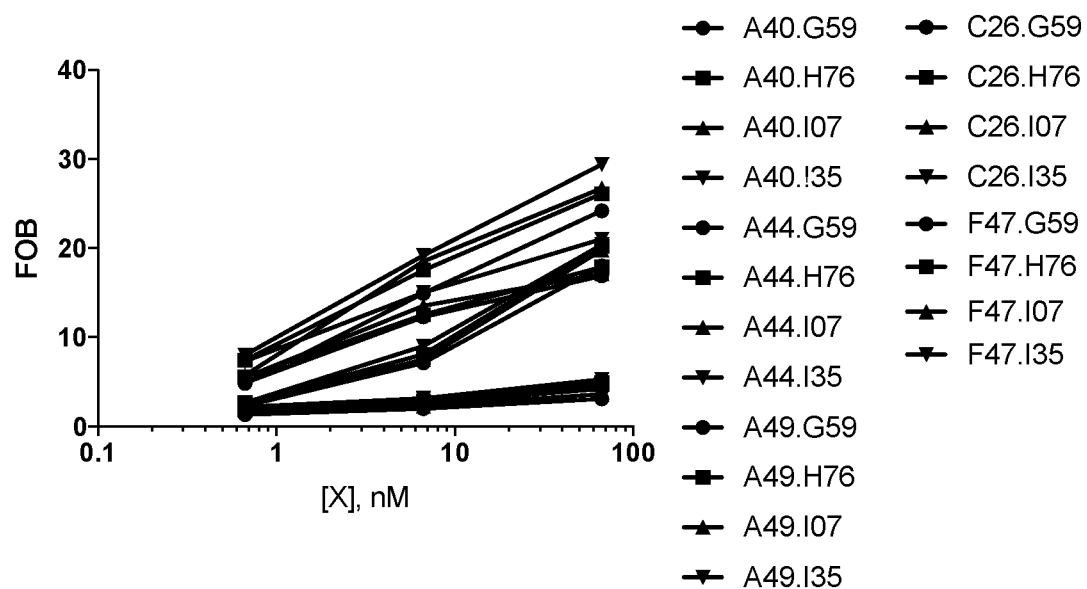
Figure 11:
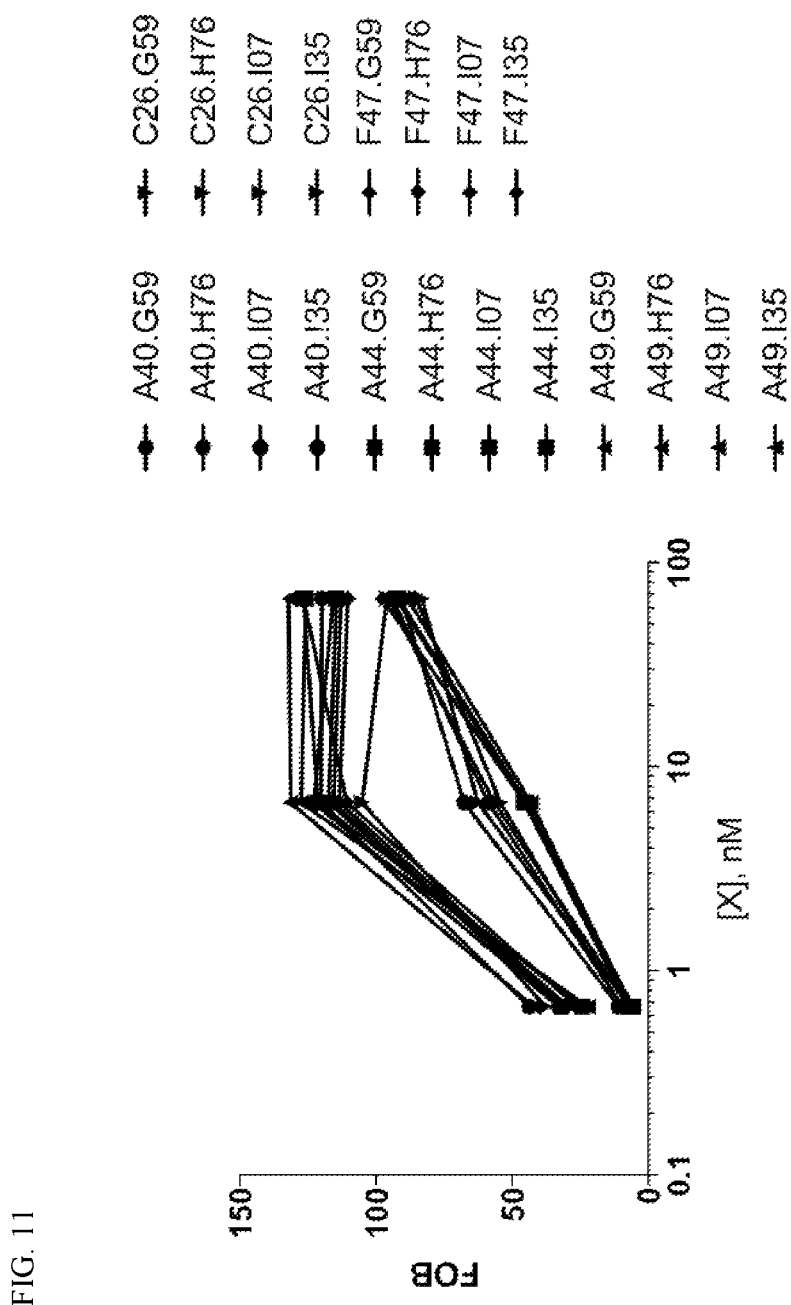
FIG. 11 shows binding of CD33-targeting TriNKETs to CD33 expressed on human AML Molm-13 cells. Four different CD33-binding clones were used with five NKG2D-binding clones to make a total of 20 different TriNKETs. NKG2D-binding domains TriNKET do not affect the binding of CD33-binding clones to CD33.

FIGS. 10A-10B show binding of CD33-targeting TriNKETs to human NKG2D expressed on EL4 (top) or KHYG-1 (bottom) cells. FOB binding signal was similar on both EL4-hNKG2D cells and KHYG-1 cells, the ranking of binding between clones was also maintain on the two cell lines. FIG. 10A shows binding of CD33-targeting TriNKETs to human NKG2D expressed on EL4 cells. FIG. 10B shows binding of CD33-targeting TriNKETs to human NKG2D expressed on KHYG-1 cells. FOB binding signal was similar on both EL4-hNKG2D cells and KHYG-1 cells, the ranking of binding between clones was also maintain on the two cell lines.

Example 4: Assessment of TriNKET or mAb Binding to Cell Expressed Human Cancer Antigens The ability of TriNKETs that include an NKG2D-binding domain and a CD33-binding domain to bind to CD33 was assayed. The Molm-13, human AML cell line, was used to assess binding of monoclonal antibodies to CD33 expressed on the cell surface. mAbs were diluted to 2 µg/mL, and mAb dilutions were used to stain cells. Bound antibody was detected using a fluorophore conjugated anti-human IgG secondary antibody. Cells were analyzed by flow cytometry, binding to cell-expressed CD33 was compared to isotype stained and unstained cell populations.

Human cancer cell lines expressing CD33 were used to assess tumor antigen binding of TriNKETs derived from different NKG2D-targeting clones. The human AML cell line Molm-13 was used to assess binding of TriNKETs to cell expressed CD33. TriNKETs were diluted, and were incubated with the respective cells. Binding of the TriNKET was detected using a fluorophore conjugated anti-human IgG secondary antibody. Cells were analyzed by flow cytometry, binding MFI to cell expressed CD33 was normalized to secondary antibody controls to obtain fold over background values.

Figure 8:
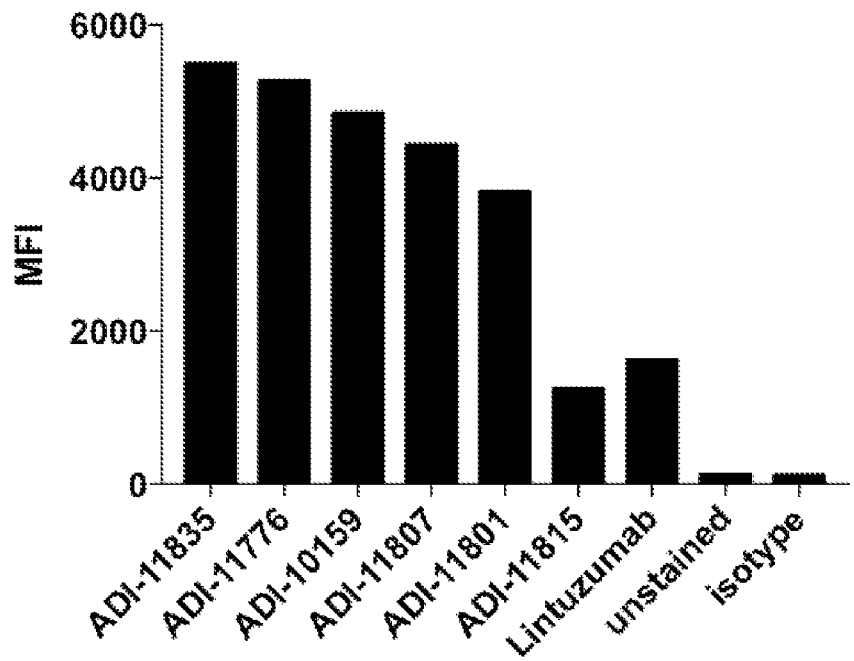
FIG. 8 are bar graphs showing binding of monoclonal antibodies comprising CD33-binding clones to CD33 expressed on Molm-13 human AML cells. CD33 antibody Lintuzumab was also tested, and mean fluorescence intensity (MFI) was plotted. Five of the six antibodies show higher binding signal to CD33 compared to Lintuzumab.

The ability of CD33 TriNKETs to bind CD33 expressed on Molm-13 cells was tested. FIG. 8 shows binding of TriNKETs targeting CD33 to Molm—shows binding MFI of six anti-CD33 antibodies to CD33 expressed on Molm-13 cells. All six antibodies bound to cell-expressed CD33. Five of the six antibodies show higher MFI binding signal compared to Lintuzumab.

The ability of CD33 TriNKETs to induce rested NK cell-mediated killing of Molm-13 AML cells was tested. Four different CD33-targeting domains were used with five NKG2D-targeting domains to make a total of 20 different TriNKETs. Regardless of the NKG2D-targeting domain used in the TriNKET, binding to CD33 was conserved for a single CD33-targeting domain.

Example 5: Assessment of TriNKET or mAb Internalization

Internalization of TriNKETs after binding to CD33 on cell surface was assayed. The Molm-13, human AML cell line, was used to assess internalization of monoclonal antibodies bound to CD33 expressed on the cell surface. Monoclonal antibodies were diluted to 2 µg/mL, and mAb dilutions were used to stain cells. Following surface staining of CD33 samples were split, half the sample was placed at 37° C. overnight to facilitate internalization, with the other half of the sample bound antibody was detected using a fluorophore conjugated anti-human IgG secondary antibody. Cells were fixed after staining with the secondary antibody, and were stored at 4° C. overnight for analysis on the following day. After 24 hours at 37° C. samples were removed from the incubator, and bound antibody on the surface of the cells was detected using a fluorophore conjugated anti-human IgG secondary antibody. Samples were fixed and all samples were analyzed on the same day. Internalization of antibodies was calculated as follows: % internalization=(1−(sample MFI 24 hours/baseline MFI))*100%.

Figure 9:
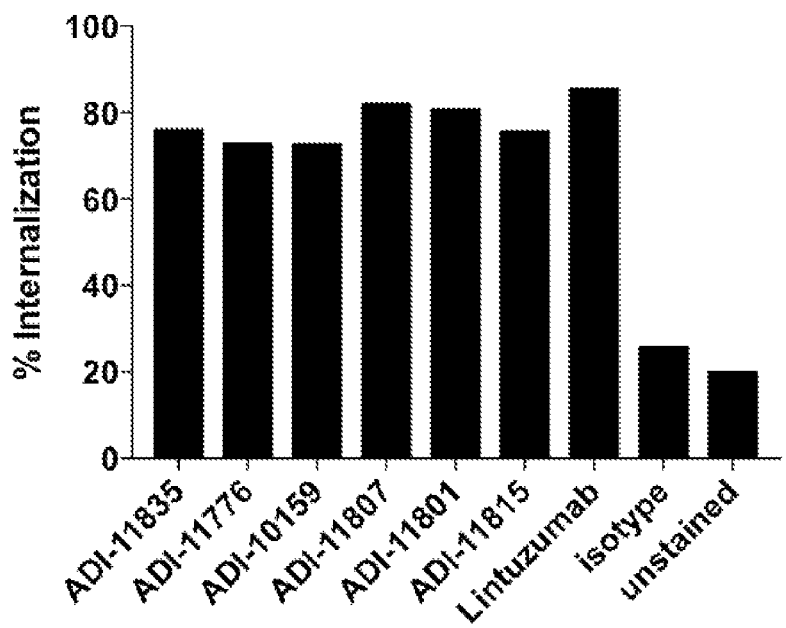
FIG. 9 are bar graphs showing internalization of CD33 antibodies on Molm-13 cells after 24 hours. All the CD33 antibodies showed similar internalization after 24 hours. Lintuzumab showed slightly higher internalization compare to other anti-CD33 antibodies.

FIG. 9 shows internalization of anti-CD33 antibodies bound to the surface of Molm-13 cells after 24 hours. All the anti-CD33 antibodies showed similar internalization after 24 hours. Lintuzumab showed slightly higher internalization compare to other anti-CD33 antibodies.

Example 6: Activation of Primary NK Cells by TriNKETs

The ability of TriNKETs that include an NKG2D-binding domain and a CD33-binding domain to activate primary NK cells was assayed. PBMCs were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3-CD56+. Isolated NK cells were cultured in media containing 100 ng/mL IL-2 for activation or rested overnight without cytokine. IL-2-activated NK cells were used either 24-48 hours later; rested NK cells were always used the day after purification.

Human cancer cell lines expressing a cancer target of interest were harvested from culture, and cells were adjusted to $2 \times 10^6$/mL. Monoclonal antibodies or TriNKETs targeting the cancer target of interest were diluted in culture media. Rested and/or activated NK cells were harvested from culture, cells were washed, and were resuspended at $2 \times 10^6$/mL in culture media. IL-2, and fluorophore-conjugated anti-CD107a was added to the NK cells for the activation culture. Brefeldin-A and monensin were diluted into culture media to block protein transport out of the cell for intracellular cytokine staining. Into a 96-well plate 50 µl of tumor targets, mAbs/TriNKETs, BFA/monensin, and NK cells were added for a total culture volume of 200 µl. Plate was cultured for 4 hours before samples were prepared for FACS analysis.

Following the 4 hour activation culture, cells were prepared for analysis by flow cytometry using fluorophore-conjugated antibodies against CD3, CD56 and IFNγ. CD107a and IFNγ staining was analyzed in CD3-CD56+ populations to assess NK cell activation.

Figure 12:
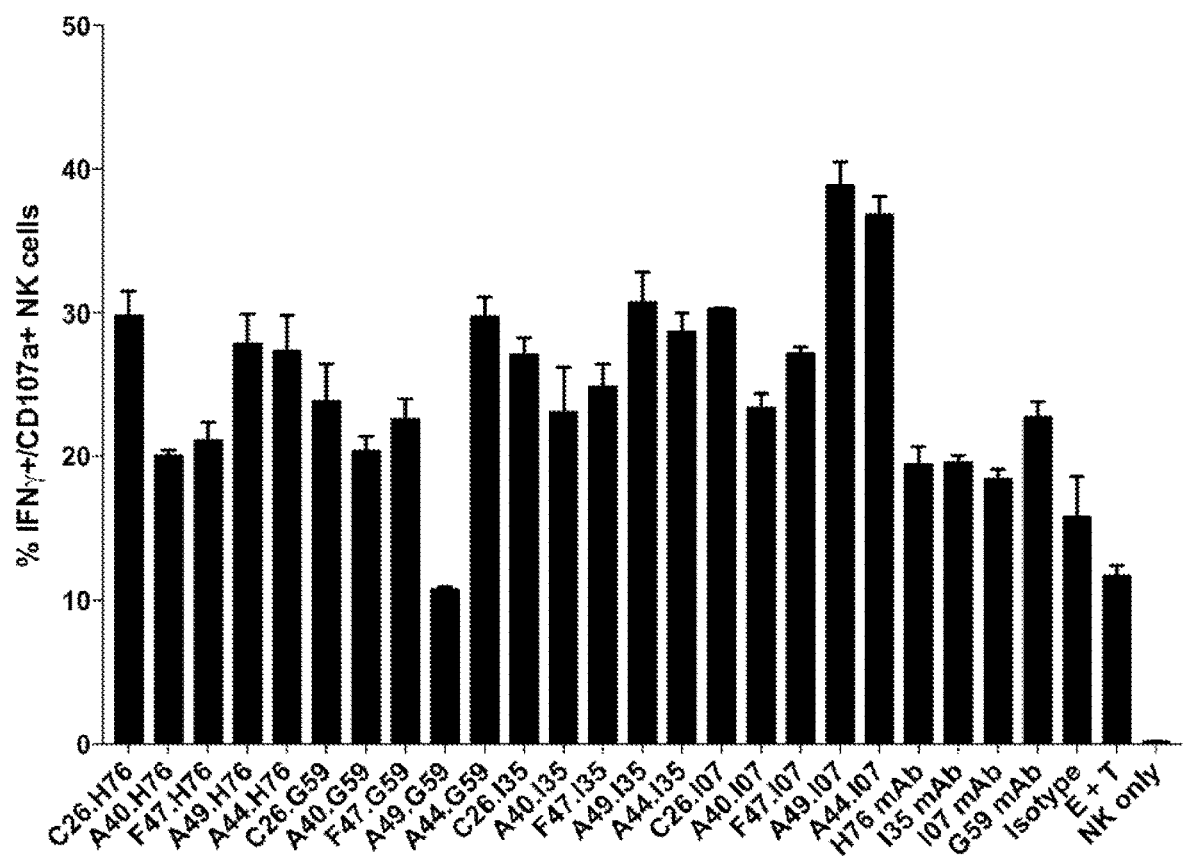
FIG. 12 is a graph showing that rested human NK cells are activated by CD33-targeting TriNKETs in co-culture with CD33-expressing THP-1 AML cells.

FIG. 12 shows TriNKET-mediated activation of rested human NK cells in co-culture with CD33-expressing THP-1 AML, cells. Human NK cell activation was assessed using IFNγ production and CD107a degranulation as markers for activation. All TriNKETs and monoclonal antibodies activated human NK cells above the isotype control. Similar activity was observed for four different anti-CD33 antibodies. TriNKET activity was dependent upon the NKG2D-targeting clone, some clones provided better TriNKET mediated activation than others. NKG2D clones provided similar activity with each of the anti-CD33 targeting domains.

Example 7: Primary Human NK Cell Cytotoxicity Assay

The ability of TriNKETs that include an NKG2D-binding domain and a CD33-binding domain to induce cytotoxicity of NK cells against CD33-expressing cells was assayed. PBMCs were isolated from human peripheral blood buffy coats using density gradient centrifugation. Isolated PBMCs were washed and prepared for NK cell isolation. NK cells were isolated using a negative selection technique with magnetic beads, purity of isolated NK cells was typically >90% CD3-CD56+. Isolated NK cells were cultured in media containing 100 ng/mL IL-2 or were rested overnight without cytokine. IL-2-activated or rested NK cells were used the following day in cytotoxicity assays.

KHYG-1 cells were maintained in 10% HI-FBS-RPMI-1640 with 10 ng/mL IL-2. The day before use as effector cells in killing assays KHYG-1 cells were harvest from culture, and cells were washed out of the IL-2-containing media. After washing KHYG-1 cells were resuspended in 10% HI-FBS-RPMI-1640, and were rested overnight without cytokine.

DELFIA Cytotoxicity Assay:

Human cancer cell lines expressing a target of interest were harvested from culture, cells were washed with HBS, and were resuspended in growth media at $10^6$/mL for labeling with BATDA reagent (Perkin Elmer AD0116). Manufacturer instructions were followed for labeling of the target cells. After labeling cells were washed 3× with HBS, and were resuspended at 0.5-1.0×$10^5$/mL in culture media. To prepare the background wells an aliquot of the labeled cells was put aside, and the cells were spun out of the media. 100 µl of the media was carefully added to wells in triplicate to avoid disturbing the pelleted cells. 100 µl of BATDA labeled cells were added to each well of the 96-well plate. Wells were saved for spontaneous release from target cells, and wells were prepared for max lysis of target cells by addition of 1% octylphenoxy polyoxyethylene ether (TRITON™-X). Monoclonal antibodies or TriNKETs against the tumor target of interest were diluted in culture media and 50 µl of diluted mAb or TriNKET was added to each well. Rested and/or activated NK cells were harvested from culture, cells were washed, and were resuspended at $10^5$-2.0×$10^6$/mL in culture media depending on the desired E:T ratio. 50 µl of NK cells was added to each well of the plate to make a total of 200 µl culture volume. The plate was incubated at 37° C. with 5% CO2 for 2-3 hours before developing the assay.

After culturing for 2-3 hours, the plate was removed from the incubator and the cells were pelleted by centrifugation at 200 g for 5 minutes. 20 µl of culture supernatant was transferred to a clean microplate provided from the manufacturer and 200 µl of room temperature europium solution was added to each well. The plate was protected from the light and incubated on a plate shaker at 250 rpm for 15 minutes. Plate was read using either Victor3™ or Spectra-Max® i3X instruments. % Specific lysis was calculated as follows: % Specific lysis=((Experimental release−Spontaneous release)/(Maximum release−Spontaneous release))*100%

Figure 13:
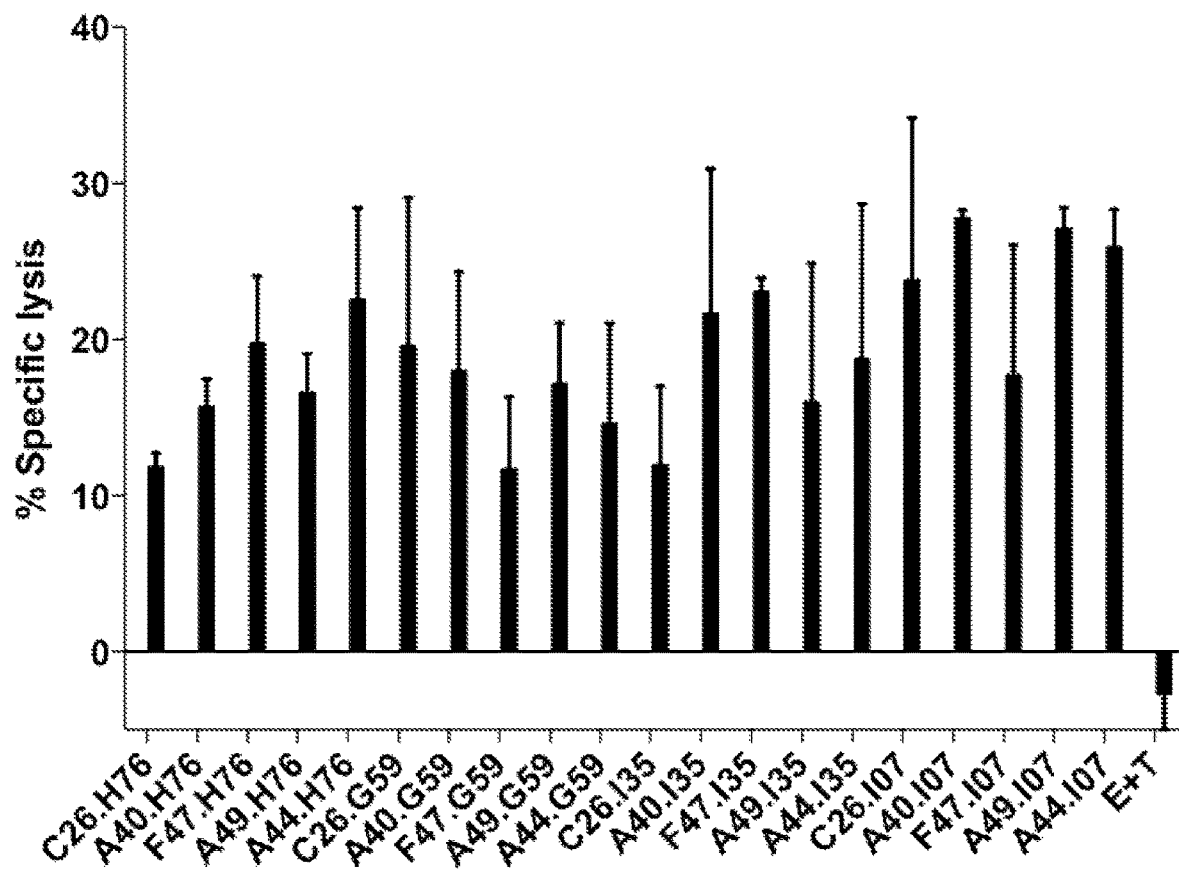
FIG. 13 is a bar graph showing that CD33 TriNKETs induce rested NK cell mediated killing of Molm-13 AML cells.
Figure 14:
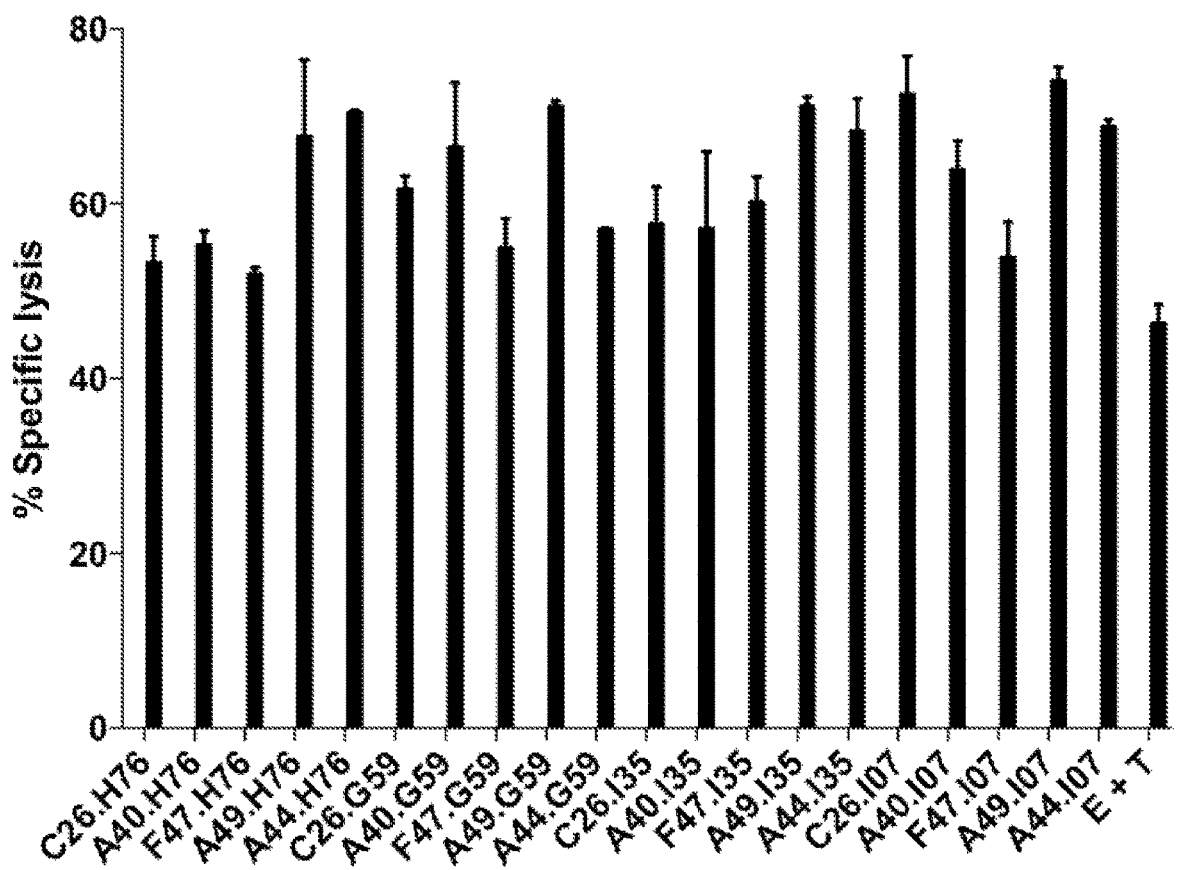
FIG. 14 is a bar graph showing that CD33 TriNKETs induce activated NK cell mediated killing of THP-1 cells.

FIG. 13 and FIG. 14 show human NK cell killing of Molm-13 (FIG. 13) and THP-1 (FIG. 14) AML target cells mediated by CD33-targeting TriNKETs. Human NK cell killing of Molm-13 AML target cells mediated by CD33-targeting TriNKETs was assayed (FIG. 13). Rested NK effector cells were used with Molm-13 target cells. Activated human NK effector cells gave higher background killing, compared to rested human NK effector cells. With NK effector cells, TriNKETs were able to increase lysis against Molm-13 AML target cells. Similar activity of each TriNKET was observed with rested and activated human NK cells, as well as with Molm-13 target cells.

Human NK cell killing of THP-1 AML target cells, mediated by CD33-targeting TriNKETs was assayed. Activated human NK effector cells were used with THP-1 cells (FIG. 14), which resulted in higher background killing, compared to rested human NK effector cells. With NK effector cells, TriNKETs were able to increase lysis against THP-1 AML target cells. Similar activity of each TriNKET was observed with rested and activated human NK cells, as well as with THP-1 target cells.

Thus, with NK effector cells TriNKETs were able to increase lysis against Molm-13 (FIG. 13) and THP-1 (FIG. 14) AML target cells. Similar activity of each TriNKET was observed with rested and activated human NK cells, as well as with Molm-13 (FIG. 13) and THP-1 (FIG. 14) target cells.

Figure 15A:
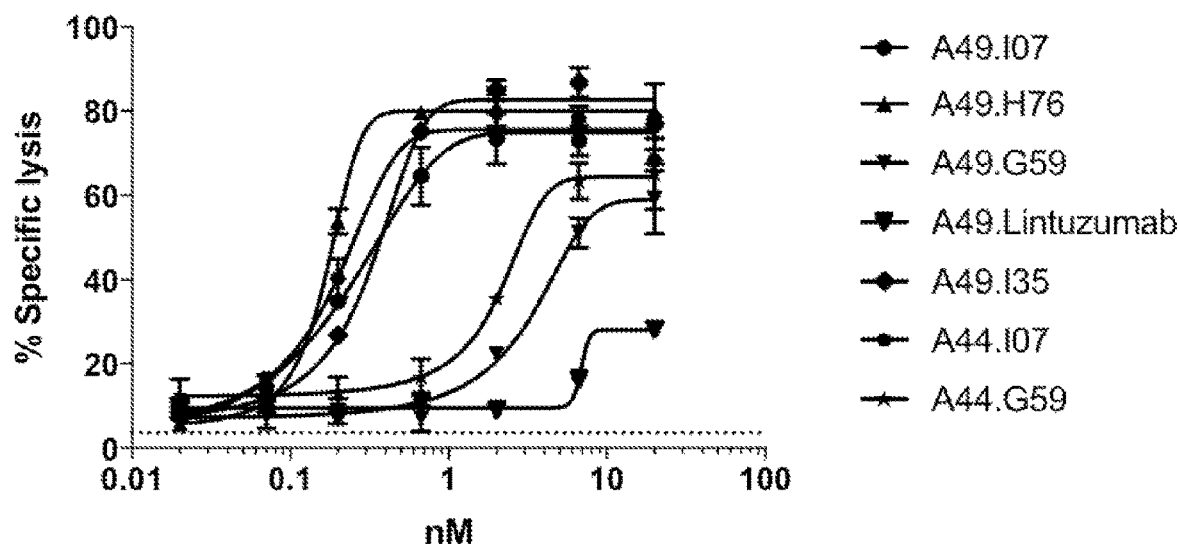
FIG. 15A are line graphs showing that TriNKETs mediate KHYG-1 killing of Molm-13 AML cells.
Figure 15B:
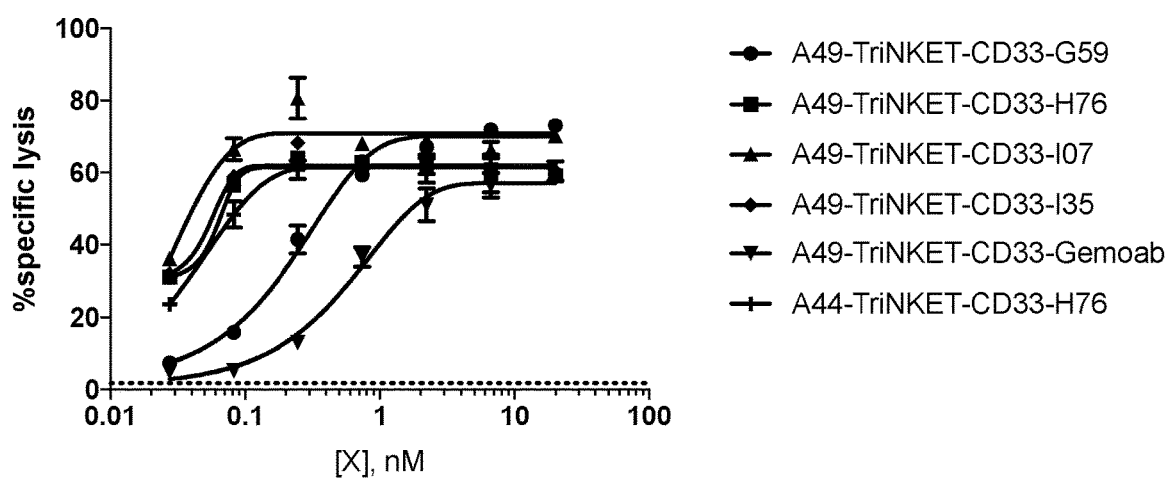
FIG. 15B are line graphs showing that TriNKETs mediate rested human NK cell killing of Molm-13 human AML cells.
Figure 16:
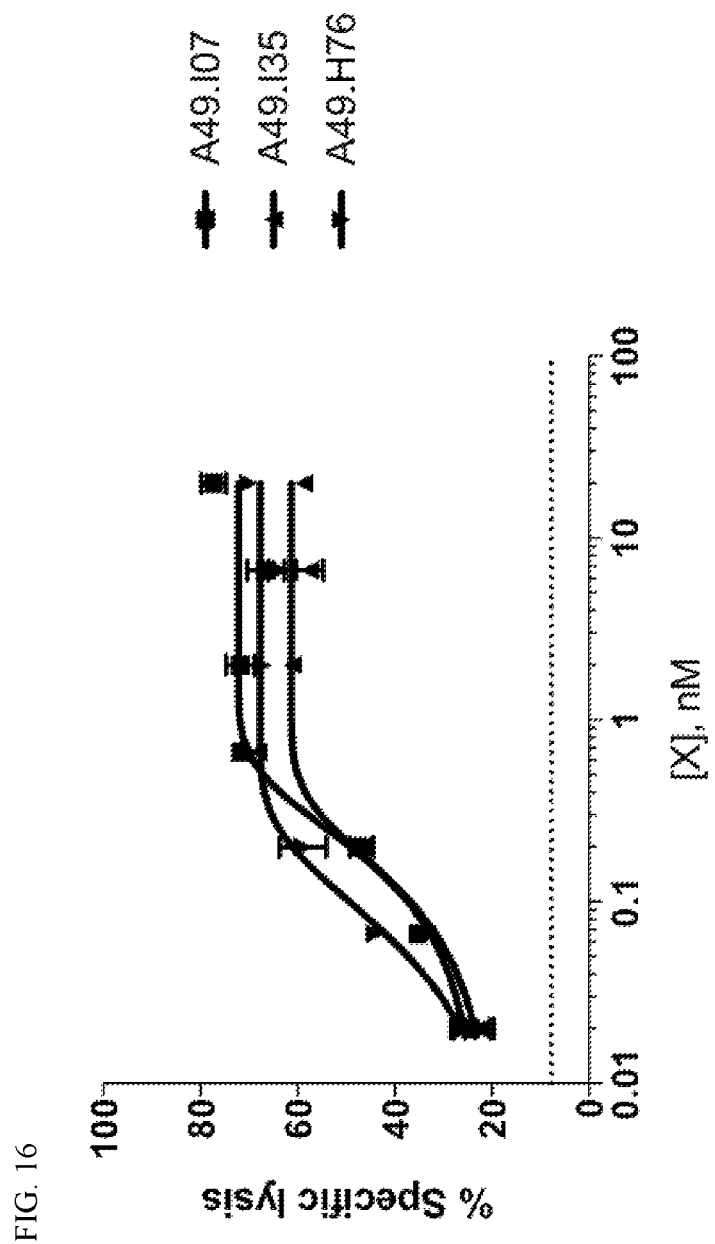
FIG. 16 are line graphs showing that TriNKETs mediate KHYG-1 killing of EOL-1 AML cells.
Figure 17A:
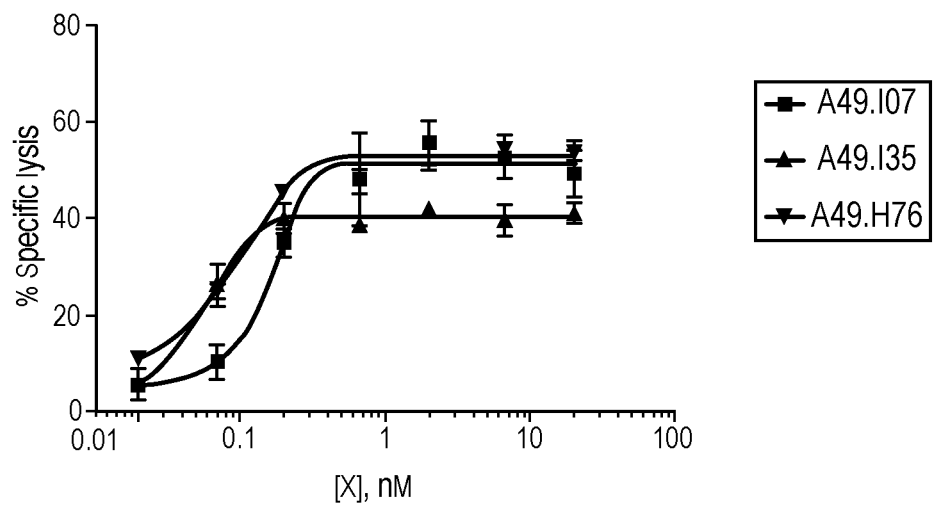
FIG. 17A are line graphs showing that TriNKETs mediate KHYG-1 killing of THP-1 cells.
Figure 17B:
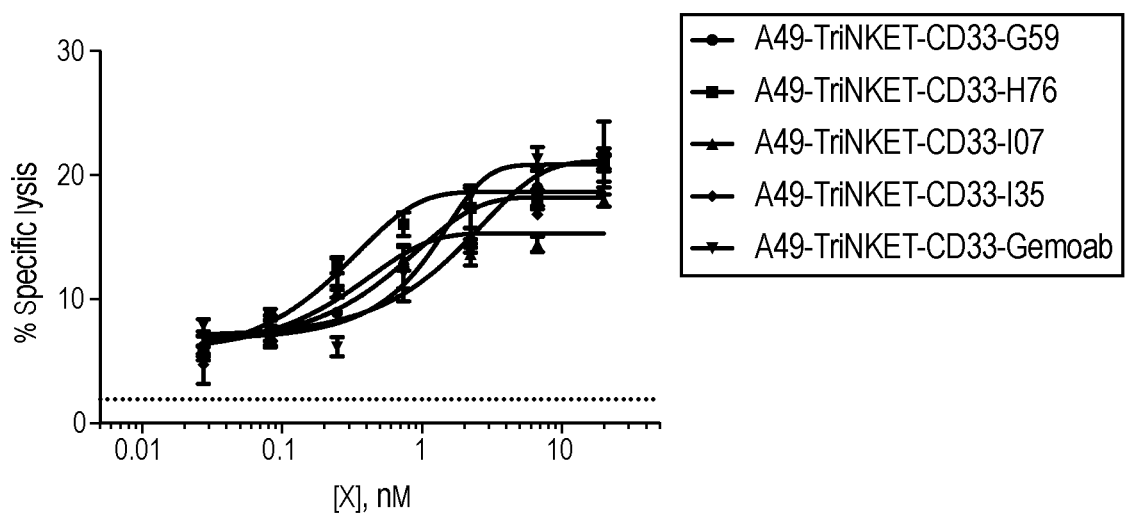
FIG. 17B are line graphs showing that TriNKETs mediate rested human NK cell killing of THP-1 human AML cells.
Figure 18:
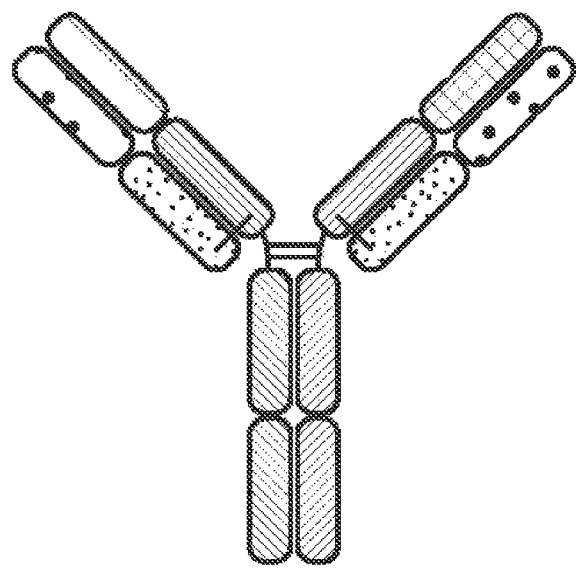
FIG. 18 is a representation of a multispecific binding protein that contains an NKG2D-binding domain (right arm), a CD33-binding domain (left arm), and an Fc domain or a portion thereof that binds to CD16.
Figure 19:
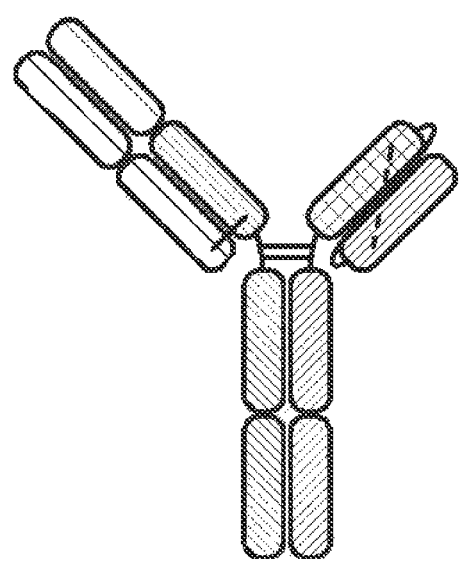
FIG. 19 is a representation of a multispecific binding protein that includes a NKG2D-binding domain or a CD33-binding domain, either one of which can be in a scFv format, and an Fc domain or a portion thereof that binds to CD16.
Figure 20:
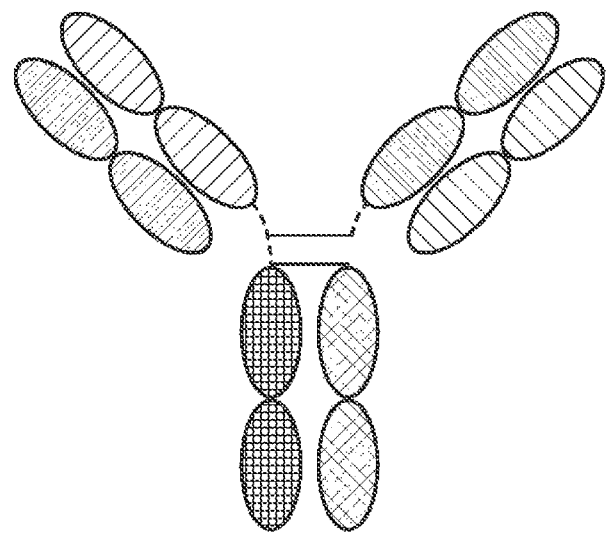
FIG. 20 is a representation of a TriNKET in the Triomab form, which is a trifunctional, bispecific antibody that maintains an IgG-like shape. This chimera consists of two half antibodies, each with one light and one heavy chain, that originate from two parental antibodies.
Figure 21:
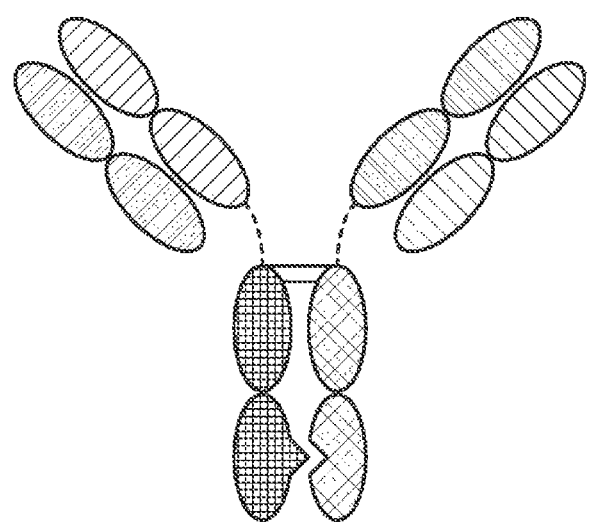
FIG. 21 is a representation of a TriNKET in the KiH Common Light Chain (LC) form, which involves the knobs-into-holes (KIHs) technology. KiH is a heterodimer containing 2 Fabs binding to target 1 and 2, and an Fc stabilized by heterodimerization mutations. TriNKET in the KiH format may be an heterodimeric construct with 2 Fabs binding to target 1 and target 2, containing two different heavy chains and a common light chain that pairs with both heavy chains.
Figure 22:
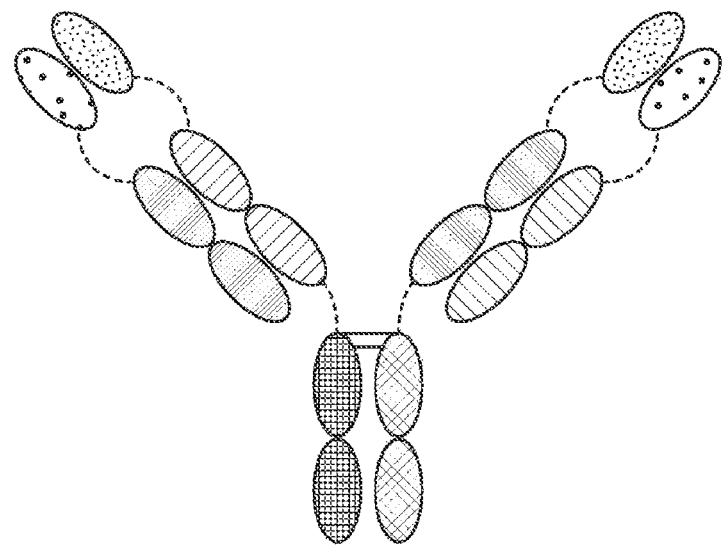
FIG. 22 is a representation of a TriNKET in the dual-variable domain immunoglobulin (DVD-Ig™) form, which combines the target binding domains of two monoclonal antibodies via flexible naturally occurring linkers, and yields a tetravalent IgG-like molecule. DVD-Ig™ is a homodimeric construct where variable domain targeting antigen 2 is fused to the N terminus of variable domain of Fab targeting antigen 1 Construct contains normal Fc.
Figure 23:
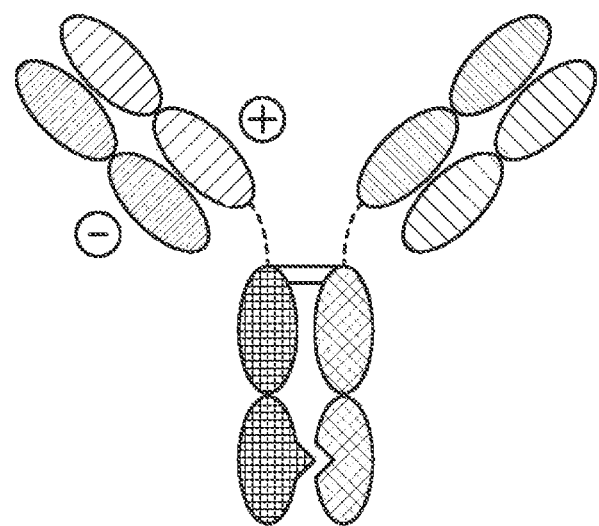
FIG. 23 is a representation of a TriNKET in the Orthogonal Fab interface (Ortho-Fab) form, which is an heterodimeric construct that contains 2 Fabs binding to target1 and target 2 fused to Fc. LC-HC pairing is ensured by orthogonal interface. Heterodimerization is ensured by mutations in the Fc.
Figure 24:
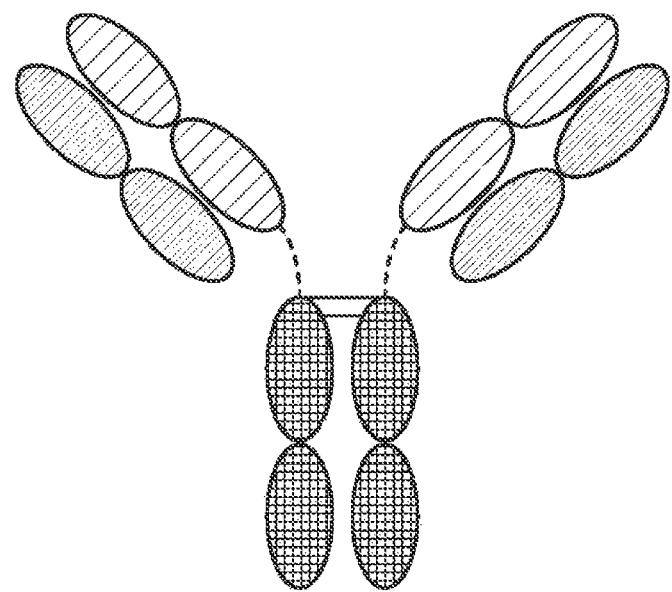
FIG. 24 is a representation of a TrinKET in the 2-in-1 Ig format.
Figure 25:
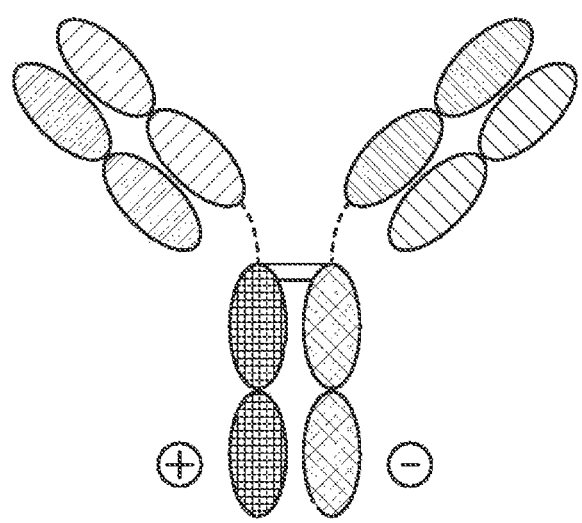
FIG. 25 is a representation of a TriNKET in the ES form, which is an heterodimeric construct containing two different Fabs binding to target 1 and target 2 fused to the Fc. Heterodimerization is ensured by electrostatic steering mutations in the Fc.
Figure 26:
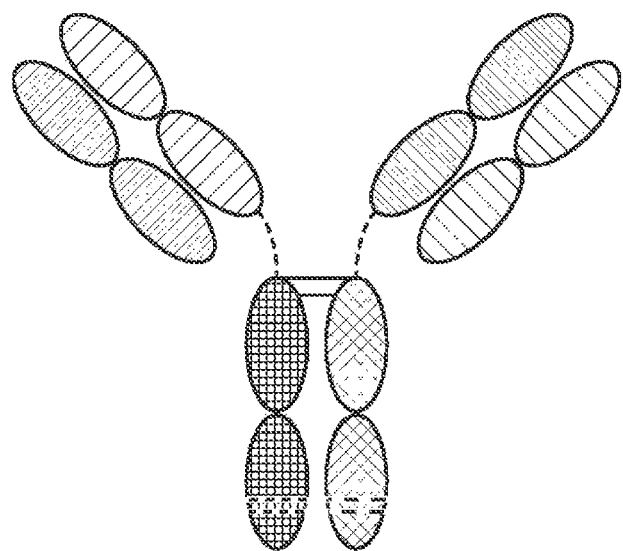
FIG. 26 is a representation of a TriNKET in the Fab Arm Exchange form: antibodies that exchange Fab arms by swapping a heavy chain and attached light chain (half-molecule) with a heavy-light chain pair from another molecule, resulting in bispecific antibodies. Fab Arm Exchange form (cFae) is a heterodimer containing 2 Fabs binding to target 1 and 2, and an Fc stabilized by heterodimerization mutations.
Figure 27:
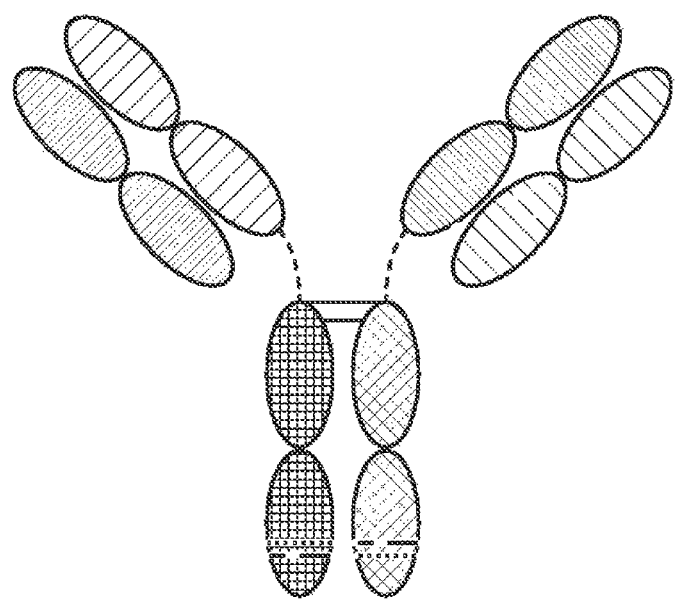
FIG. 27 is a representation of a TriNKET in the SEED Body form, which is an heterodimer containing two Fabs binding to target 1 and 2, and an Fc stabilized by heterodimerization mutations.
Figure 28:
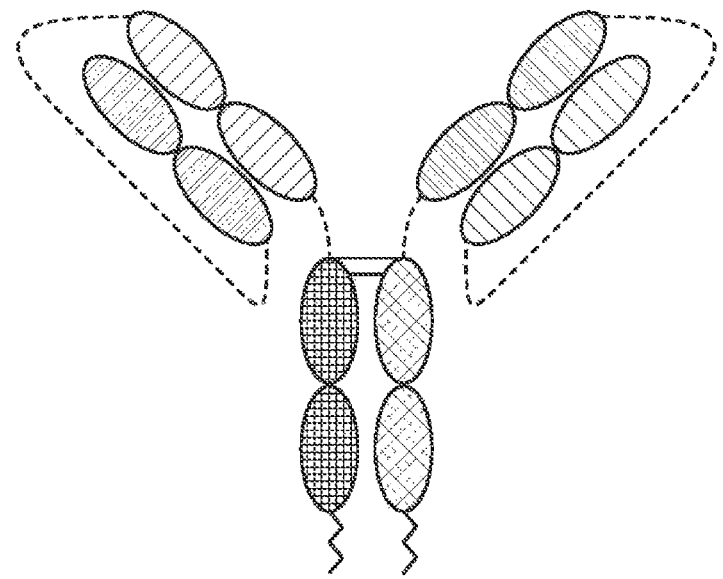
FIG. 28 is a representation of a TriNKET in the LuZ-Y form, in which leucine zipper is used to induce heterodimerization of two different HCs. LuZ-Y form is a heterodimer containing two different scFabs binding to target 1 and 2, fused to Fc.
Figure 29:
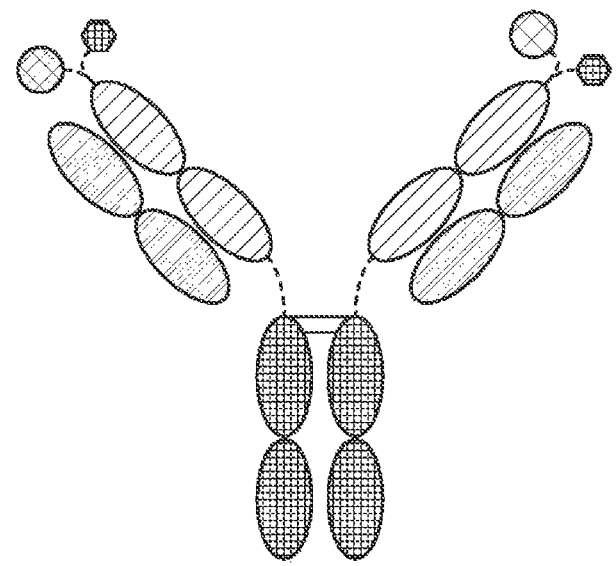
FIG. 29 is a representation of a TriNKET in the Cov-X-Body form.

FIG. 15A, FIG. 16, and FIG. 17A show KHYG-1 effector cell killing of Molm-13 (FIG. 15A), EOL-1 (FIG. 16), and THP-1 (FIG. 17A) human AML target cells respectively. KHYG-1 cells were demonstrated to express surface NKG2D, but do not express CD16. Therefore, TriNKET mediated killing here is dependent upon NKG2D mediated activation of the KHYG-1 effector cells. TriNKETs were able to mediate KHYG-1 effector cell killing of all three human AML target cell lines. Similar, TriNKET activity was demonstrated on all three target cell lines.

TriNKET mediated cytotoxicity of rested human NK cells was also tested. FIG. 15B and FIG. 17B show that TriNKETs also mediated cytotoxicity of rested human NK cells against Molm-13 (FIG. 15B) and THP-1 (FIG. 17B) human AML cells. FIG. 15B shows that TriNKETs mediated rested human NK cell killing of Molm-13 human AML cells. In FIG. 15B the rested human NK effector cell (E) to target cancer cell (T) ratio (E:T) was 10:1. The E:T ratio may reflect differences in the maximal % lysis.

TriNKETs also mediated rested human NK cell killing of THP-1 target cells, which express the high-affinity FcγRI. FIG. 17B shows that TriNKETs mediated rested human NK cell killing of THP-1 human AML cells, in which the E:T was 5:1.

Example 8: Assessment of TriNKET Binding to Cells Expressing Human NKG2D

I07 mAb was identified as a monoclonal antibody with high binding affinity to CD33. The heavy and light chain amino acid sequences of I07-F405L, an Fc variant of I07, are provided below. The I07-F405L mAb included a substitution of Leu for Phe at position 405 (under EU numbering) in the Fc CH3 domain. A Lys may be optionally included at the C-terminus of the heavy chain.

I07-F405L mAb heavy chain

[SEQ ID NO: 199]

EVQLVESGGGLVQPGGSLRLSCAASGFTFGSYWMSWVRQAPGKGLEWVAT

IKQDGSEKSYVDSVKGRFTISRDNAKNSLYLQMNSLRAEDTAVYYCARPL

NAGELDVWGQGTMVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFLLYSKLTVDKSRWQQGNVFSCSVMHEALHNHYTQKSLSLSPG

I07-F405 LmAb light chain

[SEQ ID NO: 200]

DIQMTQSPSTLSASVGDRVTITCRASQSISSWLAWYQQKPGKAPKLLIYE

ASSLESGVPSRFSGSGSGTEFTLTISSLQPDDFATYYCQQSQSYPPITFG

GGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

A49-F3'-TriNKET-I07, a TriNKET derivative of I07 mAb, is described in Section II—Multi-specific Binding Proteins. The amino acid sequences of this TriNKET are provided in SEQ ID NOs: 187, 189, and 190.

The ability of A49-F3'-TriNKET-I07 to bind to NKG2D was assessed using EL4 cells transduced with human NKG2D (EL4-hNKG2D). Briefly, A49-F3'-TriNKET-I07 and I07-F405L mAb were serially diluted. EL4-hNKG2D cells were incubated with the diluted TriNKET or mAb solutions. Binding of the TriNKET or mAb to the EL4 cells was detected using a fluorophore-conjugated anti-human IgG secondary antibody. The cells were analyzed by flow cytometry, and fold over background values were calculated by normalizing binding MFI to the MFI of a control group in which the cells were incubated with the secondary antibody only.

Figure 35:
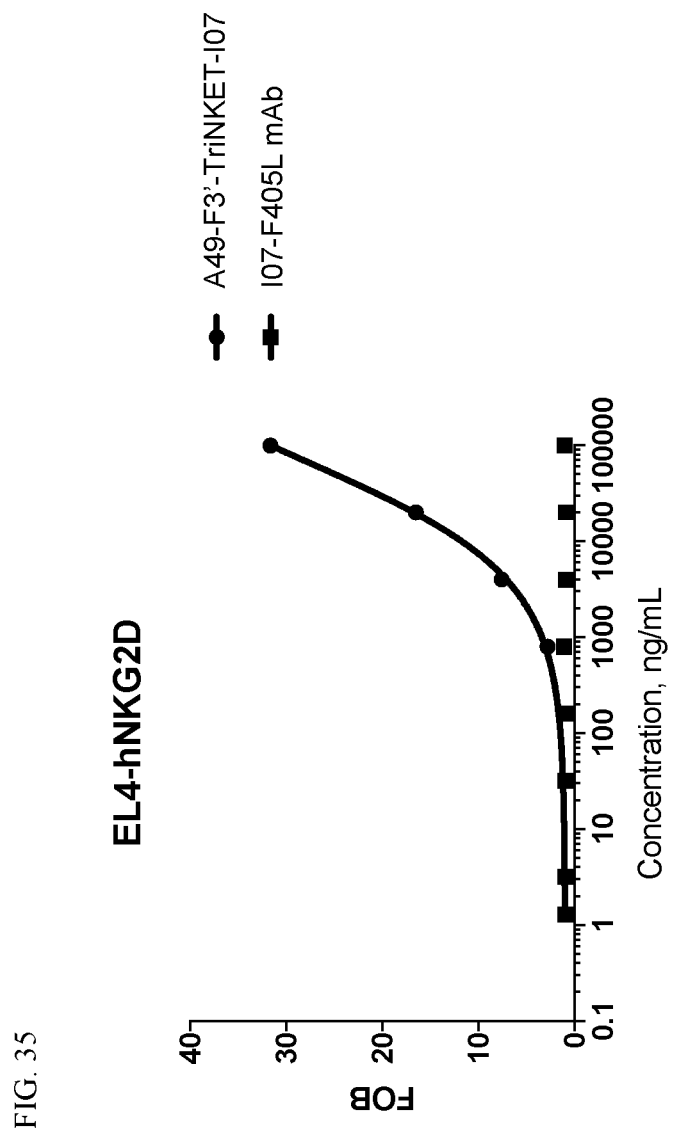
FIG. 35 is a graph showing binding of A49-F3'-TriNKET-I07 and I07-F405L mAb to cell surface human NKG2D expressed on EL4 cells.

As shown in FIG. 35, I07-F405L mAb showed no binding to EL4-hNKG2D cells. A49-F3'-TriNKET-I07 demonstrated weak binding to EL4-hNKG2D cells, without reaching saturation even at the high concentrations of 100 µg/mL.

Example 9: Assessment of TriNKET Binding to Cells Expressing Human CD33

The ability of A49-F3'-TriNKET-I07 to bind to CD33 was assessed using human cancer cell lines expressing CD33. Briefly, human AML cell lines Mv4-11 and Molm-13, which expressed CD33, were incubated with serially diluted A49-F3'-TriNKET-I07 and I07-F405L mAb solutions. Binding of A49-F3'-TriNKET-I07 or I07-F405L mAb to the AML cells was detected using a fluorophore-conjugated anti-human IgG secondary antibody. The cells were analyzed by flow cytometry, and fold over background values were calculated by normalizing binding MFI to the MFI of a control group in which the cells were incubated with the secondary antibody only.

Figure 36A:
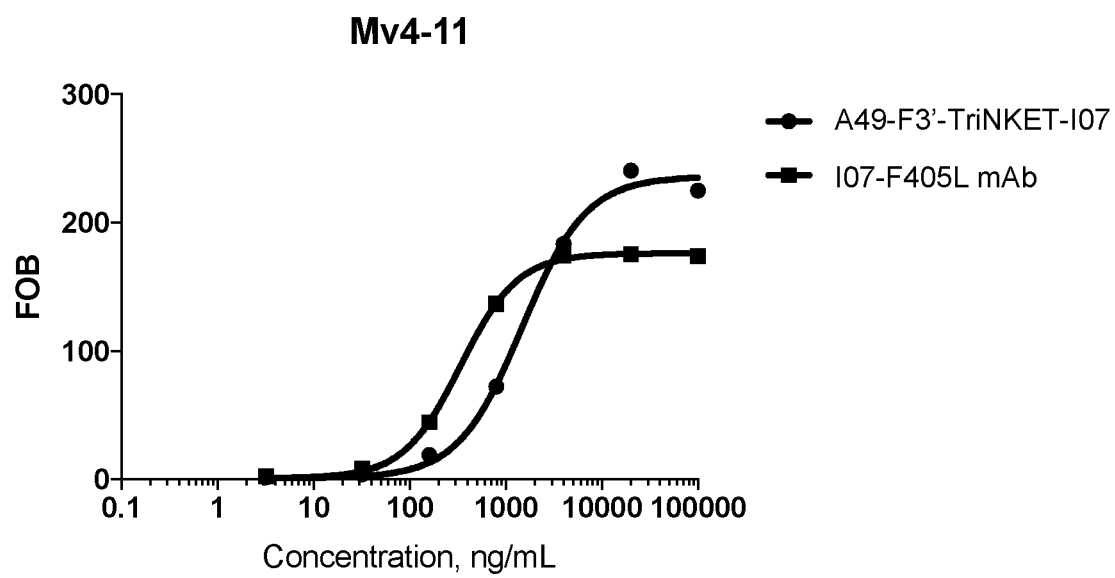
FIGS. 36A-36B are graphs showing binding of A49-F3'-TriNKET-I07 and I07-F405L mAb to CD33$^+$ human AML cell lines Mv4-11 (FIG. 36A) and Molm-13 (FIG. 36B).
Figure 36B:
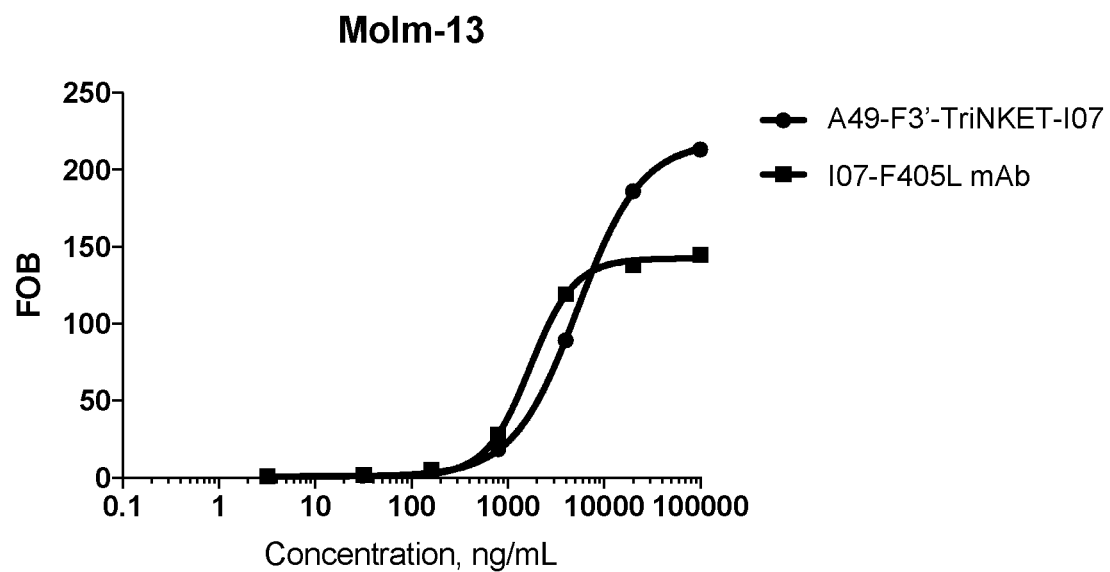

As shown in FIGS. 36A and 36B, A49-F3'-TriNKET-I07 exhibited a decrease in binding potency by three to four fold compared to I07-F405L mAb on both Molm-13 and Mv4-11 cells. A49-F3'-TriNKET-I07 was also found to bind to the cells with a higher maximum fold over background compared to I07-F405L mAb.

Example 10: Assessment of TriNKET Internalization

Internalization of A49-F3'-TriNKET-I07 and I07-F405L mAb upon binding to CD33 was assessed using human AML cell lines EOL-1 and Molm-13, which expressed CD33 on the cell surface. Briefly, the cells were incubated with 2 µg/mL A49-F3'-TriNKET-I07 or I07-F405L mAb for 20 minutes at room temperature. The cell samples were then split into three portions. The first and second portions were placed at 37° C. for 2 hours and 24 hours, respectively, to allow antibody internalization. Then the cells were incubated with a fluorophore-conjugated anti-human IgG secondary antibody, and were fixed for flow cytometry analysis. The third portion of the cell samples, used to set the baseline level, was incubated with the fluorophore-conjugated anti-human IgG secondary antibody without incubation at 37° C. The cells were fixed after staining with the secondary antibody, and were stored at 4° C. for analysis on the following day (when the first half of the samples were ready). The amount of A49-F3'-TriNKET-I07 and I07-F405L mAb bound to the cell surface was analyzed by flow cytometry on the same day. Internalization of antibodies was calculated as: % internalization=(1−(MFI of 24-hour sample/MFI of baseline sample))×100%.

Figure 37A:
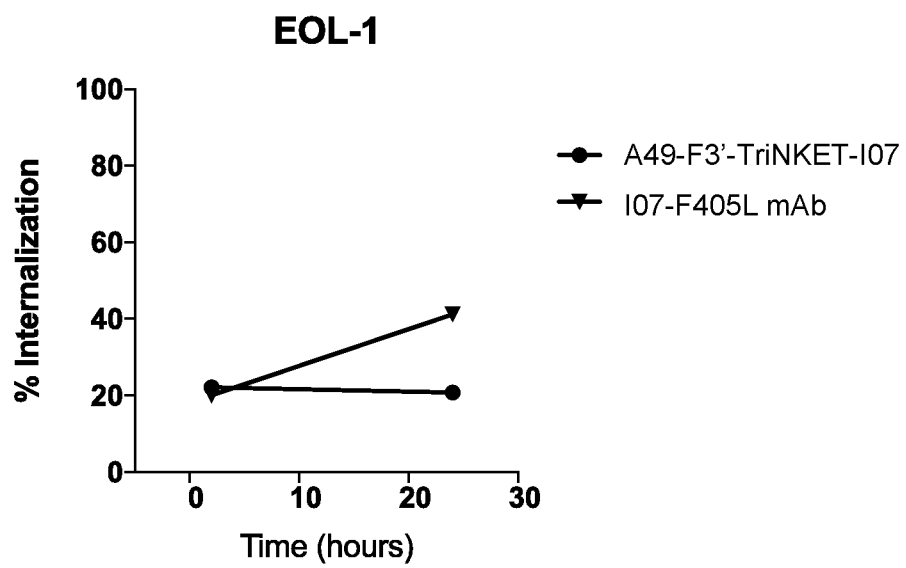
FIGS. 37A-37B are graphs showing internalization of A49-F3'-TriNKET-I07 and I07-F405L mAb after incubation with EOL-1 cells (FIG. 37A) and Molm-13 cells (FIG. 37B).
Figure 37B:
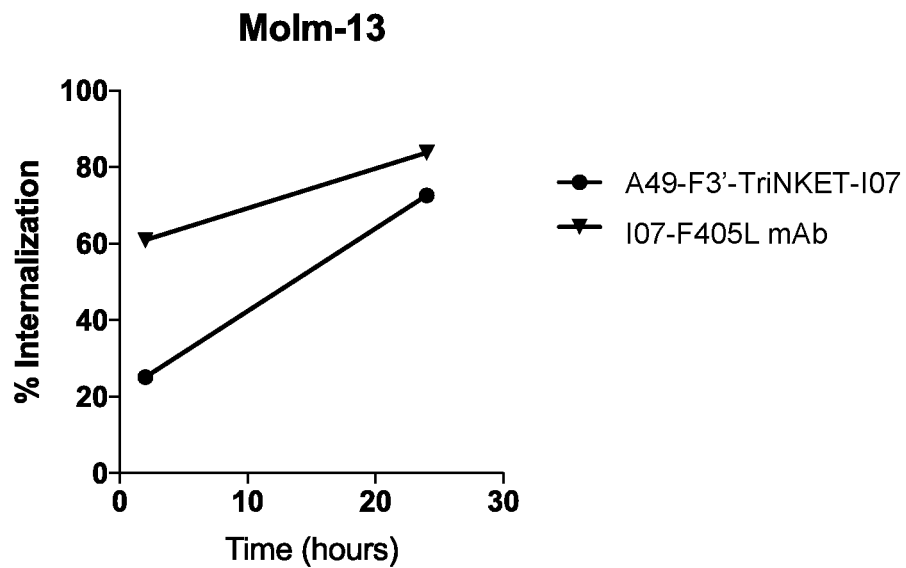

As shown in FIGS. 37A and 37B, internalization of A49-F3'-TriNKET-I07 and I07-F405L mAb after engagement of CD33 increased overtime on EOL-1 and Molm-13 cells. In both cells, I07-F405L mAb was internalized more rapidly and to a greater extent than A49-F3'-TriNKET-I07.

Example 11: Activation of Primary NK Cells by TriNKET

The ability of A49-F3'-TriNKET-I07 to elicit cytotoxicity of primary NK cells against human AML cells was assessed using the DELFIA cytotoxicity assay. Briefly, PBMCs were isolated from human peripheral blood buffy coats using density gradient centrifugation. The isolated PBMCs were washed, and NK cells were isolated using a negative selection technique with magnetic beads. The purity of the isolated NK cells was typically >90% CD3$^-$CD56$^+$. The isolated NK cells were rested without cytokine overnight.

On the following day, human AML cell lines Molm-13, THP-1, and EOL-1 were harvested from culture. The AML cells were washed with HBS, and were resuspended in growth media at $10^6$ cells/mL for labeling with BATDA reagent (Perkin Elmer AD0116) following the manufacturer instructions. After labeling, the AML cells were washed three times with HBS, and were resuspended at 0.5-1.0×10$^5$ cells/mL in culture media. 100 µl of BATDA labeled cells were added to each well of a 96-well plate.

The tested TriNKET or mAb was diluted in culture media, and 50 µl of diluted TriNKET or mAb was added to each well. Rested NK cells were harvested from culture, washed, and resuspended at $10^5$-2.0×10$^6$ cells/mL in culture media to attain a desired E:T ratio of 5:1. 50 µl of NK cells were added to each well of the plate to make a total of 200 µl culture volume in each well. The plate was incubated at 37C with 5% $CO_2$ for 2-3 hours.

After the culturing, the plate was removed from the incubator, and the cells were pelleted by centrifugation at 200×g for 5 minutes. 20 µl of culture supernatant was transferred to a clean microplate provided from the manufacturer. Supernatant from the labeled cells incubated alone was used to measure spontaneous release of TDA. Supernatant from labeled cells incubated with 1% octylphenoxy polyoxyethylene ether (TRITON™-X) was used to measure maximum lysis of the target cells. Supernatant from the labeled cells prior to the 2-3 hours of incubation was used to measure the background and for quality control purposes.

200 µl of room temperature europium solution was added to each well containing culture supernatant. The plate was protected from light and incubated on a plate shaker at 250 rpm for 15 minutes. Fluorescence was measured using a Victor3™ or SpectraMax SpectraMax® i3X instrument.

The fluorescent levels represented lysis of the target cells. The values of % specific lysis were calculated as: % specific lysis=((Experimental release−Spontaneous release)/(Maximum release−Spontaneous release))×100%.

A49-F3'-TriNKET-I07 and several monoclonal antibodies were tested in this assay. The monoclonal antibodies include I07-F405L mAb, I07-DE mAb, lintuzumab-GA, and 280-31-01(mut)-DE. I07-DE mAb is a variant of I07 mAb, with S239D and I332E substitutions in the Fc to enhance ADCC activity (bold-underlined in the sequence below). The amino acid sequence of I07-DE heavy chain is shown below, optionally with a Lys at the C-terminus.

I07-DEmAb heavy chain
[SEQ ID NO: 201]
EVQLVESGGGLVQPGGSLRLSCAASGFTFGSYWMSWVRQAPGKGLEWVAT

IKQDGSEKSYVDSVKGRFTISRDNAKNSLYLQMNSLRAEDTAVYYCARPL

NAGELDVWGQGTMVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPDVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPEEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

The light chain of I07-DE mAb is identical to that of I07-F405L mAb [SEQ ID NO:200].

280-31-01(mut)-DE is a variant of antibody clone 280-31-01 (mut) disclosed in WO2012045752, with S239D and I332E substitutions in the Fc to enhance ADCC activity (bold-underlined in the sequence below). The amino acid sequences of 280-31-01(mut)-DE heavy chain and light chain are shown below, optionally with a Lys at the C-terminus of the heavy chain.

280-31-01(mut)-DE heavy chain
(SEQ ID NO: 202)
QVQLVQSGAEVKKPGSSVKVSCKASGGTFSDYAISWVRQAPGQGLEWMGR

IIPILGVADYAQKFQGRVTITADKSTRTAYMELSSLRSEDTAVYYCARNW

ADAFDIWGQGTMVTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKRVEPKSCDKTHTCPPCPAPELLGGPDVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPEEKTISKAKGQPREPQVYT

LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPG 280-31-01(mut)-DE light chain
(SEQ ID NO: 203)
DIQLTQSPSSLSASVGDRVTITCRASQGISSVLAWYQQKPGKAPKLLIYD

ASSLESGVPSRFSGSGSGTDFTLTISSLQPEDFATYYCQQFDSSITFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

An SNP in the CD16 gene can result in V158 or F158 variants of the human CD16 protein. CD16 with F158 is known to have reduced binding affinity of CD16 to Fc than CD16 with V158, thereby decreasing antibody-dependent cell-mediated cytotoxicity (ADCC). NK cells having CD16-F158 are therefore less responsive to CD16 stimulation than NK cells expressing CD16-V158. Indeed, as shown in FIG. 38A, I07-F405L mAb only led to a low level of killing of Molm-13 cells by NK cells that only expressed the low affinity CD16 variant (CD16$^{F/F}$). In comparison, A49-F3'-TriNKET-I07 mediated more potent NK cell killing with a higher specific lysis of Molm-13 cells, likely due to its additional ability to engage NK cells by NKG2D binding. Similarly, when incubated with NK cells that had this SNP in one allele (CD16$^{V/F}$), A49-F3'-TriNKET-I07 exhibited stronger activity in killing EOL-1 cells than I07-F405L mAb (FIG. 38B).

THP-1 cells express FcγRI, which can bind to IgG1 Fc at high affinity. The competition for Fc binding by target cells can further reduce NK cell killing. Therefore, as shown in FIGS. 38C and 38D, when THP-1 cells were incubated with CD16$^{F/F}$ NK cells in the presence of I07-F405L or lintuzumab-GA mAb, no specific lysis of THP-1 cells was observed. Even I07-DE, an ADCC-enhancing variant of I07, failed to elicit NK cell cytotoxicity. Among the monoclonal antibodies tested, only 280-31-01(mut)-DE, an ADCC-enhancing variant of antibody clone 280-31-01 (mut) disclosed in WO2012045752, exhibited cell killing activity at high concentrations. Remarkably, A49-F3'-TriNKET-I07 mediated more potent NK cell killing with a higher specific lysis of THP-1 cells, likely due to its additional ability to engage NK cells by NKG2D binding.

Example 12: Activation of Primary CD8$^+$ T Cells by TriNKET

NKG2D is expressed on NK cells and many T cells, including CD8$^+$ T cells. The ability of A49-F3'-TriNKET-I07 to elicit cytotoxicity of primary CD8$^+$ T cells against human AML cells was assessed using the DELFIA cytotoxicity assay.

Briefly, human peripheral blood mononuclear cells (PBMCs) were isolated from human peripheral blood buffy coats using density gradient centrifugation. The isolated PBMCs were stimulated with 1 µg/mL Concanavalin A (ConA) at 37° C. for 18 hours. Then ConA was removed, and the PBMCs were cultured with 25 unit/mL IL-2 at 37° C. for 4 days. CD8$^+$ T cells were purified using a negative selection technique with magnetic beads, then cultured in media containing 10 ng/mL IL-15 at 37° C. for 7-13 days.

The primary human effector CD8$^+$ T cells generated above were characterized for cell markers. The cells were stained with fluorophore-conjugated antibodies against CD3, CD8, NKG2D, and CD16, and analyzed by flow cytometry. As shown in FIG. 39, the isolated CD8$^+$ T cells had high purity, as more than 99% of them were positive of CD3, CD8, and NKG2D expression, and were negative of CD16 expression.

To assess the ability of A49-F3'-TriNKET-I07 to elicit cytotoxicity of primary CD8$^+$ T cells, Molm-13 cells were harvested from culture, washed, and resuspended in growth media at 10$^6$ cells/mL. The cells were labeled with BATDA reagent (Perkin Elmer AD0116) following manufacturer instructions. After labeling, the cells were washed three times with HBS, and were resuspended at 0.5×10$^5$ cells/mL in culture media. 100 μl of BATDA labeled cells were added to each well of a 96-well plate. 50 μl of serially diluted monoclonal antibody or TriNKET was added to each well.

CD8$^+$ effector T cells were harvested from culture, washed, and resuspended at 5×10$^6$ cells/mL in culture media. 50 μl of CD8$^+$ T cells were added to each well of the plate to reach an E:T ratio of 50:1 and a total of culture volume of 200 μl. The plate was incubated at 37° C. with 5% CO$_2$ for 3.5 hours. After incubation, the cells were pelleted by centrifugation at 500×g for 5 minutes. 20 μl of culture supernatant was transferred to a clean microplate provided from the manufacturer. Supernatant from the labeled cells incubated alone was used to measure spontaneous release of TDA. Supernatant from labeled cells incubated with 1% octylphenoxy polyoxyethylene ether (TRITON™-X) was used to measure maximum lysis of the target cells.

200 μl of room temperature europium solution was added to each well. The plate was protected from light and incubated on a plate shaker at 250 rpm for 15 minutes. Fluorescence was measured using a SpectraMax® i3 X instrument.

The fluorescent levels represented lysis of the target cells. The values of % specific lysis were calculated as: % specific lysis=((Experimental release−Spontaneous release)/(Maximum release−Spontaneous release))×100%.

As shown in FIGS. 40A and 40B, A49-F3'-TriNKET-I07 enhanced the cytotoxic activity of human primary CD8$^+$ T cells in a dose-dependent manner. A49-F3'-TriNKET-H76, a protein described in Section II—Multi-specific Binding Proteins (having polypeptides comprising the sequences of SEQ ID NOs: 197, 189, and 190), was also active under the conditions but exhibited less potency than A49-F3'-TriNKET-I07. Monoclonal antibody I07-F405L and a non-target TriNKET did not show this activity.

Example 13: Binding of TriNKET to Monocytes

The expression of CD33 on blood cells is assessed by flow cytometry using the method described in Example 9. Briefly, human whole blood was incubated with A49-F3'-TriNKET-I07 or human IgG1 isotype control antibody conjugated to a fluorophore. Binding of A49-F3'-TriNKET-I07 or the isotype control antibody was detected by flow cytometry. To assess the binding levels on specific types of cells, fluorophore-conjugated antibodies that bind to surface markers of NK cells, CD8$^+$ T cells, CD4$^+$ T cells, B cells, and monocytes were added to the incubation, and the presence or absence of binding of these antibodies were used for gating when analyzing the flow cytometry data.

As shown in FIGS. 41A-41E, the binding of A49-F3'-TriNKET-I07 to NK cells was weak compared to a non-target human IgG1 isotype antibody control, whereas strong binding of the TriNKET to CD33$^+$ monocytes was observed.

Example 14: Long-Term NK Cell Cytotoxicity Mediated by TriNKET

Figure 42A:
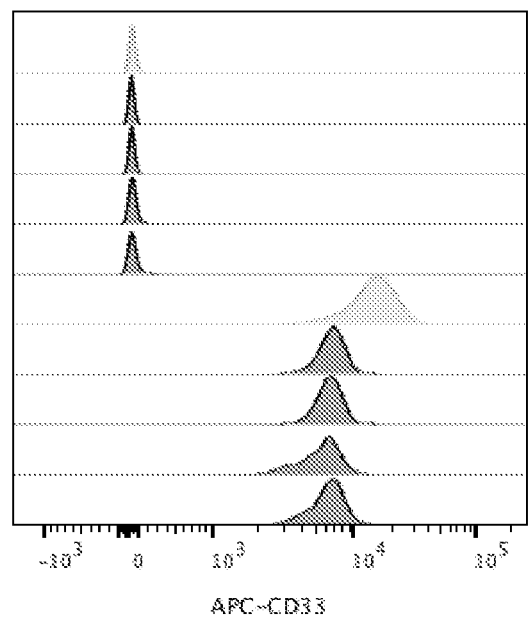
FIGS. 42A-42B are graphs showing CD33 expression on monocytes.
Figure 42B:
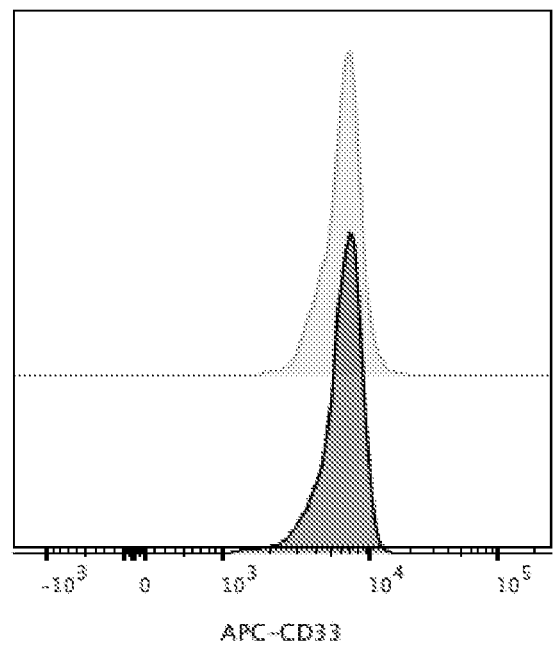

NK cells have a natural ability to sense transformed or stressed cells and kill them, but do not kill healthy cells. We tested the ability of A49-F3'-TriNKET-I07 to preserve the natural selective NK cell cytotoxicity using Molm-13 AML cells and human primary monocytes as target cells. The Molm-13 cells were obtained from DSMZ cell bank. The human primary monocytes were isolated from human peripheral blood. Briefly, PBMCs were isolated from human peripheral blood buffy coats using density gradient centrifugation. Monocytes were isolated by negative selection. CD33 expression on human primary monocytes and Molm-13 AML cells were confirmed by flow cytometry analysis (FIGS. 42A-42B).

Human primary NK cells were isolated from human peripheral blood. Briefly, PBMCs were isolated from human peripheral blood buffy coats using density gradient centrifugation. NK cells were isolated by negative selection. To distinguish target cells from NK cells in the co-culture, the target cells were fluorescently labeled. Specifically, the isolated monocytes were labeled with INCUCYTE® Cyto-Light Rapid live-cell labeling reagent according manufacturer's recommendations. The Molm-13 cells were infected with lentivirus encoding nuclear GFP, and cells with stable expression were selected with puromycin.

Isolated NK cells and target cells were mixed at an E:T ratio of 10:1 in the presence of 20 nM A49-F3'-TriNKET-I07. Non-specific activation of NK cells in the co-cultures was conducted in parallel as a positive control group for AML cell killing. The mixture was added to an Ibidi μ-slide. Time-lapse images for the phase and green channels were collected every hour, with 3 images per sample, using an INCUCYTE® S3 instrument. The images were analyzed using the INCUCYTE® S3 software. Live target cells were detected by green fluorescence, and the number of green cells at each time point was normalized to the number of green cells at time 0 from the same sample.

Figure 43A:
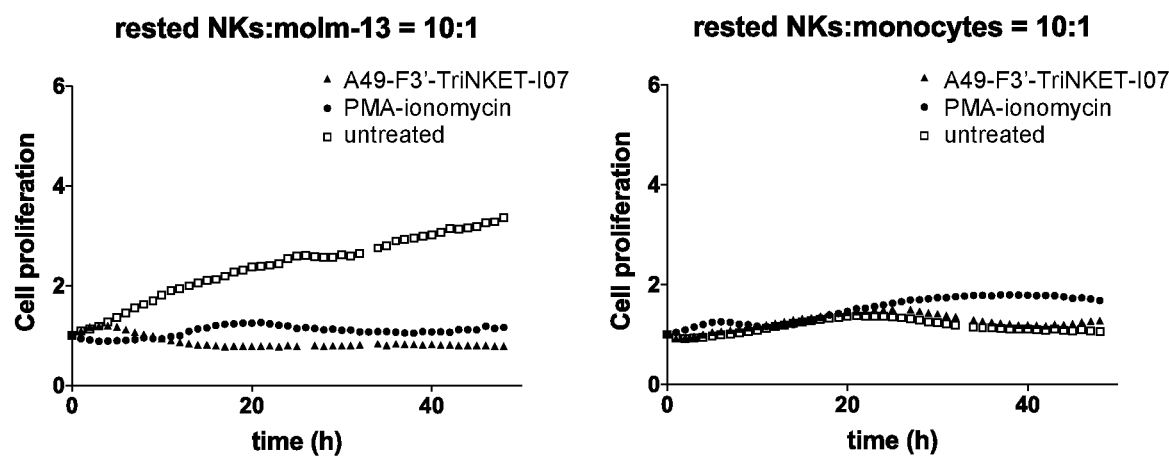
FIGS. 43A-43B are graphs showing long-term cytotoxicity of NK cells against Molm-13 AML cells and human primary monocytes in the presence of A49-F3'-TriNKET-I07. Proliferation of the target cells are plotted against the time of co-culture with NK cells in the presence of A49-F3'-TriNKET-I07 or PMA+ionomycin.
Figure 43B:
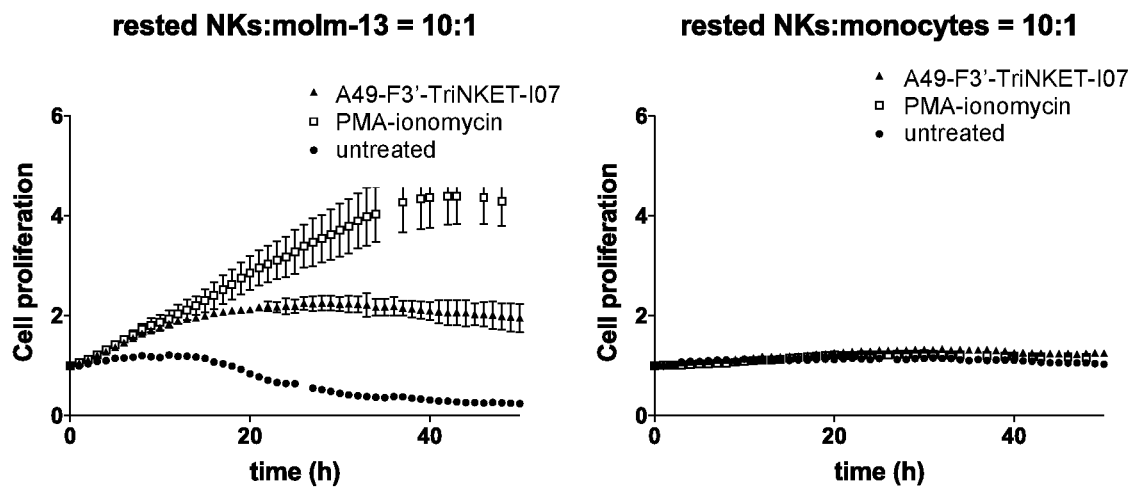
Figure 44:
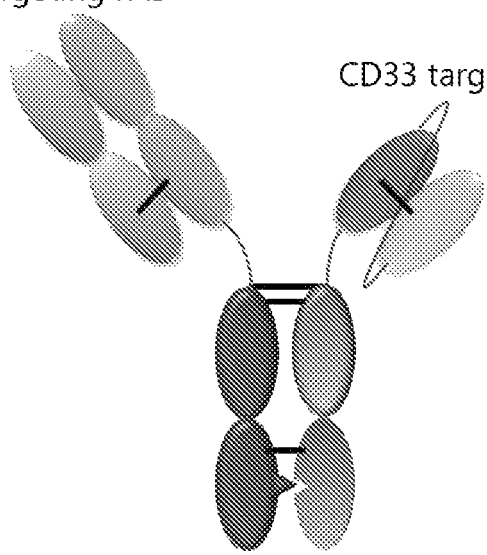
FIG. 44 illustrates a trispecific antibody (TriNKET) that contains a CD33-binding scFv, a NKG2D-targeting Fab, and a heterodimerized antibody constant domain that binds CD16. The antibody format is referred to herein as F3'-TriNKET.

As shown in FIGS. 43A and 43B, Molm-13 AML cells were able to proliferation in the presence of the NK cells alone, but target cell outgrowth was substantially inhibited by A49-F3'-TriNKET-I07. By contrast, A49-F3'-TriNKET-I07 did not mediate human NK cell killing of normal monocytes in the long-term co-culture. The activity of A49-F3'-TriNKET-I07 was similar to that of PMA+ionomycin, which also preserves the natural selectivity of NK cells. These results suggest that A49-F3'-TriNKET-I07 selectively compromised cancer cells, and potentially had a wide therapeutic window.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus

What is claimed is:

1. A protein comprising:
   (a) a first antigen-binding site that binds human NKG2D;
   (b) a second antigen-binding site that binds human CD33; and
   (c) an antibody Fc domain that binds human CD16 or a portion thereof that binds human CD16,
   wherein the first antigen-binding site that binds human NKG2D comprises a Fab fragment, and
   wherein the Fab fragment comprises a light chain complementarity-determining region 1 (CDR1) sequence comprising the amino acid sequence of SEQ ID NO:114, a light chain complementarity-determining region 2 (CDR2) sequence comprising the amino acid sequence of SEQ ID NO:115, a light chain complementarity-determining region 3 (CDR3) sequence comprising the amino acid sequence of SEQ ID NO: 116, a heavy chain complementarity-determining region 1 (CDR1) sequence comprising the amino acid sequence of SEQ ID NO:111, a heavy chain complementarity-determining region 2 (CDR2) sequence comprising the amino acid sequence of SEQ ID NO:112, and a heavy chain complementarity-determining region 3 (CDR3) sequence comprising the amino acid sequence of SEQ ID NO:113;
   and wherein the second antigen-binding site that binds human CD33 comprises a single-chain variable fragment (scFv), and wherein the scFv comprises a light chain CDR1 sequence comprising the amino acid sequence of SEQ ID NO:48, a light chain CDR2 sequence comprising the amino acid sequence of SEQ ID NO:49, a light chain CDR3 sequence comprising the amino acid sequence of SEQ ID NO:50, a heavy chain CDR1 sequence comprising the amino acid sequence of SEQ ID NO:45, a heavy chain CDR2 sequence comprising the amino acid sequence of SEQ ID NO:46, and a heavy chain CDR3 sequence comprising the amino acid sequence of SEQ ID NO:47.

2. The protein of claim 1, wherein the antibody Fc domain that binds human CD16 comprises an amino acid sequence at least 90% identical to the amino acid sequence of a human IgG1 constant region without CH1 domain, and wherein the amino acid sequence contains one or more mutations to enable heterodimerization.

3. The protein of claim 1, wherein the protein comprises
   (a) a first polypeptide comprising an amino acid sequence at least 95% identical to the amino acid sequence of SEQ ID NO: 187;
   (b) a second polypeptide comprising an amino acid sequence at least 95% identical to the amino acid sequence of SEQ ID NO:189; and
   (c) a third polypeptide comprising an amino acid sequence at least 95% identical to the amino acid sequence of SEQ ID NO:190.

4. The protein of claim 3, wherein the first polypeptide is linked to the second polypeptide via heterodimerization and at least one disulfide bond, and wherein the second polypeptide is linked to the third polypeptide via at least one disulfide bond.

5. The protein of claim 1, wherein the scFv of the second antigen-binding site is linked to the antibody Fc domain that binds human CD16 or a portion thereof that binds human CD16, via a hinge comprising Ala-Ser or Gly-Ala-Ser.

6. The protein of claim 1, wherein the first antigen-binding site that binds human NKG2D comprises a heavy chain variable region amino acid sequence at least 99% identical to the amino acid sequence of SEQ ID NO:87 and a light chain variable region amino acid sequence at least 99% identical to the amino acid sequence of SEQ ID NO:88.

7. The protein of claim 1, wherein the second antigen-binding site that binds human CD33 comprises a heavy chain variable region amino acid sequence at least 99% identical to the amino acid sequence of SEQ ID NO:9 and a light chain variable region amino acid sequence at least 99% identical to the amino acid sequence of SEQ ID NO:10.

8. The protein of claim 1, wherein the scFv of the second antigen-binding site that binds human CD33 comprises the amino acid sequence of SEQ ID NO:188.

9. The protein of claim 1, wherein the antibody Fc domain that binds human CD16 or a portion thereof that binds human CD16 comprises an amino acid sequence at least 90% identical to amino acids 234-332 of a human IgG1 antibody according to EU numbering.

10. The protein of claim 1, wherein the antibody Fc domain that binds human CD16 is an Fc domain of a human IgG1 comprising Y349C, K360E and K409W substitutions according to EU numbering.

11. The protein of claim 1, wherein the antibody Fc domain that binds human CD16 is an Fc domain of a human IgG1 comprising S354C, Q347R, D399V, and F405T substitutions according to EU numbering.

12. A protein comprising:
   (a) a first antigen-binding site that binds human NKG2D;
   (b) a second antigen-binding site that binds human CD33; and
   (c) an antibody Fc domain that binds human CD16 or a portion thereof that binds human CD16,
   wherein the first antigen-binding site that binds human NKG2D comprises a Fab fragment, and
   wherein the Fab fragment comprises a heavy chain variable region comprising the amino acid sequence of SEQ ID NO:87 and a light chain variable region comprising the amino acid sequence of SEQ ID NO:88; and
   wherein the second antigen-binding site that binds human CD33 comprises a single-chain variable fragment (scFv), and wherein the scFv comprises a heavy chain variable region comprising the amino acid sequence of SEQ ID NO:9 and a light chain variable region comprising the amino acid sequence of SEQ ID NO:10, wherein the heavy chain variable region of the scFv comprises one amino acid substitution relative to the amino acid sequence of SEQ ID NO:9 located in a framework region of the heavy chain variable region of the scFv, and wherein the light chain variable region of the scFv comprises one amino acid substitution relative to the amino acid sequence of SEQ ID NO: 10 located in a framework region of the light chain variable region of the scFv; and wherein the antibody Fc domain that binds human CD16 or a portion thereof that binds human CD16 comprises an amino acid sequence at least 90% identical to amino acids 234-332 of a human IgG1 antibody according to EU numbering.

13. A protein comprising:
(a) a first antigen-binding site that binds human NKG2D;
(b) a second antigen-binding site that binds human CD33; and
(c) an antibody Fc domain that binds human CD16 or a portion thereof that binds human CD16,
wherein the first antigen-binding site that binds human NKG2D comprises a Fab fragment, and
wherein the Fab fragment comprises a light chain complementarity-determining region 1 (CDR1) sequence comprising the amino acid sequence of SEQ ID NO:114, a light chain complementarity-determining region 2 (CDR2) sequence comprising the amino acid sequence of SEQ ID NO:115, a light chain complementarity-determining region 3 (CDR3) sequence comprising the amino acid sequence of SEQ ID NO:116, a heavy chain complementarity-determining region 1 (CDR1) sequence comprising the amino acid sequence of SEQ ID NO:192, a heavy chain complementarity-determining region 2 (CDR2) sequence comprising the amino acid sequence of SEQ ID NO:112, and a heavy chain complementarity-determining region 3 (CDR3) sequence comprising the amino acid sequence of SEQ ID NO:193;
and wherein the second antigen-binding site that binds human CD33 comprises a single-chain variable fragment (scFv), and wherein the scFv comprises a light chain CDR1 sequence comprising the amino acid sequence of SEQ ID NO:48, a light chain CDR2 sequence comprising the amino acid sequence of SEQ ID NO:49, a light chain CDR3 sequence comprising the amino acid sequence of SEQ ID NO:50, a heavy chain CDR1 sequence comprising the amino acid sequence of SEQ ID NO:181, a heavy chain CDR2 sequence comprising the amino acid sequence of SEQ ID NO:46, and a heavy chain CDR3 sequence comprising the amino acid sequence of SEQ ID NO: 182.

14. The protein of claim 13, wherein the protein comprises
(a) a first polypeptide comprising an amino acid sequence at least 95% identical to the amino acid sequence of SEQ ID NO:187;
(b) a second polypeptide comprising an amino acid sequence at least 95% identical to the amino acid sequence of SEQ ID NO:189; and
(c) a third polypeptide comprising an amino acid sequence at least 95% identical to the amino acid sequence of SEQ ID NO:190.

15. The protein of claim 13, wherein the first antigen-binding site that binds human NKG2D comprises a heavy chain variable region amino acid sequence at least 99% identical to the amino acid sequence of SEQ ID NO:87 and a light chain variable region amino acid sequence at least 99% identical to the amino acid sequence of SEQ ID NO:88.

16. The protein of claim 13, wherein the second antigen-binding site that binds human CD33 comprises a heavy chain variable region amino acid sequence at least 99% identical to the amino acid sequence of SEQ ID NO:9 and a light chain variable region amino acid sequence at least 99% identical to the amino acid sequence of SEQ ID NO:10.

17. The protein of claim 13, wherein the antibody Fc domain that binds human CD16 or a portion thereof that binds human CD16 comprises an amino acid sequence at least 90% identical to amino acids 234-332 of a human IgG1 antibody according to EU numbering.

18. The protein of claim 13, wherein the antibody Fc domain that binds human CD16 is an Fc domain of a human IgG1 comprising Y349C, K360E and K409W substitutions according to EU numbering.

19. The protein of claim 13, wherein the antibody Fc domain that binds human CD16 is an Fc domain of a human IgG1 comprising S354C, Q347R, D399V, and F405T substitutions according to EU numbering.

20. A protein comprising:
(a) a first polypeptide comprising the amino acid sequence of SEQ ID NO:187;
(b) a second polypeptide comprising the amino acid sequence of SEQ ID NO:189; and
(c) a third polypeptide comprising the amino acid sequence of SEQ ID NO:190,
wherein the first polypeptide is linked to the second polypeptide via heterodimerization and at least one disulfide bond, and wherein the second polypeptide is linked to the third polypeptide via at least one disulfide bond.

21. The protein of claim 12, wherein the one amino acid substitution in the heavy chain variable region of the scFv of the second antigen-binding site and the one amino acid substitution in the light chain variable region of the scFv of the second antigen-binding site form a disulfide bond.

22. The protein of claim 12, wherein the one amino acid substitution in the heavy chain variable region of the scFv of the second antigen-binding site is G44C numbered according to Kabat numbering, and the one amino acid substitution in the light chain variable region of the scFv of the second antigen-binding site is G100C numbered according to Kabat numbering.

23. The protein of claim 12, wherein the scFv of the second antigen-binding site that binds human CD33 comprises the amino acid sequence of SEQ ID NO:188.

24. The protein of claim 12, wherein the protein comprises
(a) a first polypeptide comprising an amino acid sequence at least 95% identical to the amino acid sequence of SEQ ID NO:187;
(b) a second polypeptide comprising an amino acid sequence at least 95% identical to the amino acid sequence of SEQ ID NO: 189; and
(c) a third polypeptide comprising an amino acid sequence at least 95% identical to the amino acid sequence of SEQ ID NO:190.

25. The protein of claim 24, wherein the first polypeptide is linked to the second polypeptide via heterodimerization and at least one disulfide bond, and wherein the second polypeptide is linked to the third polypeptide via at least one disulfide bond.

26. The protein of claim 13, wherein the antibody Fc domain that binds human CD16 comprises an amino acid sequence at least 90% identical to the amino acid sequence of a human IgG1 constant region without CHI domain, and wherein the amino acid sequence contains one or more mutations to enable heterodimerization.

27. The protein of claim 13, wherein the scFv of the second antigen-binding site that binds human CD33 comprises the amino acid sequence of SEQ ID NO: 188.

28. The protein of claim 14, wherein the first polypeptide is linked to the second polypeptide via heterodimerization and at least one disulfide bond, and wherein the second polypeptide is linked to the third polypeptide via at least one disulfide bond.

29. The protein of claim 13, wherein the scFv of the second antigen-binding site is linked to the antibody Fc domain that binds human CD16 or a portion thereof that binds human CD16, via a hinge comprising Ala-Ser or Gly-Ala-Ser.

30. The protein of claim 12, wherein the antibody Fc domain that binds human CD16 comprises an amino acid sequence at least 90% identical to the amino acid sequence of a human IgG1 constant region without CH1 domain, and wherein the amino acid sequence contains one or more mutations to enable heterodimerization.

31. The protein of claim 12, wherein the scFv of the second antigen-binding site is linked to the antibody Fc domain that binds human CD16 or a portion thereof that binds human CD16, via a hinge comprising Ala-Ser or Gly-Ala-Ser.

32. The protein of claim 12, wherein the antibody Fc domain that binds human CD16 or a portion thereof that binds human CD16 comprises an amino acid sequence at least 90% identical to amino acids 234-332 of a human IgG1 antibody according to EU numbering.

33. The protein of claim 12, wherein the antibody Fc domain that binds human CD16 is an Fc domain of a human IgG1 comprising Y349C, K360E and K409W substitutions according to EU numbering.

34. The protein of claim 12, wherein the antibody Fc domain that binds human CD16 is an Fc domain of a human IgG1 comprising S354C, Q347R, D399V, and F405T substitutions according to EU numbering.

35. The protein of claim 1, wherein the antibody Fc domain that binds human CD16 comprises an amino acid sequence at least 95% identical to the amino acid sequence of a human IgG1 constant region without CHI domain, and wherein the amino acid sequence contains one or more mutations to enable heterodimerization.

36. The protein of claim 12, wherein the antibody Fc domain that binds human CD16 comprises an amino acid sequence at least 95% identical to the amino acid sequence of a human IgGI constant region without CHI domain, and wherein the amino acid sequence contains one or more mutations to enable heterodimerization.

37. The protein of claim 13, wherein the antibody Fc domain that binds human CD16 comprises an amino acid sequence at least 95% identical to the amino acid sequence of a human IgG1 constant region without CHI domain, and wherein the amino acid sequence contains one or more mutations to enable heterodimerization.

38. The protein of claim 1, wherein the antibody Fc domain that binds human CD16 or a portion thereof that binds human CD16 comprises an amino acid sequence at least 95% identical to amino acids 234-332 of a human IgGI antibody according to EU numbering.

39. The protein of claim 12, wherein the antibody Fc domain that binds human CD16 or a portion thereof that binds human CD16 comprises an amino acid sequence at least 95% identical to amino acids 234-332 of a human IgG1 antibody according to EU numbering.

40. The protein of claim 13, wherein the antibody Fc domain that binds human CD16 or a portion thereof that binds human CD16 comprises an amino acid sequence at least 95% identical to amino acids 234-332 of a human IgG1 antibody according to EU numbering.

\* \* \* \* \*